US012497604B2

(12) United States Patent
Ledbetter et al.

(10) Patent No.: US 12,497,604 B2
(45) **Date of Patent: *Dec. 16, 2025**

(54) RNASE-PON1 FUSION POLYPEPTIDES AND RELATED COMPOSITIONS AND METHODS

(71) Applicant: Theripion, Inc., Shoreline, WA (US)

(72) Inventors: Jeffrey A. Ledbetter, Shoreline, WA (US); Martha S. Hayden-Ledbetter, Shoreline, WA (US)

(73) Assignee: Theripion, Inc., Shoreline, WA (US)

(*) Notice: Subject to any disclaimer, the term of this patent is extended or adjusted under 35 U.S.C. 154(b) by 0 days.

This patent is subject to a terminal disclaimer.

(21) Appl. No.: 19/025,781

(22) Filed: Jan. 16, 2025

(65) Prior Publication Data

US 2025/0154484 A1 May 15, 2025

Related U.S. Application Data

(60) Continuation of application No. 18/923,463, filed on Oct. 22, 2024, now Pat. No. 12,258,596, which is a division of application No. 18/546,413, filed as application No. PCT/US2022/016723 on Feb. 17, 2022, now Pat. No. 12,180,521.

(60) Provisional application No. 63/151,236, filed on Feb. 19, 2021, provisional application No. 63/151,272, filed on Feb. 19, 2021.

(51) Int. Cl.

| | |
|---|---|
| ***C12N 9/22*** | (2006.01) |
| ***A61P 11/00*** | (2006.01) |
| ***C07K 16/24*** | (2006.01) |
| ***C12N 9/16*** | (2006.01) |
| *A61K 38/00* | (2006.01) |

(52) U.S. Cl.

CPC ................ *C12N 9/22* (2013.01); *A61P 11/00* (2018.01); *C07K 16/241* (2013.01); *C12N 9/16* (2013.01); *C12Y 301/08001* (2013.01); *A61K 38/00* (2013.01); *C07K 2317/31* (2013.01); *C07K 2317/622* (2013.01); *C07K 2319/01* (2013.01); *C07K 2319/30* (2013.01); *C12Y 301/21001* (2013.01)

(58) Field of Classification Search

CPC .. C12N 9/22; C12N 9/16; A61P 11/00; C07K 16/241; C07K 2317/31; C07K 2317/622; C07K 2319/01; C07K 2319/30; C12Y 301/08001; C12Y 301/21001; A61K 38/00

See application file for complete search history.

(56) References Cited

U.S. PATENT DOCUMENTS

| | | | |
|---|---|---|---|
| 8,735,124 B2 | 5/2014 | Tawfik | |
| 8,937,157 B2 | 1/2015 | Ledbetter | |
| 10,000,745 B2 | 6/2018 | Ledbetter | |
| 2003/0092059 A1 | 5/2003 | Salfeld et al. | |
| 2003/0118592 A1 | 6/2003 | Ledbetter et al. | |
| 2010/0098693 A1 | 4/2010 | Pardridge | |
| 2012/0213834 A1 | 8/2012 | Tawfik et al. | |
| 2014/0120091 A1* | 5/2014 | Ledbetter ......... | C07K 14/70578 435/69.6 |
| 2018/0187174 A1* | 7/2018 | Ledbetter .................. | A61P 5/14 |
| 2018/0201664 A1 | 7/2018 | Hayden-Ledbetter | |
| 2019/0241878 A1 | 8/2019 | Posada et al. | |
| 2024/0101982 A1 | 3/2024 | Ledbetter | |

FOREIGN PATENT DOCUMENTS

| | | | |
|---|---|---|---|
| WO | 2011084714 | 7/2011 | |
| WO | 2014115084 | 7/2014 | |
| WO | 2018136163 | 7/2018 | |
| WO | WO-2018136163 A2 * | 7/2018 | ........... C07K 14/775 |
| WO | 2022178078 | 8/2022 | |

OTHER PUBLICATIONS

Gaidukov, L., et al., "High Affinity, Stability, and Lactonase Activity of Serum Paraoxonase PON1 Anchored on HDL with ApoA-I," Biochemistry 2005, 44: 11843-11854.

International Search Report & Written Opinion mailed Sep. 29, 2022, issued in corresponding International Application No. PCT/US2022/016723, filed Feb. 17, 2022, 20 pages.

Aharoni, A, et al., "Directed evolution of mammalian paraoxonases PON1 and PON3 for bacterial expression and catalytic specialization," Proc. Natl. Acad. Sci. USA 101 :482-487, Jan. 13, 2004, DOI: 10.1073/pnas.2536901100.

Goldsmith, M., et al., "Evolved Stereoselective Hydrolases for Broad-Spectrum G-Type Nerve Agent Detoxification," Chemistry & Biology 19:456-466, Apr. 20, 2012.

(Continued)

*Primary Examiner* — Nelson B Moseley, II
*Assistant Examiner* — Alyssa Rae Stonebraker
(74) *Attorney, Agent, or Firm* — Sherbina Intellectual Property Law, PLLC; Nicholas V. Sherbina

(57) ABSTRACT

Compositions and methods relating to paraoxonase fusion polypeptides are disclosed. In some aspects, the fusions are bispecific molecules that include a first biologically active polypeptide linked amino-terminal to a biologically active paraoxonase, wherein the first biologically active polypeptide is a DNase, an RNase, a SOD1, a CTLA-4 extracellular domain, a CD40 extracellular domain, or a polypeptide that specifically binds and neutralizes an inflammatory cytokine. Bispecific fusions may further include a second biologically active polypeptide (e.g., a dimerizing or FcRn-binding domain) linked carboxyl-terminal to the first biologically active polypeptide and amino-terminal to the paraoxonase. In other aspects, a fusion polypeptide includes a biologically active paraoxonase linked carboxyl-terminal or amino-terminal to a dimerizing or FcRn-binding domain. Also disclosed are dimeric proteins comprising first and second paraoxonase fusion polypeptides as disclosed herein. The fusion polypeptides and dimeric proteins are useful in methods for therapy.

16 Claims, 19 Drawing Sheets

Specification includes a Sequence Listing.

(56) References Cited

OTHER PUBLICATIONS

Harel, M., et al., "3-D Structure of Serum Paraoxonase 1 Sheds Light On Its Activity, Stability, Solubility and Crystallizability," Arh. Hig. Rada. Toksikol. 58:347-353, 2007.

Sarkar, M., et al., "Solubilization and Humanization of Paraoxonase-1," J. Lipids, vol. 2012, Article ID Article ID 610937, pp. 1-13, 2012, DOI: 10.1155/2012/610937.

Zharkova, O., et al., "A Flow Cytometry-Based Assay for High-Throughput Detection and Quantification of Neutrophil Extracellular Traps in Mixed Cell Populations," Cytometry Part A 95A:268-278, 2019.

Sorenson, R.C., et al., "Human Serum Paraoxonase/Arylesterase's Retained Hydrophobic N-Terminal Leader 8 Sequence Associates with HDLs by Binding Phospholipids—Apolipoprotein A-I Stabilizes Activity," Arterioscler. Thromb. Vase. Biol. 19:2214-2225, 1999.

Stoltz, D.A., et al., "*Drosophila* are protected from *Pseudomonas aeruginosa* lethality by transgenic expression of paraoxonase-1," J. Clin. Invest. 118:3123-3131, Sep. 2008.

Bacchetti, T., et al., "Plasma oxidation status and antioxidant capacity in psoriatic children," Arch. Dermatol. Res. 312:33-39, 2020.

Shakoei, S., et al., "The Serum Level of Oxidative Stress and Antioxidant Markers in Patients with Psoriasis: A Cross-sectional Study," J. Clin. Aesthet. Dermatol. 14:38-41, 2021.

Simonetti, O., et al., "Oxidative Stress and Alterations of Paraoxonases in Atopic Dermatitis," Antioxidants 10:697, pp. 1-11, 2021.

Boado, R.J., et al., "IgG-Paraoxonase-1 Fusion Protein for Targeted Drug Delivery Across the Human Blood-Brain Barrier," Mol. Pharm. 5:1037-1043, 2008.

Lee, S.J., et al., "PEP-1-paraoxonase 1 fusion protein prevents cytokine-induced cell destruction and impaired insulin secretion in rat insulinoma cells," BMB Rep. 51 :538-543, 2018.

Kim, D.S., et al. "Pharmacogenetics of paraoxonase activity: elucidating the role of high-density lipoprotein in disease," 15 Pharmacogenomics Author Manuscript; available in PMC Jul. 1, 2014; published in final edited form as Pharmacogenomics 14:1495-1515, Sep. 2013.

Stevens, R.C., et al., "Engineered recombinants human paraoxonase 1 (rHuPON1) purified from *Escherichia coli* protects against organophosphate poisoning," Proc. Natl. Acad. Sci. USA 105: 12780-12784, Sep. 2, 2008.

Eren, E., et al., "Functionally Defective High-Density Lipoprotein and Paraoxonase: A Couple for Endothelial Dysfunction in Atherosclerosis," Cholesterol, vol. 2013, Article ID 792090, 2013 DOI: 10.1155/2013/792090.

Kim, M.J., et al., "Transduced PEP-1-PON1 proteins regulate microglial activation and dopaminergic neuronal death in a Parkinson's disease model," Biomaterials 64:45-56, 2015, available online Jun. 14, 2015.

Koren-Gluzer, M., et al., "The antioxidant HDL-associated paraoxonase-1 (PON1) attenuates diabetes development and stimulates ~-cell insulin release," Atherosclerosis 219:510-518, 2011, available online Aug. 4, 2011, 001:10.1016/j.atherosclerosis.2011.07.119.

Mackness, M., et al., "Human paraoxonase-1 (PON1): Gene structure and expression, promiscuous activities and multiple physiological roles," Gene 567:12-21, 2015, available online May 9, 2015, DOI:10.1016/j.gene.2015.04.088.

Menini, T., et al., "Paraoxonase 1 in neurological disorders," Redox Report, 19:49-58, 2014, DOI: 10.1179/1351000213Y.0000000071.

Peng, W., et al., "Comparative evaluation of the protective potentials of human paraoxonase 1 and 3 against CCI4-induced liver injury," Toxicol. Lett. 193:159-166, 2010, available online Jan. 15, 2010, O01:10.1016/j.toxlet.2010.01 .003.

Rosenblat, M., et al., "Injection of paraoxonase 1 (PON1) to mice stimulates their HDL and macrophage antiatherogenicity," Biofactors 37:462-467, 2011, published online Dec. 8, 2011, DOI: 10.1002/biof.188.

Ceron, J.J., et al., "Serum paraoxonase 1 (PON1) measurement: an update," BMC Vet. Res. 10:74, 2014, DOI: 10.1186/17 46-6148-10-7 4.

Dias, C.G., et al., "Quantification of the arylesterase activity of paraoxonase-1 in human blood," Anal. Methods 6:289-294, 2014, DOI:10.1039/c3ay41527a.

Gugliucci, A., et al., "Enzymatic assessment of paraoxonase 1 activity on HDL subclasses: A practical zymogram 26 method to assess HDL function," Clin. Chim. Acta 415:162-168, 2013; available online Oct. 30, 2012;DOI: 10.1016/j.cca.2012.10.044.

Kirby, S.D., et al., "Human paraoxonase double mutants hydrolyze V and G class organophosphorus nerve agents," Chem. Biol. Interact. 203:181-185, 2013; available online Nov. 15, 2012; DOI:10.1016/j.cbi.2012.10.023.

Otto, T.C., et al., "Dramatic Differences in Organophosphorus Hydrolase Activity between Human and Chimeric Recombinant Mammalian Paraoxonase-1 Enzymes," Biochemistry 48: 10416-10422, 2009, DOI: 10.1021/bi901161 b.

Yamashita, J., et al., Paraoxonase-1 Suppresses Experimental Colitis via the Inhibition of IFN-gamma Production from CD4 T Cells, J. Immunol. 191 :949-960, 2013; prepublished Jun. 14, 2013; 001:10.4049/jimmunol.1201828.

Bojic, S., et al., "Low Paraoxonase 1 Activity Predicts Mortality in Surgical Patients with Sepsis," Disease Markers, vol. 2014, Article ID 427378, pp. 1-8, Feb. 9, 2014, 001:10.1155/2014/427378.

Inal, V., et al., "Paraoxonase 1 Activity and Survival in Sepsis Patients," Balkan Med. J. 32: 183-8, Apr. 2015, DOI: 10.5152/balkanmedj.2015.15674.

Boado, R.J., et al., "CHO Cell Expression, Long-Term Stability, and Primate Pharmacokinetics and Brain Uptake of 32 an IgG-Paraoxonase-1 Fusion Protein," Biotechnol. Bioeng. 108:186-196, Jan. 1, 2011; published online Aug. 27, 2010, OOI:10.1002/bit.22907.

Wang, X., et al., "IgG Fe engineering to modulate antibody effector functions," Protein Cell 9:63-73, 2018, 001:10.1007/s13238-017-0473-8.

Bitonti, A.J., et al., "Pulmonary delivery of an erythropoietin Fe fusion protein in non-human primates through an immunoglobulin transport pathway," Proc. Natl. Acad. Sci. USA 101 :9763-9768, Jun. 29, 2004.

Bitonti, A.J., et al., "Pulmonary administration of therapeutic proteins using an immunoglobulin transport pathway," Adv. Drug Deliv. Rev. 58:1106-1118, 2006.

Hajri, T., "Effects of oxidized lipids and lipoproteins on cardiac function," Front. Biosci. (Landmark Ed) 23: 1822-1847, Jun. 1, 2018.

Hertel, S.P., et al., "Protein stability in pulmonary drug delivery via nebulization," Adv. Drug Deliv. Rev. 93:79-94, 2015, available online Oct. 12, 2014.

Lo, M., et al., "Effector-attenuating Substitutions That Maintain Antibody Stability and Reduce Toxicity in Mice," J. Biol. Chem. 292:3900-3908, Mar. 3, 2017.

Moldogazieva, N.T., et al., "Oxidative Stress and Advanced Lipoxidation and Glycation End Products (ALEs and AGEs) in Aging and Age-Related Diseases," Oxid. Med. Cell. Longev., vol. 2019, Article ID 3085756, Aug. 14, 2019.

Padlan, E.A., "Anatomy of the Antibody Molecule," Mol. Immunol. 31: 169-217, 1994.

Tam, S.H., et al., "Functional, Biophysical, and Structural Characterization of Human IgG1 and IgG4 Fe Variants with Ablated Immune Functionality," Antibodies 6:12, 2017, DOI:10.3390/antib6030012.

Vallee, S., et al., "Pulmonary Administration of Interferon Beta-1a-Fc Fusion Protein in Non-Human Primates Using an Immunoglobulin Transport Pathway," J. Interferon Cytokine Res. 32:178-184, 2012, DOI: 10.1089/jir.2011.0048.

Bajaj, P., et al., "Characterization of human paraoxonase 1 variants suggest that His residues at 115 and 134 positions are not always needed for the lactonase/arylesterase activities of the enzyme," Protein Sci. 22: 1799-1807, 2013.

Bajaj, P., et al., "Expression and purification of biologically active recombinant human paraoxonase 1 from inclusion bodies of *Escherichia coli*," Protein Expr. Purif. 115:95-101, 2015.

(56) References Cited

OTHER PUBLICATIONS

Aalbers, F.S., and Fraaije, M.W., "Enzyme Fusions in Biocatalysis: Coupling Reactions by Pairing Enzymes," ChemBioChem 20:20-28, 2019, DOI: 10.1002/cbic.201800394.
Aviram, M., et al., "Paraoxonase Inhibits High-density Lipoprotein Oxidation and Preserves its Functions: A Possible Peroxidative Role for Paraoxonase," J. Clin. Invest. 101:1581-1590, 1998.
Bajaj, P., et al., "Refolded Recombinant Human Paraoxonase 1 Variant Exhibits Prophylactic Activity Against Organophosphate Poisoning," Appl. Biochem. Biotechnol. 180:165-176, 2016.
Bergonzi, C., et al., "The quorum-quenching lactonase from Geobacillus caldoxylosilyticus: purification, characterization, crystallization and crystallographic analysis," Acta Cryst. F72:681-686, 2016.
Bergonzi, C., et al., "Structural and Biochemical Characterization of AaL, a Quorum Quenching Lactonase with Unusual Kinetic Properties," Nature 8:11262, 2018, DOI:10.1038/s41598-018-28988-5.
Chen, X., et al., "Fusion Protein Linkers: Property, Design and Functionality," Adv. Drug Deliv. Rev. 65:1357-1369, Oct. 15, 2013, DOI:10.1016/j.addr.2012.09.039.
Cabrera-Fuentes, H.A., et al., "RNase1 as a potential mediator of remote ischaemic preconditioning for cardioprotection," Eur. J. Cardiothorac. Surg. 48:732-737, Jan. 2015 (Year: 2015).
Feng, Y., et al., "Cardiac RNA Induces Inflammatory Responses in Cardiomyocytes and Immune Cells via Toll-like 1 Receptor 7 Signaling," J. Biol. Chem. 290:26688-26698, Oct. 30, 2015; published, JBC Papers in Press, D Sep. 11, 2015. DOI: 10.107 4/jbc.M 115.661835.
Chen, C., et al., "Protective Effect of RNase on Unilateral Nephrectomy-Induced Postoperative Cognitive Dysfunction in Aged Mice," PLoS One 10:e0134307, Jul. 30, 2015, 13 pages. 001:10.1371/journal.pone.0134307.
Fischer, S., et al., "Extracellular RNA promotes leukocyte recruitment in the vascular system by mobilising proinflammatory cytokines," Thromb. Haemost. 108:730-741, 2012. DOI:10.1160/TH12-03-0186.
Lehmann, S.M., et al., "Extracellularly Delivered Single-Stranded Viral RNA Causes Neurodegeneration Dependent on TLR7," J. Immunol. 189:1448-1458, 2012, prepublished online Jun. 27, 2012. 001:10.4049/jimmunol.1201078.
Newton, D.L., et al., "Potent and specific antitumor effects of an anti-CD22-targeted cytotoxic ribonuclease: potential for the treatment of non-Hodgkin lymphoma," Blood 97(2):528-535, Jan. 15, 2001. DOI: 10.1182/blood. V97.2.528.
Simsekyilmaz, S., et al., "Role of Extracellular RNA in Atherosclerotic Plaque Formation in Mice," Circulation 129:598-606, 2013. 001:10.1161/CIRCULATIONAHA. 113.002562.
Sun, X., et al., "Increased Ribonuclease Expression Reduces Inflammation and Prolongs Survival in TLR7 Transgenic Mice," J. Immunol. 190:2536-2543, 2013, prepublished online Feb. 4, 2013. DOI: 10.4049/jimmunol.1202689.
Walberer, M., et al., "RNase therapy assessed by magnetic resonance imaging reduces cerebral edema and infarction size in acute stroke," Curr. Neurovasc. Res. 6(1):12-19, 2009, PMID 19355922, Abstract.
Bedoya, V.I., et al., "Ribonucleases in HIV Type 1 Inhibition: Effect of Recombinant RNases on Infection of Primary T Cells and Immune Activation-Induced RNase Gene and Protein Expression," AIDS Research and Human Retroviruses 22(9):897-907, 2006.
Bernard, M.A., et al., "HIV-Derived ssRNA Binds to TLR8 to Induce Inflammation-Driven Macrophage Foam Cell Formation," PLoS One 9(8):e104039, Aug. 14, 2014, 12 pages. 001:10.1371/joumal.pone.0104039.
Chen, C., et al., "Role of Extracellular RNA and TLR3-Trif Signaling in Myocardial Ischemia—Reperfusion Injury," J. Am. Heart Assoc. 3(1):e000683, 2014, 17 pages. DOI: 10.1161/JAHA.113.000683.
Rutkoski, T.J., et al., "Human Ribonuclease with a Pendant Poly(Ethylene Glycol) Inhibits Tumor Growth in Mice," Translational Oncology 6(4):392-397, 2013.
Mironova, N., et al., "The systemic tumor response to RNase A treatment affects the expression of genes involved in maintaining cell malignancy," Oncotarget 8(45):78796-78810, 2017.
Eller, C.H., et al., "Human Cancer Antigen Globo H Is a Cell-Surface Ligand for Human Ribonuclease," ACS Central Sci. 1:181-190, 2015.
Kleinert, E., et al., "Ribonuclease (RNase) Prolongs Survival of Grafts in Experimental Heart Transplantation," J. Am. Heart Assoc. 5(5):1-13, 2016. doi: 10.1161/JAHA.116.003429.
Steiger, et al., "Targeting of Extracellular RNA Reduces Edema Formation and Infarct Size and Improves Survival After Myocardial Infarction in Mice," J. Am. Heart Assoc. 6:e004541, 2017, 13 pages.
Noll, F., et al., "Self-extracellular RNA acts in synergy with exogenous danger signals to promote inflammation," PloS One 12:e0190002, 2017, 17 pages.
Murray, L.A., et al., "Deleterious Role of TLR3 during Hyperoxia-induced Acute Lung Injury," Am. J. Respir. Crit. Care Med. 178:1227-1237, 2008.
Biswas, I., et al., "Extracellular RNA facilitates hypoxia-induced leukocyte adhesion and infiltration in the lung through TLR3-IFN-γ-STAT1 signaling pathway," Eur. J. Immunol. 45:3158-3173, 2015.
Rajasekaran, S., et al., "MicroRNAs as potential targets for progressive pulmonary fibrosis," Front. Pharmacol. 6:254, 2015, 15 pages.
Thum, T., et al., "MicroRNA-21 contributes to myocardial disease by stimulating MAP kinase signalling in fibroblasts," Nature 456:980-984, 2008.
Kato, M., et al., "MicroRNAs and Their Role in Progressive Kidney Diseases," Clin. J. Am. Soc. Nephrol 4(7):1255-1266, 2009.
Lee, Y.S., and Dutta, A., "MicroRNAs in cancer," Annu. Rev. Pathol. 4:199-227, 2009.
Kumar, M., et al., "MicroRNAs: a new ray of hope for diabetes mellitus," Protein Cell. 3(10):726-738, 2012.
Noetel, A., et al., "microRNAarecentralplayersinanti-andprofibroticgeneregulationduringliverfibrosis," Front. Physiol. 3:49, 2012, 6 pages.
Zampetaki, A., and Mayr, M., "MicroRNAs in Vascular and Metabolic Disease," Circ. Res. 110:508-522, 2012.
Barna, B.P., et al., "Elevated MicroRNA-33 in Sarcoidosis and a Carbon Nanotube Model of Chronic Granulomatous Disease," Am. J. Respir. Cell Mol. Biol. 54(6):865-871, 2016.
Shikano, S., et al., "Increased extracellular vesicle miRNA-466 family in the bronchoalveolar lavage fluid as a precipitating factor of ARDS," BMC Pulmonary Med. 19:110, 2019, 11 pages.
Scheller, N., et al., "Proviral MicroRNAs Detected in Extracellular Vesicles From Bronchoalveolar Lavage Fluid of Patients With Influenza Virus-Induced Acute Respiratory Distress Syndrome," J. Inf. Dis. 219:540-543, 2019.
Rothem, L., et al., "Paraoxonases are associated with intestinal inflammatory diseases and intracellularly localized to the endoplasmic reticulum," Free Radie. Biol. Med. 43:730-739, 2007.
Seo, D., et al., "The Paraoxonase Gene Family and Atherosclerosis," Curr. Atheroscler. Rep. 11:182-187, 2009.
Sime, P.J., et al., "Fibrosis of the Lung and Other Tissues: New Concepts in Pathogenesis and Treatment," Clin. Immunol. 99:308-319, Jun. 2001.
You, Y., et al., "Effect of N-acetylcysteine on the Murine Model of Colitis Induced by Dextran Sodium Sulfate Through Up-Regulating PON1 Activity," Dig. Dis. Sci. 54:1643-1650, 2009, DOI:10.1007/s10620-008-0563-9.
GenBankAccession No. MF101816.1, Synthetic construct long-acting recombinant human paraoxonase 1 (G4Fc-L2-rhPON1) gene, complete eds, submitted May 15, 2017.
GenBank Accession No. MF101815.1, Synthetic construct long-acting recombinant human paraoxonase 1 (G4Fc-L 1-rhPON1) gene, complete eds, submitted May 15, 2017.
GenBankAccession No. MF101814.1, Synthetic construct long-acting recombinant human paraoxonase 1 (G2Fc-L2-rhPON1) gene, complete eds, submitted May 15, 2017.
GenBank Accession No. MF101813.1, Synthetic construct long-acting recombinant human paraoxonase 1 (G2Fc-L 1-rhPON1) gene, complete eds, submitted May 15, 2017.

(56) References Cited

OTHER PUBLICATIONS

GenBankAccession No. MF101812.1, Synthetic construct long-acting recombinant human paraoxonase 1 (rhPON1) gene, complete eds, submitted May 15, 2017.
Sequence Listing submitted with International Application No. PCT/IB2014/058461, filed Jan. 22, 2014 (published Jul. 31, 2014, as International Publication No. WO 2014/115084 A2).
Chen, W.-Q., et al., "Influences of PON1 on airway inflammation and remodeling in bronchial asthma," J. Cell. Biochem. 119:793-805, 2018.
Dahl, M., et al., "Protection against inhaled oxidants through scavenging of oxidized lipids by macrophage receptors MARCO and SR-AI/II," J. Clin. Invest. 117:757-764, 2007, DOI:10.1172/JCI29968.
Emin, O., et al., "Plasma paraoxonase, oxidative status level, and their relationship with asthma control test in children with asthma," Allergol. Immunopathol. (Madr). 43:346-352, 2015.
Fellner, R.C., et al., "Inhaled protein/peptide-based therapies for respiratory disease," Mol. Cell. Pediatr. 3:16, pp. 1-5, 2016, DOI: 10.1186/s40348-016-0044-8.
Fessler, M.B., et al., "A New Frontier in Immunometabolism: Cholesterol in Lung Health and Disease," Ann. Am. Thorac. Soc. 14:S399-S405, Nov. 2017.
Gaidudkov, L., et al., "In vivo administration of BL-3050: highly stable engineered PON1-HDL complexes," BMC Clin. Pharmacol. 9:18, Nov. 17, 2009, DOI:10.1186/1472-6904-9-18.
Gallego, M., et al., "*Pseudomonas aeruginosa* isolates in severe chronic obstructive pulmonary disease: characterization and risk factors," BMC Pulm. Med. 14: 103, pp. 1-12, 2014.
Golmanesh, L., et al., "Simple procedures for purification and stabilization of human serum paraoxonase-1," J. Biochem. Biophys. Methods 70, 1037-1042, 2008.
Golmanesh, L., et al., "Assessing the relationship of paraoxonase-1 Q192R polymorphisms and the severity of lung disease in SM-exposed patients," Immunopharmacol. Immunotoxicol. 35:419-425, 2013.
Gu, X., et al., "Identification of critical paraoxonase 1 residues involved in high density lipoprotein interaction," J. Biol. Chem. Manuscript M115.678334, Nov. 13, 2015.
Gupta, R.D., et al., "Directed evolution of hydrolases for prevention of G-type nerve agent intoxication," Nat. Chem. Biol. 7:120-125, Jan. 9, 2010, 001:10.1038/NCHEMBI0.510.
Harel, M., et al., "Structure and evolution of the serum paraoxonase family of detoxifying and anti-atherosclerotic enzymes," Nat. Struct. Mol. Biol. 11 :412-419, May 2004.
Hraiech, S., et al., "Inhaled Lactonase Reduces *Pseudomonas aeruginosa* Quorum Sensing and Mortality in Rat Pneumonia," 9:e107125, pp. 1-8, Oct. 2014.
Huang, Y., et al., "Myeloperoxidase, paraoxonase-1, and HDL form a functional ternary complex," J. Clin. Invest. 123:3815-3828, Sep. 2013.
Ivanisevic, J., et al., "Association of serum amyloid A and oxidative stress with paraoxonase 1 in sarcoidosis patients," Eur. J. Clin. Invest. 46:418-424, 2016.
Litvinov, D., et al., "Antioxidant and Anti-Inflammatory Role of Paraoxonase 1: Implication in Arteriosclerosis Diseases," N. Am. J. Med. Sci. 4:523-532, Nov. 2012.
Mulcahy, L.R., et al., "*Pseudomonas aeruginosa* biofilms in disease," Microb. Ecol. 68:1-12, Jul. 2014, 001:10.1007/s00248-013-0297-x.
Murugayah, S.A., and Gerth, M.L., "Engineering quorum quenching enzymes: progress and perspectives" Biochem. Soc. Trans. 47:793-800, 2019.
Okur, H.K., et al., "Lipid peroxidation and paraoxonase activity in nocturnal cyclic and sustained intermittent hypoxia," Sleep Breath. 17:365-371, 2013, DOI:10.1007/s11325-012-0703-5.
Rahman, I., et al., "Antioxidant therapies in COPD," Int. J. Chron. Obstruct. Pulmon. Dis. 1 (1 ): 15-29, 2006.
Rahman, I., et al., "Pharmacological Antioxidant Strategies as Therapeutic Interventions for COPD," Biochim. Biophys. Acta 1822:714-728, May 2012.
Rajkovic, M.G., "PON1 gene polymorphisms in patients with chronic obstructive pulmonary disease," J. Clin. Pathol. 71:963-970, 2018, DOI:10.1136/jclinpath-2018-205194 963.
Rosenblat, M., et al., "Paraoxonase 1 (PON1) inhibits monocyte-to-macrophage differentiation," Atherosclerosis 219:49-56, 2011.
Rumora, L., et al., "Paraoxonase 1 Activity in Patients with Chronic Obstructive Pulmonary Disease," COPD, 11:539-545, 2014.
Sahiner, U.M., et al., "Oxidative Stress in Asthma," World Allergy Organ. J. 4:151-158, 2011.
Sarioglu, N., et al., "Paraoxonase 1 Phenotype and Paraoxonase Activity in Asthmatic Patients," Iran J. Allergy Asthma Immunol. 14:60-66, Feb. 2015.
Szczeklik, K., et al., "Correlation of Paraoxonase-1 with the Severity of Crohn's Disease," Molecules 23:2603, pp. 1-15, 2018.
Tang, K., et al., "MomL, a Novel Marine-Derived N-Acyl Homoserine Lactonase from Muricauda olearia," Appl. Environ. Microbial. 81:774-782, Jan. 2015.
Tolgyesi, G., et al., "Gene expression profiling of experimental asthma reveals a possible role of paraoxonase-1 in the disease," Int. Immunol. 21:967-975, Jun. 25, 2009.
Uzun, H., et al., "Levels of paraoxonase, an index of antioxidant defense, in patients with active sarcoidosis," Curr. Med. Res. Opin. 24:1651-1657, 2008.
Valiyaveettil, M., et al., "Protective efficacy of catalytic bioscavenger, paraoxonase 1 against sarin and soman exposure in guinea pigs," Biochem. Pharmacol. 81 :800-809, 2011.
Valiyaveettil, M., et al., "Recombinant paraoxonase 1 protects against sarin and soman toxicity following microinstillation inhalation exposure in guinea pigs," Toxicol. Lett. 202:203-208, 2011.
Aybey, A, and Demirkan, E., "Inhibition of quorum sensing-controlled virulence factors in *Pseudomonas aeruginosa* by human serum paraoxonase," J. Med. Microbial. 65: 105-113, 2016.
Billecke, S., et al., Human Serum Paraoxonase (PON1) Isozymes Q and R Hydrolyze Lactones and Cyclic Carbonate Esters, Drug Metab. Dispos. 28:1335-1342, 2000.
Gaidukov, L., and Tawfik, D.S., "The development of human sera tests for HDL-bound serum PON1 and its lipolactonase activity," J. Lipid Res. 48:1637-1646, 2007.
Kheronsky, O., and Tawfik, D.S., "Structure-Reactivity Studies of Serum Paraoxonase PON1 Suggest that Its Native Activity Is Lactonase," Biochem. 44:6371-6382, 2005.
Martinez-Solano, L., et al., "Chronic *Pseudomonas aeruginosa* Infection in Chronic Obstructive Pulmonary Disease," Clin. Infect. Dis. 47:1526-1533, 2008.
Mayer-Hamblett, N., et al., "*Pseudomonas aeruginosa* Phenotypes Associated With Eradication Failure in Children With Cystic Fibrosis," Clin. Infect. Dis. 59:624-631, 2014.
Miller, Y.I., et al., "Context-dependent role of oxidized lipids and lipoproteins in inflammation," Trends Endocrinol. Metab. 28:143-152, Feb. 2017, DOI:10.1016/j.tem.2016.11.002.
Oran, M., et al., "Evaluation of Paraoxonase and Arylesterase activities in patients with irritable bowel syndrome," J. Pak. Med. Assoc. 64:820-822, Jul. 2014.

* cited by examiner

RNASE-PON1 FUSION POLYPEPTIDES AND RELATED COMPOSITIONS AND METHODS

CROSS-REFERENCE TO RELATED APPLICATIONS

This application is a continuation of U.S. application Ser. No. 18/923,463, filed Oct. 22, 2024, now issued as U.S. Pat. No. 12,258,596, which is a divisional of U.S. application Ser. No. 18/546,413, filed Aug. 14, 2023, now issued as U.S. Pat. No. 12,180,521, which is a national phase entry of International Application No. PCT/US2022/016723, which claims the benefit of U.S. Provisional Application Nos. 63/151,236 and 63/151,272, filed Feb. 19, 2021. Each of the foregoing applications is incorporated by reference herein in its entirety.

REFERENCE TO SEQUENCE LISTING

The instant application contains a Sequence Listing which has been submitted in XML format via Patent Center and is hereby incorporated by reference in its entirety. Said XML Copy, created on Jan. 2, 2025, is named "4346-P2US-CON_Seq_Listing_ST26" and is 455,695 bytes in size.

BACKGROUND OF THE INVENTION

Lung Disease and Fibrosis

Air pollution, primarily caused by atmospheric ozone levels, is a global health problem that is projected to increase in the future (Zhang et al., *Front. Immunol.* 10:2518, 2019). Ozone is a strong oxidant and tropospheric (ground level) ozone causes lung inflammation and damage. Ozone pollution is also linked to vascular disease and neurological disease. (Zhang et al., supra).

Lung disease is already a significant health and economic burden world-wide. Lung diseases are the third leading cause of death in the United States. Including chronic obstructive pulmonary disease (COPD) and asthma, the cost is projected to be over 80 billion dollars per year by 2020 (Foster et al., *J. COPD* 3:2011-2018, 2006; Nurmagambetov et al., *Annals of Am. Thoracic Soc.*, Center for Disease Control and Prevention, 2017). Current therapies include nebulized steroids, anticholinergics, and bronchodialators for COPD and leukotriene modulators and long acting beta agonists for asthma. Humanized antibodies, given by subcutaneous or intravenous injection, are approved as add-on therapy for hard-to-control asthma patients; these antibodies deplete IgE (Omalizumab), inhibit IL-5 (Mepolizumab and Reslizumab), or deplete eosinophils (Benralizumab). There is a need for new targets and approaches for improved therapy of lung diseases.

Lung inflammation is associated with infiltration of neutrophils, eosinophils, macrophages, and lymphocytes into the lung lumen and tissues. Extracellular DNA derived from neutrophil extracellular traps (NETS) is present in the lungs in patients with asthma, cystic fibrosis, and COPD (Liu et al., *Chinese Med. Journal* 130:730-736, 2017; Twaddell et al., *CHEST* 156:774-782, 2019; Uddin et al., *Front. Immunol.* 10:47, 2019; Yamashita et al., *J. Immunol.* 191:949-960, 2013). In addition, eosinophils contribute to extracellular traps in patients with asthma (Dworski et al., *J. Allergy Clinical Immunol.* 127:1260-1266, 2011). The traps thicken lung mucus and contain inflammatory mediators including myeloperoxidase and neutrophil elastase that promote tissue damage (Uddin et al., supra). NET-associated myeloperoxidase and elastase are increased in the sputum and bronchioalveolar lavage of cystic fibrosis patients and correlate with lung disease severity (see generally Kahn et al., *Genes* 10:183, 2019). DNase1 can digest NETS and reduce the viscosity of mucus, allowing improved lung clearance (id.).

Extracellular DNA that can be digested with DNase1 was found to be essential for silica-induced lung fibrosis (see Benmerzoug et al., *Nature Comm.* 9:5226, 2018). Silica induces cell death and release of self-DNA in the alveolar space and induces the stimulator of interferon genes (STING) inflammatory pathway leading to fibrosis (id.).

*P. aeruginosa* Infections

*P. aeruginosa* is a ubiquitous Gram-negative rod that causes severe opportunistic infections in immunocompromised individuals, burn patients, and patients with lung diseases such as COPD and cystic fibrosis (CF) (see Mulcahy et al., *Microb. Ecol.* 68:1-12, 2014). It is particularly troublesome on medical surfaces such as ventilators and is among the most common nosocomial pathogens and a frequently isolated pathogen from patients with ventilator-associated pneumonia. Because it is a major pathogen in adults with cystic fibrosis (CF) and because it is associated with increased clinical deterioration, eradication of *P. aeruginosa* would have important implications for CF therapies and other *P. aeruginosa* infections. (See, e.g., Martinez-Solano et al., *Chronic Infect. Dis.* 47:1526-1533, 2008; Meyer-Hamblett et al., *Clin Inf. Dis.* 59:624-631, 2014; Gallego et al., *BMC Pulmonary Med.* 14:103, 2014.)

Pulmonary failure, a consequence of persistent bacterial lung infections particularly with *P. aeruginosa*, accounts for 80% of deaths in CF patients. Infection with *P. aeruginosa* in CF increases the risk of early death by almost three-fold (see McColley et al., *Pediatric Pulmonology* 52:909-915, 2017). Despite intense research being focused on casing bacterial lung infections, there is still a need for additional approaches to effective treatment in the CF lung.

Quorum sensing (QS) is an important mechanism that assists in *P. aeruginosa* persistence in the CF lung and contributes significantly to its pathogenesis. QS is mediated by small molecules produced by the bacteria that allow the coordination of communitywide activities, particularly acyl homoserine lactones (or AHLs). Acyl homoserine lactones share a basic structure, consisting of a homoserine lactone ring (HSL) and an acyl chain which can vary in length and degree of saturation. The variant side chains give specificity to the QS mechanism, enabling bacteria to recognize and respond to their specific AHLs. Almost a quarter of the expressed *P. aeruginosa* proteome is controlled by QS. In *P. aeruginosa*, QS plays an essential role in the expression and regulation of numerous virulence factors. QS also plays an important role in the formation of biofilms. Biofilms essentially envelop the bacterial community in a matrix of polysaccharides, extracellular DNA, and proteins, protecting it from the host's immune responses and external antimicrobial agents like antibiotics, facilitating survival of the *P. aeruginosa*. (Mulcahy et al., supra.)

Paraoxonase 1 (PON1)

Paraoxonase 1 (PON1) is an antioxidant enzyme that inhibits oxidation of low-density lipoprotein (LDL) and preserves its function (Aviram et al., *J. Clin. Invest.* 101:1581-1590, 1998). PON1 has multiple substrates, including organophosphates and acyl homoserine lactones, the quorum sensing molecules made by *Pseudomonas aeruginosa*. PON1 activity is important in protection from arteriosclerosis and ischemic stroke (Litvinov et al., *N. Am. J. Med. Sci.* 4:523-532, 2012). In addition, PON1 activity is reduced in patients with intestinal inflammation including those with irritable bowel syndrome (IBS) or inflammatory bowel disease (IBD) such as Crohn's disease (Oran et al., *J. Pak. Med. Assoc.* 64:820-822, 2014; Szczelkik et al., *Molecules* 23:2603, 2018; Rothem et al., *Free Rad. Biol. Med.* 43:730-739, 2007). Studies in a mouse model for colitis have demonstrated that treatment with N-acetyl cysteine stimulates upregulation of PON1, and that increased PON1 activity is associated with amelioration of colon damage (You et al., *Dig. Dis. Sci.* 54:1643-1650, 2009).

PON1 is also deficient in multiple lung diseases. There is strong evidence that PON1 is important in protection from lung inflammation, and that low PON1 activity is associated with lung diseases. Oxidative stress is an important factor in the pathogenesis of asthma (see Sahiner et al., *WAO Journal* 4:151-158, 2011), and the antioxidant activity of PON1 is impaired in asthma patients. In children with asthma, PON1 levels were significantly lower than controls ($p<0.001$) (Emin et al., *Allergol. Immunopathol.* (*Madr*) 43:346-352, 2014). Additional studies have reported that PON1 activity is significantly lower in asthma patients ($p<0.024$) (Sarioglu et al., *Iran J. Asthma Immunol.* 14:60-66, 2015). Another study showed that PON1 activity is lower in asthmatic patients during active disease, but PON1 activity increases during disease remission (Tolgyesi et al., *Internat. Immunol.* 21:967-975, 2009). This study also used gene profiling in an experimental mouse asthma model to identify PON1 down-regulation as a potential target for monitoring disease activity (see id.). In addition, a mouse asthma model showed that PON1 overexpression reduced airway inflammation and remodeling, and reduced inflammatory cytokines (Chen et al., *J. Cell Biochem.* 119:793-805, 2018).

Compared to controls, patients with COPD were found to have significantly lower PON1 activity and increased oxidative stress as evidenced by lower levels of reduced thiol groups (Rumora et al., *J. COPD* 11:539-545, 2014). Another study found a polymorphism at −108 C>T in the PON1 promoter was strongly associated with COPD (Rajkovic et al., *J. Clin. Path.* 71:963-970, 2018). Both the −108 TT genotype and T allele were strongly associated ($p<0.001$), and the −108T allele could be a factor in the reduced expression of PON1 in COPD patients (id.).

PON1 activity was reported to be reduced in patients with sarcoidosis and interstitial lung disease, particularly during active disease (Ivanisevic et al., *Eur. J. Clin. Invest.* 46:418-424, 2016; Uzun et al., *Curr. Med. Res. Opin.* 24:1651-1657, 2008). Another study found lower PON1 during hypoxia (Okur et al., *Sleep Breath.* 17:365-371, 2013). PON1 activity was absent in patients with lung disease who had been exposed to sulfa mustard gas, even though the exposure was decades ago (Golmanesh et al., *Immunopharmacol. and Immunotoxicol.* 35:419-425, 2013).

PON1 and myeloperoxidase were reported to exert reciprocal control, in that an excess of PON1 inhibits myeloperoxidase, whereas an excess of myeloperoxidase inhibits PON1 (Huang et al., *J. Clin. Invest.* 123:3815-3828, 2013). Huang et al. found that both PON1 and myeloperoxidase were tightly bound to apoA-I. This provides one mechanism for the decreased PON1 activity under conditions of inflammation, where neutrophils and eosinophils produce an excess of myeloperoxidase. However, under normal conditions, PON1 is in excess and represses the activity of myeloperoxidase. (See id.)

Recombinant PON1 (rPON1) was reported to inhibit PMA-induced differentiation of monocytic cell line THP-1 (Rosenblat et al., *Atherosclerosis* 219:49-56, 2011). Mice injected IP with rPON1 had reduced differentiation of monocytes to macrophages and reduced expression of CD11b and CD36. The total cellular peroxides of peritoneal macrophages decreased by 18%. (Id.)

PON1 therapy has been studied in experimental models. One study showed that recombinant human PON1 injection was able to protect guinea pigs from sarin and soman inhalation toxicity (Valiyaveettil et al., *Biochem. Pharmacol.* 81:800-809, 2011; Valiyaveettil et al., *Toxicol. Letters* 202:203-208, 2011). Other studies showed therapy with PON1 protected from organophosphate poisoning in mice (Bajaj et al., *Appl. Biochem. Biotechnol.* 180:165, 2016; Stevens et al., *Proc. Natl. Acad. Sci. USA* 105:12780-12784, 2008). These studies used recombinant PON1 purified from bacterial inclusion bodies or made in *T. ni* larvae with a baculovirus vector. Both groups also expressed PON1 192K, a variant derived from the rabbit sequence, that helps stabilize and increase PON1 enzymatic activity. (See Bajaj et al., supra; Stevens et al., supra.)

Expression of PON1 in bacteria has also been used to select mutants that have enhanced enzymatic activity towards organophosphates and nerve agents (see Aharoni et al., *Proc. Natl. Acad. Sci. USA* 101:482-487, 2004; Goldsmith et al., *Chemistry and Biology* 19:456, 2012). Engineering of PON1 was done by directed evolution to find a variant with improved, soluble expression in bacteria. One evolved PON1 was crystallized and the PON1 structure described (see Harel et al., *Nature Struct. Mol. Biol.* 11:412-419, 2004). Another PON1 variant widely used is G3C9, a hybrid PON1 formed from shuffling mouse, rat, rabbit, and human PON1 sequences (see Aharoni et al., *Proc. Natl. Acad. Sci. USA* 101:482-487, 2004). Other PON1 variants with increased organophosphatase activity but reduced esterase activity have been described (see Aharoni et al., supra). Further evolution of G3C9 to increase activity towards G-type nerve agents tabun, sarin, soman, and cyclosarin has also been reported (Gupta et al., *Nat. Chem. Biol.* 7:120-125, 2011; Goldsmith et al., *Chemistry and Biology* 19:456-466, 2012). When compared to human PON1, G3C9 has amino acid differences at 55 positions, and the further evolved PON1 variants have even more amino acid differences (Goldsmith et al., supra).

PON1 and the PON1 variant G3C9 have been tested in mouse models of experimental colitis (Yamashita et al., *J. Immunol.* 191:949-960, 2013). PON1 therapy was effective in TNBS-induced colitis and was equivalent to anti-TNFα therapy, currently the most effective clinically used therapeutic agent in man. However, in a chronic colitis model with $CD4^{+}CD45RB^{high}$ cell transfer, PON1 was not effective but G3C9 showed strong efficacy. Efficacy of G3C9 was equivalent to anti-TNFα in the chronic colitis model. (Id.) _In another study, PON1 activity was found to correlate with severity of Crohn's disease (Sczceklik et al., *Molecules* 23:2603, 2018).

Another approach towards therapy with PON1 has been to inject HDL-like particles, formed from reconstituted apo A-I plus PON1, a therapy termed BL-3050 (Gaidukov et al., *BMC Clinical Pharmacol.* 9:18, 2009). In these studies, both G3C9 expressed in bacteria and BL-3050 complexes were protective in a mouse model of organophosphate poisoning (id.).

PON1 has been expressed as a fusion protein attached to the C-terminus of a mAb heavy chain specific for insulin receptor (see, e.g., Boado et al., *Mol. Pharm.* 5:1037, 2008). Expression of this hybrid heavy chain with an insulin receptor-specific light chain resulted in secretion of a bifunctional antibody that bound insulin receptor and had PON1 enzyme activity (id.). This hybrid molecule was expressed in mammalian cells (COS and CHO) (see id.; Boado et al.,

*Biotechnol. and Bioengineering,* 108:186, 2011). The hybrid molecule was also tested in nonhuman primates and was found to penetrate the blood/brain barrier; however, the molecule was rapidly cleared from the peripheral blood into the peripheral tissues, primarily the liver (Boado et al. (2011), supra). There are no reports of clinical testing of this molecule. Expression levels of the fusion protein in CHO cells were low (5-10 mg/liter) even after multiple transfections and subcloning (see id.).

PON1 has also been fused with a membrane transduction domain, termed PEP-1-PON1 (Kim et al., *Biomaterials* 64:45-56, 2015). This molecule inhibited the inflammatory response of a microglial cell line and protected against dopaminergic cell death in vivo in a mouse model of Parkinson's disease (id.).

Paraoxonase enzymes are able to hydrolyse QS molecules that are acyl homoserine lactones (AHL), including C12HSL (N-3-oxo-dodecanoyl-L-Homoresine Lactone), the primary QS molecule from *P. aeruginosa*. Studies of human PON1 indicate that it has pleiotropic enzyme activities, hydrolyzing a variety of substrates, including lactones (Billecke et al., *Drug Metabolism and Disposition* 28:1335-1342, 2000; Khersonsky and Tawfik, *Biochemistry* 44:6371-6382, 2005; Gaidukov and Tawfik, *J. Lipid Res.* 48:1637-1646, 2007; Bajaj et al., *Protein Science* 22:1799-1807, 2013). One study in *Drosophila melanogaster* demonstrated protection from *Pseudomonas aeruginosa* lethality by expression of a human PON1 transgene capable of hydrolyzing a critical quorum sensing molecule N-3-oxodecanoyl homoserine lactone (30C12-HSL) (Stoltz et al., *J. Clin. Invest.* 118:3123-3131, 2008).

DNase1

DNase1 is a calcium and magnesium-dependent endonuclease coded by the human DNASE1 gene. DNase1 cleaves single-stranded and double-stranded DNA and chromatin. Cleavage of chromatin occurs in hypersensitive sites where chromatin is open and accessible, and is used in genomics to identify regions likely to contain active genes (Boyle et al., *Cell* 132:311-322, 2008). DNase1 helps degrade DNA during apoptosis (Samejima et al., *Nat. Rev. Mol. Cell Biol.* 6:677-688, 2008) and also degrades neutrophil extracellular traps (NETS) (Hakkim et al., *Proc. Natl. Acad. Sci. USA* 107:9813, 2010). DNase1 can digest biofilm DNA, resulting in a reduction in biofilm biomass, and increase antibiotic mediated biofilm killing (Tetz et al., *Antimicrob. Agents Chemother.* 53:1204-1209, 2009).

Accumulation of extracellular DNA from dead and dying cells was identified as a driver of disease in patients with systemic lupus erythematosus (SLE) long ago. DNase1 was administered to SLE patients at the Rockefeller starting in 1959. However, bovine DNase1 was used, and therapy was limited by its immunogenicity (see Valle et al., *Autoimmunity Rev.* 7:359, 2008). Decreased levels of DNase1 and DNase1 mutations with reduced activity have been reported in patients with SLE (see Valle et al., supra). Reduced DNase1 activity in urine was found in patients with lupus nephritis, and reduced DNase1 activity was a biomarker of disease progression (Pedersen et al., *J. Pathol. Clin. Res.* 4:193, 2018). In SLE patients, defective clearance of apoptotic debris and accumulation of chromatin contributes to breaking of tolerance and development of autoimmune disease.

Activated neutrophils extrude DNA bound with cytoplasmic and granule proteins, called neutrophil extracellular traps (NETs), to combat infectious agents, a process also known as "NETosis" (see Brinkmann, *J. Innate Immun.* 10:422-431, 2018). However, NETs are not targeted and often cause collateral tissue damage and inflammation if not effectively cleared. NETs have been implicated in driving disease progression in multiple incurable and serious diseases. Evidence for the importance of NETs in psoriasis, cystic fibrosis, SLE, RA, type I diabetes, sepsis, small vessel vasculitis, IBD, type II diabetes, and obesity was recently reviewed (Mutua and Gershwin, *Clin. Rev. Allergy Immunol.,* 2020, DOI 10.1007/s12016-020-08804-7). See also Michailidou, *Front. Immunol.* 11:619705, 2020 (reviewing involvement of neutrophils and NETs in vasculitis). NETs also play an important role in cardiovascular disease and thrombosis, and in cancer where NETs promote tumor progression and metastasis (Brinkmann, supra). In addition to their importance in cystic fibrosis, NETs also play a role in the clinicopathology of other respiratory diseases such as asthma and chronic obstructive pulmonary disease (COPD) (see Liu et al., *Chinese Med. Journal* 130:730-736, 2017; Twaddell et al., *CHEST* 156:774-782, 2019; Uddin et al., *Front. Immunol.* 10:47, 2019). Recently, NETs were found to contribute to immunothrombosis in COVID-19 acute respiratory distress syndrome (Middleton et al., *Blood* 136:1169, 2020; Zuo et al., *JCI Insight* 5:0138999, 2020; Barnes et al., *J. Exp. Med.* 217:e20200652, 2020).

DNase1 is capable of digesting NETs and works together with another extracellular DNase called DNase1L3 to clear NETs. Mice deficient in both DNase1 and DNase1L3 were unable to clear NETs and rapidly died of massive intravascular clot formation and organ damage after neutrophil activation (Brinkmann, supra). The contribution of NETs to thrombosis has already led to a clinical trial of wild-type DNase1 (Pulmozyme®) taken by inhalation therapy in COVID-19 patients (NCT04359654).

Recombinant wild-type human DNase1 (Pulmozyme®) was produced by Genentech and first approved for cystic fibrosis (CF) to digest DNA in the lungs and reduce congestion. High levels of DNA derived primarily from NETs are pathogenic in CF lung (Law et al., *J. Inflammation,* 14:1-8, 2017). Bacterial DNA from *Pseudomonas aeruginosa* biofilm formation is also present in many CF patients and may also be digested by DNase1 (Whitchurch et al., *Science* 295:1487, 2002).

Pulmozyme is delivered directly to the lungs by nebulization and is taken daily. Pulmozyme has been studied in patients with lung diseases other than CF, but has not been approved for alternative uses (Torbic et al., *J. Pharmacy Practice* 29:480, 2016). Pulmozyme was tested in a mouse lupus model (Verthelyi et al., *Lupus* 7:223, 1998) and in a phase I clinical trial in SLE patients (Davis et al., *Lupus* 8:68-76, 1999) without a decrease in disease measurements. Systemic administration of pulmozyme therapy may be limited because the enzyme is inhibited by globular actin that is abundant in blood and lungs (Ulmer et al., *Proc. Natl. Acad. Sci. USA* 93:8225, 1996) and because of its short half-life.

Efforts have been made to enhance DNase1 for CF and SLE patients. A site-directed mutagenesis study of the DNA-binding interface identified 27 amino acid positions critical for enzyme activity and another 13 positions peripherally involved in DNA interactions with minimal impact on enzyme activity (see Pan et al., *Prot. Sci.* 7:628-636, 1998). This group also showed that increasing the local electrostatic attraction toward DNA by adding specific additional positively charged residues not only improved binding affinity to DNA but also improved functional activity and eliminated the inhibition by salt (Pan et al., *Biochemistry* 36:6624-6632, 1997; Pan and Lazarus, *J. Biol. Chem.* 273:11701-11708, 1998). Consistent with this observation, alanine replacement of two arginines (Arg-41 and Arg-111) that make critical contacts with DNA greatly reduced the DNA cleavage activity of human DNase1 (Pan et al., 1998, supra). Furthermore, the introduction of positively or negatively charged residues at sites distal to the DNA interface did not alter specific activity (Ulmer et al., *Proc. Natl. Acad. Sci. USA* 93:8225-8229, 1996).

The hyperactive DNase1 variants showed significant enhancement (up to 10,000-fold) under conditions of low DNA concentration and short DNA length (Pan and Lazarus, supra). Under optimal conditions for wild-type DNase1, however, the best variant showed activity only 7-fold higher and contained a single amino acid change (N74K). The N74K hyperactive variant showed reduced dependence on calcium (Pan and Lazarus, *Prot. Sci.* 8:1780-1788, 1999).

Ulmer et. al. (supra) and Pan et al. (1998, supra) showed that phenylalanine replacement of Ala-114 (A114F) eliminated inhibition of DNase1 by G-actin.

Actin-resistant and hyperactive DNase1 mutant enzymes are further described in U.S. Pat. Nos. 6,348,343 and 6,391,607.

DNASE1 is polymorphic, and alleles that encode for enzyme with reduced activity are associated with increased risk for autoimmune disease. However, a naturally occurring allele, G105R, was found to encode a DNase1 variant with a three-fold increase in activity (Yasuda et al., *Int. J. Biochem. Cell. Biol.* 42:1216-1225, 2010). This is a minor allele found in African populations and could confer resistance to autoimmune disease (id.).

There is great potential for DNase1 therapy using actin/salt-resistant and hyperactive DNase1. However, it was not possible to obtain stable CHO cells that constitutively express an enhanced DNase1 despite screening of thousands of clones (see Lam et al., *Biotech. Progress* 32:523-533, 2017). This was thought to be due to toxicity of the enzyme during high expression in CHO cells. Lam et al. (supra) describe an inducible expression system in CHO cells as one potential solution to the problem of manufacturing an enhanced DNase1 enzyme.

Dwyer et al. (*J. Biol. Chem.* 274:9738-43, 1999) describe DNase1-Fc fusion proteins with impaired enzyme activity due to dimerization by the Fc domain. Dwyer et al. added short linkers (up to 7 aa) between the DNase1 and the Fc domain without improving activity (see id.). U.S. Pat. No. 8,841,416 to Ledbetter et al. describe a DNase1-Fc fusion with a linker of 21 amino acids and having activity at least equivalent to recombinant DNase1 control.

Although wild-type DNase1 (Pulmozyme) therapy is FDA approved in CF, there is not a CF mouse model where DNase1 is active. Pulmozyme was approved for CF therapy without testing for activity in a relevant in vivo disease model (Greene, *Hum. Exp. Toxicol.*, May: 13 Suppl 1: S1-42, 1994). More recently, wild-type DNase1 therapy has been studied in several in vivo models with encouraging results. DNase1 was found to significantly reduce airway resistance but did not reduce inflammation in an acute asthma model (da Cunha et al., *Exp. Lung Res.* 42:66, 2016). In a silica-induced lung inflammation model, DNase1 therapy prevented DNA-mediated STING activation and blocked the downstream type I IFN response (Benmerzoug et al., *Nat. Comm.* 9:5226, 2018). In a model of acute lung injury, DNase1 therapy protected mice from lung edema and lung vascular permeability. DNase1 therapy also reduced NET formation and platelet sequestration in the lung (Caudrillier et al., *J. Clin. Invest.* 122:2661, 2012).

Studies in mouse tumor models have shown that NETs promote metastasis and that injection of DNase1 or DNase1-coated nanoparticles reduced tumor metastasis (Cools-Lartigue et al., *J. Clin. Invest.* 123:3446, 2013; Park et al., *Sci. Translational Med.* 8:361ra138, 2016). Another study showed that a combination of DNase1 and proteases significantly inhibited growth of human colon cancer cells in a nude mouse model (Trejo-Becirril et al., *Integrative Cancer Therapies* 15: NP35-NP43, 2016). In cancer patients, increased concentration of citrullinated histone H3, a marker of neutrophil NET formation, strongly predicted a poor clinical outcome (Thalin et al., *PLOS ONE* 13:e0191231, 2018).

In a murine DSS colitis model (Babicova et al., *Folia Biolica* (*Praha*) 64:10, 2018) DNase1 therapy caused a reduction in TNFα and myeloperoxidase in the colon. Another study (Li et al., *J. Crohns Colitis* 2020, 14:240-253, 2020) found that DNase1 therapy decreased cytokine production and attenuated accelerated thrombus formation and platelet activation after DSS-induced colitis.

DNase1 therapy in a hind-limb ischemia reperfusion model caused increased perfusion, decreased infiltrating inflammatory cells, and reduced a local marker of thrombosis (Albadawi et al., *J. Vasc. Surg.* 64:484, 2016). In a rat model of ischemia-reperfusion-induced acute kidney injury, DNase1 treatment showed significant renoprotective effects. Exogenous administration of DNase1 ameliorated both functional and histologic hallmarks of acute injury in kidneys of ischemic rats (Peer et al., *Am. J. Nephrol.* 43:195, 2016).

DNase1 treatment prevented organ damage and protected from death when given 4 or 6 hours after injury in a cecal ligation and puncture sepsis model in mice (Mai et al., *Shock* 44:166, 2015). Extracellular DNA from NETs has been recognized as a scaffold for thrombus formation and infusion of DNase1 prevented thrombosis in a model of inferior vena cava stenosis (Brill et al., *J. Thrombosis Haemostasis* 10:136, 2012).

RNase

RNase 1 is a member of the RNase A superfamily consisting of RNases 1 to 8 in humans. RNase A was first isolated from bovine pancreas where it functions primarily as a digestive enzyme. In humans, RNase 1 digests single stranded and double stranded RNA and RNA/DNA hybrids. RNase 1 is produced by multiple cell types in humans, and is thought to participate primarily in vascular homeostasis. RNase 1 plays a major role in polynucleotide digestion to remove inflammatory extracellular RNA. In addition, RNase 1 has anti-viral activity.

Therapy with RNase has been studied in multiple disease models. For example, growth of the human lung tumor line A549 in athymic mice was inhibited by PEG-RNase1 (Rutkoski et al., *Translational Oncology* 6:392-397, 2013). RNase therapy also showed anti-tumor activity in a syngeneic mouse tumor model with Lewis Lung carcinoma and altered microRNA profiles (Mironova et al., *Oncotarget.* 8:78796-78810, 2017). RNase1 was reported to bind to a tumor-associated antigen, Globo H, expressed on the surface of breast adenocarcinoma cells (Eller et al., *ACS Central Sci.* 1:181-190, 2015).

In addition, RNase therapy has been found effective in animal models of heart transplantation (Kleinert et al., *J. Am. Heart Assn.* doi: 10.1021, 2016), plaque formation (Simsekyilmaz et al., *Circulation* 129:598-606, 2014), and myocardial infarction (Steiger et al., *JAMA* 6:e004541, 2017). RNase1 therapy also reduced cerebral edema and infarction size in an acute stroke model (Walberer et al., *Curr. Neovas. Res.* 6:12-19, 2009).

RNase therapy was found to prevent postoperative cognitive decline in aged mice (Chen et al., *PLOS One* 10:00134307, 2015).

RNase therapy has also been studied in a mouse model of systemic lupus erythematosus (SLE) (Sun et al., *J. Immunol.* 190:2536-2543, 2013). Overexpression of TLR7, an RNA sensor, causes a lupus-like disease with autoantibodies, kidney disease, and early mortality. Crossing these mice with mice that overexpress RNase A as a transgene resulted in progeny with increased survival, reduced lymphocyte activation, reduced kidney deposits of IgG and C3, and reduced hepatic inflammation and necrosis. (Id.)

RNase-Ig in which human RNase1 is fused to a mutated human IgG1 Fc domain comprising P238S and P331S mutations (see U.S. Pat. No. 8,937,157) has been tested in phase I and phase II clinical trials in patients with systemic lupus erythematosus (SLE) and Sjogren's syndrome.

Superoxide Dismutase (SOD)

Superoxide dismutase (SOD) is an antioxidant enzyme that converts oxygen free radicals to $H_2O_2$ and $O_2$. There are three human SOD enzymes. SOD1, also called Cu/Zn SOD, is a cytoplasmic enzyme that is a homodimer stabilized by an intrachain disulfide bond and by metal binding (Doucette et al., *J. Biol. Chem.* 279:54558-54566, 2004). SOD2 is a tetramer that is localized in the mitochondria and uses manganese in its active site. SOD3 is a tetramer that is secreted and contains copper and zinc. For a review of the roles of SODs, glutathione peroxidase, and catalase in overall protection from oxidative damage, see Ighodaro and Akinolye, *Alexandria J. Med.* 54:287-293, 2018.

SOD3 is the major extracellular antioxidant enzyme in the lungs, where it protects the extracellular matrix during lung injury. Genetic variants of SOD3 are associated with decreased lung function in adults and rapid progression of COPD (see Ganguly et al., *Physiol. Genomics* 37:260-267, 2009 for review).

SOD1 has been fused with a cell membrane transduction domain in order to deliver SOD1 to the cell cytoplasm. For example, Eum et al. (*Free Rad. Biol. Med.* 37:1656-1669, 2004) made a fusion of a 21 amino acid peptide called PEP-1 with SOD, and expressed the fusion protein in bacteria. They showed that the PEP-1-SOD molecule delivered SOD through the cell membrane and was effective after IP injection in vivo in preventing neuronal death following ischemic insult. SOD1 and variant forms of SOD1 have also been fused to an enhanced green fluorescent protein (EGFP) tag to create a fusion protein which can be detected in fluorescence based binding and chaperone assays (Ganesan et al., *Cell Death and Differentiation* 15:312-321, 2008).

Cytotoxic T Lymphocyte-Associated Molecule-4 (CTLA-4)

Cytotoxic T lymphocyte-associated molecule-4 (CTLA-4) is an immunoregulatory membrane receptor resulting in the downregulation of T-cell responses by inhibiting the costimulatory interactions of CD28-B7 (Carreno et al., *J. Immunol.* 165:1352-1356, 2000). The extracellular domain of CTLA-4 fused with a human IgG1 mutant Fc domain (abatacept, Orencia™) is approved by the FDA for therapy of RA because of its ability to suppress activation of the CD28 receptor on T cells (see Linsley et al., *J. Exp. Med.* 174:561-569, 1991; Emma Hitt, FDA Approves Subcutaneous Abatacept for RA, *Medscape Medical News*, Aug. 2, 2011). Abatacept inhibits T cell production of inflammatory cytokines and inhibits B cell class switching and IgG antibody responses.

Abatacept treatment has been shown to prevent dermal fibrosis and induce regression of established inflammation-driven fibrosis (Ponsoye et al., *Ann. Rheum. Dis.* 75:2142-2149, 2016). In addition, Abatacept significantly reduced fibrogenic marker levels, T-cell proliferation, and M1/M2 macrophage infiltration in lesional lungs of Fra-2 mice, indicating it might be useful in treatment of lung fibrosis in humans (Boleto et al., *Arthritis Research and Therapy* 20:197, 2018). According to the Pulmonary Fibrosis Foundation, Abatacept is currently being tested in a phase 2 clinical trial in interstitial fibrosis patients (trial #NCT03215927), and is also being tested in a phase 3 clinical trial for treatment of relapsing non-severe granulomatosis with polyangiitis (Wegener's granulomatosis), (trial #NCT02108860). Costimulation inhibitors are being evaluated as promising candidates for suppressing the damage associated with lung inflammation and repair processes.

CD40-CD154

CD40 is a member of the TNFα receptor superfamily and is expressed on lymphocytes, hematopocitic and structural cells, including fibroblasts, epithelial cells and endothelial cells (Sime and O'Reilly, *Clin. Immunol.* 99:308-319, 2001). The ligand for CD40, (CD40L or CD154), is expressed on activated T lymphocytes, activated platelets, mast cells and eosinophils. CD154 expressed by activated T cells provides an essential signal to CD40 on B cells that is needed for class switching and IgG production. However, CD40 expressed on the surface of structural cells such as endothelial cells can be stimulated by binding CD154, resulting in the production of inflammatory cytokines (id.). Activated platelets express CD154 on their surface and are also the primary source of soluble CD154 in the blood.

The CD40-CD154 signaling pathway has been implicated in lung injury and disease processes including fibrosis (Kaufman et al., *J. Immunol.* 172:1862-1871, 2004). The interaction between CD40 receptor and CD154 can trigger cellular activation, including production of proinflammatory cytokines, expression of cell adhesion molecules, and induction of cyclooxygenase 2 (COX-2), and prostaglandin $E_2$ ($PGE_2$) (Zhang, *J. Immunol.* 160:1053-1057, 1998). These events can in turn tip the balance between Type 1 and Type 2 cytokine responses in favor of Type 2 fibrogenic responses. Suppression of the CD40-CD154 pathway has been shown to have therapeutic benefit in animal lung disease models. For example, a monoclonal anti-murine CD40L antibody, MR1, was effective in protection of hyperoxic lung injury and radiation induced lung injury and fibrosis in mouse models (Adawi et al., *Clin. Immunol. Immunopathol.* 89:222-230, 1998; Adawi et al., *Am. J. Pathol.* 152:651-657, 1998). In addition, molecules which suppress the CD40-CD40L pathway such as the CXXC5 zinc finger protein, involved in epigenetic and transcriptional regulation, have been shown to ameliorate bleomycin induced lung fibrosis in mice (Cheng et al., *BioMed. Research Intl*. Volume 2020, Article ID 7840652, 2020; Xiong et al., *J. Cell. Mol. Med.* 23:740-749, 2018), indicating an important role for the CD40-CD40L pathway in disease progression.

Tumor Necrosis Factor α (TNFα)

The tumor necrosis factor α (TNFα) cytokine is a pleotropic proinflammatory mediator that is produced by a variety of cell types including macrophages and monocytes. Macrophages are the major source of TNFα in the lung; however, epithelial cells, eosinophils, and mast cells also may release TNFα upon activation (Malaviya et al., *Pharmacol. Ther.* 180:90-98, 2017; Aggarwal et al., *Blood* 119:651-665, 2012). Increased levels of TNFα have been linked to several pulmonary inflammatory diseases including asthma, chronic obstructive pulmonary disease (COPD), acute lung injury (ALI)/acute respiratory distress syndrome (ARDS), sarcoidosis, and interstitial pulmonary fibrosis (IPF) (Malaviya et al., supra).

In addition to lung pathology, TNFα is increased and implicated in inflammatory bowel disease such as Crohn's disease (CD) and ulcerative colitis (UC). Monoclonal antibody therapy directed against tumor necrosis factor-alpha (anti-TNF) has revolutionized the care of patients with inflammatory bowel disease (IBD) (Pouillon et al., *Expert Opinion on Biological Therapy* 16:1277-1290, 2016; Peyrin-Biroulet et al., *The Lancet* 372:67-81, 2008).

Transforming Growth Factor-β (TGF-β)

The TGF-β cytokine plays an important role in immune responses and regulation (Travis and Sheppard, *Annu. Rev. Immunol.* 32:51-82, 2014). In mammals, three major isoforms of TGF-β have been identified, TGF-β1, TGF-β2, and TGF-β3 (Fernandez and Eickelberg, Proc. Amer. Thorac. Soc. 9:111-116, 2012). Many cell types express TGF-β, but it is expressed in a non-active form complexed to other molecules and requires activation to exert its functional effects. Latent TGF-β is activated upon cleavage from a preprotein form into a cytokine with pleiotropic activities, including chemotaxis, proliferation, and stimulation of cytokines associated with inflammation. TGF-β regulates cell proliferation, differentiation, migration, adhesion, survival, epithelial-mesenchymal transition (EMT), and collagen and extracellular matrix synthesis, and is essential for angiogenesis, wound healing and immune regulation, but also can drive cancer, metastasis, diabetes, and fibrosis disease progression (Varga and Pasche, *Curr. Opin.* Rheum. 20:720-728, 2008). TGF-β has also been shown to be critical in regulating adaptive T cell responses and recent studies implicate TGF-β as an important mediator of fibrosis in different organs, including the lung. Clinical trials using several antibodies which target TGF-β isoforms, such as fresolimumab (GC-1008), have been completed or are underway for cancer therapy (melanoma, glioma, breast cancer, and non-small lung cancer) and fibrosis. In addition, antibodies which target integrins such as αVβ6, involved or important in TGF-β activation, are also being used in phase 2 clinical trials to determine their efficacy for idiopathic pulmonary fibrosis (IPF) (Fernandez and Eickelberg, supra).

Expression of Enhanced DNase1 in Mammalian Cells

Wild-type DNase1, such as the FDA approved drug Pulmozyme®, is inhibited by G-actin in the lungs and plasma. An enhanced DNase1 was engineered by Genentech, creating DNase1 resistant to inhibition by actin and with increased enzyme activity (Pan and Lazarus, *Prot. Sci.* 8:1780-8, 1999). This enhanced DNase1, however, was toxic in mammalian cells, and no stable CHO cells could be established despite screening thousands of clones. Inducible expression in CHO cells was one potential solution that was reported (Lam et al., *Biotech. Progress* 32:523-33, 2017).

SUMMARY OF THE INVENTION

In one aspect, the present invention provides a fusion polypeptide comprising, from an amino terminal position to a carboxyl terminal position, T-L1-X-L2-P, wherein T is a first biologically active polypeptide selected from a DNase, an RNase, a superoxide dismutase 1 (SOD1), a cytotoxic T-lymphocyte associated molecule-4 (CTLA-4) extracellular domain, a CD40 extracellular domain, and a polypeptide that specifically binds and neutralizes tumor necrosis factor α (TNFα) or transforming growth factor-β (TGF-β); L1 is a first polypeptide linker, wherein L1 is optionally present; X is a immunoglobulin heavy chain constant region, wherein the immunoglobulin heavy chain constant region is capable of forming dimers and specifically binding the neonatal Fc receptor (FcRn); L2 is a second polypeptide linker, wherein L2 is optionally present; and P is a biologically active paraoxonase, wherein the paraoxonase has at least 80% or at least 90% identity with the amino acid sequence shown in residues 16-355 or 26-355 of SEQ ID NO:6 and does not contain an amino terminal leader sequence corresponding to residues 1-15 of SEQ ID NO:6. In some embodiments, the biologically active paraoxonase has at least 95% identity with the amino acid sequence shown in (i) residues 16-355 or 26-355 of SEQ ID NO:6, (ii) residues 16-355 or 26-355 of SEQ ID NO:124, or (iii) residues 16-355 or 26-355 of SEQ ID NO:126.

In another aspect, the present invention provides a fusion polypeptide comprising, from an amino terminal position to a carboxyl terminal position, T-L1-X-L2-P, wherein T is a first biologically active polypeptide selected from a DNase, an RNase, a superoxide dismutase 1 (SOD1), a cytotoxic T-lymphocyte associated molecule-4 (CTLA-4) extracellular domain, a CD40 extracellular domain, and a polypeptide that specifically binds and neutralizes tumor necrosis factor α (TNFα) or transforming growth factor-β (TGF-β); L1 is a first polypeptide linker, wherein L1 is optionally present; X is a second biologically active polypeptide, wherein X is optionally present; L2 is a second polypeptide linker, wherein L2 is optionally present; and P is a biologically active paraoxonase, wherein the paraoxonase has at least 80% or at least 90% identity with the amino acid sequence shown in residues 16-355 or 26-355 of SEQ ID NO:6 and does not contain an amino terminal leader sequence corresponding to residues 1-15 of SEQ ID NO:6. In some variations, the second biologically active polypeptide is present and is selected from a dimerizing domain and a domain that specifically binds to the neonatal Fc receptor (FcRn). In some embodiments, the biologically active paraoxonase has at least 95% identity with the amino acid sequence shown in (i) residues 16-355 or 26-355 of SEQ ID NO:6, (ii) residues 16-355 or 26-355 of SEQ ID NO:124, or (iii) residues 16-355 or 26-355 of SEQ ID NO:126.

In certain embodiments of a fusion polypeptide as above comprising a DNase as the first biologically active polypeptide and in which L1 is present, the DNase has at least 90% or at least 95% identity with the amino acid sequence shown in (i) residues 21-280 of SEQ ID NO:18, (ii) residues 21-280 of SEQ ID NO:152, or (iii) residues 21-290 of SEQ ID NO:136. In some embodiments wherein the DNase has at least 90% or at least 95% identity with the amino acid sequence shown in residues 21-280 of SEQ ID NO:18 or residues 21-280 of SEQ ID NO:152, the DNase contains at least one amino acid substitution at a position corresponding to an amino acid of human wild-type DNase1 (SEQ ID NO:120) selected from N74, G105, and A114, wherein (1) the amino acid substitution at a position corresponding to N74 of human DNase1 (N74 substitution), if present, increases DNA binding relative to human DNase1, (2) the amino acid substitution at a position corresponding to G105 of human DNase1 (G105 substitution), if present, increases DNA binding relative to human DNase1, and (3) the amino acid substitution at a position corresponding to A114 of human DNase1 (A114 substitution), if present, decreases G-actin-induced inhibition of endonuclease activity relative to human DNase1. In some variations, the fusion polypeptide contains both the N74 and G105 substitutions, both the G105 and A114 substitutions, or each of the N74, G105, and A114 substitutions. Particularly suitable amino acid substitutions at these positions are lysine at the position corresponding to N74 of human DNase1, arginine at the position corresponding to G105 of human DNase1, and/or phenylalanine at the position corresponding to A114 of human DNase1. In some embodiments wherein the fusion polypeptide contains both the N74 and G105 substitutions, the fusion polypeptide does not contain the A114 substitution. In some embodiments wherein the DNase has at least 90% or at least 95% identity with amino acid residues 21-290 of SEQ ID NO:136, each of the amino acids at positions corresponding to R80, R95, and N96 of SEQ ID NO:136 is alanine or serine. In more specific variations, the DNase has the amino acid sequence shown in (i) residues 21-280 of SEQ ID NO:18, (ii) residues 21-280 of SEQ ID NO:20, (iii) residues 21-280 of SEQ ID NO:152; (iv) residues 21-290 of SEQ ID NO:138, or (v) residues 21-290 of SEQ ID NO:140. In some embodiments of a fusion polypeptide comprising a DNase as above, L1 comprises at least 15 amino acid residues or at least 26 amino acid residues (e.g., an L1 linker consisting of from 26 to 60 amino acid residues or from 26 to 36 amino acid residues). In particular variations, L1 comprises three or more (e.g., four or more) tandem repeats of the amino acid sequence of SEQ ID NO:119; in some such embodiments, L1 has the amino acid sequence shown in SEQ ID NO:12 or SEQ ID NO:14.

In some embodiments of a fusion polypeptide as above comprising an RNase as the first biologically active polypeptide, the RNase has at least 90% or at least 95% identity with the amino acid sequence shown in residues 29-156 of SEQ ID NO:22. In more specific variations, the RNase has the amino acid sequence shown in residues 29-156 of SEQ ID NO:22. In certain embodiments, L1 is present and comprises at least two amino acid residues (e.g., an L1 linker consisting of from 10 to 36 amino acid residues). In particular variations, L1 comprises two or more tandem repeats of the amino acid sequence of SEQ ID NO:119; in some such embodiments, L1 has the amino acid sequence shown in SEQ ID NO:10 or SEQ ID NO:12.

In some embodiments of a fusion polypeptide as above comprising a SOD1 as the first biologically active polypeptide, the SOD1 has at least 90% or at least 95% identity with the amino acid sequence shown in residues 2-154 of SEQ ID NO:32. In some such embodiments, the SOD1 contains at least one of the following amino acid substitutions relative to human SOD1 (SEQ ID NO:32): alanine at the position corresponding to C7 of human SOD1 (C7 substitution); and serine at the position corresponding to C112 of human SOD1 (C112 substitution). In certain variations, the fusion polypeptide contains both the C7 and C112 substitutions. In more specific variations, the SOD1 has the amino acid sequence shown in residues 23-175 of SEQ ID NO:54. In certain embodiments, L1 is present and comprises at least two amino acid residues (e.g., an L1 linker consisting of from 10 to 36 amino acid residues). In particular variations, L1 comprises two or more tandem repeats of the amino acid sequence of SEQ ID NO:119; in some such embodiments, L1 has the amino acid sequence shown in SEQ ID NO:10 or SEQ ID NO:12.

In some embodiments of a fusion polypeptide as above comprising a CTLA-4 extracellular domain as the first biologically active polypeptide, the CTLA-4 extracellular domain has at least 90% or at least 95% identity with the amino acid sequence shown in residues 21-144 of SEQ ID NO:66. In more specific variations, the CTLA-4 extracellular domain has the amino acid sequence shown in residues 21-144 of SEQ ID NO:66.

In some embodiments of a fusion polypeptide as above comprising a CD40 extracellular domain as the first biologically active polypeptide, the CD40 extracellular domain has at least 90% or at least 95% identity with the amino acid sequence shown in (i) residues 21-188 of SEQ ID NO:74, (ii) residues 21-188 of SEQ ID NO:78, (iii) residues 21-188 of SEQ ID NO:82, (iv) residues 21-188 of SEQ ID NO:86, or (v) residues 21-188 of SEQ ID NO:90. In some such embodiments, the CD40 extracellular domain contains at least one amino acid substitution at a position corresponding to an amino acid of human CD40 (SEQ ID NO:68) selected from E64, K81, P85, and L121, wherein the at least one amino acid substitution increases CD40 ligand binding relative to human CD40. Particularly suitable amino acid substitutions at these positions are tyrosine at the position corresponding to E64 of human CD40, threonine, histidine, or serine at the position corresponding to K81 of human CD40, tyrosine at the position corresponding to P85 of human CD40, and/or proline at the position corresponding to L121 of human CD40. In some variations, the amino acid at the position corresponding to K81 of human CD40 is selected from threonine, histidine, and serine; the amino acid at the position corresponding to K81 of human CD40 is histidine and the amino acid at the position corresponding to L121 of human CD40 is proline; or the amino acid at the position corresponding to E64 of human CD40 is tyrosine, the amino acid at the position corresponding to K81 of human CD40 is threonine, and the amino acid at the position corresponding to P85 of human CD40 is tyrosine. In more specific variations, the CD40 extracellular domain has the amino acid sequence shown in (i) residues 21-188 of SEQ ID NO:74, (ii) residues 21-188 of SEQ ID NO:78, (iii) residues 21-188 of SEQ ID NO:82, (iv) residues 21-188 of SEQ ID NO:86, or (v) residues 21-188 of SEQ ID NO:90.

In certain embodiments of a fusion polypeptide as above, the first biologically active polypeptide is the polypeptide that specifically binds and neutralizes TNFα or TGF-β. In some such embodiments, the first biologically active polypeptide is a single-chain antibody such as, e.g., a single-chain Fv (scFv) or a single-domain antibody (sdAb).

In some embodiments of a fusion polypeptide as above comprising a single-chain antibody that specifically binds and neutralizes TNFα, the single-chain antibody comprises a VH domain comprising complementarity determining regions (CDRs) CDR-$H1_{TNF\alpha}$, CDR-$H2_{TNF\alpha}$, and CDR-$H3_{TNF\alpha}$, wherein the set of VH CDRs has three or fewer amino acid substitutions relative to a set of reference CDRs CDR-H1, CDR-H2, and CDR-H3 of the VH domain having the amino acid sequence shown in SEQ ID NO:108 (e.g., a set of VH CDRs having zero amino acid substitutions relative to CDR-H1, CDR-H2, and CDR-H3 of SEQ ID NO:108, whereby CDR-$H1_{TNF\alpha}$, CDR-$H2_{TNF\alpha}$, and CDR-$H3_{TNF\alpha}$ are, respectively, a CDR-H1, a CDR-H2, and a CDR-H3 of SEQ ID NO:108). Each VH CDR may be defined, for example, according to the Chothia definition, the Kabat definition, the AbM definition, the IMGT database definition, or the contact definition of CDR. In some variations, each VH CDR is defined according the IMGT database definition of CDR, whereby the reference CDRs CDR-H1, CDR-H2, and CDR-H3 of SEQ ID NO:108 correspond to residues 26-33, 50-59, and 97-110 of SEQ ID NO:108, respectively; in some such embodiments, CDR-$H1_{TNF\alpha}$, CDR-$H2_{TNF\alpha}$, and CDR-$H3_{TNF\alpha}$ are the VH CDRs of SEQ ID NO:108 according to the IMGT database definition, whereby CDR-$H1_{TNF\alpha}$ has the amino acid sequence shown in residues 26-33 of SEQ ID NO:108, CDR-$H2_{TNF\alpha}$ has the amino acid sequence shown in residues 50-59 of SEQ ID NO:108, and CDR-$H3_{TNF\alpha}$ has the amino acid sequence shown in residues 97-110 of SEQ ID NO:108.

In other, non-mutually exclusive embodiments of a fusion polypeptide as above comprising a single-chain antibody that specifically binds and neutralizes TNFα, the single-chain antibody comprises a VL domain comprising complementarity determining regions (CDRs) CDR-L$1_{TNF\alpha}$, CDR-L$2_{TNF\alpha}$, and CDR-L$3_{TNF\alpha}$, wherein the set of VL CDRs has three or fewer amino acid substitutions relative to a set of reference CDRs CDR-L1, CDR-L2, and CDR-L3 of the VL domain having the amino acid sequence shown in SEQ ID NO:110 (e.g., a set of VL CDRs having zero amino acid substitutions relative to CDR-L1, CDR-L2, and CDR-L3 of SEQ ID NO:110, whereby CDR-L$1_{TNF\alpha}$, CDR-L$2_{TNF\alpha}$, and CDR-L$3_{TNF\alpha}$ are, respectively, a CDR-L1, a CDR-L2, and a CDR-L3 of SEQ ID NO:110). Each VL CDR may be defined, for example, according to the Chothia definition, the Kabat definition, the AbM definition, the IMGT database definition, or the contact definition of CDR. In some variations, each VL CDR is defined according to the IMGT database definition of CDR, wherein the reference CDRs CDR-L1, CDR-L2, and CDR-L3 of SEQ ID NO:110 correspond to residues 27-32, 50-52, and 89-97 of SEQ ID NO:110, respectively; in some such embodiments, CDR-L$1_{TNF\alpha}$, CDR-L$2_{TNF\alpha}$, and CDR-L$3_{TNF\alpha}$ are VL CDRs of SEQ ID NO:110 according to the IMGT database definition, whereby CDR-L$1_{TNF\alpha}$ has the amino acid sequence shown in residues 27-32 of SEQ ID NO:110; CDR-L$2_{TNF\alpha}$ has the amino acid sequence shown in residues 50-52 of SEQ ID NO:110; and CDR-L$3_{TNF\alpha}$ has the amino acid sequence shown in residues 89-97 of SEQ ID NO:110.

In some embodiments of a fusion polypeptide as above comprising a single-chain antibody that specifically binds and neutralizes TNFα, the single-chain antibody comprises a VH domain having at least 90% or at least 95% identity with the amino acid sequence shown in SEQ ID NO:108, and/or the single-chain antibody comprises a VL domain having at least 90% or at least 95% identity with the amino acid sequence shown in SEQ ID NO:110. In more specific variations, the single-chain antibody comprises a VH domain having the amino acid sequence shown in SEQ ID NO:108, and/or the single-chain antibody comprises a VL domain having the amino acid sequence shown in SEQ ID NO:110.

In some embodiments of a fusion polypeptide as above comprising a single-chain antibody that specifically binds and neutralizes TGF-β, the single-chain antibody comprises a VH domain comprising complementarity determining regions (CDRs) CDR-H$1_{TGF\text{-}\beta}$, CDR-H$2_{TGF\text{-}\beta}$, and CDR-H$3_{TGF\text{-}\beta}$, wherein the set of VH CDRs has three or fewer amino acid substitutions relative to a set of reference CDRs CDR-H1, CDR-H2, and CDR-H3 of the VH domain having the amino acid sequence shown in SEQ ID NO:112 (e.g., a set of VH CDRs having zero amino acid substitutions relative to CDR-H1, CDR-H2, and CDR-H3 of SEQ ID NO:112, whereby CDR-H$1_{TGF\text{-}\beta}$, CDR-H$2_{TGF\text{-}\beta}$, and CDR-H$3_{TGF\text{-}\beta}$ are, respectively, a CDR-H1, a CDR-H2, and a CDR-H3 of SEQ ID NO:112). Each VH CDR may be defined, for example, according to the Chothia definition, the Kabat definition, the AbM definition, the IMGT database definition, or the contact definition of CDR. In some variations, each VH CDR is defined according the Kabat definition of CDR, whereby the reference CDRs CDR-H1, CDR-H2, and CDR-H3 of SEQ ID NO:112 correspond to residues 31-35, 50-66, and 99-106 of SEQ ID NO:112, respectively; in some such embodiments, CDR-H$1_{TGF\text{-}\beta}$, CDR-H$2_{TGF\text{-}\beta}$, and CDR-H$3_{TGF\text{-}\beta}$ are the VH CDRs of SEQ ID NO:112 according to the Kabat definition, whereby CDR-H$1_{TGF\text{-}\beta}$ has the amino acid sequence shown in residues 31-35 of SEQ ID NO:112, CDR-H$2_{TGF\text{-}\beta}$ has the amino acid sequence shown in residues 50-66 of SEQ ID NO:112, and CDR-H$3_{TGF\text{-}\beta}$ has the amino acid sequence shown in residues 99-106 of SEQ ID NO:112.

In other, non-mutually exclusive embodiments of a fusion polypeptide as above comprising a single-chain antibody that specifically binds and neutralizes TGF-β, the single-chain antibody comprises a VL domain comprising complementarity determining regions (CDRs) CDR-L$1_{TGF\text{-}\beta}$, CDR-L$2_{TGF\text{-}\beta}$, and CDR-L$3_{TGF\text{-}\beta}$, wherein the set of VL CDRs has three or fewer amino acid substitutions relative to a set of reference CDRs CDR-L1, CDR-L2, and CDR-L3 of the VL domain having the amino acid sequence shown in SEQ ID NO:114 (e.g., a set of VL CDRs having zero amino acid substitutions relative to CDR-L1, CDR-L2, and CDR-L3 of SEQ ID NO:114, whereby CDR-L$1_{TGF\text{-}\beta}$, CDR-L$2_{TGF\text{-}\beta}$, and CDR-L$3_{TGF\text{-}\beta}$ are, respectively, a CDR-L1, a CDR-L2, and a CDR-L3 of SEQ ID NO:114). Each VL CDR may be defined, for example, according to the Chothia definition, the Kabat definition, the AbM definition, the IMGT database definition, or the contact definition of CDR. In some variations, each VL CDR is defined according to the Kabat definition of CDR, wherein the reference CDRs CDR-L1, CDR-L2, and CDR-L3 of SEQ ID NO:114 correspond to residues 24-40, 56-62, and 95-102 of SEQ ID NO:114, respectively; in some such embodiments, CDR-L$1_{TGF\text{-}\beta}$, CDR-L$2_{TGF\text{-}\beta}$, and CDR-L$3_{TGF\text{-}\beta}$ are VL CDRs of SEQ ID NO:114 according to the Kabat definition, whereby CDR-L$1_{TGF\text{-}\beta}$ has the amino acid sequence shown in residues 24-40 of SEQ ID NO:114; CDR-L$2_{TGF\text{-}\beta}$ has the amino acid sequence shown in residues 56-62 of SEQ ID NO:114; and CDR-L$3_{TGF\text{-}\beta}$ has the amino acid sequence shown in residues 95-102 of SEQ ID NO:114.

In some embodiments of a fusion polypeptide as above comprising a single-chain antibody that specifically binds and neutralizes TGF-β, the single-chain antibody comprises a VH domain having at least 90% or at least 95% identity with the amino acid sequence shown in SEQ ID NO:112, and/or the single-chain antibody comprises a VL domain having at least 90% or at least 95% identity with the amino acid sequence shown in SEQ ID NO:114. In more specific variations, the single-chain antibody comprises a VH domain having the amino acid sequence shown in SEQ ID NO:112, and/or the single-chain antibody comprises a VL domain having the amino acid sequence shown in SEQ ID NO:114.

In some embodiments of a fusion polypeptide as above comprising a single-chain antibody that specifically binds and neutralizes TNFα or TGF-β, the single-chain antibody has at least 90% or at least 95% identity with the amino acid sequence shown in (i) residues 21-268 of SEQ ID NO:92, (ii) residues 21-268 of SEQ ID NO:96, (iii) residues 21-269 of SEQ ID NO:100, or (iv) residues 21-269 of SEQ ID NO:104. In more specific variations, the single-chain antibody has the amino acid sequence shown in (i) residues 21-268 of SEQ ID NO:92, (ii) residues 21-268 of SEQ ID NO:96, (iii) residues 21-269 of SEQ ID NO:100, or (iv) residues 21-269 of SEQ ID NO:104.

In another aspect, the present invention provides a fusion polypeptide comprising, from an amino terminal position to a carboxyl terminal position, X-L2-P, wherein X is an immunoglobulin heavy chain constant region, wherein the immunoglobulin heavy chain constant region is capable of forming dimers and specifically binding the neonatal Fc receptor (FcRn); L2 is a polypeptide linker, wherein L2 is optionally present; and P is a biologically active paraoxonase, wherein the paraoxonase has at least 80% or at least 90% identity with the amino acid sequence shown in residues 16-355 or 26-355 of SEQ ID NO:6 and does not contain an amino terminal leader sequence corresponding to residues 1-15 of SEQ ID NO:6, wherein the fusion polypeptide does not comprise a biologically active polypeptide N-terminal to the immunoglobulin heavy chain constant region. In some embodiments, the biologically active paraoxonase has at least 95% identity with the amino acid sequence shown in (i) residues 16-355 or 26-355 of SEQ ID NO:6, (ii) residues 16-355 or 26-355 of SEQ ID NO:124, or (iii) residues 16-355 or 26-355 of SEQ ID NO:126.

In some embodiments of a fusion polypeptide as above comprising the formula T-L1-X-L2-P or X-L2-P, the amino acid at a position corresponding to Q192 of the human paraoxonase 1 Q192 isoform (hPON1-Q192; SEQ ID NO:4) is lysine or arginine. In other, non-mutually exclusive variations, the amino acid at the position corresponding to H115 of hPON1-Q192 is tryptophan. In specific variations, the paraoxonase has an amino acid sequence selected from (i) residues n-355 of SEQ ID NO:6, (ii) residues n-355 of SEQ ID NO:124, and (iii) residues n-355 of SEQ ID NO:126, wherein n is an integer from 16 to 26, inclusive.

In certain embodiments of a fusion polypeptide as above comprising the formula T-L1-X-L2-P or X-L2-P, L2 is present and comprises at least eight amino acid residues. In some such embodiments, L2 consists of from 12 to 25 amino acid residues. A particularly suitable L2 linker has the amino acid sequence shown in SEQ ID NO:56.

In some embodiments of a fusion polypeptide as above having the formula T-L1-X-L2-P or X-L2-P and wherein X is an immunoglobulin heavy chain constant region, the immunoglobulin heavy chain constant region is an immunoglobulin Fc region. In some such embodiments, the Fc region is a human Fc region such as, e.g., a human Fc variant comprising one or more (e.g., from one to 10) amino acid substitutions relative to the wild-type human sequence. Particularly suitable Fc regions include human γ1 and γ4 Fc regions. In some variations, the Fc region is a human γ1 Fc variant in which Eu residue C220 is replaced by serine; in some such embodiments Eu residues C226 and C229 are each replaced by serine, and/or Eu residue P238 is replaced by serine. In further variations comprising an Fc region as above, the Fc region is a human γ1 Fc variant in which Eu residue P331 is replaced by serine. In some embodiments, the Fc region has at least 90% or at least 95% identity with the amino acid sequence shown in (i) residues 1-232 or 1-231 of SEQ ID NO:26, (ii) residues 1-232 or 1-231 of SEQ ID NO:28, (iii) residues 159-390 or 159-389 of SEQ ID NO:42, (iv) residues 1-232 or 1-231 of SEQ ID NO:116, or (v) residues 1-232 or 1-231 of SEQ ID NO:118. In more specific variations, the Fc region has the amino acid sequence shown in (i) residues 1-232 or 1-231 of SEQ ID NO:26, (ii) residues 1-232 or 1-231 of SEQ ID NO:28, (iii) residues 159-390 or 159-389 of SEQ ID NO:42, (iv) residues 1-232 or 1-231 of SEQ ID NO:116, or (v) residues 1-232 or 1-231 of SEQ ID NO:118.

In some embodiments of a fusion polypeptide as above having the formula T-L1-X-L2-P or X-L2-P and wherein X is an immunoglobulin heavy chain constant region, the immunoglobulin heavy chain constant region comprises an amino acid sequence having at least 90% or at least 95% identity with the amino acid sequence shown in (i) residues 16-232 or 16-231 of SEQ ID NO:26, (ii) residues 16-232 or 16-231 of SEQ ID NO:116, or (iii) residues 16-232 or 16-231 of SEQ ID NO:118. In more specific variations, the immunoglobulin heavy chain constant region comprises the amino acid sequence shown in (i) residues 16-232 or 16-231 of SEQ ID NO:26, (ii) residues 16-232 or 16-231 of SEQ ID NO:116, or (iii) residues 16-232 or 16-231 of SEQ ID NO:118.

In some embodiments of a fusion polypeptide as above having the formula T-L1-X-L2-P and wherein the first biologically active polypeptide is the DNase, the fusion polypeptide comprises an amino acid sequence having at least 90% or at least 95% identity with the amino acid sequence shown in (i) residues 21-896 of SEQ ID NO:2, (ii) residues 21-896 of SEQ ID NO:128, (iii) residues 21-896 of SEQ ID NO:130, (iv) residues 21-906 of SEQ ID NO:148, (v) residues 21-896 of SEQ ID NO:158, (vi) residues 21-906 of SEQ ID NO:160, (vii) residues 21-906 of SEQ ID NO:162, or (viii) residues 21-906 of SEQ ID NO:164; in some such embodiments, the fusion polypeptide comprises the amino acid sequence shown in (i) residues 21-896 of SEQ ID NO:2, (ii) residues 21-896 of SEQ ID NO:128, (iii) residues 21-896 of SEQ ID NO:130, (iv) residues 21-906 of SEQ ID NO:148, (v) residues 21-896 of SEQ ID NO:158, (vi) residues 21-906 of SEQ ID NO:160, (vii) residues 21-906 of SEQ ID NO:162, or (viii) residues 21-906 of SEQ ID NO:164.

In some embodiments of a fusion polypeptide as above having the formula T-L1-X-L2-P and wherein the first biologically active polypeptide is the DNase, the polypeptide region corresponding to T-L1-X ("T-L1-X region") comprises the amino acid sequence shown in SEQ ID NO:149, SEQ ID NO:150, SEQ ID NO:153, or SEQ ID NO:154. In certain variations of a T-L1-X region comprising the amino acid sequence shown in SEQ ID NO:149, SEQ ID NO:150, SEQ ID NO:153, or SEQ ID NO:154, (i) the amino acid at each of positions 315 and 316 is alanine; (ii) the amino acid at position 319 is serine; (iii) the amino acid at position 378 is alanine, glutamine, or glycine, and the amino acid at position 346 is optionally alanine; (iv) the amino acid at position 410 is alanine, glycine, or serine; (v) the amino acid at position 412 is serine or alanine; (vi) the amino acid at position 333 is tyrosine, the amino acid at position 335 is threonine, and the amino acid at position 337 is glutamate; and/or (vii) the amino acid at position 509 is leucine, and the amino acid at position 515 is serine. In other, non-mutually exclusive variations of a T-L1-X region comprising the amino acid sequence shown in SEQ ID NO:149, SEQ ID NO:150, SEQ ID NO:153, or SEQ ID NO:154, the amino acid sequence corresponding to positions 261-296 includes a Gly-Ser tandem repeat sequence having a formula selected from the group consisting of (i) $[\text{Gly-Gly-Gly-Gly-Ser}]_n$, wherein n is an integer from 4 to 7, (ii) $[\text{Gly-Gly-Gly-Ser}]_n$, wherein n is an integer from 5 to 9, and (iii) $[\text{Gly-Gly-Ser}]_n$, wherein n is an integer from 6 to 12; in some such embodiments, the amino acid sequence corresponding to positions 261-296 includes a Gly-Ser tandem repeat sequence having a formula selected from the group consisting of (i) $[\text{Gly-Gly-Gly-Gly-Ser}]_n$, wherein n is an integer from 4 to 6, (ii) $[\text{Gly-Gly-Gly-Ser}]_n$, wherein n is an integer from 5 to 7, and (iii) $[\text{Gly-Gly-Ser}]_n$, wherein n is an integer from 6 to 10. In yet other, non-mutually exclusive variations of a T-L1-X region comprising the amino acid sequence shown in SEQ ID NO:149, SEQ ID NO:150, SEQ ID NO:153, or SEQ ID NO:154, the amino acid at position 261 is aspartate, the amino acid at position 262 is leucine, the amino acid at position 263 is serine, the amino acid at position 294 is threonine, the amino acid at position is 295 is glycine, and/or the amino acid at position 296 is leucine. In other, non-mutually exclusive variations of a T-L1-X region comprising the amino acid sequence shown in SEQ ID NO:149 or SEQ ID NO:153, the amino acid at each of positions 74 and 105 is independently lysine or arginine, In other, non-mutually exclusive variations of a T-L1-X region comprising the amino acid sequence shown in SEQ ID NO:149, the amino acid at position 114 is phenylalanine.

In some embodiments of a fusion polypeptide as above having the formula T-L1-X-L2-P and wherein the first biologically active polypeptide is the RNase, the fusion polypeptide comprises an amino acid sequence having at least 90% or at least 95% identity with the amino acid sequence shown in (i) residues 21-764 of SEQ ID NO:40 or (ii) residues 21-740 of SEQ ID NO:48; in some such embodiments, the fusion polypeptide comprises the amino acid sequence shown in (i) residues 21-764 of SEQ ID NO:40 or (ii) residues 21-740 of SEQ ID NO:48.

In some embodiments of a fusion polypeptide as above having the formula T-L1-X-L2-P and wherein the first biologically active polypeptide is the SOD1, the fusion polypeptide comprises an amino acid sequence having at least 90% or at least 95% identity with the amino acid sequence shown in (i) residues 23-781 of SEQ ID NO:50, (ii) residues 23-781 of SEQ ID NO:52, or (iii) residues 23-791 of SEQ ID NO:54; in some such embodiments, the fusion polypeptide comprises the amino acid sequence shown in (i) residues 23-781 of SEQ ID NO:50, (ii) residues 23-781 of SEQ ID NO:52, or (iii) residues 23-791 of SEQ ID NO:54.

In some embodiments of a fusion polypeptide as above having the formula T-L1-X-L2-P and wherein the first biologically active polypeptide is the CTLA-4 extracellular domain, the fusion polypeptide comprises an amino acid sequence having at least 90% or at least 95% identity with the amino acid sequence shown in residues 21-736 of SEQ ID NO:66; in some such embodiments, the fusion polypeptide comprises the amino acid sequence shown in residues 21-736 of SEQ ID NO:66.

In some embodiments of a fusion polypeptide as above having the formula T-L1-X-L2-P and wherein the first biologically active polypeptide is the CD40 extracellular domain, the fusion polypeptide comprises an amino acid sequence having at least 90% or at least 95% identity with the amino acid sequence shown in (i) residues 21-804 of SEQ ID NO:74, (ii) residues 21-804 of SEQ ID NO:78, (iii) residues 21-804 of SEQ ID NO:82, (iv) residues 21-804 of SEQ ID NO:86, or (v) residues 21-804 of SEQ ID NO:90; in some such embodiments, the fusion polypeptide comprises the amino acid sequence shown in (i) residues 21-804 of SEQ ID NO:74, (ii) residues 21-804 of SEQ ID NO:78, (iii) residues 21-804 of SEQ ID NO:82, (iv) residues 21-804 of SEQ ID NO:86, or (v) residues 21-804 of SEQ ID NO:90.

In some embodiments of a fusion polypeptide as above having the formula T-L1-X-L2-P and wherein the first biologically active polypeptide is a single-chain antibody that specifically binds and neutralizes TNFα, the fusion polypeptide comprises an amino acid sequence having at least 90% or at least 95% identity with the amino acid sequence shown in (i) residues 21-860 of SEQ ID NO:94, or (ii) residues 21-860 of SEQ ID NO:98; in some such embodiments, the fusion polypeptide comprises the amino acid sequence shown in (i) residues 21-860 of SEQ ID NO:94, or (ii) residues 21-860 of SEQ ID NO:98.

In some embodiments of a fusion polypeptide as above having the formula T-L1-X-L2-P and wherein the first biologically active polypeptide is a single-chain antibody that specifically binds and neutralizes TGF-β, the fusion polypeptide comprises an amino acid sequence having at least 90% or at least 95% identity with the amino acid sequence shown in (i) residues 21-861 of SEQ ID NO:102, or (ii) residues 21-861 of SEQ ID NO:106; in some such embodiments, the fusion polypeptide comprises the amino acid sequence shown in (i) residues 21-861 of SEQ ID NO:102, or (ii) residues 21-861 of SEQ ID NO:106.

In some embodiments of a fusion polypeptide as above having the formula X-L2-P, the fusion polypeptide comprises an amino acid sequence having at least 90% or at least 95% identity with the amino acid sequence shown in (i) residues 21-613 of SEQ ID NO:122, (ii) residues 21-613 of SEQ ID NO:132, (iii) residues 21-613 of SEQ ID NO:134, (iv) residues 21-610 of SEQ ID NO:142, (v) residues 21-610 of SEQ ID NO:144, or (vi) residues 21-610 of SEQ ID NO:146; in some such embodiments, the fusion polypeptide comprises the amino acid sequence shown in (i) residues 21-613 of SEQ ID NO:122, (ii) residues 21-613 of SEQ ID NO:132, (iii) residues 21-613 of SEQ ID NO:134, (iv) residues 21-610 of SEQ ID NO:142, (v) residues 21-610 of SEQ ID NO:144, or (vi) residues 21-610 of SEQ ID NO:146.

In another aspect, the present invention provides a dimeric protein comprising a first fusion polypeptide and a second fusion polypeptide, wherein each of the first and second fusion polypeptides is (i) a fusion polypeptide as above having the formula T-L1-X-L2-P and wherein the X is a dimerizing domain (e.g., an immunoglobulin heavy chain constant region such as, for example, an immunoglobulin Fc region), or (ii) a fusion polypeptide as above having the formula X-L2-P.

In another aspect, the present invention provides a polynucleotide encoding a fusion polypeptide as described above.

In still another aspect, the present invention provides an expression cassette comprising a DNA segment encoding a fusion polypeptide as described above and which is operably linked to a promoter. In particular variations, the encoded fusion polypeptide is a fusion polypeptide as above having the formula T-L1-X-L2-P and wherein the first biologically active polypeptide is the DNase (i) having at least 90% or at least 95% identity with amino acid residues 21-280 of SEQ ID NO:18 or residues 21-280 of SEQ ID NO:152 and (ii) comprising at least one of the N74, G105, and A114 substitutions (e.g., a DNase having two or all three substitutions). Also provided is a cultured cell into which has been introduced an expression cassette as described above, wherein the cell expresses the DNA segment. In a related aspect, the present invention provides a stable cell line comprising, within its genomic DNA, an expression cassette as described above, wherein the stable cell line constitutively expresses the DNA segment. In some embodiments, the stable cell line is a Chinese hamster ovary (CHO) cell line.

In another aspect, the present invention provides a vector comprising an expression cassette as described above.

In another aspect, the present invention provides a method of making a fusion polypeptide. The method generally includes (i) culturing a cell into which has been introduced an expression cassette as described above, wherein the cell expresses the DNA segment and the encoded fusion polypeptide is produced, and (ii) recovering the fusion polypeptide. In some variations, the cultured cell is a stable cell line as described above.

In yet another aspect, the present invention provides a method of making a dimeric protein. The method generally includes (i) culturing a cell into which has been introduced an expression cassette as described above, wherein the cell expresses the DNA segment and the encoded fusion polypeptide is produced as a dimeric protein, and (ii) recovering the dimeric protein. In some variations, the cultured cell is a stable cell line as described above.

In another aspect, the present invention provides a composition comprising a fusion polypeptide as described above and a pharmaceutically acceptable carrier.

In another aspect, the present invention provides a composition comprising a dimeric protein as described above and a pharmaceutically acceptable carrier.

In some embodiments of a composition as described above, the composition is formulated for delivery to the lung by nebulization.

In still another aspect, the present invention provides a method for treating an inflammatory disease. The method generally includes administering to a subject having the inflammatory disease an effective amount of a fusion polypeptide or dimeric protein as described above. In some embodiments, the inflammatory disease is an inflammatory lung disease such as, for example, chronic obstructive pulmonary disease (COPD), asthma, cystic fibrosis (CF), bronchiectasis, hypoxia, acute respiratory distress syndrome (ARDS) (e.g., COVID-19-associated ARDS), and interstitial lung disease (e.g., idiopathic pulmonary fibrosis (IPF) or sarcoidosis); in some variations, the inflammatory lung disease is characterized by *Pseudomonas aeruginosa* infection. In other embodiments, the inflammatory disease is selected from an inflammatory bowel disease (IBD) (e.g., Crohn's disease or ulcerative colitis), systemic lupus erythematosus (SLE) (e.g., SLE with lupus nephritis), type 1 diabetes, and type 2 diabetes. In still other embodiments, the inflammatory disease is an inflammatory skin disease such as, for example, psoriasis or atopic dermatitis.

In another aspect, the present invention provides a method for treating an autoimmune disease. The method generally includes administering to a subject having the autoimmune disease an effective amount of a fusion polypeptide or dimeric protein as described above. In some embodiments, the autoimmune disease is selected from systemic lupus erythematosus (SLE) (e.g., SLE with lupus nephritis), Sjogren's syndrome, rheumatoid arthritis, psoriasis, psoriatic arthritis, antiphospholipid syndrome, type 1 diabetes, vasculitis, and systemic sclerosis.

In another aspect, the present invention provides a method for treating biofilm formation by a gram-negative bacteria. The method generally includes administering to a subject having the biofilm formation an effective amount of a fusion polypeptide or dimeric protein as described above. In some embodiments, the gram-negative bacteria is *Pseudomonas aeruginosa.*

In another aspect, the present invention provides a method for treating exposure to sulfur mustard gas or an organophosphate. The method generally includes administering to a subject exposed to the sulfur mustard gas or to the organophosphate an effective amount of a fusion polypeptide or dimeric protein as described above. In some embodiments, the organophosphate is an insecticide selected from parathion, malathion, chlorpyrifos, diazinon, dichlorvos, phosmet, fenitrothion, terbufos, tetrachlorvinphos, azamethiphos, and azinphos-methyl. In some embodiments the organophosphate is a nerve agent selected from tabun, sarin, soman, and cyclosarin.

In yet another aspect, the present invention provides a method for treating a neurological disease. The method generally includes administering to a subject having the neurological disease an effective amount of a fusion polypeptide or dimeric protein as described above. In some embodiments, the neurological disease is selected from Parkinson's disease and Alzheimer's disease. In some embodiments, the neurological disease is a disease characterized by dementia such as, for example, Alzheimer's disease.

In another aspect, the present invention provides a method for treating a cardiovascular disease. The method generally includes administering to a subject having the cardiovascular disease an effective amount of a fusion polypeptide or dimeric protein as described above. In some embodiments, the cardiovascular disease is a disease characterized by atherosclerosis such as, e.g., coronary heart disease or ischemic stroke. In some variations, the coronary heart disease is characterized by acute coronary syndrome.

In another aspect, the present invention provides a method for treating a chronic liver disease. The method generally includes administering to a subject having the chronic liver disease an effective amount of a fusion polypeptide or dimeric protein as describe above. In some embodiments, the chronic liver disease is selected from nonalcoholic fatty liver disease (NAFLD), alcohol-associated liver disease (ALD), portal hypertension, or a complication following liver transplantation. In some variations, the nonalcoholic fatty liver disease is nonalcoholic steatohepatitis (NASH).

In another aspect, the present invention provides a method for treating a fibrotic disease. The method generally includes administering to a subject having the fibrotic disease an effective amount of a fusion polypeptide or dimeric protein as described above. In some embodiments, the fibrotic disease is selected from the group consisting of systemic sclerosis, systemic lupus erythematosus (SLE), an inflammatory lung disease, a chronic liver disease, and a chronic kidney disease (e.g., lupus nephritis, IgA nephropathy, or membranous glomerulonephritis).

In still another aspect, the present invention provides a method for treating a disease or disorder characterized by NETosis. In some embodiments, the method generally includes administering to a subject having the disease or disorder characterized by NETosis an effective amount of a fusion polypeptide having the formula T-L1-X-L2-P as described above, or a dimeric protein formed by dimerization of the fusion polypeptide, wherein the fusion polypeptide or dimeric protein comprises the DNase as the first biologically active polypeptide.

In other embodiments of a method for treating a disease or disorder characterized by NETosis, the method is a combination therapy that generally includes administering to a subject having the disease or disorder characterized by NETosis (a) an effective amount of a fusion polypeptide having the formula X-L2-P as described above, or a dimeric protein formed by dimerization of the fusion polypeptide, and (b) an effective amount of a biologically active DNase. In certain embodiments of the combination therapy method, the DNase has at least 90% or at least 95% identity with the amino acid sequence shown in (i) residues 21-280 of SEQ ID NO:18, (ii) residues 21-280 of SEQ ID NO:152, or (iii) residues 21-290 of SEQ ID NO:136. In some embodiments wherein the DNase has at least 90% or at least 95% identity with the amino acid sequence shown in residues 21-280 of SEQ ID NO:18 or residues 21-280 of SEQ ID NO:152, the DNase contains at least one amino acid substitution at a position corresponding to an amino acid of human wild-type DNase1 (SEQ ID NO:120) selected from N74, G105, and A114, wherein (1) the amino acid substitution at a position corresponding to N74 of human DNase1 (N74 substitution), if present, increases DNA binding relative to human DNase1, (2) the amino acid substitution at a position corresponding to G105 of human DNase1 (G105 substitution), if present, increases DNA binding relative to human DNase1, and (3) the amino acid substitution at a position corresponding to A114 of human DNase1 (A114 substitution), if present, decreases G-actin-induced inhibition of endonuclease activity relative to human DNase1. In some variations, the DNase contains both the N74 and G105 substitutions, or each of the N74, G105, and A114 substitutions. Particularly suitable amino acid substitutions at these positions are lysine at the position corresponding to N74 of human DNase1, arginine at the position corresponding to G105 of human DNase1, and/or phenylalanine at the position corresponding to A114 of human DNase1. In some embodiments wherein the DNase has at least 90% or at least 95% identity with amino acid sequence shown in residues 21-290 of SEQ ID NO:136, each of the amino acids at positions corresponding to R80, R95, and N96 of SEQ ID NO:136 is alanine or serine. In more specific variations, the DNase has the amino acid sequence shown in (i) residues 21-280 of SEQ ID NO:18, (ii) residues 21-280 of SEQ ID NO:20, (iii) residues 21-280 of SEQ ID NO:152, (iv) residues 21-290 of SEQ ID NO:138, or (v) residues 21-290 of SEQ ID NO:140.

In certain embodiments of a combination therapy method for treating a disease or disorder characterized by NETosis as above, the DNase is contained within a DNase fusion polypeptide comprising, from an amino terminal position to a carboxyl terminal position, D-L1-Xa, wherein D is the DNase, L1 is a polypeptide linker (e.g., a linker comprising at least 15 amino acid residues or at least 26 amino acid residues), and Xa is an immunoglobulin Fc region. The immunoglobulin Fc region may be an Fc region as described above for a fusion polypeptide having the formula T-L1-X-L2-P or X-L2-P. In some variations, the DNase fusion polypeptide comprises an amino acid sequence having at least 90% or at least 95% identity with the amino acid sequence shown in (i) residues 21-538 or 21-537 of SEQ ID NO:60, (ii) residues 21-548 or 21-547 of SEQ ID NO:62, (iii) residues 21-538 or 21-537 of SEQ ID NO:155, (iv) residues 21-548 or 21-547 of SEQ ID NO:156, (v) residues 21-548 or 21-547 of SEQ ID NO:138, or (vi) residues 21-548 or 21-547 of SEQ ID NO:140; in some such embodiments, the DNase fusion polypeptide comprises the amino acid sequence shown in (i) residues 21-538 or 21-537 of SEQ ID NO:60, (ii) residues 21-548 or 21-547 of SEQ ID NO:62, (iii) residues 21-538 or 21-537 of SEQ ID NO:155, (iv) residues 21-548 or 21-547 of SEQ ID NO:156, (v) residues 21-548 or 21-547 of SEQ ID NO:138, or (vi) residues 21-548 or 21-547 of SEQ ID NO:140. In certain variations, the DNase comprises the amino acid sequence shown in SEQ ID NO:149, SEQ ID NO:150, SEQ ID NO:153, or SEQ ID NO:154.

In some embodiments of a method for treating a disease or disorder characterized by NETosis, the disease or disorder is an inflammatory lung disease such as, for example, chronic obstructive pulmonary disease (COPD), asthma, cystic fibrosis (CF), bronchiectasis, hypoxia, acute respiratory distress syndrome (ARDS) (e.g., COVID-19-associated ARDS), or interstitial lung disease (e.g., idiopathic pulmonary fibrosis (IPF) or sarcoidosis). In other embodiments, the disease or disorder is an inflammatory skin disease such as, for example, psoriasis or atopic dermatitis. In other embodiments, the disease or disorder is an autoimmune disease such as, e.g., systemic lupus erythematosus (SLE) (e.g., SLE with lupus nephritis), rheumatoid arthritis (RA), psoriasis, antiphospholipid syndrome, type 1 diabetes mellitus, vasculitis, or systemic sclerosis. In other embodiments, the disease or disorder is an autoinflammatory disease such as, for example, an inflammatory bowel disease (IBD) (e.g., Crohn's disease or ulcerative colitis) or gout. In other embodiments, the disease or disorder is a neurological disease or disorder such as, for example, a chronic neurodegenerative disease (e.g., Alzheimer's disease or multiple sclerosis), a central nervous system infection (e.g., meningitis, encephalitis, or cerebral malaria), or ischemic stroke. In other embodiments, the disease or disorder is a metabolic disease such as, e.g., type 2 diabetes or obesity. In other embodiments, the disease or disorder is a cardiovascular disease such as, for example, a cardiovascular disease characterized by atherosclerosis (e.g., coronary heart disease or ischemic stroke). In still other embodiments, the disease or disorder is selected from thrombosis, sepsis, and ischemia reperfusion. In other embodiments, the disease or disorder is a chronic liver disease such as, e.g., nonalcoholic steatohepatitis (NASH). In yet other embodiments, the disease or disorder is a fibrotic disease such as, e.g., systemic sclerosis, systemic lupus erythematosus (SLE), an inflammatory lung disease, a chronic liver disease, or a chronic kidney disease (e.g., lupus nephritis, IgA nephropathy, or membranous glomerulonephritis).

In yet other embodiments of a method for treating a disease or disorder characterized by NETosis, the disease or disorder is a cancer. In certain variations, the cancer treatment is a combination therapy. In some combination therapy embodiments, the combination therapy includes an immunomodulatory therapy comprising an anti-PD-1/PD-L1 therapy, an anti-CTLA-4 therapy, a CAR T cell therapy, or a combination thereof (e.g., both an anti-PD-1/PD-L1 therapy and an anti-CTLA-4 therapy). In other combination therapy embodiments, the combination therapy includes radiation therapy or chemotherapy. In some combination therapy embodiments, the combination therapy includes a targeted therapy; in some such embodiments, the targeted therapy includes (i) a therapeutic monoclonal antibody targeting a specific cell-surface or extracellular antigen (e.g., VEGF, EGFR, CTLA-4, PD-1, or PD-L1) or (ii) a small molecule targeting an intracellular protein such as, for example, an intracellular enzyme (e.g., a proteasome, a tyrosine kinase, a cyclin-dependent kinase, serine/threonine-protein kinase B-Raf (BRAF), or a MEK kinase).

In another aspect, the present invention provides a method for reducing lipid oxidation in a subject. The method generally includes administering to the subject an effective amount of a fusion polypeptide or dimeric protein as described above. In some embodiments, the method is a combination therapy that further reduces NETosis in the subject and that generally includes administering (a) an effective amount of a fusion polypeptide having the formula X-L2-P as described above, or a dimeric protein formed by dimerization of the fusion polypeptide, and (b) an effective amount of a biologically active DNase (e.g., a DNase fusion polypeptide having the formula D-L1-Xa as described above).

In another aspect, the present invention provides a method for protecting a subject from aging. The method generally includes administering to the subject an effective amount of a fusion polypeptide or dimeric protein as described above. In some embodiments, the method is a combination therapy that generally includes administering (a) an effective amount of a fusion polypeptide having the formula X-L2-P as described above, or a dimeric protein formed by dimerization of the fusion polypeptide, and (b) an effective amount of a biologically active DNase (e.g., a DNase fusion polypeptide having the formula D-L1-Xa as described above).

These and other aspects of the invention will become evident upon reference to the following detailed description of the invention.

DEFINITIONS

Unless defined otherwise, all technical and scientific terms used herein have the same meaning as commonly understood by one of ordinary skill in the art pertinent to the methods and compositions described. As used herein, the following terms and phrases have the meanings ascribed to them unless specified otherwise.

The terms "a," "an," and "the" include plural referents, unless the context clearly indicates otherwise.

A "polypeptide" is a polymer of amino acid residues joined by peptide bonds, whether produced naturally or synthetically. Polypeptides of less than about 50 amino acid residues may also be referred to as "peptides."

A "protein" is a macromolecule comprising one or more polypeptide chains. A protein may also comprise non-peptidic components, such as carbohydrate groups. Carbohydrates and other non-peptidic substituents may be added to a protein by the cell in which the protein is produced, and will vary with the type of cell. Proteins are defined herein in terms of their amino acid backbone structures; substituents such as carbohydrate groups are generally not specified, but may be present nonetheless.

The terms "amino-terminal" (or "N-terminal") and "carboxyl-terminal" (or "C-terminal") are used herein to denote positions within polypeptides. Where the context allows, these terms are used with reference to a particular sequence or portion of a polypeptide to denote proximity or relative position. For example, a certain sequence positioned carboxyl-terminal to a reference sequence within a polypeptide is located proximal to the carboxyl terminus of the reference sequence, but is not necessarily at the carboxyl terminus of the complete polypeptide.

The terms "polynucleotide" and "nucleic acid" are used synonymously herein and refer to a single- or double-stranded polymer of deoxyribonucleotide or ribonucleotide bases read from the 5' to the 3' end. Polynucleotides include RNA and DNA, and may be isolated from natural sources, synthesized in vitro, or prepared from a combination of natural and synthetic molecules. Sizes of polynucleotides are expressed as base pairs (abbreviated "bp"), nucleotides ("nt"), or kilobases ("kb"). Where the context allows, the latter two terms may describe polynucleotides that are single-stranded or double-stranded. It will be recognized by those skilled in the art that the two strands of a double-stranded polynucleotide may differ slightly in length and that the ends thereof may be staggered as a result of enzymatic cleavage; thus all nucleotides within a double-stranded polynucleotide molecule may not be paired. Such unpaired ends will in general not exceed 20 nt in length.

A "segment" is a portion of a larger molecule (e.g., polynucleotide or polypeptide) having specified attributes. For example, a DNA segment encoding a specified polypeptide is a portion of a longer DNA molecule, such as a plasmid or plasmid fragment that, when read from the 5' to the 3' direction, encodes the sequence of amino acids of the specified polypeptide. Also, for example, in the context of a fusion polypeptide as described herein, different components of the fusion polypeptide (e.g., a DNase, an RNase, a superoxide dismutase (SOD), linker(s), an immunoglobulin Fc region, a paraoxonase) may each be referred to as a polypeptide segment.

The term "biologically active," when used in reference to a polypeptide segment of a fusion molecule as described herein, means a polypeptide that causes a measurable or detectable physiological, biochemical, or molecular effect in a biological system. Biological activities include, for example, enzymatic activity, antigen-binding, binding to a cell-surface receptor, dimerization, activation of a signaling pathway in a eukaryotic cell, induction of cell proliferation, induction of cell differentiation, and the like. When used in specific reference to a polypeptide segment that is a DNase, RNase, paraoxonase (PON), or superoxide dismutase (SOD), "biologically active" means that the polypeptide exhibits the same type of enzymatic activity as a corresponding, naturally occurring enzyme (e.g., the same type of enzymatic activity as a full-length, wild-type human DNase1/DNase1L3, RNase1, PON1, or SOD1, respectively), allowing for differences in degree of activity, enzyme kinetics, and the like. An immunoglobulin Fc region, as referenced herein, is understood to be "biologically active" at least by virtue of its dimerizing and FcRn-binding activities.

Unless the context clearly indicates otherwise, reference herein to "paraoxonase" (e.g., "paraoxonase 1" or "PON1"), "DNase" (e.g., "DNase1" or "DNase1L3"), "RNase" (e.g., "RNase 1"), "superoxide dismutase" (e.g., "superoxide dismutase 1" or "SOD1"), "CTLA-4 extracellular domain," and "CD40 extracellular domain" is understood to include naturally occurring polypeptides of any of the foregoing, as well as functional variants and functional fragments thereof.

The term "allelic variant" is used herein to denote any of two or more alternative forms of a gene occupying the same chromosomal locus. Allelic variation arises naturally through mutation, and may result in phenotypic polymorphism within populations. Gene mutations can be silent (no change in the encoded polypeptide) or may encode polypeptides having altered amino acid sequence. The term allelic variant is also used herein to denote a protein encoded by an allelic variant of a gene.

The term "enhanced DNase1" as used herein denotes a hyperactive and/or actin-resistant variant of a naturally occurring DNase1 (e.g., human DNase1), the variant having (a) at least one amino acid substitution that decreases G-actin-induced inhibition of endonuclease activity relative to the naturally occurring DNase1, and/or (b) at least one amino acid substitution that increases DNA binding relative to the naturally occurring DNase1. In some embodiments, the enhanced DNase1 comprises the at least one amino acid substitution that decreases G-actin-induced inhibition of endonuclease activity. In some embodiments, the enhanced DNase1 comprises both the at least one amino acid substitution that decreases G-actin-induced inhibition of endonuclease activity and the at least one amino acid substitution that increases DNA binding. In some preferred embodiments, an enhanced DNase1 is a hyperactive variant of wild-type human DNase1 (mature amino acid sequence shown in SEQ ID NO:120).

The term "linker" or "polypeptide linker" is used herein to indicate two or more amino acids joined by peptide bond(s) and linking two discrete, separate polypeptide regions. The linker is typically designed to allow the separate polypeptide regions (such as, e.g., a DNase or paraoxonase polypeptide linked to an Fc region) to perform their separate functions. The linker can be a portion of a native sequence, a variant thereof, or a synthetic sequence. Linkers are also referred to herein using the abbreviation "L." The use of a numerical identifier (e.g., "1" or "2") with "L" is used herein to differentiate among linkers joining different fusion components: "L1" refers to a linker joining the C-terminus of a first biologically active polypeptide that is not a paraoxonase (e.g., a DNase, an RNase, or a SOD1) to the N-terminus of another polypeptide segment such, e.g., an immunoglobulin Fc region, and "L2" refers to a linker joining the N-terminus of a biologically active paraoxonase (e.g., a PON1) to the C-terminus of another polypeptide segment such as, e.g., an immunoglobulin Fc region. In the context of a polypeptide chain containing both L1 and L2 linkers, the linkers may be the same or different with respect to amino acid sequence. In some variations in which the carboxyl-terminus of the first biologically active polypeptide is linked directly to the amino-terminus of a biologically active paraoxonase via a single polypeptide linker (i.e., with no intervening biologically active polypeptide), such polypeptide linker may be referred to as either L1 or L2.

The term "expression cassette" is used to denote a DNA construct that comprises a segment encoding a polypeptide of interest operably linked to additional segments that provide for its transcription in an appropriate host cell. Such additional sequences include a promoter and, typically, a transcription terminator, and may also include one or more selectable markers, an enhancer, a polyadenylation signal, etc.

The term "vector" is used to denote a polynucleotide produced by recombinant DNA techniques for delivering genetic material into a cell, where it can be replicated. As is well-known in the art, it may refer, e.g., to a plasmid, a cosmid, a viral vector, an artificial chromosome, a cloning vector, or an expression vector. The term "expression vector" is used to denote a vector comprising an expression cassette.

The term "promoter" is used herein for its art-recognized meaning to denote a portion of a gene containing DNA sequences that provide for the binding of RNA polymerase and initiation of transcription. Promoter sequences are commonly, but not always, found in the 5' non-coding regions of genes.

A "secretory signal sequence" is a DNA sequence that encodes a polypeptide (a "secretory peptide") that, as a component of a larger polypeptide, directs the larger polypeptide through a secretory pathway of a cell in which it is synthesized. The larger polypeptide is commonly cleaved to remove the secretory peptide during transit through the secretory pathway.

"Operably linked" means that two or more entities are joined together such that they function in concert for their intended purposes. When referring to DNA segments, the phrase indicates, for example, that coding sequences are joined in the correct reading frame, and transcription initiates in the promoter and proceeds through the coding segment(s) to the terminator. When referring to polypeptides, "operably linked" includes both covalently (e.g., by disulfide bonding) and non-covalently (e.g., by hydrogen bonding, hydrophobic interactions, or salt-bridge interactions) linked sequences, wherein the desired function(s) of the sequences are retained.

The term "recombinant" when used with reference, e.g., to a cell, nucleic acid, protein, or vector, indicates that the cell, nucleic acid, protein, or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under-expressed or not expressed at all. By the term "recombinant nucleic acid" herein is meant nucleic acid, originally formed in vitro, in general, by the manipulation of nucleic acid using, e.g., polymerases and endonucleases, in a form not normally found in nature. In this manner, operable linkage of different sequences is achieved. Thus an isolated nucleic acid, in a linear form, or an expression vector formed in vitro by ligating DNA molecules that are not normally joined, are both considered recombinant for the purposes disclosed herein. It is understood that once a recombinant nucleic acid is made and reintroduced into a host cell or organism, it will replicate non-recombinantly, i.e., using the in vivo cellular machinery of the host cell rather than in vitro manipulations; however, such nucleic acids, once produced recombinantly, although subsequently replicated non-recombinantly, are still considered recombinant for the purposes disclosed herein. Similarly, a "recombinant protein" is a protein made using recombinant techniques, i.e., through the expression of a recombinant nucleic acid as depicted above.

The term "heterologous," when used with reference to portions of a nucleic acid, indicates that the nucleic acid comprises two or more subsequences that are not normally found in the same relationship to each other in nature. For instance, the nucleic acid is typically recombinantly produced, having two or more sequences, e.g., from unrelated genes arranged to make a new functional nucleic acid, e.g., a promoter from one source and a coding region from another source. Similarly, "heterologous," when used in reference to portions of a protein, indicates that the protein comprises two or more subsequences that are not found in the same relationship to each other in nature (e.g., two or more segments of a fusion polypeptide).

As used herein, the term "immunoglobulin" refers to a protein consisting of one or more polypeptides substantially encoded by immunoglobulin gene(s). One form of immunoglobulin constitutes the basic structural unit of an intact, native antibody. This form is a tetramer and consists of two identical pairs of immunoglobulin chains, each pair having one light and one heavy chain. In each pair, the light and heavy chain variable regions are together responsible for binding to an antigen, and the constant regions are responsible for the antibody effector functions. Immunoglobulins typically function as antibodies in a vertebrate organism. Five classes of immunoglobulin protein (IgG, IgA, IgM, IgD, and IgE) have been identified in higher vertebrates. IgG comprises the major class; it normally exists as the second most abundant protein found in plasma. In humans, IgG consists of four subclasses, designated IgG1, IgG2, IgG3, and IgG4. The heavy chain constant regions of the IgG class are identified with the Greek symbol γ. For example, immunoglobulins of the IgG1 subclass contain a γ1 heavy chain constant region. Each immunoglobulin heavy chain possesses a constant region that consists of constant region protein domains (CH1, hinge, CH2, and CH3; IgG3 also contains a CH4 domain) that are essentially invariant for a given subclass in a species. DNA sequences encoding human and non-human immunoglobulin chains are known in the art. (See, e.g., Ellison et al., DNA 1:11-18, 1981; Ellison et al., *Nucleic Acids Res.* 10:4071-4079, 1982; Kenten et al., *Proc. Natl. Acad. Sci. USA* 79:6661-6665, 1982; Seno et al., *Nuc. Acids Res.* 11:719-726, 1983; Riechmann et al., *Nature* 332:323-327, 1988; Amster et al., *Nuc. Acids Res.* 8:2055-2065, 1980; Rusconi and Kohler, *Nature* 314:330-334, 1985; Boss et al., *Nuc. Acids Res.* 12:3791-3806, 1984; Bothwell et al., *Nature* 298:380-382, 1982; van der Loo et al., *Immunogenetics* 42:333-341, 1995; Karlin et al., *J. Mol. Evol.* 22:195-208, 1985; Kindsvogel et al., DNA 1:335-343, 1982; Breiner et al., *Gene* 18:165-174, 1982; Kondo et al., *Eur. J. Immunol.* 23:245-249, 1993; and GenBank Accession No. J00228.) For a review of immunoglobulin structure and function see Putnam, *The Plasma Proteins*, Vol V, Academic Press, Inc., 49-140, 1987; and Padlan, *Mol. Immunol.* 31:169-217, 1994. The term "immunoglobulin" is used herein for its common meaning, denoting an intact antibody, its component chains, or fragments of chains, depending on the context.

The term "antibody," as used herein, refers to an immunoglobulin molecule, or a fragment and/or engineered variant thereof, which has the ability to specifically bind to an antigen. The term "antibody" includes intact monoclonal antibodies and antigen-binding antibody fragments such as, e.g., $F(ab')_2$ and Fab fragments. Genetically engineered intact antibodies and fragments, such as chimeric antibodies, humanized antibodies, single-chain Fv fragments, single-chain antibodies, diabodies, minibodies, and the like are also included. Thus, the term "antibody" is used expansively to include any protein that comprises an antigen-binding site and is capable of binding to its antigen.

The term "genetically engineered antibodies" means antibodies wherein the amino acid sequence has been varied from that of a native (i.e., naturally occurring) antibody. Because of the relevance of recombinant DNA techniques in the generation of antibodies, one need not be confined to the sequences of amino acids found in natural antibodies; antibodies can be redesigned to obtain desired characteristics. The possible variations are many and range from the changing of just one or a few amino acids to the complete redesign of, for example, the variable or constant region. Changes in the constant region will, in general, be made in order to improve or alter characteristics, such as complement fixation, interaction with cells and other effector functions. Typically, changes in the variable region will be made in order to improve the antigen binding characteristics, improve variable region stability, or reduce the risk of immunogenicity.

An "antigen-binding site" is that portion of an antibody that is sufficient to bind to its antigen. The minimum such region is typically an immunoglobulin variable domain or fragment thereof, or a genetically engineered variant of an immunoglobulin variable domain or fragment thereof. Single-domain binding sites can be generated from camelid antibodies (see Muyldermans and Lauwereys, *J. Mol. Recog.* 12:131-140, 1999; Nguyen et al., *EMBO J.* 19:921-930, 2000) or from VH domains of other species to produce single-domain antibodies ("dAbs"; see Ward et al., *Nature* 341:544-546, 1989; U.S. Pat. No. 6,248,516 to Winter et al.). In certain variations, an antigen-binding site is a polypeptide region having only 2 complementarity determining regions (CDRs) of a naturally or non-naturally (e.g., mutagenized) occurring heavy chain variable domain or light chain variable domain, or combination thereof (see, e.g., Pessi et al., *Nature* 362:367-369, 1993; Qiu et al., *Nature Biotechnol.* 25:921-929, 2007).

Full-length immunoglobulin "light chains" (about 25 Kd or 214 amino acids) are encoded by a variable region gene at the N-terminus (encoding about 110 amino acids) and by a kappa or lambda constant region gene at the C-terminus. Full-length immunoglobulin "heavy chains" (about 50 Kd or 446 amino acids) are encoded by a variable region gene (encoding about 116 amino acids) and a gamma, mu, alpha, delta, or epsilon constant region gene (encoding about 330 amino acids), the latter defining the antibody's isotype as IgG, IgM, IgA, IgD, or IgE, respectively. Within light and heavy chains, the variable and constant regions are joined by a "J" region of about 12 or more amino acids, with the heavy chain also including a "D" region of about 10 more amino acids. (See generally Fundamental Immunology (Paul, cd., Raven Press, N.Y., 2nd ed. 1989), Ch. 7).

An immunoglobulin light or heavy chain variable region consists of a framework region interrupted by three hypervariable regions. The term "hypervariable region," also referred to herein as "complementarity determining region" ("CDR"), refers to the amino acid residues of an antibody that are responsible for antigen binding. A CDR may be defined according to any of several known methods of analysis. Examples of such methods include, e.g., the Kabat definition, the Chothia definition, the AbM definition, the IMGT database definition, and the contact definition. The Kabat definition is a standard for numbering the residues in an antibody and is typically used to identify CDR regions (see, e.g., Johnson & Wu, *Nucleic Acids Res.* 28:214-8, 2000). The Chothia definition is similar to the Kabat definition, but the Chothia definition takes into account positions of certain structural loop regions (see, e.g., Chothia et al., *J. Mol. Biol.* 196:901-17, 1986; Chothia et al., *Nature* 342:877-83, 1989). The AbM definition uses an integrated suite of computer programs produced by Oxford Molecular Group that model antibody structure (see, e.g., Martin et al., 1989, *Proc. Natl. Acad. Sci. USA* 86:9268-9272, 1989; "AbM™, A Computer Program for Modeling Variable Regions of Antibodies," *Oxford, UK*; Oxford Molecular, Ltd.). The AbM definition models the tertiary structure of an antibody from primary sequence using a combination of knowledge databases and ab initio methods, such as those described by Samudrala et al., "Ab Initio Protein Structure Prediction Using a Combined Hierarchical Approach," in *PROTEINS, Structure, Function and Genetics Suppl.* 3:194-198, 1999. The IMGT database definition takes into account and combines the definition of the framework (FR) and complementarity determining regions (CDRs), structural data from X-ray diffraction studies, and characterization of hypervariable loops to number the variable regions/structures (see LeFranc, *Immunol. Today* 18:509, 1997). The contact definition is based on an analysis of the available complex crystal structures (see, e.g., MacCallum et al., *J. Mol. Biol.* 5:732-45, 1996). CDRs L1, L2, and L3 of a VL domain are also referred to herein, respectively, as CDR-L1, CDR-L2, and CDR-L3; CDRs H1, H2, and H3 of a VH domain are also referred to herein, respectively, as CDR-H1, CDR-H2, and CDR-H3.

"Framework region" are those variable domain residues other than the hypervariable region residues (e.g., other than the residues of CDRs as defined by the Kabat definition, the Chothia definition, the AbM definition, the IMGT database definition, or the contact definition of CDR). The sequences of the framework regions of different light or heavy chains are relatively conserved within a species. Thus, a "human framework region" is a framework region that is substantially identical (about 85% or more, usually 90-95% or more) to the framework region of a naturally occurring human immunoglobulin. The framework region of an antibody, that is the combined framework regions of the constituent light and heavy chains, serves to position and align the CDRs.

An "immunoglobulin hinge" is that portion of an immunoglobulin heavy chain connecting the CH1 and CH2 domains. The hinge region of human γ1 corresponds approximately to Eu residues 216-230.

The terms "Fc fragment," "Fc region," or "Fc domain," as used herein, are synonymous and refer to the portion of an immunoglobulin that is responsible for binding to antibody receptors on cells and the C1q component of complement (in the absence of any amino acid changes, relative to the naturally occurring sequence, to remove such binding activity). Fc stands for "fragment crystalline," the fragment of an antibody that will readily form a protein crystal. Distinct protein fragments, which were originally described by proteolytic digestion, can define the overall general structure of an immunoglobulin protein. As originally defined in the literature, the Fc fragment consists of the disulfide-linked heavy chain hinge regions, CH2, and CH3 domains. As used herein, the term also refers to a single chain consisting of CH3, CH2, and at least a portion of the hinge sufficient to form a disulfide-linked dimer with a second such chain. As used herein, the term Fc region further includes variants of naturally occurring hinge-CH2-CH3 sequences, wherein the variants are capable of forming dimers at least through dimerization of the CH3 domain and including such variants that have increased or decreased Fc receptor-binding or complement-binding activity while retaining at least sufficient binding to the neonatal Fc receptor (FcRn) to confer improved half-life to a fusion partner in vivo (relative to the fusion partner in the absence of the Fe region). The abbreviated term "Fc" may also be used herein to denote "Fc region" when referring to a fusion polypeptide by its general amino- to carboxyl-terminal structure (e.g., "DNase1-L1-Fc-L2-PON1").

As used herein, the term "single-chain antibody" refers to an antibody having an antigen-binding site contained within a single polypeptide chain (e.g., the variable regions from both heavy and light chains within a single polypeptide chain). The term "single-chain Fv" refers to a single-chain antibody that comprises the variable regions from both heavy and light chains but lacks constant regions. In general, a single-chain Fv further comprises a polypeptide linker between the VH and VL domains, which enables it to form the desired structure that allows for antigen binding. Single-chain antibodies are discussed in detail by, for example, Pluckthun in *The Pharmacology of Monoclonal Antibodies*, vol. 113 (Rosenburg and Moore eds., Springer-Verlag, New York, 1994), pp. 269-315. (See also International PCT Publication No. WO 88/01649; U.S. Pat. Nos. 4,946,778 and 5,260,203; Bird et al., *Science* 242:423-426, 1988.) Single-chain antibodies can also be bi-specific and/or humanized.

The term "alternative scaffold protein" refers to a non-antibody protein in which one or more regions may be diversified to produce one or more binding domains that specifically bind to a target molecule (e.g., an inflammatory cytokine such as TNFα or TGF-β). In some embodiments, the binding domain binds the target molecule with specificity and affinity similar to that of an antibody. Exemplary alternative scaffolds include those derived from fibronectin (e.g., Adnectins™), the β-sandwich (e.g., iMab), lipocalin (e.g., Anticalins®), EETI-II/AGRP, BPTI/LACI-D1/ITI-D2 (e.g., Kunitz domains), protein A (e.g., Affibody®), ankyrin repeats (e.g., DARPins), gamma-B-crystallin/ubiquitin (e.g., Affilins), $CTLD_3$ (e.g., Tetranectins), Fynomers, and Avimers. Additional information on alternative scaffolds is provided in Binz et al., *Nat. Biotechnol.* 23:1257-1268, 2005; Skerra, *Current Opin. in Biotech.* 18:295-304, 2007; and Silacci et al., *J. Biol. Chem.* 289:14392-14398, 2014.

The term "antiTNFα" or "antiTGFβ," as used herein when referring to a fusion polypeptide by its general amino- to carboxyl-terminal structure (e.g., "antiTNFα-L1-Fc-L2-PON1" or "antiTGFβ-L1-Fc-L2-PON1"), refers to a polypeptide (e.g., single-chain antibody) that specifically binds and neutralizes TNFα or TGF-β, respectively.

"Dimerizing domain," as used herein, refers to a polypeptide having affinity for a second polypeptide, such that the two polypeptides associate under physiological conditions to form a dimer. Typically, the second polypeptide is the same polypeptide, although in some variations the second polypeptide is different. The polypeptides may interact with each other through covalent and/or non-covalent association(s). Examples of dimerizing domains include an Fc region; a hinge region; a CH3 domain; a CH4 domain; a CH1 or CL domain; a leucine zipper domain (e.g., a jun/fos leucine zipper domain, see, e.g., Kostelney et al., *J. Immunol.,* 148:1547-1553, 1992; or a yeast GCN4 leucine zipper domain); an isoleucine zipper domain; a dimerizing region of a dimerizing cell-surface receptor (e.g., interleukin-8 receptor (IL-8R); or an integrin heterodimer such as LFA-1 or GPIIIb/IIIa); a dimerizing region of a secreted, dimerizing ligand (e.g., nerve growth factor (NGF), neurotrophin-3 (NT-3), interleukin-8 (IL-8), vascular endothelial growth factor (VEGF), or brain-derived neurotrophic factor (BDNF); see, e.g., Arakawa et al., *J. Biol. Chem.* 269:27833-27839, 1994, and Radziejewski et al., *Biochem.* 32:1350, 1993); and a polypeptide comprising at least one cysteine residue (e.g., from about one, two, or three to about ten cysteine residues) such that disulfide bond(s) can form between the polypeptide and a second polypeptide comprising at least one cysteine residue (hereinafter "a synthetic hinge"). A preferred dimerizing domain in accordance with the present invention is an Fc region.

The term "dimer" or "dimeric protein" as used herein, refers to a multimer of two ("first" and "second") fusion polypeptides as disclosed herein linked together via a dimerizing domain. Unless the context clearly indicates otherwise, a "dimer" or "dimeric protein" includes reference to dimerized first and second fusion polypeptides in the context of higher order multimers that may be created by inclusion of an additional dimerizing domain in a first or second fusion polypeptide (e.g., a first fusion polypeptide comprising an immunoglobulin light chain and a second fusion polypeptide comprising an immunoglobulin heavy chain can heterodimerize via the interaction between the CH1 and CL domains, and two such heterodimers may further dimerize via the Fc region of the immunoglobulin heavy chain, thereby forming a tetramer).

The term "domain that specifically binds to the neonatal Fc receptor (FcRn)" or "FcRn-binding domain," as used herein, means a polypeptide that (i) binds to FcRn with a high affinity at pH 5.8, typically with a binding affinity ($K_a$) of $10^6$ $M^{-1}$ or greater (e.g., $10^7$ $M^{-1}$ or greater, $10^8$ $M^{-1}$ or greater, or $10^9$ $M^{-1}$ or greater), and (ii) does not have affinity for FcRn at physiological pH (e.g., pH 7.4). The binding affinity of a polypeptide for FcRn can be readily determined by one of ordinary skill in the art, for example, by Scatchard analysis (Scatchard, *Ann. NY Acad. Sci.* 51:660, 1949). Typically, a FcRn-binding domain does not significantly cross-react with polypeptides related to FcRn. A polypeptide does not significantly cross-react with a polypeptide related to FcRn if, for example, it detects FcRn, but not presently known FcRn-related polypeptides, using a molecular binding assay such as, e.g., a multiwell plate assay (e.g., ELISA), a filter assay, or a surface plasmon resonance assay. Examples of known related polypeptides include known members of the major histocompatibility complex (MHC) class I protein family. An FcRn-binding domain is not mutually exclusive of a dimerizing domain, i.e., a dimerizing domain can also be an FcRn-binding domain. Examples of FcRn-binding domains that are also dimerizing domains include Fc regions that retain FcRn-binding activity.

Fusion polypeptides of the present disclosure may be referred to herein by formulae such as, for example, "DNase1-L1-Fc," "DNase1L3-L1-Fc," "DNase1-L1-Fc-L2-PON1," "DNase1L3-L1-Fc-L2-PON1," "RNase1-L1-Fc-L2-PON1," "SOD1-L1-Fc-L2-PON1," "anti-TNFα-L1-Fc-L2-PON1," or "anti-TGFβ-L1-Fc-L2-PON1." In each such case, unless the context clearly dictates otherwise, a term referring to a particular segment of a fusion polypeptide (e.g., "DNase1," "DNase1L3," "PON1," "RNase1," "SOD1," "L1" or "L2" (for first or second polypeptide linkers, respectively), "Fc" (for "Fc region"), etc.) is understood to have the meaning ascribed to such term herein and is inclusive of the various embodiments as described herein.

The term "disease or disorder characterized by NETosis," as used herein, means a disease or disorder in which NETosis—the process wherein activated neutrophils extrude DNA bound with cytoplasmic and granule proteins, called neutrophil extracellular traps (NETs)—plays at least some part of the clinicopathology.

The term "effective amount," in the context of treatment of a disease by administration of a soluble fusion polypeptide or dimeric protein to a subject as described herein, refers to an amount of such molecule that is sufficient to inhibit the occurrence or ameliorate one or more symptoms of the disease. For example, in the specific context of treatment of an inflammatory lung disease by administration of a fusion protein to a subject as described herein, the term "effective amount" refers to an amount of such molecule that is sufficient to modulate an inflammatory response in the subject so as to inhibit the occurrence or ameliorate one or more symptoms of the inflammatory lung disease. An effective amount of an agent is administered according to the methods of the present invention in an "effective regime." The term "effective regime" refers to a combination of amount of the agent being administered and dosage frequency adequate to accomplish treatment or prevention of the disease.

The term "patient" or "subject," in the context of treating a disease or disorder as described herein, includes mammals such as, for example, humans and other primates. The term also includes domesticated animals such as, e.g., cows, hogs, sheep, horses, dogs, and cats.

The term "combination therapy" refers to a therapeutic regimen that involves the provision of at least two distinct therapies to achieve an indicated therapeutic effect. For example, a combination therapy may involve the administration of two or more chemically distinct active ingredients, or agents, for example, a soluble PON1 fusion polypeptide or dimeric protein according to the present invention and another agent such as, e.g., another anti-inflammatory or immunomodulatory agent. Alternatively, a combination therapy may involve the administration of a soluble PON1 fusion polypeptide or dimeric protein according to the present invention, alone or in conjunction with another agent, as well as the delivery of another therapy (e.g., radiation therapy). The distinct therapies constituting a combination therapy may be delivered, e.g., as simultaneous, overlapping, or sequential dosing regimens. In the context of the administration of two or more chemically distinct agents, it is understood that the active ingredients may be administered as part of the same composition or as different compositions. When administered as separate compositions, the compositions comprising the different active ingredients may be administered at the same or different times, by the same or different routes, using the same or different dosing regimens, all as the particular context requires and as determined by the attending physician.

The term "targeted therapy," in the context of treating cancer, refers to a type of treatment that uses a therapeutic agent to identify and attack a specific type of cancer cell, typically with less harm to normal cells. In some embodiments, a targeted therapy blocks the action of an enzyme or other molecule involved in the growth and spread of cancer cells. In other embodiments, a targeted therapy either helps the immune system to attack cancer cells or delivers a toxic substance directly to cancer cells. In certain variations, a targeted therapy uses a small molecule drug or a monoclonal antibody as a therapeutic agent.

The phrase "protect from aging," as used herein, refers to inhibition or mitigation of any of broad aspects of aging, including, for example, age-related changes in systemic inflammation or disease risk, as indicated by accepted biomarkers. Protection from aging may also include treatment of an age-related disease where the disease is present in a subject, such as, for example, a chronic inflammatory, autoimmune, neurodegenerative, cardiovascular, or fibrotic disease Two amino acid sequences have "100% amino acid sequence identity" if the amino acid residues of the two amino acid sequences are the same when aligned for maximal correspondence. Sequence comparisons can be performed using standard software programs such as those included in the LASERGENE bioinformatics computing suite, which is produced by DNASTAR (Madison, Wisconsin). Other methods for comparing amino acid sequences by determining optimal alignment are well-known to those of skill in the art. (See, e.g., Peruski and Peruski, *The Internet and the New Biology: Tools for Genomic and Molecular Research* (ASM Press, Inc. 1997); Wu et al. (eds.), "Information Superhighway and Computer Databases of Nucleic Acids and Proteins," in *Methods in Gene Biotechnology* 123-151 (CRC Press, Inc. 1997); Bishop (cd.), *Guide to Human Genome Computing* (2nd ed., Academic Press, Inc. 1998).) Two amino acid sequences are considered to have "substantial sequence identity" if the two sequences have at least 80%, at least 90%, or at least 95% sequence identity relative to each other.

Percent sequence identity is determined by conventional methods. (See, e.g., Altschul et al., *Bull. Math. Bio.* 48:603, 1986, and Henikoff and Henikoff, *Proc. Natl. Acad. Sci. USA* 89:10915, 1992.) For example, two amino acid sequences can be aligned to optimize the alignment scores using a gap opening penalty of 10, a gap extension penalty of 1, and the "BLOSUM62" scoring matrix of Henikoff and Henikoff, supra. The percent identity is then calculated as: ([Total number of identical matches]/[length of the longer sequence plus the number of gaps introduced into the longer sequence in order to align the two sequences]) (100).

Those skilled in the art appreciate that there are many established algorithms available to align two amino acid sequences. The "FASTA" similarity search algorithm of Pearson and Lipman is a suitable protein alignment method for examining the level of identity shared by an amino acid sequence disclosed herein and a second amino acid sequence. The FASTA algorithm is described by Pearson and Lipman, *Proc. Nat'l Acad. Sci. USA* 85:2444, 1988, and by Pearson, *Meth. Enzymol.* 183:63, 1990. Briefly, FastA first characterizes sequence similarity by identifying regions shared by the query sequence (*e.g., residues* 16-355 or 26-355 of SEQ ID NO:6) and a test sequence that have either the highest density of identities (if the ktup variable is 1) or pairs of identities (if ktup=2), without considering conservative amino acid substitutions, insertions, or deletions. The ten regions with the highest density of identities are then rescored by comparing the similarity of all paired amino acids using an amino acid substitution matrix, and the ends of the regions are "trimmed" to include only those residues that contribute to the highest score. If there are several regions with scores greater than the "cutoff" value (calculated by a predetermined formula based upon the length of the sequence and the ktup value), then the trimmed initial regions are examined to determine whether the regions can be joined to form an approximate alignment with gaps. Finally, the highest scoring regions of the two amino acid sequences are aligned using a modification of the Needleman-Wunsch-Sellers algorithm (Needleman and Wunsch, *J. Mol. Biol.* 48:444, 1970; Sellers, *SIAM J. Appl. Math.* 26:787, 1974), which allows for amino acid insertions and deletions. Illustrative parameters for FASTA analysis are: ktup=1, gap opening penalty=10, gap extension penalty=1, and substitution matrix=blosum62. These parameters can be introduced into a FASTA program by modifying the scoring matrix file ("SMATRIX"), as explained in Appendix 2 of Pearson, *Meth. Enzymol.* 183:63, 1990.

The term "corresponding to," when applied to positions of amino acid residues in a reference sequence to describe positions within a subject sequence, means corresponding positions in the subject sequence when the reference and subject sequences are optimally aligned.

When such a value is expressed as "about" X or "approximately" X, the stated value of X will be understood to be accurate to +10%.

Where aspects or embodiments of the present invention are described in terms of a Markush group or other grouping of alternatives, the present invention encompasses not only the entire group listed as a whole, but each member of the group individually and all possible subgroups of the main group. The present invention also envisages the explicit exclusion of one or more of any of the group members as embodiments.

DESCRIPTION OF THE INVENTION

I. Overview

Figure 1:
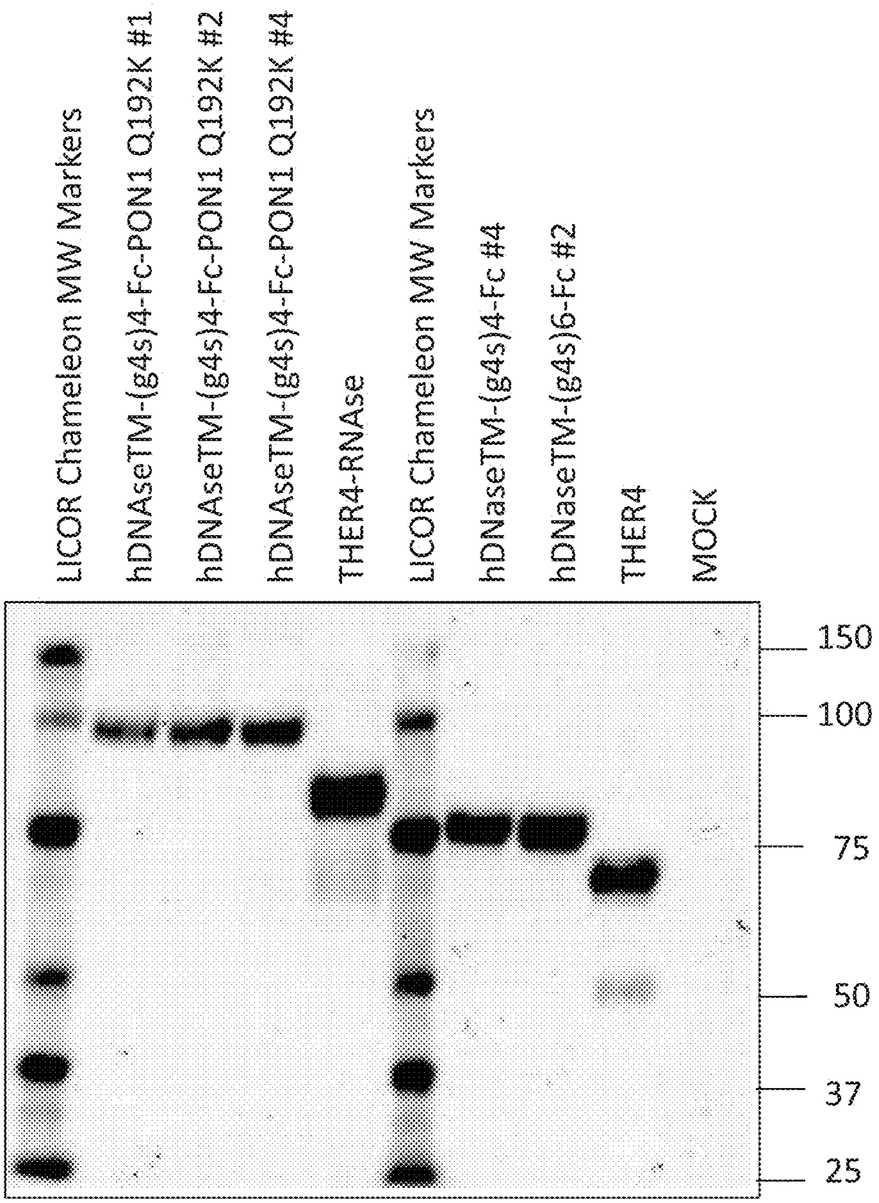
FIG. 1 shows a Western blot of culture supernatants (serum free) from transiently transfected HEK293 cells expressing DNase1-Fc and DNase1-Fc-PON1 fusion proteins. Transfections and Western blot analysis were performed as described in Example 1, infra. From left to right: Lane 1—LICOR Chameleon™ molecular weight markers; Lane 2, Lane 3, Lane 4—transfection supernatants from three different individual clones (#1, #2, #4) of hDNaseTM-(g4s)4-Fc-PON1-Q192K; Lane 5—THER4-RNase (control); Lane 6—LICOR Chameleon MW Markers; Lane 7—hDNaseTM-(g4s)4-Fc #4; Lane 8—hDNaseTM-(g4s)6-Fc #2; Lane 9—THER4 (control); Lane 10—mock transfection.

The present invention provides compositions and methods relating to paraoxonase fusion polypeptides. In certain aspects, a fusion polypeptide comprises a first biologically active polypeptide linked amino-terminal to a biologically active paraoxonase, wherein the first biologically active polypeptide is selected from a DNase, an RNase, a superoxide dismutase 1 (SOD1), a cytotoxic T-lymphocyte associated molecule-4 (CTLA-4) extracellular domain, a CD40 extracellular domain, and a polypeptide that specifically binds and neutralizes an inflammatory cytokine (e.g., a polypeptide that specifically binds and neutralizes tumor necrosis factor α (TNFα) or transforming growth factor-β (TGF-β). In some aspects, the fusion polypeptide further includes a second biologically active polypeptide linked carboxyl-terminal to the first biologically active polypeptide and amino-terminal to the paraoxonase. The second biologically active polypeptide may be, for example, a dimerizing domain or a domain that specifically binds to the neonatal Fc receptor (FcRn). A particularly suitable second biologically active polypeptide is a dimerizing and FcRn-binding immunoglobulin heavy chain constant region such as, e.g., an immunoglobulin Fc region.

In other aspects, a fusion polypeptide comprises a biologically active paraoxonase linked carboxyl-terminal to a dimerizing domain or domain that specifically binds to FcRn (for example, a dimerizing and FcRn-binding immunoglobulin heavy chain constant region such as, e.g., an immunoglobulin Fc region), wherein the fusion polypeptide does not comprise a biologically active polypeptide amino-terminal to the dimerizing or FcRn-binding domain.

In other aspects, a fusion polypeptide comprises a biologically active paraoxonase linked amino-terminal to a dimerizing domain or domain that specifically binds to FcRn (for example, a dimerizing and FcRn-binding immunoglobulin heavy chain constant region such as, e.g., an immunoglobulin Fc region).

A preferred paraoxonase in fusion polypeptides of the present disclosure is a paraoxonase 1 (PON1) polypeptide. Particularly suitable PON1 polypeptides lack an amino-terminal leader sequence corresponding to the naturally occurring, non-cleaved leader sequence of PON1 (generally corresponding to residues 1-15 of human PON1 (SEQ ID NO:4)). The association of PON1 with high density lipoprotein (HDL) in serum is primarily dependent on the direct binding of the hydrophobic, non-cleaved leader to phospholipids (see Sorenson et al., *Arterioscler. Thromb. Vasc. Biol.* 19:2214-2225, 1999). The removal of this leader sequence removes PON1 from HDL binding and facilitates the retargeting of PON1 to other sites for therapeutic benefit in accordance with the present disclosure. For example, in the context of a fusion polypeptide comprising a DNase or RNase as described herein, retargeting PON1 to DNA or RNA directs the molecule to inflammatory NETs and sites of cellular death. In addition to targeting DNA or RNA at these sites, DNase-PON1 or RNase-PON1 fusion molecules as described herein can help to direct a PON1 enzyme to myeloperoxidase, another important inflammatory NET target. Also, a fusion polypeptide comprising a superoxide dismutase 1 (SOD1) as described herein provides a molecule in which PON1 can digest the hydrogen peroxide ($H_2O_2$) produced by the action of SOD1 on superoxide, thereby providing, e.g., an improved antioxidant for lung therapy. Further, fusion molecules comprising other biologically active polypeptides in accordance with the present invention (e.g., a CTLA-4 extracellular domain, a CD40 extracellular domain, or a polypeptide that specifically binds and neutralizes an inflammatory cytokine) can target PON1 to other sites of proinflammatory and/or immune cell activation for therapeutic benefit such as described herein.

Paraoxonase fusion molecules of the present invention may be used for the treatment of various diseases or disorders through its antioxidant, anti-inflammatory, atheroprotective, and/or neuroprotective properties, including, e.g., treatment of an autoimmune or inflammatory disease. For example, studies support use of a paraoxonase for treatment of autoimmune disease such as systemic lupus erythematosus (SLE). The autoantibody titer in many patients with systemic lupus erythematosus (SLE) is correlated with loss of activity of PON1 (see Batukla et al., *Ann. NY Acad. Sci.* 1108:137-146, 2007), and SLE-disease activity assessed by SLEDAI and SLE disease related organ damage assessed by SLICC/ACR damage index are negatively correlated with PON1 activity (see Ahmed et al., *EXCLI Journal* 12:719-732, 2013). Other studies support use of a paraoxonase for treatment of inflammatory disease such as inflammatory lung diseases. Studies strongly suggest, for example, that PON1 is important in protection from lung inflammation, and further show that low PON1 activity is associated with lung diseases such as, e.g., asthma, chronic obstructive pulmonary disease (COPD), and interstitial lung disease (e.g., idiopathic pulmonary fibrosis (IPF) or sarcoidosis) (see, e.g., Sahiner et al., *WAO Journal* 4:151-158, 2011; Emin et al., *Allergol. Immunopathol.* (*Madr*) 43:346-352, 2014; Sarioglu et al., *Iran J. Asthma Immunol.* 14:60-66, 2015; Tolgyesi et al., *Internat. Immunol.* 21:967-975, 2009; Chen et al., *J. Cell Biochem.* 119:793-805, 2018; Rumora et al., *J. COPD* 11:539-545, 2014; Rajkovic et al., *J. Clin. Path.* 71:963-970, 2018; Ivanisevic et al., *Eur. J. Clin. Invest.* 46:418-424, 2016; Uzun et al., *Curr. Med. Res. Opin.* 24:1651-1657, 2008; Okur et al., *Sleep Breath.* 17:365-371, 2013; Golmanesh et al., *Immunopharmacol. And Immunotoxicol.* 35:419-425, 2013). Another study showed that low PON1 activity is correlated with the severity of Crohn's disease (Sczceklik et al., *Molecules* 23:2603, 2018). In addition, recombinant PON1 therapy has shown efficacy in animal models of organophosphate poisoning and colitis (see, e.g., Valiyaveettil et al., *Biochem. Pharmacol.* 81:800-809, 2011; Valiyaveettil et al., *Toxicol. Letters* 202:203-208, 2011; Bajaj et al., *Appl. Biochem. Biotechnol.* 180:165, 2016; Stevens et al., *Proc. Natl. Acad. Sci. USA* 105:12780-12784, 2008; Yamashita et al., *J. Immunol.* 191:949-960, 2013).

Paraoxonase fusion molecules as described herein may also be used, e.g., for treatment of a neurological disease. For example, PON1 is protective in the brain because of its antioxidant properties. A neuroprotective role of PON1 is supported by studies showing that PON1 activity is decreased in patients with Alzheimer's disease and other dementias (see, e.g., Menini et al., *Redox Rep.* 19:49-58, 2014). In addition, a study using a PON1 fusion containing a protein transduction domain to transduce PON1 into cells and tissues showed that PON1 transduction protected microglial cells in vitro from oxidative stress-induced inflammatory responses and protected against dopaminergic neuronal cell death in a Parkinson's disease model (see Kim et al., *Biomaterials* 64:45-56, 2015).

Bispecific fusions further comprising a DNase provide additional therapeutic benefit for the treatment of diseases amenable to PON-mediated therapy, including, for example, in treatment of diseases or disorders characterized by NETosis. NETs, which cause tissue damage by themselves or by increasing the pro-inflammatory response (see Mutua and Gershwin, *Clin. Rev. Allergy Immunol.,* 2020), are implicated in a variety of serious diseases and conditions. For example, NETs can play a role in enhancement of inflammation seen in autoimmune disease, including, e.g., systemic lupus erythematosus (SLE) (e.g., SLE with lupus nephritis), rheumatoid arthritis, and psoriasis, and are also associated with autoinflammatory diseases such as, for example, inflammatory bowel disease (IBD) (see id.). NETs also play a role in sepsis, metabolic diseases (e.g., type 2 diabetes and obesity), neurological diseases (e.g., Alzheimer's disease, multiple sclerosis, meningitis, cerebral malaria, and ischemic stroke), infectious disease, cardiovascular disease and thrombosis, tumor progression and metastasis, liver disease (e.g., alcohol-associated liver disease (ALD), portal hypertension, nonalcoholic fatty liver disease (NAFLD) such as nonalcoholic steatohepatitis (NASH), and complications following liver transplantation), and various inflammatory lung diseases, including, e.g., cystic fibrosis, asthma, chronic obstructive pulmonary disease (COPD), and COVID-19-associated acute respiratory distress syndrome (ARDS) (see, e.g., id.; Brinkmann, *J. Innate Immun.* 10:422-431, 2018; Liu et al., *Chinese Med. Journal* 130:730-736, 2017; Twaddell et al., *CHEST* 156:774-782, 2019; Uddin et al., *Front. Immunol.* 10:47, 2019; Middleton et al., *Blood* 136:1169, 2020; Zuo et al., *JCI Insight* 5:e138999, 2020; Barnes et al., *J. Exp. Med.* 217:e20200652, 2020; Hilscher and Shah, *Semin. Liver Dis.* 40:171-179, 2020). The use of DNase for the treatment of diseases or disorders characterized by NETosis is further supported, for example, by the use of recombinant wild-type DNase (Pulmozyme®) for treatment of cystic fibrosis, a current clinical trial of Pulmozyme in COVID-19 patients (NCT04359654), and several animal model studies, including, e.g., models of acute asthma, silica-induced lung inflammation, acute lung injury, cancer, colitis, ischemia reperfusion, sepsis, and thrombosis (see, e.g., da Cunha et al., *Exp. Lung Res.* 42:66, 2016; Benmerzoug et al., *Nat. Comm.* 9:5226, 2018; Caudrillier et al., *J. Clin. Invest.* 122:2661, 2012; Cools-Lartigue et al., *J. Clin. Invest.* 123:3446, 2013; Park et al., *Sci. Translational Med.* 8:361ra138, 2016; Trejo-Becirril et al., *Integrative Cancer Therapies* 15: NP35-NP43, 2016; Thalin et al., *PloS ONE* 13:00191231, 2018; Babicova et al., *Folia Biolica* (*Praha*) 64:10, 2018; Li et al., *J. Crohns Colitis* 2020, 14:240-253, 2020; Albadawi et al., *J. Vasc. Surg.* 64:484, 2016; Peer et al., *Am. J. Nephrol.* 43:195, 2016; Mai et al., *Shock* 44:166, 2015; Brill et al., *J. Thrombosis Haemostasis* 10:136, 2012; Manda-Handzlik and Demkow, *Cells* 8:1477, 2019; Delgado-Rizo et al., *Front. Immunol.* 8:81, 2017).

Bispecific fusions further comprising a DNase as described herein are also useful in treatment of antiphospholipid syndrome (APLS). Antiphospholipid syndrome is an autoimmune disease characterized by antibodies to phospholipids that cause a hypercoagulable state. Thrombosis occurs in both arteries and veins and causes pregnancy complications including miscarriage and stillbirths. Antiphospholipid syndrome can be primary (occurring in the absence of any other related disease) or secondary (occurring with another autoimmune disease such as, e.g., SLE). In rare cases, APLS leads to rapid organ failure due to generalized thrombosis; this is termed catastrophic antiphospholipid syndrome (CAPS or Asherson syndrome) and is associated with a high risk of death. Patients with acute respiratory distress associated with COVID-19 have antiphospholipid antibodies that promote thrombosis in vitro and in mouse thrombosis models (Zuo et al., *JCI Insight* 5:e138999, 2020; Zuo et al., *Sci. Trans. Med.* 12:eabd3876, 2020). The antiphospholipid antibodies stimulate neutrophil NET formation, providing a scaffold for thrombus formation. Digestion of NETs by DNase fusions as described herein can prevent thrombus formation and can help dissolve existing clots to restore blood flow. DNase fusion molecules of the present invention may also be used together with thrombolytics including, e.g., tPA, urokinase, and streptokinase.

Paraoxonase fusion molecules as described herein, including embodiments further comprising, e.g., a DNase, may also be used for treatment of an inflammatory skin disease. Many studies have reported the involvement of reactive oxygen species and lipid peroxidation in the pathogenesis of inflammatory skin diseases (see, e.g., Simonetti et al., *Antioxidants* 10:697, 2021). For example, significantly lower levels of paraoxonase 1 (PON1) and a significantly higher levels of myeloperoxidase (MPO) and lipid peroxides have been found in atopic dermatitis (see id.), and increased MPO and decreased PON1 activity have also been described in psoriatic children (see Bacchetti et al., *Archives of Dermatological Research* 312:33-39). In psoriasis and atopic dermatitis, neutrophil activation during inflammation leads to extruded NETs with attached MPO, causing the oxidation of lipids and damaging PON1 enzyme, which normally protects lipids from oxidation by digesting lipid peroxides. The digestion of NETs with DNase1 releases the attached MPO, allowing its clearance and removing a primary driver of oxidation, and therapy with PON1 restores protection from oxidative damage and rebalances the redox potential in patients. Thus, PON1 and DNase therapies are particularly effective as a combination.

Paraoxonase fusion molecules as described herein, including embodiments further comprising a DNase, may also be used to protect from aging. Oxidative stress is known to be a primary cause of aging. In particular, oxidized lipids are a key target for aging because of their promotion of inflammation through uptake by macrophage scavenger receptors and their damage to vascular endothelial cells. See, e.g., Moldogazieva et al. (*Oxidative Medicine and Cellular Longevity*, Volume 2019, Article ID 3085756) and Barrera et al. (*Antioxidants* 7:102, 2018) for discussions on the link between lipid oxidation and aging. See also Hajri (*Frontiers In Bioscience, Landmark* 23:1822-1847, 2018), which describes the toxic effects of oxidized lipids on inflammation and cardiac function. PON1 is known to protect lipids from oxidation by digestion of lipid peroxides. Thus, there is a direct link between increasing PON1 enzyme levels and slowing of aging. In addition, PON1 enzyme activity is known to be deficient in multiple age-related diseases including cardiovascular disease, autoimmune disease, and pulmonary disease, showing that there is a clinical need for increased PON1. In addition, embodiments further comprising a DNase are particularly useful for slowing aging because of the ability of DNase to digest NETs. NETs are a primary driver of inflammation and oxidative stress because they provide the scaffold for myeloperoxidase (MPO) and elastase produced by neutrophils and other cells. Digestion of the NETs by DNase allows the release and clearance of the inflammatory enzymes. DNase also eliminates inflammatory activation through other DNA sensing pathways (e.g., STING, TLR9).

Bispecific fusions further comprising an RNase as described herein have anti-inflammatory properties by digesting extracellular RNA derived from dead and dying cells, including, e.g., extracellular RNA associated with NETs. Extracellular RNA synergizes, for example, with TLR2 agonists to potentiate a macrophage inflammatory response and digestion of this RNA prevents inflammation through TLR2 (see Noll et al., *PloS ONE* 12:e0190002, 2017).

RNase-containing fusions provide additional therapeutic benefit for treatment of various diseases, including, e.g., autoimmune disease, inflammatory disease (e.g., inflammatory lung disease), type 2 diabetes, infectious disease, cardiovascular disease (e.g., coronary artery disease, stroke), neurodegenerative disease (e.g., Alzheimer's disease), and cancer. For example, several studies support use of an RNase for treatment of an inflammatory lung disease. One study has shown that TLR3, an RNA sensor, has a major role in the development of ARDS-like pathology in the absence of a viral pathogen (see Murray et al., *Am. J. Respir. Crit. Care Med.* 178:1227-1237, 2008). Oxygen therapy is a major therapeutic intervention in ARDS, but contributes to further lung damage and susceptibility to viral infection. Oxygen therapy was a major stimulus for increased TLR3 expression and activation in cultured human epithelial cells, and absence or blockade of TLR3 protected mice from lung injury and inflammation after exposure to hyperoxic conditions (see Murray et al., supra). Another study has shown that TLR3 activation by extracellular RNA occurs in response to acute hypoxia, and that therapy in mice with RnaseA diminished lung inflammation after acute hypoxia (see Biswas et al., *Eur. J. Immunol.* 45:3158-3173, 2015).

Other studies support use of an RNase for treatment of an autoimmune disease such as, for example, systemic lupus erythematosus (SLE). Studies show, for example, a role of RNA immune complexes and RNA receptors, including TLR7, in SLE disease pathogenesis, as well as a protective effect of RNase overexpression in mouse models of SLE (see, e.g., Sun et al., *J. Immunol.* 190:2536-2543, 2013).

RNase-containing fusion molecules as described herein can digest RNA contained in exosomes. For a review of exosomes in lung disease, see Hough et al., *Allergy* 72:534-544, 2017. RNase1 can translocate through cellular membranes into the cytosol because of its basic charge (see Chao et al., *Biochem.* 50:8374-8382, 2011; Haigas et al., *J. Cell Sci.* 116:313-324, 2003; Johnson et al., *Biochem.* 46:10308-10316, 2007). Cytoplasmic inhibitor binds to RNase1 with very high affinity and protects intact cells from RNase toxicity. However, extracellular RNA including RNA in extracellular vesicles, is not protected by cytoplasmic inhibitor (see Mironova et al., *Oncotarget* 8:78796-78810, 2017).

Fusion molecules comprising an RNase as described herein can further target microRNA (miRNA), small, extracellular noncoding RNAs involved in posttranscriptional gene regulation. miRNA dysregulations are linked to a wide spectrum of diseases, including lung disease, proliferative vascular disease, cardiac disorders, kidney diseases, diabetes mellitus, fibrosis and cancer (see Rajasekaran et al., *Front. Pharmacol.* 6:254, 2015; Thum et al., *Nature* 456:980-984, 2008; Kato et al., *Clin. J. Am. Soc. Nephrol.* 4:1255-1266, 2009*; Lee and Dutta, Annu. Rev. Pathol.* 4:199-227, 2009; Kumar et al., *Protein Cell.* 3:726-738, 2012; Noctel et al., *Front. Physiol.* 3:49, 2012; Zampetaki and Mayr, *Circ. Res.* 110:508-522, 2012). For example, microRNA-33 is overexpressed in granulomatous lung tissue in murine models and in BAL fluid of patients with sarcoidosis (Barna et al., *Am. J. Respir. Cell Mol. Biol.* 54:865-871, 2016). microRNA-33 downregulates cholesterol transporters ABCA1 and ABCG1, promoting cholesterol accumulation in alveolar macrophages and foam cell formation. Another target is microRNA-466, which has been shown to be secreted in exosomes in a mouse model of acute respiratory distress syndrome (ARDS) where it activated the NLRP3 inflammasome (Shikano et al., *BMC Pulmonary Med.* 19:110, 2019).

Other targets of RNase-containing fusions as described herein include viral RNAs such as, e.g., proviral microRNAs released in the lung during influenza virus infection (see Scheller et al., *J. Inf. Dis.* 219:540-543, 2019) or HIV single-stranded RNA that was reported to stimulate macrophage foam cell formation through TLR8 binding (see Bernard et al., *PloS ONE* 9:e104039, 2014). Other viral RNA targets include coronavirus RNA (e.g., SARS-CoV-2 RNA).

Studies also support use of RNase for treatment of, e.g., cancer, ischemia/reperfusion injury, graft rejection, atherosclerotic plaque formation, myocardial infarction, acute stroke, and postoperative cognitive decline (see, e.g., Rutkoski et al., *Translational Oncology* 6:392-397, 2013; Mironova et al., *Oncotarget.* 8:78796-78810, 2017; Eller et al., *ACS Central Sci.* 1:181-190, 2015; Kleinert et al., *J. Am. Heart Assn.* doi: 10.1021, 2016; Simsekyilmaz et al., *Circulation* 129:598-606, 2014; Steiger et al., *JAMA* 6:e004541, 2017; Walberer et al., *Curr. Neovas. Res.* 6:12-19, 2009; Chen et al., *PloS One* 10:00134307, 2015).

A bispecific paraoxonase fusion molecule comprising a superoxide dismutase 1 (SOD1) as described herein provides additional therapeutic benefit in protection from oxidative stress. The role of SOD1 in protection from oxidative damage is reviewed, e.g., by Ighodaro and Akinolye, *Alexandria J. Med.* 54:287-293, 2018. In its native form, SOD1 is an intracellular enzyme (see id.). In accordance with the present disclosure, a SOD1 polypeptide segment is used as an extracellular enzyme that works in conjunction with the paraoxonase segment of the fusion molecule to provide an improved antioxidant for therapy. For example, paraoxonase can digest hydrogen peroxide ($H_2O_2$), a product of the SOD1 enzymatic reaction. In addition, digestion of $H_2O_2$ will suppress the activity of myeloperoxidase that is associated with NETs. The coordinated activity of SOD1 and paraoxonase will improve the activity in protection from tissue damage and inflammation in patients with diseases associated with NET production. SOD1-PON molecules according to the present invention are particularly useful, for example, in treatment of inflammatory lung diseases such as, e.g., asthma, chronic obstructive pulmonary disease (COPD), sarcoidosis, and interstitial lung disease. In some preferred embodiments, the SOD1-PON fusion further includes a dimerizing domain such as, e.g., an immunoglobulin Fc region; such variations are particularly compatible with SOD1, which, in its native form, is a dimer stabilized by a disulfide bond.

A bispecific paraoxonase fusion molecule comprising a CTLA-4 extracellular domain as described herein is particularly useful for treatment of inflammatory and autoimmune disease, including, e.g., rheumatoid arthritis (RA) and inflammatory lung disease. Oxidized cholesterol activates inflammatory responses in macrophages and endothelial cells (see Miller and Shyy, *Trends Endocrinol. Metabol.* 28:143-152, 2017), and PON1 can suppress this inflammation by protecting lipoproteins from oxidation. The immunosuppressive properties of a soluble CTLA-4 (e.g., Abatacept or other CTLA4-Fc) are compatible with paraoxonase enzyme activity so that a CTLA4-PON molecule will retain the activity of both components and have improved activity in fibrotic lung disease and autoimmune/inflammatory disease. A CTLA4-PON1 molecule, for example, will bind to CD80 and CD86 that are expressed on activated antigen presenting cells, including monocytes and dendritic cells, where the PON1 enzyme will remain active. This molecule is effective in inhibiting activation of T cells, macrophages, and dendritic cells, and will also reduce oxidative stress in tissues such as, e.g., inflamed lungs.

A bispecific paraoxonase fusion molecule comprising a CD40 extracellular domain as described herein provides additional therapeutic benefit by suppressing the proinflammatory activation events associated with the CD40-CD154 signaling pathway. The CD40-CD154 pathway has been implicated, for example, in fibrotic disease, including fibrosis in inflammatory lung disease and injury (see, e.g., Kaufman et al., *J. Immunol.* 172:1862-1871, 2004), and studies support the use of molecules that suppress this pathway for treatment of fibrotic and inflammatory lung disease (see, e.g., Adawi et al., *Clin. Immunol. Immunopathol.* 89:222-230, 1998; Adawi et al., *Am. J. Pathol.* 152:651-657, 1998; Cheng et al., *BioMed. Research Intl.* Volume 2020, Article ID 7840652, 2020; Xiong et al., *J. Cell. Mol. Med.* 23:740-749, 2018). CD40-PON fusions of the present invention provide molecules that inhibit both inflammation and adaptive immunity, including e.g., molecules with improved activity in lung disease and autoimmune/inflammatory disease. For example, a CD40-PON1 fusion may provide improved activity in lung diseases where CD40 activation exacerbates inflammatory processes, and where paraoxonase levels are low or absent, including asthma, COPD, hypoxia, and interstitial lung disease (e.g., idiopathic pulmonary fibrosis (IPF) or sarcoidosis). CDO40-PON1 fusions are also beneficial, for example, for treatment of liver disease (e.g., chronic liver disease such as, for example, alcohol-associated liver disease (ALD), portal hypertension, nonalcoholic steatohepatitis (NASH), or complications following liver transplantation) and kidney disease (e.g., chronic kidney disease such as, for example, lupus nephritis, IgA nephropathy, or membranous glomerulonephritis).

In some embodiments, a paraoxonase fusion molecule of the present invention comprises a variant CD40 extracellular domain having increased binding to CD154. For example, one or more single amino acid substitutions can be made at specific residues to improve binding to CD40 ligand (see, e.g., US Patent Application Publication No. 2014/0120091, incorporated by reference herein). Such CD40 extracellular domain variants may be fused to a human IgG1 (γ1) Fc variant with impaired FcγR binding to provide CD40-Fc variants that do not induce platelet activation or aggregation in vitro, avoiding toxicity from simultaneous binding to CD40 and FcγRIIa on human platelets. Activation of platelets and thrombosis has been shown to occur due to cross-linking of FcR on platelets with antigens on the platelet surface such as VEGF, CD40, and CD40L (see Taylor et al., *Blood* 96:4254, 2020; Meyer et al., *J. Thromb. Haemost.* 7:151, 2009).

Bispecific fusion molecules comprising a polypeptide that specifically binds and neutralizes TNFα or TGF-β as described herein provide additional therapeutic benefit through inhibition of inflammatory, immune, and/or other cellular responses mediated by these cytokines. A paraoxonase fusion comprising an anti-TNFα component may be used, for example, to treat an inflammatory disease or autoimmune disease such as, e.g., rheumatoid arthritis (RA), an inflammatory lung disease (e.g., asthma, chronic obstructive pulmonary disease (COPD), acute lung injury (ALI), acute respiratory distress syndrome (ARDS), or interstitial lung disease (e.g., idiopathic pulmonary fibrosis or sarcoidosis)), an inflammatory bowel disease (IBD) (e.g., Crohn's disease or ulcerative colitis), or an inflammatory skin disease (e.g., psoriasis or atopic dermatitis). A paraoxonase fusion comprising an anti-TGF-β component may be used, for example, to treat an inflammatory disease, a fibrotic disease, or type 1 diabetes. In some embodiments, an inflammatory or fibrotic disease for treatment using an antiTGFβ-PON fusion of the present invention is an inflammatory lung disease such as, for example, asthma, chronic obstructive pulmonary disease (COPD), acute lung injury (ALI), acute respiratory distress syndrome (ARDS), or interstitial lung disease (e.g., idiopathic pulmonary fibrosis (IPF) or sarcoidosis). In some variations for treatment of an inflammatory lung disease, a fusion molecule comprising an anti-TNFα or anti-TGF-β polypeptide as describe herein is delivered by nebulization directly to the lungs rather than systemically, which may achieve efficient therapeutic activity with fewer unwanted side effects that may arise due to the pleiotropic activity of these cytokines.

In some aspects, the present invention provides compositions and methods for producing fusion polypeptides and dimeric proteins as described herein, including such compositions and methods for the constitutive expression of DNase-PON fusions in stable cells lines such as CHO. Previous efforts to obtain stable CHO cells that constitutively express an actin/salt-resistant and hyperactive DNase1 were unsuccessful despite screening thousands of clones (see Lam et al., *Biotech. Progress* 32:523-533, 2017). In certain embodiments, DNase-PON fusions comprising an enhanced DNase1 as described herein are readily expressed in stable lines with minimal screening, thereby overcoming this problem in the art. The ability to readily generate stable cell lines expressing certain enhanced DNase1-PON molecules of the present disclosure indicate that these molecules have advantages in feasibility and cost of industrial scale biologic drug manufacturing.

II. Fusion Polypeptides and Dimeric Proteins

In one aspect, the present invention provides a fusion polypeptide comprising, from an amino-terminal position to a carboxyl-terminal position, T-L1-X-L2-P, wherein T, L1, X, L2, and P are defined as follows: T is a first biologically active polypeptide selected from a DNase, an RNase, a superoxide dismutase 1 (SOD1), a cytotoxic T-lymphocyte associated molecule-4 (CLTA-4) extracellular domain, a CD40 extracellular domain, and a polypeptide that specifically binds and neutralizes an inflammatory cytokine; L1 is a first polypeptide linker that is optionally present; X is a second biologically active polypeptide that is optionally present; L2 is a second polypeptide linker that is optionally present; and P is a biologically active paraoxonase. In some embodiments of a fusion polypeptide as above wherein X is present, X is selected from a dimerizing domain and a domain that specifically binds to the neonatal Fc receptor (FcRn). Typically, the biologically active paraoxonase is a naturally occurring paraoxonase 1 (PON1) polypeptide or a functional variant or fragment thereof. In variations comprising a DNase, an RNase, a SOD1, a CLTA-4 extracellular domain, or a CD40 extracellular domain, any of the foregoing biologically active polypeptides may be selected from a naturally occurring polypeptide as specified or a functional variant or fragment thereof. In certain variations comprising a polypeptide that specifically binds and neutralizes an inflammatory cytokine (e.g., TNFα or TGF-β), the anti-cytokine polypeptide is a single-chain antibody or alternative scaffold binding protein.

In another aspect, the present invention provides a fusion polypeptide comprising, from an amino-terminal position to a carboxyl-terminal position, X-L2-P, wherein X is biologically active polypeptide selected from a dimerizing domain and a domain that specifically binds to the neonatal Fc receptor (FcRn), L2 is a polypeptide linker that is optionally present, and P is a biologically active paraoxonase, wherein the fusion polypeptide does not contain a biologically active polypeptide amino-terminal to X. Typically, the biologically active paraoxonase is a naturally occurring paraoxonase 1 (PON1) polypeptide or a functional variant or fragment thereof.

In yet another aspect, the present invention provides a fusion polypeptide comprising, from an amino-terminal position to a carboxyl-terminal position, P-L1-X, wherein P is a biologically active paraoxonase, L1 is a polypeptide linker, and X is biologically active polypeptide selected from a dimerizing domain and a domain that specifically binds to the neonatal Fc receptor (FcRn). Typically, the biologically active paraoxonase is a naturally occurring paraoxonase 1 (PON1) polypeptide or a functional variant or fragment thereof.

Functional variants of a naturally occurring paraoxonase or other biologically active polypeptides specified above can be readily identified using routine assays for assessing the variant for the corresponding biological activity. For example, paraoxonase 1 (PON1) variants may be assayed for phosphotriesterase activity using diethyl p-nitrophenol phosphate (paraoxon) as a substrate, or for arylesterase activity using phenyl acetate as a substrate (see, e.g., Graves and Scott, *Curr Chem Genomics* 2:51-61, 2008; see also Example 3, infra). In addition, DNase1 and DNase1L3 variants, including hyperactive DNase1 variants, may be assayed for nuclease activity using (i) a DNA-methyl green assay, which measures the decrease of $A_{260}$ as the methyl green dye is released from hydrolyzed DNA (see, e.g., Sinicropi et al., *Anal. Biochem.* 222:351-358; Pan and Lazarus, *J. Biol. Chem.* 273:11701-11708, 1998), (ii) a Kunitz hyperchromicity assay, in which the $A_{260}$, due to the DNA absorption, increases as a function of degradation (see, e.g., Kunitz, *J. Gen. Physiol.* 33:349-362, 1950; Pan and Lazarus, supra); (iii) a plasmid digestion assay, which uses either supercoiled or linear plasmid DNA as a substrate and measures the disappearance of substrate and/or appearance of digestion products (e.g., appearance of linear or relaxed products from supercoiled DNA) (see, e.g., Pan and Lazarus, supra), or (iv) a SYTOX™ Green fluorescence assay, which measures the decrease in fluorescence as DNA labeled with SYTOX Green dye is hydrolyzed (see Example 2, infra). DNase1 variants may also be assayed for G-actin-induced inhibition of nuclease activity using DNase preincubated with G-actin prior to addition of substrate DNA (see, e.g., Pan et al., *J. Biol. Chem.* 273:18374-18381, 1998). In the case of RNase such as human RNase 1, variants may be assayed for their ability to digest single or double-stranded RNA in known assays to assess ribonuclease activity (see, e.g., Libonati and Sorrentino, *Methods Enzymol.* 341:234-248, 2001).

SOD1 variants may be assayed using a commercially available superoxide dismutase colorimetric activity kit (ThermoFisher™ Catalog number: EIASODC). This kit is designed to measure all types of superoxide dismutase activity in a variety of sample types, including Cu/Zn, Mn, and Fe superoxide dismutase activities. Reactive oxygen species including superoxide, hydroxyl radical, and hydrogen peroxide, are produced during normal cellular aerobic metabolism, and free radicals are eliminated or converted to other products by several pathways, including the SOD enzymes. This assay should quantitatively measure SOD activity and uses a bovine erythrocyte SOD standard to generate a standard curve. A similar spectrophotometric kit is also available from Cayman Chemicals (Item number 706002), and SOD activity assays using this kit are described in Mason et al., *Free Radic. Biol. Med.* 77:130-138, 2014.

Soluble CLTA-4 and CD40 variants, as well as anti-inflammatory-cytokine polypeptides (e.g., single chain antibodies), may be assessed for desired binding activity against their respective targets (e.g., against CD80/CD86 in the case of CTLA-4, or against gp139 in the case of CD40) using any of various known assays. For example, one assay system employs a commercially available biosensor instrument (BIAcore™, Pharmacia Biosensor, Piscataway, NJ), wherein a candidate binding polypeptide (e.g., a candidate CTLA-4-Fc, CD40-Fc, or anti-cytokine antibody) is covalently attached, using amine or sulfhydryl chemistry, to dextran fibers that are attached to gold film within the flow cell. A test sample containing a soluble target molecule (e.g., CD80-Fc, CD86-Fc, CD40L-Fc (gp139-Fc), or soluble cytokine) is passed through the cell. If the immobilized protein has affinity for the target molecule, it will bind to the target causing a change in the refractive index of the medium, which is detected as a change in surface plasmon resonance of the gold film. This system allows the determination of on- and off-rates, from which binding affinity can be calculated, and assessment of stoichiometry of binding. Use of this instrument is disclosed, e.g., by Karlsson (*J. Immunol. Methods* 145:229-240, 1991) and Cunningham and Wells (*J. Mol. Biol.* 234:554-563, 1993). Binding activity of candidate polypeptides can also be assessed with other assay systems known in the art. Such systems include Scatchard analysis for determination of binding affinity (see Scatchard, *Ann. NY Acad. Sci.* 51:660-672, 1949) and calorimetric assays (see Cunningham et al., *Science* 253:545-548, 1991; Cunningham et al., *Science* 254:821-825, 1991).

Activity of soluble CTLA-4 and CD40 variants can also be assessed for function in appropriate in vitro cellular assays. For example, soluble CTLA-4 will inhibit T cell responses to stimulation by CD80- or CD86-expressing cells, such as B cells, dendritic cells, or $CD80^+$ or $CD86^+$ CHO cells (see, e.g., U.S. Pat. No. 5,434,131; Linsley et al., *J. Exp. Med.* 174:561-569, 1991). Soluble CD40 will block stimulation of CD40 positive cells by CD154 (CD40L, gp39). CD40-responsive cells can be B cells, monocytes, or dendritic cells. The response can vary depending on the cell type, and may include proliferation, suppression of antibody production, or inflammatory cytokine production (see, e.g., Noelle et al., *Proc. Natl. Acad. Sci. USA* 89:6550-6554, 1992; Grammer et al., *J. Immunol.* 154:4996-5010, 1995). A CD40L reporter cell line is also available from Invivogen (San Diego, CA). This reporter system uses HEK293 cells transfected with human CD40 and an NF-kB response element fused to secreted embryonic alkaline phosphatase (SEAP). Binding of the CD40 receptor by its ligand or antibodies leads to NF-kB activation and inducible expression of the SEAP. (See Jerome et al., *Anal. Biochem.* 585:113402, 2019.)

Neutralizing activity of inflammatory-cytokine-binding polypeptides can also be assessed using cellular assays known in the art. For example, anti-TNFα-binding proteins can be assayed for neutralizing activity using commercially available TNFα reporter cell lines available from Invivogen (San Diego, CA). These cell lines are transfected HEK-293 cells with a secreted embryonic alkaline phosphatase (SEAP) reporter gene attached to TNFα-responsive promoters. (Gregory et al., *Nature* 488 (7412): 508-511, 2012; Idress et al., *Molecules* 25:922, 2020.) In addition, anti-TGF-β-binding proteins can be assessed for neutralizing activity using similar reporter cell lines available from Invivogen (San Diego, CA), that contain TGF-β-responsive elements to drive expression of SEAP. Use of this reporter system has been described by van Noort et al. (*Cancer Res.* 74:5690-5699, 2014). Similar reporter gene assays have been reported for TNFα antagonists by Lallemand et al. (*J. Immunol. Methods* 373:229-239, 2011). The study utilized human erythroleukemic K562 cells transfected with a reporter construct incorporating TNFα response elements attached to the firefly luciferase gene. TNFα was premixed with potential antagonists for 30 minutes prior to incubation with the reporter cell line. Residual TNFα activity was quantified relative to a standard curve of TNFα alone.

Naturally occurring polypeptide segments for use in accordance with the present disclosure (e.g., a naturally occurring paraoxonase, DNase, RNase, or SOD1) include naturally occurring variants such as, for example, allelic variants and interspecies homologs consistent with the disclosure.

Functional variants of a particular reference polypeptide (e.g., a wild-type human paraoxonase 1 (PON1) as shown in residues 16-355 or 26-355 of SEQ ID NO:4, a wild-type DNase1 as shown in residues 23-282 of SEQ ID NO:16, or an enhanced DNase1 as shown in residues 21-280 of SEQ ID NO:18) are generally characterized as having one or more amino acid substitutions, deletions, or additions relative to the reference polypeptide. These changes are preferably of a minor nature, that is conservative amino acid substitutions (see, e.g., Table 1, infra, which lists some exemplary conservative amino acid substitutions) and other substitutions that do not significantly affect the folding or activity of the protein or polypeptide; small deletions, typically of one to about 30 amino acids; and small amino- or carboxyl-terminal extensions. Conservative substitutions may also be selected from the following: 1) Alanine, Glycine; 2) Aspartate, Glutamate; 3) Asparagine, Glutamine; 4) Arginine, Lysine; 5) Isoleucine, Leucine, Methionine, Valine; 6) Phenylalanine, Tyrosine, Tryptophan; 7) Serine, Threonine; and 8) Cysteine, Methionine (see, e.g., Creighton, Proteins (1984)).

TABLE 1

| Conservative amino acid substitutions | | | | | |
|---|---|---|---|---|---|
| Basic | Acidic | Polar | Hydrophobic | Aromatic | Small |
| Arginine | Glutamate | Glutamine | Leucine | Phenylalanine | Glycine |
| Lysine | Aspartate | Asparagine | Isoleucine | Tryptophan | Alanine |
| Histidine | | | Valine | Tyrosine | Serine |
| | | | Methionine | | Threonine |
| | | | | | Methionine |

Essential amino acids in a naturally occurring polypeptide can be identified according to procedures known in the art, such as site-directed mutagenesis or alanine-scanning mutagenesis (Cunningham and Wells, *Science* 244:1081-1085, 1989; Bass et al., *Proc. Natl. Acad. Sci. USA* 88:4498-4502, 1991). In the latter technique, single alanine mutations are introduced at every residue in the molecule, and the resultant mutant molecules are tested for biological activity (e.g., phosphotriesterase or arylesterase activity for PON1 variants, or nuclease activity for DNase1 variants) to identify amino acid residues that are critical to the activity of the molecule. In addition, sites of relevant protein interactions can be determined by analysis of crystal structure as determined by such techniques as nuclear magnetic resonance, crystallography or photoaffinity labeling. The identities of essential amino acids can also be inferred from analysis of homologies with related proteins (e.g., species orthologs retaining the same protein function).

Multiple amino acid substitutions can be made and tested using known methods of mutagenesis and screening, such as those disclosed by Reidhaar-Olson and Sauer *Science* 241: 53-57, 1988 or Bowie and Sauer *Proc. Natl. Acad. Sci. USA* 86:2152-2156, 1989. Briefly, these authors disclose methods for simultaneously randomizing two or more positions in a polypeptide, selecting for functional polypeptide, and then sequencing the mutagenized polypeptides to determine the spectrum of allowable substitutions at each position. Another method that can be used is region-directed mutagenesis (Derbyshire et al., *Gene* 46:145, 1986; Ner et al., DNA 7:127, 1988).

Variant nucleotide and polypeptide sequences can also be generated through DNA shuffling. (See, e.g., Stemmer, *Nature* 370:389, 1994; Stemmer, *Proc. Nat'l Acad. Sci. USA* 91:10747, 1994; International PCT Publication No. WO 97/20078.) Briefly, variant DNA molecules are generated by in vitro homologous recombination by random fragmentation of a parent DNA followed by reassembly using PCR, resulting in randomly introduced point mutations. This technique can be modified by using a family of parent DNA molecules, such as allelic variants or DNA molecules from different species, to introduce additional variability into the process. Selection or screening for the desired activity, followed by additional iterations of mutagenesis and assay provides for rapid "evolution" of sequences by selecting for desirable mutations while simultaneously selecting against detrimental changes.

As previously discussed, a polypeptide fusion in accordance with the present invention can include a polypeptide segment corresponding to a "functional fragment" of a particular polypeptide. Routine deletion analyses of nucleic acid molecules can be performed to obtain functional fragments of a nucleic acid molecule encoding a given polypeptide. As an illustration, PON1-encoding DNA molecules having the nucleotide sequence of residues 46-1099 can be digested with Bal31 nuclease to obtain a series of nested deletions. The fragments are then inserted into expression vectors in proper reading frame, and the expressed polypeptides are isolated and tested for nuclease activity. One alternative to exonuclease digestion is to use oligonucleotide-directed mutagenesis to introduce deletions or stop codons to specify production of a desired fragment. Alternatively, particular fragments of a gene encoding a polypeptide can be synthesized using the polymerase chain reaction.

Accordingly, using methods such as discussed above, one of ordinary skill in the art can prepare a variety of polypeptides that (i) are substantially identical to a reference polypeptide (e.g., a PON1 as shown in residues 16-355 or 26-355 of SEQ ID NO:6, a human wild-type DNase1 as shown in residues 23-282 of SEQ ID NO:16, or an enhanced DNase1 as shown in residues 21-280 of SEQ ID NO:18) and (ii) retains the desired functional properties of the reference polypeptide.

Polypeptide segments used within the present invention (e.g., polypeptide segments corresponding to a paraoxonase, DNase, RNase, or dimerizing or FcRn-binding domain such as, e.g., an Fc fragment) may be obtained from a variety of species. If the protein is to be used therapeutically in humans, it is preferred that human polypeptide sequences be employed. However, non-human sequences can be used, as can variant sequences. For other uses, including in vitro diagnostic uses and veterinary uses, polypeptide sequences from humans or non-human animals can be employed, although sequences from the same species as the patient may be preferred for in vivo veterinary use or for in vitro uses where species specificity of intermolecular reactions is present. Thus, polypeptide segments for use within the present invention can be, without limitation, human, non-human primate, rodent, canine, feline, equine, bovine, ovine, porcine, lagomorph, and avian polypeptides, as well as variants thereof.

In some embodiments, the paraoxonase segment is a human paraoxonase 1 (PON1) or a functional variant or fragment thereof. For example, in some embodiments, the paraoxonase (a) has at least 80%, at least 85%, at least 90%, or at least 95% identity with amino acid residues 16-355 or 26-355 of SEQ ID NO:6, SEQ ID NO:8, or SEQ ID NO:4 and (b) does not contain an amino-terminal leader sequence corresponding to residues 1-15 of SEQ ID NO:6 (also shown as residues 1-15 of SEQ ID NO:8 or SEQ ID NO:4). In some such embodiments, the biologically active paraoxonase has at least 96%, at least 97%, at least 98%, or at least 99% identity with amino acid residues 16-355, 17-355, 18-355, 19-355, 20-355, 21-355, 22-355, 23-355, 24-355, 25-355, or 26-355 of SEQ ID NO:6, SEQ ID NO:8, or SEQ ID NO:4.

In some variations of a PON1 or functional variant or fragment thereof as above, the amino acid at a position corresponding to Q192 of the human paraoxonase 1 Q192 isoform (PON1-Q192; SEQ ID NO:4) is lysine or arginine. In other, non-mutually exclusive variations, the paraoxonase contains at least one of the following amino acid substitutions relative to hPON1-Q192: (i) aspartate at the position corresponding to 18R; (ii) arginine or glycine at the position corresponding to N19; (iii) glutamine at the position corresponding to H20; (iv) lysine at the position corresponding to Q21; (v) glutamate or phenylalanine at the position corresponding to Y24; (vi) phenylalanine at the amino acid corresponding to L28; (vii) valine at the position corresponding to A30; (viii) histidine at the position corresponding to L31; (ix) threonine at the position corresponding to Q35; (x) valine at the position corresponding to I48; (xi) aspartate at the position corresponding to E49; (xii) asparagine at the position corresponding to T50; (xiii) leucine or isoleucine at the position corresponding to M55; (xiv) valine at the position corresponding to L69; (xv) methionine at the position corresponding to K75; (xvi) aspartate at the position corresponding to N78; (xvii) aspartate at the position corresponding to N80; (xviii) lysine at the position corresponding to S81; (xix) serine at the position corresponding to P82; (xx) valine at the position corresponding to T96; (xxi) serine at the position corresponding to L98; (xxii) glutamate at the position corresponding to G101; (xxiii) asparagine at the position corresponding to S105; (xxiv) threonine at the position corresponding to K106; (xxv) leucine at the position corresponding to F107; (xxvi) isoleucine at the position corresponding to V109; (xxvii) threonine at the position corresponding to S111; (xxviii) tryptophan or alanine at the position corresponding to H115; (xxix) threonine at the position corresponding to A126; (xxx) valine at the position corresponding to M127; (xxxi) arginine at the position corresponding to H134; (xxxii) glutamine at the position corresponding to D136; (xxxiii) serine at the position corresponding to A137; (xxxiv) serine at the position corresponding to K138; (xxxv) valine at the position corresponding to L143; (xxxvi) serine at the position corresponding to N166; (xxxvii) valine at the position corresponding to L167; (xxxviii) alanine at the position corresponding to G180; (xxxix) glutamate at the position corresponding to Y185; (xl) glutamine at the position corresponding to F186; (xli) lysine or alanine at the position corresponding to L187; (xlii) lysine at the position corresponding to Y190; (xxliii) glutamine at the position corresponding to L191; (xliv) lysine at the position corresponding to Q192; (xlv) lysine at the position corresponding to W194; (xlvi) histidine at the position corresponding to Y197; (xlvii) glutamate at the position corresponding to L198; (xlviii) glutamine at the position corresponding to L200; (xlix) lysine at the position corresponding to W202; (l) phenylalanine at the position corresponding to Y204; (li) threonine at the position corresponding to V206; (lii) asparagine at the position corresponding to S211; (liii) aspartate at the position corresponding to E212; (liv) serine or methionine at the position corresponding to F222; (lv) aspartate at the position corresponding to N265; (lvi) valine at the position corresponding to E276; (lvii) glutamine at the position corresponding to M289; (lviii) leucine at the position corresponding to I291; (lix) glutamate or tyrosine at the position corresponding to F293; (lx) proline at the position corresponding to S296; (lxi) lysine at the position corresponding to E297; (lxii) glycine at the position corresponding to A301; (lxiii) aspartate at the position corresponding to N309; (lxiv) serine at the position corresponding to T312; (lxv) valine at the position corresponding to Q319; (lxvi) serine at the position corresponding to T332; and alanine at the position corresponding to S335.

In some variations, the paraoxonase is a variant of human PON1 identified as G3C9 (Aharoni et al., *Proc. Natl. Acad. Sci. USA* 101:482-487, 2004; Harel et al., *Nat. Struct. Mol. Biol.* 11:412-419, 2004; Mukherjee and Gupta, *J. Toxicol.* 2020:1-16, 2020; Goldsmit et al., *Chemistry and Biology* 19:456-466, 2012), or a functional variant or fragment thereof. GC39 includes 55 amino acid substitutions from the human isoform, improving the catalytic activity against nerve agents and improving soluble expression in bacteria. The full length form of this paraoxonase sequence variant is listed in SEQ ID NO:123 (nucleotide) and SEQ ID NO:124 (amino acid). In some embodiments, a GC39 paraoxonase or functional variant thereof for use in accordance with the present invention has at least 90% or at least 95% identity with amino acid residues 16-355 or 26-355 of SEQ ID NO:124; in some such embodiments, the GC39 paraoxonase or functional variant thereof has at least 96%, at least 97%, at least 98%, or at least 99% identity with amino acid residues 16-355, 17-355, 18-355, 19-355, 20-355, 21-355, 22-355, 23-355, 24-355, 25-355, or 26-355 of SEQ ID NO:124. PON1 fusions comprising G3C9 or an active variant thereof (e.g., M-IIG1 discussed below) may be particularly useful in some short term therapy applications such as, e.g., treatment of exposure to sulfur mustard gas or exposure to an organophosphate.

In some embodiments of a fusion polypeptide as above, the paraoxonase is a modified or further variant form of GC39 identified as IIG1 (also referred to as M-IIG1 herein; see Goldsmith et al., *Chemistry & Biology* 19, 456-466, 2012), or a functional variant or fragment thereof. The full length sequence of M-IIG1 is shown in SEQ ID NO:125 (nucleotide) and SEQ ID NO:126 (amino acid). In some embodiments, a M-IIG1 paraoxonase or functional variant thereof for use in accordance with the present invention has at least 90% or at least 95% identity with amino acid residues 16-355 or 26-355 of SEQ ID NO:126; in some such embodiments, the M-IIG1 paraoxonase or functional variant thereof has at least 96%, at least 97%, at least 98%, or at least 99% identity with amino acid residues 16-355, 17-355, 18-355, 19-355, 20-355, 21-355, 22-355, 23-355, 24-355, 25-355, or 26-355 of SEQ ID NO:126.

In more specific variations, the paraoxonase has an amino acid sequence selected from (i) residues 16-355 of SEQ ID NO:6, (ii) residues 17-355 of SEQ ID NO:6, (iii) residues 18-355 of SEQ ID NO:6, (iv) residues 19-355 of SEQ ID NO:6, (v) residues 20-355 of SEQ ID NO:6, (vi) residues 21-355 of SEQ ID NO:6, (vii) residues 22-355 of SEQ ID NO:6, (viii) residues 23-355 of SEQ ID NO:6, (ix) residues 24-355 of SEQ ID NO:6, (x) residues 25-355 of SEQ ID NO:6, and (xi) residues 26-355 of SEQ ID NO:6 (i.e., an amino acid sequence selected from residues n-355 of SEQ ID NO:6, wherein n is an integer from 16 to 26, inclusive). In other variations, the paraoxonase has an amino acid sequence selected from (i) residues 16-355 of SEQ ID NO:8, (ii) residues 17-355 of SEQ ID NO:8, (iii) residues 18-355 of SEQ ID NO:8, (iv) residues 19-355 of SEQ ID NO:8, (v) residues 20-355 of SEQ ID NO:8, (vi) residues 21-355 of SEQ ID NO:8, (vii) residues 22-355 of SEQ ID NO:8, (viii) residues 23-355 of SEQ ID NO:8, (ix) residues 24-355 of SEQ ID NO:8, (x) residues 25-355 of SEQ ID NO:8, and (xi) residues 26-355 of SEQ ID NO:8 (i.e., an amino acid sequence selected from residues n-355 of SEQ ID NO:8, wherein n is an integer from 16 to 26, inclusive). In still other variations, the paraoxonase has an amino acid sequence selected from (i) residues 16-355 of SEQ ID NO:4, (ii) residues 17-355 of SEQ ID NO:4, (iii) residues 18-355 of SEQ ID NO:4, (iv) residues 19-355 of SEQ ID NO:4, (v) residues 20-355 of SEQ ID NO:4, (vi) residues 21-355 of SEQ ID NO:4, (vii) residues 22-355 of SEQ ID NO:4, (viii) residues 23-355 of SEQ ID NO:4, (ix) residues 24-355 of SEQ ID NO:4, (x) residues 25-355 of SEQ ID NO:4, and (xi) residues 26-355 of SEQ ID NO:4 (i.e., an amino acid sequence selected from residues n-355 of SEQ ID NO:4, wherein n is an integer from 16 to 26, inclusive). In still other variations, the paraoxonase has an amino acid sequence selected from (i) residues 16-355 of SEQ ID NO:124, (ii) residues 17-355 of SEQ ID NO:124, (iii) residues 18-355 of SEQ ID NO:124, (iv) residues 19-355 of SEQ ID NO:124, (v) residues 20-355 of SEQ ID NO:124, (vi) residues 21-355 of SEQ ID NO:124, (vii) residues 22-355 of SEQ ID NO:124, (viii) residues 23-355 of SEQ ID NO:124, (ix) residues 24-355 of SEQ ID NO:124, (x) residues 25-355 of SEQ ID NO:124, and (xi) residues 26-355 of SEQ ID NO:124 (i.e., an amino acid sequence selected from residues n-355 of SEQ ID NO:124, wherein n is an integer from 16 to 26, inclusive). In yet other variations, the paraoxonase has an amino acid sequence selected from (i) residues 16-355 of SEQ ID NO:126, (ii) residues 17-355 of SEQ ID NO:126, (iii) residues 18-355 of SEQ ID NO:126, (iv) residues 19-355 of SEQ ID NO:126, (v) residues 20-355 of SEQ ID NO:126, (vi) residues 21-355 of SEQ ID NO:126, (vii) residues 22-355 of SEQ ID NO:126, (viii) residues 23-355 of SEQ ID NO:126 (ix) residues 24-355 of SEQ ID NO:126, (x) residues 25-355 of SEQ ID NO:126, and (xi) residues 26-355 of SEQ ID NO:126 (i.e., an amino acid sequence selected from residues n-355 of SEQ ID NO:126, wherein n is an integer from 16 to 26, inclusive).

In some embodiments of a fusion polypeptide comprising a DNase as the first biologically active polypeptide, the DNase is a human wild-type DNase1 or a functional variant or fragment thereof. For example, in some embodiments, the DNase comprises an amino acid sequence having at least 80%, at least 85%, at least 90%, or at least 95% identity with (i) amino acid residues 23-282 of SEQ ID NO:16, (ii) amino acid residues 21-280 of SEQ ID NO:18, (iii) amino acid residues 21-280 of SEQ ID NO:20, or (iv) amino acid residues 21-280 of SEQ ID NO:152. In more particular embodiments, the DNase comprises an amino acid sequence having at least 96%, at least 97%, at least 98%, at least 99%, or 100% sequence identity with (i) amino acid residues 23-282 of SEQ ID NO:16, (ii) amino acid residues 21-280 of SEQ ID NO:18, (iii) amino acid residues 21-280 of SEQ ID NO:20, or (iv) amino acid residues 21-280 of SEQ ID NO:152.

In certain preferred embodiments, the DNase segment is a hyperactive and/or actin-resistant variant of a naturally occurring DNase1 (an "enhanced DNase1") such as, e.g., an enhanced human DNase1 variant. For example, in some variations, the DNase contains at least one amino acid substitution at a position corresponding to an amino acid of mature wild-type human DNase1 (SEQ ID NO:120) selected from N74, G105, and A114, wherein (1) the amino acid substitution at the position corresponding to N74 of human DNase1 (N74 substitution), if present, increases DNA binding of the DNase relative to human DNase1, (2) the amino acid substitution at the position corresponding to G105 of human DNase1 (G105 substitution), if present, increases DNA binding of the DNase relative to human DNase1, and (3) the amino acid substitution at the position corresponding to A114 of human DNase1 (A114 substitution), if present, decreases G-actin-induced inhibition of endonuclease activity of the DNase relative to human DNase1. Suitable amino acids for substitution at these positions include lysine at the position corresponding to N74 of human DNase1, arginine at the position corresponding to G105 of human DNase1, and/or phenylalanine at the positions corresponding to A114 of human DNase1. In some variations, an enhanced human DNase1 variant as above contains at least two of the N74, G105, and A114 substitutions (e.g., substitutions at at least the positions corresponding to both N74 and G105 or both G105 and A114 of human DNase1). In some embodiments, the enhanced human DNase1 contains each of the N74, G105, and A114 substitutions. In other variations, the enhanced human DNase1 contains the N74 and G105 substitutions but does not contain the A114 substitution. In certain embodiments, the enhanced DNase1 comprises an amino acid sequence having at least 80%, at least 85%, at least 90%, at least 95%, at least 96%, at least 97%, at least 98%, at least 99%, or 100% identity with (i) amino acid residues 21-280 of SEQ ID NO:18, (ii) amino acid residues 21-280 of SEQ ID NO:20, or (iii) residues 21-280 of SEQ ID NO:152. In some variations, the enhanced DNase1 comprises an amino acid sequence having at least 90%, at least 95%, at least 96%, at least 97%, at least 98%, or at least 99% identity with amino acid residues 21-280 of SEQ ID NO:18, wherein the enhanced DNase1 contains each of the N74, G105, and A114 substitutions but does not contain any other amino acid substitution that increases DNA binding of the DNase relative to human DNase1, and/or does not contain any other amino acid substitution that decreases G-actin-induced inhibition of endonuclease activity of the DNase relative to human DNase1. In other variations, the enhanced DNase1 comprises an amino acid sequence having at least 90%, at least 95%, at least 96%, at least 97%, at least 98%, or at least 99% identity with amino acid residues 21-280 of SEQ ID NO:152, wherein the enhanced DNase1 contains each of the N74 and G105 substitutions but does not contain any other amino acid substitution that increases DNA binding of the DNase relative to human DNase1, and/or does not contain the A114 substitution or any other amino acid substitution that decreases G-actin-induced inhibition of endonuclease activity of the DNase relative to human DNase1. Fusions comprising an enhanced DNase that lacks actin resistance are particularly beneficial for decreasing toxicity to host cells (e.g., CHO) to enable higher expression of the fusion molecule.

In other embodiments of a fusion polypeptide comprising a DNase as the first biologically active polypeptide, the DNase is a truncated form of human wild-type DNase1L3 in which the carboxyl-terminal nuclear localization signal (referred to herein as NLS2, corresponding to amino acid residues 291-305 of SEQ ID NO:136) is deleted, or a functional variant or fragment of such truncated form of human DNase1L3. For example, in some embodiments, the DNase comprises an amino acid sequence having at least 80%, at least 85%, at least 90%, or at least 95% identity with (i) amino acid residues 21-290 of SEQ ID NO:136, (ii) amino acid residues 21-290 of SEQ ID NO:138, or (iii) amino acid residues 21-290 of SEQ ID NO:140. In more particular embodiments, the DNase comprises an amino acid sequence having at least 96%, at least 97%, at least 98%, at least 99%, or 100% sequence identity with (i) amino acid residues 21-290 of SEQ ID NO:136, (ii) amino acid residues 21-290 of SEQ ID NO:138, or (iii) amino acid residues 21-290 of SEQ ID NO:140. In certain preferred embodiments comprising a truncated form of human DNase1L3 or functional variant thereof, the DNase is a variant DNase1L3 containing one or more amino acid substitutions relative to wild-type human DNase1L3 (SEQ ID NO:136) that inactivate the nuclear localization signal in the N-terminal half of the molecule (referred to herein as NLS1, corresponding to amino acid residues 80-96 of SEQ ID NO:136); in some such embodiments, each of the amino acids at positions corresponding to R80, R95, and N96 of SEQ ID NO:136 is alanine or serine (e.g., each of R80, R95, and N96 is alanine, or each of R80, R95, and N96 is serine). In more specific embodiments of a variant, truncated form of DNase1L3 as above in which the wild-type NLS1 consensus sequence is removed, the DNase has the amino acid sequence shown in (i) amino acid residues 21-290 of SEQ ID NO:138 or (ii) amino acid residues 21-290 of SEQ ID NO:140.

In some embodiments of a fusion polypeptide comprising an RNase as the first biologically active polypeptide, the RNase is a human wild-type RNase1 or a functional variant or fragment thereof. For example, in some embodiments, the RNase comprises an amino acid sequence having at least 80%, at least 85%, at least 90%, or at least 95% identity with amino acid residues 29-156 of SEQ ID NO:22. In more particular variations, the RNase comprises an amino acid sequence having at least 96%, at least 97%, at least 98%, at least 99%, or 100% identity with amino acid residues 29-156 of SEQ ID NO:22.

In some embodiments of a fusion polypeptide comprising a superoxide dismutase 1 (SOD1) as the first biologically active polypeptide, the SOD1 is a human wild-type SOD1 or a functional variant or fragment thereof. For example, in some embodiments, the SOD1 comprises an amino acid sequence having at least 80%, at least 85%, at least 90%, or at least 95% identity with amino acid residues 2-154 of SEQ ID NO:32. In more particular variations, the SOD1 comprises an amino acid sequence having at least 96%, at least 97%, at least 98%, at least 99%, or 100% identity with amino acid residues 2-154 of SEQ ID NO:32. In certain variations, the amino acid at a position corresponding to C7 of human SOD1 (SEQ ID NO:32) is not cysteine, and/or the amino acid a position corresponding to C112 of human SOD1 is not cysteine; in some such embodiments, the amino acid at a position corresponding to C7 of human SOD1 is alanine, and/or the amino acid a position corresponding to C112 of human SOD1 is serine. In more specific variations, the SOD1 comprises the amino acid sequence shown in residues 2-154 of SEQ ID NO:32 wherein the amino acid at position C7 is changed to alanine and the amino acid at position C112 is serine (also shown as residues 23-175 of SEQ ID NO:52 or residues 23-175 of SEQ ID NO:54).

In some embodiments of a fusion polypeptide comprising a CTLA-4 extracellular domain as the first biologically active polypeptide, the extracellular domain is a human wild-type CTLA-4 extracellular domain or a functional variant or fragment thereof. For example, in some embodiments, the CTLA-4 extracellular domain comprises an amino acid sequence having at least 80%, at least 85%, at least 90%, or at least 95% identity with amino acid residues 21-144 of SEQ ID NO:66. In more particular variations, the CTLA-4 extracellular domain comprises an amino acid sequence having at least 96%, at least 97%, at least 98%, at least 99%, or 100% identity with amino acid residues 21-144 of SEQ ID NO:66.

In some embodiments of a fusion polypeptide comprising a CD40 extracellular domain as the first biologically active polypeptide, the extracellular domain is a human wild-type CD40 extracellular domain or a functional variant or fragment thereof. For example, in some embodiments, the CD40 extracellular domain comprises an amino acid sequence having at least 80%, at least 85%, at least 90%, or at least 95% identity with (i) residues 21-188 of SEQ ID NO:74, (ii) residues 21-188 of SEQ ID NO:78, (iii) residues 21-188 of SEQ ID NO:82, (iv) residues 21-188 of SEQ ID NO:86, or (v) residues 21-188 of SEQ ID NO:90. In more particular embodiments, the CD40 extracellular domain comprises an amino acid sequence having at least 96%, at least 97%, at least 98%, or at least 99% identity with (i) residues 21-188 of SEQ ID NO:74, (ii) residues 21-188 of SEQ ID NO:78, (iii) residues 21-188 of SEQ ID NO:82, (iv) residues 21-188 of SEQ ID NO:86, or (v) residues 21-188 of SEQ ID NO:90.

In certain preferred embodiments, the CD40 extracellular domain contains at least one amino acid substitution at a position corresponding to an amino acid of wild-type human CD40 (SEQ ID NO:68) selected from E64, K81, P85, and L121, wherein the at least one amino acid substitution increases CD40 ligand binding relative to human CD40. Particularly suitable amino acid substitutions at these positions are tyrosine at the position corresponding to E64 of human CD40, threonine, histidine, or serine at the position corresponding to K81 of human CD40, tyrosine at the position corresponding to P85 of human CD40, and/or proline at the position corresponding to L121 of human CD40. In some variations, the CD40 extracellular domain contains at least two of the positions corresponding to E64, K81, P85, and L121 of human CD40 (e.g., substitutions at at least the positions corresponding to K81 and L121 of human CD40, or substitutions at at least the positions corresponding to E64, K81, and P85 of human CD40). In some embodiments, the amino acid at the position corresponding to K81 of human CD40 is selected from threonine, histidine, and serine. In other embodiments, the amino acid at the position corresponding to K81 of human CD40 is histidine and the amino acid the position corresponding to L121 of human CD40 is proline. In yet other embodiments, the amino acid at the position corresponding to E64 of human CD40 is tyrosine, the amino acid at the position corresponding to K81 of human CD40 is threonine, and the amino acid at the position corresponding to P85 of human CD40 is tyrosine. In specific variations, the CD40 extracellular domain comprises the amino acid sequence shown in (i) residues 21-188 of SEQ ID NO:74, (ii) residues 21-188 of SEQ ID NO:78, (iii) residues 21-188 of SEQ ID NO:82, (iv) residues 21-188 of SEQ ID NO:86, or (v) residues 21-188 of SEQ ID NO:90.

In some embodiments of a fusion polypeptide comprising a polypeptide that specifically binds and neutralizes an inflammatory cytokine as the first biologically active polypeptide, the inflammatory cytokine is a member of the tumor necrosis factor (TNF) superfamily, a member of the transforming growth factor (TGF) superfamily, an interleukin, a chemokine, a colony-stimulating factor (CSF), or an interferon. In more particular embodiments, the inflammatory cytokine is selected from the group consisting of tumor necrosis factor α (TNFα), transforming growth factor-β (TGF-β), interleukin-4 (IL-4), interleukin-5 (IL-5), interleukin-6 (IL-6), interleukin-8 (IL-8), interleukin-10 (IL-10), interleukin-11 (IL-11), interleukin-12 (IL-12), interleukin- 13 (IL-13), interleukin-17A (IL-17A), interleukin-17F (IL-17F), interleukin-1α (IL-1α), interleukin-1β (IL-1β), interleukin-18 (IL-18), interleukin-21 (IL-21), interleukin-31 (IL-31), interleukin-33 (IL-33), interleukin-36α (IL-36α), interleukin-36β (IL-36β), interleukin IL-36γ (IL-36γ), granulocyte-macrophage colony-stimulating factor (GM-CSF), and interferon γ (IFNγ). In some variations, a polypeptide that specifically binds and neutralizes an inflammatory cytokine is an antibody. In some alternative variations, a polypeptide that specifically binds and neutralizes an inflammatory cytokine is an alternative scaffold protein.

In certain embodiments of a fusion polypeptide comprising a polypeptide that specifically binds and neutralizes TNFα ("anti-TNFα polypeptide"), the anti-TNFα polypeptide competes for binding to TNFα with an antibody having the same heavy and light chain variable domains (VH and VL) as anti-TNFα monoclonal antibody adalimumab. The amino acid sequences of adalimumab VH and VL are shown herein as SEQ ID NO:108 and SEQ ID NO:110, respectively (see also GenBank Accession Nos. LQ961187 and LQ961186 for the heavy and light chain variable regions, respectively; International PCT Publication No. WO 2014/159579).

In certain embodiments of a fusion polypeptide comprising a polypeptide that specifically binds and neutralizes TGF-β ("anti-TGF-β polypeptide"), the anti-TGF-β polypeptide competes for binding to TGF-β with an antibody having the same heavy and light chain variable domains (VH and VL) as anti-TGF-β monoclonal antibody fresolimumab. The amino acid sequences of fresolimumab VH and VL are shown herein as SEQ ID NO:112 and SEQ ID NO:114, respectively (see also GenBank Accession Nos. JC232803.1 and JC232805 for the heavy and light chain variable regions, respectively; International PCT Publication No. WO 2013/065869).

The ability of a binding protein to compete for binding to TNFα or TGF-β with an antibody having the VH and VL domains of adalimumab or fresolimumab, respectively, may be determined by an assay in which a test TNFα-binding protein (e.g., an antibody), or a functional binding fragment thereof, prevents or inhibits specific binding to TNFα of a reference antibody having the VH and VL domains of adalimumab (i.e., having VH and VL domains of SEQ ID NO:108 and SEQ ID NO:110, respectively), or in which a test TNF-β-binding protein (e.g., an antibody), or a functional binding fragment thereof, prevents or inhibits specific binding to TNF-β of a reference antibody having the VH and VL domains of fresolimumab (i.e., having VH and VL domains of SEQ ID NO:112 and SEQ ID NO:114, respectively). Typically, such an assay involves the use of purified target protein bound to a solid surface or cells bearing the target protein, an unlabeled test protein (i.e., a TNFα-binding or TGF-β-binding protein or candidate TNFα-binding or TGF-β-binding protein), and a labeled reference antibody. Competitive inhibition is measured by determining the amount of label bound to the solid surface or cells in the presence of the test protein. Usually the test protein is present in excess and/or allowed to bind first. Soluble TNFα-binding or TGF-β-binding proteins identified by competition assay ("competing TNFα-binding or TGF-β-binding proteins") include proteins binding to the same epitope bound by the reference antibody, proteins binding to an epitope overlapping with the epitope bound by the reference antibody, and proteins binding to an epitope sufficiently proximal to the epitope bound by the reference antibody for steric hindrance to occur. Usually, when a competing TNFα-binding or TGF-β-binding protein (e.g., a competing anti-TNFα or anti-TGF-β antibody) is present in excess, it will inhibit specific binding of a reference antibody to TNFα or TGF-β target protein by at least 30%, at least 40%, at least 45%, at least 50%, at least 55%, at least 60%, at least 65%, at least 70%, or at least 75%; in some instances, binding is inhibited by at least 80%, at least 85%, at least 90%, at least 95%, at least 97%, or more. Conversely, when the reference antibody is bound, it will preferably inhibit binding of a subsequently added competing TNFα-binding or TGF-β-binding protein (e.g., a competing anti-TNFα or anti-TGF-β antibody) by at least 30%, at least 40%, at least 45%, at least 50%, at least 55%, at least 60%, at least 65%, at least 70%, or at least 75%; in some instances, binding is inhibited by at least 80%, at least 85%, at least 90%, at least 95%, at least 97%, or more.

In certain preferred embodiments, a polypeptide that specifically binds and neutralizes an inflammatory cytokine for use in accordance with the present invention is a single-chain antibody. Particularly suitable single-chain antibodies include single-chain Fvs (scFvs) and single-domain antibodies (sdAbs). A single-chain antibody may be, e.g., derived from an identified intact, native monoclonal antibody or antibody fragment having the desired specificity. Methods for preparing and isolating monoclonal antibodies and antigen-binding antibody fragments thereof are well-known in the art. See, e.g., *Current Protocols in Immunology*, (Cooligan et al. eds., John Wiley and Sons, Inc. 2006); Sambrook et al., *Molecular Cloning: A Laboratory Manual* (Cold Spring Harbor, NY, 2nd ed. 1989); and *Monoclonal Hybridoma Antibodies: Techniques and Applications* (Hurrell ed., CRC Press, Inc., Boca Raton, FL, 1982). Antigen-binding fragments, including scFv, can be prepared using, e.g., phage display libraries according to methods known in the art. As will be evident to persons of ordinary skill in the art, these methods are equally applicable to production of antibodies against an inflammatory cytokine for use in accordance with the present invention.

The amino acid sequence of native antibody variable regions can be varied through the application of recombinant DNA techniques. Thus, antibodies can be redesigned to obtain desired characteristics. Typically, changes in the variable region will be made in order to improve the antigen-binding characteristics, improve variable region stability, or reduce the risk of immunogenicity. Phage display techniques can also be employed. See, e.g., Huse et al., *Science* 246:1275-1281, 1989; Ladner et al., U.S. Pat. No. 5,571,698.

For therapeutic antibodies for use in humans, it is usually desirable to humanize non-human regions of an antibody according to known procedures. Methods of making humanized antibodies are disclosed, for example, in U.S. Pat. Nos. 5,530,101; 5,821,337; 5,585,089; 5,693,762; and 6,180,370. Methods of making humanized antibodies are also disclosed in, e.g., U.S. Pat. No. 7,732,578. Typically, a humanized anti-inflammatory-cytokine antibody comprises the complementarity determining regions (CDRs) of a murine donor immunoglobulin and heavy chain and light chain frameworks of a human acceptor immunoglobulin. Often, framework residues in the human framework regions will be substituted with the corresponding residue from the donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. See, e.g., Queen et al., U.S. Pat. No. 5,585,089; Riechmann et al., *Nature* 332:323, 1988.

The present invention also encompasses use of fully human antibodies such as, for example, those selected from human antibody expression libraries (e.g., phage display libraries); those made in non-human animals (e.g., mice) transgenic for a human heavy chain locus and a human light chain locus with the corresponding endogenous immunoglobulin loci inactivated; or those prepared by immortalizing human B lymphocytes producing an antibody against an inflammatory cytokine target antigen.

Antibodies for use in accordance with the present invention have binding affinities that include a dissociation constant ($K_d$) that is, e.g., less than $5\times10^{-4}$ M, less than $10^{-4}$ M, less than $5\times10^{-5}$ M, less than $10^{-5}$ M, less than $5\times10^{-6}$ M, less than $10^{-6}$ M, less than $5\times10^{-7}$ M, less than $10^{-7}$ M, less than $5\times10^{-8}$ M, less than $10^{-8}$ M, less than $5\times10^{-9}$ M, less than $10^{-9}$ M, less than $5\times10^{-10}$ M, less than $10^{-10}$ M, less than $5\times10^{-11}$ M, less than $10^{-11}$ M, less than $5\times10^{-12}$ M, less than $10^{-12}$ M, less than $5\times10^{-13}$ M, less than $10^{-13}$ M, less than $5\times10^{-14}$ M, less than $10^{-14}$ M, less than $5\times10^{-15}$ M, or less than $10^{-15}$ M.

Antibodies for use in accordance with the present invention include variants having one or more amino acid substitutions, deletions, or additions relative to a reference antibody such that the variant retains one or more biological properties of the reference antibody. In certain embodiments, an antibody is a variant having one or more amino acid substitutions, deletions, or additions relative to a reference anti-TNFα neutralizing antibody having VH and/or VL sequences as shown in SEQ ID NO:108 and SEQ ID NO:110, respectively, such that the antibody retains the ability of the reference antibody to specifically bind TNFα and neutralize TNFα activity. In other embodiments, an antibody is a variant having one or more amino acid substitutions, deletions, or additions relative to a reference anti-TNF-β neutralizing antibody having VH and/or VL sequences as shown in SEQ ID NO:112 and SEQ ID NO:114, respectively, such that the antibody retains the ability of the reference antibody to specifically bind TNF-β and neutralize TNF-β activity. A skilled person can readily produce variants having one or more amino acid substitutions, deletions, or additions relative to a reference antibody. The techniques for obtaining these variants, including genetic (suppressions, deletions, mutations, etc.), chemical, and enzymatic techniques, are known to the person having ordinary skill in the art.

In some embodiments of a fusion polypeptide as above comprising a single-chain antibody that specifically binds and neutralizes TNFα ("anti-TNFα single-chain antibody"), the anti-TNFα single-chain antibody comprises one or more CDRs of anti-TNFα monoclonal antibody adalimumab. Thus, in certain variations, an anti-TNFα single-chain antibody comprises a heavy chain CDR (at least one of the CDR-H1, CDR-H2, and CDR-H3 regions) of the adalimumab VH domain (SEQ ID NO:108) and/or a light chain CDR (at least one of CDR-L1, CDR-L2, and CDR-L3 regions) of the adalimumab VL domain (SEQ ID NO:110). In typical embodiments, the anti-TNFα single-chain antibody has two or three CDRs of the adalimumab VH domain (SEQ ID NO:108) and/or two or three CDRs of the adalimumab VL domain (SEQ ID NO:110). In some variations, where an anti-TNFα single-chain antibody has at least one CDR of the adalimumab VH domain, the antibody further comprises at least one CDR of the adalimumab VL domain; in some such embodiments, an antibody has all three heavy chain CDRs and all three light chain CDRs of adalimumab (i.e., CDR-H1, CDR-H2, and CDR-H3 of SEQ ID NO:108 and CDR-L1, CDR-L2, and CDR-L3 of SEQ ID NO:110). The one or more CDRs may be defined, for example, according to the Chothia definition, the Kabat definition, the AbM definition, the IMGT database definition, or the contact definition of CDR. Under the IMGT database definition of CDR, CDR-H1, CDR-H2, and CDR-H3 of adalimumab correspond, respectively, to residues 26-33, 50-59, and 97-110 of SEQ ID NO:108, and CDR-L1, CDR-L2, and CDR-L3 of adalimumab correspond, respectively, to residues 27-32, 50-52, and 89-97 of SEQ ID NO:110. Under the Kabat definition of CDR, CDR-H1, CDR-H2, and CDR-H3 of adalimumab correspond, respectively, to residues 31-35, 50-66, and 99-110 of SEQ ID NO:108, and CDR-L1, CDR-L2, and CDR-L3 of adalimumab correspond, respectively, to residues 24-34, 50-56, and 89-97 of SEQ ID NO:110. In particular variations of an anti-TNFα single-chain antibody as above, the single-chain antibody comprises an VH domain and/or a VL domain having a human immunoglobulin framework region, or a variant thereof having at least 85%, at least 90%, or at least 95% amino acid sequence identity to the human immunoglobulin framework region.

In some embodiments, an anti-TNFα single-chain antibody includes (a) a heavy chain variable domain that is at least 60%, at least 65%, at least 70%, at least 75%, at least 80%, at least 85%, at least 90%, at least 95%, at least 96%, at least 97%, at least 98%, at least 99%, or 100% identical to the amino acid sequence of SEQ ID NO:108, and/or (b) a light chain variable domain that is at least 60%, at least 65%, at least 70%, at least 75%, at least 80%, at least 85%, at least 90%, at least 95%, at least 96%, at least 97%, at least 98%, at least 99%, or 100% identical to the amino acid sequence of SEQ ID NO:110.

In some embodiments, an anti-TNFα single-chain antibody for use in accordance with the present invention comprises heavy chain CDRs CDR-$H1_{TNF\alpha}$, CDR-$H2_{TNF\alpha}$, and CDR-$H3_{TNF\alpha}$, wherein the set of VH CDRs has 10 or fewer amino acid substitutions relative to a set of reference CDRs CDR-H1, CDR-H2, and CDR-H3 of the adalimumab VH domain (SEQ ID NO:108). In other, non-mutually exclusive embodiments, the anti-TNFα single-chain comprises light chain CDRs CDR-$L1_{TNF\alpha}$, CDR-$L2_{TNF\alpha}$, and CDR-$L3_{TNF\alpha}$, wherein the set of VL CDRs has 10 or fewer amino acid substitutions relative to a set of reference CDRs CDR-L1, CDR-L2, and CDR-L3 of the adalimumab VL domain (SEQ ID NO:110). In certain embodiments, an anti-TNFα single-chain antibody comprises both sets of heavy chain and light chain CDRs as above. Particularly suitable anti-TNFα single-chain antibodies comprise a heavy chain variable domain comprising CDRs CDR-$H1_{TNF\alpha}$, CDR-$H2_{TNF\alpha}$, and CDR-$H3_{TNF\alpha}$ and a light chain variable domain comprising CDRs CDR-$L1_{TNF\alpha}$, CDR-$L2_{TNF\alpha}$, and CDR-$L3_{TNF\alpha}$, wherein the set of heavy chain CDRs has six or fewer, typically five or fewer, more typically four or fewer, an most typically three or fewer amino acid substitutions relative to CDR-H1, CDR-H2, and CDR-H3 of adalimumab, and wherein the set of light chain CDRs has six or fewer, typically five or fewer, more typically four or fewer, an most typically three or fewer amino acid substitutions relative to CDR-L1, CDR-L2, and CDR-L3 of adalimumab. The CDRs as above may be defined, for example, according to the Chothia definition, the Kabat definition, the AbM definition, the IMGT database definition, or the contact definition of CDR. In particular variations of an anti-TNFα antibody as above, each of the VH and VL domains has a human immunoglobulin framework region, or a variant thereof having at least 85%, at least 90%, or at least 95% amino acid sequence identity to the human immunoglobulin framework region.

In some embodiments of a fusion polypeptide as above comprising a single-chain antibody that specifically binds and neutralizes TGF-β ("anti-TGF-β single-chain antibody"), the anti-TGF-β single-chain antibody comprises one or more CDRs of anti-TGF-β monoclonal antibody fresolimumab. Thus, in certain variations, an anti-TGF-β single-chain antibody comprises a heavy chain CDR (at least one of the CDR-H1, CDR-H2, and CDR-H3 regions) of the fresolimumab VH domain (SEQ ID NO:112) and/or a light chain CDR (at least one of CDR-L1, CDR-L2, and CDR-L3 regions) of the fresolimumab VL domain (SEQ ID NO:114). In typical embodiments, the anti-TGF-single-chain antibody has two or three CDRs of the fresolimumab VH domain (SEQ ID NO:112) and/or two or three CDRs of the fresolimumab VL domain (SEQ ID NO:114). In some variations, where an anti-TGF-β single-chain antibody has at least one CDR of the fresolimumab VH domain, the antibody further comprises at least one CDR of the fresolimumab VL domain; in some such embodiments, an antibody has all three heavy chain CDRs and all three light chain CDRs of fresolimumab (i.e., CDR-H1, CDR-H2, and CDR-H3 of SEQ ID NO:112 and CDR-L1, CDR-L2, and CDR-L3 of SEQ ID NO:114). The one or more CDRs may be defined, for example, according to the Chothia definition, the Kabat definition, the AbM definition, the IMGT database definition, or the contact definition of CDR. Under the Kabat definition of CDR, CDR-H1, CDR-H2, and CDR-H3 of fresolimumab correspond, respectively, to residues 31-35, 50-66, and 99-106 of SEQ ID NO:112, and CDR-L1, CDR-L2, and CDR-L3 of fresolimumab correspond, respectively, to residues 24-40, 56-62, and 95-102 of SEQ ID NO:114. In particular variations of an anti-TGF-β single-chain antibody as above, the single-chain antibody comprises an VH domain and/or a VL domain having a human immunoglobulin framework region, or a variant thereof having at least 85%, at least 90%, or at least 95% amino acid sequence identity to the human immunoglobulin framework region.

In some embodiments, an anti-TGF-β single-chain antibody includes (a) a heavy chain variable domain that is at least 60%, at least 65%, at least 70%, at least 75%, at least 80%, at least 85%, at least 90%, at least 95%, at least 96%, at least 97%, at least 98%, at least 99%, or 100% identical to the amino acid sequence of SEQ ID NO:112, and/or (b) a light chain variable domain that is at least 60%, at least 65%, at least 70%, at least 75%, at least 80%, at least 85%, at least 90%, at least 95%, at least 96%, at least 97%, at least 98%, at least 99%, or 100% identical to the amino acid sequence of SEQ ID NO:114.

In some embodiments, an anti-TGF-β single-chain antibody for use in accordance with the present invention comprises heavy chain CDRs CDR-H1$_{TGF\text{-}\beta}$, CDR-H2$_{TGF\text{-}\beta}$, and CDR-H3$_{TGF\text{-}\beta}$, wherein the set of VH CDRs has 10 or fewer amino acid substitutions relative to a set of reference CDRs CDR-H1, CDR-H2, and CDR-H3 of the fresolimumab VH domain (SEQ ID NO:112). In other, non-mutually exclusive embodiments, the anti-TGF-β single-chain comprises light chain CDRs CDR-L1$_{TGF\text{-}\beta}$, CDR-L2$_{TGF\text{-}\beta}$, and CDR-L3$_{TGF\text{-}\beta}$, wherein the set of VL CDRs has 10 or fewer amino acid substitutions relative to a set of reference CDRs CDR-L1, CDR-L2, and CDR-L3 of the fresolimumab VL domain (SEQ ID NO:114). In certain embodiments, an anti-TGF-β single-chain antibody comprises both sets of heavy chain and light chain CDRs as above. Particularly suitable anti-TGF-β single-chain antibodies comprise a heavy chain variable domain comprising CDRs CDR-H1$_{TGF\text{-}\beta}$, CDR-H2$_{TGF\text{-}\beta}$, and CDR-H3$_{TGF\text{-}\beta}$ and a light chain variable domain comprising CDRs CDR-L1$_{TGF\text{-}\beta}$, CDR-L2$_{TGF\text{-}\beta}$, and CDR-L3$_{TGF\text{-}\beta}$, wherein the set of heavy chain CDRs has six or fewer, typically five or fewer, more typically four or fewer, and most typically three or fewer amino acid substitutions relative to CDR-H1, CDR-H2, and CDR-H3 of fresolimumab, and wherein the set of light chain CDRs has six or fewer, typically five or fewer, more typically four or fewer, and most typically three or fewer amino acid substitutions relative to CDR-L1, CDR-L2, and CDR-L3 of fresolimumab. The CDRs as above may be defined, for example, according to the Chothia definition, the Kabat definition, the AbM definition, the IMGT database definition, or the contact definition of CDR. In particular variations of an anti-TGF-β antibody as above, the each of the VH and VL domains has a human immunoglobulin framework region, or a variant thereof having at least 85%, at least 90%, or at least 95% amino acid sequence identity to the human immunoglobulin framework region.

Anti-inflammatory-cytokine antibodies for use in accordance with the present invention include affinity matured embodiments. Affinity matured antibodies can be produced by procedures known in the art (see, e.g., Marks et al., *Bio/Technology* 10:779-783, 1992; Barbas et al., *Proc Nat. Acad. Sci. USA* 91:3809-3813, 1994; Schier et al., *Gene* 169:147-155, 1995; Yelton et al., *J. Immunol.* 155:1994-2004, 1995; Jackson et al., *J. Immunol.* 154:3310-9, 1995; Hawkins et al., *J. Mol. Biol.* 226:889-896, 1992; and PCT Publication No. WO 2004/058184). One method for adjusting the affinity of an antibody is termed "library scanning mutagenesis." Generally, library scanning mutagenesis is carried out as follows. One or more amino acid positions in at least one CDR (e.g., in two, three, four, five, or six CDRs) are replaced with two or more (such as 3, 4, 5, 6, 7, 8, 9, 10, 11, 12, 13, 14, 15, 16, 17, 18, 19, or 20) amino acids using art recognized methods. This generates small libraries of clones (in some embodiments, one for every amino acid position that is analyzed), each with a complexity of two or more members (if two or more amino acids are substituted at every position). Generally, the library also includes a clone comprising the native (unsubstituted) amino acid. A small number of clones, e.g., about 20-80 clones (depending on the complexity of the library), from each library are screened for binding affinity to the target polypeptide (or other binding target), and candidates with increased, the same, decreased, or no binding are identified. Binding affinity may be determined, e.g., using Biacore™ surface plasmon resonance analysis, which detects differences in binding affinity of about 2-fold or greater. Biacore™ is particularly useful when the starting antibody already binds with a relatively high affinity, for example a $K_D$ of about 10 nM or lower.

In some embodiments of a fusion polypeptide comprising an anti-TNFα single-chain antibody as the first biologically active polypeptide, the anti-TNFα single-chain antibody comprises an amino acid sequence having at least 80%, at least 85%, at least 90%, or at least 95% identity with (i) amino acid residues 21-268 of SEQ ID NO:92 or (ii) amino acid residues 21-268 of SEQ ID NO:96. In more particular variations, the anti-TNFα single-chain antibody comprises an amino acid sequence having at least 96%, at least 97%, at least 98%, at least 99%, or 100% identity with (i) amino acid residues 21-268 of SEQ ID NO:92 or (ii) amino acid residues 21-268 of SEQ ID NO:96.

In some embodiments of a fusion polypeptide comprising an anti-TGF-β single-chain antibody as the first biologically active polypeptide, the anti-TGF-β single-chain antibody comprises an amino acid sequence having at least 80%, at least 85%, at least 90%, or at least 95% identity with (i) amino acid residues 21-269 of SEQ ID NO:100 or (ii) amino acid residues 21-269 of SEQ ID NO:104. In more particular variations, the anti-TGF-β single-chain antibody comprises an amino acid sequence having at least 96%, at least 97%, at least 98%, at least 99%, or 100% identity with (i) amino acid residues 21-269 of SEQ ID NO:100 or (ii) amino acid residues 21-269 of SEQ ID NO:104.

Polypeptide linkers for use in accordance with the present invention can be naturally occurring, synthetic, or a combination of both. The linker joins two separate polypeptide regions (e.g., an Fc region and a paraoxonase, or an Fc region and a DNase) and maintains the linked polypeptide regions as separate and discrete domains of a longer polypeptide. The linker can allow the separate, discrete domains to cooperate yet maintain separate properties (e.g., in the case of an Fc region linked to a paraoxonase or DNase, Fc receptor (e.g., FcRn) binding may be maintained for the Fc region, while functional properties of the paraoxonase (e.g., organophosphatase or arylesterase activity) or DNase (e.g., DNA binding and nuclease activity) will be maintained. For examples of the use of naturally occurring as well as artificial peptide linkers to connect heterologous polypeptides, see, e.g., Hallewell et al., *J. Biol. Chem.* 264, 5260-5268, 1989; Alfthan et al., *Protein Eng.* 8, 725-731, 1995; Robinson and Sauer, *Biochemistry* 35, 109-116, 1996; Khandekar et al., *J. Biol. Chem.* 272, 32190-32197, 1997; Fares et al., *Endocrinology* 139, 2459-2464, 1998; Smallshaw et al., *Protein Eng.* 12, 623-630, 1999; U.S. Pat. No. 5,856,456.

Typically, residues within the linker polypeptide are selected to provide an overall hydrophilic character and to be non-immunogenic and flexible. As used herein, a "flexible" linker is one that lacks a substantially stable higher-order conformation in solution, although regions of local stability are permissible. In general, small, polar, and hydrophilic residues are preferred, and bulky and hydrophobic residues are undesirable. Areas of local charge are to be avoided; if the linker polypeptide includes charged residues, they will ordinarily be positioned so as to provide a net neutral charge within a small region of the polypeptide. It is therefore preferred to place a charged residue adjacent to a residue of opposite charge. In general, preferred residues for inclusion within the linker polypeptide include Gly, Ser, Ala, Thr, Asn, and Gln; more preferred residues include Gly, Ser, Ala, and Thr; and the most preferred residues are Gly and Ser. In general, Phe, Tyr, Trp, Pro, Leu, Ile, Lys, and Arg residues will be avoided (unless present within an immunoglobulin hinge region of the linker), Pro residues due to their hydrophobicity and lack of flexibility, and Lys and Arg residues due to potential immunogenicity. The sequence of the linker will also be designed to avoid unwanted proteolysis.

In certain embodiments, linker L1 comprises at least two or at least three amino acid residues (e.g., at least five, at least 10, at least 16, at least 26, or at least 36 amino acid residues). In particular variations, L1 consists of from two to 60 amino acid residues, from three to 60 amino acid residues, from five to 40 amino acid residues, or from 15 to 40 amino acid residues. In other variations, L1 consists of from two to 50, from two to 40, from two to 36, from two to 35, from two to 30, from two to 26, from three to 50, from three to 40, from three to 36, from three to 35, from three to 30, from three to 26, from five to 60, from five to 50, from five to 40, from five to 36, from five to 35, from five to 30, from five to 26, from 10 to 60, from 10 to 50, from 10 to 40, from 10 to 36, from 10 to 35, from 10 to 30, from 10 to 26, from 15 to 60, from 15 to 50, from 15 to 36, from 15 to 35, from 15 to 30, or from 15 to 26 amino acid residues. In other variations, L1 consists of from 16 to 60, from 16 to 50, from 16 to 40, or from 16 to 36 amino acid residues. In yet other variations, L1 consists of from 20 to 60, from 20 to 50, from 20 to 40, from 20 to 36, from 25 to 60, from 25 to 50, from 25 to 40, or from 25 to 36 amino acid residues. In still other variations, L1 consists of from 26 to 60, from 26 to 50, from 26 to 40, or from 26 to 36 amino acid residues. In more specific variations, L1 consists of 16 amino acid residues, 21 amino acid residues, 26 amino acid residues, 31 amino acid residues, or 36 amino acid residues. In some embodiments, L1 comprises or consists of the amino acid sequence shown in residues SEQ ID NO:10, residues 268-288 of SEQ ID NO:12, or SEQ ID NO:14.

In typical variations of a fusion polypeptide comprising a DNase as the first biologically active polypeptide, L1 is present and comprises at least 15 amino acid residues. For example, an L1 linker joining the carboxyl-terminus of a DNase to the amino-terminus of another fusion component (e.g., an immunoglobulin Fc region) may comprise at least 20, at least 21, at least 22, at least 23, at least 24, at least 25, or at least 26 amino acid residues. In more particular variations, L1 consists of from 15 to 60 amino acid residues, from 15 to 51 amino acid residues, from 15 to 50 amino acid residues, from 15 to 46 amino acid residues, from 15 to 45 amino acid residues, from 15 to 41 amino acid residues, from 15 to 40 amino acid residues, from 15 to 36 amino acid residues, from 26 to 60 amino acid residues, from 26 to 51 amino acid residues, from 26 to 50 amino acid residues, from 26 to 46 amino acid residues, from 26 to 45 amino acid residues, from 26 to 41 amino acid residues, from 26 to 40 amino acid residues, or from 26 to 36 amino acid residues. In still more specific variations, L1 linking a DNase consists of 26 amino acid residues, 27 amino acid residues, 28 amino acid residues, 29 amino acid residues, 30 amino acid residues, 31 amino acid residues, 32 amino acid residues, 33 amino acid residues, 34 amino acid residues, 35 amino acid residues, or 36 amino acid residues. In some embodiments, L1 linking a DNase comprises or consists of the amino acid sequence shown in SEQ ID NO:12 or SEQ ID NO:14.

In some variations of a fusion polypeptide comprising an RNase or a SOD1 as the first biologically active polypeptide, L1 is present and comprises at least two amino acid residues. For example, an L1 linker joining the carboxyl-terminus of an RNase or a SOD1 to the amino-terminus of another fusion component (e.g., an immunoglobulin Fc region) may comprise at least three, at least five, or at least 10 amino acid residues. In more particular variations, L1 linking an RNase or a SOD1 consists of from two to 60 amino acid residues, from two to 51 amino acid residues, from two to 50 amino acid residues, from two to 46 amino acid residues, from two to 45 amino acid residues, from two to 41 amino acid residues, from two to 40 amino acid residues, from two to 36 amino acid residues, from 10 to 60 amino acid residues, from 10 to 51 amino acid residues, from 10 to 50 amino acid residues, from 10 to 46 amino acid residues, from 10 to 45 amino acid residues, from 10 to 41 amino acid residues, from 10 to 40 amino acid residues, or from 10 to 36 amino acid residues. In more specific variations, L1 linking an RNase or SOD1 consists of 16 or 26 amino acid residues. In some embodiments, L1 linking an RNase or a SOD1 comprises or consists of the amino acid sequence shown in SEQ ID NO:10 or SEQ ID NO:12.

In some variations of a fusion polypeptide comprising the formula P-L1-X as described herein, L1 comprises at least 20 amino acid residues. For example, an L1 linker joining the carboxyl-terminus of a paraoxonase to the amino-terminus of another fusion component (e.g., an immunoglobulin Fc region) may comprise at least 25, at least 26, at least 27, at least 28, at least 29, at least 30, at least 31, at least 32, at least 33, at least 34, at least 35, or at least 36 amino acid residues. In certain variations, L1 consists of from 20 to 60 amino acid residues, from 20 to 50 amino acid residues, from 20 to 45 amino acid residues, from 20 to 40 amino acid residues, from 20 to 36 amino acid residues, from 26 to 60 amino acid residues, from 26 to 50 amino acid residues, from 26 to 45 amino acid residues, from 26 to 40 amino acid residues, from 26 to 36 amino acid residues, from 36 to 60 amino acid residues, from 36 to 50 amino acid residues, from 36 to 45 amino acid residues, or from 36 to 40 amino acid residues. In some embodiments, L1 linking the carboxyl-terminus of a paraoxonase comprises or consists of the amino acid sequence shown in SEQ ID NO:12 or SEQ ID NO:14.

Exemplary L2 linkers comprise at least three amino acid residues and are typically up to 60 amino acid residues. In certain variations, L2 linkers comprise at least four, at least five, at least six, at least seven, at least eight, at least 9, or at least 10 amino acid residues. In more specific variations, L2 consists of from six to 30, from six to 25, from six to 20, from seven to 30, from seven to 25, from seven to 20, from eight to 30, from eight to 25, from eight to 20, from nine to 30, from nine to 25, from nine to 20, from 10 to 30, from 10 to 25, from 10 to 20, from 11 to 30, from 11 to 25, from 11 to 20, from 12 to 30, from 12 to 25, or from 12 to 20 amino acid residues. In some embodiments, L2 comprises or consists of the amino acid sequence shown in SEQ ID NO:56.

In certain embodiments, a polypeptide linker comprises a plurality of glycine residues. For example, in some embodiments, a polypeptide linker (e.g., L1) comprises a plurality of glycine residues and optionally at least one serine residue. In particular variations, a polypeptide linker (e.g., L1) comprises the sequence Gly-Gly-Gly-Gly-Ser (SEQ ID NO:29), such as, e.g., two or more tandem repeats of the amino acid sequence of SEQ ID NO:29. In some embodiments, a linker comprises the sequence [Gly-Gly-Gly-Gly-Ser]$_n$ ([SEQ ID NO:29]$_n$), where n is a positive integer such as, for example, an integer from 2 to 8, from 2 to 7, from 2 to 6, from 3 to 8, from 3 to 7, from 3 to 6, from 4 to 8, from 4 to 7, or from 4 to 6. In a specific variation of a polypeptide linker comprising the formula [Gly-Gly-Gly-Gly-Ser]$_n$, n is 4. In another specific variation of a polypeptide linker comprising the formula [Gly-Gly-Gly-Gly-Ser]$_n$, n is 6. In yet another specific variation of a polypeptide linker comprising the formula [Gly-Gly-Gly-Gly-Ser]$_n$, n is 5. In certain embodiments, a polypeptide linker comprises a series of glycine and serine residues (e.g., [Gly-Gly-Gly-Gly-Ser]$_n$, where n is defined as above) inserted between two other sequences of the polypeptide linker (e.g., inserted between Asp-Leu-Ser at the N-terminal end of the linker and Thr-Gly-Leu at the C-terminal end of the linker). In other embodiments, a polypeptide linker includes glycine and serine residues (e.g., [Gly-Gly-Gly-Gly-Ser]$_n$, where n is defined as above) attached at one or both ends of another sequence of the polypeptide linker.

In some embodiments of a fusion polypeptide as above wherein X is present, X is a dimerizing domain. Various dimerization domains are suitable for use in accordance with certain fusion polypeptide embodiments and dimeric fusion proteins as described herein. In certain embodiments of a fusion polypeptide comprising a dimerizing domain, the dimerizing domain is an immunoglobulin heavy chain constant region. The immunoglobulin heavy chain constant region may be a native sequence constant region or a variant constant region. In typical variations, an immunoglobulin heavy chain constant region is capable of binding to the neonatal Fc receptor (FcRn) with sufficient affinity to confer improved half-life to the fusion polypeptide in vivo. A particularly suitable immunoglobulin heavy chain constant region for use in accordance with the present invention is an immunoglobulin Fc region. In some embodiments, the heavy chain constant region lacks one or more effector functions (e.g., one or both of ADCC and CDC effector functions).

In some embodiments of a fusion polypeptide comprising an immunoglobulin Fc region, the immunoglobulin Fc region is a human IgG Fc region having, relative to the wild-type human IgG sequence, an amino acid substitution in the CH2 region so that the molecule is not glycosylated, including but not limited to an amino acid substitution at N297 (Eu numbering for human IgG heavy chain constant region) (corresponding to amino acid position 82 of SEQ ID NO:26, SEQ ID NO:28, SEQ ID NO:116, or SEQ ID NO:118). In another embodiment, the Fc region is human IgG1 (γ1) with the three cysteines of the hinge region (C220, C226, C229) each changed to a non-cysteine residue (e.g., serine) and, optionally, the proline at position 238 of the CH2 domain changed to a non-proline residue (e.g., serine or aspartate). In another embodiment, the Fc region is human γ1 with cysteine C220 changed to a non-cysteine residue (e.g., serine) and, optionally, the proline at position 238 of the CH2 domain changed to a non-proline residue (e.g., serine or aspartate). In another embodiment, the Fc region is human γ1 with N297 changed to a non-asparagine residue (e.g., alanine, glutamine, or glycine). In another embodiment, the Fc region is human γ1 with one or more amino acid substitutions between Eu positions 292 and 300. In another embodiment, the Fc region is human γ1 with one or more amino acid additions or deletions at any position between residues 292 and 300. In another embodiment, the Fc region is human γ1 with an SCC hinge (i.e., with cysteine C220 changed to serine and with a cysteine at each of Eu positions 226 and 229) or an SSS hinge (i.e., each of the three cysteines at Eu positions 220, 226, and 229 changed to serine). In further embodiments, the Fc region is human γ1 with an SCC hinge and an amino acid substitution at P238. In another embodiment, the Fc domain is human γ1 with amino acid substitutions that alter binding by Fc gamma receptors (I, II, III) without affecting FcRn binding important for half-life. In further embodiments, an Fc region is as disclosed in Ehrhardt and Cooper, *Curr. Top. Microbiol. Immunol.* 2010 Aug. 3 (Immunoregulatory Roles for Fc Receptor-Like Molecules); Davis et al., *Ann. Rev. Immunol.* 25:525-60, 2007 (Fc receptor-like molecules); or Swainson et al., *J. Immunol.* 184:3639-47, 2010.

In some embodiments, the Fc region comprises an amino acid substitution that alters the antigen-independent effector functions of the fusion protein. In some such embodiments, the Fc region includes an amino acid substitution that alters the circulating half-life of the resulting molecule. Such Fc variants exhibit either increased or decreased binding to FcRn when compared to an Fc region lacking these substitutions and, therefore, confer increased or decreased half-life, respectively, of the resulting molecule in serum. Fc variants with improved affinity for FcRn are anticipated to have longer serum half-lives, and such Fc variants have useful applications in methods of treating mammals where long half-life of the administered Fc fusion is desired and where increased transport through the lungs to the circulation is desired. In contrast, Fc variants with decreased FcRn binding affinity are expected to have shorter half-lives, and such variants are also useful, for example, for administration to a mammal where a shortened circulation time may be advantageous (e.g., where the fusion protein has toxic side effects when present in the circulation for prolonged periods). For treatment of conditions characterized by NETosis, fine tuning of the half-life of a DNase-Fc fusion protein through altering FcRn binding may be useful since NETs, while contributing to pathogenesis, are also beneficial in certain settings; digestion of pathogenic NETs may not require as long a half-life, so more rapid clearance of the DNase may allow neutrophils to form NETs in their protective anti-microbial function. Fc variants with decreased FcRn binding affinity are also less likely to cross the placenta and, thus, are also useful in the treatment of diseases or disorders in pregnant women. In addition, other applications in which reduced FcRn binding affinity may be desired include those applications in which localization to the brain, kidney, and/or liver is desired. In one exemplary embodiment, the fusion molecules of the invention exhibit reduced transport across the epithelium of kidney glomeruli from the vasculature. In another embodiment, the fusion molecules of the invention exhibit reduced transport across the blood brain barrier (BBB) from the brain, into the vascular space. In one embodiment, a fusion molecule with altered FcRn binding comprises an Fc region having one or more amino acid substitutions within the "FcRn binding loop" of the Fc domain. Exemplary amino acid substitutions that alter FcRn binding activity are disclosed in International PCT Publication No. WO 05/047327, which is incorporated by reference herein. Exemplary amino acid substitutions that increase FcRn binding activity are also described, e.g., by Wang et al., *Protein Cell* 9:63-73, 2018 (see, e.g., Table 1). In some embodiments, an Fc variant with increased FcRn binding activity has an amino acid substitution at each of Eu positions 252, 254, and 256 (e.g., M252Y, S254T, and T256E). In other variations, an Fc variant with increased FcRn binding activity has an amino acid substitution at each of Eu positions 428 and 434 (e.g., M428L and N434S).

In other embodiments, a fusion polypeptide of the present invention comprises an Fc variant comprising an amino acid substitution that alters one or more antigen-dependent effector functions of the polypeptide, in particular antibody-dependent cellular cytotoxicity (ADCC) or complement activation, e.g., as compared to a wild type Fc region. In an exemplary embodiment, such fusion polypeptides exhibit altered binding to an Fc gamma receptor (FcγR, e.g., CD16). Such fusion polypeptides exhibit either increased or decreased binding to FcγR when compared to wild-type polypeptides and, therefore, mediate enhanced or reduced effector function, respectively. Fc variants with improved affinity for FcγRs are anticipated to enhance effector function, and such variants have useful applications in methods of treating mammals where target molecule destruction is desired. In contrast, Fc variants with decreased FcγR binding affinity are expected to reduce effector function, and such fusion proteins are also useful, for example, for treatment of conditions in which target cell destruction is undesirable, e.g., where normal cells may express target molecules, or where chronic administration of the fusion molecule might result in unwanted immune system activation. In one embodiment, the fusion polypeptide comprising an Fc region exhibits at least one altered antigen-dependent effector function selected from the group consisting of opsonization, phagocytosis, complement dependent cytotoxicity (CDC), antibody-dependent cellular cytotoxicity (ADCC), or effector cell modulation as compared to a polypeptide comprising a wild-type Fc region. In typical embodiments of a DNase fusion molecule comprising an Fc variant with altered antigen-dependent effector function, the Fc variant has one or more reduced effector functions relative to the corresponding wild-type Fc region.

In one embodiment, a fusion polypeptide comprising an Fc region exhibits altered binding to an activating FcγR (e.g., FcγI, FcγIIa, or FcγRIIIa). In another embodiment, the fusion protein exhibits altered binding affinity to an inhibitory FcγR (e.g., FcγRIIb). Exemplary amino acid substitutions which alter FcR or complement binding activity are disclosed in International PCT Publication No. WO 05/063815, which is incorporated by reference herein. Exemplary Fc variants with reduced effector function are also described, e.g., by Tam et al., *Antibodies* 6:12, 2017 (describing variants of human IgG1 (γ1) and IgG4 (γ4)); Wang et al., *Protein Cell* 9:63-73, 2018 (see, e.g., Table 1); Lo et al., *J. Biol. Chem.* 292:3900-3908, 2017; Idusogie et al., *J. Immunol.* 164:4178-4184, 2000 (each of which is incorporated by reference herein). Suitable Fc variants that reduce antigen-dependent effector function include, for example, variants having an amino acid substitution at Eu position 238 and/or position 331 (e.g., P238S and/or P331S or P331A). In addition, amino acid substitutions at Eu positions 234 and 235 of human Fc (e.g., L234A/L235A in IgG1, or F234A/L235A in IgG4) reduce FcγR binding and have been shown to reduce cytokine storm when introduced into anti-CD3 mAb (see, e.g., Wang et al., supra), and an amino acid substitution at Eu position 329 (e.g., P329A) is highly effective at reducing C1q binding (see, e.g., Lo et al., supra). Other exemplary approaches to removing ADCC and CDC effector functions is to make hybrid Fc domains derived from human IgG2 (Eu positions 118-260) and IgG4 (Eu positions 261-447), or to modify human IgG2 to contain selected amino acid substitutions from IgG4. See Wang et al., supra.

A fusion polypeptide comprising an Fc region may also comprise an amino acid substitution that alters the glycosylation of the Fc region. For example, the Fc domain of the fusion protein may have a mutation leading to reduced glycosylation (e.g., N- or O-linked glycosylation) or may comprise an altered glycoform of the wild-type Fc domain (e.g., a low fucose or fucose-free glycan). In another embodiment, the molecule has an amino acid substitution near or within a glycosylation motif, for example, an N-linked glycosylation motif that contains the amino acid sequence NXT or NXS. Exemplary amino acid substitutions which reduce or alter glycosylation are disclosed in International PCT Publication No. WO 05/018572 and US Patent Application Publication No. 2007/0111281, which are incorporated by reference herein.

Particularly suitable amino acid substitutions to reduce glycosylation and which also reduce ADCC and CDC effector functions of Fc include amino acid substitutions at Eu position 297 (e.g., N297A, N297Q, or N297G). See, e.g., Wang et al., supra. N297 substitutions may also be paired with substitutions at position 265 (e.g., D265A) to further reduce CDC. See, e.g., Lo et al., supra.

It will be understood by those of skill in the art that various embodiments of Fc variants as described herein can be combined in the fusion polypeptides of the present invention, unless the context clearly indicates otherwise.

In some embodiments, an immunoglobulin Fc region comprises an amino acid sequence having at least 80%, at least 85%, at least 90%, or at least 95% identity with an amino acid sequence selected from sequence shown in (i) residues 1-232 or 1-231 of SEQ ID NO:26, (ii) residues 1-232 or 1-231 of SEQ ID NO:28, (iii) residues 159-390 or 159-389 of SEQ ID NO:42, (iv) residues 1-232 or 1-231 of SEQ ID NO:116, or (v) residues 1-232 or 1-231 of SEQ ID NO:118. In yet other embodiments, the Fc region comprises an amino acid sequence having at least 96%, at least 97%, at least 98%, at least 99%, or 100% identity with the amino acid sequence shown in (i) residues 1-232 or 1-231 of SEQ ID NO:26, (ii) residues 1-232 or 1-231 of SEQ ID NO:28, (iii) residues 159-390 or 159-389 of SEQ ID NO:42, (iv) residues 1-232 or 1-231 of SEQ ID NO:116, or (v) residues 1-232 or 1-231 of SEQ ID NO:118.

In some embodiments, an immunoglobulin heavy chain constant region comprises an amino acid sequence having at least 80%, at least 85%, at least 90%, or at least 95% identity with an amino acid sequence selected from sequence shown in (i) residues 16-232 or 16-231 of SEQ ID NO:26, (ii) residues 16-232 or 16-231 of SEQ ID NO:116, or (iii) residues 16-232 or 16-231 of SEQ ID NO:118. In yet other embodiments, the immunoglobulin heavy chain constant region comprises an amino acid sequence having at least 96%, at least 97%, at least 98%, at least 99%, or 100% identity with the amino acid sequence shown in (i) residues 16-232 or 16-231 of SEQ ID NO:26, (ii) residues 16-232 or 16-231 of SEQ ID NO:116, or (iii) residues 16-232 or 16-231 of SEQ ID NO:118.

In some variations of a fusion polypeptide as above wherein X is present, X is an FcRn-binding domain. Particularly suitable FcRn-binding domains include immunoglobulin heavy chain constant regions that retain FcRn-binding activity such as, e.g., an immunoglobulin Fc region; in some such variations, the Fc region is an Fc region as described herein (e.g., as described above in the context of a dimerizing domain). In other embodiments, an FcRn-binding domain is an albumin (e.g., human albumin). Yet other suitable FcRn-binding domains include single-chain antibodies (e.g., scFvs), peptide aptamers, or alternative scaffold proteins having binding affinity for FcRn; such alternative FcRn-binding molecules are readily created using, for example, display technologies that allow for selection of binding agents through screening of large expression libraries (e.g., libraries of immunoglobulin domains, randomized peptides, or other protein structures). Such display technologies are generally well-known in the art and include, for example, phage display. See, e.g., Antibody Engineering: A Practical Approach, McCafferty, Hoogenboom, and Chiswell Eds., IRL Press 1996. Alternative scaffold proteins for generating FcRn-binding domains include, e.g., avimers, ankyrin repeats, and adnectins, as well as other proteins with domains that can be evolved to generate specific affinity for a desired molecular target (see, e.g., Silverman et al., *Nature Biotechnology* 23:1556-1561, 2005; Zahnd et al., *J. Mol. Biol.* 369:1015-1028, 2007; U.S. Pat. No. 7,115,396 to Lipovsek et al.).

In some embodiments of a paraoxonase fusion polypeptide comprising a DNase as described above, the fusion polypeptide comprises an amino acid sequence having at least 80%, at least 85%, at least 90%, or at least 95% identity with the amino acid sequence shown in (i) residues 21-896 or 1-896 of SEQ ID NO:2, (ii) residues 21-896 or 1-896 of SEQ ID NO:128, (iii) residues 21-896 or 1-896 of SEQ ID NO:130, (iv) residues 21-906 or 1-906 of SEQ ID NO:148, residues 21-896 or 1-896 of SEQ ID NO:158, (vi) residues 21-906 or 1-906 of SEQ ID NO:160, (vii) residues 21-906 or 1-906 of SEQ ID NO:162, or (viii) residues 21-906 or 1-906 of SEQ ID NO:164. In yet other embodiments, the fusion polypeptide comprises an amino acid sequence having at least 96%, at least 97%, at least 98%, at least 99%, or 100% sequence identity with the amino acid sequence shown in (i) residues 21-896 or 1-896 of SEQ ID NO:2, (ii) residues 21-896 or 1-896 of SEQ ID NO:128, (iii) residues 21-896 or 1-896 of SEQ ID NO:130, (iv) residues 21-906 or 1-906 of SEQ ID NO:148, (v) residues 21-896 or 1-896 of SEQ ID NO:158, (vi) residues 21-906 or 1-906 of SEQ ID NO:160, (vii) residues 21-906 or 1-906 of SEQ ID NO:162, or (viii) residues 21-906 or 1-906 of SEQ ID NO:164.

In some embodiments of a paraoxonase fusion polypeptide comprising an RNase as described above, the fusion polypeptide comprises an amino acid sequence having at least 80%, at least 85%, at least 90%, or at least 95% identity with an amino acid sequence selected from the sequence shown in (i) residues 21-764 or 1-764 of SEQ ID NO:40 or (ii) residues 21-740 or 1-740 of SEQ ID NO:48. In yet other embodiments, the fusion polypeptide comprises an amino acid sequence having at least 96%, at least 97%, at least 98%, at least 99%, or 100% sequence identity with the amino acid sequence shown in (i) residues 21-764 or 1-764 of SEQ ID NO:40 or (ii) residues 21-740 or 1-740 of SEQ ID NO:48.

In some embodiments of a paraoxonase fusion polypeptide comprising a superoxide dismutase 1 (SOD1) as described above, the fusion polypeptide comprises an amino acid sequence having at least 80%, at least 85%, at least 90%, or at least 95% identity with an amino acid sequence selected from the sequence shown in (i) residues 23-781 or 1-781 of SEQ ID NO:50, (ii) residues 23-781 or 1-781 of SEQ ID NO:52, or (iii) residues 23-791 or 1-791 of SEQ ID NO:54. In yet other embodiments, the fusion polypeptide comprises an amino acid sequence having at least 96%, at least 97%, at least 98%, at least 99%, or 100% sequence identity with the amino acid sequence shown in (i) residues 23-781 or 1-781 of SEQ ID NO:50, (ii) residues 23-781 or 1-781 of SEQ ID NO:52, or (iii) residues 23-791 or 1-791 of SEQ ID NO:54.

In some embodiments of a paraoxonase fusion polypeptide comprising a CTLA-4 extracellular domain as described above, the fusion polypeptide comprises an amino acid sequence having at least 80%, at least 85%, at least 90%, or at least 95% identity with an amino acid sequence selected from the sequence shown in residues 21-736 or 1-736 of SEQ ID NO:66. In yet other embodiments, the fusion polypeptide comprises an amino acid sequence having at least 96%, at least 97%, at least 98%, at least 99%, or 100% sequence identity with the amino acid sequence shown in residues 21-736 or 1-736 of SEQ ID NO:66.

In some embodiments of a paraoxonase fusion polypeptide comprising a CD40 extracellular domain as described above, the fusion polypeptide comprises an amino acid sequence having at least 80%, at least 85%, at least 90%, or at least 95% identity with an amino acid sequence selected from the sequence shown in (i) residues 21-804 or 1-804 of SEQ ID NO:74, (ii) residues 21-804 or 1-804 of SEQ ID NO:78, (iii) residues 21-804 or 1-804 of SEQ ID NO:82, (iv) residues 21-804 or 1-804 of SEQ ID NO:86, or (v) residues 21-804 or 1-804 of SEQ ID NO:90. In yet other embodiments, the fusion polypeptide comprises an amino acid sequence having at least 96%, at least 97%, at least 98%, at least 99%, or 100% sequence identity with the amino acid sequence shown in (i) residues 21-804 of SEQ ID NO:74 or 1-804, (ii) residues 21-804 or 1-804 of SEQ ID NO:78, (iii)

residues 21-804 or 1-804 of SEQ ID NO:82, (iv) residues 21-804 or 1-804 of SEQ ID NO:86, or (v) residues 21-804 or 1-804 of SEQ ID NO:90.

In some embodiments of a paraoxonase fusion polypeptide comprising a polypeptide that specifically binds and neutralizes TNFα as described above, the fusion polypeptide comprises an amino acid sequence having at least 80%, at least 85%, at least 90%, or at least 95% identity with an amino acid sequence selected from the sequence shown in (i) residues 21-860 or 1-860 of SEQ ID NO:94 or (ii) residues 21-860 or 1-860 of SEQ ID NO:98. In yet other embodiments, the fusion polypeptide comprises an amino acid sequence having at least 96%, at least 97%, at least 98%, at least 99%, or 100% sequence identity with the amino acid sequence shown in (i) residues 21-860 or 1-860 of SEQ ID NO:94 or (ii) residues 21-860 or 1-860 of SEQ ID NO:98.

In some embodiments of a paraoxonase fusion polypeptide comprising a polypeptide that specifically binds and neutralizes TGF-β as described above, the fusion polypeptide comprises an amino acid sequence having at least 80%, at least 85%, at least 90%, or at least 95% identity with an amino acid sequence selected from the sequence shown in (i) residues 21-861 or 1-861 of SEQ ID NO:102 or (ii) residues 21-861 or 1-861 of SEQ ID NO:106. In yet other embodiments, the fusion polypeptide comprises an amino acid sequence having at least 96%, at least 97%, at least 98%, at least 99%, or 100% sequence identity with the amino acid sequence shown in (i) residues 21-861 or 1-861 of SEQ ID NO:102 or (ii) residues 21-861 or 1-861 of SEQ ID NO:106.

In some embodiments of a paraoxonase fusion polypeptide comprising the formula X-L2-P as described herein, the fusion polypeptide comprises an amino acid sequence having at least 80%, at least 85%, at least 90%, or at least 95% identity with the amino acid sequence shown in (i) residues 21-613 or 1-613 of SEQ ID NO:122, (ii) residues 21-613 or 1-613 of SEQ ID NO:132, (iii) 21-613 or 1-613 of SEQ ID NO:134, (iv) residues 21-610 or 1-610 of SEQ ID NO:142, (v) residues 21-610 or 1-610 of SEQ ID NO:144, or (vi) residues 21-610 or 1-610 of SEQ ID NO:146. In yet other embodiments, the fusion polypeptide comprises an amino acid sequence having at least 96%, at least 97%, at least 98%, at least 99%, or 100% sequence identity with the amino acid sequence shown in (i) residues 21-613 or 1-613 of SEQ ID NO:122, (ii) residues 21-613 or 1-613 of SEQ ID NO:132, (iii) 21-613 or 1-613 of SEQ ID NO:134, (iv) residues 21-610 or 1-610 of SEQ ID NO:142, (v) residues 21-610 or 1-610 of SEQ ID NO:144, or (vi) residues 21-610 or 1-610 of SEQ ID NO:146.

The present invention also provides dimeric proteins comprising first and second polypeptide fusions, each of the polypeptide fusions comprising a dimerizing domain, as described above. Accordingly, in another aspect, the present invention provides a dimeric protein comprising a first fusion polypeptide and a second fusion polypeptide, wherein each of the first and second fusion polypeptides comprises, from an amino-terminal position to a carboxyl-terminal position, T-L1-X-L2-P, wherein T is a first biologically active polypeptide is selected from a DNase, and RNase, a superoxide dismutase 1 (SOD1), a cytotoxic T-lymphocyte associated molecule-4 (CTLA-4) extracellular domain, a CD40 extracellular domain, and a polypeptide that specifically binds and neutralizes an inflammatory cytokine (e.g., a polypeptide that specifically binds and neutralizes tumor necrosis factor α (TNFα) or transforming growth factor-β (TGF-β)); L1 is a first polypeptide linker that is optionally present; X is a dimerizing domain; L2 is a second polypeptide linker that is optionally present; and P is a biologically active paraoxonase. In another aspect, the present invention provides a dimeric protein comprising a first fusion polypeptide and a second fusion polypeptide, wherein each of the first and second fusion polypeptides comprises, from an amino-terminal position to a carboxyl-terminal position, X-L2-P, wherein X is a dimerizing domain, L2 is a polypeptide linker that is optionally present, and P is a biologically active paraoxonase. In another aspect, the present invention provides a dimeric protein comprising a first fusion polypeptide and a second fusion polypeptide, wherein each of the first and second fusion polypeptides comprises, from an amino-terminal position to a carboxyl-terminal position, P-L1-X, wherein P is a biologically active paraoxonase, L1 is a polypeptide linker, and X is a dimerizing domain.

III. Materials and Methods for Making Polypeptide Fusions and Dimeric Proteins The present invention also provides polynucleotide molecules, including DNA and RNA molecules, that encode the fusion polypeptides disclosed above. The polynucleotides of the present invention include both single-stranded and double-stranded molecules. Polynucleotides encoding various segments of a fusion polypeptide (e.g., an Fc fragment; DNase and P polypeptide segments) can be generated and linked together to form a polynucleotide encoding a fusion polypeptide as described herein using known methods for recombinant manipulation of nucleic acids.

DNA sequences encoding fusion components in accordance with the present disclosure (for example, DNases (e.g., DNase 1), paraoxonases (e.g., PON1), RNases (e.g., RNase 1), superoxide dismutase 1 (SOD1), CTLA-4 and CD40 extracellular domains, and immunoglobulin Fc regions) are generally known in the art. Exemplary DNA sequences are disclosed herein (see Sequence Listing). Additional DNA sequences encoding any of these polypeptides can be readily generated by those of ordinary skill in the art based on the genetic code. Counterpart RNA sequences can be generated by substitution of U for T. Those skilled in the art will readily recognize that, in view of the degeneracy of the genetic code, considerable sequence variation is possible among polynucleotide molecules encoding a given polypeptide. DNA and RNA encoding functional variants and fragments of such polypeptides can also be obtained using known recombinant methods to introduce variation into a polynucleotide sequence, followed by expression of the encoded polypeptide and determination of functional activity (e.g., nuclease activity) using an appropriate screening assay.

Methods for preparing DNA and RNA are well known in the art. For example, complementary DNA (cDNA) clones can be prepared from RNA that is isolated from a tissue or cell that produces large amounts of RNA encoding a polypeptide of interest. Total RNA can be prepared using guanidine HCl extraction followed by isolation by centrifugation in a CsCl gradient (Chirgwin et al., *Biochemistry* 18:52-94, 1979). Poly $(A)^+$ RNA is prepared from total RNA using the method of Aviv and Leder (*Proc. Natl. Acad. Sci. USA* 69:1408-1412, 1972). Complementary DNA is prepared from poly$(A)^+$ RNA using known methods. In the alternative, genomic DNA can be isolated. Methods for identifying and isolating cDNA and genomic clones are well known and within the level of ordinary skill in the art, and include the use of the sequences disclosed herein, or parts thereof, for probing or priming a library. Polynucleotides encoding polypeptides of interest are identified and isolated by, for example, hybridization or polymerase chain reaction ("PCR," Mullis, U.S. Pat. No. 4,683,202). Expression libraries can be probed with antibodies to the polypeptide of interest, receptor fragments, or other specific binding partners.

The polynucleotides of the present invention can also be prepared by automated synthesis. The production of short, double-stranded segments (60 to 80 bp) is technically straightforward and can be accomplished by synthesizing the complementary strands and then annealing them. Longer segments (typically >300 bp) are assembled in modular form from single-stranded fragments that are from 20 to 100 nucleotides in length. Automated synthesis of polynucleotides is within the level of ordinary skill in the art, and suitable equipment and reagents are available from commercial suppliers. See generally Glick and Pasternak, *Molecular Biotechnology, Principles & Applications of Recombinant DNA*, ASM Press, Washington, D.C., 1994; Itakura et al., *Ann. Rev. Biochem.* 53:323-356, 1984; and Climie et al., *Proc. Natl. Acad. Sci. USA* 87:633-637, 1990.

In another aspect, materials and methods are provided for producing the polypeptide fusions of the present invention, including dimeric proteins comprising the fusion polypeptides. The fusion polypeptides can be produced in genetically engineered host cells according to conventional techniques. Suitable host cells are those cell types that can be transformed or transfected with exogenous DNA and grown in culture, and include bacteria, fungal cells, and cultured higher eukaryotic cells (including cultured cells of multicellular organisms), particularly cultured mammalian cells. Techniques for manipulating cloned DNA molecules and introducing exogenous DNA into a variety of host cells are disclosed by Sambrook et al., *Molecular Cloning: A Laboratory Manual,* 2nd ed., Cold Spring Harbor Laboratory Press, Cold Spring Harbor, NY, 1989, and Ausubel et al., eds., *Current Protocols in Molecular Biology, Green and* Wiley and Sons, NY, 1993.

In general, for production of a fusion polypeptide in a host cell, a DNA sequence encoding the fusion polypeptide is operably linked to other genetic elements required for its expression, typically including a transcription promoter and terminator, within an expression cassette. Typically, the expression cassette is contained within an expression vector for delivery into a host cell. The vector will also commonly contain one or more selectable markers and one or more origins of replication, although those skilled in the art will recognize that within certain systems selectable markers may be provided on separate vectors, and replication of the exogenous DNA may be provided by integration of an expression cassette into the host cell genome such as, e.g., in the generation of stable cell lines. Selection of promoters, terminators, selectable markers, vectors and other elements is a matter of routine design within the level of ordinary skill in the art. Many such elements are described in the literature and are available through commercial suppliers.

To direct a DNase fusion polypeptide into the secretory pathway of a host cell, a secretory signal sequence is provided in the expression cassette. The encoded secretory peptide may be that of a corresponding native protein (e.g., a native DNase secretory peptide as shown in amino acid residues 1-22 of SEQ ID NO:16, a native RNase secretory peptide as shown in amino acid residues 1-28 of SEQ ID NO:38, or a native CD40 secretory peptide as shown in amino acid residues 1-20 of SEQ ID NO:68), or may be derived from another secreted protein (e.g., t-PA; see U.S. Pat. No. 5,641,655) or synthesized de novo. An engineered cleavage site may be included at the junction between the secretory peptide and the remainder of the polypeptide fusion to optimize proteolytic processing in the host cell. The secretory signal sequence is operably linked to the DNA sequence encoding the polypeptide fusion, i.e., the two sequences are joined in the correct reading frame and positioned to direct the newly synthesized polypeptide fusion into the secretory pathway of the host cell. Secretory signal sequences are commonly positioned 5' to the DNA sequence encoding the polypeptide of interest, although certain signal sequences may be positioned elsewhere in the DNA sequence of interest (see, e.g., Welch et al., U.S. Pat. No. 5,037,743; Holland et al., U.S. Pat. No. 5,143,830). Secretory signal sequences suitable for use in accordance with the present invention include, for example, polynucleotides encoding the human VK3 leader peptide (SEQ ID NO:58).

Expression of fusion polypeptides comprising a dimerizing domain as described herein, via a host cell secretory pathway, is expected to result in the production of dimeric proteins. Accordingly, in another aspect, the present invention provides dimeric proteins comprising first and second fusion polypeptides as described above (e.g., a dimeric protein comprising a first fusion polypeptide and a second fusion polypeptide, wherein each of the first and second fusion polypeptides comprises, from an amino-terminal position to a carboxyl-terminal position, T-L1-X-L2-P, X-L2-P, or P-L1-X as described herein). Dimers may also be assembled in vitro upon incubation of component polypeptides under suitable conditions. In general, in vitro assembly will include incubating the protein mixture under denaturing and reducing conditions followed by refolding and reoxidation of the polypeptides to form dimers. Recovery and assembly of proteins expressed in bacterial cells is disclosed below.

Cultured mammalian cells are suitable hosts for use within the present invention. Methods for introducing exogenous DNA into mammalian host cells include calcium phosphate-mediated transfection (Wigler et al., *Cell* 14:725, 1978; Corsaro and Pearson, *Somatic Cell Genetics* 7:603, 1981: Graham and Van der Eb, *Virology* 52:456, 1973), electroporation (Neumann et al., *EMBO J.* 1:841-845, 1982), DEAE-dextran mediated transfection (Ausubel et al., supra), and liposome-mediated transfection (Hawley-Nelson et al., *Focus* 15:73, 1993; Ciccarone et al., *Focus* 15:80, 1993). The production of recombinant polypeptides in cultured mammalian cells is disclosed by, for example, Levinson et al., U.S. Pat. No. 4,713,339; Hagen et al., U.S. Pat. No. 4,784,950; Palmiter et al., U.S. Pat. No. 4,579,821; and Ringold, U.S. Pat. No. 4,656,134. Suitable cultured mammalian cells include the COS-1 (ATCC No. CRL 1650), COS-7 (ATCC No. CRL 1651), BHK (ATCC No. CRL 1632), BHK 570 (ATCC No. CRL 10314), 293 (ATCC No. CRL 1573; Graham et al., *J. Gen. Virol.* 36:59-72, 1977) and Chinese hamster ovary (e.g., CHO-K1, ATCC No. CCL 61; CHO-DG44, Urlaub et al., *Proc. Natl. Acad. Sci. USA* 77:4216-4220, 1980) cell lines. Additional suitable cell lines are known in the art and available from public depositories such as the American Type Culture Collection, Manassas, Virginia. Strong transcription promoters can be used, such as promoters from SV-40, cytomegalovirus, or myeloproliferative sarcoma virus. See, e.g., U.S. Pat. No. 4,956,288 and U.S. Patent Application Publication No. 20030103986. Other suitable promoters include those from metallothionein genes (U.S. Pat. Nos. 4,579,821 and 4,601,978) and the adenovirus major late promoter. Expression vectors for use in mammalian cells include pZP-1, pZP-9, and pZMP21, which have been deposited with the American Type Culture Collection, 10801 University Blvd., Manassas, VA USA under accession numbers 98669, 98668, and PTA-5266, respectively, and derivatives of these vectors.

Drug selection is generally used to select for cultured mammalian cells into which foreign DNA has been inserted. Such cells are commonly referred to as "transfectants." Cells that have been cultured in the presence of the selective agent and are able to pass the gene of interest to their progeny—by virtue of integration of the expression cassette into its genomic DNA—are referred to as "stable transfectants." An exemplary selectable marker is a gene encoding resistance to the antibiotic neomycin. Selection is carried out in the presence of a neomycin-type drug, such as G-418 or the like. Selection systems can also be used to increase the expression level of the gene of interest, a process referred to as "amplification." Amplification is carried out by culturing transfectants in the presence of a low level of the selective agent and then increasing the amount of selective agent to select for cells that produce high levels of the products of the introduced genes. An exemplary amplifiable selectable marker is dihydrofolate reductase, which confers resistance to methotrexate. Other drug resistance genes (e.g., hygromycin resistance, multi-drug resistance, puromycin acetyltransferase) can also be used. Cell-surface markers and other phenotypic selection markers can be used to facilitate identification of transfected cells (e.g., by fluorescence-activated cell sorting), and include, for example, CD8, CD4, nerve growth factor receptor, green fluorescent protein, and the like.

In some aspects, the present invention provides a stable cell line containing, within its genomic DNA, an expression cassette encoding a paraoxonase fusion polypeptide as described herein, wherein the stable cell line constitutively expresses the encoded paraoxonase fusion. Stable cell lines can be generated by methods generally known in the art, which generally include the identification of single stable cell clones from a polyclonal colony of stable transfectants by limited dilution and expansion. Protein expression of selected clones can then be assessed to identify high-expressing clones for expansion. In some embodiments, the stable cell line is a mammalian cell line such as, e.g., a Chinese hamster ovary (CHO) cell line. In some preferred embodiments of a stable cell line constitutively expressing a DNase-PON fusion polypeptide in accordance with the present disclosure, the DNase is an enhanced DNase1 as described herein; in some such embodiments, the DNase-PON fusion polypeptide is an enhanced DNase1-Fc-PON1 fusion polypeptide comprising an amino acid sequence having at least 90%, at least 95%, at least 96%, at least 97%, at least 98%, at least 99%, or 100% identity with the amino acid sequence shown in (i) residues 21-896 or 1-896 of SEQ ID NO:2, (ii) residues 21-906 or 1-906 of SEQ ID NO:148, (iii) residues 21-896 or 1-896 of SEQ ID NO:158, or (iv) residues 21-906 or 1-906 of SEQ ID NO:160. In some variations, the stable cell line is a mammalian cell line (e.g., CHO) capable of producing the fusion polypeptide (e.g., a DNase1-Fc-PON1 fusion polypeptide) at a concentration of at least 25 mg/L, at least 50 mg/L, at least 100 mg/L, at least 200 mg/L, or at least 500 mg/L of the cell culture. Typically, a DNase1-Fc fusion polypeptide as described herein can be expressed at levels of approximately 25-100 mg/L from initial isolated clones. Recloning of the initial cultures can often stabilize and increase expression by 2-3 fold. Amplification of the expression level can also be achieved by further plating of cells at low density in increasing levels of methotrexate from an initial concentration of 50 nM up to as much as 1 uM. Once cells have adapted, further rounds of limiting dilution cloning are required to maintain high expression levels.

Other higher eukaryotic cells can also be used as hosts, including insect cells, plant cells and avian cells. The use of *Agrobacterium rhizogenes* as a vector for expressing genes in plant cells has been reviewed by Sinkar et al., *J. Biosci.* (Bangalore) 11:47-58, 1987. Transformation of insect cells and production of foreign polypeptides therein is disclosed by Guarino et al., U.S. Pat. No. 5,162,222 and International PCT Publication No. WO 94/06463.

Insect cells can be infected with recombinant baculovirus, commonly derived from *Autographa californica* nuclear polyhedrosis virus (AcNPV) (see King and Possee, *The Baculovirus Expression System: A Laboratory Guide*, Chapman & Hall, London; O'Reilly et al., *Baculovirus Expression Vectors: A Laboratory Manual, Oxford University Press*., New York, 1994; and Richardson, Ed., *Baculovirus Expression Protocols. Methods in Molecular Biology*, Humana Press, Totowa, NJ, 1995). Recombinant baculovirus can also be produced through the use of a transposon-based system described by Luckow et al. (*J. Virol.* 67:4566-4579, 1993). This system, which utilizes transfer vectors, is commercially available in kit form (BAC-TO-BAC kit; Life Technologies, Gaithersburg, MD). The transfer vector (e.g., PFASTBAC1; Life Technologies) contains a Tn7 transposon to move the DNA encoding the protein of interest into a baculovirus genome maintained in *E. coli* as a large plasmid called a "bacmid" (see Hill-Perkins and Possee, *J. Gen. Virol.* 71:971-976, 1990; Bonning et al., *J. Gen. Virol.* 75:1551-1556, 1994; Chazenbalk and Rapoport, *J. Biol. Chem.* 270:1543-1549, 1995). Using techniques known in the art, a transfer vector encoding a polypeptide fusion is transformed into *E. coli* host cells, and the cells are screened for bacmids which contain an interrupted lacZ gene indicative of recombinant baculovirus. The bacmid DNA containing the recombinant baculovirus genome is isolated, using common techniques, and used to transfect *Spodoptera frugiperda* cells, such as Sf9 cells. Recombinant virus that expresses the polypeptide fusion is subsequently produced. Recombinant viral stocks are made by methods commonly used in the art.

For protein production, the recombinant virus is used to infect host cells, typically a cell line derived from the fall armyworm, *Spodoptera frugiperda* (e.g., Sf9 or Sf21 cells) or *Trichoplusia ni* (e.g., HIGH FIVE cells; Invitrogen, Carlsbad, CA) (see generally Glick and Pasternak, supra; see also U.S. Pat. No. 5,300,435). Serum-free media are used to grow and maintain the cells. Suitable media formulations are known in the art and can be obtained from commercial suppliers. The cells are grown up from an inoculation density of approximately 2-5×$10^5$ cells to a density of 1-2×$10^6$ cells, at which time a recombinant viral stock is added at a multiplicity of infection (MOI) of 0.1 to 10, more typically near 3. Procedures used are generally described in available laboratory manuals (e.g., King and Possee, supra; O'Reilly et al., supra.; Richardson, supra).

Fungal cells, including yeast cells, can also be used within the present invention. Yeast species of particular interest in this regard include *Saccharomyces cerevisiae, Pichia pastoris*, and *Pichia methanolica*. Methods for transforming *S. cerevisiae* cells with exogenous DNA and producing recombinant polypeptides therefrom are disclosed by, for example, Kawasaki, U.S. Pat. No. 4,599,311; Kawasaki et al., U.S. Pat. No. 4,931,373; Brake, U.S. Pat. No. 4,870,008; Welch et al., U.S. Pat. No. 5,037,743; and Murray et al., U.S. Pat.

No. 4,845,075. Transformed cells are selected by phenotype determined by the selectable marker, commonly drug resistance or the ability to grow in the absence of a particular nutrient (e.g., leucine). An exemplary vector system for use in *Saccharomyces cerevisiae* is the POT1 vector system disclosed by Kawasaki et al. (U.S. Pat. No. 4,931,373), which allows transformed cells to be selected by growth in glucose-containing media. Suitable promoters and terminators for use in yeast include those from glycolytic enzyme genes (see, e.g., Kawasaki, U.S. Pat. No. 4,599,311; Kingsman et al., U.S. Pat. No. 4,615,974; and Bitter, U.S. Pat. No. 4,977,092) and alcohol dehydrogenase genes. See also U.S. Pat. Nos. 4,990,446; 5,063,154; 5,139,936; and 4,661,454. Transformation systems for other yeasts, including *Hansenula polymorpha, Schizosaccharomyces pombe, Kluyveromyces lactis, Kluyveromyces fragilis, Ustilago maydis, Pichia pastoris, Pichia methanolica, Pichia guillermondii*, and *Candida maltosa* are known in the art. See, e.g., Gleeson et al., *J. Gen. Microbiol.* 132:3459-3465, 1986; Cregg, U.S. Pat. No. 4,882,279; and Raymond et al., *Yeast* 14:11-23, 1998. *Aspergillus* cells may be utilized according to the methods of McKnight et al., U.S. Pat. No. 4,935,349. Methods for transforming *Acremonium chrysogenum* are disclosed by Sumino et al., U.S. Pat. No. 5,162,228. Methods for transforming *Neurospora* are disclosed by Lambowitz, U.S. Pat. No. 4,486,533. Production of recombinant proteins in *Pichia methanolica* is disclosed in U.S. Pat. Nos. 5,716,808; 5,736,383; 5,854,039; and 5,888,768.

Prokaryotic host cells, including strains of the bacteria *Escherichia coli, Bacillus* and other genera are also useful host cells within the present invention. Techniques for transforming these hosts and expressing foreign DNA sequences cloned therein are well-known in the art (see, e.g., Sambrook et al., supra). When expressing a fusion polypeptide in bacteria such as *E. coli*, the polypeptide may be retained in the cytoplasm, typically as insoluble granules, or may be directed to the periplasmic space by a bacterial secretion sequence. In the former case, the cells are lysed, and the granules are recovered and denatured using, for example, guanidine HCl or urea. The denatured polypeptide can then be refolded and dimerized by diluting the denaturant, such as by dialysis against a solution of urea and a combination of reduced and oxidized glutathione, followed by dialysis against a buffered saline solution. In the alternative, the protein may be recovered from the cytoplasm in soluble form and isolated without the use of denaturants. The protein is recovered from the cell as an aqueous extract in, for example, phosphate buffered saline. To capture the protein of interest, the extract is applied directly to a chromatographic medium, such as an immobilized antibody or heparin-Sepharose column. Secreted polypeptides can be recovered from the periplasmic space in a soluble and functional form by disrupting the cells (by, for example, sonication or osmotic shock) and recovering the protein, thereby obviating the need for denaturation and refolding. See, e.g., Lu et al., *J. Immunol. Meth.* 267:213-226, 2002.

Transformed or transfected host cells are cultured according to conventional procedures in a culture medium containing nutrients and other components required for the growth of the chosen host cells. A variety of suitable media, including defined media and complex media, are known in the art and generally include a carbon source, a nitrogen source, essential amino acids, vitamins and minerals. Media may also contain such components as growth factors or serum, as required. The growth medium will generally select for cells containing the exogenously added DNA by, for example, drug selection or deficiency in an essential nutrient which is complemented by the selectable marker carried on the expression vector or co-transfected into the host cell.

In some variations, for production of an actin-resistant DNase1-PON fusion polypeptide as described herein (e.g., an actin-resistant DNase1-L1-Fc-L2-PON1 fusion polypeptide comprising an amino acid sequence having at least 90%, at least 95%, at least 96%, at least 97%, at least 98%, at least 99%, or 100% identity with the amino acid sequence shown in (i) residues 21-896 or 1-896 of SEQ ID NO:2 or (ii) residues 21-906 or 1-906 of SEQ ID NO:148), host cells are cultured in the presence of a DNase1 inhibitor to reduce toxicity of the enhanced DNase during its expression. DNase1 inhibitors are generally known in the art and include, for example, the inhibitor rutin (see, e.g., Kolarevic et al., *Chem. Biodiversity* 16:e1900060, 2019). In certain embodiments, the host cells cultured in the presence of a DNase1 inhibitor are mammalian cells such as, e.g., CHO.

Proteins of the present invention are purified by conventional protein purification methods, typically by a combination of chromatographic techniques. See generally *Affinity Chromatography: Principles* & Methods, Pharmacia LKB Biotechnology, Uppsala, Sweden, 1988; and Scopes, *Protein Purification: Principles and Practice*, Springer-Verlag, New York, 1994. Proteins comprising an immunoglobulin Fc region can be purified by affinity chromatography on immobilized protein A. Additional purification steps, such as gel filtration, can be used to obtain the desired level of purity or to provide for desalting, buffer exchange, and the like.

For example, fractionation and/or conventional purification methods can be used to obtain fusion polypeptides and dimeric proteins of the present invention purified from recombinant host cells. In general, ammonium sulfate precipitation and acid or chaotrope extraction may be used for fractionation of samples. Exemplary purification steps may include hydroxyapatite, size exclusion, FPLC and reverse-phase high performance liquid chromatography. Suitable chromatographic media include derivatized dextrans, agarose, cellulose, polyacrylamide, specialty silicas, and the like. PEI, DEAE, QAE and Q derivatives are suitable. Exemplary chromatographic media include those media derivatized with phenyl, butyl, or octyl groups, such as Phenyl-Sepharose FF (Pharmacia), Toyopearl butyl 650 (Toso Haas, Montgomeryville, PA), Octyl-Sepharose (Pharmacia) and the like; or polyacrylic resins, such as Amberchrom CG 71 (Toso Haas) and the like. Suitable solid supports include glass beads, silica-based resins, cellulosic resins, agarose beads, cross-linked agarose beads, polystyrene beads, cross-linked polyacrylamide resins and the like that are insoluble under the conditions in which they are to be used. These supports may be modified with reactive groups that allow attachment of proteins by amino groups, carboxyl groups, sulfhydryl groups, hydroxyl groups and/or carbohydrate moieties.

Examples of coupling chemistries include cyanogen bromide activation, N-hydroxysuccinimide activation, epoxide activation, sulfhydryl activation, hydrazide activation, and carboxyl and amino derivatives for carbodiimide coupling chemistries. These and other solid media are well-known and widely used in the art, and are available from commercial suppliers. Selection of a particular method for polypeptide isolation and purification is a matter of routine design and is determined in part by the properties of the chosen support. See, e.g., *Affinity Chromatography: Principles* & Methods (Pharmacia LKB Biotechnology 1988); Doonan, *Protein Purification Protocols* (The Humana Press 1996).

Additional variations in protein isolation and purification can be devised by those of skill in the art. For example, antibodies that specifically bind a fusion polypeptide or dimeric protein as described herein (e.g., an antibody that specifically binds a polypeptide segment corresponding to a DNase) can be used to isolate large quantities of protein by immunoaffinity purification.

The proteins of the present invention can also be isolated by exploitation of particular properties. For example, immobilized metal ion adsorption (IMAC) chromatography can be used to purify histidine-rich proteins, including those comprising polyhistidine tags. Briefly, a gel is first charged with divalent metal ions to form a chelate (Sulkowski, *Trends in Biochem.* 3:1, 1985). Histidine-rich proteins will be adsorbed to this matrix with differing affinities, depending upon the metal ion used, and will be eluted by competitive elution, lowering the pH, or use of strong chelating agents. Other methods of purification include purification of glycosylated proteins by lectin affinity chromatography and ion exchange chromatography (see, e.g., M. Deutscher, (ed.), *Meth. Enzymol.* 182:529, 1990). Within additional embodiments of the invention, a fusion of the polypeptide of interest and an affinity tag (e.g., maltose-binding protein) may be constructed to facilitate purification. Moreover, receptor- or ligand-binding properties of a fusion polypeptide or dimer thereof can be exploited for purification.

In some variations, a DNase1-PON fusion molecule comprising an enhanced but non-actin-resistant DNase1 as described herein (i.e., a DNase that does not contain any amino acid substitution, relative to human DNase1, that decreases G-actin-induced inhibition of endonuclease activity of the DNase relative to human DNase1) is treated with ethylenediamine (EDA) following purification in order to reduce the molecule's actin binging, thereby providing a DNase-Fc fusion molecule that is resistant to actin. The EDA-treated DNase1-PON fusion molecule is then further treated to remove EDA using methods generally known in the art (see, e.g., U.S. Pat. No. 11,225,648). Such embodiments are advantageous for achieving higher expression of the DNase1-PON fusion for pharmaceutical use, since expression of the non-actin-resistant form of enhanced DNase1 would be less toxic to host cells (e.g., CHO). In particular embodiments, the purified DNase1-PON to be treated with EDA comprises an amino acid sequence having at least 90%, at least 95%, at least 96%, at least 97%, at least 98%, at least 99%, or 100% identity with the amino acid sequence shown in (i) residues 21-896 of SEQ ID NO:158 or (ii) residues 21-906 of SEQ ID NO:160.

The polypeptides of the present invention are typically purified to at least about 80% purity, more typically to at least about 90% purity and preferably to at least about 95%, at least about 96%, at least about 97%, at least about 98%, or at least about 99% purity with respect to contaminating macromolecules, particularly other proteins and nucleic acids, and free of infectious and pyrogenic agents. The polypeptides of the present invention may also be purified to a pharmaceutically pure state, which is greater than 99.9% pure. In certain preparations, purified polypeptide is substantially free of other polypeptides, particularly other polypeptides of animal origin.

IV. Methods of Use and Pharmaceutical Compositions

The fusion polypeptides and dimeric proteins of the present invention can be used to provide therapy for the treatment of various diseases or disorders. The paraoxonase fusion polypeptides are particularly useful, e.g., for treatment of inflammatory, autoimmune, neurological, cardiovascular, and/or fibrotic diseases and disorders. In aspects relating to bispecific fusions further comprising a first biologically active polypeptide as described herein (e.g., a DNase, RNase, or SOD1), the fusion polypeptides and dimeric proteins may further provide one or more additional biological activities for treatment. For example, paraoxonase fusion polypeptides comprising a DNase or an RNase are particularly useful, e.g., for treatment of diseases and disorders characterized by NETosis. In addition, paraoxonase fusion polypeptides comprising a CTLA-4 or CD40 extracellular domain are particularly useful, e.g., for treatment of diseases or disorders characterized by an aberrant adaptive immune response. As yet another example, paraoxonase fusion polypeptides comprising a CD40 extracellular domain or a polypeptide that specifically binds and neutralizes TGF-β are particularly useful, e.g., for treatment of diseases and disorders characterized by a fibrotic inflammatory response.

In some aspects, the present invention provides methods for treating a disease or disorder selected from an inflammatory disease, an autoimmune disease, a neurological disease, an infectious disease, a metabolic disease, a cardiovascular disease, a liver disease, a fibrotic disease, thrombosis, sepsis, ischemia reperfusion, biofilm formation by a gram-negative bacteria, exposure to sulfur mustard gas, exposure to an organophosphate, and cancer. The methods generally include administering to a subject having the disease or disorder an effective amount of a fusion polypeptide or dimeric protein as described herein.

Inflammatory diseases amenable to treatment in accordance with the present invention include, for example, inflammatory lung diseases such as, for example, asthma, cystic fibrosis (CF), chronic obstructive pulmonary disease (COPD), bronchiectasis, hypoxia, interstitial lung disease (e.g., idiopathic pulmonary fibrosis (IPF) or sarcoidosis), and acute respiratory distress syndrome (ARDS). In particular embodiments comprising treatment of ARDS, the ARDS is associated with COVID-19. In some embodiments, the inflammatory lung disease is characterized by *Pseudomonas aeruginosa* infection. In some variations, a patient having the inflammatory lung disease is a patient that has been exposed to sulfur mustard gas (SM). In other variations, a patient having the inflammatory lung disease is a patient that has been exposed to an organophosphate, such as an insecticide (e.g., parathion, malathion, chlorpyrifos, diazinon, dichlorvos, phosmet, fenitrothion, terbufos, tetrachlorvinphos, azamethiphos, or azinphos-methyl) or other neurotoxin (e.g., tabun, sarin, soman, or cyclosarin).

Other inflammatory diseases amenable to treatment in accordance with the present invention include autoinflammatory diseases (i.e., innate immune system activation disorders characterized by seemingly unprovoked episodes of inflammation and a relative lack of obvious autoimmune pathology). Exemplary autoinflammatory diseases include inflammatory bowel disease (IBD) (e.g., Crohn's disease, ulcerative colitis), Behcet's disease, systemic onset juvenile idiopathic arthritis (JIA), gout, pseudogout, storage (Gaucher's) disorders, hereditary angioedema (HAE), atypical hemolytic uremic syndrome, familial Mediterranean fever (FMF), TNF-receptor associated periodic fever syndrome (TRAPS), cryopyrin-associated periodic syndromes (CAPS)), NOD2-associated autoinflammatory disease (NAID), and Blau syndrome.

In yet other embodiments, an inflammatory disease or disorder for treatment in accordance with the present invention is selected from rheumatoid arthritis, systemic lupus erythematosus, multiple sclerosis, type 1 diabetes, type 2 diabetes, hepatitis (e.g., non-alcoholic steatohepatitis (NASH)), ankylosing spondylitis, psoriasis, psoriatic arthritis, dermatitis (e.g., atopic dermatitis), diverticulitis, irritable bowel syndrome, and nephritis. In still other variations, the inflammatory disease or disorder is an inflammatory skin disease such as, e.g., psoriasis or atopic dermatitis.

In more particular embodiments of a method for treating an inflammatory disease, a fusion molecule for the inflammatory disease treatment is a polypeptide having the structure DNase1-L1-Fc-L2-PON1, DNase1L3-L1-Fc-L2-PON1, RNase1-L1-Fc-L2-PON1, RNase 1-Fc-L2-PON1, SOD1-L1-Fc-L2-PON1, SOD1-Fc-L2-PON1, CTLA4-L1-Fc-L2-PON1, CTLA4-Fc-L2-PON1, CD40-L1-Fc-L2-PON1, CD40-Fc-L2-PON1, antiTNFα-L1-Fc-L2-PON1, antiTNFα-Fc-L2-PON1, antiTGFβ-L1-Fc-L2-PON1, antiTGFβ-Fc-L2-PON1, Fc-L2-PON1, or PON1-L1-Fc, or a dimeric protein formed by dimerization of any of the foregoing fusion polypeptides; in some such embodiments, the fusion polypeptide comprises or consists of an amino acid sequence having at least 90%, at least 95%, or 100% identity with the amino acid sequence shown in (i) residues 21-896 of SEQ ID NO:2, (ii) residues 21-764 of SEQ ID NO:40, (iii) residues 21-740 of SEQ ID NO:48, (iv) residues 23-781 of SEQ ID NO:50, (v) residues 23-781 of SEQ ID NO:52, (vi) residues 23-791 of SEQ ID NO:54, (vii) residues 21-736 of SEQ ID NO:66, (viii) residues 21-804 of SEQ ID NO:74, (ix) residues 21-804 of SEQ ID NO:78, (x) residues 21-804 of SEQ ID NO:82, (xi) residues 21-804 of SEQ ID NO:86, (xii) residues 21-804 of SEQ ID NO:90, (xiii) residues 21-860 of SEQ ID NO:94, (xiv) residues 21-860 of SEQ ID NO:98, (xv) residues 21-861 of SEQ ID NO:102, (xvi) residues 21-861 of SEQ ID NO:106, (xvii) residues 21-613 of SEQ ID NO:122, (xviii) residues 21-610 of SEQ ID NO:142, (xix) residues 21-906 of SEQ ID NO:148, (xx) residues 21-896 of SEQ ID NO:158, (xxi) residues 21-906 of SEQ ID NO:160, (xxii) residues 21-906 of SEQ ID NO:162, or (xxiii) residues 21-906 of SEQ ID NO:164. In some embodiments of a method for treating an autoinflammatory disease, the fusion molecule is a polypeptide having the structure DNase1-L1-Fc-L2-PON1, DNase1L3-L1-Fc-L2-PON1, RNase1-L1-Fc-L2-PON1, or RNase 1-Fc-L2-PON1, or a dimeric protein formed by dimerization of any of the foregoing fusion polypeptides. In some embodiments of a method for treating rheumatoid arthritis, psoriatic arthritis, or juvenile idiopathic arthritis, the fusion molecule is a polypeptide having the structure CTLA4-L1-Fc-L2-PON1 or CTLA4-Fc-L2-PON1, or a dimeric protein formed by dimerization of either of the foregoing fusion polypeptides. In some embodiments of a method for treating an inflammatory bowel disease (IBD) (e.g., Crohn's disease or ulcerative colitis), the fusion molecule is a polypeptide having the structure DNase1-L1-Fc-L2-PON1, DNase1L3-L1-Fc-L2-PON1, antiTNFα-L1-Fc-L2-PON1, or antiTNFα-Fc-L2-PON1, or a dimeric protein formed by dimerization of any of the foregoing fusion polypeptides. In some embodiments of a method for treating an inflammatory skin disease (e.g., psoriasis or atopic dermatitis), the fusion molecule is a polypeptide having the structure DNase1-L1-Fc-L2-PON1, DNase1L3-L1-Fc-L2-PON1, antiTNFα-L1-Fc-L2-PON1, antiTNFα-Fc-L2-PON1, Fc-L2-PON1, or PON1-L1-Fc, or a dimeric protein formed by dimerization of any of the foregoing fusion polypeptides.

Autoimmune diseases amenable to treatment in accordance with the present invention include, for example, rheumatoid arthritis, systemic lupus erythematosus, psoriasis, multiple sclerosis, type 1 diabetes, vasculitis, and systemic sclerosis (also known as scleroderma). In other embodiments, the autoimmune disease is selected from coeliac disease, neuritis, polymyositis, juvenile rheumatoid arthritis, psoriatic arthritis, vitiligo, Sjogren's syndrome, autoimmune pancreatitis, autoimmune hepatitis, glomerulonephritis, lupus nephritis, scleroderma, antiphospholipid syndrome, autoimmune vasculitis, sarcoidosis, autoimmune thyroid diseases, Hashimoto's thyroiditis, Graves disease, Wegener's granulomatosis, myasthenia gravis, Addison's disease, autoimmune uveoretinitis, pemphigus vulgaris, primary biliary cirrhosis, pernicious anemia, sympathetic opthalmia, uveitis, autoimmune hemolytic anemia, pulmonary fibrosis, chronic beryllium disease, and idiopathic pulmonary fibrosis. In some variations comprising treatment of vasculitis, the vasculitis is selected from small vessel vasculitis and medium vessel vasculitis; in other variations, the vasculitis is large vessel vasculitis.

In more particular embodiments of a method for treating an autoimmune disease, a fusion molecule for the autoimmune disease treatment is a polypeptide having the structure DNase1-L1-Fc-L2-PON1, DNase1L3-L1-Fc-L2-PON1, RNase1-L1-Fc-L2-PON1, RNase 1-Fc-L2-PON1, SOD1-L1-Fc-L2-PON1, SOD1-Fc-L2-PON1, CTLA4-L1-Fc-L2-PON1, CTLA4-Fc-L2-PON1, CD40-L1-Fc-L2-PON1, CD40-Fc-L2-PON1, antiTNFα-L1-Fc-L2-PON1, antiTNFα-Fc-L2-PON1, antiTGFβ-L1-Fc-L2-PON1, antiTGFβ-Fc-L2-PON1, Fc-L2-PON1, or PON1-L1-Fc, or a dimeric protein formed by dimerization of any of the foregoing fusion polypeptides; in some such embodiments, the fusion polypeptide comprises or consists of an amino acid sequence having at least 90%, at least 95%, or 100% identity with the amino acid sequence shown in (i) residues 21-896 of SEQ ID NO:2, (ii) residues 21-764 of SEQ ID NO:40, (iii) residues 21-740 of SEQ ID NO:48, (iv) residues 23-781 of SEQ ID NO:50, (v) residues 23-781 of SEQ ID NO:52, (vi) residues 23-791 of SEQ ID NO:54, (vii) residues 21-736 of SEQ ID NO:66, (viii) residues 21-804 of SEQ ID NO:74, (ix) residues 21-804 of SEQ ID NO:78, (x) residues 21-804 of SEQ ID NO:82, (xi) residues 21-804 of SEQ ID NO:86, (xii) residues 21-804 of SEQ ID NO:90, (xiii) residues 21-860 of SEQ ID NO:94, (xiv) residues 21-860 of SEQ ID NO:98, (xv) residues 21-861 of SEQ ID NO:102, (xvi) residues 21-861 of SEQ ID NO:106, (xvii) residues 21-613 of SEQ ID NO:122, (xviii) residues 21-610 of SEQ ID NO:142, (xix) residues 21-906 of SEQ ID NO:148, (xx) residues 1-896 of SEQ ID NO:158, (xxi) residues 21-906 of SEQ ID NO:160, (xxii) residues 21-906 of SEQ ID NO:162, or (xxiii) residues 21-906 of SEQ ID NO:164. In some embodiments of a method for treating systemic lupus erythematosus, rheumatoid arthritis, psoriasis, type 1 diabetes, or small vessel vasculitis, the fusion molecule is a fusion polypeptide having the structure DNase1-L1-Fc-L2-PON1 or DNase1L3-L1-Fc-L2-PON1, or a dimeric protein formed by dimerization thereof. In some embodiments of a method for treating systemic lupus erythematosus, Sjogren's syndrome, or type 1 diabetes, the fusion molecule is a polypeptide having the structure RNase1-L1-Fc-L2-PON1 or RNase1-Fc-L2-PON1, or a dimeric protein formed by dimerization of either of the foregoing fusion polypeptides. In some embodiments of a method for treating rheumatoid arthritis or psoriatic arthritis, the fusion molecule is a polypeptide having the structure CLTA4-L1-Fc-L2-PON1 or CTLA4-Fc-L2-PON1, or a dimeric protein formed by dimerization of either of the foregoing fusion polypeptides.

Neurological diseases amenable to treatment in accordance with the present invention include, for example, neurodegenerative diseases characterized by inflammation in the CNS such as, e.g., multiple sclerosis, Alzheimer's disease, Parkinson's disease, or amylotrophic lateral sclerosis (ALS). In some embodiments, the neurological disease is a neurodegenerative disease characterized by dementia such as, e.g., Alzheimer's disease. In more specific variations of a method for treating multiple sclerosis (MS), the MS is spino-optical MS, primary progressive MS (PPMS), or relapsing remitting MS (RRMS). In other embodiments, a neurological disease for treatment in accordance with the present invention is a CNS infection such as, e.g., meningitis, encephalitis, or cerebral malaria. In more particular variations of a method for treating meningitis, the meningitis is a bacterial meningitis; in some such embodiments, the CNS infection is an *S. pneumoniae, N. meningitis, S. aureus, E. coli, A. baumanii, S. oralis, S. capitis*, or *S. epidermidis* infection. Other neurological diseases or disorders amenable to treatment with fusion molecules as described herein include, for example, acute brain injury such as, e.g., ischemic stroke. In still other embodiments, the neurological disease is a brain cancer such as, e.g., an intracranial tumor selected from astrocytoma, anaplastic astrocytoma, glioblastoma, oligodendroglioma, anaplastic oligodendroglioma, ependymoma, primary CNS lymphoma, medulloblastoma, germ cell tumor, pineal gland neoplasm, meningioma, pituitary tumor, tumor of the nerve sheath (e.g., schwannoma), chordoma, craniopharyngioma, and a choroid plexus tumor (e.g., choroid plexus carcinoma).

In more particular embodiments of a method for treating a neurological disease, a fusion molecule for the neurological disease treatment is a polypeptide having the structure DNase1-L1-Fc-L2-PON1, DNase1L3-L1-Fc-L2-PON1, RNase1-L1-Fc-L2-PON1, RNase1-Fc-L2-PON1, SOD1-L1-Fc-L2-PON1, SOD1-Fc-L2-PON1, CTLA4-L1-Fc-L2-PON1, CTLA4-Fc-L2-PON1, CD40-L1-Fc-L2-PON1, CD40-Fc-L2-PON1, antiTNFα-L1-Fc-L2-PON1, antiTNFα-Fc-L2-PON1, antiTGFβ-L1-Fc-L2-PON1, antiTGFβ-Fc-L2-PON1, Fc-L2-PON1, or PON1-L1-Fc, or a dimeric protein formed by dimerization of any of the foregoing fusion polypeptides; in some such embodiments, the fusion polypeptide comprises or consists of an amino acid sequence having at least 90%, at least 95%, or 100% identity with the amino acid sequence shown in (i) residues 21-896 of SEQ ID NO:2, (ii) residues 21-764 of SEQ ID NO:40, (iii) residues 21-740 of SEQ ID NO:48, (iv) residues 23-781 of SEQ ID NO:50, (v) residues 23-781 of SEQ ID NO:52, (vi) residues 23-791 of SEQ ID NO:54, (vii) residues 21-736 of SEQ ID NO:66, (viii) residues 21-804 of SEQ ID NO:74, (ix) residues 21-804 of SEQ ID NO:78, (x) residues 21-804 of SEQ ID NO:82, (xi) residues 21-804 of SEQ ID NO:86, (xii) residues 21-804 of SEQ ID NO:90, (xiii) residues 21-860 of SEQ ID NO:94, (xiv) residues 21-860 of SEQ ID NO:98, (xv) residues 21-861 of SEQ ID NO:102, (xvi) residues 21-861 of SEQ ID NO:106, (xvii) residues 21-613 of SEQ ID NO:122, (xviii) residues 21-610 of SEQ ID NO:142, (xix) residues 21-906 of SEQ ID NO:148, (xx) residues 21-896 of SEQ ID NO:158, (xxi) residues 21-906 of SEQ ID NO:160, (xxii) residues 21-906 of SEQ ID NO:162, or (xxiii) residues 21-906 of SEQ ID NO:164. In some embodiments of a method for treating a neurodegenerative disease characterized by dementia (e.g., Alzheimer's disease), acute brain injury (e.g., ischemic stroke), or a brain cancer, the fusion molecule is a polypeptide having the structure DNase-L1-Fc-L2-PON1, DNase1L3-L1-Fc-L2-PON1, RNase1-L1-Fc-L2-PON1, or RNase 1-Fc-L2-PON1, or a dimeric protein formed by dimerization of any of the foregoing fusion polypeptides. In some embodiments of a method for treating multiple sclerosis, Alzheimer's disease, Parkinson's disease, amylotrophic lateral sclerosis, or a CNS infection, the fusion molecule is a polypeptide having the structure DNase1-L1-Fc-L2-PON1 or DNase1L3-L1-Fc-L2-PON1, or a dimeric protein formed by dimerization thereof.

Infectious diseases amenable to treatment in accordance with the present invention include, for example, bacterial infections, viral infections, fungal infections, and parasitic infections. In some embodiments comprising treatment of a parasitic infection, the infection is a *Trypanosoma brucei, Leishmania, Plasmodium falciparum*, or *Toxoplasma gondii* infection. In some embodiments comprising treatment of a bacterial infection, the infection is a *Staphylococcus aureus, Streptococcus pneumoniae*, or *Mycobacterium tuberculosis* infection. In other embodiments, the bacterial infection is a *Pseudomonas aeruginosa* infection. In yet other embodiments, the bacterial infection is a *Borrelia burgdorferi* infection (Lyme disease). In some embodiments comprising treatment of a viral infection, the infection is an influenza virus (e.g., influenza A virus) or respiratory syncytial virus (RSV) infection. In still other embodiments, the infection is a CNS infection such as, for example, meningitis (e.g., a bacterial meningitis), encephalitis, or cerebral malaria.

Paraoxonase fusion molecules for treating an infectious disease typically comprise a DNase, RNase, SOD1, or anti-TGF-β neutralizing polypeptide as the first biologically active polypeptide, or may be a monospecific paraoxonase fusion molecule. In more particular variations, a fusion molecule for infectious disease treatment is a polypeptide having the structure DNase1-L1-Fc-L2-PON1, DNase1L3-L1-Fc-L2-PON1, RNase1-L1-Fc-L2-PON1, RNase1-Fc-L2-PON1, SOD1-L1-Fc-L2-PON1, SOD1-Fc-L2-PON1, antiTNFα-L1-Fc-L2-PON1, antiTNFα-Fc-L2-PON1, antiTGFβ-L1-Fc-L2-PON1, antiTGFβ-Fc-L2-PON1, Fc-L2-PON1, or PON1-L1-Fc, or a dimeric protein formed by dimerization of any of the foregoing fusion polypeptides. In some such embodiments, the fusion polypeptide comprises or consists of an amino acid sequence having at least 90%, at least 95%, or 100% identity with the amino acid sequence shown in (i) residues 21-896 of SEQ ID NO:2, (ii) residues 21-764 of SEQ ID NO:40, (iii) residues 21-740 of SEQ ID NO:48, (iv) residues 23-781 of SEQ ID NO:50, (v) residues 23-781 of SEQ ID NO:52, (vi) residues 23-791 of SEQ ID NO:54, (vii) residues 21-860 of SEQ ID NO:94, (viii) residues 21-860 of SEQ ID NO:98, (ix) residues 21-861 of SEQ ID NO:102, (x) residues 21-861 of SEQ ID NO:106, (xi) residues 21-613 of SEQ ID NO:122, (xii) residues 21-610 of SEQ ID NO:142, (xiii) residues 21-906 of SEQ ID NO:148, (xiv) residues 21-896 of SEQ ID NO:158, (xv) residues 21-906 of SEQ ID NO:160, (xvi) residues 21-906 of SEQ ID NO:162, or (xvii) residues 21-906 of SEQ ID NO:164.

In some embodiments of a method for treating biofilm formation by a gram negative bacteria, the gram negative bacteria is *Pseudomonas aeruginosa*. In particular variations for treating biofilm formation by a gram negative bacteria, a fusion molecule for the biofilm formation treatment is a polypeptide having the structure DNase1-L1-Fc-L2-PON1, DNase1L3-L1-Fc-L2-PON1, Fc-L2-PON1, or PON1-L1-Fc, or a dimeric protein formed by dimerization of either of the foregoing fusion polypeptides; in some such embodiments, the fusion polypeptide comprises or consists of an amino acid sequence having at least 90%, at least 95%, or 100% identity with the amino acid sequence shown in (i) residues 21-896 of SEQ ID NO:2, (ii) residues 21-613 of SEQ ID NO:122, (iii) residues 21-610 of SEQ ID NO:142, (xix) residues 21-906 of SEQ ID NO:148, (xx) residues 21-896 of SEQ ID NO:158, (xxi) residues 21-906 of SEQ ID NO:160, (xxii) residues 21-906 of SEQ ID NO:162, or (xxiii) residues 21-906 of SEQ ID NO:164.

Metabolic diseases that may be treated in accordance with the present invention include, for example, type 2 diabetes and obesity. In particular variations of a method for treating a metabolic disease, a fusion molecule for the metabolic disease treatment is a polypeptide having the structure DNase1-L1-Fc-L2-PON1, DNase1L3-L1-Fc-L2-PON1, RNase 1-L1-Fc-L2-PON1, RNase1-Fc-L2-PON1, Fc-L2-PON1, or PON1-L1-Fc, or a dimeric protein formed by dimerization of any of the foregoing fusion polypeptides; in some such embodiments, the fusion polypeptide comprises or consists of an amino acid sequence having at least 90%, at least 95%, or 100% identity with the amino acid sequence shown in (i) residues 21-896 of SEQ ID NO:2, (ii) residues 21-764 of SEQ ID NO:40, (iii) residues 21-740 of SEQ ID NO:48, (iv) residues 21-613 of SEQ ID NO:122, (v) residues 21-610 of SEQ ID NO:142, (vi) residues 21-906 of SEQ ID NO:148, (vii) residues 21-896 of SEQ ID NO:158, (viii) residues 21-906 of SEQ ID NO:160, (ix) residues 21-906 of SEQ ID NO:162, or (x) residues 21-906 of SEQ ID NO:164.

Cardiovascular diseases that may be treated in accordance with the present invention include, for example, cardiovascular diseases characterized by atherosclerosis. In some embodiments, the cardiovascular disease characterized by atherosclerosis is coronary heart disease or ischemic stroke. In more particular variations comprising treatment of coronary heart disease, the coronary heart disease is characterized by acute coronary syndrome. In certain variations of a method for treating a cardiovascular disease, a fusion molecule for the cardiovascular disease treatment is a polypeptide having the structure DNase1-L1-Fc-L2-PON1, DNase1L3-L1-Fc-L2-PON1, RNase 1-L1-Fc-L2-PON1, RNase1-Fc-L2-PON1, Fc-L2-PON1, or PON1-L1-Fc, or a dimeric protein formed by dimerization of any of the foregoing fusion polypeptides; in some such embodiments, the fusion polypeptide comprises or consists of an amino acid sequence having at least 90%, at least 95%, or 100% identity with the amino acid sequence shown in (i) residues 21-896 of SEQ ID NO:2, (ii) residues 21-764 of SEQ ID NO:40, (iii) residues 21-740 of SEQ ID NO:48, (iv) residues 21-613 of SEQ ID NO:122, (v) residues 21-610 of SEQ ID NO:142, (vi) residues 21-906 of SEQ ID NO:148, (vii) residues 21-896 of SEQ ID NO:158, (viii) residues 21-906 of SEQ ID NO:160, (ix) residues 21-906 of SEQ ID NO:162, or (x) residues 21-906 of SEQ ID NO:164.

In some embodiments of a method for treating thrombosis, sepsis, or ischemia reperfusion, a fusion molecule for such treatment is a polypeptide having the structure DNase1-L1-Fc-L2-PON1, DNase1L3-L1-Fc-L2-PON1, RNase1-L1-Fc-L2-PON1, or RNase 1-Fc-L2-PON1, or a dimeric protein formed by dimerization of any of the foregoing fusion polypeptides; in some such embodiments, the fusion polypeptide comprises or consists of an amino acid sequence having at least 90%, at least 95%, or 100% identity with the amino acid sequence shown in (i) residues 21-896 of SEQ ID NO:2, (ii) residues 21-764 of SEQ ID NO:40, (iii) residues 21-740 of SEQ ID NO:48, (iv) residues 21-906 of SEQ ID NO:148, (v) residues 21-896 of SEQ ID NO:158, (vi) residues 21-906 of SEQ ID NO:160, (vii) residues 21-906 of SEQ ID NO:162, or (viii) residues 21-906 of SEQ ID NO:164.

In some embodiments of a method for treating antiphospholipid syndrome, thrombosis, or ischemic stroke, a DNase-containing fusion molecule as described herein is administered to a patient as one of the distinct therapies of a combination therapy comprising a thrombolytic agent. In some such embodiments, the thrombolytic agent is selected from anistreplase, reteplase, streptokinase, t-PA, tenecteplase, and rokinase.

In some embodiments of a method for treating exposure to sulfur mustard gas (SM) or exposure to an organophosphate (e.g., tabun, sarin, soman, or cyclosarin), a fusion molecule for such exposure treatment is a polypeptide having the structure DNase1-L1-Fc-L2-PON1, DNase1L3-L1-Fc-L2-PON1, RNase1-L1-Fc-L2-PON1, RNase1-Fc-L2-PON1, SOD1-L1-Fc-L2-PON1, SOD1-Fc-L2-PON1, CTLA4-L1-Fc-L2-PON1, CTLA4-Fc-L2-PON1, CD40-L1-Fc-L2-PON1, CD40-Fc-L2-PON1, antiTNFα-L1-Fc-L2-PON1, antiTNFα-Fc-L2-PON1, antiTGFβ-L1-Fc-L2-PON1, antiTGFβ-Fc-L2-PON1, Fc-L2-PON1, or PON1-L1-Fc, or a dimeric protein formed by dimerization of any of the foregoing fusion polypeptides; in some such embodiments, the fusion polypeptide comprises or consists of an amino acid sequence having at least 90%, at least 95%, or 100% identity with the amino acid sequence shown in (i) residues 21-896 of SEQ ID NO:2, (ii) residues 21-896 of SEQ ID NO:128, (iii) residues 21-896 of SEQ ID NO:130, (iv) residues 21-764 of SEQ ID NO:40, (v) residues 21-740 of SEQ ID NO:48, (vi) residues 23-781 of SEQ ID NO:50, (vii) residues 23-781 of SEQ ID NO:52, (viii) residues 23-791 of SEQ ID NO:54, (ix) residues 21-736 of SEQ ID NO:66, (x) residues 21-804 of SEQ ID NO:74, (xi) residues 21-804 of SEQ ID NO:78, (xii) residues 21-804 of SEQ ID NO:82, (xiii) residues 21-804 of SEQ ID NO:86, (xiv) residues 21-804 of SEQ ID NO:90, (xv) residues 21-860 of SEQ ID NO:94, (xvi) residues 21-860 of SEQ ID NO:98, (xvii) residues 21-861 of SEQ ID NO:102, (xviii) residues 21-861 of SEQ ID NO:106, (xix) residues 21-613 of SEQ ID NO:122, (xx) residues 21-613 of SEQ ID NO:132, (xxi) residues 21-613 of SEQ ID NO:134, (xxii) residues 21-610 of SEQ ID NO:142, (xxiii) residues 21-610 of SEQ ID NO:144, (xxiv) residues 21-610 of SEQ ID NO:146, (xxv) residues 21-906 of SEQ ID NO:148, (xxvi) residues 21-896 of SEQ ID NO:158, (xxvii) residues 21-906 of SEQ ID NO:160, (xxviii) residues 21-906 of SEQ ID NO:162, or (xxix) residues 21-906 of SEQ ID NO:164.

Liver diseases or disorders that may be treated in accordance with the present invention include chronic liver diseases such as, e.g., nonalcoholic fatty liver disease (NAFLD), alcohol-associated liver disease (ALD), portal hypertension, and complications following liver transplantation. In some variations comprising treatment of nonalcoholic fatty liver disease (NAFLD), the NAFLD is nonalcoholic steatohepatitis (NASH). In particular variations of a method for treating a liver disease, a fusion molecule for the liver disease treatment is a polypeptide having the structure DNase1-L1-Fc-L2-PON1, DNase1L3-L1-Fc-L2-PON1, CD40-L1-Fc-L2-PON1, CD40-Fc-L2-PON1, antiTGFβ-L1-Fc-L2-PON1, antiTGFβ-Fc-L2-PON1, Fc-L2-PON1, or PON1-L1-Fc, or a dimeric protein formed by dimerization of any of the foregoing fusion polypeptides; in some such embodiments, the fusion polypeptide comprises or consists of an amino acid sequence having at least 90%, at least 95%, or 100% identity with the amino acid sequence shown in (i) residues 21-896 of SEQ ID NO:2, (ii) residues 21-804 of SEQ ID NO:74, (iii) residues 21-804 of SEQ ID NO:78, (iv) residues 21-804 of SEQ ID NO:82, (v) residues 21-804 of SEQ ID NO:86, (vi) residues 21-804 of SEQ ID NO:90, (vii) residues 21-861 of SEQ ID NO:102, (viii) residues 21-861 of SEQ ID NO:106, (ix) residues 21-613 of SEQ ID NO:122, (x) residues 21-610 of SEQ ID NO:142, (xi) residues 21-906 of SEQ ID NO:148, (xii) residues 21-896 of SEQ ID NO:158, (xiii) residues 21-906 of SEQ ID NO:160, (xiv) residues 21-906 of SEQ ID NO:162, or (xv) residues 21-906 of SEQ ID NO:164.

Fibrotic diseases or disorders amenable to treatment in accordance with the present invention include systemic sclerosis, systemic lupus erythematosus, inflammatory lung diseases, chronic liver diseases, and chronic kidney diseases. In some variations comprising treatment of an inflammatory lung disease, the fibrotic disease is cystic fibrosis, chronic obstructive pulmonary disease, interstitial lung disease (e.g., idiopathic pulmonary fibrosis or sarcoidosis), acute respiratory distress syndrome, or asthma. In some variations comprising treatment of a chronic liver disease, the fibrotic disease is nonalcoholic steatohepatitis, alcohol-associated liver disease, portal hypertension, or a complication following liver transplantation. In some variations comprising treatment of a chronic kidney disease, the fibrotic disease is lupus nephritis, IgA nephropathy, or membranous glomerulonephritis. In particular variations of a method for treating a liver disease, a fusion molecule for the liver disease treatment is a polypeptide having the structure DNase1-L1-Fc-L2-PON1, DNase1L3-L1-Fc-L2-PON1, CD40-L1-Fc-L2-PON1, CD40-Fc-L2-PON1, antiTGFβ-L1-Fc-L2-PON1, antiTGFβ-Fc-L2-PON1, Fc-L2-PON1, or PON1-L1-Fc, or a dimeric protein formed by dimerization of any of the foregoing fusion polypeptides; in some such embodiments, the fusion polypeptide comprises or consists of an amino acid sequence having at least 90%, at least 95%, or 100% identity with the amino acid sequence shown in (i) residues 21-896 of SEQ ID NO:2, (ii) residues 21-804 of SEQ ID NO:74, (iii) residues 21-804 of SEQ ID NO:78, (iv) residues 21-804 of SEQ ID NO:82, (v) residues 21-804 of SEQ ID NO:86, (vi) residues 21-804 of SEQ ID NO:90, (vii) residues 21-861 of SEQ ID NO:102, (viii) residues 21-861 of SEQ ID NO:106, (ix) residues 21-613 of SEQ ID NO:122, (x) residues 21-610 of SEQ ID NO:142, (xi) residues 21-906 of SEQ ID NO:148, (xii) residues 21-896 of SEQ ID NO:158, (xiii) residues 21-906 of SEQ ID NO:160, (xiv) residues 21-906 of SEQ ID NO:162, or (xv) residues 21-906 of SEQ ID NO:164.

Paraoxonase fusion molecules for treating cancer typically comprise a DNase, RNase, or anti-TGF-β neutralizing polypeptide as the first biologically active polypeptide. In more particular variations, a fusion molecule for cancer treatment is a polypeptide having the structure DNase1-L1-Fc-L2-PON1, DNase1L3-L1-Fc-L2-PON1, RNase1-L1-Fc-L2-PON1, RNase 1-Fc-L2-PON1, antiTGFβ-L1-Fc-L2-PON1, or antiTGFβ-Fc-L2-PON1, or a dimeric protein formed by dimerization of any of the foregoing fusion polypeptides; in some such embodiments, the fusion polypeptide comprises or consists of an amino acid sequence having at least 90%, at least 95%, or 100% identity with the amino acid sequence shown in (i) residues 21-896 of SEQ ID NO:2, (ii) residues 21-764 of SEQ ID NO:40, (iii) residues 21-740 of SEQ ID NO:48, (ix) residues 21-861 of SEQ ID NO:102, (v) residues 21-861 of SEQ ID NO:106, (vi) residues 21-906 of SEQ ID NO:148, (vii) residues 21-896 of SEQ ID NO:158, (viii) residues 21-906 of SEQ ID NO:160, (ix) residues 21-906 of SEQ ID NO:162, or (x) residues 21-906 of SEQ ID NO:164.

Cancers that may be treated in accordance with the present invention include, for example, the following: a cancer of the head and neck (e.g., a cancer of the oral cavity, orophyarynx, nasopharynx, hypopharynx, nasal cavity or paranasal sinuses, larynx, lip, or salivary gland); a lung cancer (e.g., non-small cell lung cancer, small cell carcinoma, or mesothelimia); a gastrointestinal tract cancer (e.g., colorectal cancer, gastric cancer, esophageal cancer, or anal cancer); gastrointestinal stromal tumor (GIST); pancreatic adenocarcinoma; pancreatic acinar cell carcinoma; a cancer of the small intestine; a cancer of the liver or biliary tree (e.g., liver cell adenoma, hepatocellular carcinoma, hemangiosarcoma, extrahepatic or intrahepatic cholangiosarcoma, cancer of the ampulla of vater, or gallbladder cancer); a breast cancer (e.g., metastatic breast cancer or inflammatory breast cancer); a gynecologic cancer (e.g., cervical cancer, ovarian cancer, fallopian tube cancer, peritoneal carcinoma, vaginal cancer, vulvar cancer, gestational trophoblastic neoplasia, or uterine cancer, including endometrial cancer or uterine sarcoma); a cancer of the urinary tract (e.g., prostate cancer; bladder cancer; penile cancer; urethral cancer, or kidney cancer such as, for example, renal cell carcinoma or transitional cell carcinoma, including renal pelvis and ureter); testicular cancer; a cancer of the central nervous system (CNS) such as an intracranial tumor (e.g., astrocytoma, anaplastic astrocytoma, glioblastoma, oligodendroglioma, anaplastic oligodendroglioma, ependymoma, primary CNS lymphoma, medulloblastoma, germ cell tumor, pineal gland neoplasm, meningioma, pituitary tumor, tumor of the nerve sheath (e.g., schwannoma), chordoma, craniopharyngioma, a chloroid plexus tumor (e.g., chloroid plexus carcinoma), or other intracranial tumor of neuronal or glial origin) or a tumor of the spinal cord (e.g., schwannoma, meningioma); an endocrine neoplasm (e.g., thyroid cancer such as, for example, thyroid carcinoma, medullary cancer, or thyroid lymphoma; a pancreatic endocrine tumor such as, for example, an insulinoma or glucagonoma; an adrenal carcinoma such as, for example, pheochromocytoma; a carcinoid tumor; or a parathyroid carcinoma); a skin cancer (e.g., squamous cell carcinoma; basal cell carcinoma; Kaposi's sarcoma; or a malignant melanoma such as, for example, an intraocular melanoma); a bone cancer (e.g., a bone sarcoma such as, for example, osteosarcoma, osteochondroma, or Ewing's sarcoma); multiple myeloma; a chloroma; a soft tissue sarcoma (e.g., a fibrous tumor or fibrohistiocytic tumor); a tumor of the smooth muscle or skeletal muscle; a blood or lymph vessel perivascular tumor (e.g., Kaposi's sarcoma); a synovial tumor; a mesothelial tumor; a neural tumor; a paraganglionic tumor; an extraskeletal cartilaginous or osseous tumor; and a pluripotential mesenchymal tumor. In some such embodiments, a paraoxonase fusion molecule as described herein is administered to a cancer patient as one of the distinct therapies of a combination therapy such as, for example, a combination therapy comprising an immunomodulatory therapy (e.g., a CAR T cell therapy (see, e.g., June et al., *Science* 359:1361-1365, 2018) or a therapy comprising an immune checkpoint inhibitor), a radiation therapy, or a chemotherapy.

In certain embodiments, a combination cancer therapy comprises a DNase-PON, RNase-PON, or antiTGFβ-PON fusion molecule as described herein and a targeted therapy such as, e.g., a therapeutic monoclonal antibody targeting a specific cell-surface or extracellular antigen, or a small molecule targeting an intracellular protein (e.g., an intracellular enzyme). Exemplary antibody targeted therapies include anti-VEGF (e.g., bevacizumab), anti-EGFR (e.g., cetuximab), anti-CTLA-4 (e.g., ipilimumab), anti-PD-1 (e.g., nivolumab), and anti-PD-L1 (e.g., pembrolizumab). Exemplary small molecule targeted therapies include proteasome inhibitors (e.g., bortezomib), tyrosine kinase inhibitors (e.g., imatinib), cyclin-dependent kinase inhibitors (e.g., seliciclib); BRAF inhibitors (e.g., vemurafenib or dabrafenib); and MEK kinase inhibitors (e.g., trametnib).

In some cancer combination therapy variations comprising an immune checkpoint inhibitor, the combination therapy includes an anti-PD-1/PD-L1 therapy, an anti-CTLA-4 therapy, or both. In certain aspects, a DNase-PON, RNase-PON, or antiTGFβ-PON fusion molecule as described herein can increase the response rate to either anti-CTLA-4 or anti-PD-1/PD-L1 therapy, as well as the response rate to the combination of anti-CTLA-4 plus anti-PD-1/PD-L1 therapy. Fusion molecules of the invention may also be useful for reducing the toxicity associated with anti-CTLA-4, anti-PD-1/PD-L1, or the combination thereof.

In certain variations, a cancer treated in accordance with the present invention is selected from malignant melanoma, renal cell carcinoma, non-small cell lung cancer, bladder cancer, and head and neck cancer. These cancers have shown responses to immune checkpoint inhibitors anti-PD-1/PD-L1 and anti-CTLA-4. See Grimaldi et al., *Expert Opin. Biol. Ther.* 16:433-41, 2016; Gunturi et al., *Curr. Treat. Options Oncol.* 15:137-46, 2014; Topalian et al., *Nat. Rev. Cancer* 16:275-87, 2016. Thus, in some more specific variations, any of these cancers is treated with a DNase-PON, RNase-PON, or antiTGFβ-PON fusion molecule as described herein in combination with an anti-PD-1/PD-L1 therapy, an anti-CTLA-4 therapy, or both.

In other aspects, the present invention provides methods for reducing lipid oxidation in a subject. The method generally includes administering to the subject an effective amount of a fusion polypeptide or dimeric protein as described herein, wherein one or more oxidized lipids in the subject are reduced. In some embodiments, the method reduces one or more oxidized lipids associated with the presence of a disease or disorder in the subject (e.g., a disease or disorder discussed above). In other embodiments, the one or more oxidized lipids are associated with a risk of developing such a disease or disorder; in particular variations, treatment with the fusion molecule reduces the risk of developing the disease or disorder in the subject.

In another aspect, the present invention provides a method for protecting a subject from aging. The method generally includes administering to the subject an effective amount of a fusion polypeptide of a fusion polypeptide or dimeric protein as described herein. In some embodiments, the subject has an age-related disease or disorder (e.g., an inflammatory disease, an autoimmune disease, a neurodegenerative disease, a cardiovascular disease, or a fibrotic disease). In other embodiments, the subject is at risk of developing such an age-related disease or disorder, and treatment with the fusion molecule reduces the risk of the disease or disorder in the subject.

In some embodiments of a method for treating a disease or disorder, reducing lipid oxidation, or protecting from aging as above, the method is a combination therapy comprising administering to the patient (a) an effective amount of a paraoxonase fusion polypeptide having the formula X-L2-P or P-L1-X as described above, or a dimeric protein formed by dimerization of the fusion polypeptide, and (b) an effective amount of a biologically active DNase. Such embodiments are particularly useful, e.g., for treatment of diseases and disorder characterized by NETosis. In some variations, the method comprises administration of a paraoxonase fusion polypeptide having the structure Fc-L2-PON1 or PON1-L1-Fc, or a dimeric protein formed by dimerization thereof; in some such embodiments, the paraoxonase fusion polypeptide has the structure Fc-L2-PON1 and comprises or consists of an amino acid sequence having at least 90%, at least 95%, or 100% identity with the amino acid sequence shown in (i) residues 21-613 of SEQ ID NO:122, (ii) residues 21-613 of SEQ ID NO:132, (iii) residues 21-613 of SEQ ID NO:134, (iv) residues 21-610 of SEQ ID NO:142, (v) residues 21-610 of SEQ ID NO:144, or (vi) residues 21-610 of SEQ ID NO:146. The biologically active DNase may be, for example, a DNase1 or DNase1L3 polypeptide as described herein (e.g., a polypeptide corresponding to the DNase component of a DNase-containing paraoxonase fusion as described herein such as, for example, an enhanced DNase1 polypeptide comprising or consisting of an amino acid sequence having at least 90%, at least 95%, or 100% identity with the amino acid sequence shown in residues 21-280 of SEQ ID NO:18, residues 21-280 of SEQ ID NO:20, or residues 21-280 of SEQ ID NO:152. In some embodiments, the DNase is contained within a fusion polypeptide comprising, from an amino terminal position to a carboxyl terminal position, D-L1-Xa, wherein D is the DNase, L1 is a polypeptide linker (e.g., an L1 linker as described herein for a DNase-containing paraoxonase fusion molecule), and $X_a$ is an immunoglobulin Fc region as described herein (or contained with a dimeric protein formed by dimerization of the fusion polypeptide); in some such embodiments, the DNase fusion polypeptide comprises or consists of an amino acid sequence having at least 90%, at least 95%, or 100% identity with the amino acid sequence shown in (i) residues 21-538 or 21-537 of SEQ ID NO:60, (ii) residues 21-548 or 21-547 of SEQ ID NO:62, (iii) residues 21-538 or 21-537 of SEQ ID NO:155, (iv) residues 21-548 or 21-547 of SEQ ID NO:156, (v) residues 21-548 or 21-547 of SEQ ID NO:138, or (vi) residues 21-548 or 21-547 of SEQ ID NO:140.

In some embodiments of a combination therapy comprising administration of a paraoxonase fusion molecule and a DNase as described above, the DNase is contained within a DNase1-L1-Fc fusion polypeptide comprising the amino acid sequence shown in SEQ ID NO:149, SEQ ID NO:150, SEQ ID NO:153, or SEQ ID NO:154. In certain variations of the combination therapy method wherein DNase fusion polypeptide comprises the amino acid sequence shown in SEQ ID NO:149, SEQ ID NO:150, SEQ ID NO:153, or SEQ ID NO:154, (i) the amino acid at each of positions 315 and 316 is alanine; (ii) the amino acid at position 319 is serine; (iii) the amino acid at position 378 is alanine, glutamine, or glycine, and the amino acid at position 346 is optionally alanine; (iv) the amino acid at position 410 is alanine, glycine, or serine; (v) the amino acid at position 412 is serine or alanine; (vi) the amino acid at position 333 is tyrosine, the amino acid at position 335 is threonine, and the amino acid at position 337 is glutamate; and/or (vii) the amino acid at position 509 is leucine, and the amino acid at position 515 is serine. In other, non-mutually exclusive variations of the combination therapy method wherein the DNase fusion polypeptide comprises the amino acid sequence shown in SEQ ID NO:149, SEQ ID NO:150, SEQ ID NO:153, or SEQ ID NO154, the amino acid sequence corresponding to positions 261-296 includes a Gly-Ser tandem repeat sequence having a formula selected from the group consisting of (i) $[\text{Gly-Gly-Gly-Gly-Ser}]_n$, wherein n is an integer from 4 to 7, (ii) $[\text{Gly-Gly-Gly-Ser}]_n$, wherein n is an integer from 5 to 9, and (iii) $[\text{Gly-Gly-Ser}]_n$, wherein n is an integer from 6 to 12; in some such embodiments, the amino acid sequence corresponding to positions 261-296 includes a Gly-Ser tandem repeat sequence having a formula selected from the group consisting of (i) $[\text{Gly-Gly-Gly-Gly-Ser}]_n$, wherein n is an integer from 4 to 6, (ii) $[\text{Gly-Gly-Gly-Ser}]_n$, wherein n is an integer from 5 to 7, and (iii) $[\text{Gly-Gly-Ser}]_n$, wherein n is an integer from 6 to 10. In yet other, non-mutually exclusive variations of the combination therapy method wherein the DNase fusion polypeptide comprises the amino acid sequence shown in SEQ ID NO:149, SEQ ID NO:150, SEQ ID NO:153, or SEQ ID NO:154, the amino acid at position 261 is aspartate, the amino acid at position 262 is leucine, the amino acid at position 263 is serine, the amino acid at position 294 is threonine, the amino acid at position is 295 is glycine, and/or the amino acid at position 296 is leucine. In other, non-mutually exclusive variations of the combination therapy method where the DNase fusion polypeptide comprises the amino acid sequence shown in SEQ ID NO:149 or SEQ ID NO:153, (i) the amino acid at each of positions 74 and 105 is independently lysine or arginine, and/or (ii) the amino acid at position 114 is phenylalanine.

In some embodiments of a method for treating a disease or disorder, reducing lipid oxidation, or protecting from aging as above, the method is a combination therapy comprising administering to the patient (a) an effective amount of a paraoxonase fusion polypeptide having the formula X-L2-P or P-L1-X as described above, or a dimeric protein formed by dimerization of the fusion polypeptide, and (b) an effective amount of a biologically active apolipoprotein A-1 (ApoA1) (e.g., an ApoA1-Fc fusion polypeptide as described in International PCT Publication No. WO 2017/044424, or a dimeric protein formed by dimerization of the fusion polypeptide).

For therapeutic use, a fusion polypeptide or dimeric protein as described herein is delivered in a manner consistent with conventional methodologies associated with management of the disease or disorder for which treatment is sought. In accordance with the disclosure herein, an effective amount of the fusion polypeptide or dimeric protein is administered to a subject in need of such treatment for a time and under conditions sufficient to prevent or treat the disease or disorder.

Subjects for administration of fusion polypeptides or dimeric proteins as described herein include patients at high risk for developing a particular disease or disorder as well as patients presenting with an existing disease or disorder. In certain embodiments, the subject has been diagnosed as having the disease or disorder for which treatment is sought. Further, subjects can be monitored during the course of treatment for any change in the disease or disorder (e.g., for an increase or decrease in clinical symptoms of the disease or disorder). Also, in some variations, the subject does not suffer from another disease or disorder requiring treatment that involves administration of a protein selected from a paraoxonase, a DNase, an RNase, a SOD1, a CTLA-4 extracellular domain, a CD40 extracellular domain, or a polypeptide (e.g, antibody) that specifically binds and neutralizes TNFα or TGF-β.

In prophylactic applications, pharmaceutical compositions or medicants are administered to a patient susceptible to, or otherwise at risk of, a particular disease in an amount sufficient to eliminate or reduce the risk or delay the onset of the disease. In therapeutic applications, compositions or medicants are administered to a patient suspected of, or already suffering from such a disease in an amount sufficient to cure, or at least partially arrest, the symptoms of the disease and its complications. An amount adequate to accomplish this is referred to as a therapeutically or pharmaceutically effective dose or amount. In both prophylactic and therapeutic regimes, agents are usually administered in several dosages until a sufficient response (e.g., enhanced alveolar fluid clearance in inflammatory lung disease) has been achieved. Typically, the response is monitored and repeated dosages are given if the desired response starts to fade.

To identify subject patients for treatment according to the methods of the invention, accepted screening methods may be employed to determine risk factors associated with a specific disease or to determine the status of an existing disease identified in a subject. Such methods can include, for example, determining whether an individual has relatives who have been diagnosed with a particular disease. Screening methods can also include, for example, conventional work-ups to determine familial status for a particular disease known to have a heritable component. Toward this end, nucleotide probes can be routinely employed to identify individuals carrying genetic markers associated with a particular disease of interest. In addition, a wide variety of immunological methods are known in the art that are useful to identify markers for specific diseases. Screening may be implemented as indicated by known patient symptomology, age factors, related risk factors, etc. These methods allow the clinician to routinely select patients in need of the methods described herein for treatment. In accordance with these methods, treatment using a fusion polypeptide or dimeric protein of the present invention may be implemented as an independent treatment program or as a follow-up, adjunct, or coordinate treatment regimen to other treatments.

For treatment of a disease or disorder characterized by NETosis, subject patients likely to benefit from NET-targeted therapy may be identified, for example, by measuring NETs in candidate patients. There are multiple ways to measure NETs in vivo (for a review, see, e.g., Masuda et al., *Clin. Chim. Acta* 459:89-93, 2016). One method uses flow cytometry to measure cell-associated DNA by staining with a non-cell permeable DNA dye (Zharkova et al., *Cytometry A* 95:268-278, 2019). Other methods include measuring myeloperoxidase activity associated with DNA or measuring citrullinated histone H3 (see, e.g., Matsuda et al., supra). Yet another method measures NETosis by incubating blood neutrophils with autologous plasma (Abrams et al., *Am. J. Resp. Crit. Care Med.* 200:869, 2019). This method was able to predict disseminated intravascular coagulation in critically ill patients (id.).

For administration, a fusion polypeptide or dimeric protein in accordance with the present invention is formulated as a pharmaceutical composition. A pharmaceutical composition comprising a fusion polypeptide or dimeric protein as described herein can be formulated according to known methods to prepare pharmaceutically useful compositions, whereby the therapeutic molecule is combined in a mixture with a pharmaceutically acceptable carrier. A composition is said to be a "pharmaceutically acceptable carrier" if its administration can be tolerated by a recipient patient. Sterile phosphate-buffered saline is one example of a pharmaceutically acceptable carrier. Other suitable carriers are well-known to those in the art. See, e.g., Gennaro (ed.), *Remington's Pharmaceutical Sciences* (Mack Publishing Company, 19th ed. 1995). Formulations may further include one or more excipients, preservatives, solubilizers, buffering agents, albumin to prevent protein loss on vial surfaces, etc.

A pharmaceutical composition comprising a fusion polypeptide or dimeric protein of the present invention is administered to a subject in an effective amount. The fusion polypeptide or dimeric protein may be administered to subjects by a variety of administration modes, including, for example, by intramuscular, subcutaneous, intravenous, intra-atrial, intra-articular, parenteral, intranasal, intrapulmonary, transdermal, intrapleural, intrathecal, and oral routes of administration. For prevention and treatment purposes, the fusion polypeptide or dimeric protein may be administered to a subject in a single bolus delivery, via continuous delivery (e.g., continuous transdermal delivery) over an extended time period, or in a repeated administration protocol (e.g., on an hourly, daily, or weekly basis).

In some embodiments, a pharmaceutical composition comprising a fusion molecule or dimeric protein of the present invention is formulated for delivery to the lung by nebulization. Previous studies of pulmonary delivery of Fc fusion proteins, including erythropoietin-Fc, interferon Beta1a-Fc, and FSH-Fc, have shown that the immunoglobulin transport FcRn pathway is active in the lungs and provides 20% to 50% bioavailability (see Bitonti et al., *Proc. Natl. Acad. Sci. USA* 101:9763-9768, 2004; Bitonti and Dumont, *Adv. Drug Deliv. Rev.* 58:1106, 2006; Valle et al., *J. Interferon Cytokine Res.* 32:178-184, 2012). Pulmonary delivery of FcRn-binding paraoxonase fusion molecules as described herein (e.g., paraoxonase fusion molecules containing an Fc region) could act both locally and in circulation and peripheral organs. In certain embodiments wherein the treatment is a combination therapy with a paraoxonase fusion molecule and a DNase as described herein, both the paraoxonase fusion molecule (e.g., an Fc-L2-PON1 fusion as described herein) and the DNase (e.g., a DNase-Fc fusion as described herein) are delivered by a nebulizer. In some variations comprising delivery to the lung by a nebulizer, the disease or disorder to the treated is selected from an inflammatory lung disease (e.g., cystic fibrosis, interstitial lung disease (e.g., idiopathic pulmonary fibrosis or sarcoidosis), acute respiratory distress syndrome (ARDS), chronic obstructive pulmonary disease (COPD), asthma, exposure to sulfur mustard gas, or exposure to an organophosphate), biofilm formation by a gram-negative bacteria (e.g., *Pseudomonas aeruginosa*), and sepsis. In other, non-mutually exclusive variations, an FcRn-binding fusion molecule for delivery to the lung by nebulization (e.g., an Fc-L2-PON1 fusion as described herein) comprises an Fc variant with increased FcRn-binding affinity relative to the corresponding wild-type Fc, thereby increasing fusion molecule half-life and increasing concentration in the blood after inhalation with a nebulizer.

Multiple biologics have been successfully formulated to retain biologic activity after nebulization (see, e.g., Hertel et al., *Adv. Drug Deliv. Rev.* 93:79-94, 2015). Formulations for delivery of a paraoxonase fusion molecule of the present invention may include an excipient suitable for pulmonary delivery such as, e.g., Polysorbate 80 (PS80) or Polysorbate 20 (PS20), surfactants that are included in many biopharmaceutical formulations. Such stabilizing excipients protect proteins from degradation at the air-liquid interface when applied above their critical micelle concentration (for example, PS80 above 0.01% was effective in stabilizing G-CSF, LDH, rhConIFN, and t-Pa; and PS20 applied at 0.04% was effective for protection of Fc-gamma RIIb). Another suitable stabilizing excipient is HP-beta-cyclodextrin (HP-beta-CD) applied at, e.g., 0.35% or above (see Hertel et al., supra). In some variations, a stabilizing excipient is not required for nebulized delivery of a paraoxonase fusion molecule (e.g., DNase1-Fc-PON1) as described herein (for example, wild-type human DNase 1 (Pulmozyme®) has been shown to not aggregate and remain stable after nebulization with either jet or vibrating mesh (VM) nebulizers without requiring excipients, see Cipolla et al., *Pharm. Res.* 11:491-498, 1994; Scherer et al., *J. Pharm. Sci.* 100:98-109, 2011).

Determination of effective dosages is typically based on animal model studies followed up by human clinical trials and is guided by determining effective dosages and administration protocols that significantly reduce the occurrence or severity of the subject disease or disorder in model subjects. Effective doses of the compositions of the present invention vary depending upon many different factors, including means of administration, target site, physiological state of the patient, whether the patient is human or an animal, other medications administered, whether treatment is prophylactic or therapeutic, as well as the specific activity of the composition itself and its ability to elicit the desired response in the individual. Usually, the patient is a human, but in some diseases, the patient can be a nonhuman mammal. Typically, dosage regimens are adjusted to provide an optimum therapeutic response, i.e., to optimize safety and efficacy. Accordingly, a therapeutically or prophylactically effective amount is also one in which any undesired collateral effects are outweighed by beneficial effects (e.g., in the case of treatment of inflammatory lung disease, where any undesired collateral effects are outweighed by any beneficial effects such as, for example, improved alveolar fluid clearance, improved lung physiology and function, etc.). For administration of a fusion polypeptide or dimeric protein of the present invention, a dosage typically ranges from about 0.1 μg to 100 mg/kg or 1 μg/kg to about 50 mg/kg, and more usually 10 μg to 5 mg/kg of the subject's body weight. In more specific embodiments, an effective amount of the agent is between about 1 μg/kg and about 20 mg/kg, between about 10 μg/kg and about 10 mg/kg, or between about 0.1 mg/kg and about 5 mg/kg. Dosages within this range can be achieved by single or multiple administrations, including, e.g., multiple administrations per day or daily, weekly, bi-weekly, or monthly administrations. For example, in certain variations, a regimen consists of an initial administration followed by multiple, subsequent administrations at weekly or bi-weekly intervals. Another regimen consists of an initial administration followed by multiple, subsequent administrations at monthly or bi-monthly intervals. Alternatively, administrations can be on an irregular basis as indicated by monitoring of clinical symptoms of the disease or disorder and/or monitoring of disease biomarkers or other disease correlates.

In some specific embodiments comprising delivery by inhalation with a nebulizer (for example, for treatment of an inflammatory lung disease such as, e.g., cystic fibrosis or interstitial lung disease), a fusion polypeptide or dimeric protein of the present invention is administered to the lung by a nebulizer at a dose of from about 1 mg to about 5 mg or from about 2 mg to about 4 mg per day. In other specific embodiments comprising systemic administration (for example, for treatment of systemic lupus erythematosus, lupus nephritis, rheumatoid arthritis, or inflammatory bowel disease), a fusion polypeptide or dimeric protein of the present invention is administered (e.g., by intravenous or subcutaneous injection) at a dose of from about 50 mg to about 1,000 mg, from about 50 mg to about 800 mg, from about 50 mg to about 500 mg, from about 100 mg to about 500 mg, from about 100 mg to about 400 mg, from about 100 mg to about 300 mg, from about 150 mg to about 250 mg, or about 200 mg every month to six weeks. For combination therapy with a paraoxonase fusion molecule and a DNase as described herein, each of the paraoxonase fusion molecule (e.g., an Fc-L2-PON1 fusion as described herein) and the DNase (e.g., a DNase-Fc fusion as described herein) may be administered at these doses.

Particularly suitable animal models for evaluating efficacy of a paraoxonase fusion composition of the present invention for treatment of inflammatory lung disease include, for example, a murine ovalbumin-induced acute asthma model as described by da Cunha et al. (*Exp. Lung*

*Res.* 42:66, 2016) (showing significantly reduced airway resistance with wild-type (wt) DNase1 treatment), a murine silica-induced lung inflammation model as described by Benmerzoug et al. (*Nat. Comm.* 9:5226, 2018) (showing prevention of DNA-mediated STING activation and blockade of the downstream type I IFN response with wt DNase1 treatment), and a murine model of transfusion-related acute lung injury as described by Caudrillier et al. (*J. Clin. Invest.* 122:2661, 2012) (showing protection from lung edema and lung vascular permeability as well as reduced NET formation and platelet sequestration in the lung with wt DNase1 treatment).

Suitable animal models for evaluating efficacy of a paraoxonase fusion composition as described herein for treatment of exposure to exposure to sulfur mustard gas or an organophosphate include, for example, a guinea pig model as describe by Valiyaveettil et al. (*Biochem. Pharmocol.* 81:800-809, 2011*; Toxicol. Letters* 202:203-208, 2011) (showing protection from sarin and soman inhalation toxicity with recombinant human PON1 injection) and mouse models as described by Bajaj et al. (*Appl. Biochem. Biotechnol.* 180:165-176, 2016) and Stevens et al. (*Proc. Natl. Acad. Sci. USA* 105:12780-12784, 2008) (showing protection from organophosphate poisoning using a recombinant Q192K variant of PON1).

Particularly suitable animal models for evaluating efficacy of a paraoxonase composition as described herein for treatment of an inflammatory bowel disease include a TNBS-induced colitis model and a chronic colitis model with $CD4^{+}CD45RB^{high}$ cell transfer in mice. See, e.g., Yamashita et al., *J. Immunol.* 191:949-960, 2013 (showing efficacy of PON1 therapy in the TNBS-induced colitis model and a PON1 variant (G3C9) in the chronic colitis model). Another suitable model is a dextran sulfate sodium (DSS)-induced colitis model in mice. See, e.g., Babicova et al., *Folia Biolica* (*Praha*) 64:10, 2018 (showing reduction in TNFα and myeloperoxidase in the colon with wt DNase1 treatment of DSS-induced colitis); Li et al., *J. Crohns Colitis* 2020, 14:240-253, 2020 (showing decreased cytokine production and attenuated accelerated thrombus formation and platelet activation with DNase1 treatment of DSS-induced colitis).

Also known is the collagen-induced arthritis (CIA) model for rheumatoid arthritis (RA) (see, e.g., Brand et al., *Nat. Protoc.* 2:1269-1275, 2007). CIA shares similar immunological and pathological features with RA, making it an ideal model for evaluating efficacy of DNase compositions. Another suitable model for RA is PG-PS (proteoglycan-polysaccharide)-induced arthritis in Lewis rats (see, e.g., Esser et al., *Arthritis and Rheumatism* 28:1402-1411, 1985; Brooks et al., *Proc. Intl. Soc. Mag. Reason. Med.* 11:1526, 2003).

Suitable animal models for multiple sclerosis (MS) include, for example, experimental allergic encephalomyelitis (EAE) models that rely on the induction of an autoimmune response in the CNS by immunization with a CNS antigen (also referred to as an "encephalitogen" in the context of EAE), which leads to inflammation, demyelination, and weakness (see, e.g., Constantinescu et al., *British Journal of Pharmacology* 164:1079-1106, 2011).

Other known animal models for evaluating efficacy of paraoxonase fusion molecules of the present invention include, e.g., a hind-limb ischemia reperfusion model as described by Albadawi et al. (*J. Vasc. Surg.* 64:484, 2016) (showing increased perfusion, decreased infiltrating inflammatory cells, and reduction of a local thrombosis marker with wt DNase1 therapy), a rat model of ischemia-reperfusion-induced acute kidney injury as described by Peer et al. (*Am. J. Nephrol.* 43:195, 2016) (showing renoprotective effects with wt DNase1 therapy), a cecal ligation and puncture sepsis model in mice as described by Mai et al. (*Shock* 44:166, 2015) (showing prevention of organ damage and protection from death with wt DNase1 therapy), and a model of inferior vena cava stenosis as described by Brill et al. (*J. Thrombosis Haemostasis* 10:136, 2012) (showing prevention of thrombosis with wt DNase1 therapy). Still other exemplary animal models include models of heart transplantation rejection, plaque formation, and myocardial infarction used to show efficacy of RNase therapy (see, e.g., Kleinert et al., *J. Am. Heart Assn.* doi: 10.1021, 2016; Simsekyilmaz et al., *Circulation* 129:598-606, 2014; Steiger et al., *JAMA* 6:0004541, 2017) as well as an acute stroke model as described by Walberer et al. (*Curr. Neovas. Res.* 6:12-19, 2009) (showing reduced cerebral edema and infarction size with RNase1 therapy).

Fusion molecules of the present invention can also be evaluated for anti-tumor activity in animal tumor models. For example, efficacy of DNase-PON treatment in reducing tumor metastasis associated with NET formation can be evaluated in mouse models as described by, e.g., Cools-Lartigue et al. (*J. Clin. Invest.* 123:3446, 2013) (showing reduction in metastasis of injected tumor (lung carcinoma) cells with systemic administration of wt DNase1 in a model of severe postoperative infection) and Park et al. (*Sci. Translational Med.* 8:361ra138, 2016) (showing reduction in metastasis of breast cancer cells to the lung with systemic administration of wt DNase1-coated nanoparticles). Also known is a model utilizing nude mice subcutaneously grafted with the human colon cancer cell line SW480 as described, e.g., by Trejo-Becirril et al. (*Integrative Cancer Therapies* 15: NP35-NP43, 2016) (showing inhibition of tumor growth with a combination of DNase1 and proteases). Other suitable models include a human lung tumor xenograft model described by Rutkoski et al. (*Translational Oncology* 6:392-397, 2013) (showing inhibition of tumor growth in mice using PEG-RNase1) and a syngeneic mouse tumor model with Lewis lung carcinoma described by Mironova et al., *Oncotarget* 8:78796-78810, 2017 (showing anti-tumor activity with RNase therapy).

Another known animal tumor model is B16 melanoma, a poorly immunogenic tumor. Multiple models of tumor immunotherapy have been studied. See Ngiow et al., *Adv. Immunol.* 130:1-24, 2016. The B16 melanoma model has been studied extensively with checkpoint inhibitors anti-CTLA-4, anti-PD-1, and the combination thereof. Anti-CTLA-4 alone has a potent therapeutic effect in this model only when combined with GM-CSF transduced tumor vaccine, or combined with anti-PD-1. See Weber, *Semin. Oncol.* 37:430-439, 2010; Ai et al., *Cancer Immunol. Immunother.* 64:885-92, 2015; Haanen et al., *Prog. Tumor Res.* 42:55-66, 2015. Efficacy of a DNase-PON, RNase-PON, or antiTGFβ-PON fusion molecule for treatment of malignant melanoma is shown, for example, by slowed tumor growth following administration to B16 melanoma mice that have formed palpable subcutaneous tumor nodules. Efficacy of a paraoxonase fusion molecule can be evaluated in B16 melanoma mice either alone or, alternatively, in combination with another anti-cancer therapy (e.g., anti-CTLA-4, with or without tumor vaccine or with or without anti-PD-1/PD-L1). For example, tumor rejection in B16 melanoma mice using a combination of a DNase-PON, RNase-PON, or antiTGFβ-PON fusion molecule as described herein and anti-CTLA-4, in the absence of tumor vaccine, demonstrates an enhanced response to anti-CTLA-4 using the paraoxonase fusion therapy. In exemplary studies to evaluate paraoxonase fusion molecules comprising human protein sequences, which are functionally active in mice but are expected to be immunogenic in these models (and thereby likely to result in formation of neutralizing antibodies after 7-10 days), mice may be administered a fusion molecule of the present invention for a short period (for example, one week, administered in, e.g., two doses of about 40 mg/kg three days apart), and tumor growth then monitored, typically for two to three weeks after injection with the fusion molecule.

Dosage of the pharmaceutical composition may be varied by the attending clinician to maintain a desired concentration at a target site. For example, if an intravenous mode of delivery is selected, local concentration of the agent in the bloodstream at the target tissue may be between about 1-50 nanomoles of the composition per liter, sometimes between about 1.0 nanomole per liter and 10, 15, or 25 nanomoles per liter depending on the subject's status and projected measured response. Higher or lower concentrations may be selected based on the mode of delivery, e.g., trans-epidermal delivery versus delivery to a mucosal surface. Dosage should also be adjusted based on the release rate of the administered formulation, e.g., nasal spray versus powder, sustained release oral or injected particles, transdermal formulations, etc. To achieve the same serum concentration level, for example, slow-release particles with a release rate of 5 nanomolar (under standard conditions) would be administered at about twice the dosage of particles with a release rate of 10 nanomolar. Dosing may also vary, e.g., depending on the activity of the fusion molecule being administered. For example, in the context of a DNase1-PON fusion molecule in which the DNase1 is not actin-resistant (i.e., in which the DNase1 does not contain any amino acid substitution, relative to human DNase1, that decreases G-actin-induced inhibition of endonuclease activity of the DNase relative to human DNase1), inhibition by actin may be overcome by increasing the dose relative to a dose that is effective for a similar but actin-resistant DNase1-PON fusion molecule.

A pharmaceutical composition comprising a fusion polypeptide or dimeric protein as described herein can be furnished in liquid form, in an aerosol, or in solid form. Liquid forms, are illustrated by injectable solutions, aerosols, droplets, topological solutions and oral suspensions. Exemplary solid forms include capsules, tablets, and controlled-release forms. The latter form is illustrated by miniosmotic pumps and implants. See, e.g., Bremer et al., *Pharm. Biotechnol.* 10:239, 1997; Ranade, "Implants in Drug Delivery," in *Drug Delivery Systems* 95-123 (Ranade and Hollinger, eds., CRC Press 1995); Bremer et al., "Protein Delivery with Infusion Pumps," in *Protein Delivery: Physical Systems* 239-254 (Sanders and Hendren, eds., Plenum Press 1997); Yewey et al., "Delivery of Proteins from a Controlled Release Injectable Implant," in *Protein Delivery: Physical Systems* 93-117 (Sanders and Hendren, eds., Plenum Press 1997). Other solid forms include creams, pastes, other topological applications, and the like.

Degradable polymer microspheres have been designed to maintain high systemic levels of therapeutic proteins. Microspheres are prepared from degradable polymers such as poly(lactide-co-glycolide) (PLG), polyanhydrides, poly (ortho esters), nonbiodegradable ethylvinyl acetate polymers, in which proteins are entrapped in the polymer. See, e.g., Gombotz and Pettit, *Bioconjugate Chem.* 6:332, 1995; Ranade, "Role of Polymers in Drug Delivery," in *Drug Delivery Systems* 51-93 (Ranade and Hollinger, eds., CRC Press 1995); Roskos and Maskiewicz, "Degradable Controlled Release Systems Useful for Protein Delivery," in Protein Delivery: Physical Systems 45-92 (Sanders and Hendren, eds., Plenum Press 1997); Bartus et al., *Science* 281:1161, 1998; Putney and Burke, *Nature Biotechnology* 16:153, 1998; Putney, *Curr. Opin. Chem. Biol.* 2:548, 1998. Polyethylene glycol (PEG)-coated nanospheres can also provide carriers for intravenous administration of therapeutic proteins. See, e.g., Gref et al., *Pharm. Biotechnol.* 10:167, 1997.

Other dosage forms can be devised by those skilled in the art, as shown by, e.g., Ansel and Popovich, *Pharmaceutical Dosage Forms and Drug Delivery Systems* (Lea & Febiger, 5th ed. 1990); Gennaro (ed.), *Remington's Pharmaceutical Sciences* (Mack Publishing Company, 19th ed. 1995), and Ranade and Hollinger, *Drug Delivery Systems* (CRC Press 1996).

In some embodiments comprising systemic administration of a fusion polypeptide or dimeric protein as described herein, the fusion molecule is formulated in a buffered saline (for example, saline buffered with 2 mM carbonate, pH 7.5, plus 1 mM calcium chloride).

Pharmaceutical compositions as described herein may also be used in the context of combination therapy. For example, for a combination therapy comprising administration of a paraoxonase fusion molecule and a DNase as described herein, each of the paraoxonase fusion molecule and the DNase (e.g., a DNase-Fc fusion as described herein) may be formulated in a buffered saline (for example, saline buffered with 2 mM carbonate, pH 7.5, plus 1 mM calcium chloride), either separately or as a mixture.

Pharmaceutical compositions may be supplied as a kit comprising a container that comprises a fusion polypeptide or dimeric protein as described herein. A therapeutic molecule can be provided, for example, in the form of an injectable solution for single or multiple doses, or as a sterile powder that will be reconstituted before injection. Alternatively, such a kit can include a dry-powder disperser, liquid aerosol generator, or nebulizer for administration of a therapeutic protein. Such a kit may further comprise written information on indications and usage of the pharmaceutical composition.

The invention is further illustrated by the following non-limiting examples.

Example 1: Construction and Expression of DNase1-Fc and DNase1-Fc-PON1 Fusion Proteins Constructs were designed and synthesized and cassettes with the correct sequences were combined to generate synthetic fusion genes encoding unique DNase1 fusion molecules. Each construct included a variant of wild-type human DNase1 (nucleotide and encoded amino acid sequences as shown in SEQ ID NOs: 15 and 16; see also GenBank accession number NM_005223). The DNase1 variant contained amino acid substitutions, relative to the mature wild-type human sequence (SEQ ID NO:120), at positions N74 (N74K), G105 (G105R), and A114 (A114F); the variant DNase1 nucleotide and encoded amino acid sequences corresponding to the mature protein are shown in residues 61-840 of SEQ ID NO:17 and residues 21-280 of SEQ ID NO:18, respectively). The signal peptide sequence utilized was the human VK3 leader peptide (nucleotide and amino acid sequences as shown in SEQ ID NO:57 and SEQ ID NO:58), an efficient heterologous leader peptide that drives high level expression and secretion of fusion proteins. The DNase1 cassette was fused to the N-terminus of a human IgG1 Fc variant (SSS hinge, P238S, P331S) using a peptide linker, either a $(Gly_4Ser)_4$ linker ((g4s)4; nucleotide and amino acid sequences as shown in SEQ ID NO: 11 and SEQ ID NO:12) or a $(Gly_4Ser)_6$ linker ((g4s)6; nucleotide and amino acid sequences as shown in SEQ ID NO:13 and SEQ ID NO:14). The Fc variant nucleotide and amino acid sequences are shown in SEQ ID NO:27 and SEQ ID NO:28. The completed DNase1-Fc constructs generated are as follows:

[hVK3LP]-[hDNase1 N74K-G105R-A114F]-(g4s)4-[SSShinge-P238S-P331S Fc] (also referred to hereinbelow as hDNaseTM-(g4s)4-Fc; nucleotide and amino acid sequences as shown in SEQ ID NO:59 and SEQ ID NO:60); and

[hVK3LP]-[hDNase1 N74K-G105R-A114F]-(g4s)6-[SSShinge-P238S-P331S Fc] (also referred to hereinbelow as hDNaseTM-(g4s)6-Fc; nucleotide and amino acid sequences as shown in SEQ ID NO:61 and SEQ ID NO:62).

Bispecific constructs further comprising a functional PON1 enzyme were also generated by fusing the carboxyl end of hDNaseTM-(g4s)4-Fc or hDNaseTM-(gs)6-Fc to a peptide linker containing an N-linked glycosylation site (NGS; nucleotide and amino acid sequences as shown in SEQ ID NO:55 and SEQ ID NO:56) followed by a variant of human PON1 (PON1 Q192K; nucleotide and amino acid sequences as shown in SEQ ID NO:5 and SEQ ID NO:6) in which the first 15 amino acids of the uncleaved leader peptide were deleted. The completed DNase-Fc-PON1 constructs are as follows:

[Human VK3LP]-[hDNase1 N974K-G105R-A114F]-(g4s)4-[SSShinge-P238S-P331S Fc]-NGS-[PON1 Q192K], (nucleotide and amino acid sequences as shown in SEQ ID NO:1 and SEQ ID NO:2) (also referred to hereinbelow as hDNaseTM-(g4s)4-Fc-PON1-Q192K, hDNaseTM-(g4s)4-Fc-PON1-K, or DNaseTM-(g4s)4-Fc-P1-K); and

[Human VK3LP]-[hDNase1 N974K-G105R-A114F]-(g4s)6-[SSShinge-P238S-P331S Fc]-NGS-[PON1 Q192K], (nucleotide and amino acid sequences as shown in SEQ ID NO:147 and SEQ ID NO:148) (also referred to hereinbelow as DNaseTM-(g4s)6-Fc-P1-K).

Transient Expression of DNase1-Fc and DNase1-Fc-PON1 Fusion Proteins

All fusion genes were assembled in a pUC based vector, then inserted into a multiple cloning site of the mammalian expression vector pDG, a pcDNA3 plasmid derivative containing a CMV promoter to drive expression of the fusion gene. Plasmid DNA was prepared using QIAGEN (Germantown, MD) mini or maxiprep plasmid DNA kits. Purified plasmid DNA was transfected into HEK293 cells plated at approximately 50-75% confluence, using Polyfect (QIAGEN, Germantown, MD) transfection reagent according to the manufacturer's instructions. Culture media was changed to DMEM Fluorobrite™ (Life Technologies, Carlsbad, CA) serum free media on the day after transfections, and transfected cells incubated for an additional 48 hours prior to harvest of culture supernatants.

FIG. 1 shows the results of Western blot analysis of fusion protein expression from a representative set of HEK293 transient transfections. Culture supernatants were loaded directly for gel electrophoresis as follows: supernatants were collected, ¼ sample volume 4× reducing LDS sample buffer added (Life Technologies, Carlsbad, CA), samples heated for 10 minutes at 72° C., the samples centrifuged for 1 minute at 3000 rpm in a microfuge, and 30 μl sample in loading buffer (one half) from each sample was loaded onto 4-12% Bis-Tris NuPAGE gels (Life Technologies, Carlsbad, CA). Protein molecular weight markers were included on each gel (Chameleon® DUO molecular weight markers; LI-COR Biosciences, Lincoln, NE). SDS-PAGE gels were run in NuPAGE MOPS running buffer (Life Technologies, Carlsbad, CA) under reducing conditions at 185 volts for approximately 1-1.5 hours. Gels were blotted to nitrocellulose membranes using the XCell blot module (Life Technologies, Carlsbad, CA) and NUPAGE-MOPS (Life Technologies, Carlsbad, CA) transfer buffer containing 10% methanol. Blots were blocked in LI-COR Odyssey Intercept™ blocking buffer, followed by incubation with diluted goat anti-human IgG (Fc specific) secondary antibodies (Jackson Immunoresearch, West Grove, PA). Secondary antibody was conjugated with Alexafluor 790 near IR dye (LI-COR Odyssey detection) and diluted in blocking buffer 1:25,000 at 4° C. and rocked overnight. Blots were washed four times with Tris buffered saline (TBS) containing 0.1% Tween 20. Blots were then rinsed in TBS buffer and scanned with a LICOR Odyssey™ scanner. Transfection samples were loaded as follows: Lane 1—LICOR Chameleon™ molecular weight markers; Lane 2, Lane 3, Lane 4—transfection supernatants from three different individual clones (#1, #2, #4) of hDNaseTM-(g4s)4-Fc-PON1-Q192K; Lane 5—THER4-RNase (control; apoA1-(g4s)4-SSShinge-P238S-P331S-Fc-NGS-RNase1; see US Patent Application Publication No. 2018/0201664); Lane 6—LICOR Chameleon MW Markers; Lane 7—hDNaseTM-(g4s)4-Fc #4; Lane 8—hDNaseTM-(g4s)6-Fc #2; Lane 9—THER4 (control; apoA1-(g4s)4-SSShinge-P238S-P331S-Fc; see International PCT Publication No. WO 2017/044424); Lane 10—mock transfection. The approximate molecular weight (kDa) of each marker band is indicated on the right side of the Western blot.

Stable Expression of DNase1-Fc and DNase1-Fc-PON1 Fusion Proteins

Stable production of the DNase1 fusion proteins was achieved by electroporation of a selectable, amplifiable plasmid, pDG, containing the DNase1 fusion molecule cDNAs under the control of the CMV promoter, into Chinese Hamster Ovary (CHO) DG44 cells. The PDG vector is a modified version of pcDNA3 encoding the DHFR selectable marker with an attenuated promoter to increase selection pressure for the plasmid. Plasmid DNA (200 μg) was prepared using QIAGEN HISPEED maxiprep kits. Purified plasmid was linearized at a unique AscI site (New England Biolabs, Ipswich, MA Catalog #R0558), purified by phenol extraction (Sigma-Aldrich, St Louis, MO), ethanol precipitated, washed, and resuspended in tissue culture media, Excell 302 (Catalog #14324, SAFC/Sigma Aldrich, St Louis, MO). Salmon sperm DNA (Sigma-Aldrich, St. Louis, MO) was added as carrier DNA just prior to phenol extraction and ethanol precipitation. Plasmid and carrier DNA were coprecipitated, and the 400 μg was used to transfect $2\times10^7$ CHO DG44 cells by electroporation.

For electroporation, cells were grown to logarithmic phase in Excell 302 media (Catalog #13424C, SAFC Biosciences/Sigma-Aldrich, St. Louis, MO) containing glutamine (4 mM), pyruvate, recombinant insulin (1 μg/ml), penicillin-streptomycin, and 2×DMEM nonessential amino acids (all from Life Technologies, Grand Island, NY), hereinafter referred to as "Excell 302 complete" media. Media for untransfected cells and cells to be transfected also contained HT (diluted from a 100× solution of hypoxanthine and thymidine) (Invitrogen/Life Technologies, Grand Island, NY). Electroporations were performed at 280 volts, 950 microFarads, using a BioRad (Hercules, CA) GenePulser electroporation unit with capacitance extender.

Electroporation was performed in 0.4 cm gap sterile, disposable cuvettes. Electroporated cells were incubated for 5 minutes after electroporation prior to transfer of the treated cells to non-selective Excell 302 complete media in T75 flasks. Transfected cells were incubated overnight at 37° C., 5% $CO_2$ in non-selective media to permit recovery, prior to selective plating in 96-well flat-bottom plates (Costar) at varying serial dilutions ranging from 250 cells/well (2500 cells/ml) to 2000 cells/well (20,000 cells/ml). Culture media for cell cloning was Excell 302 complete containing 50 nM methotrexate. Transfection plates were fed at five-day intervals with 80 μl fresh media. After the first couple of feedings, 100 μl media was removed and replaced with fresh media. Plates were monitored and individual wells with clones were fed until clonal outgrowth became close to confluent, after which clones were expanded into 24-well dishes containing 1 ml media/well. Aliquots of the culture supernatants from the original 96-well plate were harvested to a second 96-well plate prior to transfer and expansion of the cells in the 24-well plates. This second plate was frozen until performing dilutions for ELISA analysis to estimate IgG concentrations.

Screening Culture Supernatants for Production Levels of Recombinant Fusion Proteins: Once clonal outgrowth of initial transfectants was sufficient, serial dilutions of culture supernatants from master wells were thawed and the dilutions screened for expression of DNase1 fusion protein by use of an -IgG sandwich ELISA. Briefly, NUNC Maxisorp plates were coated overnight at 4° C. with 2 microgram/ml F(ab'2) goat anti-human IgG (Jackson Immunoresearch, West Grove, PA; Catalog #109-006-098) in PBS. Plates were blocked in PBS/3% BSA, and serial dilutions of culture supernatants incubated at room temperature for 2-3 hours or overnight at 4° C. Plates were washed three times in PBS/0.05% Tween 20, and incubated with horseradish-peroxidase-conjugated F(ab'2) goat anti-human IgG (Jackson Immunoresearch, West Grove, PA, Catalog #109-036-098) at 1:7500-1:10,000 in PBS/0.5% BSA, for 1-2 hours at room temperature. Plates were washed five times in PBS/0.05% Tween 20, and binding detected with SureBlue Reserve™ TMB substrate (KPL Labs/SeraCare, Gaithersburg, MD; catalog #53-00-02). Reactions were stopped by addition of equal volume of 1N HCl, and absorbance per well on each plate was read at 450 nM on a VarioSkan LUX plate reader (ThermoFisher Scientific, Waltham, MA). Concentrations were estimated by comparing the OD450 of the dilutions of culture supernatants to a standard curve generated using serial dilutions of a known standard, a protein-A-purified human -IgG fusion protein with the identical -Ig tail to clones described in this disclosure, typically THER4 (apoA1-(g4s)4-SSShinge-P238S-P331S Fc; see International PCT Publication No. WO 2017/044424) or an scFv-Fc targeted to human CD180 (G28-8). Data was collected and analyzed using platereader software and Microsoft Office Excel or GraphPad Prism 8.4.3 (San Diego, CA). The best expressing DNase-lnk-Fc clones expressed in the range of 25-55 μg/ml, while the best expressing DNase-lnk-Fc-PON1-K clones expressed at approximately 10-30 μg/ml.

Protein A purification supernatants were collected from spent CHO cell cultures expressing the fusion proteins, filtered through 0.2 μm PES express filters (Nalgene, Rochester, NY) and subjected to affinity chromatography using slow rotation of culture supernatants with Protein A-agarose (IPA 300 crosslinked agarose) slurry in 50 ml sterile, conical centrifuge tubes at 4° C. (Repligen, Waltham, MA). Fusion protein bound to protein A agarose was recovered by centrifugation, and culture supernatants removed, replaced, and the incubation process repeated until the desired volume of supernatant was processed. The final protein A agarose slurry was then loaded into sterile, acid-washed econocolumns (BioRad, Hercules, CA) to wash the resin. Columns were then washed with several column volumes of column wash buffer (Gentle Ag-Ab binding buffer, Pierce/ThermoFisher, Waltham, MA) to remove any residual culture supernatant, prior to elution. Bound protein was then eluted from the resin using gentle Ag/Ab elution buffer (Pierce/ThermoFisher, Waltham, MA). Fractions (0.8-1.0 ml) were collected and protein concentration of aliquots (2 μl) from each fraction were determined at 280 nM using a Nanodrop (Wilmington DE) microsample spectrophotometer, with blank determination using elution buffer alone. Fractions containing fusion protein were pooled, and buffer exchange was performed by dialysis using Spectrum Laboratories G2 (Ranch Dominguez, CA, Catalog #G235057, Fisher Scientific catalog #08-607-007) float-a-lyzer units (MWCO 20 kDa) against [0.9% sodium chloride, 5 mM sodium bicarbonate, 1 mM HEPES buffer, 1 mM calcium chloride, pH 7.5]. Dialysis was performed in sterile, 2.2-liter Corning roller bottles at 4° C. overnight. After dialysis, protein was filtered using 0.2 μM filter units, and aliquots tested for endotoxin contamination using Pyrotell LAL gel clot system single test vials (STV) (Catalog #G2006, Associates of Cape Cod, East Falmouth, MA).

Figure 2:
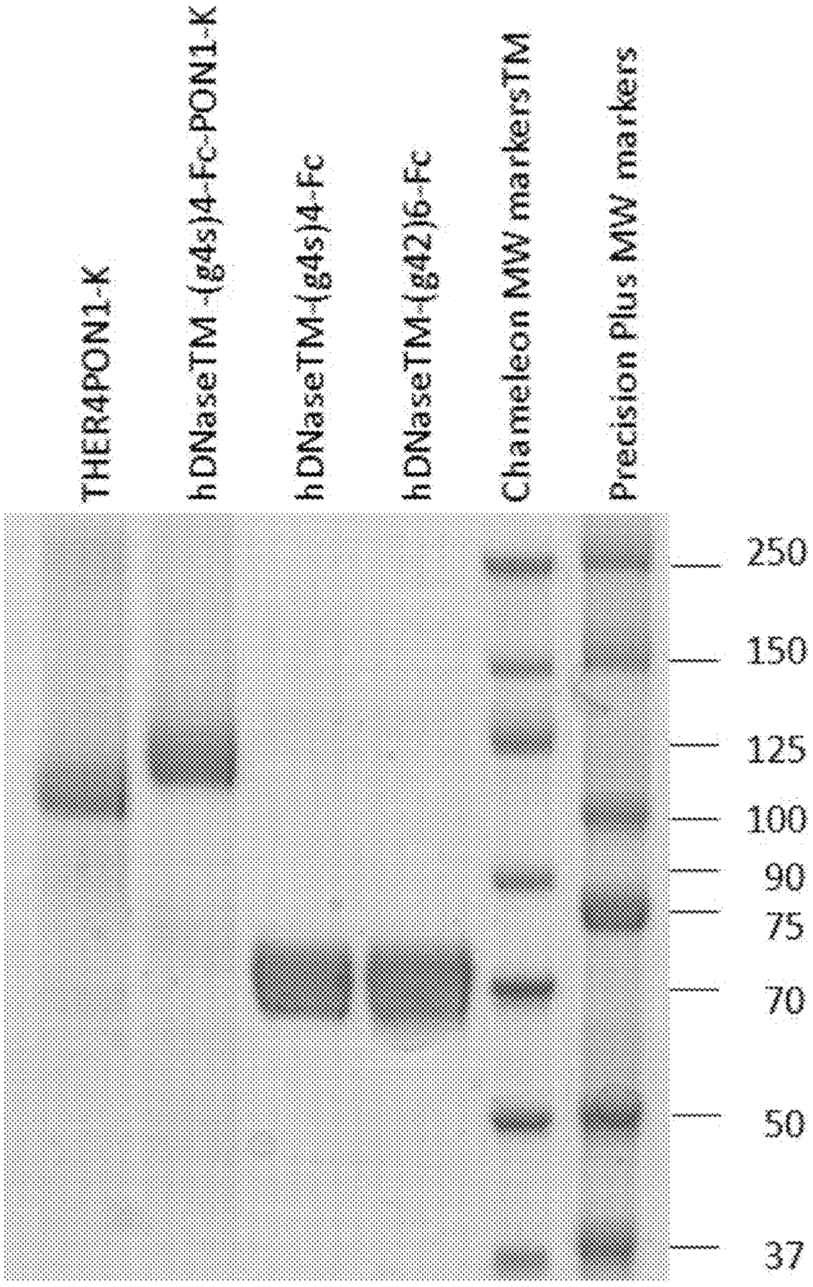
FIG. 2 shows reducing SDS-PAGE analysis of DNase1-Fc and DNase1-Fc-PON1 fusion proteins purified from CHO clone spent culture supernatants. Stable CHO cell generation, Protein A purification of fusion proteins, and SDS-PAGE were performed as described in Example 1, infra. From left to right: Lane 1—THER4PON1-K (control); Lane 2—hDNaseTM-(g4s)4-Fc-PON1-K; Lane 3—hDNaseTM-(g4s)4-Fc; Lane 4—hDNaseTM-(g4s)6-Fc; Lane 5—LI-COR Chameleon® MW markers; Lane 6—BioRad Precision Plus Kaleidoscope MW markers.

FIG. 2 shows purified proteins from stable CHO transfections after SDS-PAGE electrophoresis and staining with Imperial Protein Stain (Pierce/ThermoFisher, Waltham, MA/Rockville, MD; Catalog #24615). Five micrograms each protein-A-purified fusion protein was incubated in 1×LDS reducing sample buffer at 72° C. for 10 minutes followed by loading onto 4-12% Bis-Tris NuPAGE gels (Life Technologies, Carlsbad, CA). Protein molecular weight markers were included on each gel (Chameleon® DUO molecular weight markers (L1-COR Biosciences, Lincoln, NE) and Precision Plus molecular weight markers (BioRad, Hercules, CA)). SDS-PAGE gels were run in NuPAGE MOPS running buffer (Life Technologies, Carlsbad, CA) under reducing conditions at 175 volts for approximately 2 hours. Gels were washed three times in 100 ml distilled water, then stained in 30 ml Imperial Stain (Pierce/ThermoFisher, Waltham, MA) at room temperature with rocking for 2.5 hours. Gels were destained by washing 4 times in 100-200 ml distilled water and placed in a plastic sleeve prior to photographing/scanning of the stained gel. Lanes were loaded as follows: Lane 1—THER4PON1-K (apoA1-(g4s)4-SSShinge-P238S-P331S-Fc-NGS-PON1-K; see International PCT Publication No. WO 2017/044424); Lane2—hDNaseTM-(g4s)4-Fc-PON1-K; Lane 3—hDNaseTM-(g4s)4-Fc; Lane 4—hDNaseTM-(g4s)6-Fc; Lane5—LI-COR Chameleon® MW markers; Lane 6—BioRad Precision Plus Kaleidoscope MW markers. The approximate molecular weight (kDa) of each marker band is indicated on the right side of the stained gel.

Example 2: DNase Activity of DNase1-Fc and DNase1-Fc-PON1 Fusion Proteins

Nuclease activity of DNase1 fusion proteins was assessed using a modified SYTOX™ Green fluorescence assay. SYTOX Green dye (5 mM solution in DMSO, Catalog #S7020) was obtained from Molecular Probes/Invitrogen (ThermoFisher Scientific, Waltham, MA). Salmon sperm DNA was also obtained from ThermoFisher Scientific (UltraPure, sheared, phenol purified, Catalog #15632011). Enzyme activity assays were performed either by titrating the substrate concentration with a fixed enzyme concentration, or by titrating the enzyme concentration with a fixed substrate concentration. For substrate titration experiments, salmon sperm DNA was mixed with SYTOX Green stain at a ratio of 14 μM sytox green to 400 μM (140 ug/ml) salmon sperm DNA in 1× DNase reaction buffer (10 mM Tris, pH 7.5, 5 mM $MgCl_2$, 1 mM $CaCl_2$)), and the mixture was incubated at 37° C. for approximately 2 hours to label and equilibrate. Appropriate dilutions of the stock labeled DNA were made for enzyme activity assays. One-third fold serial dilutions of SYTOX Green labeled DNA were prepared in a separate plate and 50 μl of each dilution was transferred to the assay plate to generate the following substrate concentrations in the final reactions: 1) 220 μM salmon sperm DNA (SS DNA) and 10 μM SYTOX Green; 2) 147 μM SS DNA and 6.7 μM SYTOX Green; 3) 98.78 μM SS DNA and 4.4 μM SYTOX Green; 4) 66 μM SS DNA and 3.01 μM SYTOX Green; and 5) 44 μM SS DNA and 2.05 UM SYTOX Green.

Each fusion protein or recombinant DNase 1 enzyme was prepared at two times the desired final concentration (9 nM initial, or 4.5 nM final concentration) to be assessed in 1× DNase reaction buffer. Fifty microliters of each fusion protein or recombinant enzyme were added to each well of the assay plate containing the labeled substrate. Plates were immediately transferred to the plate reader, and fluorescence was measured using 485 nm excitation and 528 nm emission wavelengths. Sample fluorescence was monitored using a kinetic assay on a VarioSkan LUX fluorescent plate reader (Thermo Scientific, Waltham, MA) with readings every 45 seconds for a total of 40 minutes. RFU (Relative Fluorescence Units) were plotted as a function of time for each well. The fluorescence signal in each well decreased more rapidly with increasing nuclease activity.

Figure 3A:
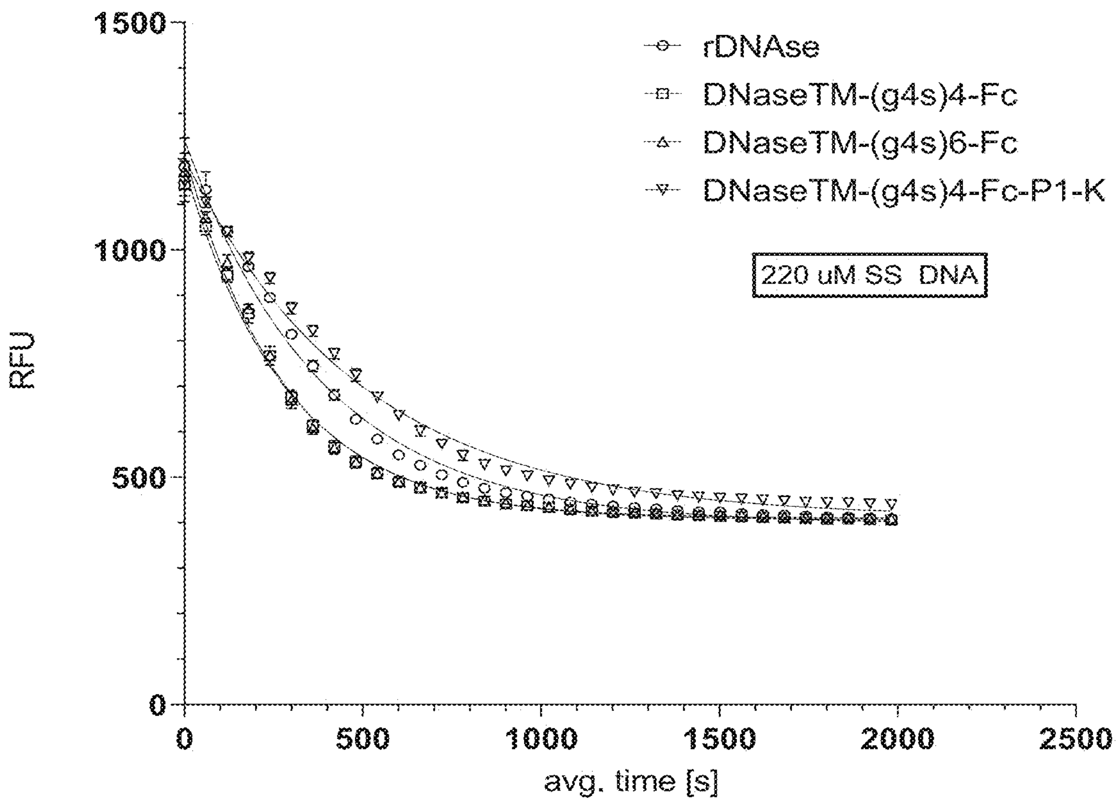
FIGS. 3A and 3B show raw data from a modified SYTOX™ Green fluorescence assay assessing nuclease activity of DNase1 fusion proteins at two different substrate concentrations, 220 μM or 66 μM salmon sperm DNA (see Example 2, infra).
Figure 3B:
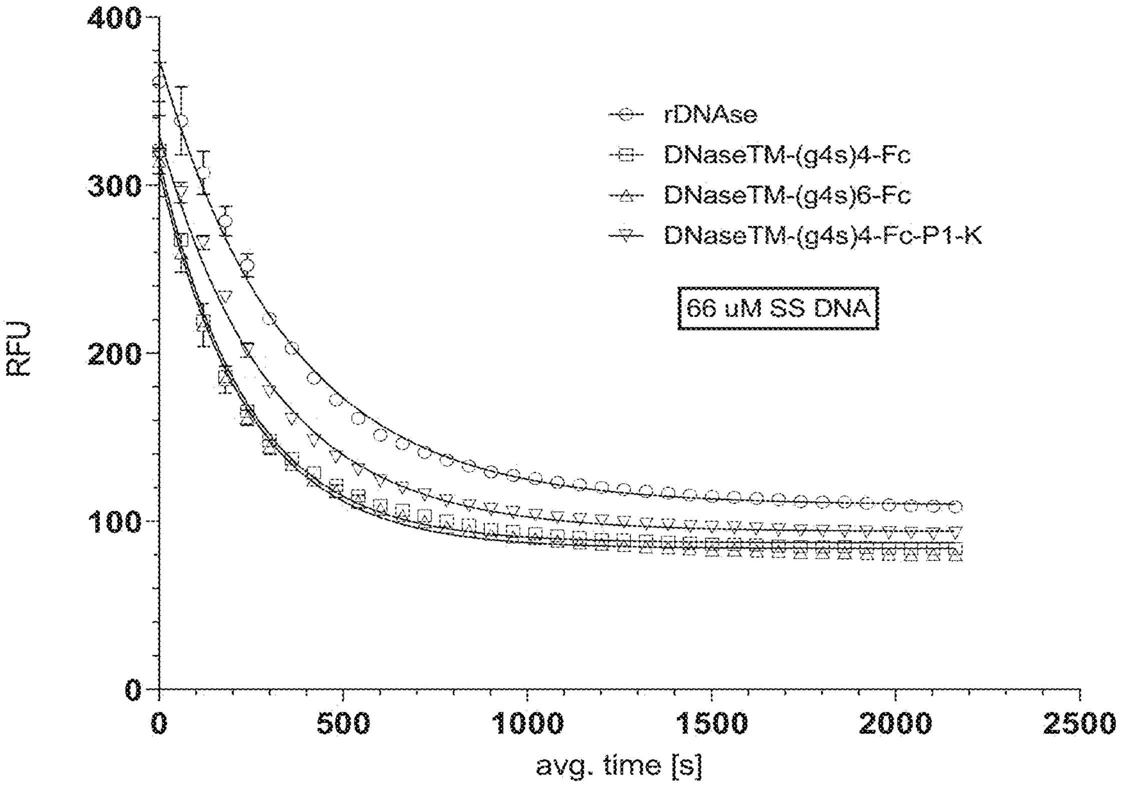

FIG. 3 shows a graphical representation of the raw data analyzing the relative fluorescence units (RFU) as a function of time at two different substrate concentrations, 220 μM or 66 μM salmon sperm DNA. For these experiments, the enzyme concentration used was fixed at 4.5 nM. The specific activity of the DNase1TM-(g4s)4-Fc and DNase1TM-(g4s)6-Fc fusion proteins was higher than the recombinant wild-type human DNase1 at all substrate concentrations. At lower concentrations of substrate (the more physiologically relevant levels), the bispecific fusion protein (DNase1TM-(g4s)4-Fc-P1-K) showed higher activity than the recombinant wild-type DNase1, while at higher concentrations of DNA substrate, the wild-type DNase1 had higher activity than the bispecific fusion protein.

Figure 4A:
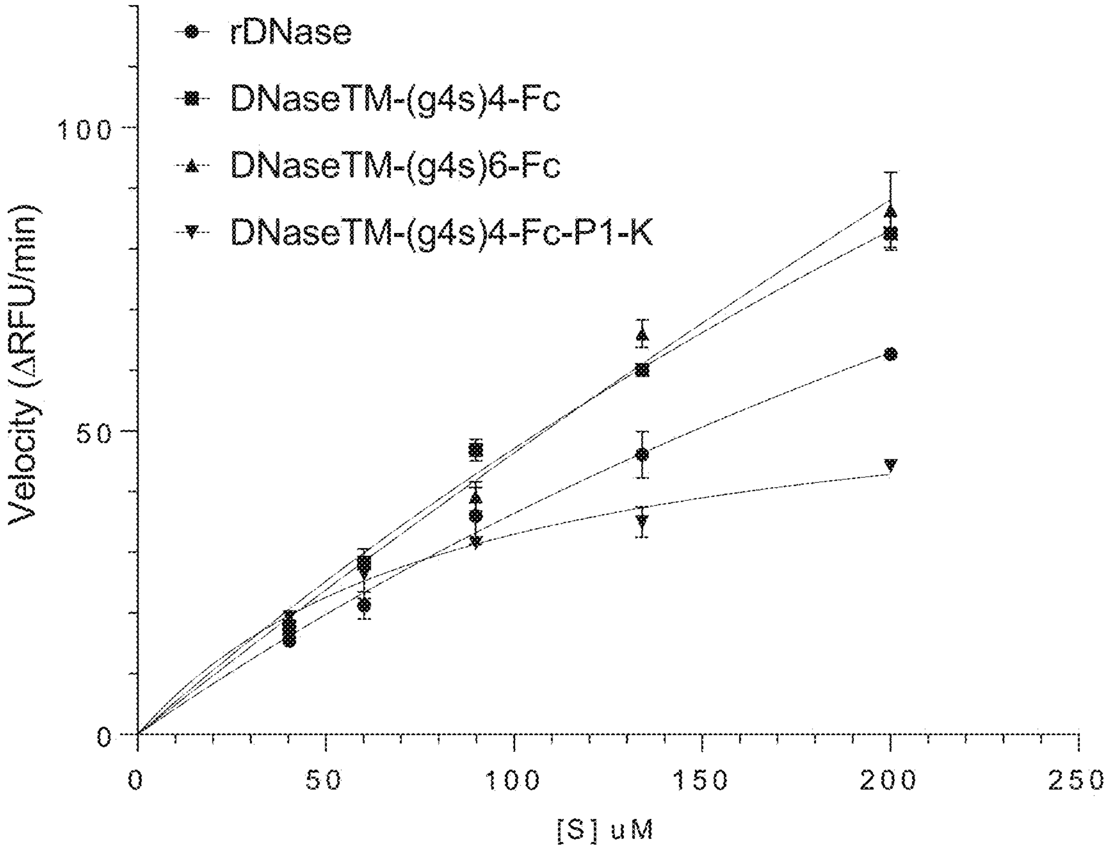
FIGS. 4A and 4B show Michaelis-Menten plots of data from two different DNase activity experiments using a modified SYTOX™ Green fluorescence assay (see Example 2, infra).
Figure 4B:
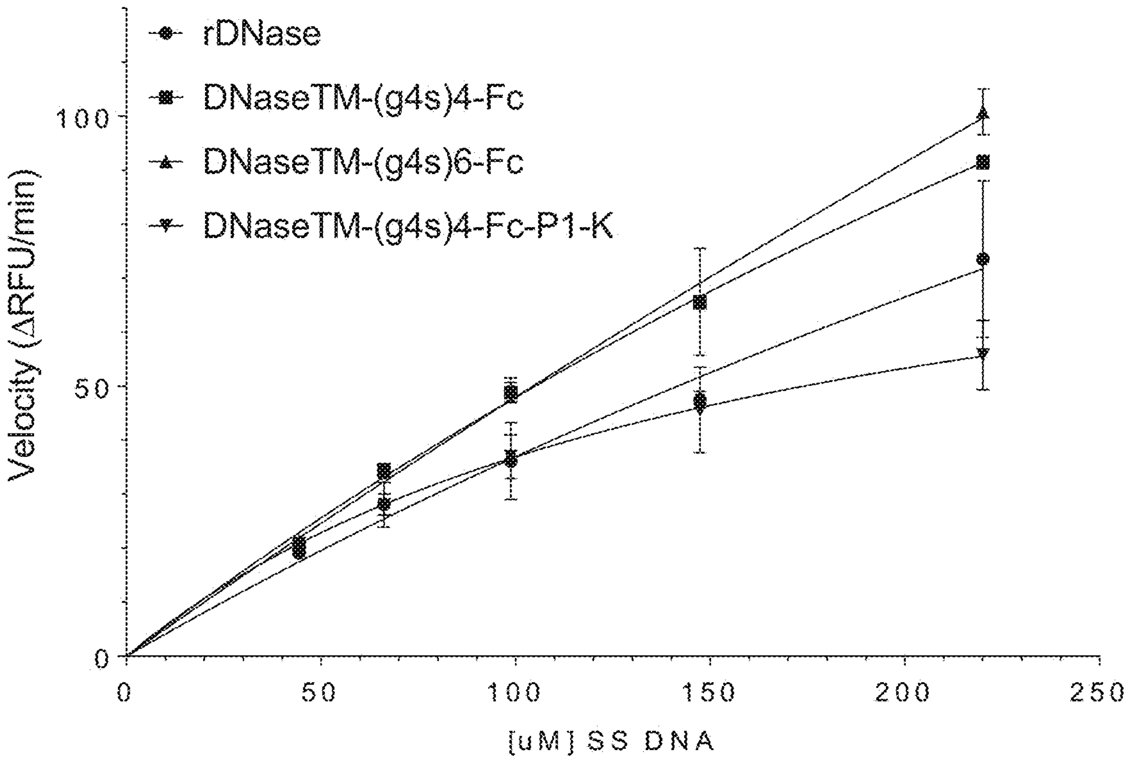

FIGS. 4A and 4B show Michaelis Menten plots of the data from two different DNase activity experiments ("Experiment #1" and "Experiment #2") using these conditions. The estimated Km and Vmax for each fusion protein in Experiment #1 and Experiment #2 are shown below in Table 2, with the tabulated data for each experiment listed. The units for the Vmax or maximal velocity are in μmoles SYTOX-labeled salmon DNA digested/min, and the units for the Km are in μmoles labeled salmon sperm DNA. Raw data was analyzed using the SkanIt™ software for the VarioSkan LUX plate reader (Thermo Scientific, Waltham, MA), then the data further analyzed using Microsoft Excel (Redmond, WA) and GraphPad Prism 8.4.3 (San Diego CA).

TABLE 2

Tabulated Michaelis Menten Data for DNase Fusion Proteins at 4.5 nM

| | rDNase | DNaseTM-(g4s)4-Fc | DNaseTM-(g4s)6-Fc | DNaseTM-(g4s)4Fc-P1-K |
|---|---|---|---|---|
| Experiment #1 | | | | |
| Vmax | 332.5 | 374.7 | 968.9 | 95.91 |
| Km | 533.6 | 681.9 | 1919 | 159.7 |
| Experiment #2 | | | | |
| Vmax | 230.8 | 349.4 | 874.3 | 61.13 |
| Km | 533.6 | 641.6 | 1785 | 85.29 |

Vmax: μmol salmon sperm DNA digested/min
Km: μmol salmon sperm DNA

Enzyme activity assays were also performed in the presence or absence of actin to assess whether the DNase fusion proteins were sensitive to actin inhibition. These assays were performed either by titrating the substrate concentration with a fixed enzyme concentration, or by titrating the enzyme concentration with a fixed substrate concentration. For substrate titration experiments, salmon sperm DNA was mixed with SYTOX Green stain at a ratio of 14 μM sytox green to 400 μM (140 ug/ml) salmon sperm DNA in 1× DNase reaction buffer (10 mM Tris, pH 7.5, 5 mM $MgCl_2$, 1 mM $CaCl_2$)), and the mixture was incubated at 37° C. for approximately 2 hours to label and equilibrate.

Figure 5A:
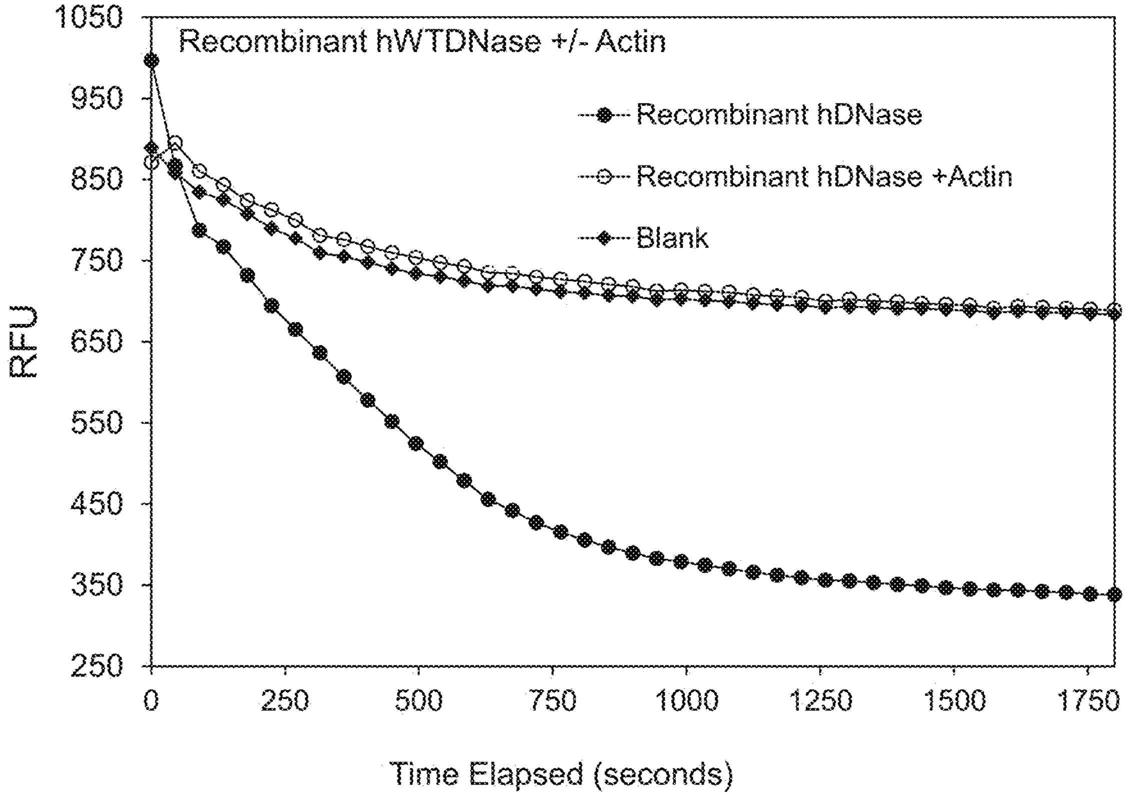
FIGS. 5A and 5B show results from a SYTOX™ Green fluorescence assay comparing relative actin-induced inhibition of DNase activity of recombinant human DNase1 and a DNase1-Fc fusion protein (see Example 2, infra).
Figure 5B:
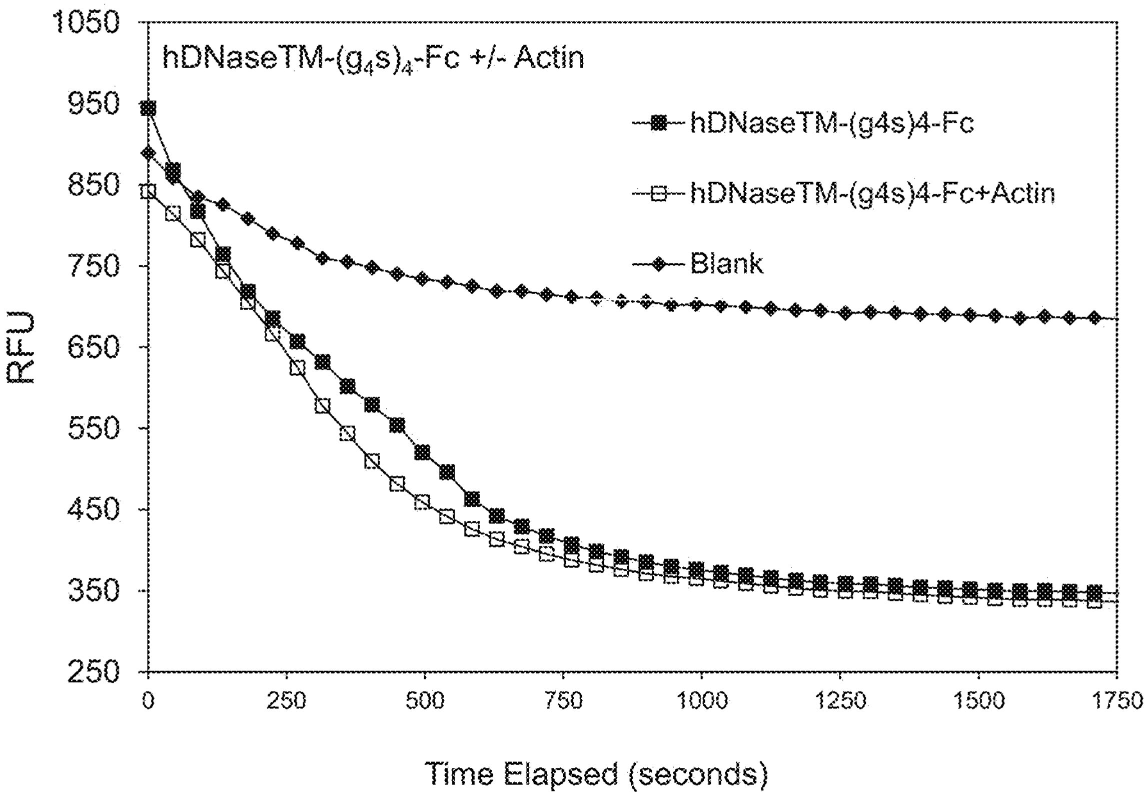

Each fusion protein or recombinant DNase1 enzyme was prepared at four times the desired final concentration (18 nM initial, or 4.5 nM final concentration) to be assessed in 1× DNase reaction buffer. Each 4× sample was then mixed 1:1 with a solution containing rabbit skeletal muscle actin protein (Cytoskeleton, Denver, CO., Catalog #AKL99-A) at 4×=160 g/ml, or a final concentration in the nuclease reaction of 40 μg/ml; or reaction buffer containing no actin. Samples containing 9 nM fusion protein with 80 μg/ml actin were incubated at 37° C. for 45-60 minutes prior to addition of the labeled SYTOX green substrate. Sytox green substrate was prepared by adding 160 μg/ml salmon sperm DNA to 14 μM Sytox green dye in 1× DNase reaction buffer and equilibrating at 37° C. for 60-120 minutes. Fifty microliters of each actin-treated fusion protein or recombinant enzyme were added to each well of the assay plate containing 50 μl of the labeled substrate. Plates were immediately transferred to the plate reader, and fluorescence was measured using 485 nm excitation and 528 nm emission wavelengths. Sample fluorescence was monitored using a kinetic assay on a VarioSkan LUX fluorescent plate reader (Thermo Scientific, Waltham, MA) with readings every 45 seconds for a total of 40 minutes. RFU (Relative Fluorescence Units) were plotted as a function of time for each well. The fluorescence signal in each well decreased more rapidly with increasing nuclease activity. FIGS. 5A and 5B show graphs plotting the RFU as a function of time for the DNaseTM-(g4s)4-Fc molecule and for the recombinant human DNase. The nuclease activity of the recombinant human DNase1 was inhibited by actin, while the fusion protein variants were not inhibited under these conditions.

Example 3: Paraoxonase Activity of DNase1-Fc-PON1 Fusion Protein

Arylesterase Activity

Phenyl acetate was used as a substrate to assess arylesterase activity of the DNase1TM-(g4s)4-Fc-PON1-Q192K fusion protein. Enzyme activity assays were performed either by titrating the substrate concentration with a fixed enzyme concentration, or by titrating the enzyme concentration with a fixed substrate concentration. For the phenyl acetate activity assays, reaction buffer contained 20 mM Tris-HCl, pH 8.0, 1 mM $CaCl_2$). Substrate solution contained reaction butter and 10 mM phenyl acetate, while enzyme solution contained reaction buffer and enzyme(s) at the appropriate concentrations. Substrate solution was diluted 1:1 with enzyme solutions for a final concentration of 5 mM phenyl acetate substrate in the reactions. Fusion protein (enzyme) concentration was present in the assays titrated in 1/3 serial dilutions from 40 μg/ml (40, 26.8, 17.96, 12.05, 8.06, 5.4, 3.62, and 2.4 ug/ml). Sample absorption was monitored using a kinetic assay on a VarioSkan LUX fluorescent plate reader, with readings every 45 seconds for a total of 10 minutes. Molar absorptivity at 270 nm serves as a measure of phenol formed as a function of time. The change in absorption was converted into a reaction rate using the molar extinction coefficient of 1310 $M^{-1}$ $cm^{-1}$ for phenol.

Figure 6A:
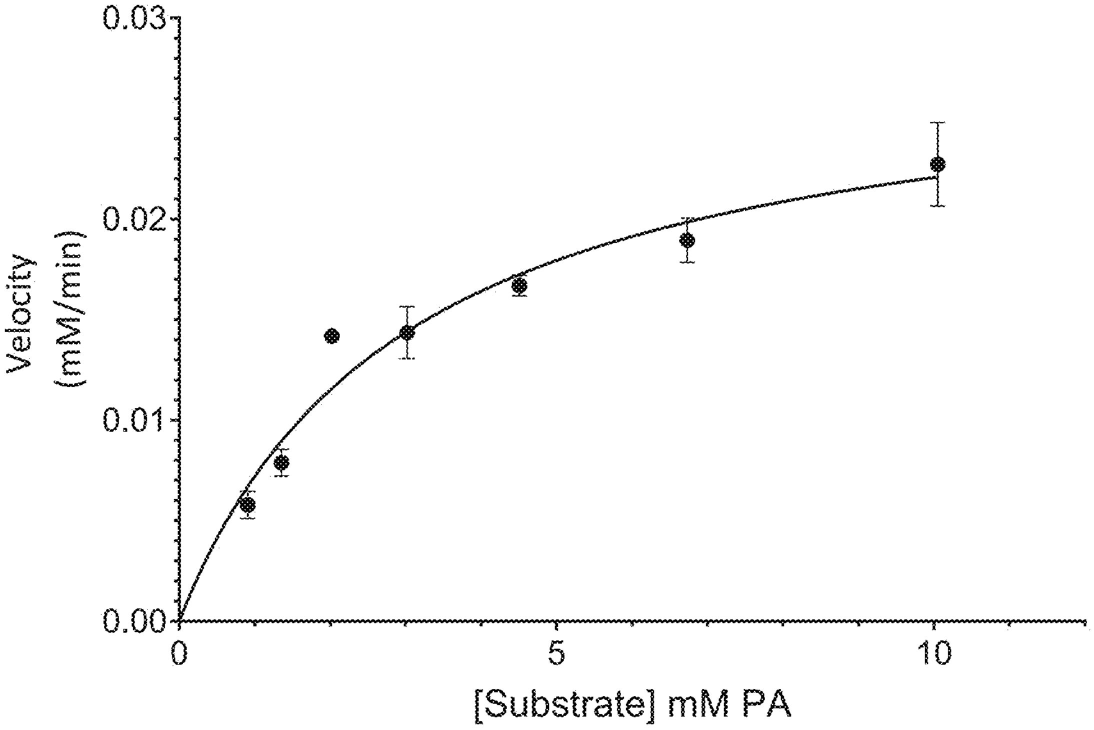
FIGS. 6A and 6B show Michaelis-Menten and Lineweaver-Burk plots, respectively, for a representative experiment measuring the arylesterase activity of a DNase1-Fc-PON1 fusion protein (see Example 3, infra).
Figure 6B:
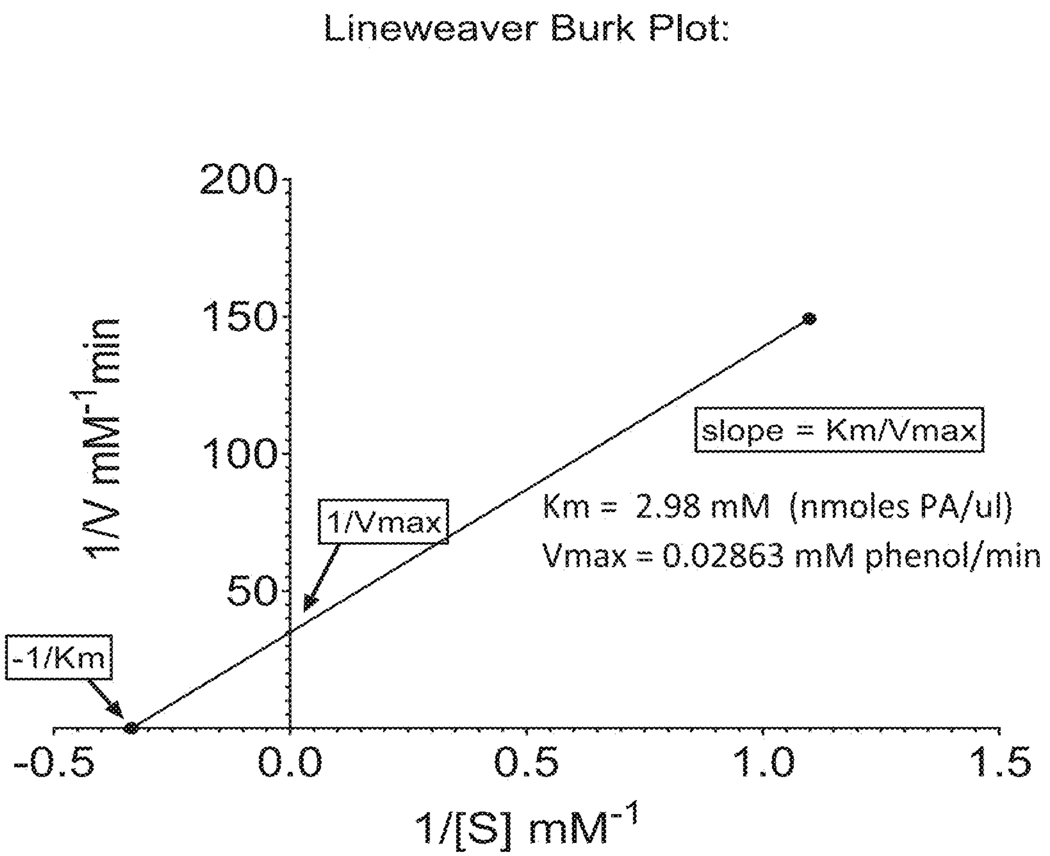

In addition, arylesterase activity assays were performed titrating the amount of phenyl acetate substrate present in 1/3-fold serial increments as follows: 15 mM, 10.05 mM, 6.73 mM, 4.51 mM, 3.02 mM, 2.03 mM, 1.36 mM, and 0.91 mM substrate. In each case, the amount of fusion protein (enzyme) present was 7.5 ug/ml. For the DNase1TM-(g4s)4-Fc-PON1-Q192K molecules, this concentration corresponds to 75 nM. FIGS. 6A and 6B show Michaelis Menten analysis and Lineweaver Burk plots for a representative experiment measuring the arylesterase activity of the DNaseTM-(g4s)4-Fc-PON1-Q192K fusion protein. When multiple experiments were compared, the Vmax average was approximately 0.027 mM phenol/min (mmoles/liter=nmoles/ul) and the Km was approximately 2.7 mM phenyl acetate (mmoles/liter=nmoles phenyl acetate/ul).

Organophosphatase Activity

Figure 7:
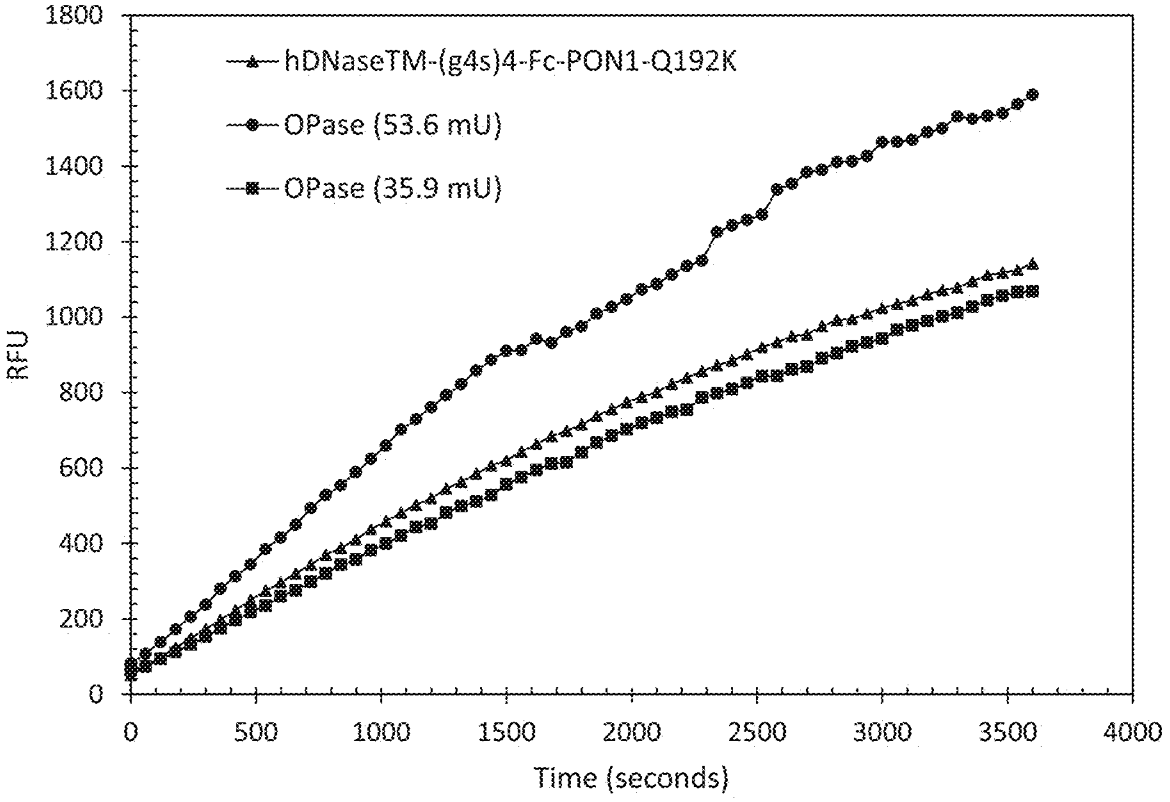
FIG. 7 shows the results of a fluorometric assay measuring the organophosphatase activity of a DNase1-Fc-PON1 fusion protein and an organophosphatase positive control enzyme (see Example 3, infra).

The Enzcheck paraoxonase activity assay (Catalog #E33702, ThermoFisher Scientific, Waltham, MA) was used to assess organophosphatase activity of the DNase1TM-(g4s)4-Fc-PON1-Q192K fusion protein. This assay is a very sensitive fluorometric assay for the organophosphatase activity of paraoxonase that uses excitation/emission maxima of 360/450 nm to measure the conversion of a fluorogenic organophosphate analog provided with the kit. The assay can either be set up as a kinetic assay or terminated after a particular period of time for an endpoint assay. The change in relative fluorescence units (RFU) per unit time is converted to the units of paraoxonase in the sample using the standard curve generated from the fluorescent standard and the conversion factor that 1 U unit of paraoxonase generates 1 nmol of fluorescent product per minute at 37° C. The amount of paraoxonase present in the fusion protein samples can be compared to the paraoxonase positive control provided with the kit. FIG. 7 shows a graphical representation of the organophosphatase activity of the DNase1TM-(g4s)4-Fc-PON1-Q192K fusion protein compared to the RFU curves generated by two different dilutions of the organophosphatase positive control in the average to above average activity range for human serum sample comparisons. The fusion protein tested had been kept at 4° C. for 11 months, but still had activity above average in the PON1 assay.

Similar activity assays to the arylesterase and organophosphatase can be performed for the PON1 enzyme activities present in fusion proteins as described herein, such as, e.g., peroxidase activity assays (Amplex Red peroxide/peroxidase assay, ThermoFisher Scientific, Waltham MA, Catalog number: A22188) or a general phosphatase assay (ENzChek phosphatase assay, ThermoFisher Scientific, Waltham MA, Catalog number: 12020).

Example 4: Assays to Assess Inhibition of Biofilm Formation by DNase-Fc and DNase-Fc-PON1 Fusion Proteins DNase-Fc and DNase-Fc-PON1 fusion proteins are characterized in biofilm formation assays to evaluate inhibition of *Pseudomonas aeruginosa* biofilm formation. *Pseudomonas aeruginosa* cultures are grown from an isolated bacterial colony by inoculation into rich media such as 2×YT or LB media. Overnight cultures are diluted 1:100 in tryptic soy broth/0.5% glucose (Teknova, Hollister, CA), and the diluted cultures used to inoculate 100 μl/well into a 96 well tissue culture plate. Wells are precoated with each fusion protein of interest at different concentrations, prior to inoculation with the diluted bacterial culture. Alternatively, fusion proteins are added directly to diluted bacterial cultures to assess inhibition activity in solution. Plates are incubated at 37° C. for 4-8 hours prior to assay. All conditions are performed in replicates of 6-8 in order to control for well-to-well variation. After the incubation, cultures are removed by aspiration or turning the plate over and shaking out the liquid. The plate is then washed with PBS to remove unattached cells and media. After washing, 125 μl of 0.1% solution crystal violet is added to each well, and the plate is incubated for 15 minutes at room temperature. Plates are rinsed 3-4 times with water or PBS using a plate washer. After the final wash, microtiter plates are inverted and left to dry for a few hours or overnight. To quantify biofilms, 125 μl 30% acetic acid is added to each dried well in order to solubilize the crystal violet. Plates are incubated at room temperature for 15 minutes, and the 125 μl of crystal violet is transferred to a new flat bottom microtiter dish. Well absorbance is then measured at 550 nm in a Varioskan plate reader using 30% acetic acid as a blank solution. Percent biofilm inhibition is estimated by subtracting the ratio of [fusion protein treated absorbance average/untreated absorbance average] from 1 and multiplying by 100.

A commercially available biofilm formation kit is also available from Dojindo (Donjindo Laboratories, Kumamoto, Japan) that uses pegged microtiter plates for biofilm formation, simplifying washing steps.

Example 5: Construction of SOD1-Fc-PON1 Fusion Proteins

The sequence for wild-type human SOD1 (see GenBank Accession Nos. NM_000454.5, CR450355.1, and CR4541742.1) is obtained from the NCBI sequence database and is designed and synthesized as an expression cassette for insertion into a molecule already containing a partial fusion gene encoding a $(Gly_4Ser)_2$ linker ((g4s)2; nucleotide and amino acid sequences as shown in SEQ ID NO:9 and SEQ ID NO:10) attached to the N-terminus of a human IgG1 Fc variant (SSS hinge, P238S, P331S Fc; nucleotide and amino acid sequences as shown in SEQ ID NO:27 and SEQ ID NO:28). The carboxyl end of the human Fc variant is fused to a peptide linker containing an N-linked glycosylation site (NGS; nucleotide and amino acid sequences as shown in SEQ ID NO:55 and SEQ ID NO:56) followed by a variant of human PON1 (PON1 Q192K; nucleotide and amino acid sequences as shown in SEQ ID NO:5 and SEQ ID NO:6) in which the first 15 amino acids of the uncleaved leader peptide are deleted. The predicted amino acid sequence of SOD1 does not contain a signal peptide for secretion, so a modified version of the human VK3 signal sequence is designed with additional amino acids at the junction site with SOD1 in order to achieve cleavage of the heterologous signal peptide at the correct location. The amino terminal methionine for SOD1 is absent in the mature secreted version of this modified SOD1, so that the predicted N-terminal amino acid after cleavage of the modified signal peptide is alanine. The encoded, modified VK3 leader and N-terminal SOD1 sequence is MET-PAQLLFLLLLWLPDTTGMA/ATKAVCVL (residues 1-30 of SEQ ID NO:50), where the slash mark indicates the junction between the VK3 leader peptide (VK3LP) and SOD1. The completed SOD1 fusion construct is [Human VK3LP]-[hSOD1]-(g4s)2-[SSShinge-P238S-P331S Fc]-NGS-[PON1 Q192K] (nucleotide and amino acid sequences as shown in SEQ ID NO:49 and SEQ ID NO:50).

Additional SOD1 fusion genes containing a sequence variant of SOD1 are also constructed. The variant substitutes alternative amino acids for cysteines at positions 7 and 112 of human SOD1 (amino acid numbering according to the full-length immature SOD1 sequence of SEQ ID NO:32), creating a C7A and C112S double mutant form of the predicted amino acid sequence. This sequence was originally described by Parge et al. (*Proc. Natl. Acad. Sci. USA* 89:6109-6113, 1992) as a thermostable mutant of SOD1 with improved solubility and stability. The SOD1 double mutant variant is fused to the N-terminus of the human Fc variant (SSS hinge, P238S, P331S Fc; see above) using either the $(Gly_4Ser)_2$ linker (see above) or a $(Gly_4Ser)_4$ linker ((g4s)4; nucleotide and amino acid sequences as shown in SEQ ID NO:11 and SEQ ID NO:12). The carboxyl end of the Fc is fused to the NGS linker followed by the PON1 Q192K variant as described above for the wild-type SOD1 fusion. The completed double mutant SOD1 fusion constructs are [Human VK3LP]-[hSOD1 C7A C112S]-(g4s)2-[SSShinge-P238S-P331S Fc]-NGS-[PON1 Q192K] (nucleotide and amino acid sequences as shown in SEQ ID NO:51 and SEQ ID NO:52) and [Human VK3LP]-[hSOD1 C7A C112S]-(g4s)4-[SSShinge-P238S-P331S Fc]-NGS-[PON1 Q192K] (also referred to hereinbelow as SOD1-P1-K; nucleotide and amino acid sequences as shown in SEQ ID NO:53 and SEQ ID NO:54).

Superoxide dismutase activity of the SOD1-Fc-PON1 fusion proteins is measured using a commercially available kit such as the SOD colorimetric activity kit (ThermoFisher Scientific, Waltham MA, Catalog number: EIASODC) or a similar kit available from Cayman Chemical, (Cayman Chemical, Ann Arbor, MI; Catalog number: 706002).

Example 6: Construction of RNase1-Fc-PON1 Fusion Proteins

The sequence for wild-type human RNase 1 (see GenBank Accession Nos. NM_198235.3, NM_198234.3, NM_198232.3, and NM_002933.5) is obtained from the NCBI sequence database and is designed and synthesized as an expression cassette encoding wild-type RNase 1 with its native leader sequence (nucleotide and amino acid sequences as shown in SEQ ID NO:21 and SEQ ID NO:22) or RNase 1 attached to the human VK3 leader peptide (VK3LP) sequence (nucleotide and amino acid sequences as shown in SEQ ID NO:23 and SEQ ID NO:24). These RNase 1-encoding cassettes are then fused to a human IgG1 Fc variant with C220S, C226S, C229S, and P238S amino acid substitutions, but wild-type CH2 and CH3 domains (SSS hinge, P238S Fc; nucleotide and amino acid sequences as shown in residues 475-1170 of SEQ ID NO:41 and residues 159-390 of SEQ ID NO:42). The nucleotide and amino acid sequences for the wild-type RNase 1-Fc construct (with the native leader) are shown in SEQ ID NO:41 and SEQ ID NO:42, and the nucleotide and amino acid sequences for the VK3LP-RNase1-Fc construct are shown in SEQ ID NO:43 and SEQ ID NO:44. These constructs contain two heterologous, restriction-site-encoded amino acids (Asp-Leu; residues 157-158 of SEQ ID NO:42 or residues 149-150 of SEQ ID NO:44) linking the carboxyl end of RNase1 to the N-terminus of the Fc.

The RNase1-encoding cassettes are also fused to the SSS hinge, P238S Fc variant via a $(Gly_4Ser)_4$ linker peptide ((g4s)4; nucleotide and amino acid sequences as shown in SEQ ID NO:11 and SEQ ID NO:12). The resulting RNase1-(g4s)4-Fc nucleotide and predicted amino acid sequences are shown in SEQ ID NO:33 and SEQ ID NO:34 (for the wild-type RNase1 with the native leader) and SEQ ID NO:35 and SEQ ID NO:36 (for the mature wild-type RNase1 fused to the human VK3 leader).

The carboxyl end of the human Fc variant in each of the RNase1-Fc constructs described above is fused to a peptide linker containing an N-linked glycosylation site (NGS; nucleotide and amino acid sequences as shown in SEQ ID NO:55 and SEQ ID NO:56) followed by a variant of human PON1 (PON1 Q192K; nucleotide and amino acid sequences as shown in SEQ ID NO:5 and SEQ ID NO:6) in which the first 15 amino acids of the uncleaved leader peptide are deleted. The completed RNase1-Fc-PON1 constructs generated are as follows:

- hRNase1-[SSShinge-P238S Fc]-NGS-[PON1 Q192K] (nucleotide and amino acid sequences as shown in SEQ ID NO:45 and SEQ ID NO:46);
- hVK3LP-hRNase1-[SSShinge-P238S Fc]-NGS-[PON1 Q192K] (nucleotide and amino acid sequences as shown in SEQ ID NO:47 and SEQ ID NO:48);
- hRNase1-(g4s)4-[SSShinge-P238S Fc]-NGS-[PON1 Q192K] (nucleotide and amino acid sequences as shown in SEQ ID NO:37 and SEQ ID NO:38); and
- hVK3LP-hRNase1-(g4s)4-[SSShinge-P238S Fc]-NGS-[PON1 Q192K] (nucleotide and amino acid sequences as shown in SEQ ID NO:39 and SEQ ID NO:40).

Example 7: Construction of CTLA4-Fc-PON1 Fusion Proteins

The sequence for wild-type, full length, human CTLA-4 (see GenBank Accession Nos. AF414120.1 and L15006.1) is obtained from the NCBI sequence database and is used in the design and synthesis of an expression cassette encoding the human CTLA-4 extracellular domain attached to the human VK3 leader peptide (VK3LP) sequence (nucleotide and amino acid sequences as shown in SEQ ID NO:57 and SEQ ID NO:58). These CTLA-4-encoding cassettes are then fused to a human IgG1 Fc variant with C220S, C226S, C229S, P238S and P331S amino acid substitutions in the Fc domain (SSS hinge, P238S, P331S Fc; nucleotide and amino acid sequences as shown in SEQ ID NO:27 and SEQ ID NO:28). The nucleotide and amino acid sequences for the VK3LP-CTLA4-Fc construct are shown in SEQ ID NO:63 and SEQ ID NO:64. These constructs contain two heterologous, restriction-site-encoded amino acids (Asp-Leu or DL; residues 433-438 of SEQ ID NO:63 or residues 145-146 of SEQ ID NO:64) linking the carboxyl end of CTLA-4 to the N-terminus of the Fc region.

The carboxyl end of the human Fc variant in each of the CTLA4-Fc constructs described above is fused to a peptide linker containing an N-linked glycosylation site (NGS; nucleotide and amino acid sequences as shown in SEQ ID NO:55 and SEQ ID NO:56) followed by a variant of human PON1 (PON1 Q192K; nucleotide and amino acid sequences as shown in SEQ ID NO:5 and SEQ ID NO:6) in which the first 15 amino acids of the uncleaved leader peptide are deleted. The nucleotide and amino acid sequences of the completed CTLA4-Fc-PON1 construct generated (hVK3LP-[hCTLA-4EC]-[SSShinge-P238S-P331S Fc]-NGS-[PON1 Q192K]; also referred to hereinbelow as CTLA4-Fc-P1-K) are listed in SEQ ID NO:65 and SEQ ID NO:66.

Example 8: Construction of CD40-Fc-PON1 Fusion Proteins

The sequence for wild-type, full length, human CD40 (nucleotide and amino acid sequences shown in SEQ ID NO:67 and SEQ ID NO:68; see GenBank Accession No. NM_001250) is obtained from the NCBI sequence database and is used in the design and synthesis of an expression cassette encoding the human CD40 extracellular domain with its native leader sequence or the human CD40 extracellular domain attached to the human VK3 leader peptide (VK3LP) sequence (nucleotide and amino acid sequences as shown in SEQ ID NO:57 and SEQ ID NO:58). These CD40-encoding cassettes are then fused to a $(Gly_4Ser)_4$ peptide linker (nucleotide and amino acid sequences as shown in SEQ ID NO:11 and SEQ ID NO:12, including flanking restriction sites and encoded amino acids) and a human IgG1 Fc variant with C220S, C226S, C229S, P238S and P331S amino acid substitutions in the Fc domain (SSS hinge, P238S, P331S Fc; nucleotide and amino acid sequences as shown in SEQ ID NO:27 and SEQ ID NO:28). The nucleotide and amino acid sequences for the wild-type CD40-Fc construct with the native leader ([hCD40 EC]-(g4s)4-[SSShinge-P238S Fc]) are shown in SEQ ID NO:69 and SEQ ID NO:70, and the nucleotide and amino acid sequences for the CD40-Fc construct with the VK3LP leader (hVK3LP-[hCD40 EC]-(g4s)4-[SSShinge-P238S Fc]) are shown in SEQ ID NO:71 and SEQ ID NO:72.

In addition to the wild-type form of CD40, several variants were generated which show improved binding avidity for the CD40 ligand (CD154 or gp39). Using the amino acid numbering according to the wild-type, full-length human CD40 (SEQ ID NO:68), the amino acid substitution(s) for each of these CD40 variants relative to the wild-type sequence are (i) K81T, (ii) K81H, L121P, (iii) K81S, and (iv) E64Y, K81T, P85Y. The variant CD40-Fc constructs are as follows:

hVK3LP-[hCD40 EC K81T]-(g4s)4-[SSShinge-P238S Fc] (nucleotide and amino acid sequences as shown in SEQ ID NO:75 and SEQ ID NO:76);

hVK3LP-[hCD40 EC K81H-L121P]-(g4s)4-[SSShinge-P238S Fc] (nucleotide and amino acid sequences as shown in SEQ ID NO:79 and SEQ ID NO:80);

hVK3LP-[hCD40 EC K81S]-(g4s)4-[SSShinge-P238S Fc] (nucleotide and amino acid sequences as shown in SEQ ID NO:83 and SEQ ID NO:84); and hVK3LP-[hCD40 EC E64Y-K81T-P85Y]-(g4s)4-[SSShinge-P238S Fc] (nucleotide and amino acid sequences as shown in SEQ ID NO:87 and SEQ ID NO:88).

The carboxyl end of the human Fc variant in each of the CD40-Fc constructs described above is fused to a peptide linker containing an N-linked glycosylation site (NGS; nucleotide and amino acid sequences as shown in SEQ ID NO:55 and SEQ ID NO:56) followed by a variant of human PON1 (PON1 Q192K; nucleotide and amino acid sequences as shown in SEQ ID NO:5 and SEQ ID NO:6) in which the first 15 amino acids of the uncleaved leader peptide are deleted. The completed CD40-Fc-PON1 constructs generated are as follows:

hVK3LP-[hCD40 EC]-(g4s)4-[SSShinge-P238S Fc]-NGS-[PON1 Q192K] (nucleotide and amino acid sequences as shown in SEQ ID NO:73 and SEQ ID NO:74);

hVK3LP-[hCD40 EC K81T]-(g4s)4-[SSShinge-P238S Fc]-NGS-[PON1 Q192K] (nucleotide and amino acid sequences as shown in SEQ ID NO:77 and SEQ ID NO:78);

hVK3LP-[hCD40 EC K81H-L121P]-(g4s)4-[SSShinge-P238S Fc]-NGS-[PON1 Q192K] (nucleotide and amino acid sequences as shown in SEQ ID NO:81 and SEQ ID NO:82);

hVK3LP-[hCD40 EC K81S]-(g4s)4-[SSShinge-P238S Fc]-NGS-[PON1 Q192K] (nucleotide and amino acid sequences as shown in SEQ ID NO:85 and SEQ ID NO:86); and hVK3LP-[hCD40EC E64Y-K81T-P85Y]-(g4s)4-[SSShinge-P238S Fc]-NGS-[PON1 Q192K] (nucleotide and amino acid sequences as shown in SEQ ID NO:89 and SEQ ID NO:90) (also referred to hereinbelow as CD40TM-Fc-P1-K).

Example 9: Construction of Anti-TNF-α scFv-Fc-PON1 Fusion Proteins

The sequence for Humira™ or the adalimumab antibody targeted to human TNF-α is obtained from the IMGT database INN number 7860, chain numbers INN 7860_H and INN 7860_L. The GenBank Accession numbers for the adalimumab anti-TNF-α antibody sequences are LQ961187 for the heavy chain variable region and LQ961186 for the light chain variable region. See also International PCT Publication No. WO 2014/159579. The sequences are used to design and synthesize an expression cassette encoding an scFv including the heavy and light chain V regions for the adalimumab antibody attached to the human VK3 leader peptide (VK3LP) sequence (nucleotide and amino acid sequences as shown in SEQ ID NO:57 and SEQ ID NO:58). The V region sequences are joined by a (gly4ser)4 linker segment to construct the scFv. The anti-TNF-α scFv is constructed in both the VL-VH and VH-VL orientations. The nucleotide and amino acid sequences for the human VK3LP anti-TNF-α VL-VH scFv are shown in SEQ ID NO:91 and SEQ ID NO:92, and the nucleotide and amino acid sequences for the human VK3LP anti-TNF-α VH-VL scFv are shown in SEQ ID NO:95 and SEQ ID NO:96.

These TNF-α scFv-encoding cassettes are then linked at the carboxyl end of the scFv to the N-terminus of the Fc domain using two heterologous, restriction-site-encoded amino acids (Asp-Leu; residues 816-822 of SEQ ID NO:93 and SEQ ID NO:97 or residues 269-270 of SEQ ID NO:94 and SEQ ID NO:98). The Fc domain encodes a human IgG1 Fc variant with C220S, C226S, C229S, and P238S amino acid substitutions, but wild-type for the remaining residues of the CH2 and CH3 domains (SSS hinge, P238S Fc; nucleotide and amino acid sequences as shown in residues 475-1170 of SEQ ID NO:41 and residues 159-390 of SEQ ID NO:42). The carboxyl end of the human Fc variant in each of the scFv-Fc constructs is fused to a peptide linker containing an N-linked glycosylation site (NGS; nucleotide and amino acid sequences as shown in SEQ ID NO:55 and SEQ ID NO:56) followed by a variant of human PON1 (PON1 Q192K; nucleotide and amino acid sequences as shown in SEQ ID NO:5 and SEQ ID NO:6) in which the first 15 amino acids of the uncleaved leader peptide are deleted. The completed anti-TNF-α scFv-Fc-PON1 constructs generated are as follows:

hVK3LP-[VL-VH anti-TNFalpha scFv]-[SSShinge-P238S-P331S Fc]-NGS-[PON1 Q192K] (nucleotide and amino acid sequences as shown in SEQ ID NO:93 and SEQ ID NO:94) (also referred to hereinbelow as Adalimumab scFv-Fc-P1-K); and hVK3LP-[VH-VL anti-TNFalpha scFv]-[SSShinge-P238S-P331S Fc]-NGS-[PON1 Q192K] (nucleotide and amino acid sequences as shown in SEQ ID NO:97 and SEQ ID NO:98).

Example 10: Construction of Anti-TGF-β scFv-Fc-PON1 Fusion Proteins

The sequence for humanized fresolimumab antibody (GC1008) targeted to human TGF-β cytokine isoforms is obtained from the IMGT sequence database. The chain ID designations are INN 9158_H and INN 9158_L. The GenBank Accession numbers for the fresolimumab anti-TGF-antibody sequences are JC 232803.1 for the heavy chain and JC 232805 for the light chain. The sequences for the antibody are also listed in U.S. Pat. No. 7,723,486 and International PCT Publication No. WO 2013/065869. The sequences are used to design and synthesize an expression cassette encoding an scFv including the heavy and light chain V regions for the GC1008/fresolimumab antibody attached to the human VK3 leader peptide (VK3LP) sequence (nucleotide and amino acid sequences as shown in SEQ ID NO:57 and SEQ ID NO:58). The V region sequences are joined by a (gly4ser)4 linker segment to construct the scFv. The anti-TGF-scFv is constructed in both the VL-VH and VH-VL orientations. The nucleotide and amino acid sequences for the human VK3LP anti-TGF-β VH-VL scFv are shown in SEQ ID NO:99 and SEQ ID NO:100, and the nucleotide and amino acid sequences for the human VK3LP anti-TGF-β VL-VH scFv are shown in SEQ ID NO:103 and SEQ ID NO:104.

These TGF-β scFv-encoding cassettes are then fused at the carboxyl end of the scFv to the N-terminus of the Fc domain using two heterologous, restriction-site-encoded amino acids (Asp-Leu; residues 819-825 of SEQ ID NO:101 and SEQ ID NO:105 or residues 270-271 of SEQ ID NO:102 and SEQ ID NO:106). The Fc domain encodes a human IgG1 Fc variant with C220S, C226S, C229S, and P238S amino acid substitutions, but wild-type for the remaining residues of the CH2 and CH3 domains (SSS hinge, P238S Fc; nucleotide and amino acid sequences as shown in residues 475-1170 of SEQ ID NO:41 and residues 159-390 of SEQ ID NO:42). The carboxyl end of the human Fc variant in each of the scFc-Fc constructs is fused to a peptide linker containing an N-linked glycosylation site (NGS; nucleotide and amino acid sequences as shown in SEQ ID NO:55 and SEQ ID NO:56) followed by a variant of human PON1 (PON1 Q192K; nucleotide and amino acid sequences as shown in SEQ ID NO:5 and SEQ ID NO:6) in which the first 15 amino acids of the uncleaved leader peptide are deleted. The completed anti-TGF-β scFv-Fc-PON1 constructs generated are as follows:

hVK3LP-[anti-hTGFbeta VH-VL scFv]-SSShinge-P238S-P331S Fc]-NGS-PON1 Q192K] (nucleotide and amino acid sequences as shown in SEQ ID NO:101 and SEQ ID NO:102); and hVK3LP-[anti-hTGFbeta VL-VH scFv]-SSShinge-P238S-P331S Fc]-NGS-PON1 Q192K] (nucleotide and amino acid sequences as shown in SEQ ID NO:105 and SEQ ID NO:106).

Example 11: Construction of DNase1L3-Fc and DNase1L3-Fc-PON1 Fusion Proteins

Constructs were designed and synthesized and cassettes with the correct sequences are combined to generate two synthetic fusion genes encoding unique DNase1L3 fusion molecules. Each construct includes a variant of wild-type human DNase1L3 (nucleotide and encoded amino acid sequences as shown in SEQ ID NOs: 135 and 136). Each DNase1L3 sequence is modified to remove amino acid residues 291-305 of the wild-type sequence, corresponding to the C-terminal nuclear localization signal (NLS2). Each DNase1L3 variant also contains amino acid substitutions, relative to the wild-type human sequence (SEQ ID NO:136), at positions R80, R95, and N96 (either all three positions changed to alanine or all three changed to serine) to inactivate a nuclear localization signal (NLS1) located in the N-terminal half of the molecule. The nucleotide and encoded amino acid sequences corresponding to the mature DNase1L3 variant containing the R80A/R95A/N96A mutations are shown in residues 61-870 of SEQ ID NO:137 and residues 21-290 of SEQ ID NO:138, respectively; the nucleotide and encoded amino acid sequences corresponding to the mature DNase1L3 variant containing the R80S/R95S/N96S mutations are shown in residues 61-870 of SEQ ID NO:139 and residues 21-290 of SEQ ID NO:140, respectively. The signal peptide sequence utilized was the human VK3 leader peptide (nucleotide and amino acid sequences as shown in SEQ ID NO:57 and SEQ ID NO:58). The DNase1 cassette was fused to the N-terminus of a human IgG1 Fc variant (SSS hinge, P238S, P331S) using a $(Gly_4Ser)_4$ peptide linker ((g4s)4; nucleotide and amino acid sequences as shown in SEQ ID NO:11 and SEQ ID NO:12). The Fc variant nucleotide and amino acid sequences are shown in SEQ ID NO:27 and SEQ ID NO:28. The completed DNase1 L3-Fc constructs generated are as follows:

hVK3LP-[hDNase1L3 R80A-R95A-N96A NLS2delta]-(g4s)4-[SSShinge-P238S-P331S Fc] (nucleotide and amino acid sequences as shown in SEQ ID NO:137 and SEQ ID NO:138); and hVK3LP-[hDNase1L3 R80S-R95S-N96S NLS2delta]-(g4s)4-[SSShinge-P238S-P331S Fc] (nucleotide and amino acid sequences as shown in SEQ ID NO:139 and SEQ ID NO:140).

Bispecific constructs further comprising a functional PON1 enzyme are also generated by fusing the carboxyl end of each variant DNase1L3-Fc sequence above to a peptide linker containing an N-linked glycosylation site (NGS; nucleotide and amino acid sequences as shown in SEQ ID NO:55 and SEQ ID NO:56) followed by a variant of human PON1 (PON1 Q192K; nucleotide and amino acid sequences as shown in SEQ ID NO:5 and SEQ ID NO:6) in which the first 15 amino acids of the uncleaved leader peptide are deleted. The completed DNase1L3-Fc-PON1 constructs are as follows:

hVK3LP-[hDNase1L3 R80A-R95A-N96A NLS2delta]-(g4s)4-[SSShinge-P238S-P331S Fc]-NGS-[PON1 Q192K] (nucleotide and amino acid sequences as shown in SEQ ID NO:161 and SEQ ID NO:162); and hVK3LP-[hDNase1L3 R80S-R95S-N96S NLS2delta]-(g4s)4-[SSShinge-P238S-P331S Fc]-NGS-[PON1 Q192K] (nucleotide and amino acid sequences as shown in SEQ ID NO:163 and SEQ ID NO:164) (also referred to hereinbelow as DNase1L3-Fc-P1-K).

Example 12: Construction and Expression of Bispecific and Monospecific PON1 Fusion Proteins Various Fc fusion genes as described in Examples 1, 5, 7-9, and 11 were assembled in a pUC based vector, and assembled genes screened by DNA sequencing prior to further manipulations. Assembled genes included both a monospecific (T-L1-Fc) and a bispecific PON1 (T-L1-Fc-L2-PON1) form for each of the DNase1, SOD1, CTLA-4, CD40, anti-TNFα scFv, and DNase1L3 "T" region fusion partners. The assembled PON1 fusion constructs included the following: DNaseTM-(g4s)6-Fc-P1-K, SOD1-Fc-P1-K, CTLA4-Fc-P1-K, CD40TM-Fc-P1-K, Adalimumab scFv-Fc-P1-K, and DNase1L3-Fc-P1-K. In addition, a monospecific Fc-PON1 fusion construct was assembled (nucleotide and amino acid sequences as shown in SEQ ID NO:121 and SEQ ID NO:122; also referred to hereinbelow as Fc-PON1-K or Fc-P1-K). Also assembled were two ApoA1-Fc-PON1 fusions: THER4-P1-K (nucleotide and amino acid sequences shown in SEQ ID NO:45 and SEQ ID NO:46 of PCT Publication No. WO 2017/044424) and THER6-P1-K (identical to THER4-P1-K but with six repeats of ($Gly_4$Ser) in the linker sequence instead of four ($Gly_4$Ser) repeats). Fusion gene cassettes containing the desired sequences were then inserted into a multiple cloning site of the mammalian expression vector pDG, a pcDNA3 plasmid derivative containing a CMV promoter to drive expression of the fusion gene. Plasmid DNA was prepared using QIAGEN (Germantown, MD) mini or maxiprep plasmid DNA kits. Purified plasmid DNA was transfected into HEK293 cells plated at approximately 50-75% confluence, using Polyfect (QIAGEN, Germantown, MD) transfection reagent according to the manufacturer's instructions. Culture media was changed to DMEM Fluorobrite™ (Life Technologies, Carlsbad, CA) serum free media on the day after transfections, and transfected cells incubated for an additional 48 hours prior to harvest of culture supernatants. Culture supernatants were filtered through 0.2 μm PES syringe filters prior to analysis.

Figure 8:
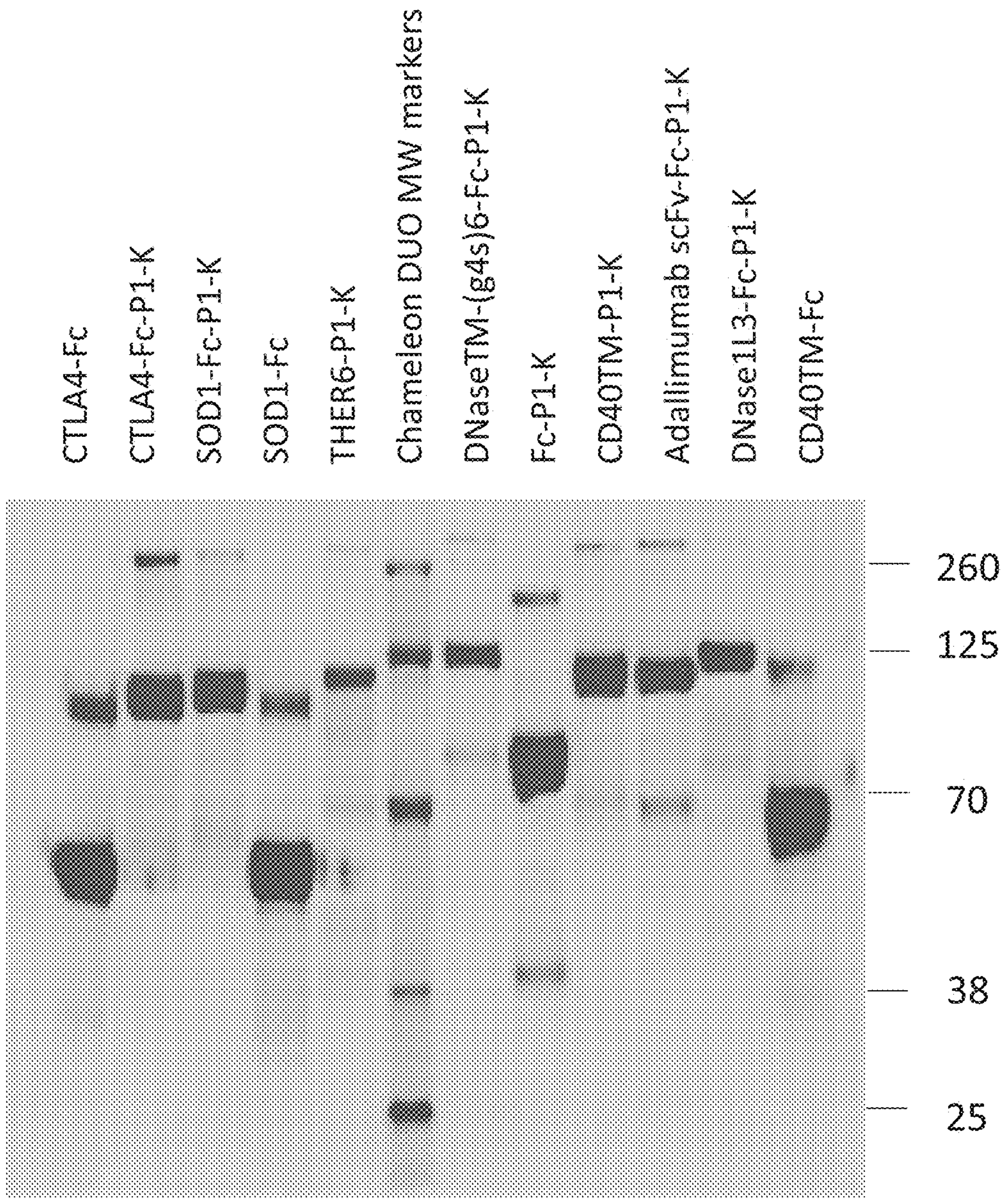
FIGS. 8 and 9 show Western blot analysis of PON1 fusion proteins immunoprecipitated from HEK293 transfection supernatants. Transfections, Protein A immunoprecipitation, and Western blot analysis were performed as described in Example 12, infra.
Figure 9:
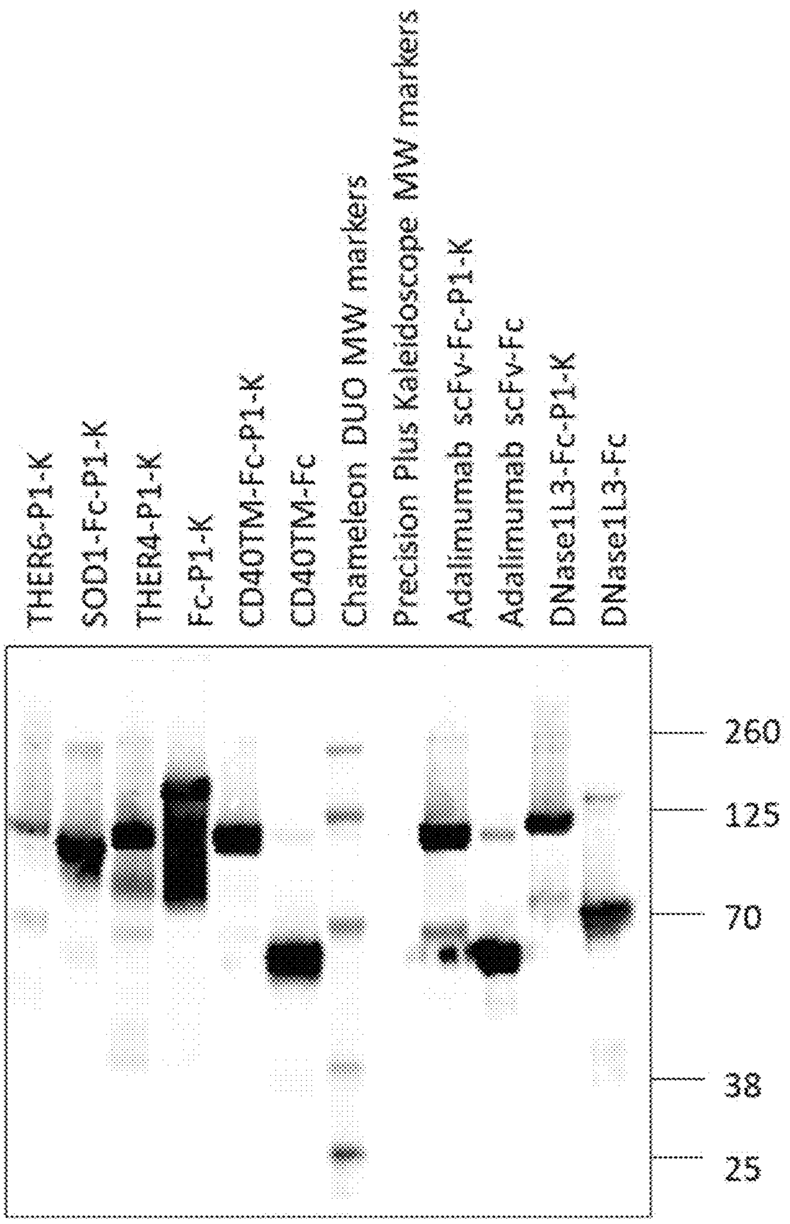

FIG. 8 and FIG. 9 show the results of Western blot analysis of fusion protein expression from a representative set of HEK293 transient transfections. Culture supernatants were immunoprecipitated with 60 μl protein A agarose (Repligen, Waltham MA) washed in gentle antigen-antibody binding buffer pH 8.0, (Pierce/Life Technologies, Carlsbad, CA) and 0.5 ml 293 transfection supernatants in Fluorobrite DMEM added to each microfuge tube. Immunoprecipitates were rotated overnight at 4° C., centrifuged at 3000 rpm, and washed in Binding Buffer pH 8.0, prior to addition of 60 μl 2×LDS sample buffer (Life Technologies, Carlsbad, CA), samples heated for 10 minutes at 72° C., the samples centrifuged for 1 minute at 3000 rpm in a microfuge, and 15 μl sample in loading buffer (one fourth) from each sample was loaded onto 4-12% Bis-Tris NuPAGE gels (Life Technologies, Carlsbad, CA). Protein molecular weight markers were included on each gel (Chameleon® DUO molecular weight markers; LI-COR Biosciences, Lincoln, NE and/or Precision Plus Kaleidoscope MW markers; BIORAD, Hercules, CA). SDS-PAGE gels were run in NuPAGE MOPS running buffer (Life Technologies, Carlsbad, CA) under reducing conditions at 185 volts for approximately 1-1.5 hours. Gels were blotted to nitrocellulose membranes using the XCell blot module (Life Technologies, Carlsbad, CA) and NUPAGE-MOPS (Life Technologies, Carlsbad, CA) transfer buffer containing 10% methanol. Blots were blocked in LI-COR Odyssey Intercept™ blocking buffer, followed by incubation with diluted goat anti-human IgG (Fc specific) secondary antibodies (Jackson Immunoresearch, West Grove, PA). Secondary antibody was conjugated with Alexafluor 790 near IR dye (LI-COR Odyssey detection) and diluted in blocking buffer 1:35,000 at 4° C. and rocked overnight. Blots were washed four times with Tris buffered saline (TBS) containing 0.1% Tween 20. Blots were then rinsed in TBS buffer and scanned with a LICOR Odyssey™ scanner. For the Western Blot shown in FIG. 8, transfection samples were loaded as follows: Lane 1—CTLA4-Fc, Lane 2—CTLA4-Fc-P1-K, Lane 3—SOD1-Fc-P1-K, Lane 4—SOD1-Fc, Lane 5—THER6-P1-K, Lane 6—LICOR Chameleon DUO MW Markers, Lane 7—DNaseTM-(g4s)6-Fc-P1-K, Lane 8—Fc-P1-K, Lane 9—CD40TM-Fc-P1-K; Lane 10—Adalimumab scFv-Fc-P1-K, Lane 11—DNase1L3-Fc-P1-K, Lane 12—CD40TM-Fc. The approximate molecular weight (kDa) of each marker band is indicated on the right side of the Western blot. For the Western Blot shown in FIG. 9, transfection samples were loaded as follows: Lane 1—THER6-P1-K, Lane 2—SOD1-Fc-P1-K, Lane 3—THER4-P1-K, Lane 4—Fc-P1-K, Lane 5—CD40TM-Fc-P1-K; Lane 6—CD40TM-Fc, Lane 7—LI-COR Chameleon DUO MW Markers, Lane 8—BIORAD Precision Plus Kaleidoscope MW markers, Lane 9—Adalimumab scFv-Fc-P1-K, Lane 10—Adalimumab scFv-Fc, Lane 11—DNase1L3-Fc-P1-K, Lane 12—DNase1L3-Fc. The approximate molecular weight (kDa) of each marker band is indicated on the right side of the Western blot.

Figure 10:
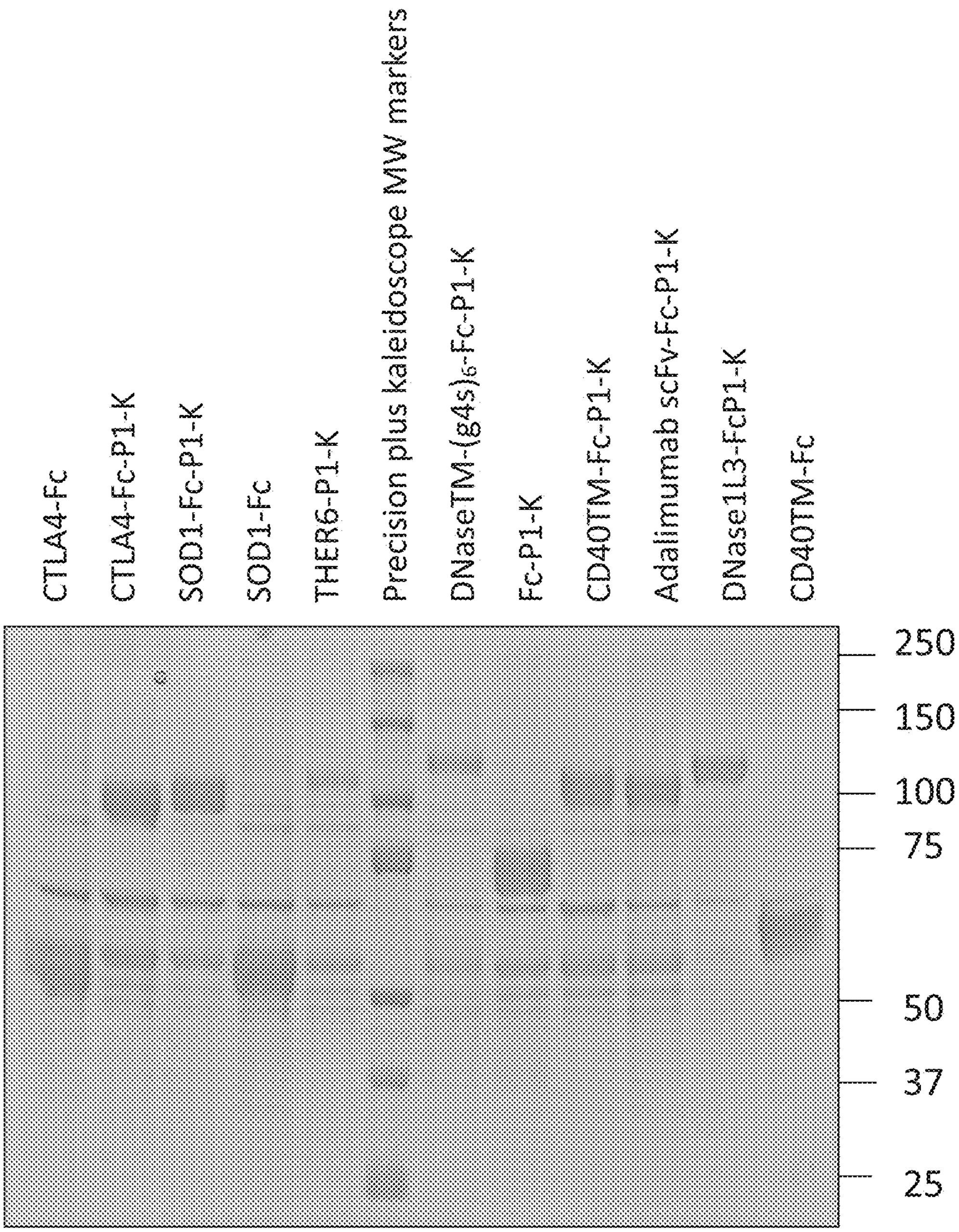
FIG. 10 shows reducing SDS-PAGE analysis of PON1 fusion proteins immunoprecipitated from HEK293 transfection supernatants. Transfections, Protein A immunoprecipitation, and SDS-PAGE were performed as described in Example 12, infra.

FIG. 10 shows the results of SDS-PAGE analysis of immunoprecipitated protein from HEK293 transfection supernatants. Culture supernatants were immunoprecipitated with 60 μl protein A agarose (Repligen, Waltham, MA), washed in gentle antigen-antibody binding buffer pH 8.0, (Pierce/Life Technologies, Carlsbad, CA) and 0.5 ml 293 transfection supernatants in Fluorobrite DMEM (ThermoFisher Scientific, Waltham, MA) added to each microfuge tube. Immunoprecipitates were rotated overnight at 4° C., centrifuged at 3000 rpm, and washed in Binding Buffer pH 8.0, prior to addition of 60 μl 2×LDS sample buffer (Life Technologies, Carlsbad, CA), samples heated for 10 minutes at 72° C., the samples centrifuged for 1 minute at 3000 rpm in a microfuge, and 15 μl sample in loading buffer (one fourth) from each sample was loaded onto 4-12% Bis-Tris NuPAGE gels (Life Technologies, Carlsbad, CA). SDS-PAGE gels were run in NuPAGE MOPS running buffer (Life Technologies, Carlsbad, CA) under reducing conditions at 185 volts for approximately 1-1.5 hours. After electrophoresis, gels were washed in distilled water several times, then incubated for 2 hours in Imperial Protein Stain (Pierce/ThermoFisher Scientific, Waltham MA). Gels were destained by washing several times in distilled water to remove nonspecific stain. Gels were then scanned using a Canon PIXMA MG8220 scanner to visualize the bands. Lanes were loaded as follows: Lane 1—CTLA4-Fc, Lane 2—CTLA4-Fc-P1-K, Lane 3—SOD1-Fc-P1-K, Lane 4—SOD1-Fc, Lane 5—THER6-P1-K, Lane 6—BIORAD Precision Plus Kaleidoscope molecular weight markers, Lane 7—DNaseTM-(g4s)6-Fc-P1-K, Lane 8—Fc-P1-K, Lane 9—CD40TM-Fc-P1-K; Lane 10—Adalimumab scFv-Fc-P1-K, Lane 11—DNase1L3-Fc-P1-K, Lane 12—CD40TM-Fc. The approximate molecular weight (kDa) of each marker band is indicated on the right side of the gel image.

Example 13: In Vitro Assessment of PON1 Fusion Proteins for Functional Activity

Functional activity of the PON1 fusion proteins was assessed with a series of in vitro assays. For several of the assays, protein activity was often analyzed directly from culture supernatants of transiently transfected HEK 293 cells. For other in vitro assays, fusion proteins were first purified from culture supernatants (either HEK 293 or CHO DG44 transfected cells) prior to assessment of functional activity. Fusion proteins were purified from culture supernatants by protein A affinity chromatography. Culture supernatants were filtered through 0.2 μm PES express filters (Nalgene, Rochester, NY) and subjected to affinity chromatography using slow rotation of culture supernatants with Protein A-agarose (IPA 300 crosslinked agarose) slurry in 50 ml sterile, conical centrifuge tubes at 4° C. (Repligen, Waltham, MA). Fusion protein bound to protein A agarose was recovered by centrifugation, and culture supernatants removed, replaced, and the incubation process repeated until the desired volume of supernatant was processed. The final protein A agarose slurry was then loaded into sterile, acid-washed econocolumns (BioRad, Hercules, CA) to wash the resin. Columns were then washed with several column volumes of column wash buffer (Gentle Ag-Ab binding buffer, Pierce/ThermoFisher, Waltham, MA) to remove any residual culture supernatant, prior to elution. Bound protein was then eluted from the resin using gentle Ag/Ab elution buffer (Pierce/ThermoFisher, Waltham, MA). Fractions (0.8-1.0 ml) were collected and protein concentration of aliquots (2 μl) from each fraction were determined at 280 nM using a Nanodrop (Wilmington DE) microsample spectrophotometer, with blank determination using elution buffer alone. Fractions containing fusion protein were pooled, and buffer exchange was performed by dialysis using Spectrum Laboratories G2 (Ranch Dominguez, CA, Catalog #G235057, Fisher Scientific catalog #08-607-007) float-a-lyzer units (MWCO 20 kDa) against [0.9% sodium chloride, 5 mM sodium bicarbonate, 1 mM HEPES buffer, 1 mM calcium chloride, pH 7.5]. Dialysis was performed in sterile, 2.2-liter Corning roller bottles at 4° C. overnight. After dialysis, protein was filtered using 0.2 μM filter units, and aliquots tested for endotoxin contamination using Pyrotell LAL gel clot system single test vials (STV) (Catalog #G2006, Associates of Cape Cod, East Falmouth, MA).

Figure 11:
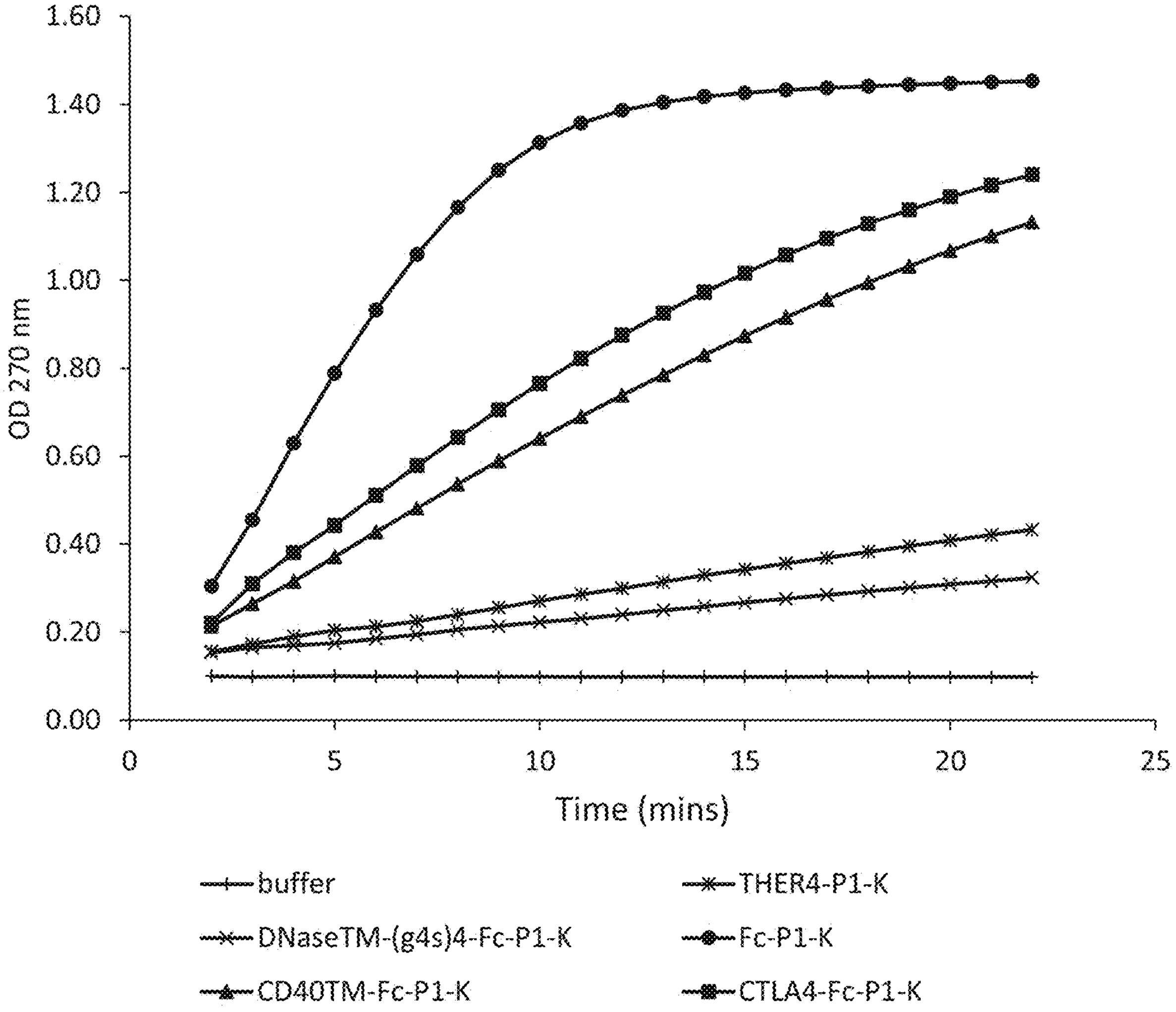
FIGS. 11-13 show arylesterase activity (FIG. 11), organophosphatase activity (FIG. 12), and lactonase activity (FIG. 13) of PON1 fusion proteins assayed directly from HEK293 culture supernatants (see Example 13, infra).

FIG. 11 shows the results from a representative assay of the PON1 arylesterase activity directly from HEK 293 culture supernatants. For this assay, culture supernatants were harvested in Fluorobrite DMEM (serum free) 72 hours after transfection, and sterile filtered with 0.2 μm syringe filters prior to use. Supernatants were diluted with reaction buffer for the assay to two times the final desired dilution. Diluted supernatants were aliquoted to individual wells of a UV transparent, 96 well flat bottom microtiter plate (ThermoFisher Scientific, Waltham, MA). Reactions were performed at 25° C. Just prior to measurement, appropriate dilutions of the arylesterase substrate phenyl acetate were added to each well with a multichannel pipettor. For the data shown in the graph, culture supernatants were diluted 1:8 and 50 μl added to each well. The substrate was then added in 50 μl/well to begin the assay. For most assays, 6-10 mM phenyl acetate was used, so that the final concentration of substrate was 3-5 mM. To monitor conversion of phenyl acetate to phenol, the absorbance change at 270 nm was monitored in a kinetic assay, with readings taken every 45 seconds for 22.5 minutes (30 measurements/well). The absorbance at each time point was then plotted as a function of time.

Figure 12:
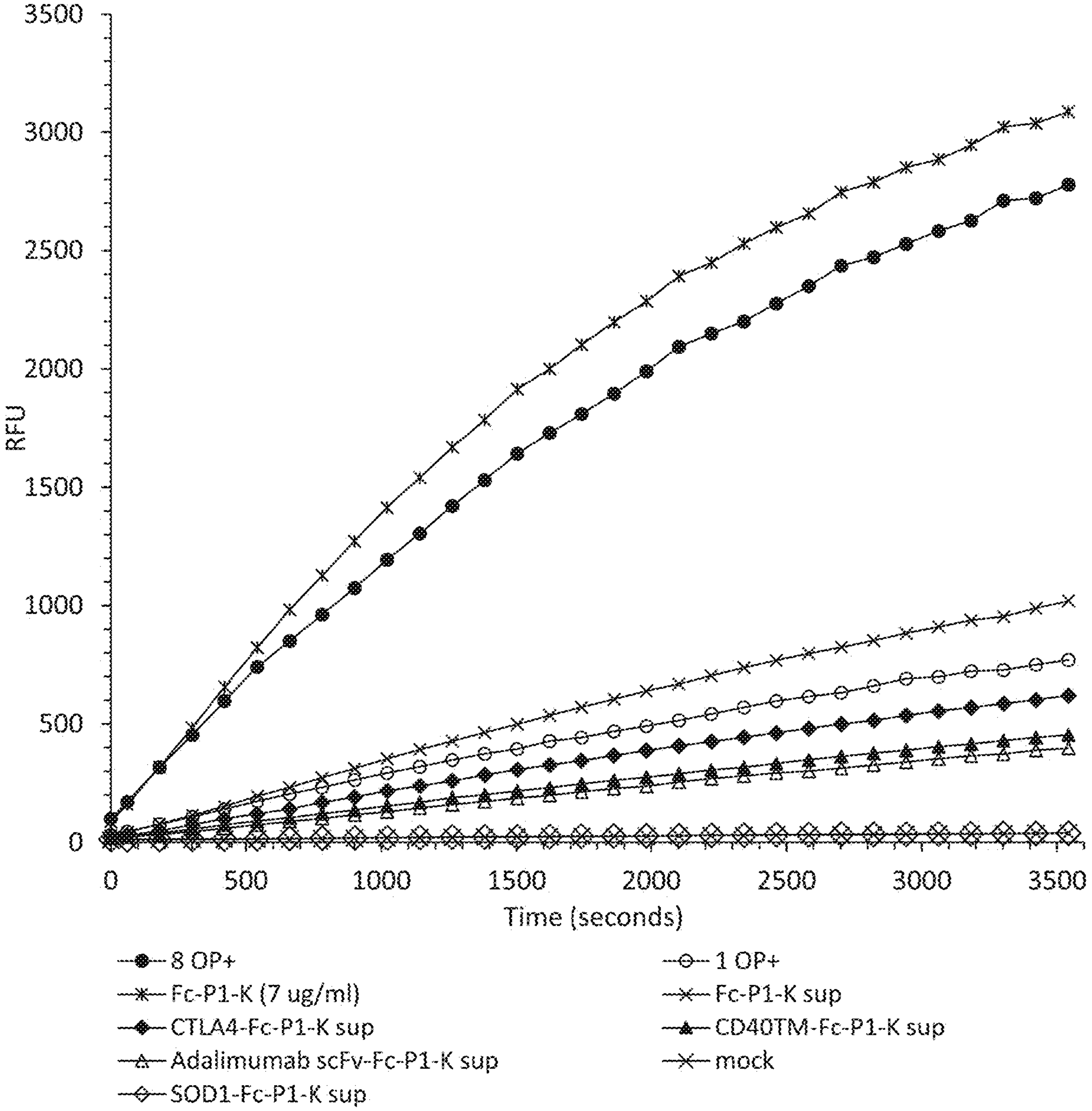

FIG. 12 shows a similar assessment measuring organophosphatase activity of the PON1 moiety in bispecific and monospecific PON1 fusion proteins. In these assays, the substrate used was a proprietary organophosphatase substrate contained in the EnzCHEK paraoxonase assay kit (Molecular Probes/ThermoFisher Scientific, Waltham, MA). This assay is a very sensitive fluorometric assay for the organophosphatase activity of paraoxonase that uses excitation/emission maxima of 360/450 nm to measure the conversion of a fluorogenic organophosphate analog provided with the kit. The assay can either be set up as a kinetic assay or terminated after a particular period of time for an endpoint assay. The change in relative fluorescence units (RFU) per unit time is converted to the units of paraoxonase in the sample using the standard curve generated from the fluorescent standard and the conversion factor that 1 U unit of paraoxonase generates 1 nmol of fluorescent product per minute at 37° C. The amount of paraoxonase present in the fusion protein samples can be compared to the paraoxonase positive control provided with the kit. FIG. 12 shows a graphical representation of the organophosphatase activity present in serial dilutions of culture supernatant from several of the SOD1-Fc-P1-K, CTLA4-Fc-P1-K, and CD40TM-Fc-P1-K fusion proteins expressed in HEK 293 transient transfections and from a purified batch of the Fc-PON1-K (Fc-P1-K) fusion protein. The organophosphatase activity is compared to the RFU curves generated by two different dilutions of the organophosphatase positive control in the average to above average activity range for human serum sample comparisons. Fc-PON1-K purified fusion protein showed high activity in this assay, and calculations relative to the fluorescent standard curve indicate that the PON1 organophosphatase activity is 700 mU/μg, or 40 U/umole, Fc-P1-K. Culture supernatants from HEK293 transfections were also included in the assay. Although they are not shown on the graph, the supernatant from the Adalimumab scFv-Fc-P1-K transfections mirrored the activity profile observed for the CD40TM-Fc-P1-K transfection. Similarly, the supernatant from the DNase1L3-Fc-P1-K transfection mirrored the negligible activity level observed for the SOD1-Fc-P1-K transfection shown on the graph.

Figure 13:
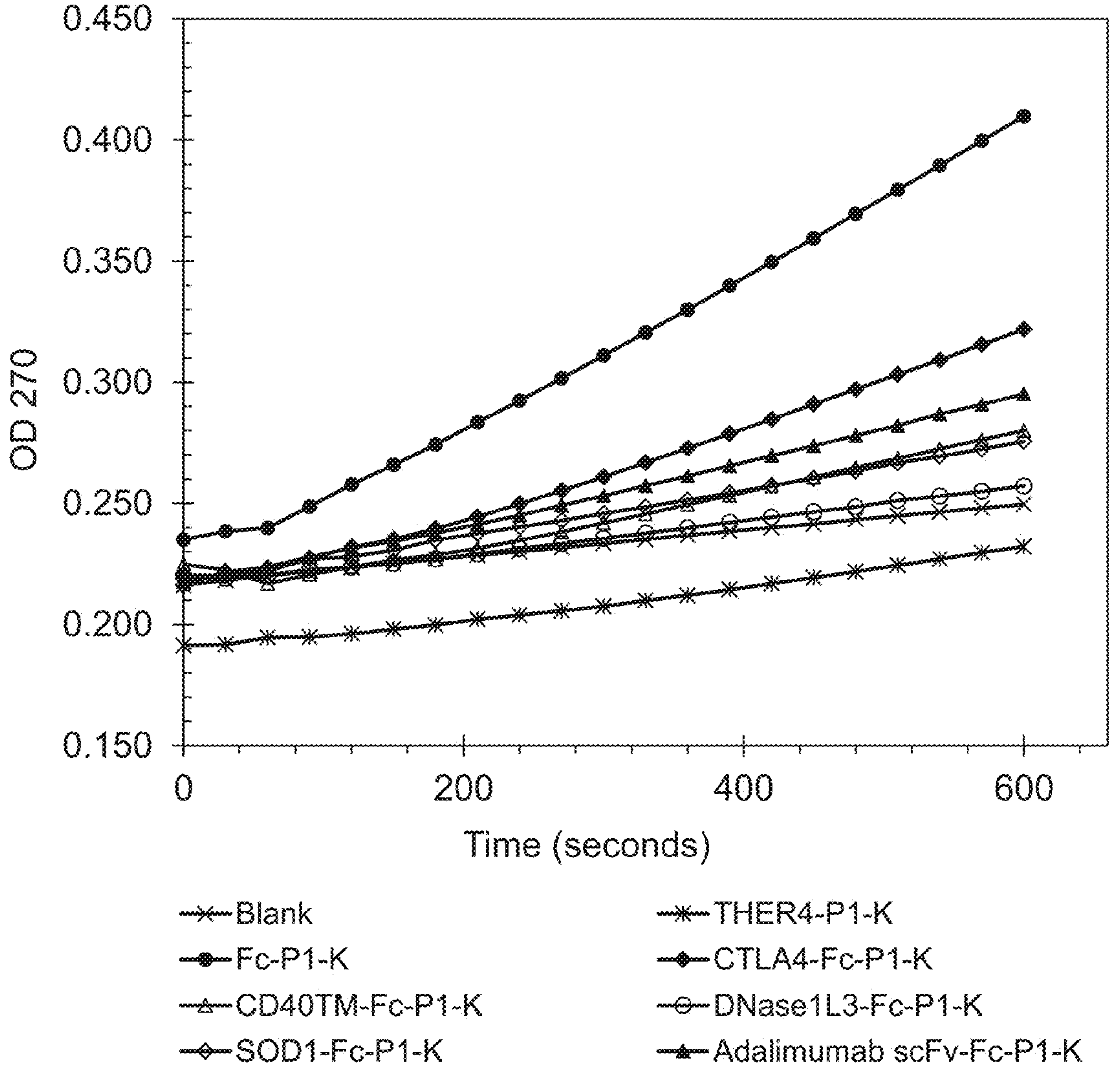

FIG. 13 shows results of an assay measuring lactonase activity of the PON1 moiety in bispecific and monospecific PON1 fusion proteins. In these assays, the substrate used was dihydrocoumarin (DHC) (Millipore-Sigma, St. Louis, MO) at a final concentration of 1 mM in 1× reaction buffer. Reaction buffer for the DHC assays was 50 mM Tris HCl (pH 7.4), 1 mM $CaCl_2$). HEK293 culture supernatants were diluted 1:4 in reaction buffer and 25 μl added to individual wells of a 96 well UV STAR (Greiner BioOne, Thomas Scientific) microtiter plate. Substrate dihydrocoumarin (DHC) solution in reaction buffer was added to each well (75 μl) to generate a final volume of 100 μl. Hydrolysis of the substrate was monitored at OD 270 for 15 minutes. Hydrolysis of DHC by the fusion proteins was monitored as the change in OD270 as a function of time.

Figure 14:
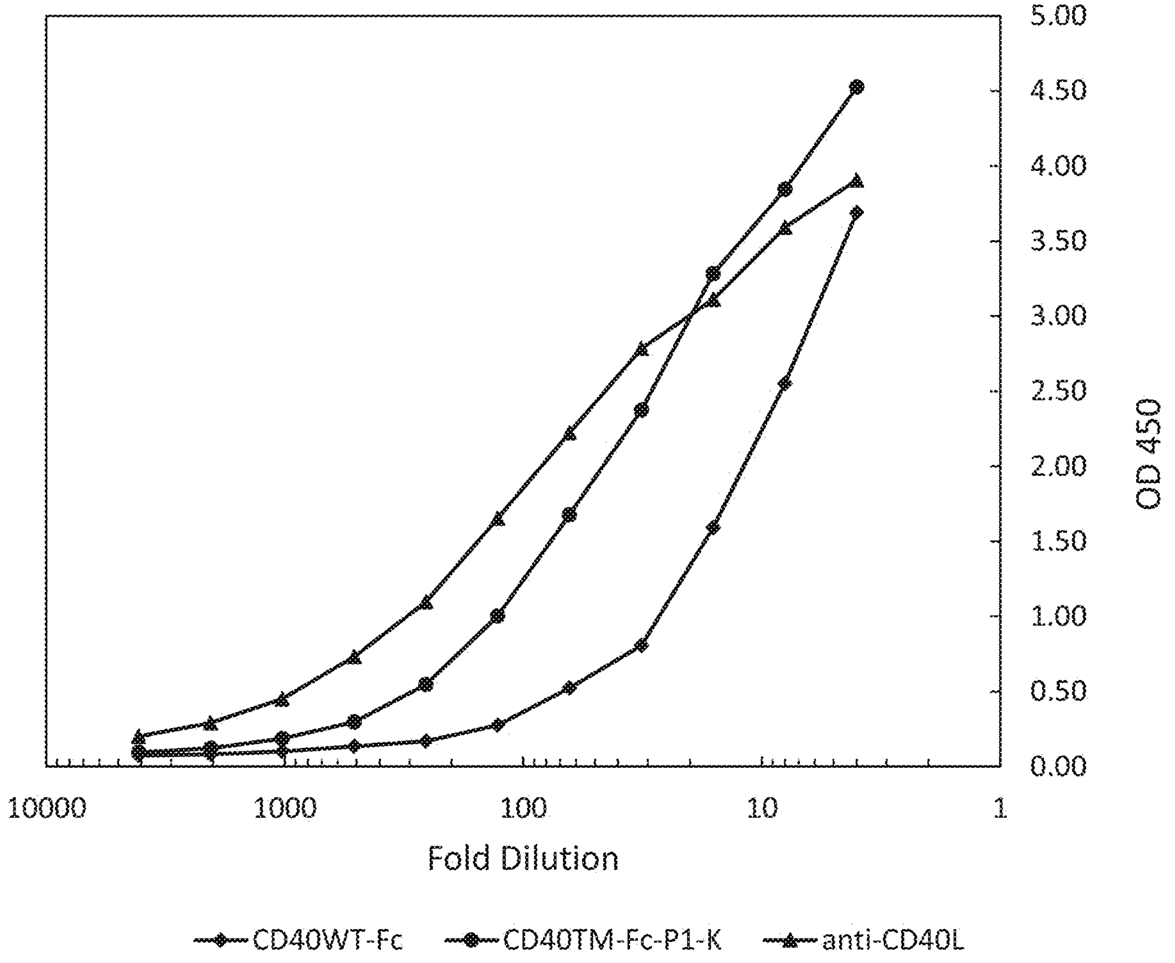
FIG. 14 shows high affinity binding of immobilized CD40 ligand to CD40-Fc-PON1 fusion protein present in HEK293 transfection supernatant (see Example 14, infra).

In addition to the paraoxonase enzyme activity, the functional properties of the different "T" domains positioned at the amino terminus of the T-L1-X-L2-P fusion proteins were also assessed. Depending on the identity of the "T" domain, binding to a target antigen or enzyme activity was monitored. FIG. 14 shows the results of an antigen binding assay to CD40 ligand for the human CD40 receptor extracellular domain triple mutant in the CD40TM-Fc-P1-K fusion proteins. The antigen binding ELISA assay was performed as follows: Human CD40 ligand was obtained from BioLegend (San Diego, CA). The human CD40 ligand was diluted in 0.1 M carbonate buffer (pH 9.0) to a concentration of 2 μg/ml and 100 μl/well aliquoted to each well to be used in the assay in a 96 well NUNC immulon II MaxiSorp plate (ThermoFisher Scientific, Waltham, MA). Plates were incubated overnight at 4° C., prior to blocking in 200 μl/well PBS/2.0% BSA, overnight at 4° C. Plates were washed in wash buffer (PBS, 0.5% Tween-20, 0.005% Kathon), and serial dilutions of the HEK 293 transfection supernatants added to wells of the plate. As a positive control for antigen binding, a mouse antibody targeted to the CD40 ligand was also serially diluted on the plate Plates were incubated with supernatant or antibody dilutions at 4° C., overnight. Plates were washed four times in wash buffer, then incubated with horseradish peroxidase conjugated goat anti-human IgG Fc specific, or goat anti-mouse IgG1 at a dilution of 1:10,000 (Jackson Immunoresearch, West Grove, PA). FIG. 14 shows the CD40 ligand binding curves for the CD40WT-Fc, the CD40TM-Fc-P1-K transfection supernatants, and the CD40L specific antibody dilutions by plotting the absorbance at 450 nm as a function of dilution. The CD40 mutant form shows improved binding activity to CD40 ligand when compared to the wild type CD40Fc containing supernatants.

Figure 15:
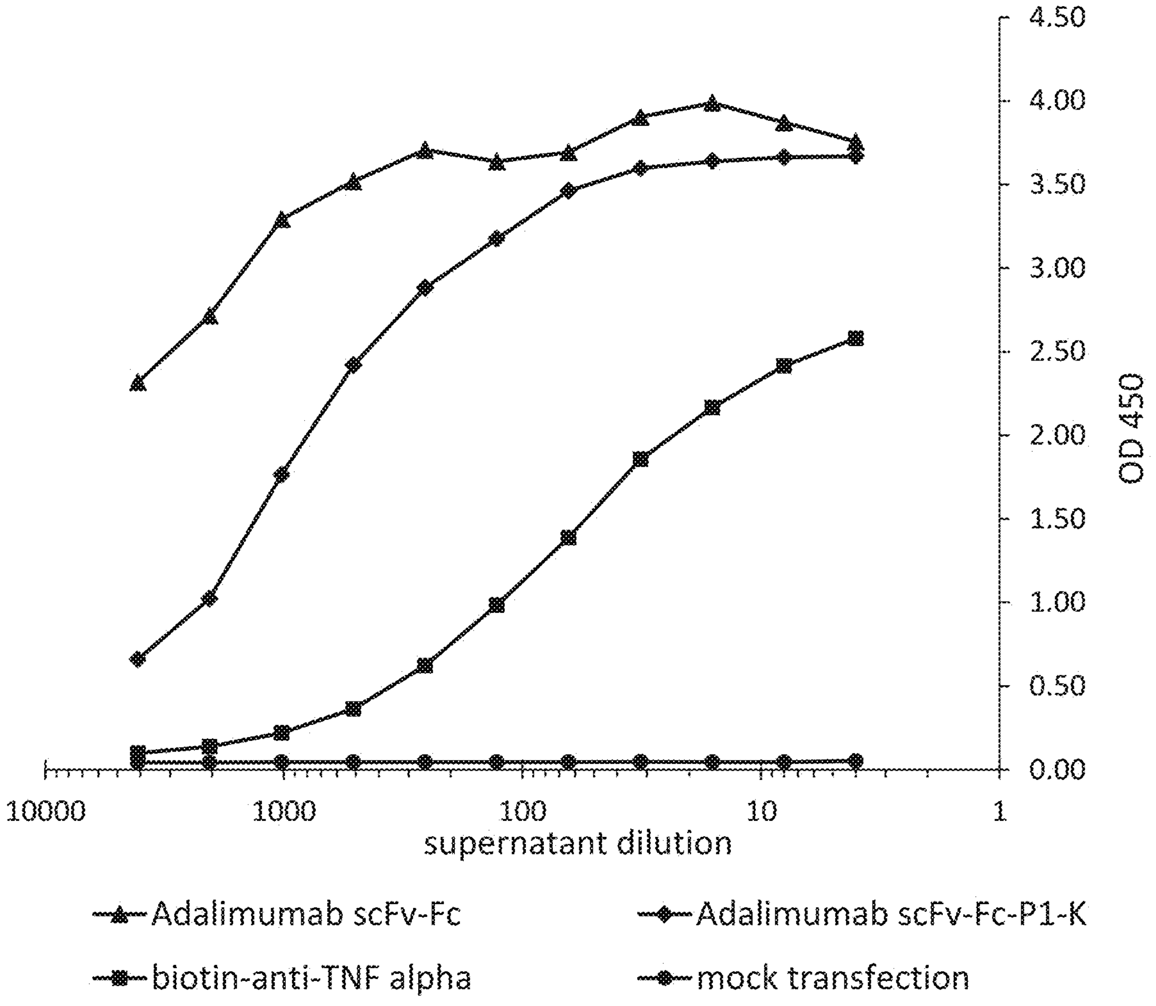
FIG. 15 shows high affinity binding of immobilized TNFα to anti-TNF-α scFv-Fc-PON1 fusion protein present in HEK293 transfection supernatant (see Example 14, infra).

FIG. 15 shows binding data for the Humira™ (adalimumab) scFv containing fusion protein supernatants to TNF-alpha (TNF-α) in an antigen binding ELISA with immobilized TNF-α. The antigen binding ELISA assay was performed as follows: Human TNF-α was obtained from BioLegend (San Diego, CA). The TNF-α protein was diluted in 0.1 M carbonate buffer (pH 9.0) to a concentration of 1 μg/ml and 100 μl/well aliquoted to each well to be used in the assay in a 96 well NUNC immulon II MaxiSorp plate (ThermoFisher Scientific, Waltham, MA). Plates were incubated overnight at 4° C., prior to blocking in 200 μl/well blocking buffer (PBS/2.0% BSA), overnight at 4° C. Plates were washed in wash buffer (PBS, 0.5% Tween-20, 0.005% Kathon), and serial dilutions of either the HEK293 transfection supernatants or mouse anti-human TNF antibody (BioLegend, San Diego, CA) added to wells of the plate. Plates were incubated with supernatant or antibody dilutions at 4° C., overnight. Plates were washed four times in wash buffer, then incubated with horseradish peroxidase conjugated goat anti-human IgG Fc specific, or goat anti-mouse IgG1 at a dilution of 1:10,000 (Jackson Immunoresearch, West Grove, PA). FIG. 15 shows the TNF-α binding curves for the adalimumab scFv-Fc transfection supernatant, the adalimumab scFv-Fc-P1-K transfection supernatant, or the TNF-α specific antibody, in which the absorbance at 450 nm was plotted as a function of dilution. The adalimumab scFv-containing fusion proteins expressed in HEK293 transient transfections bind to human TNF-α immobilized on the plate(s).

Example 15: Treatment of Lung Fibrosis by Administration of PON1 Fusion Proteins Effects of different PON1 fusion proteins on lung fibrosis are assessed using in vivo mouse models of disease. One such model involves in vivo assessment of the efficacy of the purified fusion proteins for treatment of pulmonary fibrosis in a bleomycin induced lung fibrosis mouse model. Bleomycin (BLM)-induced pulmonary fibrosis is the most well-established disease model for IPF and is widely used to investigate the efficacy and mechanism of therapeutic candidates. In the model, alveolar injury and interstitial inflammation/fibrosis are induced by intratracheal BLM administration. The aim of this study is to examine the effect of PON1 fusion test compounds on lung inflammation and fibrosis in BLM-induced pulmonary fibrosis model and compare responses to a control preparation of nintedanib. At day 0, mice are induced to develop pulmonary fibrosis by a single intratracheal administration of bleomycin hydrochloride in saline at a dose of 3.0 mg/kg, in a volume of 50 μl per animal using Microsprayer. Mice are divided into groups of 12 mice based on the body weight changes on the day before the start of treatments with the test compounds on day 7. Mice are intranasally/intravenously/intraperitoneally administered test compounds (depending on the test group). Compounds are administered daily from Day 7 to 20, animals sacrificed on Day 21 and samples analyzed for fibrotic markers.

At study termination, whole blood samples without anticoagulant are obtained via abdominal vena cava under a mixture of medetomidine, midazolam and butorphanol anesthesia. The supernatants from separated blood are collected and stored at −80° C. until further processing. Lungs are harvested from the mice and two lobes left unfixed, one lobe is frozen and another harvested for biochemical assays such as measurements of hydroxyproline or inflammatory markers. Remaining lung lobes are fixed in 10% neutral buffered formalin, paraffin emedded for Masson's trichrome staining and histology. For quantitative analysis of lung fibrosis area, bright field images of Masson's Trichrome-stained sections are randomly captured using a digital camera at 100-fold magnification, and the subpleural regions in 20 fields/mouse are evaluated according to the criteria for grading lung fibrosis (Ashcroft, T., et al., *J Clin Pathol,* 1988; 41:467-70), to generate an Ashcroft score. All sections are blindly analyzed by an experimenter. Statistics are performed on each treatment group, calculating an average Aschroft score, and comparing the scores in the different treatment groups to the Vehicle group.

Alternative methods of fusion protein delivery may be utilized. As an example, rather than intranasal spray delivery which is confined to the upper airways, nebulization of the fusion proteins may improve delivery of the fusion molecules deeper into the lungs, thereby more effectively targeting all areas of the lung. Fusion proteins can be nebulized with or without excipients and tested for protein recovery, aggregation, and enzyme activity. A vibrating mesh (VM) nebulizer (PARI eFlow. Omron NE-U100, Lake Forest, IL) can be used since other proteins have been successfully nebulized using this apparatus and because VM nebulizers are small and portable. Nebulized proteins (500 μl) at 1 mg/ml in saline plus 1 mM $CaCl_2$) (Pulmozyme® buffer) are collected on a sterile 60 mm low protein binding tissue culture dish. Recovered fusion proteins are analyzed by SDS gels, size exclusion HPLC (SEC), and for protein concentration and enzyme activity before and after nebulization to evaluate the effects of the excipients and the effects of nebulization on the protein.

From the foregoing, it will be appreciated that, although specific embodiments of the invention have been described herein for purposes of illustration, various modifications may be made without deviating from the spirit and scope of the invention. Accordingly, the invention is not limited except as by the appended claims. All publications, patents, and patent applications cited herein are hereby incorporated by reference in their entireties for all purposes.

SEQUENCE LISTING

```
Sequence total quantity: 164
SEQ ID NO: 1            moltype = DNA  length = 2688
FEATURE                 Location/Qualifiers
misc_feature            1..2688
                        note = hVK3LP-[hDNase1
                         N74K-G105R-A114F]-(g4s)4-[SSShinge-P238S-P331S
                         Fc]-NGS-[PON1 Q192K] DNA
sig_peptide             1..60
                        note = human VK3 leader peptide
misc_feature            61..840
                        note = human DNase 1 (N74K, G105R, A114F) without leader
                         peptide
misc_feature            280..283
                        note = human DNase 1 N74K substitution
misc_feature            373..375
                        note = human DNase 1 G105R substitution
misc_feature            399..401
                        note = human DNase 1 A114F substitution
misc_feature            841..918
                        note = (gly4ser)4 linker peptide sequence with additional
                         restriction site amino acids
misc_feature            919..1614
                        note = human IgG1 variant Fc (SSS hinge, P238S, P331S)
misc_feature            931..933
                        note = human IgG1 hinge C220S substitution
misc_feature            949..951
                        note = human IgG1 hinge C226S substitution
misc_feature            958..960
                        note = human IgG1 hinge C229S substitution
misc_feature            985..987
                        note = human IgG1 lower hinge-CH2 P238S substitution
misc_feature            1264..1266
                        note = human IgG1 Fc P331S substitution
misc_feature            1615..1672
                        note = peptide linker containing N-linked glycosylation site
misc_feature            1673..2688
                        note = human PON1 Q192K without uncleaved leader peptide
misc_feature            2197..2199
                        note = PON1 Q192K substitution
source                  1..2688
                        mol_type = other DNA
                        organism = synthetic construct
SEQUENCE: 1
atggaaaccc cagcgcagct tctcttcctc ctgctactct ggctcccaga taccaccggt  60
ctgaagatcg cagccttcaa catccagaca tttggggaga ccaagatgtc caatgccacc  120
ctcgtcagct acattgtgca gatcctgagc cgctatgaca tcgccctggt ccaggaggtc  180
agagacagcc acctgactgc cgtggggaag ctgctggaca acctcaatca ggatgcacca  240
gacacctatc actacgtggt cagtgagcca ctgggacgga agagctataa ggagcgctac  300
ctgttcgtgt acaggcctga ccaggtgtct gcggtggaca gctactacta cgatgatggc  360
tgcgagccct gcaggaacga caccttcaac cgagagccat tcattgtcag gttcttctcc  420
cggttcacag aggtcaggga gtttgccatt gttcccctgc atgcggcccc gggggacgca  480
gtagccgaga tcgacgctct ctatgacgtc tacctggatg tccaagagaa atggggcttg  540
gaggacgtca tgttgatggg cgacttcaat gcgggctgca gctatgtgag accctcccag  600
tggtcatcca tccgcctgtg gacaagcccc accttccagt ggctgatccc cgacagcgct  660
gacaccacag ctacacccac gcactgtgcc tatgacagga tcgtggttgc agggatgctg  720
ctccgaggcg ccgttgttcc cgactcggct cttcccttta acttccaggc tgcctatggc  780
ctgagtgacc aactggccca agccatcagt gaccactatc cagtggaggt gatgctgaaa  840
gatctctccg gaggaggtgg ctcaggtggt ggaggatctg gaggaggtgg gagtggtgga  900
ggtggttcta ccggtctcga gcccaaatct tctgacaaaa ctcacacatc tccaccgtcc  960
ccagcacctg aactcctggg aggatcgtca gtcttcctct tcccccccaaa acccaaggac  1020
accctcatga tctcccggac ccctgaggtc acatgcgtgg tggtggacgt gagccacgaa  1080
gaccctgagg tcaagttcaa ctggtacgtg gacggcgtgg aggtgcataa tgccaagaca  1140
aagccgcggg aggagcagta caacagcacg taccgtgtgg tcagcgtcct caccgtcctg  1200
caccaggact ggctgaatgg caaggagtac aagtgcaagg tctccaacaa agccctccca  1260
gcctccatcg agaaaaccat ctccaaagcc aaagggcagc cccgagaacc acaggtgtac  1320
accctgcccc catcccggga tgagctgacc aagaaccagg tcagcctgac ctgcctggtc  1380
aaaggcttct atcccagcga catcgccgtg gagtgggaga gcaatgggca gccggagaac  1440
aactacaaga ccacgcctcc cgtgctggac tccgacggct ccttcttcct ctacagcaag  1500
ctcaccgtgg acaagagcag gtggcagcag gggaacgtct tctcatgctc cgtgatgcat  1560
gaggctctgc acaaccacta cacgcagaag agcctctctc tctctccggg taaagtcgac  1620
ggagctagca gccccgtgaa cgtgagcagc cccagcgtgc aggatatcct cttcaggaac  1680
caccagtctt cttaccaaac acgacttaat gctctccgag aggtacaacc cgtagaactt  1740
cctaactgta atttagttaa aggaatcgaa actggctctg aagacttgga gatactgcct  1800
aatggactgg ctttcattag ctctggatta aagtatcctg gaataaagag cttcaacccc  1860
aacagtcctg gaaaaatact tctgatggac ctgaatgaag aagatccaac agtgttggaa  1920
ttggggatca ctggaagtaa atttgatgta tcttcattta accctcatgg gattagcaca  1980
ttcacagatg aagataatgc catgtacctc ctggtggtga accatccaga tgccaagtcc  2040
acagtggagt tgtttaaatt tcaagaagaa gaaaaatcgc ttttgcatct aaaaaccatc  2100
```

```
agacataaac ttctgcctaa tttgaatgat attgttgctg tgggacctga gcacttttat  2160
ggcacaaatg atcactattt tcttgacccc tacttaaaat cctgggagat gtatttgggt  2220
ttagcgtggt cgtatgttgt ctactatagt ccaagtgaag ttcgagtggt ggcagaagga  2280
tttgattttg ctaatggaat caacatttca cccgatggca agtatgtcta tatagctgag  2340
ttgctggctc ataagattca tgtgtatgaa aagcatgcta attggacttt aactccattg  2400
aagtcccttg actttaatac cctcgtggat aacatatctg tggatcctga gacaggagac  2460
ctttgggttg gatgccatcc caatggcatg aaaatcttct tctatgactc agagaatcct  2520
cctgcatcag aggtgcttcg aatccagaac attctaacag aagaacctaa agtgacacag  2580
gtttatgcag aaaatggcac agtgttgcaa ggcagtacag ttgcctctgt gtacaaaggg  2640
aaactgctga ttggcacagt gtttcacaaa gctctttact gtgagctc              2688

SEQ ID NO: 2            moltype = AA  length = 896
FEATURE                 Location/Qualifiers
REGION                  1..896
                        note = hVK3LP-[hDNase1
                         N74K-G105R-A114F]-(g4s)4-[SSShinge-P238S-P331S
                         Fc]-NGS-[PON1 Q192K]
SIGNAL                  1..20
                        note = human VK3 leader peptide
REGION                  21..280
                        note = human DNase 1 (N74K, G105R, A114F) without leader
                         peptide
SITE                    94
                        note = human DNase 1 N74K substitution
SITE                    125
                        note = human DNase 1 G105R substitution
SITE                    134
                        note = human DNase 1 A114F substitution
REGION                  281..306
                        note = MISC_FEATURE - (gly4ser)4 linker peptide with
                         restriction site amino acids
REGION                  307..538
                        note = MISC_FEATURE - human IgG1 variant Fc (SSS hinge,
                         P238S, P331S)
SITE                    311
                        note = human IgG1 C220S substitution
SITE                    317
                        note = human IgG1 C226S substitution
SITE                    320
                        note = human IgG1 C229S substitution
SITE                    329
                        note = P238S lower hinge-CH2 mutation
SITE                    422
                        note = human IgG1 P331S substitution
REGION                  539..557
                        note = MISC_FEATURE - peptide linker containing N-linked
                         glycosylation site
REGION                  558..896
                        note = MISC_FEATURE - human PON1 Q192K without uncleaved
                         leader peptide
SITE                    733
                        note = PON1 Q192K substitution
source                  1..896
                        mol_type = protein
                        organism = synthetic construct
SEQUENCE: 2
METPAQLLFL LLLWLPDTTG LKIAAFNIQT FGETKMSNAT LVSYIVQILS RYDIALVQEV  60
RDSHLTAVGK LLDNLNQDAP DTYHYVVSEP LGRKSYKERY LFVYRPDQVS AVDSYYYDDG  120
CEPCRNDTFN REPFIVRFFS RFTEVREFAI VPLHAAPGDA VAEIDALYDV YLDVQEKWGL  180
EDVMLMGDFN AGCSYVRPSQ WSSIRLWTSP TFQWLIPDSA DTTATPTHCA YDRIVVAGML  240
LRGAVVPDSA LPFNFQAAYG LSDQLAQAIS DHYPVEVMLK DLSGGGGSGG GGSGGGGSGG  300
GGSTGLEPKS SDKTHTSPPS PAPELLGGSS VFLFPPKPKD TLMISRTPEV TCVVVDVSHE  360
DPEVKFNWYV DGVEVHNAKT KPREEQYNST YRVVSVLTVL HQDWLNGKEY KCKVSNKALP  420
ASIEKTISKA KGQPREPQVY TLPPSRDELT KNQVSLTCLV KGFYPSDIAV EWESNGQPEN  480
NYKTTPPVLD SDGSFFLYSK LTVDKSRWQQ GNVFSCSVMH EALHNHYTQK SLSLSPGKVD  540
GASSPVNVSS PSVQDILFRN HQSSYQTRLN ALREVQPVEL PNCNLVKGIE TGSEDLEILP  600
NGLAFISSGL KYPGIKSFNP NSPGKILLMD LNEEDPTVLE LGITGSKFDV SSFNPHGIST  660
FTDEDNAMYL LVVNHPDAKS TVELFKFQEE EKSLLHLKTI RHKLLPNLND IVAVGPEHFY  720
GTNDHYFLDP YLKSWEMYLG LAWSYVVYYS PSEVRVVAEG FDFANGINIS PDGKYVYIAE  780
LLAHKIHVYE KHANWTLTPL KSLDFNTLVD NISVDPETGD LWVGCHPNGM KIFFYDSENP  840
PASEVLRIQN ILTEEPKVTQ VYAENGTVLQ GSTVASVYKG KLLIGTVFHK ALYCEL      896

SEQ ID NO: 3            moltype = DNA  length = 1065
FEATURE                 Location/Qualifiers
source                  1..1065
                        mol_type = other DNA
                        organism = Homo sapiens
SEQUENCE: 3
atggcgaagc tgattgcgct caccctcttg ggatgggac tggcactctt caggaaccac  60
```

```
cagtcttctt accaaacacg acttaatgct ctccgagagg tacaacccgt agaacttcct  120
aactgtaatt tagttaaagg aatcgaaact ggctctgaag acttggagat actgcctaat  180
ggactggctt tcattagctc tggattaaag tatcctggaa taaagagctt caaccccaac  240
agtcctggaa aaatacttct gatggacctg aatgaagaag atccaacagt gttggaattg  300
gggatcactg gaagtaaatt tgatgtatct tcatttaacc ctcatgggat tagcacattc  360
acagatgaag ataatgccat gtacctcctg gtggtgaacc atccagatgc caagtccaca  420
gtggagttgt ttaaatttca agaagaagaa aaatcgcttt tgcatctaaa aaccatcaga  480
cataaacttc tgcctaattt gaatgatatt gttgctgtgg gacctgagca cttttatggc  540
acaaatgatc actattttct tgacccctac ttacaatcct gggagatgta tttgggttta  600
gcgtggtcgt atgttgtcta ctatagtcca agtgaagttc gagtggtggc agaaggattt  660
gattttgcta atggaatcaa catttcaccc gatggcaagt atgtctatat agctgagttg  720
ctggctcata agattcatgt gtatgaaaag catgctaatt ggactttaac tccattgaag  780
tcccttgact ttaataccct cgtggataac atatctgtgg atcctgagac aggagacctt  840
tgggttggat gccatcccaa tggcatgaaa atcttcttct atgactcaga gaatcctcct  900
gcatcagagg tgcttcgaat ccagaacatt ctaacagaag aacctaaagt gacacaggtt  960
tatgcagaaa atggcacagt gttgcaaggc agtacagttg cctctgtgta caaagggaaa  1020
ctgctgattg gcacagtgtt tcacaaagct ctttactgtg agctc                  1065

SEQ ID NO: 4           moltype = AA  length = 355
FEATURE                Location/Qualifiers
SIGNAL                 1..16
                       note = PON1 noncleaved signal peptide
REGION                 1..355
                       note = mat_peptide - PON1 coding sequence
REGION                 17..355
                       note = PON1 sequence without uncleaved leader sequence
SITE                   192
                       note = PON1 sequence variant Q192
source                 1..355
                       mol_type = protein
                       organism = Homo sapiens
SEQUENCE: 4
MAKLIALTLL GMGLALFRNH QSSYQTRLNA LREVQPVELP NCNLVKGIET GSEDLEILPN  60
GLAFISSGLK YPGIKSFNPN SPGKILLMDL NEEDPTVLEL GITGSKFDVS SFNPHGISTF  120
TDEDNAMYLL VVNHPDAKST VELFKFQEEE KSLLHLKTIR HKLLPNLNDI VAVGPEHFYG  180
TNDHYFLDPY LQSWEMYLGL AWSYVVYYSP SEVRVVAEGF DFANGINISP DGKYVYIAEL  240
LAHKIHVYEK HANWTLTPLK SLDFNTLVDN ISVDPETGDL WVGCHPNGMK IFFYDSENPP  300
ASEVLRIQNI LTEEPKVTQV YAENGTVLQG STVASVYKGK LLIGTVFHKA LYCEL       355

SEQ ID NO: 5           moltype = DNA  length = 1065
FEATURE                Location/Qualifiers
misc_feature           1..1065
                       note = Human PON1 Q192K DNA
source                 1..1065
                       mol_type = other DNA
                       organism = synthetic construct
SEQUENCE: 5
atggcgaagc tgattgcgct caccctcttg gggatgggac tggcactctt caggaaccac  60
cagtcttctt accaaacacg acttaatgct ctccgagagg tacaacccgt agaacttcct  120
aactgtaatt tagttaaagg aatcgaaact ggctctgaag acttggagat actgcctaat  180
ggactggctt tcattagctc tggattaaag tatcctggaa taaagagctt caaccccaac  240
agtcctggaa aaatacttct gatggacctg aatgaagaag atccaacagt gttggaattg  300
gggatcactg gaagtaaatt tgatgtatct tcatttaacc ctcatgggat tagcacattc  360
acagatgaag ataatgccat gtacctcctg gtggtgaacc atccagatgc caagtccaca  420
gtggagttgt ttaaatttca agaagaagaa aaatcgcttt tgcatctaaa aaccatcaga  480
cataaacttc tgcctaattt gaatgatatt gttgctgtgg gacctgagca cttttatggc  540
acaaatgatc actattttct tgacccctac ttaaaatcct gggagatgta tttgggttta  600
gcgtggtcgt atgttgtcta ctatagtcca agtgaagttc gagtggtggc agaaggattt  660
gattttgcta atggaatcaa catttcaccc gatggcaagt atgtctatat agctgagttg  720
ctggctcata agattcatgt gtatgaaaag catgctaatt ggactttaac tccattgaag  780
tcccttgact ttaataccct cgtggataac atatctgtgg atcctgagac aggagacctt  840
tgggttggat gccatcccaa tggcatgaaa atcttcttct atgactcaga gaatcctcct  900
gcatcagagg tgcttcgaat ccagaacatt ctaacagaag aacctaaagt gacacaggtt  960
tatgcagaaa atggcacagt gttgcaaggc agtacagttg cctctgtgta caaagggaaa  1020
ctgctgattg gcacagtgtt tcacaaagct ctttactgtg agctc                  1065

SEQ ID NO: 6           moltype = AA  length = 355
FEATURE                Location/Qualifiers
REGION                 1..355
                       note = Human PON1 Q192K
SIGNAL                 1..16
                       note = PON1 uncleaved leader sequence
REGION                 1..355
                       note = mat_peptide - PON1 mature polypeptide with uncleaved
                        leader
REGION                 17..355
                       note = PON1 sequence without uncleaved signal peptide
SITE                   192
                       note = PON1 mutant Q192K
```

```
source                  1..355
                        mol_type = protein
                        organism = synthetic construct
SEQUENCE: 6
MAKLIALTLL GMGLALFRNH QSSYQTRLNA LREVQPVELP NCNLVKGIET GSEDLEILPN  60
GLAFISSGLK YPGIKSFNPN SPGKILLMDL NEEDPTVLEL GITGSKFDVS SFNPHGISTF  120
TDEDNAMYLL VVNHPDAKST VELFKFQEEE KSLLHLKTIR HKLLPNLNDI VAVGPEHFYG  180
TNDHYFLDPY LKSWEMYLGL AWSYVVYYSP SEVRVVAEGF DFANGINISP DGKYVYIAEL  240
LAHKIHVYEK HANWTLTPLK SLDFNTLVDN ISVDPETGDL WVGCHPNGMK IFFYDSENPP  300
ASEVLRIQNI LTEEPKVTQV YAENGTVLQG STVASVYKGK LLIGTVFHKA LYCEL       355

SEQ ID NO: 7            moltype = DNA  length = 1065
FEATURE                 Location/Qualifiers
source                  1..1065
                        mol_type = other DNA
                        organism = Homo sapiens
SEQUENCE: 7
atggcgaagc tgattgcgct caccctcttg ggatgggac tggcactctt caggaaccac  60
cagtcttctt accaaacacg acttaatgct ctccgagagg tacaacccgt agaacttcct  120
aactgtaatt tagttaaagg aatcgaaact ggctctgaag acttggagat actgcctaat  180
ggactggctt tcattagctc tggattaaag tatcctggaa taaagagctt caaccccaac  240
agtcctggaa aaatacttct gatggacctg aatgaagaag atccaacagt gttggaattg  300
gggatcactg gaagtaaatt tgatgtatct tcatttaacc ctcatgggat tagcacattc  360
acagatgaag ataatgccat gtacctcctg gtggtgaacc atccagatgc caagtccaca  420
gtggagttgt ttaaatttca agaagaagaa aaatcgcttt tgcatctaaa aaccatcaga  480
cataaacttc tgcctaattt gaatgatatt gttgctgtgg gacctgagca cttttatggc  540
acaaatgatc actattttct tgacccctac ttaagatcct gggagatgta tttgggttta  600
gcgtggtcgt atgttgtcta ctatagtcca agtgaagttc gagtggtggc agaaggattt  660
gattttgcta atggaatcaa catttcaccc gatggcaagt atgtctatat agctgagttg  720
ctggctcata agattcatgt gtatgaaaag catgctaatt ggactttaac tccattgaag  780
tcccttgact ttaatacccct cgtggataac atatctgtgg atcctgagac aggagacctt  840
tgggttggat gccatcccaa tggcatgaaa atcttcttct atgactcaga gaatcctcct  900
gcatcagagg tgcttcgaat ccagaacatt ctaacagaag aacctaaagt gacacaggtt  960
tatgcagaaa atggcacagt gttgcaaggc agtacagttg cctctgtgta caaagggaaa  1020
ctgctgattg gcacagtgtt tcacaaagct ctttactgtg agctc                  1065

SEQ ID NO: 8            moltype = AA  length = 355
FEATURE                 Location/Qualifiers
SIGNAL                  1..16
                        note = PON1 uncleaved signal peptide
source                  1..355
                        mol_type = protein
                        organism = Homo sapiens
SEQUENCE: 8
MAKLIALTLL GMGLALFRNH QSSYQTRLNA LREVQPVELP NCNLVKGIET GSEDLEILPN  60
GLAFISSGLK YPGIKSFNPN SPGKILLMDL NEEDPTVLEL GITGSKFDVS SFNPHGISTF  120
TDEDNAMYLL VVNHPDAKST VELFKFQEEE KSLLHLKTIR HKLLPNLNDI VAVGPEHFYG  180
TNDHYFLDPY LRSWEMYLGL AWSYVVYYSP SEVRVVAEGF DFANGINISP DGKYVYIAEL  240
LAHKIHVYEK HANWTLTPLK SLDFNTLVDN ISVDPETGDL WVGCHPNGMK IFFYDSENPP  300
ASEVLRIQNI LTEEPKVTQV YAENGTVLQG STVASVYKGK LLIGTVFHKA LYCEL       355

SEQ ID NO: 9            moltype = DNA  length = 52
FEATURE                 Location/Qualifiers
misc_feature            1..52
                        note = (gly4ser)2 linker DNA
source                  1..52
                        mol_type = other DNA
                        organism = synthetic construct
SEQUENCE: 9
agatctctcc ggaggaggtg gctcaggtgg tggaggatct accggtctcg ag          52

SEQ ID NO: 10           moltype = AA  length = 16
FEATURE                 Location/Qualifiers
REGION                  1..16
                        note = (gly4ser)2 linker
source                  1..16
                        mol_type = protein
                        organism = synthetic construct
SEQUENCE: 10
DLSGGGGSGG GGSTGL                                                  16

SEQ ID NO: 11           moltype = DNA  length = 82
FEATURE                 Location/Qualifiers
misc_feature            1..82
                        note = (gly4ser)4 linker DNA
source                  1..82
                        mol_type = other DNA
                        organism = synthetic construct
SEQUENCE: 11
```

```
agatctctcc ggaggaggtg gctcaggtgg tggaggatct ggaggaggtg ggagtggtgg  60
aggtggttct accggtctcg ag                                            82

SEQ ID NO: 12          moltype = AA  length = 26
FEATURE                Location/Qualifiers
REGION                 1..26
                       note = (gly4ser)4 linker
source                 1..26
                       mol_type = protein
                       organism = synthetic construct
SEQUENCE: 12
DLSGGGGSGG GGSGGGGSGG GGSTGL                                        26

SEQ ID NO: 13          moltype = DNA  length = 112
FEATURE                Location/Qualifiers
misc_feature           1..112
                       note = (gly4ser)6 linker DNA
source                 1..112
                       mol_type = other DNA
                       organism = synthetic construct
SEQUENCE: 13
agatctctcc ggaggaggtg gctcaggtgg tggaggatct ggaggaggtg ggagtggtgg  60
aggtggttct ggaggaggtg gtagtggagg tggaggttct accggtctcg ag          112

SEQ ID NO: 14          moltype = AA  length = 36
FEATURE                Location/Qualifiers
REGION                 1..36
                       note = (gly4ser)6 linker
source                 1..36
                       mol_type = protein
                       organism = synthetic construct
SEQUENCE: 14
DLSGGGGSGG GGSGGGGSGG GGSGGGGSGG GGSTGL                             36

SEQ ID NO: 15          moltype = DNA  length = 846
FEATURE                Location/Qualifiers
source                 1..846
                       mol_type = other DNA
                       organism = Homo sapiens
SEQUENCE: 15
atgaggggca tgaagctgct gggggcgctg ctggcactgg cggccctact gcagggggcc  60
gtgtccctga agatcgcagc cttcaacatc cagacatttg gggagaccaa gatgtccaat  120
gccaccctcg tcagctacat tgtgcagatc ctgagccgct atgacatcgc cctggtccag  180
gaggtcagag acagccacct gactgccgtg gggaagctgc tggacaacct caatcaggat  240
gcaccagaca cctatcacta cgtggtcagt gagccactgg gacggaacag ctataaggag  300
cgctacctgt tcgtgtacag gcctgaccag gtgtctgcgg tggacagcta ctactacgat  360
gatggctgcg agccctgcgg gaacgacacc ttcaaccgag agccagccat tgtcaggttc  420
ttctcccggt tcacagaggt cagggagttt gccattgttc ccctgcatgc ggccccgggg  480
gacgcagtag ccgagatcga cgctctctat gacgtctacc tggatgtcca agagaaatgg  540
ggcttggagg acgtcatgtt gatgggcgac ttcaatgcgg gctgcagcta tgtgagaccc  600
tcccagtggt catccatccg cctgtggaca agccccacct tccagtggct gatccccgac  660
agcgctgaca ccacagctac acccacgcac tgtgcctatg acaggatcgt ggttgcaggg  720
atgctgctcc gaggcgccgt tgttcccgac tcggctcttc cctttaactt ccaggctgcc  780
tatggcctga gtgaccaact ggcccaagcc atcagtgacc actatccagt ggaggtgatg  840
ctgaag                                                              846

SEQ ID NO: 16          moltype = AA  length = 282
FEATURE                Location/Qualifiers
SIGNAL                 1..22
                       note = human DNase 1 signal peptide
SIGNAL                 1..22
source                 1..282
                       mol_type = protein
                       organism = Homo sapiens
SEQUENCE: 16
MRGMKLLGAL LALAALLQGA VSLKIAAFNI QTFGETKMSN ATLVSYIVQI LSRYDIALVQ  60
EVRDSHLTAV GKLLDNLNQD APDTYHYVVS EPLGRNSYKE RYLFVYRPDQ VSAVDSYYYD  120
DGCEPCGNDT FNREPAIVRF FSRFTEVREF AIVPLHAAPG DAVAEIDALY DVYLDVQEKW  180
GLEDVMLMGD FNAGCSYVRP SQWSSIRLWT SPTFQWLIPD SADTTATPTH CAYDRIVVAG  240
MLLRGAVVPD SALPFNFQAA YGLSDQLAQA ISDHYPVEVM LK                      282

SEQ ID NO: 17          moltype = DNA  length = 840
FEATURE                Location/Qualifiers
misc_feature           1..840
                       note = hVK3LP-[hDNase1 N74K-G105R-A114F] DNA
source                 1..840
                       mol_type = other DNA
                       organism = synthetic construct
SEQUENCE: 17
```

```
atggaaaccc cagcgcagct tctcttcctc ctgctactct ggctcccaga taccaccggt  60
ctgaagatcg cagccttcaa catccagaca tttggggaga ccaagatgtc caatgccacc  120
ctcgtcagct acattgtgca gatcctgagc cgctatgaca tcgccctggt ccaggaggtc  180
agagacagcc acctgactgc cgtggggaag ctgctggaca acctcaatca ggatgcacca  240
gacacctatc actacgtggt cagtgagcca ctgggacgga agagctataa ggagcgctac  300
ctgttcgtgt acaggcctga ccaggtgtct gcggtggaca gctactacta cgatgatggc  360
tgcgagccct gcaggaacga caccttcaac cgagagccat tcattgtcag gttcttctcc  420
cggttcacag aggtcaggga gtttgccatt gttcccctgc atgcggcccc gggggacgca  480
gtagccgaga tcgacgctct ctatgacgtc tacctggatg tccaagagaa atggggcttg  540
gaggacgtca tgttgatggg cgacttcaat gcgggctgca gctatgtgag accctcccag  600
tggtcatcca tccgcctgtg gacaagcccc accttccagt ggctgatccc cgacagcgct  660
gacaccacag ctacacccac gcactgtgcc tatgacagga tcgtggttgc agggatgctg  720
ctccgaggcg ccgttgttcc cgactcggct cttcccttta acttccaggc tgcctatggc  780
ctgagtgacc aactggccca agccatcagt gaccactatc cagtggaggt gatgctgaaa  840

SEQ ID NO: 18           moltype = AA  length = 280
FEATURE                 Location/Qualifiers
REGION                  1..280
                        note = hVK3LP-[hDNase1 N74K-G105R-A114F]
SIGNAL                  1..20
                        note = human VK3 leader peptide
SITE                    94
                        note = N74K substitution
SITE                    125
                        note = G105R substitution
SITE                    134
                        note = A114F substitution
source                  1..280
                        mol_type = protein
                        organism = synthetic construct
SEQUENCE: 18
METPAQLLFL LLLWLPDTTG LKIAAFNIQT FGETKMSNAT LVSYIVQILS RYDIALVQEV  60
RDSHLTAVGK LLDNLNQDAP DTYHYVVSEP LGRKSYKERY LFVYRPDQVS AVDSYYYDDG  120
CEPCRNDTFN REPFIVRFFS RFTEVREFAI VPLHAAPGDA VAEIDALYDV YLDVQEKWGL  180
EDVMLMGDFN AGCSYVRPSQ WSSIRLWTSP TFQWLIPDSA DTTATPTHCA YDRIVVAGML  240
LRGAVVPDSA LPFNFQAAYG LSDQLAQAIS DHYPVEVMLK                       280

SEQ ID NO: 19           moltype = DNA  length = 840
FEATURE                 Location/Qualifiers
misc_feature            1..840
                        note = hVK3LP-[hDNase1 G105R-A114F] DNA
source                  1..840
                        mol_type = other DNA
                        organism = synthetic construct
SEQUENCE: 19
atggaaaccc cagcgcagct tctcttcctc ctgctactct ggctcccaga taccaccggt  60
ctgaagatcg cagccttcaa catccagaca tttggggaga ccaagatgtc caatgccacc  120
ctcgtcagct acattgtgca gatcctgagc cgctatgaca tcgccctggt ccaggaggtc  180
agagacagcc acctgactgc cgtggggaag ctgctggaca acctcaatca ggatgcacca  240
gacacctatc actacgtggt cagtgagcca ctgggacgga acagctataa ggagcgctac  300
ctgttcgtgt acaggcctga ccaggtgtct gcggtggaca gctactacta cgatgatggc  360
tgcgagccct gcaggaacga caccttcaac cgagagccat tcattgtcag gttcttctcc  420
cggttcacag aggtcaggga gtttgccatt gttcccctgc atgcggcccc gggggacgca  480
gtagccgaga tcgacgctct ctatgacgtc tacctggatg tccaagagaa atggggcttg  540
gaggacgtca tgttgatggg cgacttcaat gcgggctgca gctatgtgag accctcccag  600
tggtcatcca tccgcctgtg gacaagcccc accttccagt ggctgatccc cgacagcgct  660
gacaccacag ctacacccac gcactgtgcc tatgacagga tcgtggttgc agggatgctg  720
ctccgaggcg ccgttgttcc cgactcggct cttcccttta acttccaggc tgcctatggc  780
ctgagtgacc aactggccca agccatcagt gaccactatc cagtggaggt gatgctgaaa  840

SEQ ID NO: 20           moltype = AA  length = 280
FEATURE                 Location/Qualifiers
REGION                  1..280
                        note = hVK3LP-[hDNase1 G105R-A114F]
SIGNAL                  1..20
                        note = human VK3 leader peptide
SITE                    125
                        note = G105R substitution
SITE                    134
                        note = A114F substitution
source                  1..280
                        mol_type = protein
                        organism = synthetic construct
SEQUENCE: 20
METPAQLLFL LLLWLPDTTG LKIAAFNIQT FGETKMSNAT LVSYIVQILS RYDIALVQEV  60
RDSHLTAVGK LLDNLNQDAP DTYHYVVSEP LGRNSYKERY LFVYRPDQVS AVDSYYYDDG  120
CEPCRNDTFN REPFIVRFFS RFTEVREFAI VPLHAAPGDA VAEIDALYDV YLDVQEKWGL  180
EDVMLMGDFN AGCSYVRPSQ WSSIRLWTSP TFQWLIPDSA DTTATPTHCA YDRIVVAGML  240
LRGAVVPDSA LPFNFQAAYG LSDQLAQAIS DHYPVEVMLK                       280
```

```
SEQ ID NO: 21          moltype = DNA  length = 468
FEATURE                Location/Qualifiers
source                 1..468
                       mol_type = other DNA
                       organism = Homo sapiens
SEQUENCE: 21
atggctctgg agaagtctct tgtccggctc cttctgcttg tcctgatact gctggtgctg  60
ggctgggtcc agccttccct gggcaaggaa tcccgggcca agaaattcca gcggcagcat  120
atggactcag acagttcccc cagcagcagc tccacctact gtaaccaaat gatgaggcgc  180
cggaatatga cacaggggcg gtgcaaacca gtgaacacct ttgtgcacga gccccctggta  240
gatgtccaga atgtctgttt ccaggaaaag gtcacctgca agaacgggca gggcaactgc  300
tacaagagca actccagcat gcacatcaca gactgccgcc tgacaaacgg ctccaggtac  360
cccaactgtg cataccggac cagcccgaag gagagacaca tcattgtggc ctgtgaaggg  420
agcccatatg tgccagtcca ctttgatgct tctgtggagg actctacc             468

SEQ ID NO: 22          moltype = AA  length = 156
FEATURE                Location/Qualifiers
SIGNAL                 1..28
                       note = human RNase signal peptide
source                 1..156
                       mol_type = protein
                       organism = Homo sapiens
SEQUENCE: 22
MALEKSLVRL LLLVLILLVL GWVQPSLGKE SRAKKFQRQH MDSDSSPSSS STYCNQMMRR  60
RNMTQGRCKP VNTFVHEPLV DVQNVCFQEK VTCKNGQGNC YKSNSSMHIT DCRLTNGSRY  120
PNCAYRTSPK ERHIIVACEG SPYVPVHFDA SVEDST                          156

SEQ ID NO: 23          moltype = DNA  length = 444
FEATURE                Location/Qualifiers
misc_feature           1..444
                       note = hVK3LP-RNase1 DNA
source                 1..444
                       mol_type = other DNA
                       organism = synthetic construct
SEQUENCE: 23
atggaaaccc cagcgcagct tctcttcctc ctgctactct ggctcccaga taccaccggt  60
aaggaatccc gggccaagaa attccagcgg cagcatatgg actcagacag ttcccccagc  120
agcagctcca cctactgtaa ccaaatgatg aggcgccgga atatgacaca ggggcggtgc  180
aaaccagtga acacctttgt gcacgagccc ctggtagatg tccagaatgt ctgtttccag  240
gaaaaggtca cctgcaagaa cgggcagggc aactgctaca agagcaactc cagcatgcac  300
atcacagact gccgcctgac aaacgactcc aggtacccca actgtgcata ccggaccagc  360
ccgaaggaga gacacatcat tgtggcctgt gaagggagcc catatgtgcc agtccacttt  420
gatgcttctg tggaggactc taca                                       444

SEQ ID NO: 24          moltype = AA  length = 148
FEATURE                Location/Qualifiers
REGION                 1..148
                       note = hVK3LP-RNase1
SIGNAL                 1..20
                       note = human VK3 leader peptide
source                 1..148
                       mol_type = protein
                       organism = synthetic construct
SEQUENCE: 24
METPAQLLFL LLLWLPDTTG KESRAKKFQR QHMDSDSSPS SSSTYCNQMM RRRNMTQGRC  60
KPVNTFVHEP LVDVQNVCFQ EKVTCKNGQG NCYKSNSSMH ITDCRLTNGS RYPNCAYRTS  120
PKERHIIVAC EGSPYVPVHF DASVEDST                                   148

SEQ ID NO: 25          moltype = DNA  length = 696
FEATURE                Location/Qualifiers
misc_feature           1..696
                       note = Human IgG1 variant Fc DNA (SCC hinge, wild-type CH2
                        and CH3)
source                 1..696
                       mol_type = other DNA
                       organism = synthetic construct
SEQUENCE: 25
gagcccaaat cttctgacaa aactcacaca tgtccaccgt gcccagcacc tgaactcctg  60
gggggaccgt cagtcttcct cttcccccca aaacccaagg acaccctcat gatctcccgg  120
acccctgagg tcacatgcgt ggtggtggac gtgagccacg aagaccctga ggtcaagttc  180
aactggtacg tggacggcgt ggaggtgcat aatgccaaga caaagccgcg ggaggagcag  240
tacaacagca cgtaccgtgt ggtcagcgtc ctcaccgtcc tgcaccagga ctggctgaat  300
ggcaaggagt acaagtgcaa ggtctccaac aaagccctcc cagcccccat cgagaaaacc  360
atctccaaag ccaaagggca gccccgagaa ccacaggtgt acaccctgcc cccatcccgg  420
gatgagctga ccaagaacca ggtcagcctg acctgcctgg tcaaaggctt ctatcccagc  480
gacatcgccg tggagtggga gagcaatggg cagccggaga acaactacaa gaccacgcct  540
cccgtgctgg actccgacgg ctccttcttc ctctacagca agctcaccgt ggacaagagc  600
aggtggcagc aggggaacgt cttctcatgc tccgtgatgc atgaggctct gcacaaccac  660
```

-continued

```
tacacgcaga agagcctctc tctgtctccg ggtaaa                        696

SEQ ID NO: 26          moltype = AA  length = 232
FEATURE                Location/Qualifiers
REGION                 1..232
                       note = Human IgG1 variant Fc (SCC hinge, wild-type CH2 and
                        CH3)
source                 1..232
                       mol_type = protein
                       organism = synthetic construct
SEQUENCE: 26
EPKSSDKTHT CPPCPAPELL GGPSVFLFPP KPKDTLMISR TPEVTCVVVD VSHEDPEVKF  60
NWYVDGVEVH NAKTKPREEQ YNSTYRVVSV LTVLHQDWLN GKEYKCKVSN KALPAPIEKT  120
ISKAKGQPRE PQVYTLPPSR DELTKNQVSL TCLVKGFYPS DIAVEWESNG QPENNYKTTP  180
PVLDSDGSFF LYSKLTVDKS RWQQGNVFSC SVMHEALHNH YTQKSLSLSP GK          232

SEQ ID NO: 27          moltype = DNA  length = 696
FEATURE                Location/Qualifiers
misc_feature           1..696
                       note = Human IgG1 variant Fc DNA (SSS hinge, P238S, P331S)
source                 1..696
                       mol_type = other DNA
                       organism = synthetic construct
SEQUENCE: 27
gagcccaaat cttctgacaa aactcacaca tctccaccgt ccccagcacc tgaactcctg  60
ggaggatcgt cagtcttcct cttcccccca aaacccaagg acaccctcat gatctcccgg  120
acccctgagg tcacatgcgt ggtggtggac gtgagccacg aagaccctga ggtcaagttc  180
aactggtacg tggacggcgt ggaggtgcat aatgccaaga caaagccgcg ggaggagcag  240
tacaacagca cgtaccgtgt ggtcagcgtc ctcaccgtcc tgcaccagga ctggctgaat  300
ggcaaggagt acaagtgcaa ggtctccaac aaagccctcc cagcctccat cgagaaaacc  360
atctccaaag ccaaagggca gccccgagaa ccacaggtgt acaccctgcc cccatcccgg  420
gatgagctga ccaagaacca ggtcagcctg acctgcctgg tcaaaggctt ctatcccagc  480
gacatcgccg tggagtggga gagcaatggg cagccggaga acaactacaa gaccacgcct  540
cccgtgctgg actccgacgg ctccttcttc ctctacagca agctcaccgt ggacaagagc  600
aggtggcagc aggggaacgt cttctcatgc tccgtgatgc atgaggctct gcacaaccac  660
tacacgcaga agagcctctc tctctctccg ggtaaa                        696

SEQ ID NO: 28          moltype = AA  length = 232
FEATURE                Location/Qualifiers
REGION                 1..232
                       note = Human IgG1 variant Fc (SSS hinge, P238S, P331S)
SITE                   5
                       note = IgG1 hinge C220S substitution
SITE                   11
                       note = IgG1 hinge C226S substitution
SITE                   14
                       note = IgG1 hinge C229S substitution
SITE                   23
                       note = IgG1 lower hinge-CH2 P238S substitution
SITE                   116
                       note = IgG1 Fc P331S substitution
source                 1..232
                       mol_type = protein
                       organism = synthetic construct
SEQUENCE: 28
EPKSSDKTHT SPPSPAPELL GGSSVFLFPP KPKDTLMISR TPEVTCVVVD VSHEDPEVKF  60
NWYVDGVEVH NAKTKPREEQ YNSTYRVVSV LTVLHQDWLN GKEYKCKVSN KALPASIEKT  120
ISKAKGQPRE PQVYTLPPSR DELTKNQVSL TCLVKGFYPS DIAVEWESNG QPENNYKTTP  180
PVLDSDGSFF LYSKLTVDKS RWQQGNVFSC SVMHEALHNH YTQKSLSLSP GK          232

SEQ ID NO: 29          moltype = DNA  length = 774
FEATURE                Location/Qualifiers
misc_feature           1..774
                       note = (g4s)4-[SSShinge-P238S-P331S Fc] DNA
source                 1..774
                       mol_type = other DNA
                       organism = synthetic construct
SEQUENCE: 29
gatctctccg gaggaggtgg ctcaggtggt ggaggatctg gaggaggtgg gagtggtgga  60
ggtggttcta ccggtctcga gcccaaatct tctgacaaaa ctcacacatc tccaccgtcc  120
ccagcacctg aactcctggg aggatcgtca gtcttcctct tccccccaaa acccaaggac  180
accctcatga tctcccggac ccctgaggtc acatgcgtgg tggtggacgt gagccacgaa  240
gaccctgagg tcaagttcaa ctggtacgtg gacggcgtgg aggtgcataa tgccaagaca  300
aagccgcggg aggagcagta caacagcacg taccgtgtgg tcagcgtcct caccgtcctg  360
caccaggact ggctgaatgg caaggagtac aagtgcaagg tctccaacaa agccctccca  420
gcctccatcg agaaaaccat ctccaaagcc aaagggcagc cccgagaacc acaggtgtac  480
accctgcccc catcccggga tgagctgacc aagaaccagg tcagcctgac ctgcctggtc  540
aaaggcttct atcccagcga catcgccgtg gagtgggaga gcaatgggca gccggagaac  600
aactacaaga ccacgcctcc cgtgctggac tccgacggct ccttcttcct ctacagcaag  660
```

```
ctcaccgtgg acaagagcag gtggcagcag gggaacgtct tctcatgctc cgtgatgcat  720
gaggctctgc acaaccacta cacgcagaag agcctctctc tctctccggg taaa        774

SEQ ID NO: 30          moltype = AA  length = 258
FEATURE                Location/Qualifiers
REGION                 1..258
                       note = (g4s)4-[SSShinge-P238S-P331S Fc]
REGION                 1..26
                       note = (Gly4Ser)4 linker (including additional restriction
                        site amino acids)
REGION                 27..258
                       note = human IgG1 hinge-CH2-CH3 with substituted amino acids
SITE                   31
                       note = human IgG1 hinge C220S substitution
SITE                   37
                       note = human IgG1 hinge C226S substitution
SITE                   40
                       note = human IgG1 hinge C229S substitution
SITE                   49
                       note = human IgG1 lower hinge-CH2 P238S substitution
SITE                   142
                       note = human IgG1 P331S substitution
source                 1..258
                       mol_type = protein
                       organism = synthetic construct
SEQUENCE: 30
DLSGGGGSGG GGSGGGGSGG GGSTGLEPKS SDKTHTSPPS PAPELLGGSS VFLFPPKPKD  60
TLMISRTPEV TCVVVDVSHE DPEVKFNWYV DGVEVHNAKT KPREEQYNST YRVVSVLTVL  120
HQDWLNGKEY KCKVSNKALP ASIEKTISKA KGQPREPQVY TLPPSRDELT KNQVSLTCLV  180
KGFYPSDIAV EWESNGQPEN NYKTTPPVLD SDGSFFLYSK LTVDKSRWQQ GNVFSCSVMH  240
EALHNHYTQK SLSLSPGK                                                258

SEQ ID NO: 31          moltype = DNA  length = 462
FEATURE                Location/Qualifiers
source                 1..462
                       mol_type = other DNA
                       organism = Homo sapiens
SEQUENCE: 31
atggcgacga aggccgtgtg cgtgctgaag ggcgacggcc cagtgcaggg catcatcaat  60
ttcgagcaga aggaaagtaa tggaccagtg aaggtgtggg gaagcattaa aggactgact  120
gaaggcctgc atggattcca tgttcatgag tttggagata atacagcagg ctgtaccagt  180
gcaggtcctc actttaatcc tctatccaga aaacacggtg ggccaaagga tgaagagagg  240
catgttggag acttgggcaa tgtgactgct gacaaagatg gtgtggccga tgtgtctatt  300
gaagattctg tgatctcact ctcaggagac cattgcatca ttggccgcac actggtggtc  360
catgaaaaag cagatgactt gggcaaaggt ggaaatgaag aaagtacaaa gacaggaaac  420
gctggaagtc gtttggcttg tggtgtaatt gggatcgccc aa                     462

SEQ ID NO: 32          moltype = AA  length = 154
FEATURE                Location/Qualifiers
REGION                 1..154
                       note = mat_peptide - human SOD1 wild type sequence
source                 1..154
                       mol_type = protein
                       organism = Homo sapiens
SEQUENCE: 32
MATKAVCVLK GDGPVQGIIN FEQKESNGPV KVWGSIKGLT EGLHGFHVHE FGDNTAGCTS  60
AGPHFNPLSR KHGGPKDEER HVGDLGNVTA DKDGVADVSI EDSVISLSGD HCIIGRTLVV  120
HEKADDLGKG GNEESTKTGN AGSRLACGVI GIAQ                              154

SEQ ID NO: 33          moltype = DNA  length = 1242
FEATURE                Location/Qualifiers
misc_feature           1..1242
                       note = hRNase1-(g4s)4-[SSShinge-P238S Fc] DNA
source                 1..1242
                       mol_type = other DNA
                       organism = synthetic construct
SEQUENCE: 33
atggctctgg agaagtctct tgtccggctc cttctgcttg tcctgatact gctggtgctg  60
ggctgggtcc agccttccct gggcaaggaa tcccgggcca agaaattcca gcggcagcat  120
atggactcag acagttcccc cagcagcagc tccacctact gtaaccaaat gatgaggcgc  180
cggaatatga cacaggggcg gtgcaaacca gtgaacacct ttgtgcacga gcccctggta  240
gatgtccaga atgtctgttt ccaggaaaag gtcacctgca agaacgggca gggcaactgc  300
tacaagagca actccagcat gcacatcaca gactgccgcc tgacaaacgg ctccaggtac  360
cccaactgtg cataccggac cagcccgaag gagagacaca tcattgtggc ctgtgaaggg  420
agcccatatg tgccagtcca ctttgatgct tctgtggagg actctacaga tctctccgga  480
ggaggtggct caggtggtgg aggatctgga ggaggtggga gtggtggagg tggttctacc  540
ggtctcgagc ccaaatcttc tgacaaaact cacacatctc caccgtcccc agcacctgaa  600
ctcctggggg gatcgtcagt cttcctcttc cccccaaaac ccaaggacac cctcatgatc  660
tcccggaccc ctgaggtcac atgcgtggtg gtggacgtga gccacgaaga ccctgaggtc  720
```

-continued

```
aagttcaact ggtacgtgga cggcgtggag gtgcataatg ccaagacaaa gccgcgggag  780
gagcagtaca acagcacgta ccgtgtggtc agcgtcctca ccgtcctgca ccaggactgg  840
ctgaatggca aggagtacaa gtgcaaggtc tccaacaaag ccctcccagc ccccatcgag  900
aaaaccatct ccaaagccaa agggcagccc cgagaaccac aggtgtacac cctgccccca  960
tcccgggatg agctgaccaa gaaccaggtc agcctgacct gcctggtcaa aggcttctat  1020
cccagcgaca tcgccgtgga gtgggagagc aatgggcagc cggagaacaa ctacaagacc  1080
acgcctcccg tgctggactc cgacggctcc ttcttcctct acagcaagct caccgtggac  1140
aagagcaggt ggcagcaggg gaacgtcttc tcatgctccg tgatgcatga ggctctgcac  1200
aaccactaca cgcagaagag cctctctctg tctccgggta aa  1242

SEQ ID NO: 34          moltype = AA  length = 414
FEATURE                Location/Qualifiers
REGION                 1..414
                       note = hRNase1-(g4s)4-[SSShinge-P238S Fc]
SIGNAL                 1..28
                       note = human RNase signal sequence
REGION                 29..166
                       note = human RNase1 mature polypeptide
REGION                 167..182
                       note = human (gly4ser)4 linker peptide with additional
                        restriction site amino acids
REGION                 183..414
                       note = human IgG1 variant Fc (SSS hinge, P238S)
SITE                   187
                       note = human IgG1 hinge C220S substitution
SITE                   193
                       note = human IgG1 hinge C226S substitution
SITE                   196
                       note = human IgG1 hinge C229S substitution
SITE                   205
                       note = human IgG1lower hinge-CH2 P238S substitution
source                 1..414
                       mol_type = protein
                       organism = synthetic construct
SEQUENCE: 34
MALEKSLVRL LLLVLILLVL GWVQPSLGKE SRAKKFQRQH MDSDSSPSSS STYCNQMMRR  60
RNMTQGRCKP VNTFVHEPLV DVQNVCFQEK VTCKNGQGNC YKSNSSMHIT DCRLTNGSRY  120
PNCAYRTSPK ERHIIVACEG SPYVPVHFDA SVEDSTDLSG GGGSGGGGSG GGGSGGGGST  180
GLEPKSSDKT HTSPPSPAPE LLGGSSVFLF PPKPKDTLMI SRTPEVTCVV VDVSHEDPEV  240
KFNWYVDGVE VHNAKTKPRE EQYNSTYRVV SVLTVLHQDW LNGKEYKCKV SNKALPAPIE  300
KTISKAKGQP REPQVYTLPP SRDELTKNQV SLTCLVKGFY PSDIAVEWES NGQPENNYKT  360
TPPVLDSDGS FFLYSKLTVD KSRWQQGNVF SCSVMHEALH NHYTQKSLSL SPGK  414

SEQ ID NO: 35          moltype = DNA  length = 1218
FEATURE                Location/Qualifiers
misc_feature           1..1218
                       note = hVK3LP-hRNase1-(g4s)4-[SSShinge-P238S Fc] DNA
source                 1..1218
                       mol_type = other DNA
                       organism = synthetic construct
SEQUENCE: 35
atggaaaccc cagcgcagct tctcttcctc ctgctactct ggctcccaga taccaccggt  60
aaggaatccc gggccaagaa attccagcgg cagcatatgg actcagacag ttcccccagc  120
agcagctcca cctactgtaa ccaaatgatg aggcgccgga atatgacaca ggggcggtgc  180
aaaccagtga acacctttgt gcacgagccc ctggtagatg tccagaatgt ctgtttccag  240
gaaaaggtca cctgcaagaa cggcagggc aactgctaca agagcaactc cagcatgcac  300
atcacagact gccgcctgac aaacgactcc aggtacccca actgtgcata ccggaccagc  360
ccgaaggaga gacacatcat tgtggcctgt gaagggagcc catatgtgcc agtccacttt  420
gatgcttctg tggaggactc tacagatctc tccggaggag gtggctcagg tggtggagga  480
tctggaggag gtgggagtgg tggaggtggt tctaccggtc tcgagcccaa atcttctgac  540
aaaactcaca catctccacc gtccccagca cctgaactcc tgggggatc gtcagtcttc  600
ctcttccccc caaaacccaa ggacaccctc atgatctccc ggacccctga ggtcacatgc  660
gtggtggtgg acgtgagcca cgaagaccct gaggtcaagt tcaactggta cgtggacggc  720
gtggaggtgc ataatgccaa gacaaagccg cgggaggagc agtacaacag cacgtaccgt  780
gtggtcagcg tcctcaccgt cctgcaccag gactggctga atggcaagga gtacaagtgc  840
aaggtctcca acaaagccct cccagccccc atcgagaaaa ccatctccaa agccaaaggg  900
cagccccgag aaccacaggt gtacaccctg cccccatccc gggatgagct gaccaagaac  960
caggtcagcc tgacctgcct ggtcaaaggc ttctatccca gcgacatcgc cgtggagtgg  1020
gagagcaatg ggcagccgga gaacaactac aagaccacgc ctcccgtgct ggactccgac  1080
ggctccttct tcctctacag caagctcacc gtggacaaga gcaggtggca gcaggggaac  1140
gtcttctcat gctccgtgat gcatgaggct ctgcacaacc actacacgca gaagagcctc  1200
tctctgtctc cgggtaaa  1218

SEQ ID NO: 36          moltype = AA  length = 406
FEATURE                Location/Qualifiers
REGION                 1..406
                       note = hVK3LP-hRNase1-(g4s)4-[SSShinge-P238S Fc]
SIGNAL                 1..20
                       note = human VK3 signal peptide
```

```
REGION              21..158
                    note = human RNase 1 mature polypeptide
REGION              159..174
                    note = (gly4ser)4 linker peptide with additional
                     restriction site amino acids
REGION              175..406
                    note = human IgG1 variant Fc (SSS hinge, P238S)
SITE                179
                    note = human IgG1 hinge C220S substitution
SITE                185
                    note = human IgG1 hinge C226S substitution
SITE                188
                    note = human IgG1 hinge C229S substitution
SITE                197
                    note = human IgG1 lower hinge-CH2 P238S substitution
source              1..406
                    mol_type = protein
                    organism = synthetic construct
SEQUENCE: 36
METPAQLLFL LLLWLPDTTG KESRAKKFQR QHMDSDSSPS SSSTYCNQMM RRRNMTQGRC  60
KPVNTFVHEP LVDVQNVCFQ EKVTCKNGQG NCYKSNSSMH ITDCRLTNDS RYPNCAYRTS  120
PKERHIIVAC EGSPYVPVHF DASVEDSTDL SGGGGSGGGG SGGGGSGGGG STGLEPKSSD  180
KTHTSPPSPA PELLGGSSVF LFPPKPKDTL MISRTPEVTC VVVDVSHEDP EVKFNWYVDG  240
VEVHNAKTKP REEQYNSTYR VVSVLTVLHQ DWLNGKEYKC KVSNKALPAP IEKTISKAKG  300
QPREPQVYTL PPSRDELTKN QVSLTCLVKG FYPSDIAVEW ESNGQPENNY KTTPPVLDSD  360
GSFFLYSKLT VDKSRWQQGN VFSCSVMHEA LHNHYTQKSL SLSPGK                406

SEQ ID NO: 37       moltype = DNA  length = 2316
FEATURE             Location/Qualifiers
misc_feature        1..2316
                    note = hRNase1-(g4s)4-[SSSH-P238S Fc]-NGS-[PON1 Q192K) DNA
source              1..2316
                    mol_type = other DNA
                    organism = synthetic construct
SEQUENCE: 37
atggctctgg agaagtctct tgtccggctc cttctgcttg tcctgatact gctggtgctg  60
ggctgggtcc agccttccct gggcaaggaa tcccgggcca agaaattcca gcggcagcat  120
atggactcag acagttcccc cagcagcagc tccacctact gtaaccaaat gatgaggcgc  180
cggaatatga cacaggggcg gtgcaaacca gtgaacacct ttgtgcacga gccccctggta  240
gatgtccaga atgtctgttt ccaggaaaag gtcacctgca agaacgggca gggcaactgc  300
tacaagagca actccagcat gcacatcaca gactgccgcc tgacaaacgg ctccaggtac  360
cccaactgtg cataccggac cagcccgaag gagagacaca tcattgtggc ctgtgaaggg  420
agcccatatg tgccagtcca ctttgatgct tctgtggagg actctacaga tctctccgga  480
ggaggtggct caggtggtgg aggatctgga ggaggtggga gtggtggagg tggttctacc  540
ggtctcgagc ccaaatcttc tgacaaaact cacacatctc caccgtcccc agcacctgaa  600
ctcctgggag gatcgtcagt cttcctcttc cccccaaaac ccaaggacac cctcatgatc  660
tcccggaccc ctgaggtcac atgcgtggtg gtggacgtga gccacgaaga ccctgaggtc  720
aagttcaact ggtacgtgga cggcgtggag gtgcataatg ccaagacaaa gccgcgggag  780
gagcagtaca acagcacgta ccgtgtggtc agcgtcctca ccgtcctgca ccaggactgg  840
ctgaatggca aggagtacaa gtgcaaggtc tccaacaaag ccctcccagc ccccatcgag  900
aaaaccatct ccaaagccaa agggcagccc cgagaaccac aggtgtacac cctgccccca  960
tcccgggatg agctgaccaa gaaccaggtc agcctgacct gcctggtcaa aggcttctat  1020
cccagcgaca tcgccgtgga gtgggagagc aatgggcagc cggagaacaa ctacaagacc  1080
acgcctcccg tgctggactc cgacggctcc ttcttcctct acagcaagct caccgtggac  1140
aagagcaggt ggcagcaggg gaacgtcttc tcatgctccg tgatgcatga ggctctgcac  1200
aaccactaca cgcagaagag cctctctctc tctccgggta aagtcgacgg agctagcagc  1260
cccgtgaacg tgagcagccc cagcgtgcag gatatcctct tcaggaacca ccagtcttct  1320
taccaaacac gacttaatgc tctccgagag gtacaacccg tagaacttcc taactgtaat  1380
ttagttaaag gaatcgaaac tggctctgaa gacttggaga tactgcctaa tggactggct  1440
ttcattagct ctggattaaa gtatcctgga ataaagagct tcaaccccaa cagtcctgga  1500
aaaatacttc tgatggacct gaatgaagaa gatccaacag tgttggaatt ggggatcact  1560
ggaagtaaat ttgatgtatc ttcatttaac cctcatggga ttagcacatt cacagatgaa  1620
gataatgcca tgtacctcct ggtggtgaac catccagatg ccaagtccac agtggagttg  1680
tttaaatttc aagaagaaga aaaatcgctt ttgcatctaa aaaccatcag acataaactt  1740
ctgcctaatt tgaatgatat tgttgctgtg ggacctgagc acttttatgg cacaaatgat  1800
cactattttc ttgacccccta cttaaaatcc tgggagatgt atttgggttt agcgtggtcg  1860
tatgttgtct actatagtcc aagtgaagtt cgagtggtgg cagaaggatt tgattttgct  1920
aatggaatca acatttcacc cgatggcaag tatgtctata tagctgagtt gctggctcat  1980
aagattcatg tgtatgaaaa gcatgctaat tggactttaa ctccattgaa gtcccttgac  2040
tttaataccc tcgtggataa catatctgtg gatcctgaga caggagacct ttgggttgga  2100
tgccatccca atggcatgaa aatcttcttc tatgactcag agaatcctcc tgcatcagag  2160
gtgcttcgaa tccagaacat tctaacagaa gaacctaaag tgacacaggt ttatgcagaa  2220
aatggcacag tgttgcaagg cagtacagtt gcctctgtgt acaaagggaa actgctgatt  2280
ggcacagtgt ttcacaaagc tctttactgt gagctc                           2316

SEQ ID NO: 38       moltype = AA  length = 772
FEATURE             Location/Qualifiers
REGION              1..772
                    note = hRNase1-(g4s)4-[SSSH-P238S Fc]-NGS-[PON1 Q192K)
```

```
SIGNAL                    1..28
                          note = human RNase 1 signal peptide
REGION                    29..156
                          note = human RNase 1 mature polypeptide
REGION                    157..182
                          note = (gly4ser)4 linker peptide with additional
                           restriction site amino acids
REGION                    183..414
                          note = human IgG1 variant Fc (SSS hinge, P238S)
SITE                      187
                          note = Human IgG1 hinge C220S substitution
SITE                      193
                          note = Human IgG1 hinge C226S substitution
SITE                      196
                          note = Human IgG1 hinge C229S substitution
SITE                      205
                          note = Human IgG1 lower hinge-CH2 P238S substitution
REGION                    415..433
                          note = peptide linker containing N-linked glyscosylation
                           site
REGION                    434..772
                          note = human PON1 Q192K without uncleaved leader peptide
SITE                      609
                          note = PON1 Q192K amino acid substitution
source                    1..772
                          mol_type = protein
                          organism = synthetic construct
SEQUENCE: 38
MALEKSLVRL LLLVLILLVL GWVQPSLGKE SRAKKFQRQH MDSDSSPSSS STYCNQMMRR  60
RNMTQGRCKP VNTFVHEPLV DVQNVCFQEK VTCKNGQGNC YKSNSSMHIT DCRLTNGSRY  120
PNCAYRTSPK ERHIIVACEG SPYVPVHFDA SVEDSTDLSG GGGSGGGGSG GGGSGGGGST  180
GLEPKSSDKT HTSPPSPAPE LLGGSSVFLF PPKPKDTLMI SRTPEVTCVV VDVSHEDPEV  240
KFNWYVDGVE VHNAKTKPRE EQYNSTYRVV SVLTVLHQDW LNGKEYKCKV SNKALPAPIE  300
KTISKAKGQP REPQVYTLPP SRDELTKNQV SLTCLVKGFY PSDIAVEWES NGQPENNYKT  360
TPPVLDSDGS FFLYSKLTVD KSRWQQGNVF SCSVMHEALH NHYTQKSLSL SPGKVDGASS  420
PVNVSSPSVQ DILFRNHQSS YQTRLNALRE VQPVELPNCN LVKGIETGSE DLEILPNGLA  480
FISSGLKYPG IKSFNPNSPG KILLMDLNEE DPTVLELGIT GSKFDVSSFN PHGISTFTDE  540
DNAMYLLVVN HPDAKSTVEL FKFQEEEKSL LHLKTIRHKL LPNLNDIVAV GPEHFYGTND  600
HYFLDPYLKS WEMYLGLAWS YVVYYSPSEV RVVAEGFDFA NGINISPDGK YVYIAELLAH  660
KIHVYEKHAN WTLTPLKSLD FNTLVDNISV DPETGDLWVG CHPNGMKIFF YDSENPPASE  720
VLRIQNILTE EPKVTQVYAE NGTVLQGSTV ASVYKGKLLI GTVFHKALYC EL          772

SEQ ID NO: 39             moltype = DNA  length = 2292
FEATURE                   Location/Qualifiers
misc_feature              1..2292
                          note = hVK3LP-hRNase1-(g4s)4-[SSShinge-P238S Fc]-NGS-[PON1
                           Q192K] DNA
source                    1..2292
                          mol_type = other DNA
                          organism = synthetic construct
SEQUENCE: 39
atggaaaccc cagcgcagct tctcttcctc ctgctactct ggctcccaga taccaccggt  60
aaggaatccc gggccaagaa attccagcgg cagcatatgg actcagacag ttcccccagc  120
agcagctcca cctactgtaa ccaaatgatg aggcgccgga atatgacaca ggggcggtgc  180
aaaccagtga acacctttgt gcacgagccc ctggtagatg tccagaatgt ctgtttccag  240
gaaaaggtca cctgcaagaa cggccagggc aactgctaca agagcaactc cagcatgcac  300
atcacagact gccgcctgac aaacggctcc aggtacccca actgtgcata ccggaccagc  360
ccgaaggaga gacacatcat tgtggcctgt gaagggagcc catatgtgcc agtccacttt  420
gatgcttctg tggaggactc tacagatctc tccggaggag gtggctcagg tggtggagga  480
tctggaggag gtgggagtgg tggaggtggt tctaccggtc tcgagcccaa atcttctgac  540
aaaactcaca catctccacc gtccccagca cctgaactcc tgggaggatc gtcagtcttc  600
ctcttccccc caaaacccaa ggacaccctc atgatctccc ggacccctga ggtcacatgc  660
gtggtggtgg acgtgagcca cgaagaccct gaggtcaagt tcaactggta cgtggacggc  720
gtggaggtgc ataatgccaa gacaaagccg cgggaggagc agtacaacag cacgtaccgt  780
gtggtcagcg tcctcaccgt cctgcaccag gactggctga atggcaagga gtacaagtgc  840
aaggtctcca acaaagccct cccagccccc atcgagaaaa ccatctccaa agccaaaggg  900
cagccccgag aaccacaggt gtacaccctg cccccatccc gggatgagct gaccaagaac  960
caggtcagcc tgacctgcct ggtcaaaggc ttctatccca gcgacatcgc cgtggagtgg  1020
gagagcaatg ggcagccgga gaacaactac aagaccacgc ctcccgtgct ggactccgac  1080
ggctccttct tcctctacag caagctcacc gtggacaaga gcaggtggca gcaggggaac  1140
gtcttctcat gctccgtgat gcatgaggct ctgcacaacc actacacgca gaagagcctc  1200
tctctctctc cgggtaaagt cgacggagct agcagccccg tgaacgtgag cagccccagc  1260
gtgcaggata tcctcttcag gaaccaccag tcttcttacc aaacacgact taatgctctc  1320
cgagaggtac aacccgtaga acttcctaac tgtaatttag ttaaaggaat cgaaactggc  1380
tctgaagact tggagatact gcctaatgga ctggctttca ttagctctgg attaaagtat  1440
cctggaataa agagcttcaa ccccaacagt cctggaaaaa tacttctgat ggacctgaat  1500
gaagaagatc caacagtgtt ggaattgggg atcactggaa gtaaatttga tgtatcttca  1560
tttaaccctc atgggattag cacattcaca gatgaagata atgccatgta cctcctggtg  1620
gtgaaccatc cagatgccaa gtccacagtg gagttgttta aatttcaaga agaagaaaaa  1680
```

```
tcgcttttgc atctaaaaac catcagacat aaacttctgc ctaatttgaa tgatattgtt  1740
gctgtgggac ctgagcactt ttatggcaca aatgatcact attttcttga cccctactta  1800
aaatcctggg agatgtattt gggtttagcg tggtcgtatg ttgtctacta tagtccaagt  1860
gaagttcgag tggtggcaga aggatttgat tttgctaatg gaatcaacat ttcacccgat  1920
ggcaagtatg tctatatagc tgagttgctg gctcataaga ttcatgtgta tgaaaagcat  1980
gctaattgga ctttaactcc attgaagtcc cttgacttta ataccctcgt ggataacata  2040
tctgtggatc ctgagacagg agacctttgg gttggatgcc atcccaatgg catgaaaatc  2100
ttcttctatg actcagagaa tcctcctgca tcagaggtgc ttcgaatcca gaacattcta  2160
acagaagaac ctaaagtgac acaggtttat gcagaaaatg gcacagtgtt gcaaggcagt  2220
acagttgcct ctgtgtacaa agggaaactg ctgattggca cagtgtttca caaagctctt  2280
tactgtgagc tc                                                     2292

SEQ ID NO: 40          moltype = AA  length = 764
FEATURE                Location/Qualifiers
REGION                 1..764
                       note = hVK3LP-hRNase1-(g4s)4-[SSShinge-P238S Fc]-NGS-[PON1
                        Q192K]
SIGNAL                 1..20
                       note = human VK3 signal peptide
REGION                 21..148
                       note = human RNase1 mature polypeptide
REGION                 149..174
                       note = (gly4ser)4 linker peptide with addtional restriction
                        site amino acids
REGION                 175..406
                       note = human IgG1 variant Fc (SSS hinge, P238S)
SITE                   179
                       note = human IgG1 hinge C220S amino acid substitution
SITE                   185
                       note = human IgG1 hinge C226S amino acid substitution
SITE                   188
                       note = human IgG1 hinge C229S amino acid substitution
SITE                   197
                       note = human IgG1 lower hinge-CH2 P238S amino acid
                        substitution
REGION                 407..425
                       note = peptide linker containing N linked glyscosylation
                        site
REGION                 426..764
                       note = human PON1 Q192K without uncleaved leader peptide
SITE                   601
                       note = PON1 Q192K amino acid substitution
source                 1..764
                       mol_type = protein
                       organism = synthetic construct
SEQUENCE: 40
METPAQLLFL LLLWLPDTTG KESRAKKFQR QHMDSDSSPS SSSTYCNQMM RRRNMTQGRC  60
KPVNTFVHEP LVDVQNVCFQ EKVTCKNGQG NCYKSNSSMH ITDCRLTNGS RYPNCAYRTS  120
PKERHIIVAC EGSPYVPVHF DASVEDSTDL SGGGGSGGGG SGGGGSGGGG STGLEPKSSD  180
KTHTSPPSPA PELLGGSSVF LFPPKPKDTL MISRTPEVTC VVVDVSHEDP EVKFNWYVDG  240
VEVHNAKTKP REEQYNSTYR VVSVLTVLHQ DWLNGKEYKC KVSNKALPAP IEKTISKAKG  300
QPREPQVYTL PPSRDELTKN QVSLTCLVKG FYPSDIAVEW ESNGQPENNY KTTPPVLDSD  360
GSFFLYSKLT VDKSRWQQGN VFSCSVMHEA LHNHYTQKSL SLSPGKVDGA SSPVNVSSPS  420
VQDILFRNHQ SSYQTRLNAL REVQPVELPN CNLVKGIETG SEDLEILPNG LAFISSGLKY  480
PGIKSFNPNS PGKILLMDLN EEDPTVLELG ITGSKFDVSS FNPHGISTFT DEDNAMYLLV  540
VNHPDAKSTV ELFKFQEEEK SLLHLKTIRH KLLPNLNDIV AVGPEHFYGT NDHYFLDPYL  600
KSWEMYLGLA WSYVVYYSPS EVRVVAEGFD FANGINISPD GKYVYIAELL AHKIHVYEKH  660
ANWTLTPLKS LDFNTLVDNI SVDPETGDLW VGCHPNGMKI FFYDSENPPA SEVLRIQNIL  720
TEEPKVTQVY AENGTVLQGS TVASVYKGKL LIGTVFHKAL YCEL                  764

SEQ ID NO: 41          moltype = DNA  length = 1170
FEATURE                Location/Qualifiers
misc_feature           1..1170
                       note = hRNase1-[SSShinge-P238S Fc] DNA
source                 1..1170
                       mol_type = other DNA
                       organism = synthetic construct
SEQUENCE: 41
atggctctgg agaagtctct tgtccggctc cttctgcttg tcctgatact gctggtgctg  60
ggctgggtcc agccttccct gggcaaggaa tcccgggcca agaaattcca gcggcagcat  120
atggactcag acagttcccc cagcagcagc tccacctact gtaaccaaat gatgaggcgc  180
cggaatatga cacaggggcg gtgcaaacca gtgaacacct ttgtgcacga gcccctggta  240
gatgtccaga atgtctgttt ccaggaaaag gtcacctgca agaacgggca gggcaactgc  300
tacaagagca actccagcat gcacatcaca gactgccgcc tgacaaacgg ctccaggtac  360
cccaactgtg cataccggac cagcccgaag gagagacaca tcattgtggc ctgtgaaggg  420
agcccatatg tgccagtcca ctttgatgct tctgtggagg actctacaga tctcgagccc  480
aaatcttctg acaaaactca cacatctcca ccgtccccag cacctgaact cctgggggga  540
tcgtcagtct tcctcttccc cccaaaaccc aaggacaccc tcatgatctc ccggacccct  600
gaggtcacat gcgtggtggt ggacgtgagc cacgaagacc ctgaggtcaa gttcaactgg  660
```

```
tacgtggacg gcgtggaggt gcataatgcc aagacaaagc cgcgggagga gcagtacaac  720
agcacgtacc gtgtggtcag cgtcctcacc gtcctgcacc aggactggct gaatggcaag  780
gagtacaagt gcaaggtctc caacaaagcc ctcccagccc ccatcgagaa aaccatctcc  840
aaagccaaag ggcagccccg agaaccacag gtgtacaccc tgcccccatc ccgggatgag  900
ctgaccaaga accaggtcag cctgacctgc ctggtcaaag gcttctatcc cagcgacatc  960
gccgtggagt gggagagcaa tgggcagccg gagaacaact acaagaccac gcctcccgtg  1020
ctggactccg acggctcctt cttcctctac agcaagctca ccgtggacaa gagcaggtgg  1080
cagcagggga acgtcttctc atgctccgtg atgcatgagg ctctgcacaa ccactacacg  1140
cagaagagcc tctctctgtc tccgggtaaa                                  1170

SEQ ID NO: 42          moltype = AA  length = 390
FEATURE                Location/Qualifiers
REGION                 1..390
                       note = hRNase1-[SSShinge-P238S Fc]
SIGNAL                 1..28
                       note = human RNase1 signal peptide
REGION                 29..156
                       note = human RNase1 mature polypeptide
REGION                 157..158
                       note = restriction site amino acids
REGION                 159..390
                       note = human IgG1 variant Fc (SSS hinge, P238S)
SITE                   163
                       note = human IgG1 hinge domain C220S substitution
SITE                   169
                       note = human IgG1 hinge domain C226S substitution
SITE                   172
                       note = human IgG1 hinge domain C229S substitution
SITE                   181
                       note = human IgG1 lower hinge-CH2 domain P238S substitution
source                 1..390
                       mol_type = protein
                       organism = synthetic construct
SEQUENCE: 42
MALEKSLVRL LLLVLILLVL GWVQPSLGKE SRAKKFQRQH MDSDSSPSSS STYCNQMMRR  60
RNMTQGRCKP VNTFVHEPLV DVQNVCFQEK VTCKNGQGNC YKSNSSMHIT DCRLTNGSRY  120
PNCAYRTSPK ERHIIVACEG SPYVPVHFDA SVEDSTDLEP KSSDKTHTSP PSPAPELLGG  180
SSVFLFPPKP KDTLMISRTP EVTCVVVDVS HEDPEVKFNW YVDGVEVHNA KTKPREEQYN  240
STYRVVSVLT VLHQDWLNGK EYKCKVSNKA LPAPIEKTIS KAKGQPREPQ VYTLPPSRDE  300
LTKNQVSLTC LVKGFYPSDI AVEWESNGQP ENNYKTTPPV LDSDGSFFLY SKLTVDKSRW  360
QQGNVFSCSV MHEALHNHYT QKSLSLSPGK                                  390

SEQ ID NO: 43          moltype = DNA  length = 1146
FEATURE                Location/Qualifiers
misc_feature           1..1146
                       note = hVK3LP-hRNase1-[SSShinge-P238S Fc] DNA
source                 1..1146
                       mol_type = other DNA
                       organism = synthetic construct
SEQUENCE: 43
atggaaaccc cagcgcagct tctcttcctc ctgctactct ggctcccaga taccaccggt  60
aaggaatccc gggccaagaa attccagcgg cagcatatgg actcagacag ttcccccagc  120
agcagctcca cctactgtaa ccaaatgatg aggcgccgga atatgacaca ggggcggtgc  180
aaaccagtga acacctttgt gcacgagccc ctggtagatg tccagaatgt ctgtttccag  240
gaaaaggtca cctgcaagaa cgggcagggc aactgctaca agagcaactc cagcatgcac  300
atcacagact gccgcctgac aaacgactcc aggtacccca actgtgcata ccggaccagc  360
ccgaaggaga gacacatcat tgtggcctgt gaagggagcc catatgtgcc agtccacttt  420
gatgcttctg tggaggactc tacagatctc gagcccaaat cttctgacaa aactcacaca  480
tctccaccgt ccccagcacc tgaactcctg gggggatcgt cagtcttcct cttcccccca  540
aaacccaagg acaccctcat gatctcccgg acccctgagg tcacatgcgt ggtggtggac  600
gtgagccacg aagaccctga ggtcaagttc aactggtacg tggacggcgt ggaggtgcat  660
aatgccaaga caaagccgcg ggaggagcag tacaacagca cgtaccgtgt ggtcagcgtc  720
ctcaccgtcc tgcaccagga ctggctgaat ggcaaggagt acaagtgcaa ggtctccaac  780
aaagccctcc cagcccccat cgagaaaacc atctccaaag ccaaagggca gccccgagaa  840
ccacaggtgt acaccctgcc cccatcccgg gatgagctga ccaagaacca ggtcagcctg  900
acctgcctgg tcaaaggctt ctatcccagc gacatcgccg tggagtggga gagcaatggg  960
cagccggaga acaactacaa gaccacgcct cccgtgctgg actccgacgg ctccttcttc  1020
ctctacagca agctcaccgt ggacaagagc aggtggcagc aggggaacgt cttctcatgc  1080
tccgtgatgc atgaggctct gcacaaccac tacacgcaga agagcctctc tctgtctccg  1140
ggtaaa                                                            1146

SEQ ID NO: 44          moltype = AA  length = 382
FEATURE                Location/Qualifiers
REGION                 1..382
                       note = hVK3LP-hRNase1-[SSShinge-P238S Fc]
SIGNAL                 1..20
                       note = Human VK3 leader peptide
REGION                 21..148
                       note = human RNase 1 mature polytpeptide
```

```
REGION                  149..150
                        note = restriction site amino acids
REGION                  151..382
                        note = human IgG1 variant Fc (SSS hinge, P238S)
SITE                    155
                        note = human IgG1 hinge C220S amino acid substitution
SITE                    161
                        note = human IgG1 hinge C226S amino acid substitution
SITE                    164
                        note = human IgG1 hinge C229S amino acid substitution
SITE                    173
                        note = human IgG1 lower hinge-CH2 P238S amino acid
                         substitution
source                  1..382
                        mol_type = protein
                        organism = synthetic construct
SEQUENCE: 44
METPAQLLFL LLLWLPDTTG KESRAKKFQR QHMDSDSSPS SSSTYCNQMM RRRNMTQGRC  60
KPVNTFVHEP LVDVQNVCFQ EKVTCKNGQG NCYKSNSSMH ITDCRLTNDS RYPNCAYRTS  120
PKERHIIVAC EGSPYVPVHF DASVEDSTDL EPKSSDKTHT SPPSPAPELL GGSSVFLFPP  180
KPKDTLMISR TPEVTCVVVD VSHEDPEVKF NWYVDGVEVH NAKTKPREEQ YNSTYRVVSV  240
LTVLHQDWLN GKEYKCKVSN KALPAPIEKT ISKAKGQPRE PQVYTLPPSR DELTKNQVSL  300
TCLVKGFYPS DIAVEWESNG QPENNYKTTP PVLDSDGSFF LYSKLTVDKS RWQQGNVFSC  360
SVMHEALHNH YTQKSLSLSP GK                                           382

SEQ ID NO: 45           moltype = DNA  length = 2244
FEATURE                 Location/Qualifiers
misc_feature            1..2244
                        note = hRNase1-[SSShinge-P238S Fc]-NGS-[PON1 Q192K] DNA
source                  1..2244
                        mol_type = other DNA
                        organism = synthetic construct
SEQUENCE: 45
atggctctgg agaagtctct tgtccggctc cttctgcttg tcctgatact gctggtgctg  60
ggctgggtcc agccttccct gggcaaggaa tcccgggcca agaaattcca gcggcagcat  120
atggactcag acagttcccc cagcagcagc tccacctact gtaaccaaat gatgaggcgc  180
cggaatatga cacaggggcg gtgcaaacca gtgaacacct ttgtgcacga gcccctggta  240
gatgtccaga atgtctgttt ccaggaaaag gtcacctgca agaacgggca gggcaactgc  300
tacaagagca actccagcat gcacatcaca gactgccgcc tgacaaacgg ctccaggtac  360
cccaactgtg cataccggac cagcccgaag gagagacaca tcattgtggc ctgtgaaggg  420
agcccatatg tgccagtcca ctttgatgct tctgtggagg actctacaga tctcgagccc  480
aaatcttctg acaaaactca cacatctcca ccgtccccag cacctgaact cctgggagga  540
tcgtcagtct tcctcttccc cccaaaaccc aaggacaccc tcatgatctc ccggacccct  600
gaggtcacat gcgtggtggt ggacgtgagc cacgaagacc ctgaggtcaa gttcaactgg  660
tacgtggacg gcgtggaggt gcataatgcc aagacaaagc cgcgggagga gcagtacaac  720
agcacgtacc gtgtggtcag cgtcctcacc gtcctgcacc aggactggct gaatggcaag  780
gagtacaagt gcaaggtctc caacaaagcc ctcccagccc ccatcgagaa aaccatctcc  840
aaagccaaag ggcagccccg agaaccacag gtgtacaccc tgcccccatc ccgggatgag  900
ctgaccaaga accaggtcag cctgacctgc ctggtcaaag gcttctatcc cagcgacatc  960
gccgtggagt gggagagcaa tgggcagccg gagaacaact acaagaccac gcctcccgtg  1020
ctggactccg acggctcctt cttcctctac agcaagctca ccgtggacaa gagcaggtgg  1080
cagcagggga acgtcttctc atgctccgtg atgcatgagg ctctgcacaa ccactacacg  1140
cagaagagcc tctctctctc tccgggtaaa gtcgacggag ctagcagccc cgtgaacgtg  1200
agcagcccca gcgtgcagga tatcctcttc aggaaccacc agtcttctta ccaaacacga  1260
cttaatgctc tccgagaggt acaacccgta gaacttccta actgtaattt agttaaagga  1320
atcgaaactg gctctgaaga cttggagata ctgcctaatg gactggcttt cattagctct  1380
ggattaaagt atcctggaat aaagagcttc aaccccaaca gtcctggaaa aatacttctg  1440
atggacctga atgaagaaga tccaacagtg ttggaattgg ggatcactgg aagtaaattt  1500
gatgtatctt catttaaccc tcatgggatt agcacattca cagatgaaga taatgccatg  1560
tacctcctgg tggtgaacca tccagatgcc aagtccacag tggagttgtt taaatttcaa  1620
gaagaagaaa aatcgctttt gcatctaaaa accatcagac ataaacttct gcctaatttg  1680
aatgatattg ttgctgtggg acctgagcac ttttatggca caaatgatca ctattttctt  1740
gacccctact taaaatcctg ggagatgtat ttgggtttag cgtggtcgta tgttgtctac  1800
tatagtccaa gtgaagttcg agtggtggca gaaggatttg attttgctaa tggaatcaac  1860
atttcacccg atggcaagta tgtctatata gctgagttgc tggctcataa gattcatgtg  1920
tatgaaaagc atgctaattg gactttaact ccattgaagt cccttgactt taataccctc  1980
gtggataaca tatctgtgga tcctgagaca ggagaccttt gggttggatg ccatcccaat  2040
ggcatgaaaa tcttcttcta tgactcagag aatcctcctg catcagaggt gcttcgaatc  2100
cagaacattc taacagaaga acctaaagtg acacaggttt atgcagaaaa tggcacagtg  2160
ttgcaaggca gtacagttgc ctctgtgtac aaagggaaac tgctgattgg cacagtgttt  2220
cacaaagctc tttactgtga gctc                                         2244

SEQ ID NO: 46           moltype = AA  length = 748
FEATURE                 Location/Qualifiers
REGION                  1..748
                        note = hRNase1-[SSShinge-P238S Fc]-NGS-[PON1 Q192K]
SIGNAL                  1..28
                        note = human RNase 1 signal peptide
REGION                  29..156
```

```
                        note = human RNase 1 mature polypeptide
REGION                  157..158
                        note = restriction site amino acids
REGION                  159..390
                        note = human IgG1 variant Fc (SSS hinge, P238S)
SITE                    163
                        note = human IgG1 hinge C220S amino acid substitution
SITE                    169
                        note = human IgG1 hinge C226S amino acid substitution
SITE                    172
                        note = human IgG1 hinge C229S amino acid substitution
SITE                    182
                        note = human IgG1lower hinge-CH2 P238S amino acid
                         substitution
REGION                  391..409
                        note = peptide linker containing N-linked glycosylation site
REGION                  410..748
                        note = human PON1 Q192K without uncleaved leader peptide
SITE                    585
                        note = human PON1 Q192K amino acid substitution
source                  1..748
                        mol_type = protein
                        organism = synthetic construct
SEQUENCE: 46
MALEKSLVRL LLLVLILLVL GWVQPSLGKE SRAKKFQRQH MDSDSSPSSS STYCNQMMRR  60
RNMTQGRCKP VNTFVHEPLV DVQNVCFQEK VTCKNGQGNC YKSNSSMHIT DCRLTNGSRY  120
PNCAYRTSPK ERHIIVACEG SPYVPVHFDA SVEDSTDLEP KSSDKTHTSP PSPAPELLGG  180
SSVFLFPPKP KDTLMISRTP EVTCVVVDVS HEDPEVKFNW YVDGVEVHNA KTKPREEQYN  240
STYRVVSVLT VLHQDWLNGK EYKCKVSNKA LPAPIEKTIS KAKGQPREPQ VYTLPPSRDE  300
LTKNQVSLTC LVKGFYPSDI AVEWESNGQP ENNYKTTPPV LDSDGSFFLY SKLTVDKSRW  360
QQGNVFSCSV MHEALHNHYT QKSLSLSPGK VDGASSPVNV SSPSVQDILF RNHQSSYQTR  420
LNALREVQPV ELPNCNLVKG IETGSEDLEI LPNGLAFISS GLKYPGIKSF NPNSPGKILL  480
MDLNEEDPTV LELGITGSKF DVSSFNPHGI STFTDEDNAM YLLVVNHPDA KSTVELFKFQ  540
EEEKSLLHLK TIRHKLLPNL NDIVAVGPEH FYGTNDHYFL DPYLKSWEMY LGLAWSYVVY  600
YSPSEVRVVA EGFDFANGIN ISPDGKYVYI AELLAHKIHV YEKHANWTLT PLKSLDFNTL  660
VDNISVDPET GDLWVGCHPN GMKIFFYDSE NPPASEVLRI QNILTEEPKV TQVYAENGTV  720
LQGSTVASVY KGKLLIGTVF HKALYCEL                                    748

SEQ ID NO: 47           moltype = DNA  length = 2220
FEATURE                 Location/Qualifiers
misc_feature            1..2220
                        note = hVK3LP-hRNase1-[SSShinge-P238S Fc]-NGS-[PON1 Q192K]
                         DNA
source                  1..2220
                        mol_type = other DNA
                        organism = synthetic construct
SEQUENCE: 47
atggaaaccc cagcgcagct tctcttcctc ctgctactct ggctcccaga taccaccggt  60
aaggaatccc gggccaagaa attccagcgg cagcatatgg actcagacag ttcccccagc  120
agcagctcca cctactgtaa ccaaatgatg aggcgccgga atatgacaca ggggcggtgc  180
aaaccagtga acacctttgt gcacgagccc ctggtagatg tccagaatgt ctgtttccag  240
gaaaaggtca cctgcaagaa cgggcagggc aactgctaca agagcaactc cagcatgcac  300
atcacagact gccgcctgac aaacggctcc aggtacccca actgtgcata ccggaccagc  360
ccgaaggaga gacacatcat tgtggcctgt gaagggagcc catatgtgcc agtccacttt  420
gatgcttctg tggaggactc tacagatctc gagcccaaat cttctgacaa aactcacaca  480
tctccaccgt ccccagcacc tgaactcctg ggaggatcgt cagtcttcct cttcccccca  540
aaacccaagg acaccctcat gatctcccgg acccctgagg tcacatgcgt ggtggtggac  600
gtgagccacg aagaccctga ggtcaagttc aactggtacg tggacggcgt ggaggtgcat  660
aatgccaaga caaagccgcg ggaggagcag tacaacagca cgtaccgtgt ggtcagcgtc  720
ctcaccgtcc tgcaccagga ctggctgaat ggcaaggagt acaagtgcaa ggtctccaac  780
aaagccctcc cagcccccat cgagaaaacc atctccaaag ccaaagggca gccccgagaa  840
ccacaggtgt acaccctgcc cccatcccgg gatgagctga ccaagaacca ggtcagcctg  900
acctgcctgg tcaaaggctt ctatcccagc gacatcgccg tggagtggga gagcaatggg  960
cagccggaga acaactacaa gaccacgcct cccgtgctgg actccgacgg ctccttcttc  1020
ctctacagca agctcaccgt ggacaagagc aggtggcagc aggggaacgt cttctcatgc  1080
tccgtgatgc atgaggctct gcacaaccac tacacgcaga agagcctctc tctctctccg  1140
ggtaaagtcg acggagctag cagccccgtg aacgtgagca gccccagcgt gcaggatatc  1200
ctcttcagga accaccagtc ttcttaccaa acacgactta atgctctccg agaggtacaa  1260
cccgtagaac ttcctaactg taatttagtt aaaggaatcg aaactggctc tgaagacttg  1320
gagatactgc ctaatggact ggctttcatt agctctggat taaagtatcc tggaataaag  1380
agcttcaacc ccaacagtcc tggaaaaata cttctgatgg acctgaatga agaagatcca  1440
acagtgttgg aattggggat cactggaagt aaatttgatg tatcttcatt taaccctcat  1500
gggattagca cattcacaga tgaagataat gccatgtacc tcctggtggt gaaccatcca  1560
gatgccaagt ccacagtgga gttgtttaaa tttcaagaag aagaaaaatc gcttttgcat  1620
ctaaaaacca tcagacataa acttctgcct aatttgaatg atattgttgc tgtgggacct  1680
gagcactttt atggcacaaa tgatcactat tttcttgacc cctacttaaa atcctgggag  1740
atgtatttgg gtttagcgtg gtcgtatgtt gtctactata gtccaagtga agttcgagtg  1800
gtggcagaag gatttgattt tgctaatgga atcaacattt cacccgatgg caagtatgtc  1860
tatatagctg agttgctggc tcataagatt catgtgtatg aaaagcatgc taattggact  1920
```

```
ttaactccat tgaagtccct tgactttaat accctcgtgg ataacatatc tgtggatcct  1980
gagacaggag acctttgggt tggatgccat cccaatggca tgaaaatctt cttctatgac  2040
tcagagaatc ctcctgcatc agaggtgctt cgaatccaga acattctaac agaagaacct  2100
aaagtgacac aggtttatgc agaaaatggc acagtgttgc aaggcagtac agttgcctct  2160
gtgtacaaag ggaaactgct gattggcaca gtgtttcaca aagctcttta ctgtgagctc  2220

SEQ ID NO: 48          moltype = AA  length = 740
FEATURE                Location/Qualifiers
REGION                 1..740
                       note = hVK3LP-hRNase1-[SSShinge-P238S Fc]-NGS-[PON1 Q192K]
SIGNAL                 1..20
                       note = human VK3 leader peptide
REGION                 21..148
                       note = human RNase 1 mature polypeptide
REGION                 149..150
                       note = restriction site amino acids
REGION                 151..382
                       note = human IgG1 variant Fc (SSS hinge, P238S)
SITE                   155
                       note = human IgG1 hinge C220S amino acid substitution
SITE                   161
                       note = human IgG1 hinge C226S amino acid substitution
SITE                   164
                       note = human IgG1 hinge C229S amino acid substitution
SITE                   173
                       note = human IgG1 lower hinge-CH2 P238S amino acid
                        substitution
REGION                 383..401
                       note = peptide linker containing N-linked glycosylation site
REGION                 402..740
                       note = human PON1 Q192K without uncleaved leader peptide
SITE                   577
                       note = human PON1 Q192K amino acid substitution
source                 1..740
                       mol_type = protein
                       organism = synthetic construct
SEQUENCE: 48
METPAQLLFL LLLWLPDTTG KESRAKKFQR QHMDSDSSPS SSSTYCNQMM RRRNMTQGRC  60
KPVNTFVHEP LVDVQNVCFQ EKVTCKNGQG NCYKSNSSMH ITDCRLTNGS RYPNCAYRTS  120
PKERHIIVAC EGSPYVPVHF DASVEDSTDL EPKSSDKTHT SPPSPAPELL GGSSVFLFPP  180
KPKDTLMISR TPEVTCVVVD VSHEDPEVKF NWYVDGVEVH NAKTKPREEQ YNSTYRVVSV  240
LTVLHQDWLN GKEYKCKVSN KALPAPIEKT ISKAKGQPRE PQVYTLPPSR DELTKNQVSL  300
TCLVKGFYPS DIAVEWESNG QPENNYKTTP PVLDSDGSFF LYSKLTVDKS RWQQGNVFSC  360
SVMHEALHNH YTQKSLSLSP GKVDGASSPV NVSSPSVQDI LFRNHQSSYQ TRLNALREVQ  420
PVELPNCNLV KGIETGSEDL EILPNGLAFI SSGLKYPGIK SFNPNSPGKI LLMDLNEEDP  480
TVLELGITGS KFDVSSFNPH GISTFTDEDN AMYLLVVNHP DAKSTVELFK FQEEEKSLLH  540
LKTIRHKLLP NLNDIVAVGP EHFYGTNDHY FLDPYLKSWE MYLGLAWSYV VYYSPSEVRV  600
VAEGFDFANG INISPDGKYV YIAELLAHKI HVYEKHANWT LTPLKSLDFN TLVDNISVDP  660
ETGDLWVGCH PNGMKIFFYD SENPPASEVL RIQNILTEEP KVTQVYAENG TVLQGSTVAS  720
VYKGKLLIGT VFHKALYCEL                                            740

SEQ ID NO: 49          moltype = DNA  length = 2343
FEATURE                Location/Qualifiers
misc_feature           1..2343
                       note = hVK3LP-hSOD1-(g4s)2-[SSShinge-P238S-P331S
                        Fc]-NGS-[PON1 Q192K] DNA
source                 1..2343
                       mol_type = other DNA
                       organism = synthetic construct
SEQUENCE: 49
atggaaaccc cagcgcagct tctcttcctc ctgctactct ggctcccaga taccaccggt  60
atggcggcaa cgaaggccgt gtgcgtgctg aagggcgacg gcccagtgca gggcatcatc  120
aatttcgagc agaaggaaag taatggacca gtgaaggtgt ggggaagcat taaaggactg  180
actgaaggcc tgcatggatt ccatgttcat gagtttggag ataatacagc aggctgtacc  240
agtgcaggtc ctcactttaa tcctctatcc agaaaacacg gtgggccaaa ggatgaagag  300
aggcatgttg gagacttggg caatgtgact gctgacaaag atggtgtggc cgatgtgtct  360
attgaagatt ctgtgatctc actctcagga gaccattgca tcattggccg cacactggtg  420
gtccatgaaa aagcagatga cttgggcaaa ggtggaaatg aagaaagtac aaagacagga  480
aacgctggaa gtcgtttggc ttgtggtgta attgggatcg cccaagatct ctccggagga  540
ggtggctcag gtggtggagg atctaccggt ctcgagccca aatcttctga caaaactcac  600
acatctccac cgtccccagc acctgaactc ctgggaggat cgtcagtctt cctcttcccc  660
ccaaaaccca aggacaccct catgatctcc cggacccctg aggtcacatg cgtggtggtg  720
gacgtgagcc acgaagaccc tgaggtcaag ttcaactggt acgtggacgg cgtggaggtg  780
cataatgcca agacaaagcc gcgggaggag cagtacaaca gcacgtaccg tgtggtcagc  840
gtcctcaccg tcctgcacca ggactggctg aatggcaagg agtacaagtg caaggtctcc  900
aacaaagccc tcccagcctc catcgagaaa accatctcca aagccaaagg gcagccccga  960
gaaccacagg tgtacaccct gcccccatcc cgggatgagc tgaccaagaa ccaggtcagc  1020
ctgacctgcc tggtcaaagg cttctatccc agcgacatcg ccgtggagtg ggagagcaat  1080
gggcagccgg agaacaacta caagaccacg cctcccgtgc tggactccga cggctccttc  1140
```

```
ttcctctaca gcaagctcac cgtggacaag agcaggtggc agcaggggaa cgtcttctca  1200
tgctccgtga tgcatgaggc tctgcacaac cactacacgc agaagagcct ctctctctct  1260
ccgggtaaag tcgacggagc tagcagcccc gtgaacgtga gcagccccag cgtgcaggat  1320
atcctcttca ggaaccacca gtcttcttac caaacacgac ttaatgctct ccgagaggta  1380
caacccgtag aacttcctaa ctgtaattta gttaaaggaa tcgaaactgg ctctgaagac  1440
ttggagatac tgcctaatgg actggctttc attagctctg gattaaagta tcctggaata  1500
aagagcttca accccaacag tcctggaaaa atacttctga tggacctgaa tgaagaagat  1560
ccaacagtgt tggaattggg gatcactgga agtaaatttg atgtatcttc atttaaccct  1620
catgggatta gcacattcac agatgaagat aatgccatgt acctcctggt ggtgaaccat  1680
ccagatgcca agtccacagt ggagttgttt aaatttcaag aagaagaaaa atcgcttttg  1740
catctaaaaa ccatcagaca taaacttctg cctaatttga atgatattgt tgctgtggga  1800
cctgagcact tttatggcac aaatgatcac tattttcttg acccctactt aaaatcctgg  1860
gagatgtatt tgggtttagc gtggtcgtat gttgtctact atagtccaag tgaagttcga  1920
gtggtggcag aaggatttga ttttgctaat ggaatcaaca tttcacccga tggcaagtat  1980
gtctatatag ctgagttgct ggctcataag attcatgtgt atgaaaagca tgctaattgg  2040
actttaactc cattgaagtc ccttgacttt aataccctcg tggataacat atctgtggat  2100
cctgagacag gagacctttg ggttggatgc catcccaatg gcatgaaaat cttcttctat  2160
gactcagaga atcctcctgc atcagaggtg cttcgaatcc agaacattct aacagaagaa  2220
cctaaagtga cacaggttta tgcagaaaat ggcacagtgt tgcaaggcag tacagttgcc  2280
tctgtgtaca aagggaaact gctgattggc acagtgtttc acaaagctct ttactgtgag  2340
ctc                                                                2343

SEQ ID NO: 50           moltype = AA  length = 781
FEATURE                 Location/Qualifiers
REGION                  1..781
                        note = hVK3LP-hSOD1-(g4s)2-[SSShinge-P238S-P331S
                         Fc]-NGS-[PON1 Q192K]
SIGNAL                  1..22
                        note = human VK3 leader peptide with 2 additional amino
                         acids to drive correct cleavage
REGION                  23..175
                        note = human SOD 1 without N-terminal methionine
REGION                  176..191
                        note = (gly4ser)2 linker peptide with additional
                         restriction site amino acids
REGION                  192..483
                        note = human IgG1 variant Fc (SSS hinge, P238S, P331S)
SITE                    196
                        note = human IgG1 hinge C220S amino acid substitution
SITE                    202
                        note = human IgG1 hinge C226S amino acid substitution
SITE                    205
                        note = human IgG1 hinge C229S amino acid substitution
SITE                    224
                        note = human IgG1 lower hinge-CH2 P238S amino acid
                         substitution
SITE                    307
                        note = human IgG1 Fc P331S amino acid substitution
REGION                  424..442
                        note = peptide linker containing N-linked glycosylation site
REGION                  443..781
                        note = human PON1 Q192K without uncleaved leader peptide
SITE                    618
                        note = human PON1 Q192K amino acid substitution
source                  1..781
                        mol_type = protein
                        organism = synthetic construct
SEQUENCE: 50
METPAQLLFL LLLWLPDTTG MAATKAVCVL KGDGPVQGII NFEQKESNGP VKVWGSIKGL  60
TEGLHGFHVH EFGDNTAGCT SAGPHFNPLS RKHGGPKDEE RHVGDLGNVT ADKDGVADVS  120
IEDSVISLSG DHCIIGRTLV VHEKADDLGK GGNEESTKTG NAGSRLACGV IGIAQDLSGG  180
GGSGGGGSTG LEPKSSDKTH TSPPSPAPEL LGGSSVFLFP PKPKDTLMIS RTPEVTCVVV  240
DVSHEDPEVK FNWYVDGVEV HNAKTKPREE QYNSTYRVVS VLTVLHQDWL NGKEYKCKVS  300
NKALPASIEK TISKAKGQPR EPQVYTLPPS RDELTKNQVS LTCLVKGFYP SDIAVEWESN  360
GQPENNYKTT PPVLDSDGSF FLYSKLTVDK SRWQQGNVFS CSVMHEALHN HYTQKSLSLS  420
PGKVDGASSP VNVSSPSVQD ILFRNHQSSY QTRLNALREV QPVELPNCNL VKGIETGSED  480
LEILPNGLAF ISSGLKYPGI KSFNPNSPGK ILLMDLNEED PTVLELGITG SKFDVSSFNP  540
HGISTFTDED NAMYLLVVNH PDAKSTVELF KFQEEEKSLL HLKTIRHKLL PNLNDIVAVG  600
PEHFYGTNDH YFLDPYLKSW EMYLGLAWSY VVYYSPSEVR VVAEGFDFAN GINISPDGKY  660
VYIAELLAHK IHVYEKHANW TLTPLKSLDF NTLVDNISVD PETGDLWVGC HPNGMKIFFY  720
DSENPPASEV LRIQNILTEE PKVTQVYAEN GTVLQGSTVA SVYKGKLLIG TVFHKALYCE  780
L                                                                  781

SEQ ID NO: 51           moltype = DNA  length = 2343
FEATURE                 Location/Qualifiers
misc_feature            1..2343
                        note = hVK3LP-[hSOD1 C6A
                         C111S]-(g4s)2-[SSShinge-P238S-P331S Fc]-NGS-[PON1 Q192K]
                         DNA
```

```
source                1..2343
                      mol_type = other DNA
                      organism = synthetic construct
SEQUENCE: 51
atggaaaccc cagcgcagct tctcttcctc ctgctactct ggctcccaga taccaccggt  60
atggcggcaa cgaaggccgt ggctgtgctg aagggcgacg gcccagtgca gggcatcatc  120
aatttcgagc agaaggaaag taatggacca gtgaaggtgt ggggaagcat taaaggactg  180
actgaaggcc tgcatggatt ccatgttcat gagtttggag ataatacagc aggctgtacc  240
agtgcaggtc ctcactttaa tcctctatcc agaaaacacg gtgggccaaa ggatgaagag  300
aggcatgttg gagacttggg caatgtgact gctgacaaag atggtgtggc cgatgtgtct  360
attgaagatt ctgtgatctc actctcagga gaccattcaa tcattggccg cacactggtg  420
gtccatgaaa aagcagatga cttgggcaaa ggtggaaatg aagaaagtac aaagacagga  480
aacgctggaa gtcgtttggc ttgtggtgta attgggatcg cccaagatct ctccggagga  540
ggtggctcag gtggtggagg atctaccggt ctcgagccca aatcttctga caaaactcac  600
acatctccac cgtccccagc acctgaactc ctgggaggat cgtcagtctt cctcttcccc  660
ccaaaaccca aggacaccct catgatctcc cggacccctg aggtcacatg cgtggtggtg  720
gacgtgagcc acgaagaccc tgaggtcaag ttcaactggt acgtggacgg cgtggaggtg  780
cataatgcca agacaaagcc gcgggaggag cagtacaaca gcacgtaccg tgtggtcagc  840
gtcctcaccg tcctgcacca ggactggctg aatggcaagg agtacaagtg caaggtctcc  900
aacaaagccc tcccagcctc catcgagaaa accatctcca aagccaaagg gcagccccga  960
gaaccacagg tgtacaccct gcccccatcc cgggatgagc tgaccaagaa ccaggtcagc  1020
ctgacctgcc tggtcaaagg cttctatccc agcgacatcg ccgtggagtg ggagagcaat  1080
gggcagccgg agaacaacta caagaccacg cctcccgtgc tggactccga cggctccttc  1140
ttcctctaca gcaagctcac cgtggacaag agcaggtggc agcaggggaa cgtcttctca  1200
tgctccgtga tgcatgaggc tctgcacaac cactacacgc agaagagcct ctctctctct  1260
ccgggtaaag tcgacggagc tagcagcccc gtgaacgtga gcagccccag cgtgcaggat  1320
atcctcttca ggaaccacca gtcttcttac caaacacgac ttaatgctct ccgagaggta  1380
caacccgtag aacttcctaa ctgtaattta gttaaaggaa tcgaaactgg ctctgaagac  1440
ttggagatac tgcctaatgg actggctttc attagctctg gattaaagta tcctggaata  1500
aagagcttca accccaacag tcctggaaaa atacttctga tggacctgaa tgaagaagat  1560
ccaacagtgt tggaattggg gatcactgga agtaaatttg atgtatcttc atttaaccct  1620
catgggatta gcacattcac agatgaagat aatgccatgt acctcctggt ggtgaaccat  1680
ccagatgcca agtccacagt ggagttgttt aaatttcaag aagaagaaaa atcgcttttg  1740
catctaaaaa ccatcagaca taaacttctg cctaatttga atgatattgt tgctgtggga  1800
cctgagcact tttatggcac aaatgatcac tattttcttg acccctactt aaaatcctgg  1860
gagatgtatt tgggtttagc gtggtcgtat gttgtctact atagtccaag tgaagttcga  1920
gtggtggcag aaggatttga ttttgctaat ggaatcaaca tttcacccga tggcaagtat  1980
gtctatatag ctgagttgct ggctcataag attcatgtgt atgaaaagca tgctaattgg  2040
actttaactc cattgaagtc ccttgacttt aataccctcg tggataacat atctgtggat  2100
cctgagacag gagacctttg ggttggatgc catcccaatg gcatgaaaat cttcttctat  2160
gactcagaga atcctcctgc atcagaggtg cttcgaatcc agaacattct aacagaagaa  2220
cctaaagtga cacaggttta tgcagaaaat ggcacagtgt tgcaaggcag tacagttgcc  2280
tctgtgtaca aagggaaact gctgattggc acagtgtttc acaaagctct ttactgtgag  2340
ctc                                                                 2343

SEQ ID NO: 52         moltype = AA  length = 781
FEATURE               Location/Qualifiers
REGION                1..781
                      note = hVK3LP-[hSOD1 C6A
                       C111S]-(g4s)2-[SSShinge-P238S-P331S Fc]-NGS-[PON1 Q192K]
SIGNAL                1..22
                      note = human VK3 leader peptide with 2 additional amino
                       acids to drive correct cleavage
REGION                23..175
                      note = human SOD1 C6A-C111S without N-terminal methionine
SITE                  28
                      note = human SOD 1 C6A amino acid substitution
SITE                  133
                      note = human SOD 1 C111S amino acid substitution
REGION                176..191
                      note = (gly4ser)2 linker peptide with additional
                       restriction site amino acids
REGION                192..423
                      note = human IgG1 variant Fc (SSS hinge, P238S, P331S)
SITE                  196
                      note = human IgG1 hinge C220S amino acid substitution
SITE                  202
                      note = human IgG1 hinge C226S amino acid substitution
SITE                  205
                      note = human IgG1 hinge C229S amino acid substitution
SITE                  215
                      note = human IgG1 lower hinge-CH2 P238S amino acid
                       substitution
SITE                  307
                      note = human IgG1 Fc P331S amino acid substitution
REGION                424..442
                      note = linker peptide containing N-linked glycosylation site
REGION                443..781
                      note = human PON1 Q192K without uncleaved leader peptide
```

```
SITE                    618
                        note = human PON1 Q192K amino acid substitution
source                  1..781
                        mol_type = protein
                        organism = synthetic construct
SEQUENCE: 52
METPAQLLFL LLLWLPDTTG MAATKAVAVL KGDGPVQGII NFEQKESNGP VKVWGSIKGL  60
TEGLHGFHVH EFGDNTAGCT SAGPHFNPLS RKHGGPKDEE RHVGDLGNVT ADKDGVADVS  120
IEDSVISLSG DHSIIGRTLV VHEKADDLGK GGNEESTKTG NAGSRLACGV IGIAQDLSGG  180
GGSGGGGSTG LEPKSSDKTH TSPPSPAPEL LGGSSVFLFP PKPKDTLMIS RTPEVTCVVV  240
DVSHEDPEVK FNWYVDGVEV HNAKTKPREE QYNSTYRVVS VLTVLHQDWL NGKEYKCKVS  300
NKALPASIEK TISKAKGQPR EPQVYTLPPS RDELTKNQVS LTCLVKGFYP SDIAVEWESN  360
GQPENNYKTT PPVLDSDGSF FLYSKLTVDK SRWQQGNVFS CSVMHEALHN HYTQKSLSLS  420
PGKVDGASSP VNVSSPSVQD ILFRNHQSSY QTRLNALREV QPVELPNCNL VKGIETGSED  480
LEILPNGLAF ISSGLKYPGI KSFNPNSPGK ILLMDLNEED PTVLELGITG SKFDVSSFNP  540
HGISTFTDED NAMYLLVVNH PDAKSTVELF KFQEEEKSLL HLKTIRHKLL PNLNDIVAVG  600
PEHFYGTNDH YFLDPYLKSW EMYLGLAWSY VVYYSPSEVR VVAEGFDFAN GINISPDGKY  660
VYIAELLAHK IHVYEKHANW TLTPLKSLDF NTLVDNISVD PETGDLWVGC HPNGMKIFFY  720
DSENPPASEV LRIQNILTEE PKVTQVYAEN GTVLQGSTVA SVYKGKLLIG TVFHKALYCE  780
L                                                                 781

SEQ ID NO: 53           moltype = DNA  length = 2373
FEATURE                 Location/Qualifiers
misc_feature            1..2373
                        note = hVK3LP-[hSOD1 C6A
                         C111S]-(g4s)4-[SSShinge-P238S-P331S Fc]-NGS-[PON1 Q192K]
                         DNA
source                  1..2373
                        mol_type = other DNA
                        organism = synthetic construct
SEQUENCE: 53
atggaaaccc cagcgcagct tctcttcctc ctgctactct ggctcccaga taccaccggt  60
atggcggcaa cgaaggccgt ggctgtgctg aagggcgacg gcccagtgca gggcatcatc  120
aatttcgagc agaaggaaag taatggacca gtgaaggtgt ggggaagcat taaaggactg  180
actgaaggcc tgcatggatt ccatgttcat gagtttggag ataatacagc aggctgtacc  240
agtgcaggtc ctcactttaa tcctctatcc agaaaacacg gtgggccaaa ggatgaagag  300
aggcatgttg gagacttggg caatgtgact gctgacaaag atggtgtggc cgatgtgtct  360
attgaagatt ctgtgatctc actctcagga gaccattcaa tcattggccg cacactggtg  420
gtccatgaaa aagcagatga cttgggcaaa ggtggaaatg aagaaagtac aaagacagga  480
aacgctggaa gtcgtttggc ttctggtgta attgggatcg cccaagatct ctccggagga  540
ggtggctcag gtggtggagg atctggagga ggtgggagtg gtggaggtgg ttctaccggt  600
ctcgagccca aatcttctga caaaactcac acatctccac cgtccccagc acctgaactc  660
ctgggaggat cgtcagtctt cctcttcccc ccaaaaccca aggacaccct catgatctcc  720
cggacccctg aggtcacatg cgtggtggtg gacgtgagcc acgaagaccc tgaggtcaag  780
ttcaactggt acgtggacgg cgtggaggtg cataatgcca agacaaagcc gcgggaggag  840
cagtacaaca gcacgtaccg tgtggtcagc gtcctcaccg tcctgcacca ggactggctg  900
aatggcaagg agtacaagtg caaggtctcc aacaaagccc tcccagcctc catcgagaaa  960
accatctcca aagccaaagg gcagccccga gaaccacagg tgtacaccct gcccccatcc  1020
cgggatgagc tgaccaagaa ccaggtcagc ctgacctgcc tggtcaaagg cttctatccc  1080
agcgacatcg ccgtggagtg ggagagcaat gggcagccgg agaacaacta caagaccacg  1140
cctcccgtgc tggactccga cggctccttc ttcctctaca gcaagctcac cgtggacaag  1200
agcaggtggc agcaggggaa cgtcttctca tgctccgtga tgcatgaggc tctgcacaac  1260
cactacacgc agaagagcct ctctctctct ccgggtaaag tcgacggagc tagcagcccc  1320
gtgaacgtga gcagccccag cgtgcaggat atcctcttca ggaaccacca gtcttcttac  1380
caaacacgac ttaatgctct ccgagaggta caacccgtag aacttcctaa ctgtaattta  1440
gttaaaggaa tcgaaactgg ctctgaagac ttggagatac tgcctaatgg actggctttc  1500
attagctctg gattaaagta tcctggaata aagagcttca accccaacag tcctggaaaa  1560
atacttctga tggacctgaa tgaagaagat ccaacagtgt tggaattggg gatcactgga  1620
agtaaatttg atgtatcttc atttaaccct catgggatta gcacattcac agatgaagat  1680
aatgccatgt acctcctggt ggtgaaccat ccagatgcca agtccacagt ggagttgttt  1740
aaatttcaag aagaagaaaa atcgcttttg catctaaaaa ccatcagaca taaacttctg  1800
cctaatttga atgatattgt tgctgtggga cctgagcact tttatggcac aaatgatcac  1860
tattttcttg acccctactt aaaatcctgg gagatgtatt tgggtttagc gtggtcgtat  1920
gttgtctact atagtccaag tgaagttcga gtggtggcag aaggatttga ttttgctaat  1980
ggaatcaaca tttcacccga tggcaagtat gtctatatag ctgagttgct ggctcataag  2040
attcatgtgt atgaaaagca tgctaattgg actttaactc cattgaagtc ccttgacttt  2100
aataccctcg tggataacat atctgtggat cctgagacag gagacctttg ggttggatgc  2160
catcccaatg gcatgaaaat cttcttctat gactcagaga atcctcctgc atcagaggtg  2220
cttcgaatcc agaacattct aacagaagaa cctaaagtga cacaggttta tgcagaaaat  2280
ggcacagtgt tgcaaggcag tacagttgcc tctgtgtaca aagggaaact gctgattggc  2340
acagtgtttc acaaagctct ttactgtgag ctc                              2373

SEQ ID NO: 54           moltype = AA  length = 791
FEATURE                 Location/Qualifiers
REGION                  1..791
                        note = hVK3LP-[hSOD1 C6A
                         C111S]-(g4s)4-[SSShinge-P238S-P331S Fc]-NGS-[PON1 Q192K]
SIGNAL                  1..22
                        note = human VK3 leader peptide with 2 additional amino
```

```
                         acids to drive correct cleavage
REGION                  23..175
                        note = human SOD1 C6A-C111S without N-terminal methionine
SITE                    28
                        note = human SOD 1 C6A amino acid substitution
SITE                    133
                        note = human SOD 1 C111S amino acid substitution
REGION                  176..201
                        note = (gly4ser)4 linker peptide with additional
                         restriction site amino acids
REGION                  202..433
                        note = human IgG1 variant Fc (SSS hinge, P238S, P331S)
SITE                    206
                        note = human IgG1 hinge C220S amino acid substitution
SITE                    212
                        note = human IgG1 hinge C226S amino acid substitution
SITE                    215
                        note = human IgG1 hinge C229S amino acid substitution
SITE                    225
                        note = human IgG1 lower hinge-CH2 P238S amino acid
                         substitution
SITE                    317
                        note = human IgG1 Fc P331S amino acid substitution
REGION                  434..452
                        note = peptide linker containing N-linked glycosylation site
REGION                  453..791
                        note = human PON1 Q192K without uncleaved leader peptide
SITE                    628
                        note = human PON1 Q192K amino acid substitution
source                  1..791
                        mol_type = protein
                        organism = synthetic construct
SEQUENCE: 54
METPAQLLFL LLLWLPDTTG MAATKAVAVL KGDGPVQGII NFEQKESNGP VKVWGSIKGL  60
TEGLHGFHVH EFGDNTAGCT SAGPHFNPLS RKHGGPKDEE RHVGDLGNVT ADKDGVADVS  120
IEDSVISLSG DHSIIGRTLV VHEKADDLGK GGNEESTKTG NAGSRLASGV IGIAQDLSGG  180
GGSGGGGSGG GGSGGGGSTG LEPKSSDKTH TSPPSPAPEL LGGSSVFLFP PKPKDTLMIS  240
RTPEVTCVVV DVSHEDPEVK FNWYVDGVEV HNAKTKPREE QYNSTYRVVS VLTVLHQDWL  300
NGKEYKCKVS NKALPASIEK TISKAKGQPR EPQVYTLPPS RDELTKNQVS LTCLVKGFYP  360
SDIAVEWESN GQPENNYKTT PPVLDSDGSF FLYSKLTVDK SRWQQGNVFS CSVMHEALHN  420
HYTQKSLSLS PGKVDGASSP VNVSSPSVQD ILFRNHQSSY QTRLNALREV QPVELPNCNL  480
VKGIETGSED LEILPNGLAF ISSGLKYPGI KSFNPNSPGK ILLMDLNEED PTVLELGITG  540
SKFDVSSFNP HGISTFTDED NAMYLLVVNH PDAKSTVELF KFQEEEKSLL HLKTIRHKLL  600
PNLNDIVAVG PEHFYGTNDH YFLDPYLKSW EMYLGLAWSY VVYYSPSEVR VVAEGFDFAN  660
GINISPDGKY VYIAELLAHK IHVYEKHANW TLTPLKSLDF NTLVDNISVD PETGDLWVGC  720
HPNGMKIFFY DSENPPASEV LRIQNILTEE PKVTQVYAEN GTVLQGSTVA SVYKGKLLIG  780
TVFHKALYCE L                                                      791

SEQ ID NO: 55           moltype = DNA  length = 54
FEATURE                 Location/Qualifiers
misc_feature            1..54
                        note = Peptide linker containing N-linked glycosylation
                         site (NGS linker) DNA
source                  1..54
                        mol_type = other DNA
                        organism = synthetic construct
SEQUENCE: 55
gtcgacggag ctagcagccc cgtgaacgtg agcagcccca gcgtgcagga tatc       54

SEQ ID NO: 56           moltype = AA  length = 18
FEATURE                 Location/Qualifiers
REGION                  1..18
                        note = Peptide linker containing N-linked glycosylation
                         site (NGS linker)
source                  1..18
                        mol_type = protein
                        organism = synthetic construct
SEQUENCE: 56
VDGASSPVNV SSPSVQDI                                               18

SEQ ID NO: 57           moltype = DNA  length = 72
FEATURE                 Location/Qualifiers
source                  1..72
                        mol_type = other DNA
                        organism = Homo sapiens
SEQUENCE: 57
aagcttgccg ccatggaaac cccagcgcag cttctcttcc tcctgctact ctggctccca  60
gataccaccg gt                                                     72
```

```
SEQ ID NO: 58           moltype = AA  length = 20
FEATURE                 Location/Qualifiers
source                  1..20
                        mol_type = protein
                        organism = Homo sapiens
SEQUENCE: 58
METPAQLLFL LLLWLPDTTG                                              20

SEQ ID NO: 59           moltype = DNA  length = 1614
FEATURE                 Location/Qualifiers
misc_feature            1..1614
                        note = hVK3LP-[hDNase1
                         N74K-G105R-A114F]-(g4s)4-[SSShinge-P238S-P331S Fc] DNA
source                  1..1614
                        mol_type = other DNA
                        organism = synthetic construct
SEQUENCE: 59
atggaaaccc cagcgcagct tctcttcctc ctgctactct ggctcccaga taccaccggt  60
ctgaagatcg cagccttcaa catccagaca tttggggaga ccaagatgtc caatgccacc  120
ctcgtcagct acattgtgca gatcctgagc cgctatgaca tcgccctggt ccaggaggtc  180
agagacagcc acctgactgc cgtggggaag ctgctggaca acctcaatca ggatgcacca  240
gacacctatc actacgtggt cagtgagcca ctgggacgga agagctataa ggagcgctac  300
ctgttcgtgt acaggcctga ccaggtgtct gcggtggaca gctactacta cgatgatggc  360
tgcgagccct gcaggaacga caccttcaac cgagagccat tcattgtcag gttcttctcc  420
cggttcacag aggtcaggga gtttgccatt gttcccctgc atgcggcccc gggggacgca  480
gtagccgaga tcgacgctct ctatgacgtc tacctggatg tccaagagaa atggggcttg  540
gaggacgtca tgttgatggg cgacttcaat gcgggctgca gctatgtgag accctcccag  600
tggtcatcca tccgcctgtg gacaagcccc accttccagt ggctgatccc cgacagcgct  660
gacaccacag ctacacccac gcactgtgcc tatgacagga tcgtggttgc agggatgctg  720
ctccgaggcg ccgttgttcc cgactcggct cttcccttta acttccaggc tgcctatggc  780
ctgagtgacc aactggccca agccatcagt gaccactatc cagtggaggt gatgctgaaa  840
gatctctccg gaggaggtgg ctcaggtggt ggaggatctg gaggaggtgg gagtggtgga  900
ggtggttcta ccggtctcga gcccaaatct tctgacaaaa ctcacacatc tccaccgtcc  960
ccagcacctg aactcctggg aggatcgtca gtcttcctct tcccccccaaa acccaaggac  1020
accctcatga tctcccggac ccctgaggtc acatgcgtgg tggtggacgt gagccacgaa  1080
gaccctgagg tcaagttcaa ctggtacgtg gacggcgtgg aggtgcataa tgccaagaca  1140
aagccgcggg aggagcagta caacagcacg taccgtgtgg tcagcgtcct caccgtcctg  1200
caccaggact ggctgaatgg caaggagtac aagtgcaagg tctccaacaa agccctccca  1260
gcctccatcg agaaaaccat ctccaaagcc aaagggcagc cccgagaacc acaggtgtac  1320
accctgcccc catcccggga tgagctgacc aagaaccagg tcagcctgac ctgcctggtc  1380
aaaggcttct atcccagcga catcgccgtg gagtgggaga gcaatgggca gccggagaac  1440
aactacaaga ccacgcctcc cgtgctggac tccgacggct ccttcttcct ctacagcaag  1500
ctcaccgtgg acaagagcag gtggcagcag gggaacgtct tctcatgctc cgtgatgcat  1560
gaggctctgc acaaccacta cacgcagaag agcctctctc tctctccggg taaa        1614

SEQ ID NO: 60           moltype = AA  length = 538
FEATURE                 Location/Qualifiers
REGION                  1..538
                        note = hVK3LP-[hDNase1
                         N74K-G105R-A114F]-(g4s)4-[SSShinge-P238S-P331S Fc]
source                  1..538
                        mol_type = protein
                        organism = synthetic construct
SEQUENCE: 60
METPAQLLFL LLLWLPDTTG LKIAAFNIQT FGETKMSNAT LVSYIVQILS RYDIALVQEV  60
RDSHLTAVGK LLDNLNQDAP DTYHYVVSEP LGRKSYKERY LFVYRPDQVS AVDSYYYDDG  120
CEPCRNDTFN REPFIVRFFS RFTEVREFAI VPLHAAPGDA VAEIDALYDV YLDVQEKWGL  180
EDVMLMGDFN AGCSYVRPSQ WSSIRLWTSP TFQWLIPDSA DTTATPTHCA YDRIVVAGML  240
LRGAVVPDSA LPFNFQAAYG LSDQLAQAIS DHYPVEVMLK DLSGGGGSGG GGSGGGGSGG  300
GGSTGLEPKS SDKTHTSPPS PAPELLGGSS VFLFPPKPKD TLMISRTPEV TCVVVDVSHE  360
DPEVKFNWYV DGVEVHNAKT KPREEQYNST YRVVSVLTVL HQDWLNGKEY KCKVSNKALP  420
ASIEKTISKA KGQPREPQVY TLPPSRDELT KNQVSLTCLV KGFYPSDIAV EWESNGQPEN  480
NYKTTPPVLD SDGSFFLYSK LTVDKSRWQQ GNVFSCSVMH EALHNHYTQK SLSLSPGK    538

SEQ ID NO: 61           moltype = DNA  length = 1644
FEATURE                 Location/Qualifiers
misc_feature            1..1644
                        note = hVK3LP-[hDNase1
                         N74K-G105R-A114F]-(g4s)6-[SSShinge-P238S-P331S Fc] DNA
source                  1..1644
                        mol_type = other DNA
                        organism = synthetic construct
SEQUENCE: 61
atggaaaccc cagcgcagct tctcttcctc ctgctactct ggctcccaga taccaccggt  60
ctgaagatcg cagccttcaa catccagaca tttggggaga ccaagatgtc caatgccacc  120
ctcgtcagct acattgtgca gatcctgagc cgctatgaca tcgccctggt ccaggaggtc  180
agagacagcc acctgactgc cgtggggaag ctgctggaca acctcaatca ggatgcacca  240
gacacctatc actacgtggt cagtgagcca ctgggacgga agagctataa ggagcgctac  300
ctgttcgtgt acaggcctga ccaggtgtct gcggtggaca gctactacta cgatgatggc  360
```

```
tgcgagccct gcaggaacga caccttcaac cgagagccat tcattgtcag gttcttctcc  420
cggttcacag aggtcaggga gtttgccatt gttcccctgc atgcggcccc gggggacgca  480
gtagccgaga tcgacgctct ctatgacgtc tacctggatg tccaagagaa atggggcttg  540
gaggacgtca tgttgatggg cgacttcaat gcgggctgca gctatgtgag accctcccag  600
tggtcatcca tccgcctgtg gacaagcccc accttccagt ggctgatccc cgacagcgct  660
gacaccacag ctacacccac gcactgtgcc tatgacagga tcgtggttgc agggatgctg  720
ctccgaggcg ccgttgttcc cgactcggct cttcccttta acttccaggc tgcctatggc  780
ctgagtgacc aactggccca agccatcagt gaccactatc cagtggaggt gatgctgaaa  840
gatctctccg gaggaggtgg ctcaggtggt ggaggatctg gaggaggtgg gagtggtgga  900
ggtggttctg gaggaggtgg tagtggaggt ggaggttcta ccggtctcga gcccaaatct  960
tctgacaaaa ctcacacatc tccaccgtcc ccagcacctg aactcctggg aggatcgtca  1020
gtcttcctct tcccccccaaa acccaaggac accctcatga tctcccggac ccctgaggtc  1080
acatgcgtgg tggtggacgt gagccacgaa gaccctgagg tcaagttcaa ctggtacgtg  1140
gacggcgtgg aggtgcataa tgccaagaca aagccgcggg aggagcagta caacagcacg  1200
taccgtgtgg tcagcgtcct caccgtcctg caccaggact ggctgaatgg caaggagtac  1260
aagtgcaagg tctccaacaa agccctccca gcctccatcg agaaaaccat ctccaaagcc  1320
aaagggcagc cccgagaacc acaggtgtac accctgcccc catcccggga tgagctgacc  1380
aagaaccagg tcagcctgac ctgcctggtc aaaggcttct atcccagcga catcgccgtg  1440
gagtgggaga gcaatgggca gccggagaac aactacaaga ccacgcctcc cgtgctggac  1500
tccgacggct ccttcttcct ctacagcaag ctcaccgtgg acaagagcag gtggcagcag  1560
gggaacgtct tctcatgctc cgtgatgcat gaggctctgc acaaccacta cacgcagaag  1620
agcctctctc tctctccggg taaa                                         1644

SEQ ID NO: 62           moltype = AA  length = 548
FEATURE                 Location/Qualifiers
REGION                  1..548
                        note = hVK3LP-[hDNase1
                         N74K-G105R-A114F]-(g4s)6-[SSShinge-P238S-P331S Fc]
source                  1..548
                        mol_type = protein
                        organism = synthetic construct
SEQUENCE: 62
METPAQLLFL LLLWLPDTTG LKIAAFNIQT FGETKMSNAT LVSYIVQILS RYDIALVQEV  60
RDSHLTAVGK LLDNLNQDAP DTYHYVVSEP LGRKSYKERY LFVYRPDQVS AVDSYYYDDG  120
CEPCRNDTFN REPFIVRFFS RFTEVREFAI VPLHAAPGDA VAEIDALYDV YLDVQEKWGL  180
EDVMLMGDFN AGCSYVRPSQ WSSIRLWTSP TFQWLIPDSA DTTATPTHCA YDRIVVAGML  240
LRGAVVPDSA LPFNFQAAYG LSDQLAQAIS DHYPVEVMLK DLSGGGGSGG GGSGGGGSGG  300
GGSGGGGSGG GGSTGLEPKS SDKTHTSPPS PAPELLGGSS VFLFPPKPKD TLMISRTPEV  360
TCVVVDVSHE DPEVKFNWYV DGVEVHNAKT KPREEQYNST YRVVSVLTVL HQDWLNGKEY  420
KCKVSNKALP ASIEKTISKA KGQPREPQVY TLPPSRDELT KNQVSLTCLV KGFYPSDIAV  480
EWESNGQPEN NYKTTPPVLD SDGSFFLYSK LTVDKSRWQQ GNVFSCSVMH EALHNHYTQK  540
SLSLSPGK                                                           548

SEQ ID NO: 63           moltype = DNA  length = 1137
FEATURE                 Location/Qualifiers
misc_feature            1..1137
                        note = hVK3LP-[hCTLA-4 EC]-[SSShinge-P238S-P331S Fc] DNA
source                  1..1137
                        mol_type = other DNA
                        organism = synthetic construct
SEQUENCE: 63
atggaaaccc cagcgcagct tctcttcctc ctgctactct ggctcccgga taccaccggt  60
gcaatgcacg tggcccagcc tgctgtggta ctggccagca gccgaggcat cgccagcttt  120
gtgtgtgagt atgcatctcc aggcaaagcc actgaggtcc gggtgacagt gcttcggcag  180
gctgacagcc aggtgactga agtctgtgcg gcaacctaca tgatggggaa tgagttgacc  240
ttcctagatg attccatctg cacgggcacc tccagtggaa atcaagtgaa cctcactatc  300
caaggactga gggccatgga cacgggactc tacatctgca aggtggagct catgtaccca  360
ccgccatact acctgggcat aggcaacgga acccagattt atgtaattga tccagaaccg  420
tgcccagatt cagatctcga gcccaaatct tctgacaaaa ctcacacatc tccaccgtcc  480
ccagcacctg aactcctggg aggatcgtca gtcttcctct tcccccccaaa acccaaggac  540
accctcatga tctcccggac ccctgaggtc acatgcgtgg tggtggacgt gagccacgaa  600
gaccctgagg tcaagttcaa ctggtacgtg gacggcgtgg aggtgcataa tgccaagaca  660
aagccgcggg aggagcagta caacagcacg taccgtgtgg tcagcgtcct caccgtcctg  720
caccaggact ggctgaatgg caaggagtac aagtgcaagg tctccaacaa agccctccca  780
gcctccatcg agaaaaccat ctccaaagcc aaagggcagc cccgagaacc acaggtgtac  840
accctgcccc catcccggga tgagctgacc aagaaccagg tcagcctgac ctgcctggtc  900
aaaggcttct atcccagcga catcgccgtg gagtgggaga gcaatgggca gccggagaac  960
aactacaaga ccacgcctcc cgtgctggac tccgacggct ccttcttcct ctacagcaag  1020
ctcaccgtgg acaagagcag gtggcagcag gggaacgtct tctcatgctc cgtgatgcat  1080
gaggctctgc acaaccacta cacgcagaag agcctctctc tctctccggg taaataa     1137

SEQ ID NO: 64           moltype = AA  length = 378
FEATURE                 Location/Qualifiers
REGION                  1..378
                        note = hVK3LP-[hCTLA-4 EC]-[SSShinge-P238S-P331S Fc]
source                  1..378
                        mol_type = protein
                        organism = synthetic construct
SEQUENCE: 64
```

```
METPAQLLFL LLLWLPDTTG AMHVAQPAVV LASSRGIASF VCEYASPGKA TEVRVTVLRQ  60
ADSQVTEVCA ATYMMGNELT FLDDSICTGT SSGNQVNLTI QGLRAMDTGL YICKVELMYP  120
PPYYLGIGNG TQIYVIDPEP CPDSDLEPKS SDKTHTSPPS PAPELLGGSS VFLFPPKPKD  180
TLMISRTPEV TCVVVDVSHE DPEVKFNWYV DGVEVHNAKT KPREEQYNST YRVVSVLTVL  240
HQDWLNGKEY KCKVSNKALP ASIEKTISKA KGQPREPQVY TLPPSRDELT KNQVSLTCLV  300
KGFYPSDIAV EWESNGQPEN NYKTTPPVLD SDGSFFLYSK LTVDKSRWQQ GNVFSCSVMH  360
EALHNHYTQK SLSLSPGK                                              378

SEQ ID NO: 65          moltype = DNA  length = 2211
FEATURE                Location/Qualifiers
misc_feature           1..2211
                       note = hVK3LP-[hCTLA-4 EC]-[SSShinge-P238S-P331S
                        Fc]-NGS-[PON1 Q192K] DNA
source                 1..2211
                       mol_type = other DNA
                       organism = synthetic construct
SEQUENCE: 65
atggaaaccc cagcgcagct tctcttcctc ctgctactct ggctcccgga taccaccggt  60
gcaatgcacg tggcccagcc tgctgtggta ctggccagca gccgaggcat cgccagcttt  120
gtgtgtgagt atgcatctcc aggcaaagcc actgaggtcc gggtgacagt gcttcggcag  180
gctgacagcc aggtgactga agtctgtgcg gcaacctaca tgatggggaa tgagttgacc  240
ttcctagatg attccatctg cacgggcacc tccagtggaa atcaagtgaa cctcactatc  300
caaggactga gggccatgga cacgggactc tacatctgca aggtggagct catgtaccca  360
ccgccatact acctgggcat aggcaacgga acccagattt atgtaattga tccagaaccg  420
tgcccagatt cagatctcga gcccaaatct tctgacaaaa ctcacacatc tccaccgtcc  480
ccagcacctg aactcctggg aggatcgtca gtcttcctct tcccccaaa acccaaggac  540
accctcatga tctcccggac ccctgaggtc acatgcgtgg tggtggacgt gagccacgaa  600
gaccctgagg tcaagttcaa ctggtacgtg gacggcgtgg aggtgcataa tgccaagaca  660
aagccgcggg aggagcagta caacagcacg taccgtgtgg tcagcgtcct caccgtcctg  720
caccaggact ggctgaatgg caaggagtac aagtgcaagg tctccaacaa agccctccca  780
gcctccatcg agaaaaccat ctccaaagcc aaagggcagc cccgagaacc acaggtgtac  840
accctgcccc catcccggga tgagctgacc aagaaccagg tcagcctgac ctgcctggtc  900
aaaggcttct atcccagcga catcgccgtg gagtgggaga gcaatgggca gccggagaac  960
aactacaaga ccacgcctcc cgtgctggac tccgacggct ccttcttcct ctacagcaag  1020
ctcaccgtgg acaagagcag gtggcagcag gggaacgtct tctcatgctc cgtgatgcat  1080
gaggctctgc acaaccacta cacgcagaag agcctctctc tctctccggg taaagtcgac  1140
ggagctagca gccccgtgaa cgtgagcagc cccagcgtgc aggatatcct cttcaggaac  1200
caccagtctt cttaccaaac acgacttaat gctctccgag aggtacaacc cgtagaactt  1260
cctaactgta atttagttaa aggaatcgaa actggctctg aagacttgga gatactgcct  1320
aatggactgg ctttcattag ctctggatta aagtatcctg gaataaagag cttcaacccc  1380
aacagtcctg gaaaaatact tctgatggac ctgaatgaag aagatccaac agtgttggaa  1440
ttggggatca ctggaagtaa atttgatgta tcttcattta accctcatgg gattagcaca  1500
ttcacagatg aagataatgc catgtacctc ctggtggtga accatccaga tgccaagtcc  1560
acagtggagt tgtttaaatt tcaagaagaa gaaaaatcgc ttttgcatct aaaaaccatc  1620
agacataaac ttctgcctaa tttgaatgat attgttgctg tgggacctga gcacttttat  1680
ggcacaaatg atcactattt tcttgacccc tacttaaaat cctgggagat gtatttgggt  1740
ttagcgtggt cgtatgttgt ctactatagt ccaagtgaag ttcgagtggt ggcagaagga  1800
tttgattttg ctaatggaat caacatttca cccgatggca agtatgtcta tatagctgag  1860
ttgctggctc ataagattca tgtgtatgaa aagcatgcta attggacttt aactccattg  1920
aagtcccttg actttaatac cctcgtggat aacatatctg tggatcctga gacaggagac  1980
ctttgggttg gatgccatcc caatggcatg aaaatcttct tctatgactc agagaatcct  2040
cctgcatcag aggtgcttcg aatccagaac attctaacag aagaacctaa agtgacacag  2100
gtttatgcag aaaatggcac agtgttgcaa ggcagtacag ttgcctctgt gtacaaaggg  2160
aaactgctga ttggcacagt gtttcacaaa gctctttact gtgagctcta a          2211

SEQ ID NO: 66          moltype = AA  length = 736
FEATURE                Location/Qualifiers
REGION                 1..736
                       note = hVK3LP-[hCTLA-4 EC]-[SSShinge-P238S-P331S
                        Fc]-NGS-[PON1 Q192K]
source                 1..736
                       mol_type = protein
                       organism = synthetic construct
SEQUENCE: 66
METPAQLLFL LLLWLPDTTG AMHVAQPAVV LASSRGIASF VCEYASPGKA TEVRVTVLRQ  60
ADSQVTEVCA ATYMMGNELT FLDDSICTGT SSGNQVNLTI QGLRAMDTGL YICKVELMYP  120
PPYYLGIGNG TQIYVIDPEP CPDSDLEPKS SDKTHTSPPS PAPELLGGSS VFLFPPKPKD  180
TLMISRTPEV TCVVVDVSHE DPEVKFNWYV DGVEVHNAKT KPREEQYNST YRVVSVLTVL  240
HQDWLNGKEY KCKVSNKALP ASIEKTISKA KGQPREPQVY TLPPSRDELT KNQVSLTCLV  300
KGFYPSDIAV EWESNGQPEN NYKTTPPVLD SDGSFFLYSK LTVDKSRWQQ GNVFSCSVMH  360
EALHNHYTQK SLSLSPGKVD GASSPVNVSS PSVQDILFRN HQSSYQTRLN ALREVQPVEL  420
PNCNLVKGIE TGSEDLEILP NGLAFISSGL KYPGIKSFNP NSPGKILLMD LNEEDPTVLE  480
LGITGSKFDV SSFNPHGIST FTDEDNAMYL LVVNHPDAKS TVELFKFQEE EKSLLHLKTI  540
RHKLLPNLND IVAVGPEHFY GTNDHYFLDP YLKSWEMYLG LAWSYVVYYS PSEVRVVAEG  600
FDFANGINIS PDGKYVYIAE LLAHKIHVYE KHANWTLTPL KSLDFNTLVD NISVDPETGD  660
LWVGCHPNGM KIFFYDSENP PASEVLRIQN ILTEEPKVTQ VYAENGTVLQ GSTVASVYKG  720
KLLIGTVFHK ALYCEL                                                736

SEQ ID NO: 67          moltype = DNA  length = 835
```

```
FEATURE                Location/Qualifiers
source                 1..835
                       mol_type = other DNA
                       organism = Homo sapiens
SEQUENCE: 67
atggttcgtc tgcctctgca gtgcgtcctc tggggctgct tgctgaccgc tgtccatcca  60
gaaccaccca ctgcatgcag agaaaaacag tacctaataa acagtcagtg ctgttctttg  120
tgccagccag gacagaaact ggtgagtgac tgcacagagt tcactgaaac ggaatgcctt  180
ccttgcggtg aaagcgaatt cctagacacc tggaacagag agacacactg ccaccagcac  240
aaatactgcg accccaacct agggcttcgg gtccagcaga agggcacctc agaaacagac  300
accatctgca cctgtgaaga aggctggcac tgtacgagtg aggcctgtga gagctgtgtc  360
ctgcaccgct catgctcgcc cggctttggg gtcaagcaga ttgctacagg ggtttctgat  420
accatctgcg agccctgccc agtcggcttc ttctccaatg tgtcatctgc tttcgaaaaa  480
tgtcaccctt ggacaagctg tgagaccaaa gacctggttg tgcaacaggc aggcacaaac  540
aagactgatg ttgtctgtgg tccccaggat cggctgagag ccctggtggt gatccccatc  600
atcttcggga tcctgtttgc catcctcttg gtgctggtct ttatcaaaaa ggtggccaag  660
aagccaacca ataaggcccc ccaccccaag caggaacccc aggagatcaa ttttcccgac  720
gatcttcctg gctccaacac tgctgctcca gtgcaggaga ctttacatgg atgccaaccg  780
gtcacccagg aggatggcaa agagagtcgc atctcagtgc aggagagaca gtgag       835

SEQ ID NO: 68          moltype = AA  length = 277
FEATURE                Location/Qualifiers
source                 1..277
                       mol_type = protein
                       organism = Homo sapiens
SEQUENCE: 68
MVRLPLQCVL WGCLLTAVHP EPPTACREKQ YLINSQCCSL CQPGQKLVSD CTEFTETECL  60
PCGESEFLDT WNRETHCHQH KYCDPNLGLR VQQKGTSETD TICTCEEGWH CTSEACESCV  120
LHRSCSPGFG VKQIATGVSD TICEPCPVGF FSNVSSAFEK CHPWTSCETK DLVVQQAGTN  180
KTDVVCGPQD RLRALVVIPI IFGILFAILL VLVFIKKVAK KPTNKAPHPK QEPQEINFPD  240
DLPGSNTAAP VQETLHGCQP VTQEDGKESR ISVQERQ                          277

SEQ ID NO: 69          moltype = DNA  length = 1351
FEATURE                Location/Qualifiers
misc_feature           1..1351
                       note = [hCD40 EC]-(g4s)4-[SSShinge-P238S Fc] DNA
source                 1..1351
                       mol_type = other DNA
                       organism = synthetic construct
SEQUENCE: 69
atggttcgtc tgcctctgca gtgcgtcctc tggggctgct tgctgaccgc tgtccatcca  60
gaaccaccca ctgcatgcag agaaaaacag tacctaataa acagtcagtg ctgttctttg  120
tgccagccag gacagaaact ggtgagtgac tgcacagagt tcactgaaac ggaatgcctt  180
ccttgcggtg aaagcgaatt cctagacacc tggaacagag agacacactg ccaccagcac  240
aaatactgcg accccaacct agggcttcgg gtccagcaga agggcacctc agaaacagac  300
accatctgca cctgtgaaga aggctggcac tgtacgagtg aggcctgtga gagctgtgtc  360
ctgcaccgct catgctcgcc cggctttggg gtcaagcaga ttgctacagg ggtttctgat  420
accatctgcg agccctgccc agtcggcttc ttctccaatg tgtcatctgc tttcgaaaaa  480
tgtcaccctt ggacaagctg tgagaccaaa gacctggttg tgcaacaggc aggcacaaac  540
aagactgatg ttgtctgtgg tccagatctc tccggaggag gtggctcagg tggtggagga  600
tctggaggag gtgggagtgg tggaggtggt tctaccggtc tcgagcccaa atcttctgac  660
aaaactcaca catctccacc gtccccagca cctgaactcc tgggaggatc gtcagtcttc  720
ctcttccccc caaaacccaa ggacaccctc atgatctccc ggacccctga ggtcacatgc  780
gtggtggtgg acgtgagcca cgaagaccct gaggtcaagt tcaactggta cgtggacggc  840
gtggaggtgc ataatgccaa gacaaagccg cgggaggagc agtacaacag cacgtaccgt  900
gtggtcagcg tcctcaccgt cctgcaccag gactggctga atggcaagga gtacaagtgc  960
aaggtctcca acaaagccct cccagcctcc atcgagaaaa ccatctccaa agccaaaggg  1020
cagccccgag aaccacaggt gtacaccctg cccccatccc gggatgagct gaccaagaac  1080
caggtcagcc tgacctgcct ggtcaaaggc ttctatccca gcgacatcgc cgtggagtgg  1140
gagagcaatg ggcagccgga gaacaactac aagaccacgc ctcccgtgct ggactccgac  1200
ggctccttct tcctctacag caagctcacc gtggacaaga gcaggtggca gcaggggaac  1260
gtcttctcat gctccgtgat gcatgaggct ctgcacaacc actacacgca gaagagcctc  1320
tctctctctc cgggtaaata ataatctaga a                                1351

SEQ ID NO: 70          moltype = AA  length = 446
FEATURE                Location/Qualifiers
REGION                 1..446
                       note = [hCD40 EC]-(g4s)4-[SSShinge-P238S Fc]
source                 1..446
                       mol_type = protein
                       organism = synthetic construct
SEQUENCE: 70
MVRLPLQCVL WGCLLTAVHP EPPTACREKQ YLINSQCCSL CQPGQKLVSD CTEFTETECL  60
PCGESEFLDT WNRETHCHQH KYCDPNLGLR VQQKGTSETD TICTCEEGWH CTSEACESCV  120
LHRSCSPGFG VKQIATGVSD TICEPCPVGF FSNVSSAFEK CHPWTSCETK DLVVQQAGTN  180
KTDVVCGPDL SGGGGSGGGG SGGGGSGGGG STGLEPKSSD KTHTSPPSPA PELLGGSSVF  240
LFPPKPKDTL MISRTPEVTC VVVDVSHEDP EVKFNWYVDG VEVHNAKTKP REEQYNSTYR  300
VVSVLTVLHQ DWLNGKEYKC KVSNKALPAS IEKTISKAKG QPREPQVYTL PPSRDELTKN  360
QVSLTCLVKG FYPSDIAVEW ESNGQPENNY KTTPPVLDSD GSFFLYSKLT VDKSRWQQGN  420
```

```
VFSCSVMHEA LHNHYTQKSL SLSPGK                                      446

SEQ ID NO: 71           moltype = DNA  length = 1341
FEATURE                 Location/Qualifiers
misc_feature            1..1341
                        note = hVK3LP-[hCD40 EC]-(g4s)4-[SSShinge-P238S Fc] DNA
source                  1..1341
                        mol_type = other DNA
                        organism = synthetic construct
SEQUENCE: 71
atggaaaccc cagcgcagct tctcttcctc ctgctactct ggctcccaga taccaccggt  60
gaaccaccca ctgcatgcag agaaaaacag tacctaataa acagtcagtg ctgttctttg  120
tgccagccag gacagaaact ggtgagtgac tgcacagagt tcactgaaac ggaatgcctt  180
ccttgcggtg aaagcgaatt cctagacacc tggaacagag agacacactg ccaccagcac  240
aaatactgcg accccaacct agggcttcgg gtccagcaga agggcacctc agaaacagac  300
accatctgca cctgtgaaga aggctggcac tgtacgagtg aggcctgtga gagctgtgtc  360
ctgcaccgct catgctcgcc cggctttggg gtcaagcaga ttgctacagg ggtttctgat  420
accatctgcg agccctgccc agtcggcttc ttctccaatg tgtcatctgc tttcgaaaaa  480
tgtcaccctt ggacaagctg tgagaccaaa gacctggttg tgcaacaggc aggcacaaac  540
aagactgatg ttgtctgtgg tccagatctc tccggaggag gtggctcagg tggtggagga  600
tctggaggag gtgggagtgg tggaggtggt tctaccggtc tcgagcccaa atcttctgac  660
aaaactcaca catctccacc gtccccagca cctgaactcc tgggaggatc gtcagtcttc  720
ctcttccccc caaaacccaa ggacaccctc atgatctccc ggacccctga ggtcacatgc  780
gtggtggtgg acgtgagcca cgaagaccct gaggtcaagt tcaactggta cgtggacggc  840
gtggaggtgc ataatgccaa gacaaagccg cgggaggagc agtacaacag cacgtaccgt  900
gtggtcagcg tcctcaccgt cctgcaccag gactggctga atggcaagga gtacaagtgc  960
aaggtctcca acaaagccct cccagcctcc atcgagaaaa ccatctccaa agccaaaggg  1020
cagccccgag aaccacaggt gtacaccctg cccccatccc gggatgagct gaccaagaac  1080
caggtcagcc tgacctgcct ggtcaaaggc ttctatccca gcgacatcgc cgtggagtgg  1140
gagagcaatg ggcagccgga gaacaactac aagaccacgc ctcccgtgct ggactccgac  1200
ggctccttct tcctctacag caagctcacc gtggacaaga gcaggtggca gcaggggaac  1260
gtcttctcat gctccgtgat gcatgaggct ctgcacaacc actacacgca gaagagcctc  1320
tctctctctc cgggtaaata a                                           1341

SEQ ID NO: 72           moltype = AA  length = 446
FEATURE                 Location/Qualifiers
REGION                  1..446
                        note = hVK3LP-[hCD40 EC]-(g4s)4-[SSShinge-P238S Fc]
source                  1..446
                        mol_type = protein
                        organism = synthetic construct
SEQUENCE: 72
METPAQLLFL LLLWLPDTTG EPPTACREKQ YLINSQCCSL CQPGQKLVSD CTEFTETECL  60
PCGESEFLDT WNRETHCHQH KYCDPNLGLR VQQKGTSETD TICTCEEGWH CTSEACESCV  120
LHRSCSPGFG VKQIATGVSD TICEPCPVGF FSNVSSAFEK CHPWTSCETK DLVVQQAGTN  180
KTDVVCGPDL SGGGGSGGGG SGGGGSGGGG STGLEPKSSD KTHTSPPSPA PELLGGSSVF  240
LFPPKPKDTL MISRTPEVTC VVVDVSHEDP EVKFNWYVDG VEVHNAKTKP REEQYNSTYR  300
VVSVLTVLHQ DWLNGKEYKC KVSNKALPAS IEKTISKAKG QPREPQVYTL PPSRDELTKN  360
QVSLTCLVKG FYPSDIAVEW ESNGQPENNY KTTPPVLDSD GSFFLYSKLT VDKSRWQQGN  420
VFSCSVMHEA LHNHYTQKSL SLSPGK                                      446

SEQ ID NO: 73           moltype = DNA  length = 2425
FEATURE                 Location/Qualifiers
misc_feature            1..2425
                        note = hVK3LP-[hCD40 EC]-(g4s)4-[SSShinge-P238S
                         Fc]-NGS-[PON1 Q192K] DNA
source                  1..2425
                        mol_type = other DNA
                        organism = synthetic construct
SEQUENCE: 73
atggaaaccc cagcgcagct tctcttcctc ctgctactct ggctcccaga taccaccggt  60
gaaccaccca ctgcatgcag agaaaaacag tacctaataa acagtcagtg ctgttctttg  120
tgccagccag gacagaaact ggtgagtgac tgcacagagt tcactgaaac ggaatgcctt  180
ccttgcggtg aaagcgaatt cctagacacc tggaacagag agacacactg ccaccagcac  240
aaatactgcg accccaacct agggcttcgg gtccagcaga agggcacctc agaaacagac  300
accatctgca cctgtgaaga aggctggcac tgtacgagtg aggcctgtga gagctgtgtc  360
ctgcaccgct catgctcgcc cggctttggg gtcaagcaga ttgctacagg ggtttctgat  420
accatctgcg agccctgccc agtcggcttc ttctccaatg tgtcatctgc tttcgaaaaa  480
tgtcaccctt ggacaagctg tgagaccaaa gacctggttg tgcaacaggc aggcacaaac  540
aagactgatg ttgtctgtgg tccagatctc tccggaggag gtggctcagg tggtggagga  600
tctggaggag gtgggagtgg tggaggtggt tctaccggtc tcgagcccaa atcttctgac  660
aaaactcaca catctccacc gtccccagca cctgaactcc tgggaggatc gtcagtcttc  720
ctcttccccc caaaacccaa ggacaccctc atgatctccc ggacccctga ggtcacatgc  780
gtggtggtgg acgtgagcca cgaagaccct gaggtcaagt tcaactggta cgtggacggc  840
gtggaggtgc ataatgccaa gacaaagccg cgggaggagc agtacaacag cacgtaccgt  900
gtggtcagcg tcctcaccgt cctgcaccag gactggctga atggcaagga gtacaagtgc  960
aaggtctcca acaaagccct cccagcctcc atcgagaaaa ccatctccaa agccaaaggg  1020
cagccccgag aaccacaggt gtacaccctg cccccatccc gggatgagct gaccaagaac  1080
caggtcagcc tgacctgcct ggtcaaaggc ttctatccca gcgacatcgc cgtggagtgg  1140
```

```
gagagcaatg ggcagccgga gaacaactac aagaccacgc ctcccgtgct ggactccgac  1200
ggctccttct tcctctacag caagctcacc gtggacaaga gcaggtggca gcaggggaac  1260
gtcttctcat gctccgtgat gcatgaggct ctgcacaacc actacacgca gaagagcctc  1320
tctctctctc cgggtaaagt cgacggagct agcagccccg tgaacgtgag cagccccagc  1380
gtgcaggata tcctcttcag gaaccaccag tcttcttacc aaacacgact taatgctctc  1440
cgagaggtac aacccgtaga acttcctaac tgtaatttag ttaaaggaat cgaaactggc  1500
tctgaagact tggagatact gcctaatgga ctggctttca ttagctctgg attaaagtat  1560
cctggaataa agagcttcaa ccccaacagt cctggaaaaa tacttctgat ggacctgaat  1620
gaagaagatc caacagtgtt ggaattgggg atcactggaa gtaaatttga tgtatcttca  1680
tttaaccctc atgggattag cacattcaca gatgaagata atgccatgta cctcctggtg  1740
gtgaaccatc cagatgccaa gtccacagtg gagttgttta aatttcaaga agaagaaaaa  1800
tcgcttttgc atctaaaaac catcagacat aaacttctgc ctaatttgaa tgatattgtt  1860
gctgtgggac ctgagcactt ttatggcaca aatgatcact attttcttga cccctactta  1920
aaatcctggg agatgtattt gggtttagcg tggtcgtatg ttgtctacta tagtccaagt  1980
gaagttcgag tggtggcaga aggatttgat tttgctaatg gaatcaacat ttcacccgat  2040
ggcaagtatg tctatatagc tgagttgctg gctcataaga ttcatgtgta tgaaaagcat  2100
gctaattgga ctttaactcc attgaagtcc cttgacttta ataccctcgt ggataacata  2160
tctgtggatc ctgagacagg agacctttgg gttggatgcc atcccaatgg catgaaaatc  2220
ttcttctatg actcagagaa tcctcctgca tcagaggtgc ttcgaatcca gaacattcta  2280
acagaagaac ctaaagtgac acaggtttat gcagaaaatg gcacagtgtt gcaaggcagt  2340
acagttgcct ctgtgtacaa agggaaactg ctgattggca cagtgtttca caaagctctt  2400
tactgtgagc tctaataatc tagaa                                  2425

SEQ ID NO: 74           moltype = AA  length = 804
FEATURE                 Location/Qualifiers
REGION                  1..804
                        note = hVK3LP-[hCD40 EC]-(g4s)4-[SSShinge-P238S
                         Fc]-NGS-[PON1 Q192K]
source                  1..804
                        mol_type = protein
                        organism = synthetic construct
SEQUENCE: 74
METPAQLLFL LLLWLPDTTG EPPTACREKQ YLINSQCCSL CQPGQKLVSD CTEFTETECL  60
PCGESEFLDT WNRETHCHQH KYCDPNLGLR VQQKGTSETD TICTCEEGWH CTSEACESCV  120
LHRSCSPGFG VKQIATGVSD TICEPCPVGF FSNVSSAFEK CHPWTSCETK DLVVQQAGTN  180
KTDVVCGPDL SGGGGSGGGG SGGGGSGGGG STGLEPKSSD KTHTSPPSPA PELLGGSSVF  240
LFPPKPKDTL MISRTPEVTC VVVDVSHEDP EVKFNWYVDG VEVHNAKTKP REEQYNSTYR  300
VVSVLTVLHQ DWLNGKEYKC KVSNKALPAS IEKTISKAKG QPREPQVYTL PPSRDELTKN  360
QVSLTCLVKG FYPSDIAVEW ESNGQPENNY KTTPPVLDSD GSFFLYSKLT VDKSRWQQGN  420
VFSCSVMHEA LHNHYTQKSL SLSPGKVDGA SSPVNVSSPS VQDILFRNHQ SSYQTRLNAL  480
REVQPVELPN CNLVKGIETG SEDLEILPNG LAFISSGLKY PGIKSFNPNS PGKILLMDLN  540
EEDPTVLELG ITGSKFDVSS FNPHGISTFT DEDNAMYLLV VNHPDAKSTV ELFKFQEEEK  600
SLLHLKTIRH KLLPNLNDIV AVGPEHFYGT NDHYFLDPYL KSWEMYLGLA WSYVVYYSPS  660
EVRVVAEGFD FANGINISPD GKYVYIAELL AHKIHVYEKH ANWTLTPLKS LDFNTLVDNI  720
SVDPETGDLW VGCHPNGMKI FFYDSENPPA SEVLRIQNIL TEEPKVTQVY AENGTVLQGS  780
TVASVYKGKL LIGTVFHKAL YCEL                                   804

SEQ ID NO: 75           moltype = DNA  length = 1341
FEATURE                 Location/Qualifiers
misc_feature            1..1341
                        note = hVK3LP-[hCD40 K81T EC]-(g4s)4-[SSShinge-P238S Fc] DNA
source                  1..1341
                        mol_type = other DNA
                        organism = synthetic construct
SEQUENCE: 75
atggaaaccc cagcgcagct tctcttcctc ctgctactct ggctcccaga taccaccggt  60
gaaccaccca ctgcatgcag agaaaaacag tacctaataa acagtcagtg ctgttctttg  120
tgccagccag gacagaaact ggtgagtgac tgcacagagt tcactgaaac ggaatgcctt  180
ccttgcggtg aaagcgaatt cctagacacc tggaacagag agacacactg ccaccagcac  240
acatactgcg accccaacct agggcttcgg gtccagcaga agggcacctc agaaacagac  300
accatctgca cctgtgaaga aggctggcac tgtacgagtg aggcctgtga gagctgtgtc  360
ctgcaccgct catgctcgcc cggctttggg gtcaagcaga ttgctacagg ggtttctgat  420
accatctgcg agccctgccc agtcggcttc ttctccaatg tgtcatctgc tttcgaaaaa  480
tgtcaccctt ggacaagctg tgagaccaaa gacctggttg tgcaacaggc aggcacaaac  540
aagactgatg ttgtctgtgg tccagatctc tccggaggag gtggctcagg tggtggagga  600
tctggaggag gtgggagtgg tggaggtggt tctaccggtc tcgagcccaa atcttctgac  660
aaaactcaca catctccacc gtccccagca cctgaactcc tgggaggatc gtcagtcttc  720
ctcttccccc caaaacccaa ggacaccctc atgatctccc ggacccctga ggtcacatgc  780
gtggtggtgg acgtgagcca cgaagaccct gaggtcaagt tcaactggta cgtggacggc  840
gtggaggtgc ataatgccaa gacaaagccg cgggaggagc agtacaacag cacgtaccgt  900
gtggtcagcg tcctcaccgt cctgcaccag gactggctga atggcaagga gtacaagtgc  960
aaggtctcca acaaagccct cccagcctcc atcgagaaaa ccatctccaa agccaaaggg  1020
cagccccgag aaccacaggt gtacaccctg cccccatccc gggatgagct gaccaagaac  1080
caggtcagcc tgacctgcct ggtcaaaggc ttctatccca gcgacatcgc cgtggagtgg  1140
gagagcaatg ggcagccgga gaacaactac aagaccacgc ctcccgtgct ggactccgac  1200
ggctccttct tcctctacag caagctcacc gtggacaaga gcaggtggca gcaggggaac  1260
gtcttctcat gctccgtgat gcatgaggct ctgcacaacc actacacgca gaagagcctc  1320
tctctctctc cgggtaaata a                                      1341
```

```
SEQ ID NO: 76           moltype = AA  length = 446
FEATURE                 Location/Qualifiers
REGION                  1..446
                        note = hVK3LP-[hCD40 K81T EC]-(g4s)4-[SSShinge-P238S Fc]
source                  1..446
                        mol_type = protein
                        organism = synthetic construct
SEQUENCE: 76
METPAQLLFL LLLWLPDTTG EPPTACREKQ YLINSQCCSL CQPGQKLVSD CTEFTETECL  60
PCGESEFLDT WNRETHCHQH TYCDPNLGLR VQQKGTSETD TICTCEEGWH CTSEACESCV  120
LHRSCSPGFG VKQIATGVSD TICEPCPVGF FSNVSSAFEK CHPWTSCETK DLVVQQAGTN  180
KTDVVCGPDL SGGGGSGGGG SGGGGSGGGG STGLEPKSSD KTHTSPPSPA PELLGGSSVF  240
LFPPKPKDTL MISRTPEVTC VVVDVSHEDP EVKFNWYVDG VEVHNAKTKP REEQYNSTYR  300
VVSVLTVLHQ DWLNGKEYKC KVSNKALPAS IEKTISKAKG QPREPQVYTL PPSRDELTKN  360
QVSLTCLVKG FYPSDIAVEW ESNGQPENNY KTTPPVLDSD GSFFLYSKLT VDKSRWQQGN  420
VFSCSVMHEA LHNHYTQKSL SLSPGK                                      446

SEQ ID NO: 77           moltype = DNA  length = 2418
FEATURE                 Location/Qualifiers
misc_feature            1..2418
                        note = hVK3LP-[hCD40 K81T EC]-(g4s)4-[SSShinge-P238S
                         Fc]-NGS-[PON1 Q192K] DNA
source                  1..2418
                        mol_type = other DNA
                        organism = synthetic construct
SEQUENCE: 77
atggaaaccc cagcgcagct tctcttcctc ctgctactct ggctcccaga taccaccggt  60
gaaccaccca ctgcatgcag agaaaaacag tacctaataa acagtcagtg ctgttctttg  120
tgccagccag gacagaaact ggtgagtgac tgcacagagt tcactgaaac ggaatgcctt  180
ccttgcggtg aaagcgaatt cctagacacc tggaacagag agacacactg ccaccagcac  240
acatactgcg accccaacct agggcttcgg gtccagcaga agggcacctc agaaacagac  300
accatctgca cctgtgaaga aggctggcac tgtacgagtg aggcctgtga gagctgtgtc  360
ctgcaccgct catgctcgcc cggctttggg gtcaagcaga ttgctacagg ggtttctgat  420
accatctgcg agccctgccc agtcggcttc ttctccaatg tgtcatctgc tttcgaaaaa  480
tgtcaccctt ggacaagctg tgagaccaaa gacctggttg tgcaacaggc aggcacaaac  540
aagactgatg ttgtctgtgg tccagatctc tccggaggag gtggctcagg tggtggagga  600
tctggaggag gtgggagtgg tggaggtggt tctaccggtc tcgagcccaa atcttctgac  660
aaaactcaca catctccacc gtccccagca cctgaactcc tgggaggatc gtcagtcttc  720
ctcttccccc caaaacccaa ggacaccctc atgatctccc ggacccctga ggtcacatgc  780
gtggtggtgg acgtgagcca cgaagaccct gaggtcaagt tcaactggta cgtggacggc  840
gtggaggtgc ataatgccaa gacaaagccg cgggaggagc agtacaacag cacgtaccgt  900
gtggtcagcg tcctcaccgt cctgcaccag gactggctga atggcaagga gtacaagtgc  960
aaggtctcca acaaagccct cccagcctcc atcgagaaaa ccatctccaa agccaaaggg  1020
cagccccgag aaccacaggt gtacaccctg cccccatccc gggatgagct gaccaagaac  1080
caggtcagcc tgacctgcct ggtcaaaggc ttctatccca gcgacatcgc cgtggagtgg  1140
gagagcaatg ggcagccgga gaacaactac aagaccacgc ctcccgtgct ggactccgac  1200
ggctccttct tcctctacag caagctcacc gtggacaaga gcaggtggca gcaggggaac  1260
gtcttctcat gctccgtgat gcatgaggct ctgcacaacc actacacgca gaagagcctc  1320
tctctctctc cgggtaaagt cgacggagct agcagccccg tgaacgtgag cagccccagc  1380
gtgcaggata tcctcttcag gaaccaccag tcttcttacc aaacacgact taatgctctc  1440
cgagaggtac aacccgtaga acttcctaac tgtaatttag ttaaaggaat cgaaactggc  1500
tctgaagact tggagatact gcctaatgga ctggctttca ttagctctgg attaaagtat  1560
cctggaataa agagcttcaa ccccaacagt cctggaaaaa tacttctgat ggacctgaat  1620
gaagaagatc caacagtgtt ggaattgggg atcactggaa gtaaatttga tgtatcttca  1680
tttaaccctc atgggattag cacattcaca gatgaagata atgccatgta cctcctggtg  1740
gtgaaccatc cagatgccaa gtccacagtg gagttgttta aatttcaaga agaagaaaaa  1800
tcgcttttgc atctaaaaac catcagacat aaacttctgc ctaatttgaa tgatattgtt  1860
gctgtgggac ctgagcactt ttatggcaca aatgatcact attttcttga cccctactta  1920
aaatcctggg agatgtattt gggtttagcg tggtcgtatg ttgtctacta tagtccaagt  1980
gaagttcgag tggtggcaga aggatttgat tttgctaatg gaatcaacat ttcacccgat  2040
ggcaagtatg tctatatagc tgagttgctg gctcataaga ttcatgtgta tgaaaagcat  2100
gctaattgga ctttaactcc attgaagtcc cttgacttta ataccctcgt ggataacata  2160
tctgtggatc ctgagacagg agacctttgg gttggatgcc atcccaatgg catgaaaatc  2220
ttcttctatg actcagagaa tcctcctgca tcagaggtgc ttcgaatcca gaacattcta  2280
acagaagaac ctaaagtgac acaggtttat gcagaaaatg gcacagtgtt gcaaggcagt  2340
acagttgcct ctgtgtacaa agggaaactg ctgattggca cagtgtttca caaagctctt  2400
tactgtgagc tctaataa                                                2418

SEQ ID NO: 78           moltype = AA  length = 804
FEATURE                 Location/Qualifiers
REGION                  1..804
                        note = hVK3LP-[hCD40 K81T EC]-(g4s)4-[SSShinge-P238S
                         Fc]-NGS-[PON1 Q192K]
source                  1..804
                        mol_type = protein
                        organism = synthetic construct
SEQUENCE: 78
METPAQLLFL LLLWLPDTTG EPPTACREKQ YLINSQCCSL CQPGQKLVSD CTEFTETECL  60
PCGESEFLDT WNRETHCHQH TYCDPNLGLR VQQKGTSETD TICTCEEGWH CTSEACESCV  120
```

```
LHRSCSPGFG VKQIATGVSD TICEPCPVGF FSNVSSAFEK CHPWTSCETK DLVVQQAGTN  180
KTDVVCGPDL SGGGGSGGGG SGGGGSGGGG STGLEPKSSD KTHTSPPSPA PELLGGSSVF  240
LFPPKPKDTL MISRTPEVTC VVVDVSHEDP EVKFNWYVDG VEVHNAKTKP REEQYNSTYR  300
VVSVLTVLHQ DWLNGKEYKC KVSNKALPAS IEKTISKAKG QPREPQVYTL PPSRDELTKN  360
QVSLTCLVKG FYPSDIAVEW ESNGQPENNY KTTPPVLDSD GSFFLYSKLT VDKSRWQQGN  420
VFSCSVMHEA LHNHYTQKSL SLSPGKVDGA SSPVNVSSPS VQDILFRNHQ SSYQTRLNAL  480
REVQPVELPN CNLVKGIETG SEDLEILPNG LAFISSGLKY PGIKSFNPNS PGKILLMDLN  540
EEDPTVLELG ITGSKFDVSS FNPHGISTFT DEDNAMYLLV VNHPDAKSTV ELFKFQEEEK  600
SLLHLKTIRH KLLPNLNDIV AVGPEHFYGT NDHYFLDPYL KSWEMYLGLA WSYVVYYSPS  660
EVRVVAEGFD FANGINISPD GKYVYIAELL AHKIHVYEKH ANWTLTPLKS LDFNTLVDNI  720
SVDPETGDLW VGCHPNGMKI FFYDSENPPA SEVLRIQNIL TEEPKVTQVY AENGTVLQGS  780
TVASVYKGKL LIGTVFHKAL YCEL                                         804

SEQ ID NO: 79          moltype = DNA  length = 1341
FEATURE                Location/Qualifiers
misc_feature           1..1341
                       note = hVK3LP-[hCD40 K81H-L121P EC]-(g4s)4-[SSShinge-P238S
                        Fc] DNA
source                 1..1341
                       mol_type = other DNA
                       organism = synthetic construct
SEQUENCE: 79
atggaaaccc cagcgcagct tctcttcctc ctgctactct ggctcccagg taccaccggt  60
gaaccaccca ctgcatgcag agaaaaacag tacctaataa acagtcagtg ctgttctttg  120
tgccagccag gacagaaact ggtgagtgac tgcacagagt tcactgaaac ggaatgcctt  180
ccttgcggtg aaagcgaatt cctagacacc tggaacagag agacacactg ccaccagcac  240
cactactgcg accccaacct agggcttcgg gtccagcaga agggcacctc agaaacagac  300
accatctgca cctgtgaaga aggctggcac tgtacgagtg aggcctgtga gagctgtgtc  360
ccgcaccgct catgctcgcc cggctttggg gtcaagcaga ttgctacagg ggtttctgat  420
accatctgcg agccctgccc agtcggcttc ttctccaatg tgtcatctgc tttcgaaaaa  480
tgtcaccctt ggacaagctg tgagaccaaa gacctggttg tgcaacaggc aggcacaaac  540
aagactgatg ttgtctgtgg tccagatctc tccggaggag gtggctcagg tggtggagga  600
tctggaggag gtgggagtgg tggaggtggt tctaccggtc tcgagcccaa atcttctgac  660
aaaactcaca catctccacc gtccccagca cctgaactcc tgggaggatc gtcagtcttc  720
ctcttccccc caaaacccaa ggacaccctc atgatctccc ggacccctga ggtcacatgc  780
gtggtggtgg acgtgagcca cgaagaccct gaggtcaagt tcaactggta cgtggacggc  840
gtggaggtgc ataatgccaa gacaaagccg cgggaggagc agtacaacag cacgtaccgt  900
gtggtcagcg tcctcaccgt cctgcaccag gactggctga atggcaagga gtacaagtgc  960
aaggtctcca acaaagccct cccagcctcc atcgagaaaa ccatctccaa agccaaaggg  1020
cagccccgag aaccacaggt gtacaccctg cccccatccc gggatgagct gaccaagaac  1080
caggtcagcc tgacctgcct ggtcaaaggc ttctatccca gcgacatcgc cgtggagtgg  1140
gagagcaatg ggcagccgga gaacaactac aagaccacgc ctcccgtgct ggactccgac  1200
ggctccttct tcctctacag caagctcacc gtggacaaga gcaggtggca gcaggggaac  1260
gtcttctcat gctccgtgat gcatgaggct ctgcacaacc actacacgca gaagagcctc  1320
tctctctctc cgggtaaata a                                            1341

SEQ ID NO: 80          moltype = AA  length = 446
FEATURE                Location/Qualifiers
REGION                 1..446
                       note = hVK3LP-[hCD40 K81H-L121P EC]-(g4s)4-[SSShinge-P238S
                        Fc]
source                 1..446
                       mol_type = protein
                       organism = synthetic construct
SEQUENCE: 80
METPAQLLFL LLLWLPGTTG EPPTACREKQ YLINSQCCSL CQPGQKLVSD CTEFTETECL  60
PCGESEFLDT WNRETHCHQH HYCDPNLGLR VQQKGTSETD TICTCEEGWH CTSEACESCV  120
PHRSCSPGFG VKQIATGVSD TICEPCPVGF FSNVSSAFEK CHPWTSCETK DLVVQQAGTN  180
KTDVVCGPDL SGGGGSGGGG SGGGGSGGGG STGLEPKSSD KTHTSPPSPA PELLGGSSVF  240
LFPPKPKDTL MISRTPEVTC VVVDVSHEDP EVKFNWYVDG VEVHNAKTKP REEQYNSTYR  300
VVSVLTVLHQ DWLNGKEYKC KVSNKALPAS IEKTISKAKG QPREPQVYTL PPSRDELTKN  360
QVSLTCLVKG FYPSDIAVEW ESNGQPENNY KTTPPVLDSD GSFFLYSKLT VDKSRWQQGN  420
VFSCSVMHEA LHNHYTQKSL SLSPGK                                       446

SEQ ID NO: 81          moltype = DNA  length = 2415
FEATURE                Location/Qualifiers
misc_feature           1..2415
                       note = hVK3LP-[hCD40 K81H-L121P EC]-(g4s)4-[SSShinge-P238S
                        Fc]-NGS-[PON1 Q192K] DNA
source                 1..2415
                       mol_type = other DNA
                       organism = synthetic construct
SEQUENCE: 81
atggaaaccc cagcgcagct tctcttcctc ctgctactct ggctcccagg taccaccggt  60
gaaccaccca ctgcatgcag agaaaaacag tacctaataa acagtcagtg ctgttctttg  120
tgccagccag gacagaaact ggtgagtgac tgcacagagt tcactgaaac ggaatgcctt  180
ccttgcggtg aaagcgaatt cctagacacc tggaacagag agacacactg ccaccagcac  240
cactactgcg accccaacct agggcttcgg gtccagcaga agggcacctc agaaacagac  300
accatctgca cctgtgaaga aggctggcac tgtacgagtg aggcctgtga gagctgtgtc  360
```

```
ccgcaccgct catgctcgcc cggctttggg gtcaagcaga ttgctacagg ggtttctgat  420
accatctgcg agccctgccc agtcggcttc ttctccaatg tgtcatctgc tttcgaaaaa  480
tgtcaccctt ggacaagctg tgagaccaaa gacctggttg tgcaacaggc aggcacaaac  540
aagactgatg ttgtctgtgg tccagatctc tccggaggag gtggctcagg tggtggagga  600
tctggaggag gtgggagtgg tggaggtggt tctaccggtc tcgagcccaa atcttctgac  660
aaaactcaca catctccacc gtccccagca cctgaactcc tgggaggatc gtcagtcttc  720
ctcttccccc caaaacccaa ggacaccctc atgatctccc ggacccctga ggtcacatgc  780
gtggtggtgg acgtgagcca cgaagaccct gaggtcaagt tcaactggta cgtggacggc  840
gtggaggtgc ataatgccaa gacaaagccg cgggaggagc agtacaacag cacgtaccgt  900
gtggtcagcg tcctcaccgt cctgcaccag gactggctga atggcaagga gtacaagtgc  960
aaggtctcca acaaagccct cccagcctcc atcgagaaaa ccatctccaa agccaaaggg  1020
cagccccgag aaccacaggt gtacaccctg cccccatccc gggatgagct gaccaagaac  1080
caggtcagcc tgacctgcct ggtcaaaggc ttctatccca gcgacatcgc cgtggagtgg  1140
gagagcaatg ggcagccgga gaacaactac aagaccacgc ctcccgtgct ggactccgac  1200
ggctccttct tcctctacag caagctcacc gtggacaaga gcaggtggca gcaggggaac  1260
gtcttctcat gctccgtgat gcatgaggct ctgcacaacc actacacgca gaagagcctc  1320
tctctctctc cgggtaaagt cgacggagct agcagccccg tgaacgtgag cagccccagc  1380
gtgcaggata tcctcttcag gaaccaccag tcttcttacc aaacacgact taatgctctc  1440
cgagaggtac aacccgtaga acttcctaac tgtaatttag ttaaaggaat cgaaactggc  1500
tctgaagact tggagatact gcctaatgga ctggctttca ttagctctgg attaaagtat  1560
cctggaataa agagcttcaa ccccaacagt cctggaaaaa tacttctgat ggacctgaat  1620
gaagaagatc caacagtgtt ggaattgggg atcactggaa gtaaatttga tgtatcttca  1680
tttaaccctc atgggattag cacattcaca gatgaagata atgccatgta cctcctggtg  1740
gtgaaccatc cagatgccaa gtccacagtg gagttgttta aatttcaaga agaagaaaaa  1800
tcgcttttgc atctaaaaac catcagacat aaacttctgc ctaatttgaa tgatattgtt  1860
gctgtgggac ctgagcactt ttatggcaca aatgatcact attttcttga cccctactta  1920
aaatcctggg agatgtattt gggtttagcg tggtcgtatg ttgtctacta tagtccaagt  1980
gaagttcgag tggtggcaga aggatttgat tttgctaatg gaatcaacat ttcacccgat  2040
ggcaagtatg tctatatagc tgagttgctg gctcataaga ttcatgtgta tgaaaagcat  2100
gctaattgga ctttaactcc attgaagtcc cttgacttta ataccctcgt ggataacata  2160
tctgtggatc ctgagacagg agacctttgg gttggatgcc atcccaatgg catgaaaatc  2220
ttcttctatg actcagagaa tcctcctgca tcagaggtgc ttcgaatcca gaacattcta  2280
acagaagaac ctaaagtgac acaggtttat gcagaaaatg gcacagtgtt gcaaggcagt  2340
acagttgcct ctgtgtacaa agggaaactg ctgattggca cagtgtttca caaagctctt  2400
tactgtgagc tctaa                                                  2415

SEQ ID NO: 82           moltype = AA  length = 804
FEATURE                 Location/Qualifiers
REGION                  1..804
                        note = hVK3LP-[hCD40 K81H-L121P EC]-(g4s)4-[SSShinge-P238S
                         Fc]-NGS-[PON1 Q192K]
source                  1..804
                        mol_type = protein
                        organism = synthetic construct
SEQUENCE: 82
METPAQLLFL LLLWLPGTTG EPPTACREKQ YLINSQCCSL CQPGQKLVSD CTEFTETECL  60
PCGESEFLDT WNRETHCHQH HYCDPNLGLR VQQKGTSETD TICTCEEGWH CTSEACESCV  120
PHRSCSPGFG VKQIATGVSD TICEPCPVGF FSNVSSAFEK CHPWTSCETK DLVVQQAGTN  180
KTDVVCGPDL SGGGGSGGGG SGGGGSGGGG STGLEPKSSD KTHTSPPSPA PELLGGSSVF  240
LFPPKPKDTL MISRTPEVTC VVVDVSHEDP EVKFNWYVDG VEVHNAKTKP REEQYNSTYR  300
VVSVLTVLHQ DWLNGKEYKC KVSNKALPAS IEKTISKAKG QPREPQVYTL PPSRDELTKN  360
QVSLTCLVKG FYPSDIAVEW ESNGQPENNY KTTPPVLDSD GSFFLYSKLT VDKSRWQQGN  420
VFSCSVMHEA LHNHYTQKSL SLSPGKVDGA SSPVNVSSPS VQDILFRNHQ SSYQTRLNAL  480
REVQPVELPN CNLVKGIETG SEDLEILPNG LAFISSGLKY PGIKSFNPNS PGKILLMDLN  540
EEDPTVLELG ITGSKFDVSS FNPHGISTFT DEDNAMYLLV VNHPDAKSTV ELFKFQEEEK  600
SLLHLKTIRH KLLPNLNDIV AVGPEHFYGT NDHYFLDPYL KSWEMYLGLA WSYVVYYSPS  660
EVRVVAEGFD FANGINISPD GKYVYIAELL AHKIHVYEKH ANWTLTPLKS LDFNTLVDNI  720
SVDPETGDLW VGCHPNGMKI FFYDSENPPA SEVLRIQNIL TEEPKVTQVY AENGTVLQGS  780
TVASVYKGKL LIGTVFHKAL YCEL                                        804

SEQ ID NO: 83           moltype = DNA  length = 1341
FEATURE                 Location/Qualifiers
misc_feature            1..1341
                        note = hVK3LP-[hCD40 K81S EC]-(g4s)4-[SSShinge-P238S Fc] DNA
source                  1..1341
                        mol_type = other DNA
                        organism = synthetic construct
SEQUENCE: 83
atggaaaccc cagcgcagct tctcttcctc ctgctactct ggctcccaga taccaccggt  60
gaaccaccca ctgcatgcag agaaaaacag tacctaataa acagtcagtg ctgttctttg  120
tgccagccag gacagaaact ggtgagtgac tgcacagagt tcactgaaac ggaatgcctt  180
ccttgcggtg aaagcgaatt cctagacacc tggaacagag agacacactg ccaccagcac  240
tcctactgcg accccaacct agggcttcgg gtccagcaga agggcacctc agaaacagac  300
accatctgca cctgtgaaga aggctggcac tgtacgagtg aggcctgtga gagctgtgtc  360
ctgcaccgct catgctcgcc cggctttggg gtcaagcaga ttgctacagg ggtttctgat  420
accatctgcg agccctgccc agtcggcttc ttctccaatg tgtcatctgc tttcgaaaaa  480
tgtcaccctt ggacaagctg tgagaccaaa gacctggttg tgcaacaggc aggcacaaac  540
aagactgatg ttgtctgtgg tccagatctc tccggaggag gtggctcagg tggtggagga  600
tctggaggag gtgggagtgg tggaggtggt tctaccggtc tcgagcccaa atcttctgac  660
```

```
aaaactcaca catctccacc gtccccagca cctgaactcc tgggaggatc gtcagtcttc  720
ctcttccccc caaaacccaa ggacaccctc atgatctccc ggacccctga ggtcacatgc  780
gtggtggtgg acgtgagcca cgaagaccct gaggtcaagt tcaactggta cgtggacggc  840
gtggaggtgc ataatgccaa gacaaagccg cgggaggagc agtacaacag cacgtaccgt  900
gtggtcagcg tcctcaccgt cctgcaccag gactggctga atggcaagga gtacaagtgc  960
aaggtctcca acaaagccct cccagcctcc atcgagaaaa ccatctccaa agccaaaggg  1020
cagccccgag aaccacaggt gtacaccctg cccccatccc gggatgagct gaccaagaac  1080
caggtcagcc tgacctgcct ggtcaaaggc ttctatccca gcgacatcgc cgtggagtgg  1140
gagagcaatg ggcagccgga gaacaactac aagaccacgc ctcccgtgct ggactccgac  1200
ggctccttct tcctctacag caagctcacc gtggacaaga gcaggtggca gcaggggaac  1260
gtcttctcat gctccgtgat gcatgaggct ctgcacaacc actacacgca gaagagcctc  1320
tctctctctc cgggtaaata a                                            1341
```

```
SEQ ID NO: 84          moltype = AA  length = 446
FEATURE                Location/Qualifiers
REGION                 1..446
                       note = hVK3LP-[hCD40 K81S EC]-(g4s)4-[SSShinge-P238S Fc]
source                 1..446
                       mol_type = protein
                       organism = synthetic construct
SEQUENCE: 84
METPAQLLFL LLLWLPDTTG EPPTACREKQ YLINSQCCSL CQPGQKLVSD CTEFTETECL  60
PCGESEFLDT WNRETHCHQH SYCDPNLGLR VQQKGTSETD TICTCEEGWH CTSEACESCV  120
LHRSCSPGFG VKQIATGVSD TICEPCPVGF FSNVSSAFEK CHPWTSCETK DLVVQQAGTN  180
KTDVVCGPDL SGGGGSGGGG SGGGGSGGGG STGLEPKSSD KTHTSPPSPA PELLGGSSVF  240
LFPPKPKDTL MISRTPEVTC VVVDVSHEDP EVKFNWYVDG VEVHNAKTKP REEQYNSTYR  300
VVSVLTVLHQ DWLNGKEYKC KVSNKALPAS IEKTISKAKG QPREPQVYTL PPSRDELTKN  360
QVSLTCLVKG FYPSDIAVEW ESNGQPENNY KTTPPVLDSD GSFFLYSKLT VDKSRWQQGN  420
VFSCSVMHEA LHNHYTQKSL SLSPGK                                       446
```

```
SEQ ID NO: 85          moltype = DNA  length = 2415
FEATURE                Location/Qualifiers
misc_feature           1..2415
                       note = hVK3LP-[hCD40 K81S EC]-(g4s)4-[SSShinge-P238S
                        Fc]-NGS-[PON1 Q192K] DNA
source                 1..2415
                       mol_type = other DNA
                       organism = synthetic construct
SEQUENCE: 85
atggaaaccc cagcgcagct tctcttcctc ctgctactct ggctcccaga taccaccggt  60
gaaccaccca ctgcatgcag agaaaaacag tacctaataa acagtcagtg ctgttctttg  120
tgccagccag gacagaaact ggtgagtgac tgcacagagt tcactgaaac ggaatgcctt  180
ccttgcggtg aaagcgaatt cctagacacc tggaacagag agacacactg ccaccagcac  240
tcctactgcg accccaacct agggcttcgg gtccagcaga agggcacctc agaaacagac  300
accatctgca cctgtgaaga aggctggcac tgtacgagtg aggcctgtga gagctgtgtc  360
ctgcaccgct catgctcgcc cggctttggg gtcaagcaga ttgctacagg ggtttctgat  420
accatctgcg agccctgccc agtcggcttc ttctccaatg tgtcatctgc tttcgaaaaa  480
tgtcaccctt ggacaagctg tgagaccaaa gacctggttg tgcaacaggc aggcacaaac  540
aagactgatg ttgtctgtgg tccagatctc tccggaggag gtggctcagg tggtggagga  600
tctggaggag gtgggagtgg tggaggtggt tctaccggtc tcgagcccaa atcttctgac  660
aaaactcaca catctccacc gtccccagca cctgaactcc tgggaggatc gtcagtcttc  720
ctcttccccc caaaacccaa ggacaccctc atgatctccc ggacccctga ggtcacatgc  780
gtggtggtgg acgtgagcca cgaagaccct gaggtcaagt tcaactggta cgtggacggc  840
gtggaggtgc ataatgccaa gacaaagccg cgggaggagc agtacaacag cacgtaccgt  900
gtggtcagcg tcctcaccgt cctgcaccag gactggctga atggcaagga gtacaagtgc  960
aaggtctcca acaaagccct cccagcctcc atcgagaaaa ccatctccaa agccaaaggg  1020
cagccccgag aaccacaggt gtacaccctg cccccatccc gggatgagct gaccaagaac  1080
caggtcagcc tgacctgcct ggtcaaaggc ttctatccca gcgacatcgc cgtggagtgg  1140
gagagcaatg ggcagccgga gaacaactac aagaccacgc ctcccgtgct ggactccgac  1200
ggctccttct tcctctacag caagctcacc gtggacaaga gcaggtggca gcaggggaac  1260
gtcttctcat gctccgtgat gcatgaggct ctgcacaacc actacacgca gaagagcctc  1320
tctctctctc cgggtaaagt cgacggagct agcagccccg tgaacgtgag cagccccagc  1380
gtgcaggata tcctcttcag gaaccaccag tcttcttacc aaacacgact taatgctctc  1440
cgagaggtac aacccgtaga acttcctaac tgtaatttag ttaaaggaat cgaaactggc  1500
tctgaagact tggagatact gcctaatgga ctggctttca ttagctctgg attaaagtat  1560
cctggaataa agagcttcaa ccccaacagt cctggaaaaa tacttctgat ggacctgaat  1620
gaagaagatc caacagtgtt ggaattgggg atcactggaa gtaaatttga tgtatcttca  1680
tttaaccctc atgggattag cacattcaca gatgaagata atgccatgta cctcctggtg  1740
gtgaaccatc cagatgccaa gtccacagtg gagttgttta aatttcaaga agaagaaaaa  1800
tcgcttttgc atctaaaaac catcagacat aaacttctgc ctaatttgaa tgatattgtt  1860
gctgtgggac ctgagcactt ttatggcaca aatgatcact attttcttga cccctactta  1920
aaatcctggg agatgtattt gggtttagcg tggtcgtatg ttgtctacta tagtccaagt  1980
gaagttcgag tggtggcaga aggatttgat tttgctaatg gaatcaacat ttcacccgat  2040
ggcaagtatg tctatatagc tgagttgctg gctcataaga ttcatgtgta tgaaaagcat  2100
gctaattgga ctttaactcc attgaagtcc cttgacttta ataccctcgt ggataacata  2160
tctgtggatc ctgagacagg agacctttgg gttggatgcc atcccaatgg catgaaaatc  2220
ttcttctatg actcagagaa tcctcctgca tcagaggtgc ttcgaatcca gaacattcta  2280
acagaagaac ctaaagtgac acaggtttat gcagaaaatg gcacagtgtt gcaaggcagt  2340
acagttgcct ctgtgtacaa agggaaactg ctgattggca cagtgtttca caaagctctt  2400
```

```
tactgtgagc tctaa                                                  2415

SEQ ID NO: 86           moltype = AA  length = 804
FEATURE                 Location/Qualifiers
REGION                  1..804
                        note = hVK3LP-[hCD40 K81S EC]-(g4s)4-[SSShinge-P238S
                         Fc]-NGS-[PON1 Q192K]
source                  1..804
                        mol_type = protein
                        organism = synthetic construct
SEQUENCE: 86
METPAQLLFL LLLWLPDTTG EPPTACREKQ YLINSQCCSL CQPGQKLVSD CTEFTETECL  60
PCGESEFLDT WNRETHCHQH SYCDPNLGLR VQQKGTSETD TICTCEEGWH CTSEACESCV  120
LHRSCSPGFG VKQIATGVSD TICEPCPVGF FSNVSSAFEK CHPWTSCETK DLVVQQAGTN  180
KTDVVCGPDL SGGGGSGGGG SGGGGSGGGG STGLEPKSSD KTHTSPPSPA PELLGGSSVF  240
LFPPKPKDTL MISRTPEVTC VVVDVSHEDP EVKFNWYVDG VEVHNAKTKP REEQYNSTYR  300
VVSVLTVLHQ DWLNGKEYKC KVSNKALPAS IEKTISKAKG QPREPQVYTL PPSRDELTKN  360
QVSLTCLVKG FYPSDIAVEW ESNGQPENNY KTTPPVLDSD GSFFLYSKLT VDKSRWQQGN  420
VFSCSVMHEA LHNHYTQKSL SLSPGKVDGA SSPVNVSSPS VQDILFRNHQ SSYQTRLNAL  480
REVQPVELPN CNLVKGIETG SEDLEILPNG LAFISSGLKY PGIKSFNPNS PGKILLMDLN  540
EEDPTVLELG ITGSKFDVSS FNPHGISTFT DEDNAMYLLV VNHPDAKSTV ELFKFQEEEK  600
SLLHLKTIRH KLLPNLNDIV AVGPEHFYGT NDHYFLDPYL KSWEMYLGLA WSYVVYYSPS  660
EVRVVAEGFD FANGINISPD GKYVYIAELL AHKIHVYEKH ANWTLTPLKS LDFNTLVDNI  720
SVDPETGDLW VGCHPNGMKI FFYDSENPPA SEVLRIQNIL TEEPKVTQVY AENGTVLQGS  780
TVASVYKGKL LIGTVFHKAL YCEL                                        804

SEQ ID NO: 87           moltype = DNA  length = 1341
FEATURE                 Location/Qualifiers
misc_feature            1..1341
                        note = hVK3LP-[hCD40 E64Y-K81T-P85Y
                         EC]-(g4s)4-[SSShinge-P238S Fc] DNA
source                  1..1341
                        mol_type = other DNA
                        organism = synthetic construct
SEQUENCE: 87
atggaaaccc cagcgcagct tctcttcctc ctgctactct ggctcccaga taccaccggt  60
gaaccaccca ctgcatgcag agaaaaacag tacctaataa acagtcagtg ctgttctttg  120
tgccagccag gacagaaact ggtgagtgac tgcacagagt tcactgaaac ggaatgcctt  180
ccttgcggtt acagcgaatt cctagacacc tggaacagag agacacactg ccaccagcac  240
acatactgcg actacaacct agggcttcgg gtccagcaga agggcacctc agaaacagac  300
accatctgca cctgtgaaga aggctggcac tgtacgagtg aggcctgtga gagctgtgtc  360
ctgcaccgct catgctcgcc cggctttggg gtcaagcaga ttgctacagg ggtttctgat  420
accatctgcg agccctgccc agtcggcttc ttctccaatg tgtcatctgc tttcgaaaaa  480
tgtcaccctt ggacaagctg tgagaccaaa gacctggttg tgcaacaggc aggcacaaac  540
aagactgatg ttgtctgtgg tccagatctc tccggaggag gtggctcagg tggtggagga  600
tctggaggag gtgggagtgg tggaggtggt tctaccggtc tcgagcccaa atcttctgac  660
aaaactcaca catctccacc gtccccagca cctgaactcc tgggaggatc gtcagtcttc  720
ctcttccccc caaaacccaa ggacaccctc atgatctccc ggacccctga ggtcacatgc  780
gtggtggtgg acgtgagcca cgaagaccct gaggtcaagt tcaactggta cgtggacggc  840
gtggaggtgc ataatgccaa gacaaagccg cgggaggagc agtacaacag cacgtaccgt  900
gtggtcagcg tcctcaccgt cctgcaccag gactggctga atggcaagga gtacaagtgc  960
aaggtctcca acaaagccct cccagcctcc atcgagaaaa ccatctccaa agccaaaggg  1020
cagccccgag aaccacaggt gtacaccctg cccccatccc gggatgagct gaccaagaac  1080
caggtcagcc tgacctgcct ggtcaaaggc ttctatccca gcgacatcgc cgtggagtgg  1140
gagagcaatg ggcagccgga gaacaactac aagaccacgc ctcccgtgct ggactccgac  1200
ggctccttct tcctctacag caagctcacc gtggacaaga gcaggtggca gcaggggaac  1260
gtcttctcat gctccgtgat gcatgaggct ctgcacaacc actacacgca gaagagcctc  1320
tctctctctc cgggtaaata a                                           1341

SEQ ID NO: 88           moltype = AA  length = 446
FEATURE                 Location/Qualifiers
REGION                  1..446
                        note = hVK3LP-[hCD40 E64Y-K81T-P85Y
                         EC]-(g4s)4-[SSShinge-P238S Fc]
source                  1..446
                        mol_type = protein
                        organism = synthetic construct
SEQUENCE: 88
METPAQLLFL LLLWLPDTTG EPPTACREKQ YLINSQCCSL CQPGQKLVSD CTEFTETECL  60
PCGYSEFLDT WNRETHCHQH TYCDYNLGLR VQQKGTSETD TICTCEEGWH CTSEACESCV  120
LHRSCSPGFG VKQIATGVSD TICEPCPVGF FSNVSSAFEK CHPWTSCETK DLVVQQAGTN  180
KTDVVCGPDL SGGGGSGGGG SGGGGSGGGG STGLEPKSSD KTHTSPPSPA PELLGGSSVF  240
LFPPKPKDTL MISRTPEVTC VVVDVSHEDP EVKFNWYVDG VEVHNAKTKP REEQYNSTYR  300
VVSVLTVLHQ DWLNGKEYKC KVSNKALPAS IEKTISKAKG QPREPQVYTL PPSRDELTKN  360
QVSLTCLVKG FYPSDIAVEW ESNGQPENNY KTTPPVLDSD GSFFLYSKLT VDKSRWQQGN  420
VFSCSVMHEA LHNHYTQKSL SLSPGK                                      446

SEQ ID NO: 89           moltype = DNA  length = 2415
FEATURE                 Location/Qualifiers
```

```
misc_feature          1..2415
                      note = hVK3LP-[hCD40 E64Y-K81T-P85Y
                       EC]-(g4s)4-[SSShinge-P238S Fc]-NGS-[PON1 Q192K] DNA
source                1..2415
                      mol_type = other DNA
                      organism = synthetic construct
SEQUENCE: 89
atggaaaccc cagcgcagct tctcttcctc ctgctactct ggctcccaga taccaccggt  60
gaaccaccca ctgcatgcag agaaaaacag tacctaataa acagtcagtg ctgttctttg  120
tgccagccag gacagaaact ggtgagtgac tgcacagagt tcactgaaac ggaatgcctt  180
ccttgcggtt acagcgaatt cctagacacc tggaacagag agacacactg ccaccagcac  240
acatactgcg actacaacct agggcttcgg gtccagcaga agggcacctc agaaacagac  300
accatctgca cctgtgaaga aggctggcac tgtacgagtg aggcctgtga gagctgtgtc  360
ctgcaccgct catgctcgcc cggctttggg gtcaagcaga ttgctacagg ggtttctgat  420
accatctgcg agccctgccc agtcggcttc ttctccaatg tgtcatctgc tttcgaaaaa  480
tgtcaccctt ggacaagctg tgagaccaaa gacctggttg tgcaacaggc aggcacaaac  540
aagactgatg ttgtctgtgg tccagatctc tccggaggag gtggctcagg tggtggagga  600
tctggaggag gtgggagtgg tggaggtggt tctaccggtc tcgagcccaa atcttctgac  660
aaaactcaca catctccacc gtccccagca cctgaactcc tgggaggatc gtcagtcttc  720
ctcttccccc caaaacccaa ggacaccctc atgatctccc ggacccctga ggtcacatgc  780
gtggtggtgg acgtgagcca cgaagaccct gaggtcaagt tcaactggta cgtggacggc  840
gtggaggtgc ataatgccaa gacaaagccg cgggaggagc agtacaacag cacgtaccgt  900
gtggtcagcg tcctcaccgt cctgcaccag gactggctga atggcaagga gtacaagtgc  960
aaggtctcca acaaagccct cccagcctcc atcgagaaaa ccatctccaa agccaaaggg  1020
cagccccgag aaccacaggt gtacaccctg cccccatccc gggatgagct gaccaagaac  1080
caggtcagcc tgacctgcct ggtcaaaggc ttctatccca gcgacatcgc cgtggagtgg  1140
gagagcaatg ggcagccgga gaacaactac aagaccacgc ctcccgtgct ggactccgac  1200
ggctccttct tcctctacag caagctcacc gtggacaaga gcaggtggca gcaggggaac  1260
gtcttctcat gctccgtgat gcatgaggct ctgcacaacc actacacgca gaagagcctc  1320
tctctctctc cgggtaaagt cgacggagct agcagccccg tgaacgtgag cagccccagc  1380
gtgcaggata tcctcttcag gaaccaccag tcttcttacc aaacacgact taatgctctc  1440
cgagaggtac aacccgtaga acttcctaac tgtaatttag ttaaaggaat cgaaactggc  1500
tctgaagact tggagatact gcctaatgga ctggctttca ttagctctgg attaaagtat  1560
cctggaataa agagcttcaa ccccaacagt cctggaaaaa tacttctgat ggacctgaat  1620
gaagaagatc caacagtgtt ggaattgggg atcactggaa gtaaatttga tgtatcttca  1680
tttaaccctc atgggattag cacattcaca gatgaagata atgccatgta cctcctggtg  1740
gtgaaccatc cagatgccaa gtccacagtg gagttgttta aatttcaaga agaagaaaaa  1800
tcgcttttgc atctaaaaac catcagacat aaacttctgc ctaatttgaa tgatattgtt  1860
gctgtgggac ctgagcactt ttatggcaca aatgatcact atttcttgga cccctactta  1920
aaatcctggg agatgtattt gggtttagcg tggtcgtatg ttgtctacta tagtccaagt  1980
gaagttcgag tggtggcaga aggatttgat tttgctaatg gaatcaacat ttcacccgat  2040
ggcaagtatg tctatatagc tgagttgctg gctcataaga ttcatgtgta tgaaaagcat  2100
gctaattgga ctttaactcc attgaagtcc cttgacttta ataccctcgt ggataacata  2160
tctgtggatc ctgagacagg agacctttgg gttggatgcc atcccaatgg catgaaaatc  2220
ttcttctatg actcagagaa tcctcctgca tcagaggtgc ttcgaatcca gaacattcta  2280
acagaagaac ctaaagtgac acaggtttat gcagaaaatg gcacagtgtt gcaaggcagt  2340
acagttgcct ctgtgtacaa agggaaactg ctgattggca cagtgtttca caaagctctt  2400
tactgtgagc tctaa                                                   2415

SEQ ID NO: 90         moltype = AA  length = 804
FEATURE               Location/Qualifiers
REGION                1..804
                      note = hVK3LP-[hCD40 E64Y-K81T-P85Y
                       EC]-(g4s)4-[SSShinge-P238S Fc]-NGS-[PON1 Q192K]
source                1..804
                      mol_type = protein
                      organism = synthetic construct
SEQUENCE: 90
METPAQLLFL LLLWLPDTTG EPPTACREKQ YLINSQCCSL CQPGQKLVSD CTEFTETECL  60
PCGYSEFLDT WNRETHCHQH TYCDYNLGLR VQQKGTSETD TICTCEEGWH CTSEACESCV  120
LHRSCSPGFG VKQIATGVSD TICEPCPVGF FSNVSSAFEK CHPWTSCETK DLVVQQAGTN  180
KTDVVCGPDL SGGGGSGGGG SGGGGSGGGG STGLEPKSSD KTHTSPPSPA PELLGGSSVF  240
LFPPKPKDTL MISRTPEVTC VVVDVSHEDP EVKFNWYVDG VEVHNAKTKP REEQYNSTYR  300
VVSVLTVLHQ DWLNGKEYKC KVSNKALPAS IEKTISKAKG QPREPQVYTL PPSRDELTKN  360
QVSLTCLVKG FYPSDIAVEW ESNGQPENNY KTTPPVLDSD GSFFLYSKLT VDKSRWQQGN  420
VFSCSVMHEA LHNHYTQKSL SLSPGKVDGA SSPVNVSSPS VQDILFRNHQ SSYQTRLNAL  480
REVQPVELPN CNLVKGIETG SEDLEILPNG LAFISSGLKY PGIKSFNPNS PGKILLMDLN  540
EEDPTVLELG ITGSKFDVSS FNPHGISTFT DEDNAMYLLV VNHPDAKSTV ELFKFQEEEK  600
SLLHLKTIRH KLLPNLNDIV AVGPEHFYGT NDHYFLDPYL KSWEMYLGLA WSYVVYYSPS  660
EVRVVAEGFD FANGINISPD GKYVYIAELL AHKIHVYEKH ANWTLTPLKS LDFNTLVDNI  720
SVDPETGDLW VGCHPNGMKI FFYDSENPPA SEVLRIQNIL TEEPKVTQVY AENGTVLQGS  780
TVASVYKGKL LIGTVFHKAL YCEL                                         804

SEQ ID NO: 91         moltype = DNA  length = 816
FEATURE               Location/Qualifiers
misc_feature          1..816
                      note = hVK3LP-[VL-VH anti-TNFalpha scFv] DNA
source                1..816
                      mol_type = other DNA
```

```
                         organism = synthetic construct
SEQUENCE: 91
aagcttgccg ccatggaaac cccagcgcag cttctcttcc tcctgctact ctggctcccg  60
gataccaccg gtgacatcca gatgacccag tctccatcct ccctgtctgc atctgtaggg  120
gacagagtca ccatcacttg tcgggcaagt cagggcatca gaaattactt agcctggtat  180
cagcaaaaac cagggaaagc ccctaagctc ctgatctatg ctgcatccac tttgcaatca  240
ggggtcccat ctcggttcag tggcagtgga tctgggacag atttcactct caccatcagc  300
agcctacagc ctgaagatgt tgcaacttat tactgtcaaa ggtataaccg tgcaccgtat  360
acttttggcc aggggaccaa ggtggaaatc aaaggaggtg gtggatctgg tggaggaggt  420
tcaggtggtg gaggatctgg gggtggaggt agtgaggtgc agctggtgga gtctgggggga  480
ggcttggtac agcccggcag gtccctgaga ctctcctgtg cggcctctgg attcaccttt  540
gatgattatg ccatgcactg ggtccggcaa gctccaggga agggcctgga atgggtctca  600
gctatcactt ggaatagtgg tcacatagac tatgcggact ctgtggaggg ccgattcacc  660
atctccagag acaacgccaa gaactccctg tatctgcaaa tgaacagtct gagagctgag  720
gatacggccg tatattactg tgcgaaagtc tcgtacctta gcaccgcgtc ctcccttgac  780
tattggggcc aaggtaccct ggtcaccgtc tcgtca                          816

SEQ ID NO: 92            moltype = AA  length = 268
FEATURE                  Location/Qualifiers
REGION                   1..268
                         note = hVK3LP-[VL-VH anti-TNFalpha scFv]
source                   1..268
                         mol_type = protein
                         organism = synthetic construct
SEQUENCE: 92
METPAQLLFL LLLWLPDTTG DIQMTQSPSS LSASVGDRVT ITCRASQGIR NYLAWYQQKP  60
GKAPKLLIYA ASTLQSGVPS RFSGSGSGTD FTLTISSLQP EDVATYYCQR YNRAPYTFGQ  120
GTKVEIKGGG GSGGGGSGGG GSGGGGSEVQ LVESGGGLVQ PGRSLRLSCA ASGFTFDDYA  180
MHWVRQAPGK GLEWVSAITW NSGHIDYADS VEGRFTISRD NAKNSLYLQM NSLRAEDTAV  240
YYCAKVSYLS TASSLDYWGQ GTLVTVSS                                    268

SEQ ID NO: 93            moltype = DNA  length = 2605
FEATURE                  Location/Qualifiers
misc_feature             1..2605
                         note = hVK3LP-[VL-VH anti-TNFalpha
                          scFv]-[SSShinge-P238S-P331S Fc]-NGS-[PON1 Q192K] DNA
source                   1..2605
                         mol_type = other DNA
                         organism = synthetic construct
SEQUENCE: 93
aagcttgccg ccatggaaac cccagcgcag cttctcttcc tcctgctact ctggctcccg  60
gataccaccg gtgacatcca gatgacccag tctccatcct ccctgtctgc atctgtaggg  120
gacagagtca ccatcacttg tcgggcaagt cagggcatca gaaattactt agcctggtat  180
cagcaaaaac cagggaaagc ccctaagctc ctgatctatg ctgcatccac tttgcaatca  240
ggggtcccat ctcggttcag tggcagtgga tctgggacag atttcactct caccatcagc  300
agcctacagc ctgaagatgt tgcaacttat tactgtcaaa ggtataaccg tgcaccgtat  360
acttttggcc aggggaccaa ggtggaaatc aaaggaggtg gtggatctgg tggaggaggt  420
tcaggtggtg gaggatctgg gggtggaggt agtgaggtgc agctggtgga gtctgggggga  480
ggcttggtac agcccggcag gtccctgaga ctctcctgtg cggcctctgg attcaccttt  540
gatgattatg ccatgcactg ggtccggcaa gctccaggga agggcctgga atgggtctca  600
gctatcactt ggaatagtgg tcacatagac tatgcggact ctgtggaggg ccgattcacc  660
atctccagag acaacgccaa gaactccctg tatctgcaaa tgaacagtct gagagctgag  720
gatacggccg tatattactg tgcgaaagtc tcgtacctta gcaccgcgtc ctcccttgac  780
tattggggcc aaggtaccct ggtcaccgtc tcgtcagatc tcgagcccaa atcttctgac  840
aaaactcaca catctccacc gtccccagca cctgaactcc tgggaggatc gtcagtcttc  900
ctcttccccc caaaacccaa ggacaccctc atgatctccc ggacccctga ggtcacatgc  960
gtggtggtgg acgtgagcca cgaagaccct gaggtcaagt tcaactggta cgtggacggc  1020
gtggaggtgc ataatgccaa gacaaagccg cgggaggagc agtacaacag cacgtaccgt  1080
gtggtcagcg tcctcaccgt cctgcaccag gactggctga atggcaagga gtacaagtgc  1140
aaggtctcca acaaagccct cccagcctcc atcgagaaaa ccatctccaa agccaaaggg  1200
cagccccgag aaccacaggt gtacaccctg cccccatccc gggatgagct gaccaagaac  1260
caggtcagcc tgacctgcct ggtcaaaggc ttctatccca gcgacatcgc cgtggagtgg  1320
gagagcaatg ggcagccgga gaacaactac aagaccacgc ctcccgtgct ggactccgac  1380
ggctccttct tcctctacag caagctcacc gtggacaaga gcaggtggca gcaggggaac  1440
gtcttctcat gctccgtgat gcatgaggct ctgcacaacc actacacgca gaagagcctc  1500
tctctctctc cgggtaaagt cgacggagct agcagccccg tgaacgtgag cagccccagc  1560
gtgcaggata tcctcttcag gaaccaccag tcttcttacc aaacacgact taatgctctc  1620
cgagaggtac aacccgtaga acttcctaac tgtaatttag ttaaaggaat cgaaactggc  1680
tctgaagact tggagatact gcctaatgga ctggctttca ttagctctgg attaaagtat  1740
cctggaataa agagcttcaa ccccaacagt cctggaaaaa tacttctgat ggacctgaat  1800
gaagaagatc caacagtgtt ggaattgggg atcactggaa gtaaatttga tgtatcttca  1860
tttaaccctc atgggattag cacattcaca gatgaagata atgccatgta cctcctggtg  1920
gtgaaccatc cagatgccaa gtccacagtg gagttgttta aatttcaaga agaagaaaaa  1980
tcgcttttgc atctaaaaac catcagacat aaacttctgc ctaatttgaa tgatattgtt  2040
gctgtgggac ctgagcactt ttatggcaca aatgatcact attttcttga cccctactta  2100
aaatcctggg agatgtattt gggtttagcg tggtcgtatg ttgtctacta tagtccaagt  2160
gaagttcgag tggtggcaga aggatttgat tttgctaatg gaatcaacat ttcacccgat  2220
ggcaagtatg tctatatagc tgagttgctg gctcataaga ttcatgtgta tgaaaagcat  2280
gctaattgga ctttaactcc attgaagtcc cttgacttta ataccctcgt ggataacata  2340
```

```
tctgtggatc ctgagacagg agacctttgg gttggatgcc atcccaatgg catgaaaatc  2400
ttcttctatg actcagagaa tcctcctgca tcagaggtgc ttcgaatcca gaacattcta  2460
acagaagaac ctaaagtgac acaggtttat gcagaaaatg gcacagtgtt gcaaggcagt  2520
acagttgcct ctgtgtacaa agggaaactg ctgattggca cagtgtttca caaagctctt  2580
tactgtgagc tctaataatc tagaa                                        2605

SEQ ID NO: 94          moltype = AA  length = 860
FEATURE                Location/Qualifiers
REGION                 1..860
                       note = hVK3LP-[VL-VH anti-TNFalpha
                        scFv]-[SSShinge-P238S-P331S Fc]-NGS-[PON1 Q192K]
source                 1..860
                       mol_type = protein
                       organism = synthetic construct
SEQUENCE: 94
METPAQLLFL LLLWLPDTTG DIQMTQSPSS LSASVGDRVT ITCRASQGIR NYLAWYQQKP  60
GKAPKLLIYA ASTLQSGVPS RFSGSGSGTD FTLTISSLQP EDVATYYCQR YNRAPYTFGQ  120
GTKVEIKGGG GSGGGGSGGG GSGGGGSEVQ LVESGGGLVQ PGRSLRLSCA ASGFTFDDYA  180
MHWVRQAPGK GLEWVSAITW NSGHIDYADS VEGRFTISRD NAKNSLYLQM NSLRAEDTAV  240
YYCAKVSYLS TASSLDYWGQ GTLVTVSSDL EPKSSDKTHT SPPSPAPELL GGSSVFLFPP  300
KPKDTLMISR TPEVTCVVVD VSHEDPEVKF NWYVDGVEVH NAKTKPREEQ YNSTYRVVSV  360
LTVLHQDWLN GKEYKCKVSN KALPASIEKT ISKAKGQPRE PQVYTLPPSR DELTKNQVSL  420
TCLVKGFYPS DIAVEWESNG QPENNYKTTP PVLDSDGSFF LYSKLTVDKS RWQQGNVFSC  480
SVMHEALHNH YTQKSLSLSP GKVDGASSPV NVSSPSVQDI LFRNHQSSYQ TRLNALREVQ  540
PVELPNCNLV KGIETGSEDL EILPNGLAFI SSGLKYPGIK SFNPNSPGKI LLMDLNEEDP  600
TVLELGITGS KFDVSSFNPH GISTFTDEDN AMYLLVVNHP DAKSTVELFK FQEEEKSLLH  660
LKTIRHKLLP NLNDIVAVGP EHFYGTNDHY FLDPYLKSWE MYLGLAWSYV VYYSPSEVRV  720
VAEGFDFANG INISPDGKYV YIAELLAHKI HVYEKHANWT LTPLKSLDFN TLVDNISVDP  780
ETGDLWVGCH PNGMKIFFYD SENPPASEVL RIQNILTEEP KVTQVYAENG TVLQGSTVAS  840
VYKGKLLIGT VFHKALYCEL                                              860

SEQ ID NO: 95          moltype = DNA  length = 816
FEATURE                Location/Qualifiers
misc_feature           1..816
                       note = hVK3LP-[VH-VL anti-TNFalpha scFv] DNA
source                 1..816
                       mol_type = other DNA
                       organism = synthetic construct
SEQUENCE: 95
aagcttgccg ccatggaaac cccagcgcag cttctcttcc tcctgctact ctggctcccg  60
gataccaccg gtgaggtgca gctggtggag tctgggggag gcttggtaca gcccggcagg  120
tccctgagac tctcctgtgc ggcctctgga ttcacctttg atgattatgc catgcactgg  180
gtccggcaag ctccagggaa gggcctggaa tgggtctcag ctatcacttg gaatagtggt  240
cacatagact atgcggactc tgtggagggc cgattcacca tctccagaga caacgccaag  300
aactccctgt atctgcaaat gaacagtctg agagctgagg atacggccgt atattactgt  360
gcgaaagtct cgtaccttag caccgcgtcc tcccttgact attggggcca aggtaccctg  420
gtcaccgtct cgagtggagg tggtggatct ggtggaggag gttcaggtgg tggaggatct  480
gggggtggag gtagtgacat ccagatgacc cagtctccat cctccctgtc tgcatctgta  540
ggggacagag tcaccatcac ttgtcgggca agtcagggca tcagaaatta cttagcctgg  600
tatcagcaaa aaccagggaa agcccctaag ctcctgatct atgctgcatc cactttgcaa  660
tcaggggtcc catctcggtt cagtggcagt ggatctggga cagatttcac tctcaccatc  720
agcagcctac agcctgaaga tgttgcaact tattactgtc aaaggtataa ccgtgcaccg  780
tatacttttg gccaggggac caaggtggaa atcaaa                            816

SEQ ID NO: 96          moltype = AA  length = 268
FEATURE                Location/Qualifiers
REGION                 1..268
                       note = hVK3LP-[VH-VL anti-TNFalpha scFv]
source                 1..268
                       mol_type = protein
                       organism = synthetic construct
SEQUENCE: 96
METPAQLLFL LLLWLPDTTG EVQLVESGGG LVQPGRSLRL SCAASGFTFD DYAMHWVRQA  60
PGKGLEWVSA ITWNSGHIDY ADSVEGRFTI SRDNAKNSLY LQMNSLRAED TAVYYCAKVS  120
YLSTASSLDY WGQGTLVTVS SGGGGSGGGG SGGGGSGGGG SDIQMTQSPS SLSASVGDRV  180
TITCRASQGI RNYLAWYQQK PGKAPKLLIY AASTLQSGVP SRFSGSGSGT DFTLTISSLQ  240
PEDVATYYCQ RYNRAPYTFG QGTKVEIK                                     268

SEQ ID NO: 97          moltype = DNA  length = 2605
FEATURE                Location/Qualifiers
misc_feature           1..2605
                       note = hVK3LP-[VH-VL anti-TNFalpha
                        scFv]-[SSShinge-P238S-P331S Fc]-NGS-[PON1 Q192K] DNA
source                 1..2605
                       mol_type = other DNA
                       organism = synthetic construct
SEQUENCE: 97
aagcttgccg ccatggaaac cccagcgcag cttctcttcc tcctgctact ctggctcccg  60
gataccaccg gtgaggtgca gctggtggag tctgggggag gcttggtaca gcccggcagg  120
```

-continued

```
tccctgagac tctcctgtgc ggcctctgga ttcacctttg atgattatgc catgcactgg  180
gtccggcaag ctccagggaa gggcctggaa tgggtctcag ctatcacttg gaatagtggt  240
cacatagact atgcggactc tgtggagggc cgattcacca tctccagaga caacgccaag  300
aactccctgt atctgcaaat gaacagtctg agagctgagg atacggccgt atattactgt  360
gcgaaagtct cgtaccttag caccgcgtcc tcccttgact attggggcca aggtaccctg  420
gtcaccgtct cgagtggagg tggtggatct ggtggaggag gttcaggtgg tggaggatct  480
gggggtggag gtagtgacat ccagatgacc cagtctccat cctccctgtc tgcatctgta  540
ggggacagag tcaccatcac ttgtcgggca agtcagggca tcagaaatta cttagcctgg  600
tatcagcaaa aaccagggaa agcccctaag ctcctgatct atgctgcatc cactttgcaa  660
tcaggggtcc catctcggtt cagtggcagt ggatctggga cagatttcac tctcaccatc  720
agcagcctac agcctgaaga tgttgcaact tattactgtc aaaggtataa ccgtgcaccg  780
tatacttttg gccaggggac caaggtggaa atcaaagatc tcgagcccaa atcttctgac  840
aaaactcaca catctccacc gtccccagca cctgaactcc tgggaggatc gtcagtcttc  900
ctcttccccc caaaacccaa ggacaccctc atgatctccc ggacccctga ggtcacatgc  960
gtggtggtgg acgtgagcca cgaagaccct gaggtcaagt tcaactggta cgtggacggc  1020
gtggaggtgc ataatgccaa gacaaagccg cgggaggagc agtacaacag cacgtaccgt  1080
gtggtcagcg tcctcaccgt cctgcaccag gactggctga atggcaagga gtacaagtgc  1140
aaggtctcca acaaagccct cccagcctcc atcgagaaaa ccatctccaa agccaaaggg  1200
cagccccgag aaccacaggt gtacaccctg cccccatccc gggatgagct gaccaagaac  1260
caggtcagcc tgacctgcct ggtcaaaggc ttctatccca gcgacatcgc cgtggagtgg  1320
gagagcaatg ggcagccgga gaacaactac aagaccacgc ctcccgtgct ggactccgac  1380
ggctccttct tcctctacag caagctcacc gtggacaaga gcaggtggca gcaggggaac  1440
gtcttctcat gctccgtgat gcatgaggct ctgcacaacc actacacgca gaagagcctc  1500
tctctctctc cgggtaaagt cgacggagct agcagccccg tgaacgtgag cagccccagc  1560
gtgcaggata tcctcttcag gaaccaccag tcttcttacc aaacacgact taatgctctc  1620
cgagaggtac aacccgtaga acttcctaac tgtaatttag ttaaaggaat cgaaactggc  1680
tctgaagact tggagatact gcctaatgga ctggctttca ttagctctgg attaaagtat  1740
cctggaataa agagcttcaa ccccaacagt cctggaaaaa tacttctgat ggacctgaat  1800
gaagaagatc caacagtgtt ggaattgggg atcactggaa gtaaatttga tgtatcttca  1860
tttaaccctc atgggattag cacattcaca gatgaagata atgccatgta cctcctggtg  1920
gtgaaccatc cagatgccaa gtccacagtg gagttgttta aatttcaaga agaagaaaaa  1980
tcgcttttgc atctaaaaac catcagacat aaacttctgc ctaatttgaa tgatattgtt  2040
gctgtgggac ctgagcactt ttatggcaca aatgatcact attttcttga cccctactta  2100
aaatcctggg agatgtattt gggtttagcg tggtcgtatg ttgtctacta tagtccaagt  2160
gaagttcgag tggtggcaga aggatttgat tttgctaatg gaatcaacat ttcacccgat  2220
ggcaagtatg tctatatagc tgagttgctg gctcataaga ttcatgtgta tgaaaagcat  2280
gctaattgga ctttaactcc attgaagtcc cttgacttta ataccctcgt ggataacata  2340
tctgtggatc ctgagacagg agacctttgg gttggatgcc atcccaatgg catgaaaatc  2400
ttcttctatg actcagagaa tcctcctgca tcagaggtgc ttcgaatcca gaacattcta  2460
acagaagaac ctaaagtgac acaggtttat gcagaaaatg gcacagtgtt gcaaggcagt  2520
acagttgcct ctgtgtacaa agggaaactg ctgattggca cagtgtttca caaagctctt  2580
tactgtgagc tctaataatc tagaa                                     2605

SEQ ID NO: 98          moltype = AA  length = 860
FEATURE                Location/Qualifiers
REGION                 1..860
                       note = hVK3LP-[VH-VL anti-TNFalpha
                        scFv]-[SSShinge-P238S-P331S Fc]-NGS-[PON1 Q192K]
source                 1..860
                       mol_type = protein
                       organism = synthetic construct
SEQUENCE: 98
METPAQLLFL LLLWLPDTTG EVQLVESGGG LVQPGRSLRL SCAASGFTFD DYAMHWVRQA  60
PGKGLEWVSA ITWNSGHIDY ADSVEGRFTI SRDNAKNSLY LQMNSLRAED TAVYYCAKVS  120
YLSTASSLDY WGQGTLVTVS SGGGGSGGGG SGGGGSGGGG SDIQMTQSPS SLSASVGDRV  180
TITCRASQGI RNYLAWYQQK PGKAPKLLIY AASTLQSGVP SRFSGSGSGT DFTLTISSLQ  240
PEDVATYYCQ RYNRAPYTFG QGTKVEIKDL EPKSSDKTHT SPPSPAPELL GGSSVFLFPP  300
KPKDTLMISR TPEVTCVVVD VSHEDPEVKF NWYVDGVEVH NAKTKPREEQ YNSTYRVVSV  360
LTVLHQDWLN GKEYKCKVSN KALPASIEKT ISKAKGQPRE PQVYTLPPSR DELTKNQVSL  420
TCLVKGFYPS DIAVEWESNG QPENNYKTTP PVLDSDGSFF LYSKLTVDKS RWQQGNVFSC  480
SVMHEALHNH YTQKSLSLSP GKVDGASSPV NVSSPSVQDI LFRNHQSSYQ TRLNALREVQ  540
PVELPNCNLV KGIETGSEDL EILPNGLAFI SSGLKYPGIK SFNPNSPGKI LLMDLNEEDP  600
TVLELGITGS KFDVSSFNPH GISTFTDEDN AMYLLVVNHP DAKSTVELFK FQEEEKSLLH  660
LKTIRHKLLP NLNDIVAVGP EHFYGTNDHY FLDPYLKSWE MYLGLAWSYV VYYSPSEVRV  720
VAEGFDFANG INISPDGKYV YIAELLAHKI HVYEKHANWT LTPLKSLDFN TLVDNISVDP  780
ETGDLWVGCH PNGMKIFFYD SENPPASEVL RIQNILTEEP KVTQVYAENG TVLQGSTVAS  840
VYKGKLLIGT VFHKALYCEL                                           860

SEQ ID NO: 99          moltype = DNA  length = 819
FEATURE                Location/Qualifiers
misc_feature           1..819
                       note = hVK3LP-[anti-hTGFbeta VH-VL scFv] DNA
source                 1..819
                       mol_type = other DNA
                       organism = synthetic construct
SEQUENCE: 99
aagcttgccg ccatggaaac cccagcgcag cttctcttcc tcctgctact ctggctcccg  60
gataccaccg gtgaagttca gctggtggag tctggcggtg gcctggtgca gccagggggc  120
tcactccgtt tgtcctgtgc agcttctggc tacgcattca ccaactatct gatcgagtgg  180
```

```
gtccgtcagg ccccgggtaa gggcctcgag tgggttggtg ttaacaatcc tggatccgga  240
ggctccaact ataacgagaa gttcaagggg cgcgccacta tcagtgcaga caattcgaaa  300
aacacattat acctgcagat gaacagcctg cgtgctgagg acactgccgt ctattattgt  360
gctcgatccg gaggcttcta cttcgactac tggggtcaag gaaccctggt caccgtctcc  420
tcgggaggtg gtggatctgg tggaggaggt tcaggtggtg gaggatctgg gggtggaggt  480
agtgatatcc agatgaccca gtccccgagc tccctgtccg cctctgtggg cgatagggtc  540
accatcacct gcagagccag tcagagcgtg ctgtatagtt cgaatcagaa gaactacctg  600
gcctggtatc aacagaaacc aggaaaagct ccgaaactac tgatttactg ggctagcact  660
agagaatctg gagtcccttc tcgcttctct ggatccggtt ctgggacgga tttcactctg  720
accatcagca gtctgcagcc agaagacttc gcaacttatt actgtcacca gtatctgagc  780
tctgacacat ttggacaggg taccaaggtg gagatcaaa                         819

SEQ ID NO: 100          moltype = AA  length = 269
FEATURE                 Location/Qualifiers
REGION                  1..269
                        note = hVK3LP-[anti-hTGFbeta VH-VL scFv]
source                  1..269
                        mol_type = protein
                        organism = synthetic construct
SEQUENCE: 100
METPAQLLFL LLLWLPDTTG EVQLVESGGG LVQPGGSLRL SCAASGYAFT NYLIEWVRQA  60
PGKGLEWVGV NNPGSGGSNY NEKFKGRATI SADNSKNTLY LQMNSLRAED TAVYYCARSG  120
GFYFDYWGQG TLVTVSSGGG GSGGGGSGGG GSGGGGSDIQ MTQSPSSLSA SVGDRVTITC  180
RASQSVLYSS NQKNYLAWYQ QKPGKAPKLL IYWASTRESG VPSRFSGSGS GTDFTLTISS  240
LQPEDFATYY CHQYLSSDTF GQGTKVEIK                                    269

SEQ ID NO: 101          moltype = DNA  length = 2608
FEATURE                 Location/Qualifiers
misc_feature            1..2608
                        note = hVK3LP-[anti-hTGFbeta VH-VL
                         scFv]-SSShinge-P238S-P331S Fc]-NGS-PON1 Q192K] DNA
source                  1..2608
                        mol_type = other DNA
                        organism = synthetic construct
SEQUENCE: 101
aagcttgccg ccatggaaac cccagcgcag cttctcttcc tcctgctact ctggctcccg  60
gataccaccg gtgaagttca gctggtggag tctggcggtg gcctggtgca gccagggggc  120
tcactccgtt tgtcctgtgc agcttctggc tacgcattca ccaactatct gatcgagtgg  180
gtccgtcagg ccccgggtaa gggcctcgag tgggttggtg ttaacaatcc tggatccgga  240
ggctccaact ataacgagaa gttcaagggg cgcgccacta tcagtgcaga caattcgaaa  300
aacacattat acctgcagat gaacagcctg cgtgctgagg acactgccgt ctattattgt  360
gctcgatccg gaggcttcta cttcgactac tggggtcaag gaaccctggt caccgtctcc  420
tcgggaggtg gtggatctgg tggaggaggt tcaggtggtg gaggatctgg gggtggaggt  480
agtgatatcc agatgaccca gtccccgagc tccctgtccg cctctgtggg cgatagggtc  540
accatcacct gcagagccag tcagagcgtg ctgtatagtt cgaatcagaa gaactacctg  600
gcctggtatc aacagaaacc aggaaaagct ccgaaactac tgatttactg ggctagcact  660
agagaatctg gagtcccttc tcgcttctct ggatccggtt ctgggacgga tttcactctg  720
accatcagca gtctgcagcc agaagacttc gcaacttatt actgtcacca gtatctgagc  780
tctgacacat ttggacaggg taccaaggtg gagatcaaag atctcgagcc caaatcttct  840
gacaaaactc acacatctcc accgtcccca gcacctgaac tcctgggagg atcgtcagtc  900
ttcctcttcc ccccaaaacc caaggacacc ctcatgatct cccggacccc tgaggtcaca  960
tgcgtggtgg tggacgtgag ccacgaagac cctgaggtca agttcaactg gtacgtggac  1020
ggcgtggagg tgcataatgc caagacaaag ccgcgggagg agcagtacaa cagcacgtac  1080
cgtgtggtca gcgtcctcac cgtcctgcac caggactggc tgaatggcaa ggagtacaag  1140
tgcaaggtct ccaacaaagc cctcccagcc tccatcgaga aaaccatctc caaagccaaa  1200
gggcagcccc gagaaccaca ggtgtacacc ctgcccccat cccgggatga gctgaccaag  1260
aaccaggtca gcctgacctg cctggtcaaa ggcttctatc ccagcgacat cgccgtggag  1320
tgggagagca atgggcagcc ggagaacaac tacaagacca cgcctcccgt gctggactcc  1380
gacggctcct tcttcctcta cagcaagctc accgtggaca agagcaggtg gcagcagggg  1440
aacgtcttct catgctccgt gatgcatgag gctctgcaca accactacac gcagaagagc  1500
ctctctctct ctccgggtaa agtcgacgga gctagcagcc ccgtgaacgt gagcagcccc  1560
agcgtgcagg atatcctctt caggaaccac cagtcttctt accaaacacg acttaatgct  1620
ctccgagagg tacaacccgt agaacttcct aactgtaatt tagttaaagg aatcgaaact  1680
ggctctgaag acttggagat actgcctaat ggactggctt tcattagctc tggattaaag  1740
tatcctggaa taaagagctt caaccccaac agtcctggaa aaatacttct gatggacctg  1800
aatgaagaag atccaacagt gttggaattg gggatcactg gaagtaaatt tgatgtatct  1860
tcatttaacc ctcatgggat tagcacattc acagatgaag ataatgccat gtacctcctg  1920
gtggtgaacc atccagatgc caagtccaca gtggagttgt ttaaatttca agaagaagaa  1980
aaatcgcttt tgcatctaaa aaccatcaga cataaacttc tgcctaattt gaatgatatt  2040
gttgctgtgg gacctgagca cttttatggc acaaatgatc actattttct tgacccctac  2100
ttaaaatcct gggagatgta tttgggttta gcgtggtcgt atgttgtcta ctatagtcca  2160
agtgaagttc gagtggtggc agaaggattt gattttgcta atggaatcaa catttcaccc  2220
gatggcaagt atgtctatat agctgagttg ctggctcata agattcatgt gtatgaaaag  2280
catgctaatt ggactttaac tccattgaag tcccttgact ttaataccct cgtggataac  2340
atatctgtgg atcctgagac aggagacctt tgggttggat gccatcccaa tggcatgaaa  2400
atcttcttct atgactcaga gaatcctcct gcatcagagg tgcttcgaat ccagaacatt  2460
ctaacagaag aacctaaagt gacacaggtt tatgcagaaa atggcacagt gttgcaaggc  2520
agtacagttg cctctgtgta caaagggaaa ctgctgattg gcacagtgtt tcacaaagct  2580
ctttactgtg agctctaata atctagaa                                     2608
```

```
SEQ ID NO: 102          moltype = AA  length = 861
FEATURE                 Location/Qualifiers
REGION                  1..861
                        note = hVK3LP-[anti-hTGFbeta VH-VL
                         scFv]-SSShinge-P238S-P331S Fc]-NGS-PON1 Q192K]
source                  1..861
                        mol_type = protein
                        organism = synthetic construct
SEQUENCE: 102
METPAQLLFL LLLWLPDTTG EVQLVESGGG LVQPGGSLRL SCAASGYAFT NYLIEWVRQA  60
PGKGLEWVGV NNPGSGGSNY NEKFKGRATI SADNSKNTLY LQMNSLRAED TAVYYCARSG  120
GFYFDYWGQG TLVTVSSGGG GSGGGGSGGG GSGGGGSDIQ MTQSPSSLSA SVGDRVTITC  180
RASQSVLYSS NQKNYLAWYQ QKPGKAPKLL IYWASTRESG VPSRFSGSGS GTDFTLTISS  240
LQPEDFATYY CHQYLSSDTF GQGTKVEIKD LEPKSSDKTH TSPPSPAPEL LGGSSVFLFP  300
PKPKDTLMIS RTPEVTCVVV DVSHEDPEVK FNWYVDGVEV HNAKTKPREE QYNSTYRVVS  360
VLTVLHQDWL NGKEYKCKVS NKALPASIEK TISKAKGQPR EPQVYTLPPS RDELTKNQVS  420
LTCLVKGFYP SDIAVEWESN GQPENNYKTT PPVLDSDGSF FLYSKLTVDK SRWQQGNVFS  480
CSVMHEALHN HYTQKSLSLS PGKVDGASSP VNVSSPSVQD ILFRNHQSSY QTRLNALREV  540
QPVELPNCNL VKGIETGSED LEILPNGLAF ISSGLKYPGI KSFNPNSPGK ILLMDLNEED  600
PTVLELGITG SKFDVSSFNP HGISTFTDED NAMYLLVVNH PDAKSTVELF KFQEEEKSLL  660
HLKTIRHKLL PNLNDIVAVG PEHFYGTNDH YFLDPYLKSW EMYLGLAWSY VVYYSPSEVR  720
VVAEGFDFAN GINISPDGKY VYIAELLAHK IHVYEKHANW TLTPLKSLDF NTLVDNISVD  780
PETGDLWVGC HPNGMKIFFY DSENPPASEV LRIQNILTEE PKVTQVYAEN GTVLQGSTVA  840
SVYKGKLLIG TVFHKALYCE L                                          861

SEQ ID NO: 103          moltype = DNA  length = 819
FEATURE                 Location/Qualifiers
misc_feature            1..819
                        note = hVK3LP-[anti-hTGFbeta VL-VH scFv] DNA
source                  1..819
                        mol_type = other DNA
                        organism = synthetic construct
SEQUENCE: 103
aagcttgccg ccatggaaac cccagcgcag cttctcttcc tcctgctact ctggctcccg  60
gataccaccg gtgatatcca gatgacccag tccccgagct ccctgtccgc ctctgtgggc  120
gatagggtca ccatcacctg cagagccagt cagagcgtgc tgtatagttc gaatcagaag  180
aactacctgg cctggtatca acagaaacca ggaaaagctc cgaaactact gatttactgg  240
gctagcacta gagaatctgg agtcccttct cgcttctctg gatccggttc tgggacggat  300
ttcactctga ccatcagcag tctgcagcca gaagacttcg caacttatta ctgtcaccag  360
tatctgagct ctgacacatt tggacagggt accaaggtgg agatcaaagg aggtggtgga  420
tctggtggag gaggttcagg tggtggagga tctgggggtg gaggtagtga agttcagctg  480
gtggagtctg gcggtggcct ggtgcagcca gggggctcac tccgtttgtc ctgtgcagct  540
tctggctacg cattcaccaa ctatctgatc gagtgggtcc gtcaggcccc gggtaagggc  600
ctcgagtggg ttggtgttaa caatcctgga tccggaggct ccaactataa cgagaagttc  660
aaggggcgcg ccactatcag tgcagacaat tcgaaaaaca cattatacct gcagatgaac  720
agcctgcgtg ctgaggacac tgccgtctat tattgtgctc gatccggagg cttctacttc  780
gactactggg gtcaaggaac cctggtcacc gtctcctcg                       819

SEQ ID NO: 104          moltype = AA  length = 269
FEATURE                 Location/Qualifiers
REGION                  1..269
                        note = hVK3LP-[anti-hTGFbeta VL-VH scFv]
source                  1..269
                        mol_type = protein
                        organism = synthetic construct
SEQUENCE: 104
METPAQLLFL LLLWLPDTTG DIQMTQSPSS LSASVGDRVT ITCRASQSVL YSSNQKNYLA  60
WYQQKPGKAP KLLIYWASTR ESGVPSRFSG SGSGTDFTLT ISSLQPEDFA TYYCHQYLSS  120
DTFGQGTKVE IKGGGGSGGG GSGGGGSGGG GSEVQLVESG GGLVQPGGSL RLSCAASGYA  180
FTNYLIEWVR QAPGKGLEWV GVNNPGSGGS NYNEKFKGRA TISADNSKNT LYLQMNSLRA  240
EDTAVYYCAR SGGFYFDYWG QGTLVTVSS                                  269

SEQ ID NO: 105          moltype = DNA  length = 2608
FEATURE                 Location/Qualifiers
misc_feature            1..2608
                        note = hVK3LP-[anti-hTGFbeta VL-VH
                         scFv]-SSShinge-P238S-P331S Fc]-NGS-PON1 Q192K] DNA
source                  1..2608
                        mol_type = other DNA
                        organism = synthetic construct
SEQUENCE: 105
aagcttgccg ccatggaaac cccagcgcag cttctcttcc tcctgctact ctggctcccg  60
gataccaccg gtgatatcca gatgacccag tccccgagct ccctgtccgc ctctgtgggc  120
gatagggtca ccatcacctg cagagccagt cagagcgtgc tgtatagttc gaatcagaag  180
aactacctgg cctggtatca acagaaacca ggaaaagctc cgaaactact gatttactgg  240
gctagcacta gagaatctgg agtcccttct cgcttctctg gatccggttc tgggacggat  300
ttcactctga ccatcagcag tctgcagcca gaagacttcg caacttatta ctgtcaccag  360
tatctgagct ctgacacatt tggacagggt accaaggtgg agatcaaagg aggtggtgga  420
```

```
tctggtggag gaggttcagg tggtggagga tctgggggtg gaggtagtga agttcagctg  480
gtggagtctg gcggtggcct ggtgcagcca gggggctcac tccgtttgtc ctgtgcagct  540
tctggctacg cattcaccaa ctatctgatc gagtgggtcc gtcaggcccc gggtaagggc  600
ctcgagtggg ttggtgttaa caatcctgga tccggaggct ccaactataa cgagaagttc  660
aaggggcgcg ccactatcag tgcagacaat tcgaaaaaca cattatacct gcagatgaac  720
agcctgcgtg ctgaggacac tgccgtctat tattgtgctc gatccggagg cttctacttc  780
gactactggg gtcaaggaac cctggtcacc gtctcctcag atctcgagcc caaatcttct  840
gacaaaactc acacatctcc accgtcccca gcacctgaac tcctgggagg atcgtcagtc  900
ttcctcttcc ccccaaaacc caaggacacc ctcatgatct cccggacccc tgaggtcaca  960
tgcgtggtgg tggacgtgag ccacgaagac cctgaggtca agttcaactg gtacgtggac  1020
ggcgtggagg tgcataatgc caagacaaag ccgcgggagg agcagtacaa cagcacgtac  1080
cgtgtggtca gcgtcctcac cgtcctgcac caggactggc tgaatggcaa ggagtacaag  1140
tgcaaggtct ccaacaaagc cctcccagcc tccatcgaga aaaccatctc caaagccaaa  1200
gggcagcccc gagaaccaca ggtgtacacc ctgcccccat cccgggatga gctgaccaag  1260
aaccaggtca gcctgacctg cctggtcaaa ggcttctatc ccagcgacat cgccgtggag  1320
tgggagagca atgggcagcc ggagaacaac tacaagacca cgcctcccgt gctggactcc  1380
gacggctcct tcttcctcta cagcaagctc accgtggaca agagcaggtg gcagcagggg  1440
aacgtcttct catgctccgt gatgcatgag gctctgcaca accactacac gcagaagagc  1500
ctctctctct ctccgggtaa agtcgacgga gctagcagcc ccgtgaacgt gagcagcccc  1560
agcgtgcagg atatcctctt caggaaccac cagtcttctt accaaacacg acttaatgct  1620
ctccgagagg tacaacccgt agaacttcct aactgtaatt tagttaaagg aatcgaaact  1680
ggctctgaag acttggagat actgcctaat ggactggctt tcattagctc tggattaaag  1740
tatcctggaa taaagagctt caaccccaac agtcctggaa aaatacttct gatggacctg  1800
aatgaagaag atccaacagt gttggaattg gggatcactg gaagtaaatt tgatgtatct  1860
tcatttaacc ctcatgggat tagcacattc acagatgaag ataatgccat gtacctcctg  1920
gtggtgaacc atccagatgc caagtccaca gtggagttgt ttaaatttca agaagaagaa  1980
aaatcgcttt tgcatctaaa aaccatcaga cataaacttc tgcctaattt gaatgatatt  2040
gttgctgtgg gacctgagca cttttatggc acaaatgatc actattttct tgacccctac  2100
ttaaaatcct gggagatgta tttgggttta gcgtggtcgt atgttgtcta ctatagtcca  2160
agtgaagttc gagtggtggc agaaggattt gattttgcta atggaatcaa catttcaccc  2220
gatggcaagt atgtctatat agctgagttg ctggctcata agattcatgt gtatgaaaag  2280
catgctaatt ggactttaac tccattgaag tcccttgact ttaataccct cgtggataac  2340
atatctgtgg atcctgagac aggagacctt tgggttggat gccatcccaa tggcatgaaa  2400
atcttcttct atgactcaga gaatcctcct gcatcagagg tgcttcgaat ccagaacatt  2460
ctaacagaag aacctaaagt gacacaggtt tatgcagaaa atggcacagt gttgcaaggc  2520
agtacagttg cctctgtgta caaagggaaa ctgctgattg gcacagtgtt tcacaaagct  2580
ctttactgtg agctctaata atctagaa                                    2608
```

```
SEQ ID NO: 106          moltype = AA  length = 861
FEATURE                 Location/Qualifiers
REGION                  1..861
                        note = hVK3LP-[anti-hTGFbeta VL-VH
                         scFv]-SSShinge-P238S-P331S Fc]-NGS-PON1 Q192K]
source                  1..861
                        mol_type = protein
                        organism = synthetic construct
SEQUENCE: 106
METPAQLLFL LLLWLPDTTG DIQMTQSPSS LSASVGDRVT ITCRASQSVL YSSNQKNYLA  60
WYQQKPGKAP KLLIYWASTR ESGVPSRFSG SGSGTDFTLT ISSLQPEDFA TYYCHQYLSS  120
DTFGQGTKVE IKGGGGSGGG GSGGGGSGGG GSEVQLVESG GGLVQPGGSL RLSCAASGYA  180
FTNYLIEWVR QAPGKGLEWV GVNNPGSGGS NYNEKFKGRA TISADNSKNT LYLQMNSLRA  240
EDTAVYYCAR SGGFYFDYWG QGTLVTVSSD LEPKSSDKTH TSPPSPAPEL LGGSSVFLFP  300
PKPKDTLMIS RTPEVTCVVV DVSHEDPEVK FNWYVDGVEV HNAKTKPREE QYNSTYRVVS  360
VLTVLHQDWL NGKEYKCKVS NKALPASIEK TISKAKGQPR EPQVYTLPPS RDELTKNQVS  420
LTCLVKGFYP SDIAVEWESN GQPENNYKTT PPVLDSDGSF FLYSKLTVDK SRWQQGNVFS  480
CSVMHEALHN HYTQKSLSLS PGKVDGASSP VNVSSPSVQD ILFRNHQSSY QTRLNALREV  540
QPVELPNCNL VKGIETGSED LEILPNGLAF ISSGLKYPGI KSFNPNSPGK ILLMDLNEED  600
PTVLELGITG SKFDVSSFNP HGISTFTDED NAMYLLVVNH PDAKSTVELF KFQEEEKSLL  660
HLKTIRHKLL PNLNDIVAVG PEHFYGTNDH YFLDPYLKSW EMYLGLAWSY VVYYSPSEVR  720
VVAEGFDFAN GINISPDGKY VYIAELLAHK IHVYEKHANW TLTPLKSLDF NTLVDNISVD  780
PETGDLWVGC HPNGMKIFFY DSENPPASEV LRIQNILTEE PKVTQVYAEN GTVLQGSTVA  840
SVYKGKLLIG TVFHKALYCE L                                           861
```

```
SEQ ID NO: 107          moltype = DNA  length = 363
FEATURE                 Location/Qualifiers
source                  1..363
                        mol_type = other DNA
                        organism = Homo sapiens
SEQUENCE: 107
gataccaccg gtgaggtgca gctggtggag tctgggggag gcttggtaca gcccggcagg  60
tccctgagac tctcctgtgc ggcctctgga ttcacctttg atgattatgc catgcactgg  120
gtccggcaag ctccagggaa gggcctggaa tgggtctcag ctatcacttg gaatagtggt  180
cacatagact atgcggactc tgtggagggc cgattcacca tctccagaga caacgccaag  240
aactccctgt atctgcaaat gaacagtctg agagctgagg atacggccgt atattactgt  300
gcgaaagtct cgtaccttag caccgcgtcc tcccttgact attggggcca aggtaccctg  360
gtc                                                               363
```

```
SEQ ID NO: 108          moltype = AA  length = 121
FEATURE                 Location/Qualifiers
```

```
source                  1..121
                        mol_type = protein
                        organism = Homo sapiens
SEQUENCE: 108
EVQLVESGGG LVQPGRSLRL SCAASGFTFD DYAMHWVRQA PGKGLEWVSA ITWNSGHIDY  60
ADSVEGRFTI SRDNAKNSLY LQMNSLRAED TAVYYCAKVS YLSTASSLDY WGQGTLVTVS  120
S                                                                 121

SEQ ID NO: 109          moltype = DNA  length = 321
FEATURE                 Location/Qualifiers
source                  1..321
                        mol_type = other DNA
                        organism = Homo sapiens
SEQUENCE: 109
gataccaccg gtgacatcca gatgacccag tctccatcct ccctgtctgc atctgtaggg  60
gacagagtca ccatcacttg tcgggcaagt cagggcatca gaaattactt agcctggtat  120
cagcaaaaac cagggaaagc ccctaagctc ctgatctatg ctgcatccac tttgcaatca  180
ggggtcccat ctcggttcag tggcagtgga tctgggacag atttcactct caccatcagc  240
agcctacagc ctgaagatgt tgcaacttat tactgtcaaa ggtataaccg tgcaccgtat  300
acttttggcc aggggaccaa g                                           321

SEQ ID NO: 110          moltype = AA  length = 107
FEATURE                 Location/Qualifiers
source                  1..107
                        mol_type = protein
                        organism = Homo sapiens
SEQUENCE: 110
DIQMTQSPSS LSASVGDRVT ITCRASQGIR NYLAWYQQKP GKAPKLLIYA ASTLQSGVPS  60
RFSGSGSGTD FTLTISSLQP EDVATYYCQR YNRAPYTFGQ GTKVEIK               107

SEQ ID NO: 111          moltype = DNA  length = 351
FEATURE                 Location/Qualifiers
misc_feature            1..351
                        note = Humanized anti-hTGFbeta VH DNA
source                  1..351
                        mol_type = other DNA
                        organism = synthetic construct
SEQUENCE: 111
gataccaccg gtgaagttca gctggtggag tctggcggtg gcctggtgca gccagggggc  60
tcactccgtt tgtcctgtgc agcttctggc tacgcattca ccaactatct gatcgagtgg  120
gtccgtcagg ccccgggtaa gggcctcgag tgggttggtg ttaacaatcc tggatccgga  180
ggctccaact ataacgagaa gttcaagggg cgcgccacta tcagtgcaga caattcgaaa  240
aacacattat acctgcagat gaacagcctg cgtgctgagg acactgccgt ctattattgt  300
gctcgatccg gaggcttcta cttcgactac tggggtcaag gaaccctggt c          351

SEQ ID NO: 112          moltype = AA  length = 117
FEATURE                 Location/Qualifiers
REGION                  1..117
                        note = Humanized anti-hTGFbeta VH
source                  1..117
                        mol_type = protein
                        organism = synthetic construct
SEQUENCE: 112
EVQLVESGGG LVQPGGSLRL SCAASGYAFT NYLIEWVRQA PGKGLEWVGV NNPGSGGSNY  60
NEKFKGRATI SADNSKNTLY LQMNSLRAED TAVYYCARSG GFYFDYWGQG TLVTVSS     117

SEQ ID NO: 113          moltype = DNA  length = 336
FEATURE                 Location/Qualifiers
misc_feature            1..336
                        note = Humanized anti-hTGFbeta VL DNA
source                  1..336
                        mol_type = other DNA
                        organism = synthetic construct
SEQUENCE: 113
gataccaccg gtgatatcca gatgacccag tccccgagct ccctgtccgc ctctgtgggc  60
gatagggtca ccatcacctg cagagccagt cagagcgtgc tgtatagttc gaatcagaag  120
aactacctgg cctggtatca acagaaacca ggaaaagctc cgaaactact gatttactgg  180
gctagcacta gagaatctgg agtcccttct cgcttctctg gatccggttc tgggacggat  240
ttcactctga ccatcagcag tctgcagcca gaagacttcg caacttatta ctgtcaccag  300
tatctgagct ctgacacatt tggacagggt accaag                           336

SEQ ID NO: 114          moltype = AA  length = 112
FEATURE                 Location/Qualifiers
REGION                  1..112
                        note = Humanized anti-hTGFbeta VL
source                  1..112
                        mol_type = protein
                        organism = synthetic construct
SEQUENCE: 114
```

```
DIQMTQSPSS LSASVGDRVT ITCRASQSVL YSSNQKNYLA WYQQKPGKAP KLLIYWASTR  60
ESGVPSRFSG SGSGTDFTLT ISSLQPEDFA TYYCHQYLSS DTFGQGTKVE IK          112

SEQ ID NO: 115         moltype = DNA  length = 696
FEATURE                Location/Qualifiers
misc_feature           1..696
                       note = Human IgG1 variant Fc DNA (SCC hinge, P238S, P331S)
source                 1..696
                       mol_type = other DNA
                       organism = synthetic construct
SEQUENCE: 115
gagcccaaat cttctgacaa aactcacaca tgtccaccgt gcccagcacc tgaactcctg  60
ggaggatcgt cagtcttcct cttcccccca aaacccaagg acaccctcat gatctcccgg  120
acccctgagg tcacatgcgt ggtggtggac gtgagccacg aagaccctga ggtcaagttc  180
aactggtacg tggacggcgt ggaggtgcat aatgccaaga caaagccgcg ggaggagcag  240
tacaacagca cgtaccgtgt ggtcagcgtc ctcaccgtcc tgcaccagga ctggctgaat  300
ggcaaggagt acaagtgcaa ggtctccaac aaagccctcc cagcctccat cgagaaaacc  360
atctccaaag ccaaagggca gccccgagaa ccacaggtgt acaccctgcc cccatcccgg  420
gatgagctga ccaagaacca ggtcagcctg acctgcctgg tcaaaggctt ctatcccagc  480
gacatcgccg tggagtggga gagcaatggg cagccggaga acaactacaa gaccacgcct  540
cccgtgctgg actccgacgg ctccttcttc ctctacagca agctcaccgt ggacaagagc  600
aggtggcagc aggggaacgt cttctcatgc tccgtgatgc atgaggctct gcacaaccac  660
tacacgcaga agagcctctc tctctctccg ggtaaa                            696

SEQ ID NO: 116         moltype = AA  length = 232
FEATURE                Location/Qualifiers
REGION                 1..232
                       note = Human IgG1 variant Fc (SCC hinge, P238S, P331S)
source                 1..232
                       mol_type = protein
                       organism = synthetic construct
SEQUENCE: 116
EPKSSDKTHT CPPCPAPELL GGSSVFLFPP KPKDTLMISR TPEVTCVVVD VSHEDPEVKF  60
NWYVDGVEVH NAKTKPREEQ YNSTYRVVSV LTVLHQDWLN GKEYKCKVSN KALPASIEKT  120
ISKAKGQPRE PQVYTLPPSR DELTKNQVSL TCLVKGFYPS DIAVEWESNG QPENNYKTTP  180
PVLDSDGSFF LYSKLTVDKS RWQQGNVFSC SVMHEALHNH YTQKSLSLSP GK          232

SEQ ID NO: 117         moltype = DNA  length = 696
FEATURE                Location/Qualifiers
misc_feature           1..696
                       note = Human IgG1 variant Fc DNA (SCC hinge, P238S)
source                 1..696
                       mol_type = other DNA
                       organism = synthetic construct
SEQUENCE: 117
gagcccaaat cttctgacaa aactcacaca tgtccaccgt gcccagcacc tgaactcctg  60
ggaggatcgt cagtcttcct cttcccccca aaacccaagg acaccctcat gatctcccgg  120
acccctgagg tcacatgcgt ggtggtggac gtgagccacg aagaccctga ggtcaagttc  180
aactggtacg tggacggcgt ggaggtgcat aatgccaaga caaagccgcg ggaggagcag  240
tacaacagca cgtaccgtgt ggtcagcgtc ctcaccgtcc tgcaccagga ctggctgaat  300
ggcaaggagt acaagtgcaa ggtctccaac aaagccctcc cagcccccat cgagaaaacc  360
atctccaaag ccaaagggca gccccgagaa ccacaggtgt acaccctgcc cccatcccgg  420
gatgagctga ccaagaacca ggtcagcctg acctgcctgg tcaaaggctt ctatcccagc  480
gacatcgccg tggagtggga gagcaatggg cagccggaga acaactacaa gaccacgcct  540
cccgtgctgg actccgacgg ctccttcttc ctctacagca agctcaccgt ggacaagagc  600
aggtggcagc aggggaacgt cttctcatgc tccgtgatgc atgaggctct gcacaaccac  660
tacacgcaga agagcctctc tctctctccg ggtaaa                            696

SEQ ID NO: 118         moltype = AA  length = 232
FEATURE                Location/Qualifiers
REGION                 1..232
                       note = Human IgG1 variant Fc (SCC hinge, P238S)
source                 1..232
                       mol_type = protein
                       organism = synthetic construct
SEQUENCE: 118
EPKSSDKTHT CPPCPAPELL GGSSVFLFPP KPKDTLMISR TPEVTCVVVD VSHEDPEVKF  60
NWYVDGVEVH NAKTKPREEQ YNSTYRVVSV LTVLHQDWLN GKEYKCKVSN KALPAPIEKT  120
ISKAKGQPRE PQVYTLPPSR DELTKNQVSL TCLVKGFYPS DIAVEWESNG QPENNYKTTP  180
PVLDSDGSFF LYSKLTVDKS RWQQGNVFSC SVMHEALHNH YTQKSLSLSP GK          232

SEQ ID NO: 119         moltype = AA  length = 5
FEATURE                Location/Qualifiers
REGION                 1..5
                       note = (gly4ser) tandem repeat sequence
source                 1..5
                       mol_type = protein
                       organism = synthetic construct
SEQUENCE: 119
```

```
GGGGS                                                             5

SEQ ID NO: 120         moltype = AA  length = 260
FEATURE                Location/Qualifiers
source                 1..260
                       mol_type = protein
                       organism = Homo sapiens
SEQUENCE: 120
LKIAAFNIQT FGETKMSNAT LVSYIVQILS RYDIALVQEV RDSHLTAVGK LLDNLNQDAP  60
DTYHYVVSEP LGRNSYKERY LFVYRPDQVS AVDSYYYDDG CEPCGNDTFN REPAIVRFFS  120
RFTEVREFAI VPLHAAPGDA VAEIDALYDV YLDVQEKWGL EDVMLMGDFN AGCSYVRPSQ  180
WSSIRLWTSP TFQWLIPDSA DTTATPTHCA YDRIVVAGML LRGAVVPDSA LPFNFQAAYG  240
LSDQLAQAIS DHYPVEVMLK                                             260

SEQ ID NO: 121         moltype = DNA  length = 1842
FEATURE                Location/Qualifiers
misc_feature           1..1842
                       note = hVK3LP-[KDL-SCChinge-P238S-P331S Fc]-NGS-[PON1
                        Q192K] DNA
source                 1..1842
                       mol_type = other DNA
                       organism = synthetic construct
SEQUENCE: 121
atggaaaccc cagcgcagct tctcttcctc ctgctactct ggctcccaga taccaccggt  60
aaagatctcg agcccaaatc ttctgacaaa actcacacat gtccaccgtg cccagcacct  120
gaactcctgg gaggatcgtc agtcttcctc ttccccccaa aacccaagga caccctcatg  180
atctcccgga cccctgaggt cacatgcgtg gtggtggacg tgagccacga agaccctgag  240
gtcaagttca actggtacgt ggacggcgtg gaggtgcata atgccaagac aaagccgcgg  300
gaggagcagt acaacagcac gtaccgtgtg gtcagcgtcc tcaccgtcct gcaccaggac  360
tggctgaatg gcaaggagta caagtgcaag gtctccaaca aagccctccc agcctccatc  420
gagaaaacca tctccaaagc caaagggcag ccccgagaac cacaggtgta caccctgccc  480
ccatcccggg atgagctgac caagaaccag gtcagcctga cctgcctggt caaaggcttc  540
tatcccagcg acatcgccgt ggagtgggag agcaatgggc agccggagaa caactacaag  600
accacgcctc ccgtgctgga ctccgacggc tccttcttcc tctacagcaa gctcaccgtg  660
gacaagagca ggtggcagca ggggaacgtc ttctcatgct ccgtgatgca tgaggctctg  720
cacaaccact acacgcagaa gagcctctct ctctctccgg gtaaagtcga cggagctagc  780
agccccgtga acgtgagcag ccccagcgtg caggatatcc tcttcaggaa ccaccagtct  840
tcttaccaaa cacgacttaa tgctctccga gaggtacaac ccgtagaact tcctaactgt  900
aatttagtta aaggaatcga aactggctct gaagacttgg agatactgcc taatggactg  960
gctttcatta gctctggatt aaagtatcct ggaataaaga gcttcaaccc caacagtcct  1020
ggaaaaatac ttctgatgga cctgaatgaa gaagatccaa cagtgttgga attggggatc  1080
actggaagta aatttgatgt atcttcattt aaccctcatg ggattagcac attcacagat  1140
gaagataatg ccatgtacct cctggtggtg aaccatccag atgccaagtc cacagtggag  1200
ttgtttaaat ttcaagaaga agaaaaatcg cttttgcatc taaaaaccat cagacataaa  1260
cttctgccta atttgaatga tattgttgct gtgggacctg agcactttta tggcacaaat  1320
gatcactatt ttcttgaccc ctacttaaaa tcctgggaga tgtatttggg tttagcgtgg  1380
tcgtatgttg tctactatag tccaagtgaa gttcgagtgg tggcagaagg atttgatttt  1440
gctaatggaa tcaacatttc acccgatggc aagtatgtct atatagctga gttgctggct  1500
cataagattc atgtgtatga aaagcatgct aattggactt taactccatt gaagtccctt  1560
gactttaata ccctcgtgga taacatatct gtggatcctg agacaggaga cctttgggtt  1620
ggatgccatc ccaatggcat gaaaatcttc ttctatgact cagagaatcc tcctgcatca  1680
gaggtgcttc gaatccagaa cattctaaca gaagaaccta aagtgacaca ggtttatgca  1740
gaaaatggca cagtgttgca aggcagtaca gttgcctctg tgtacaaagg gaaactgctg  1800
attggcacag tgtttcacaa agctctttac tgtgagctct aa                    1842

SEQ ID NO: 122         moltype = AA  length = 613
FEATURE                Location/Qualifiers
REGION                 1..613
                       note = hVK3LP-[KDL-SCChinge-P238S-P331S Fc]-NGS-[PON1 Q192K]
source                 1..613
                       mol_type = protein
                       organism = synthetic construct
SEQUENCE: 122
METPAQLLFL LLLWLPDTTG KDLEPKSSDK THTCPPCPAP ELLGGSSVFL FPPKPKDTLM  60
ISRTPEVTCV VVDVSHEDPE VKFNWYVDGV EVHNAKTKPR EEQYNSTYRV VSVLTVLHQD  120
WLNGKEYKCK VSNKALPASI EKTISKAKGQ PREPQVYTLP PSRDELTKNQ VSLTCLVKGF  180
YPSDIAVEWE SNGQPENNYK TTPPVLDSDG SFFLYSKLTV DKSRWQQGNV FSCSVMHEAL  240
HNHYTQKSLS LSPGKVDGAS SPVNVSSPSV QDILFRNHQS SYQTRLNALR EVQPVELPNC  300
NLVKGIETGS EDLEILPNGL AFISSGLKYP GIKSFNPNSP GKILLMDLNE EDPTVLELGI  360
TGSKFDVSSF NPHGISTFTD EDNAMYLLVV NHPDAKSTVE LFKFQEEEKS LLHLKTIRHK  420
LLPNLNDIVA VGPEHFYGTN DHYFLDPYLK SWEMYLGLAW SYVVYYSPSE VRVVAEGFDF  480
ANGINISPDG KYVYIAELLA HKIHVYEKHA NWTLTPLKSL DFNTLVDNIS VDPETGDLWV  540
GCHPNGMKIF FYDSENPPAS EVLRIQNILT EEPKVTQVYA ENGTVLQGST VASVYKGKLL  600
IGTVFHKALY CEL                                                    613

SEQ ID NO: 123         moltype = DNA  length = 1065
FEATURE                Location/Qualifiers
misc_feature           1..1065
                       note = Human PON1 variant G3C9 DNA
```

```
source                  1..1065
                        mol_type = other DNA
                        organism = synthetic construct
SEQUENCE: 123
atggctaaac tgacagcgct cacactcttg gggctgggat tggcactctt cgatggacag  60
aagtcttctt tccaaacacg atttaatgtt caccgtgaag taactccagt ggaacttcct  120
aactgtaatt tagttaaagg ggttgacaat ggttctgaag acttggaaat actgcccaat  180
ggactggctt tcatcagctc cggattaaag tatcctggaa taatgagctt tgaccctgat  240
aagtctggaa agatacttct aatggacctg aatgaggaag acccagtagt gttggaactg  300
ggcattactg gaaatacatt ggatatatct tcatttaacc ctcatgggat tagcacattc  360
acagatgaag ataacactgt gtacctactg gtggtaaacc atccagactc ctcgtccacc  420
gtggaggtgt ttaaatttca agaagaagaa aaatcacttt tgcatctgaa aaccatcaga  480
cacaagcttc tgcctagtgt gaatgacatt gtcgctgtgg gacctgaaca cttttatgcc  540
acaaatgatc actattttgc tgacccttac ttaaaatcct gggaaatgca tttgggatta  600
gcgtggtcat ttgttactta ttatagtccc aatgatgttc gagtagtggc agaaggattt  660
gattttgcta acggaatcaa catctcacca gacggcaagt atgtctatat agctgagttg  720
ctggctcata agatccatgt gtatgaaaag cacgctaatt ggactttaac tccattgaag  780
tccctcgact ttgacaccct tgtggataac atctctgtgg atcctgtgac aggggacctc  840
tgggtgggat gccatcccaa cggaatgcga atcttctact atgacccaaa gaatcctccc  900
ggctcagagg tgcttcgaat ccaggacatt ttatccgaag agcccaaagt gacagtggtt  960
tatgcagaaa atggcactgt gttacagggc agcacggtgg ccgctgtgta caaagggaaa  1020
ctgctgattg gcacagtgtt tcacaaagct ctttactgtg agctg  1065

SEQ ID NO: 124          moltype = AA  length = 355
FEATURE                 Location/Qualifiers
REGION                  1..355
                        note = Human PON1 variant G3C9
source                  1..355
                        mol_type = protein
                        organism = synthetic construct
SEQUENCE: 124
MAKLTALTLL GLGLALFDGQ KSSFQTRFNV HREVTPVELP NCNLVKGVDN GSEDLEILPN  60
GLAFISSGLK YPGIMSFDPD KSGKILLMDL NEEDPVVLEL GITGNTLDIS SFNPHGISTF  120
TDEDNTVYLL VVNHPDSSST VEVFKFQEEE KSLLHLKTIR HKLLPSVNDI VAVGPEHFYA  180
TNDHYFADPY LKSWEMHLGL AWSFVTYYSP NDVRVVAEGF DFANGINISP DGKYVYIAEL  240
LAHKIHVYEK HANWTLTPLK SLDFDTLVDN ISVDPVTGDL WVGCHPNGMR IFYYDPKNPP  300
GSEVLRIQDI LSEEPKVTVV YAENGTVLQG STVAAVYKGK LLIGTVFHKA LYCEL  355

SEQ ID NO: 125          moltype = DNA  length = 1065
FEATURE                 Location/Qualifiers
misc_feature            1..1065
                        note = PON1 variant M-IIG1 DNA
source                  1..1065
                        mol_type = other DNA
                        organism = synthetic construct
SEQUENCE: 125
atggctaaac tgacagcgct cacactcttg gggctgggat tggcactctt cgatggacag  60
aagtcttctt tccaaacacg atttaatgtt caccgtgaag taactccagt ggaacttcct  120
aactgtaatt tagttaaagg ggttgacaat ggttctgaag acattgaaat actgcccaat  180
ggactggctt tcatcagctc cggagttaag tatcctggaa taatgagctt tgaccctgat  240
aagtctggaa agatacttct aatggacctg aatgaggaag acccagtagt gttggaactg  300
ggcattactg gaaatacatt ggatatatct tcatttaacc ctgctgggat tagcacattc  360
acagatgaag ataacactgt gtacctactg gtggtaaacc gaccagactc ctcgtccacc  420
gtggaggtgt ttaaatttca agaagaagaa aaatcacttt tgcatctgaa aaccatcaga  480
cacaagcttc tgcctagtgt gaatgacatt gtcgctgtgg gacctgaaca cttttatgcc  540
acaaatgatc actattttgc tgacccttac ttaaaatcct gggaaatgca tttgggatta  600
gcgtggtcat ttgttactta ttatagtccc aatgatgttc gagtagtggc agaaggattt  660
gatatggcta acggaatcaa catctcacca gacggcaagt atgtctatat agctgagttg  720
ctggctcata agatccatgt gtatgaaaag cacgctaatt ggactttaac tccattgaag  780
tccctcgact ttgacaccct tgtggataac atctctgtgg atcctgtgac aggggacctc  840
tgggtgggat gccatcccaa cggaatgcga ttattctact atgacccaaa gaatcctccc  900
ggctcagagg tgcttcgaat ccaggacatt ttatccgaag agcccaaagt gacagtggtt  960
tatgcagaaa atggcactgt gttacagggc agcagtgtgg ccgctgtgta caaagggaaa  1020
ctgctgattg gcacagtgtt tcacaaagct ctttactgtg agctg  1065

SEQ ID NO: 126          moltype = AA  length = 355
FEATURE                 Location/Qualifiers
REGION                  1..355
                        note = PON1 variant M-IIG1
source                  1..355
                        mol_type = protein
                        organism = synthetic construct
SEQUENCE: 126
MAKLTALTLL GLGLALFDGQ KSSFQTRFNV HREVTPVELP NCNLVKGVDN GSEDIEILPN  60
GLAFISSGVK YPGIMSFDPD KSGKILLMDL NEEDPVVLEL GITGNTLDIS SFNPAGISTF  120
TDEDNTVYLL VVNRPDSSST VEVFKFQEEE KSLLHLKTIR HKLLPSVNDI VAVGPEHFYA  180
TNDHYFADPY LKSWEMHLGL AWSFVTYYSP NDVRVVAEGF DMANGINISP DGKYVYIAEL  240
LAHKIHVYEK HANWTLTPLK SLDFDTLVDN ISVDPVTGDL WVGCHPNGMR LFYYDPKNPP  300
GSEVLRIQDI LSEEPKVTVV YAENGTVLQG SSVAAVYKGK LLIGTVFHKA LYCEL  355
```

```
SEQ ID NO: 127          moltype = DNA  length = 2713
FEATURE                 Location/Qualifiers
misc_feature            1..2713
                        note = hVK3LP-[hDNase1
                         N74K-G105R-A114F]-(g4s)4-[SSShinge-P238S-P331S
                         Fc]-NGS-[G3C9 PON1] DNA
source                  1..2713
                        mol_type = other DNA
                        organism = synthetic construct
SEQUENCE: 127
aagcttgccg ccatggaaac cccagcgcag cttctcttcc tcctgctact ctggctccca  60
gataccaccg gtctgaagat cgcagccttc aacatccaga catttgggga gaccaagatg  120
tccaatgcca ccctcgtcag ctacattgtg cagatcctga gccgctatga catcgccctg  180
gtccaggagg tcagagacag ccacctgact gccgtgggga agctgctgga caacctcaat  240
caggatgcac cagacaccta tcactacgtg gtcagtgagc cactgggacg gaagagctat  300
aaggagcgct acctgttcgt gtacaggcct gaccaggtgt ctgcggtgga cagctactac  360
tacgatgatg gctgcgagcc ctgcaggaac gacaccttca accgagagcc attcattgtc  420
aggttcttct cccggttcac agaggtcagg gagtttgcca ttgttcccct gcatgcggcc  480
ccgggggacg cagtagccga gatcgacgct ctctatgacg tctacctgga tgtccaagag  540
aaatggggct tggaggacgt catgttgatg ggcgacttca atgcgggctg cagctatgtg  600
agaccctccc agtggtcatc catccgcctg tggacaagcc ccaccttcca gtggctgatc  660
cccgacagcg ctgacaccac agctacaccc acgcactgtg cctatgacag gatcgtggtt  720
gcagggatgc tgctccgagg cgccgttgtt cccgactcgg ctcttccctt taacttccag  780
gctgcctatg gcctgagtga ccaactggcc caagccatca gtgaccacta tccagtggag  840
gtgatgctga aagatctctc cggaggaggt ggctcaggtg gtggaggatc tggaggaggt  900
gggagtggtg gaggtggttc taccggtctc gagcccaaat cttctgacaa aactcacaca  960
tctccaccgt ccccagcacc tgaactcctg ggaggatcgt cagtcttcct cttcccccca  1020
aaacccaagg acaccctcat gatctcccgg acccctgagg tcacatgcgt ggtggtggac  1080
gtgagccacg aagaccctga ggtcaagttc aactggtacg tggacggcgt ggaggtgcat  1140
aatgccaaga caaagccgcg ggaggagcag tacaacagca cgtaccgtgt ggtcagcgtc  1200
ctcaccgtcc tgcaccagga ctggctgaat ggcaaggagt acaagtgcaa ggtctccaac  1260
aaagccctcc cagcctccat cgagaaaacc atctccaaag ccaaagggca gccccgagaa  1320
ccacaggtgt acaccctgcc cccatcccgg gatgagctga ccaagaacca ggtcagcctg  1380
acctgcctgg tcaaaggctt ctatcccagc gacatcgccg tggagtggga gagcaatggg  1440
cagccggaga acaactacaa gaccacgcct cccgtgctgg actccgacgg ctccttcttc  1500
ctctacagca agctcaccgt ggacaagagc aggtggcagc aggggaacgt cttctcatgc  1560
tccgtgatgc atgaggctct gcacaaccac tacacgcaga agagcctctc tctctctccg  1620
ggtaaagtcg acggagctag cagccccgtg aacgtgagca gccccagcgt gcaggatatc  1680
ctcttcgatg gacagaagtc ttctttccaa acacgattta atgttcaccg tgaagtaact  1740
ccagtggaac ttcctaactg taatttagtt aaaggggttg acaatggttc tgaagacttg  1800
gaaatactgc ccaatggact ggctttcatc agctccggat taaagtatcc tggaataatg  1860
agctttgacc ctgataagtc tggaaagata cttctaatgg acctgaatga ggaagaccca  1920
gtagtgttgg aactgggcat tactggaaat acattggata tatcttcatt taaccctcat  1980
gggattagca cattcacaga tgaagataac actgtgtacc tactggtggt aaaccatcca  2040
gactcctcgt ccaccgtgga ggtgtttaaa tttcaagaag aagaaaaatc acttttgcat  2100
ctgaaaacca tcagacacaa gcttctgcct agtgtgaatg acattgtcgc tgtgggacct  2160
gaacactttt atgccacaaa tgatcactat tttgctgacc cttacttaaa atcctgggaa  2220
atgcatttgg gattagcgtg gtcatttgtt acttattata gtcccaatga tgttcgagta  2280
gtggcagaag gatttgattt tgctaacgga atcaacatct caccagacgg caagtatgtc  2340
tatatagctg agttgctggc tcataagatc catgtgtatg aaaagcacgc taattggact  2400
ttaactccat tgaagtccct cgactttgac acccttgtgg ataacatctc tgtggatcct  2460
gtgacagggg acctctgggt gggatgccat cccaacggaa tgcgaatctt ctactatgac  2520
ccaaagaatc ctcccggctc agaggtgctt cgaatccagg acattttatc cgaagagccc  2580
aaagtgacag tggtttatgc agaaaatggc actgtgttac agggcagcac ggtggccgct  2640
gtgtacaaag ggaaactgct gattggcaca gtgtttcaca aagctcttta ctgtgagctg  2700
taataatcta gaa                                                     2713

SEQ ID NO: 128          moltype = AA  length = 896
FEATURE                 Location/Qualifiers
REGION                  1..896
                        note = hVK3LP-[hDNase1
                         N74K-G105R-A114F]-(g4s)4-[SSShinge-P238S-P331S
                         Fc]-NGS-[G3C9 PON1]
source                  1..896
                        mol_type = protein
                        organism = synthetic construct
SEQUENCE: 128
METPAQLLFL LLLWLPDTTG LKIAAFNIQT FGETKMSNAT LVSYIVQILS RYDIALVQEV  60
RDSHLTAVGK LLDNLNQDAP DTYHYVVSEP LGRKSYKERY LFVYRPDQVS AVDSYYYDDG  120
CEPCRNDTFN REPFIVRFFS RFTEVREFAI VPLHAAPGDA VAEIDALYDV YLDVQEKWGL  180
EDVMLMGDFN AGCSYVRPSQ WSSIRLWTSP TFQWLIPDSA DTTATPTHCA YDRIVVAGML  240
LRGAVVPDSA LPFNFQAAYG LSDQLAQAIS DHYPVEVMLK DLSGGGGSGG GGSGGGGSGG  300
GGSTGLEPKS SDKTHTSPPS PAPELLGGSS VFLFPPKPKD TLMISRTPEV TCVVVDVSHE  360
DPEVKFNWYV DGVEVHNAKT KPREEQYNST YRVVSVLTVL HQDWLNGKEY KCKVSNKALP  420
ASIEKTISKA KGQPREPQVY TLPPSRDELT KNQVSLTCLV KGFYPSDIAV EWESNGQPEN  480
NYKTTPPVLD SDGSFFLYSK LTVDKSRWQQ GNVFSCSVMH EALHNHYTQK SLSLSPGKVD  540
GASSPVNVSS PSVQDILFDG QKSSFQTRFN VHREVTPVEL PNCNLVKGVD NGSEDLEILP  600
NGLAFISSGL KYPGIMSFDP DKSGKILLMD LNEEDPVVLE LGITGNTLDI SSFNPHGIST  660
```

```
FTDEDNTVYL LVVNHPDSSS TVEVFKFQEE EKSLLHLKTI RHKLLPSVND IVAVGPEHFY  720
ATNDHYFADP YLKSWEMHLG LAWSFVTYYS PNDVRVVAEG FDFANGINIS PDGKYVYIAE  780
LLAHKIHVYE KHANWTLTPL KSLDFDTLVD NISVDPVTGD LWVGCHPNGM RIFYYDPKNP  840
PGSEVLRIQD ILSEEPKVTV VYAENGTVLQ GSTVAAVYKG KLLIGTVFHK ALYCEL      896

SEQ ID NO: 129          moltype = DNA  length = 2688
FEATURE                 Location/Qualifiers
misc_feature            1..2688
                        note = hVK3LP-[hDNase1
                         N74K-G105R-A114F]-(g4s)4-[SSShinge-P238S-P331S
                         Fc]-NGS-[M-IIG1 PON1] DNA
source                  1..2688
                        mol_type = other DNA
                        organism = synthetic construct
SEQUENCE: 129
atggaaaccc cagcgcagct tctcttcctc ctgctactct ggctcccaga taccaccggt  60
ctgaagatcg cagccttcaa catccagaca tttggggaga ccaagatgtc caatgccacc  120
ctcgtcagct acattgtgca gatcctgagc cgctatgaca tcgccctggt ccaggaggtc  180
agagacagcc acctgactgc cgtggggaag ctgctggaca acctcaatca ggatgcacca  240
gacacctatc actacgtggt cagtgagcca ctgggacgga agagctataa ggagcgctac  300
ctgttcgtgt acaggcctga ccaggtgtct gcggtggaca gctactacta cgatgatggc  360
tgcgagccct gcaggaacga caccttcaac cgagagccat tcattgtcag gttcttctcc  420
cggttcacag aggtcaggga gtttgccatt gttcccctgc atgcggcccc gggggacgca  480
gtagccgaga tcgacgctct ctatgacgtc tacctggatg tccaagagaa atggggcttg  540
gaggacgtca tgttgatggg cgacttcaat gcgggctgca gctatgtgag accctcccag  600
tggtcatcca tccgcctgtg gacaagcccc accttccagt ggctgatccc cgacagcgct  660
gacaccacag ctacacccac gcactgtgcc tatgacagga tcgtggttgc agggatgctg  720
ctccgaggcg ccgttgttcc cgactcggct cttcccttta acttccaggc tgcctatggc  780
ctgagtgacc aactggccca agccatcagt gaccactatc cagtggaggt gatgctgaaa  840
gatctctccg gaggaggtgg ctcaggtggt ggaggatctg gaggaggtgg gagtggtgga  900
ggtggttcta ccggtctcga gcccaaatct tctgacaaaa ctcacacatc tccaccgtcc  960
ccagcacctg aactcctggg aggatcgtca gtcttcctct tcccccccaaa acccaaggac  1020
accctcatga tctcccggac ccctgaggtc acatgcgtgg tggtggacgt gagccacgaa  1080
gaccctgagg tcaagttcaa ctggtacgtg gacggcgtgg aggtgcataa tgccaagaca  1140
aagccgcggg aggagcagta caacagcacg taccgtgtgg tcagcgtcct caccgtcctg  1200
caccaggact ggctgaatgg caaggagtac aagtgcaagg tctccaacaa agccctccca  1260
gcctccatcg agaaaaccat ctccaaagcc aaagggcagc cccgagaacc acaggtgtac  1320
accctgcccc catcccggga tgagctgacc aagaaccagg tcagcctgac ctgcctggtc  1380
aaaggcttct atcccagcga catcgccgtg gagtgggaga gcaatgggca gccggagaac  1440
aactacaaga ccacgcctcc cgtgctggac tccgacggct ccttcttcct ctacagcaag  1500
ctcaccgtgg acaagagcag gtggcagcag gggaacgtct tctcatgctc cgtgatgcat  1560
gaggctctgc acaaccacta cacgcagaag agcctctctc tctctccggg taaagtcgac  1620
ggagctagca gccccgtgaa cgtgagcagc cccagcgtgc aggatatcct cttcgatgga  1680
cagaagtctt ctttccaaac acgatttaat gttcaccgtg aagtaactcc agtggaactt  1740
cctaactgta atttagttaa aggggttgac aatggttctg aagacattga aatactgccc  1800
aatggactgg ctttcatcag ctccggagtt aagtatcctg gaataatgag ctttgaccct  1860
gataagtctg gaaagatact tctaatggac ctgaatgagg aagacccagt agtgttggaa  1920
ctgggcatta ctggaaatac attggatata tcttcattta accctgctgg gattagcaca  1980
ttcacagatg aagataacac tgtgtaccta ctggtggtaa accgaccaga ctcctcgtcc  2040
accgtggagg tgtttaaatt tcaagaagaa gaaaaatcac ttttgcatct gaaaaccatc  2100
agacacaagc ttctgcctag tgtgaatgac attgtcgctg tgggacctga acacttttat  2160
gccacaaatg atcactattt tgctgaccct tacttaaaat cctgggaaat gcatttggga  2220
ttagcgtggt catttgttac ttattatagt cccaatgatg ttcgagtagt ggcagaagga  2280
tttgatatgg ctaacggaat caacatctca ccagacggca agtatgtcta tatagctgag  2340
ttgctggctc ataagatcca tgtgtatgaa aagcacgcta attggacttt aactccattg  2400
aagtccctcg actttgacac ccttgtggat aacatctctg tggatcctgt gacaggggac  2460
ctctgggtgg gatgccatcc caacggaatg cgattattct actatgaccc aaagaatcct  2520
cccggctcag aggtgcttcg aatccaggac attttatccg aagagcccaa agtgacagtg  2580
gtttatgcag aaaatggcac tgtgttacag ggcagcagtg tggccgctgt gtacaaaggg  2640
aaactgctga ttggcacagt gtttcacaaa gctctttact gtgagctg            2688

SEQ ID NO: 130          moltype = AA  length = 896
FEATURE                 Location/Qualifiers
REGION                  1..896
                        note = hVK3LP-[hDNase1
                         N74K-G105R-A114F]-(g4s)4-[SSShinge-P238S-P331S
                         Fc]-NGS-[M-IIG1 PON1]
source                  1..896
                        mol_type = protein
                        organism = synthetic construct
SEQUENCE: 130
METPAQLLFL LLLWLPDTTG LKIAAFNIQT FGETKMSNAT LVSYIVQILS RYDIALVQEV  60
RDSHLTAVGK LLDNLNQDAP DTYHYVVSEP LGRKSYKERY LFVYRPDQVS AVDSYYYDDG  120
CEPCRNDTFN REPFIVRFFS RFTEVREFAI VPLHAAPGDA VAEIDALYDV YLDVQEKWGL  180
EDVMLMGDFN AGCSYVRPSQ WSSIRLWTSP TFQWLIPDSA DTTATPTHCA YDRIVVAGML  240
LRGAVVPDSA LPFNFQAAYG LSDQLAQAIS DHYPVEVMLK DLSGGGGSGG GGSGGGGSGG  300
GGSTGLEPKS SDKTHTSPPS PAPELLGGSS VFLFPPKPKD TLMISRTPEV TCVVVDVSHE  360
DPEVKFNWYV DGVEVHNAKT KPREEQYNST YRVVSVLTVL HQDWLNGKEY KCKVSNKALP  420
ASIEKTISKA KGQPREPQVY TLPPSRDELT KNQVSLTCLV KGFYPSDIAV EWESNGQPEN  480
```

```
NYKTTPPVLD SDGSFFLYSK LTVDKSRWQQ GNVFSCSVMH EALHNHYTQK SLSLSPGKVD  540
GASSPVNVSS PSVQDILFDG QKSSFQTRFN VHREVTPVEL PNCNLVKGVD NGSEDIEILP  600
NGLAFISSGV KYPGIMSFDP DKSGKILLMD LNEEDPVVLE LGITGNTLDI SSFNPAGIST  660
FTDEDNTVYL LVVNRPDSSS TVEVFKFQEE EKSLLHLKTI RHKLLPSVND IVAVGPEHFY  720
ATNDHYFADP YLKSWEMHLG LAWSFVTYYS PNDVRVVAEG FDMANGINIS PDGKYVYIAE  780
LLAHKIHVYE KHANWTLTPL KSLDFDTLVD NISVDPVTGD LWVGCHPNGM RLFYYDPKNP  840
PGSEVLRIQD ILSEEPKVTV VYAENGTVLQ GSSVAAVYKG KLLIGTVFHK ALYCEL      896

SEQ ID NO: 131          moltype = DNA  length = 1839
FEATURE                 Location/Qualifiers
misc_feature            1..1839
                        note = hVK3LP-[KDL-SCChinge-P238S-P331S Fc]-NGS-[G3C9 PON1]
                         DNA
source                  1..1839
                        mol_type = other DNA
                        organism = synthetic construct
SEQUENCE: 131
atggaaaccc cagcgcagct tctcttcctc ctgctactct ggctcccaga taccaccggt  60
aaagatctcg agcccaaatc ttctgacaaa actcacacat gtccaccgtg cccagcacct  120
gaactcctgg gaggatcgtc agtcttcctc ttccccccaa aacccaagga caccctcatg  180
atctcccgga cccctgaggt cacatgcgtg gtggtggacg tgagccacga agaccctgag  240
gtcaagttca actggtacgt ggacggcgtg gaggtgcata atgccaagac aaagccgcgg  300
gaggagcagt acaacagcac gtaccgtgtg gtcagcgtcc tcaccgtcct gcaccaggac  360
tggctgaatg gcaaggagta caagtgcaag gtctccaaca aagccctccc agcctccatc  420
gagaaaacca tctccaaagc caaagggcag ccccgagaac cacaggtgta caccctgccc  480
ccatcccggg atgagctgac caagaaccag gtcagcctga cctgcctggt caaaggcttc  540
tatcccagcg acatcgccgt ggagtgggag agcaatgggc agccggagaa caactacaag  600
accacgcctc ccgtgctgga ctccgacggc tccttcttcc tctacagcaa gctcaccgtg  660
gacaagagca ggtggcagca ggggaacgtc ttctcatgct ccgtgatgca tgaggctctg  720
cacaaccact acacgcagaa gagcctctct ctctctccgg gtaaagtcga cggagctagc  780
agccccgtga acgtgagcag ccccagcgtg caggatatcc tcttcgatgg acagaagtct  840
tctttccaaa cacgatttaa tgttcaccgt gaagtaactc cagtggaact tcctaactgt  900
aatttagtta aggggttga caatggttct gaagacttgg aaatactgcc caatggactg  960
gctttcatca gctccggatt aaagtatcct ggaataatga gctttgaccc tgataagtct  1020
ggaaagatac ttctaatgga cctgaatgag gaagacccag tagtgttgga actgggcatt  1080
actggaaata cattggatat atcttcattt aaccctcatg ggattagcac attcacagat  1140
gaagataaca ctgtgtacct actggtggta aaccatccag actcctcgtc caccgtggag  1200
gtgtttaaat ttcaagaaga agaaaaatca cttttgcatc tgaaaaccat cagacacaag  1260
cttctgccta gtgtgaatga cattgtcgct gtgggacctg aacactttta tgccacaaat  1320
gatcactatt ttgctgaccc ttacttaaaa tcctgggaaa tgcatttggg attagcgtgg  1380
tcatttgtta cttattatag tcccaatgat gttcgagtag tggcagaagg atttgatttt  1440
gctaacggaa tcaacatctc accagacggc aagtatgtct atatagctga gttgctggct  1500
cataagatcc atgtgtatga aaagcacgct aattggactt taactccatt gaagtccctc  1560
gactttgaca cccttgtgga taacatctct gtggatcctg tgacagggga cctctgggtg  1620
ggatgccatc ccaacggaat gcgaatcttc tactatgacc caaagaatcc tcccggctca  1680
gaggtgcttc gaatccagga cattttatcc gaagagccca aagtgacagt ggtttatgca  1740
gaaaatggca ctgtgttaca gggcagcacg gtggccgctg tgtacaaagg gaaactgctg  1800
attggcacag tgtttcacaa agctctttac tgtgagctg                        1839

SEQ ID NO: 132          moltype = AA  length = 613
FEATURE                 Location/Qualifiers
REGION                  1..613
                        note = hVK3LP-[KDL-SCChinge-P238S-P331S Fc]-NGS-[G3C9 PON1]
source                  1..613
                        mol_type = protein
                        organism = synthetic construct
SEQUENCE: 132
METPAQLLFL LLLWLPDTTG KDLEPKSSDK THTCPPCPAP ELLGGSSVFL FPPKPKDTLM  60
ISRTPEVTCV VVDVSHEDPE VKFNWYVDGV EVHNAKTKPR EEQYNSTYRV VSVLTVLHQD  120
WLNGKEYKCK VSNKALPASI EKTISKAKGQ PREPQVYTLP PSRDELTKNQ VSLTCLVKGF  180
YPSDIAVEWE SNGQPENNYK TTPPVLDSDG SFFLYSKLTV DKSRWQQGNV FSCSVMHEAL  240
HNHYTQKSLS LSPGKVDGAS SPVNVSSPSV QDILFDGQKS SFQTRFNVHR EVTPVELPNC  300
NLVKGVDNGS EDLEILPNGL AFISSGLKYP GIMSFDPDKS GKILLMDLNE EDPVVLELGI  360
TGNTLDISSF NPHGISTFTD EDNTVYLLVV NHPDSSSTVE VFKFQEEEKS LLHLKTIRHK  420
LLPSVNDIVA VGPEHFYATN DHYFADPYLK SWEMHLGLAW SFVTYYSPND VRVVAEGFDF  480
ANGINISPDG KYVYIAELLA HKIHVYEKHA NWTLTPLKSL DFDTLVDNIS VDPVTGDLWV  540
GCHPNGMRIF YYDPKNPPGS EVLRIQDILS EEPKVTVVYA ENGTVLQGST VAAVYKGKLL  600
IGTVFHKALY CEL                                                    613

SEQ ID NO: 133          moltype = DNA  length = 1839
FEATURE                 Location/Qualifiers
misc_feature            1..1839
                        note = hVK3LP-[KDL-SCChinge-P238S-P331S Fc]-NGS-[M-IIG1
                         PON1] DNA
source                  1..1839
                        mol_type = other DNA
                        organism = synthetic construct
SEQUENCE: 133
atggaaaccc cagcgcagct tctcttcctc ctgctactct ggctcccaga taccaccggt  60
```

```
aaagatctcg agcccaaatc ttctgacaaa actcacacat gtccaccgtg cccagcacct  120
gaactcctgg gaggatcgtc agtcttcctc ttccccccaa aacccaagga caccctcatg  180
atctcccgga cccctgaggt cacatgcgtg gtggtggacg tgagccacga agaccctgag  240
gtcaagttca actggtacgt ggacggcgtg gaggtgcata atgccaagac aaagccgcgg  300
gaggagcagt acaacagcac gtaccgtgtg gtcagcgtcc tcaccgtcct gcaccaggac  360
tggctgaatg gcaaggagta caagtgcaag gtctccaaca aagccctccc agcctccatc  420
gagaaaacca tctccaaagc caaagggcag ccccgagaac cacaggtgta caccctgccc  480
ccatcccggg atgagctgac caagaaccag gtcagcctga cctgcctggt caaaggcttc  540
tatcccagcg acatcgccgt ggagtgggag agcaatgggc agccggagaa caactacaag  600
accacgcctc ccgtgctgga ctccgacggc tccttcttcc tctacagcaa gctcaccgtg  660
gacaagagca ggtggcagca ggggaacgtc ttctcatgct ccgtgatgca tgaggctctg  720
cacaaccact acacgcagaa gagcctctct ctctctccgg gtaaagtcga cggagctagc  780
agccccgtga acgtgagcag ccccagcgtg caggatatcc tcttcgatgg acagaagtct  840
tctttccaaa cacgatttaa tgttcaccgt gaagtaactc cagtggaact tcctaactgt  900
aatttagtta aggggttga caatggttct gaagacattg aaatactgcc caatggactg  960
gctttcatca gctccggagt taagtatcct ggaataatga gctttgaccc tgataagtct  1020
ggaaaagatac ttctaatgga cctgaatgag gaagacccag tagtgttgga actgggcatt  1080
actggaaata cattggatat atcttcattt aaccctgctg ggattagcac attcacagat  1140
gaagataaca ctgtgtacct actggtggta aaccgaccag actcctcgtc caccgtggag  1200
gtgtttaaat ttcaagaaga agaaaaatca cttttgcatc tgaaaaccat cagacacaag  1260
cttctgccta gtgtgaatga cattgtcgct gtgggacctg aacactttta tgccacaaat  1320
gatcactatt ttgctgaccc ttacttaaaa tcctgggaaa tgcatttggg attagcgtgg  1380
tcatttgtta cttattatag tcccaatgat gttcgagtag tggcagaagg atttgatatg  1440
gctaacggaa tcaacatctc accagacggc aagtatgtct atatagctga gttgctggct  1500
cataagatcc atgtgtatga aaagcacgct aattggactt taactccatt gaagtccctc  1560
gactttgaca cccttgtgga taacatctct gtggatcctg tgacagggga cctctgggtg  1620
ggatgccatc ccaacggaat gcgattattc tactatgacc caaagaatcc tcccggctca  1680
gaggtgcttc gaatccagga cattttatcc gaagagccca aagtgacagt ggtttatgca  1740
gaaaatggca ctgtgttaca gggcagcagt gtggccgctg tgtacaaagg gaaactgctg  1800
attggcacag tgtttcacaa agctctttac tgtgagctg                        1839
```

SEQ ID NO: 134 moltype = AA length = 613
FEATURE Location/Qualifiers
REGION 1..613
note = hVK3LP-[KDL-SCChinge-P238S-P331S Fc]-NGS-[M-IIG1 PON1]
source 1..613
mol_type = protein
organism = synthetic construct
SEQUENCE: 134

```
METPAQLLFL LLLWLPDTTG KDLEPKSSDK THTCPPCPAP ELLGGSSVFL FPPKPKDTLM  60
ISRTPEVTCV VVDVSHEDPE VKFNWYVDGV EVHNAKTKPR EEQYNSTYRV VSVLTVLHQD  120
WLNGKEYKCK VSNKALPASI EKTISKAKGQ PREPQVYTLP PSRDELTKNQ VSLTCLVKGF  180
YPSDIAVEWE SNGQPENNYK TTPPVLDSDG SFFLYSKLTV DKSRWQQGNV FSCSVMHEAL  240
HNHYTQKSLS LSPGKVDGAS SPVNVSSPSV QDILFDGQKS SFQTRFNVHR EVTPVELPNC  300
NLVKGVDNGS EDIEILPNGL AFISSGVKYP GIMSFDPDKS GKILLMDLNE EDPVVLELGI  360
TGNTLDISSF NPAGISTFTD EDNTVYLLVV NRPDSSSTVE VFKFQEEEKS LLHLKTIRHK  420
LLPSVNDIVA VGPEHFYATN DHYFADPYLK SWEMHLGLAW SFVTYYSPND VRVVAEGFDM  480
ANGINISPDG KYVYIAELLA HKIHVYEKHA NWTLTPLKSL DFDTLVDNIS VDPVTGDLWV  540
GCHPNGMRLF YYDPKNPPGS EVLRIQDILS EEPKVTVVYA ENGTVLQGSS VAAVYKGKLL  600
IGTVFHKALY CEL                                                    613
```

SEQ ID NO: 135 moltype = DNA length = 982
FEATURE Location/Qualifiers
source 1..982
mol_type = other DNA
organism = Homo sapiens
SEQUENCE: 135

```
atgtcacggg agctggcccc actgctgctt ctcctcctct ccatccacag cgccctggcc  60
atgaggatct gctccttcaa cgtcaggtcc tttggggaaa gcaagcagga agacaagaat  120
gccatggatg tcattgtgaa ggtcatcaaa cgctgtgaca tcatactcgt gatggaaatc  180
aaggacagca acaacaggat ctgccccata ctgatggaga agctgaacag aaattcaagg  240
agaggcataa cgtacaacta tgtgattagc tctcggcttg gaagaaacac atataaagaa  300
caatatgcct ttctctacaa ggaaaagctg gtgtctgtga agaggagtta tcactaccat  360
gactatcagg atggagacgc agatgtgttt tccagggagc cctttgtggt ctggttccaa  420
tctccccaca ctgctgtcaa agacttcgtg attatccccc tgcacaccac cccagagaca  480
tccgttaagg agatcgatga gttggttgag gtctacacgg acgtgaaaca ccgctggaag  540
gcggagaatt tcattttcat gggtgacttc aatgccggct gcagctacgt ccccaagaag  600
gcctggaaga acatccgctt gaggactgac cccaggtttg tttggctgat cggggaccaa  660
gaggacacca cggtgaagaa gagcaccaac tgtgcatatg acaggattgt gcttagagga  720
caagaaatcg tcagttctgt tgttcccaag tcaaacagtg tttttgactt ccagaaagct  780
tacaagctga ctgaagagga ggccctggat gtcagcgacc actttccagt tgaatttaaa  840
ctacagtctt caagggcctt caccaacagc aaaaaatctg tcactctaag gaagaaaaca  900
aagaggaaac gctcctaccc aactttcttg tacaaagttg gcattataag aaagcattgc  960
ttatcaattt gttgcaacga ac                                          982
```

SEQ ID NO: 136 moltype = AA length = 305
FEATURE Location/Qualifiers
source 1..305

```
                         mol_type = protein
                         organism = Homo sapiens
SEQUENCE: 136
MSRELAPLLL LLLSIHSALA MRICSFNVRS FGESKQEDKN AMDVIVKVIK RCDIILVMEI  60
KDSNNRICPI LMEKLNRNSR RGITYNYVIS SRLGRNTYKE QYAFLYKEKL VSVKRSYHYH  120
DYQDGDADVF SREPFVVWFQ SPHTAVKDFV IIPLHTTPET SVKEIDELVE VYTDVKHRWK  180
AENFIFMGDF NAGCSYVPKK AWKNIRLRTD PRFVWLIGDQ EDTTVKKSTN CAYDRIVLRG  240
QEIVSSVVPK SNSVFDFQKA YKLTEEEALD VSDHFPVEFK LQSSRAFTNS KKSVTLRKKT  300
KRKRS                                                              305

SEQ ID NO: 137           moltype = DNA  length = 1647
FEATURE                  Location/Qualifiers
misc_feature             1..1647
                         note = hVK3LP-[hDNase1L3 NLS1mutAAA,
                          NLS2delta]-(g4s)4-[SSShinge-P238S-P331S Fc] DNA
source                   1..1647
                         mol_type = other DNA
                         organism = synthetic construct
SEQUENCE: 137
atggaaaccc cagcgcagct tctcttcctc ctgctactct ggctcccaga taccaccggt  60
atgaggatct gctccttcaa cgtcaggtcc tttggggaaa gcaagcagga agacaagaat  120
gccatggatg tcattgtgaa ggtcatcaaa cgctgtgaca tcatactcgt gatggaaatc  180
aaggacagca acaacaggat ctgccccata ctgatggaga agctgaacag aaattcagca  240
agaggcataa cgtacaacta tgtgattagc tctcggcttg gagcagctac atataaagaa  300
caatatgcct ttctctacaa ggaaaagctg gtgtctgtga agaggagtta tcactaccat  360
gactatcagg atggagacgc agatgtgttt tccagggagc cctttgtggt ctggttccaa  420
tctccccaca ctgctgtcaa agacttcgtg attatccccc tgcacaccac cccagagaca  480
tccgttaagg agatcgatga gttggttgag gtctacacgg acgtgaaaca ccgctggaag  540
gcggagaatt tcattttcat gggtgacttc aatgccggct gcagctacgt ccccaagaag  600
gcctggaaga acatccgctt gaggactgac cccaggtttg tttggctgat cggggaccaa  660
gaggacacca cggtgaagaa gagcaccaac tgtgcatatg acaggattgt gcttagagga  720
caagaaatcg tcagttctgt tgttcccaag tcaaacagtg tttttgactt ccagaaagct  780
tacaagctga ctgaagagga ggccctggat gtcagcgacc actttccagt tgaatttaaa  840
ctacagtctt caagggcctt caccaactca gatctctccg gaggaggtgg ctcaggtggt  900
ggaggatctg gaggaggtgg gagtggtgga ggtggttcta ccggtctcga gcccaaatct  960
tctgacaaaa ctcacacatc tccaccgtcc ccagcacctg aactcctggg aggatcgtca  1020
gtcttcctct tcccccccaaa acccaaggac accctcatga tctcccggac ccctgaggtc  1080
acatgcgtgg tggtggacgt gagccacgaa gaccctgagg tcaagttcaa ctggtacgtg  1140
gacggcgtgg aggtgcataa tgccaagaca aagccgcggg aggagcagta caacagcacg  1200
taccgtgtgg tcagcgtcct caccgtcctg caccaggact ggctgaatgg caaggagtac  1260
aagtgcaagg tctccaacaa agccctccca gcctccatcg agaaaaccat ctccaaagcc  1320
aaagggcagc cccgagaacc acaggtgtac accctgcccc catcccggga tgagctgacc  1380
aagaaccagg tcagcctgac ctgcctggtc aaaggcttct atcccagcga catcgccgtg  1440
gagtgggaga gcaatgggca gccggagaac aactacaaga ccacgcctcc cgtgctggac  1500
tccgacggct ccttcttcct ctacagcaag ctcaccgtgg acaagagcag gtggcagcag  1560
gggaacgtct tctcatgctc cgtgatgcat gaggctctgc acaaccacta cacgcagaag  1620
agcctctctc tctctccggg taaataa                                     1647

SEQ ID NO: 138           moltype = AA  length = 548
FEATURE                  Location/Qualifiers
REGION                   1..548
                         note = hVK3LP-[hDNase1L3 NLS1mutAAA,
                          NLS2delta]-(g4s)4-[SSShinge-P238S-P331S Fc]
source                   1..548
                         mol_type = protein
                         organism = synthetic construct
SEQUENCE: 138
METPAQLLFL LLLWLPDTTG MRICSFNVRS FGESKQEDKN AMDVIVKVIK RCDIILVMEI  60
KDSNNRICPI LMEKLNRNSA RGITYNYVIS SRLGAATYKE QYAFLYKEKL VSVKRSYHYH  120
DYQDGDADVF SREPFVVWFQ SPHTAVKDFV IIPLHTTPET SVKEIDELVE VYTDVKHRWK  180
AENFIFMGDF NAGCSYVPKK AWKNIRLRTD PRFVWLIGDQ EDTTVKKSTN CAYDRIVLRG  240
QEIVSSVVPK SNSVFDFQKA YKLTEEEALD VSDHFPVEFK LQSSRAFTNS DLSGGGGSGG  300
GGSGGGGSGG GGSTGLEPKS SDKTHTSPPS PAPELLGGSS VFLFPPKPKD TLMISRTPEV  360
TCVVVDVSHE DPEVKFNWYV DGVEVHNAKT KPREEQYNST YRVVSVLTVL HQDWLNGKEY  420
KCKVSNKALP ASIEKTISKA KGQPREPQVY TLPPSRDELT KNQVSLTCLV KGFYPSDIAV  480
EWESNGQPEN NYKTTPPVLD SDGSFFLYSK LTVDKSRWQQ GNVFSCSVMH EALHNHYTQK  540
SLSLSPGK                                                           548

SEQ ID NO: 139           moltype = DNA  length = 1647
FEATURE                  Location/Qualifiers
misc_feature             1..1647
                         note = hVK3LP-[hDNase1L3 NLS1mutSSS,
                          NLS2delta]-(g4s)4-[SSShinge-P238S-P331S Fc] DNA
source                   1..1647
                         mol_type = other DNA
                         organism = synthetic construct
SEQUENCE: 139
atggaaaccc cagcgcagct tctcttcctc ctgctactct ggctcccaga taccaccggt  60
atgaggatct gctccttcaa cgtcaggtcc tttggggaaa gcaagcagga agacaagaat  120
```

```
gccatggatg tcattgtgaa ggtcatcaaa cgctgtgaca tcatactcgt gatggaaatc  180
aaggacagca acaacaggat ctgccccata ctgatggaga agctgaacag aaattcatca  240
agaggcataa cgtacaacta tgtgattagc tctcggcttg gaagttctac atataaagaa  300
caatatgcct ttctctacaa ggaaaagctg gtgtctgtga agaggagtta tcactaccat  360
gactatcagg atggagacgc agatgtgttt tccagggagc cctttgtggt ctggttccaa  420
tctccccaca ctgctgtcaa agacttcgtg attatccccc tgcacaccac cccagagaca  480
tccgttaagg agatcgatga gttggttgag gtctacacgg acgtgaaaca ccgctggaag  540
gcggagaatt tcattttcat gggtgacttc aatgccggct gcagctacgt ccccaagaag  600
gcctggaaga acatccgctt gaggactgac cccaggtttg tttggctgat cggggaccaa  660
gaggacacca cggtgaagaa gagcaccaac tgtgcatatg acaggattgt gcttagagga  720
caagaaatcg tcagttctgt tgttcccaag tcaaacagtg tttttgactt ccagaaagct  780
tacaagctga ctgaagagga ggccctggat gtcagcgacc actttccagt tgaatttaaa  840
ctacagtctt caagggcctt caccaactca gatctctccg gaggaggtgg ctcaggtggt  900
ggaggatctg gaggaggtgg gagtggtgga ggtggttcta ccggtctcga gcccaaatct  960
tctgacaaaa ctcacacatc tccaccgtcc ccagcacctg aactcctggg aggatcgtca  1020
gtcttcctct tccccccaaa acccaaggac accctcatga tctcccggac ccctgaggtc  1080
acatgcgtgg tggtggacgt gagccacgaa gaccctgagg tcaagttcaa ctggtacgtg  1140
gacggcgtgg aggtgcataa tgccaagaca aagccgcggg aggagcagta caacagcacg  1200
taccgtgtgg tcagcgtcct caccgtcctg caccaggact ggctgaatgg caaggagtac  1260
aagtgcaagg tctccaacaa agccctccca gcctccatcg agaaaaccat ctccaaagcc  1320
aaagggcagc cccgagaacc acaggtgtac accctgcccc catcccggga tgagctgacc  1380
aagaaccagg tcagcctgac ctgcctggtc aaaggcttct atcccagcga catcgccgtg  1440
gagtgggaga gcaatgggca gccggagaac aactacaaga ccacgcctcc cgtgctggac  1500
tccgacggct ccttcttcct ctacagcaag ctcaccgtgg acaagagcag gtggcagcag  1560
gggaacgtct tctcatgctc cgtgatgcat gaggctctgc acaaccacta cacgcagaag  1620
agcctctctc tctctccggg taaataa                                      1647

SEQ ID NO: 140          moltype = AA  length = 548
FEATURE                 Location/Qualifiers
REGION                  1..548
                        note = hVK3LP-[hDNase1L3 NLS1mutSSS,
                         NLS2delta]-(g4s)4-[SSShinge-P238S-P331S Fc]
source                  1..548
                        mol_type = protein
                        organism = synthetic construct
SEQUENCE: 140
METPAQLLFL LLLWLPDTTG MRICSFNVRS FGESKQEDKN AMDVIVKVIK RCDIILVMEI  60
KDSNNRICPI LMEKLNRNSS RGITYNYVIS SRLGSSTYKE QYAFLYKEKL VSVKRSYHYH  120
DYQDGDADVF SREPFVVWFQ SPHTAVKDFV IIPLHTTPET SVKEIDELVE VYTDVKHRWK  180
AENFIFMGDF NAGCSYVPKK AWKNIRLRTD PRFVWLIGDQ EDTTVKKSTN CAYDRIVLRG  240
QEIVSSVVPK SNSVFDFQKA YKLTEEEALD VSDHFPVEFK LQSSRAFTNS DLSGGGGSGG  300
GGSGGGGSGG GGSTGLEPKS SDKTHTSPPS PAPELLGGSS VFLFPPKPKD TLMISRTPEV  360
TCVVVDVSHE DPEVKFNWYV DGVEVHNAKT KPREEQYNST YRVVSVLTVL HQDWLNGKEY  420
KCKVSNKALP ASIEKTISKA KGQPREPQVY TLPPSRDELT KNQVSLTCLV KGFYPSDIAV  480
EWESNGQPEN NYKTTPPVLD SDGSFFLYSK LTVDKSRWQQ GNVFSCSVMH EALHNHYTQK  540
SLSLSPGK                                                           548

SEQ ID NO: 141          moltype = DNA  length = 1842
FEATURE                 Location/Qualifiers
misc_feature            1..1842
                        note = hVK3LP-[SCChinge-P238S-P331S Fc]-NGS-[PON1 Q192K] DNA
source                  1..1842
                        mol_type = other DNA
                        organism = synthetic construct
SEQUENCE: 141
atggaaaccc cagcgcagct tctcttcctc ctgctactct ggctcccaga taccaccggt  60
gagcccaaat cttctgacaa aactcacaca tgtccaccgt gcccagcacc tgaactcctg  120
ggaggatcgt cagtcttcct cttcccccca aaacccaagg acaccctcat gatctcccgg  180
acccctgagg tcacatgcgt ggtggtggac gtgagccacg aagaccctga ggtcaagttc  240
aactggtacg tggacggcgt ggaggtgcat aatgccaaga caaagccgcg ggaggagcag  300
tacaacagca cgtaccgtgt ggtcagcgtc ctcaccgtcc tgcaccagga ctggctgaat  360
ggcaaggagt acaagtgcaa ggtctccaac aaagccctcc cagcctccat cgagaaaacc  420
atctccaaag ccaaagggca gccccgagaa ccacaggtgt acaccctgcc cccatcccgg  480
gatgagctga ccaagaacca ggtcagcctg acctgcctgg tcaaaggctt ctatcccagc  540
gacatcgccg tggagtggga gagcaatggg cagccggaga acaactacaa gaccacgcct  600
cccgtgctgg actccgacgg ctccttcttc ctctacagca agctcaccgt ggacaagagc  660
aggtggcagc aggggaacgt cttctcatgc tccgtgatgc atgaggctct gcacaaccac  720
tacacgcaga agagcctctc tctctctccg ggtaaagtcg acggagctag cagccccgtg  780
aacgtgagca gccccagcgt gcaggatatc ctcttcagga accaccagtc ttcttaccaa  840
acacgactta atgctctccg agaggtacaa cccgtagaac ttcctaactg taatttagtt  900
aaaggaatcg aaactggctc tgaagacttg gagatactgc ctaatggact ggctttcatt  960
agctctggat taaagtatcc tggaataaag agcttcaacc ccaacagtcc tggaaaaata  1020
cttctgatgg acctgaatga agaagatcca acagtgttgg aattggggat cactggaagt  1080
aaatttgatg tatcttcatt taaccctcat gggattagca cattcacaga tgaagataat  1140
gccatgtacc tcctggtggt gaaccatcca gatgccaagt ccacagtgga gttgtttaaa  1200
tttcaagaag aagaaaaatc gcttttgcat ctaaaaacca tcagacataa acttctgcct  1260
aatttgaatg atattgttgc tgtgggacct gagcactttt atggcacaaa tgatcactat  1320
tttcttgacc cctacttaaa atcctgggag atgtatttgg gtttagcgtg gtcgtatgtt  1380
gtctactata gtccaagtga agttcgagtg gtggcagaag gatttgattt tgctaatgga  1440
```

```
atcaacattt cacccgatgg caagtatgtc tatatagctg agttgctggc tcataagatt  1500
catgtgtatg aaaagcatgc taattggact ttaactccat tgaagtccct tgactttaat  1560
accctcgtgg ataacatatc tgtggatcct gagacaggag acctttgggt tggatgccat  1620
cccaatggca tgaaaatctt cttctatgac tcagagaatc ctcctgcatc agaggtgctt  1680
cgaatccaga acattctaac agaagaacct aaagtgacac aggtttatgc agaaaatggc  1740
acagtgttgc aaggcagtac agttgcctct gtgtacaaag ggaaactgct gattggcaca  1800
gtgtttcaca aagctcttta ctgtgagctc taataatcta ga                     1842

SEQ ID NO: 142         moltype = AA  length = 610
FEATURE                Location/Qualifiers
REGION                 1..610
                       note = hVK3LP-[SCChinge-P238S-P331S Fc]-NGS-[PON1 Q192K]
source                 1..610
                       mol_type = protein
                       organism = synthetic construct
SEQUENCE: 142
METPAQLLFL LLLWLPDTTG EPKSSDKTHT CPPCPAPELL GGSSVFLFPP KPKDTLMISR  60
TPEVTCVVVD VSHEDPEVKF NWYVDGVEVH NAKTKPREEQ YNSTYRVVSV LTVLHQDWLN  120
GKEYKCKVSN KALPASIEKT ISKAKGQPRE PQVYTLPPSR DELTKNQVSL TCLVKGFYPS  180
DIAVEWESNG QPENNYKTTP PVLDSDGSFF LYSKLTVDKS RWQQGNVFSC SVMHEALHNH  240
YTQKSLSLSP GKVDGASSPV NVSSPSVQDI LFRNHQSSYQ TRLNALREVQ PVELPNCNLV  300
KGIETGSEDL EILPNGLAFI SSGLKYPGIK SFNPNSPGKI LLMDLNEEDP TVLELGITGS  360
KFDVSSFNPH GISTFTDEDN AMYLLVVNHP DAKSTVELFK FQEEEKSLLH LKTIRHKLLP  420
NLNDIVAVGP EHFYGTNDHY FLDPYLKSWE MYLGLAWSYV VYYSPSEVRV VAEGFDFANG  480
INISPDGKYV YIAELLAHKI HVYEKHANWT LTPLKSLDFN TLVDNISVDP ETGDLWVGCH  540
PNGMKIFFYD SENPPASEVL RIQNILTEEP KVTQVYAENG TVLQGSTVAS VYKGKLLIGT  600
VFHKALYCEL                                                         610

SEQ ID NO: 143         moltype = DNA  length = 1830
FEATURE                Location/Qualifiers
misc_feature           1..1830
                       note = hVK3LP-[SCChinge-P238S-P331S Fc]-NGS-[G3C9 PON1] DNA
source                 1..1830
                       mol_type = other DNA
                       organism = synthetic construct
SEQUENCE: 143
atggaaaccc cagcgcagct tctcttcctc ctgctactct ggctcccaga taccaccggt  60
gagcccaaat cttctgacaa aactcacaca tgtccaccgt gcccagcacc tgaactcctg  120
ggaggatcgt cagtcttcct cttcccccca aaacccaagg acaccctcat gatctcccgg  180
acccctgagg tcacatgcgt ggtggtggac gtgagccacg aagaccctga ggtcaagttc  240
aactggtacg tggacggcgt ggaggtgcat aatgccaaga caaagccgcg ggaggagcag  300
tacaacagca cgtaccgtgt ggtcagcgtc ctcaccgtcc tgcaccagga ctggctgaat  360
ggcaaggagt acaagtgcaa ggtctccaac aaagccctcc cagcctccat cgagaaaacc  420
atctccaaag ccaaagggca gccccgagaa ccacaggtgt acaccctgcc cccatcccgg  480
gatgagctga ccaagaacca ggtcagcctg acctgcctgg tcaaaggctt ctatcccagc  540
gacatcgccg tggagtggga gagcaatggg cagccggaga acaactacaa gaccacgcct  600
cccgtgctgg actccgacgg ctccttcttc ctctacagca agctcaccgt ggacaagagc  660
aggtggcagc aggggaacgt cttctcatgc tccgtgatgc atgaggctct gcacaaccac  720
tacacgcaga agagcctctc tctctctccg ggtaaagtcg acggagctag cagccccgtg  780
aacgtgagca gccccagcgt gcaggatatc ctcttcgatg gacagaagtc ttctttccaa  840
acacgattta atgttcaccg tgaagtaact ccagtggaac ttcctaactg taatttagtt  900
aaagggggttg acaatggttc tgaagacttg gaaatactgc ccaatggact ggctttcatc  960
agctccggat taaagtatcc tggaataatg agctttgacc ctgataagtc tggaaagata  1020
cttctaatgg acctgaatga ggaagaccca gtagtgttgg aactgggcat tactggaaat  1080
acattggata tatcttcatt taaccctcat gggattagca cattcacaga tgaagataac  1140
actgtgtacc tactggtggt aaaccatcca gactcctcgt ccaccgtgga ggtgtttaaa  1200
tttcaagaag aagaaaaatc acttttgcat ctgaaaacca tcagacacaa gcttctgcct  1260
agtgtgaatg acattgtcgc tgtgggacct gaacactttt atgccacaaa tgatcactat  1320
tttgctgacc cttacttaaa atcctgggaa atgcatttgg gattagcgtg gtcatttgtt  1380
acttattata gtcccaatga tgttcgagta gtggcagaag gatttgattt tgctaacgga  1440
atcaacatct caccagacgg caagtatgtc tatatagctg agttgctggc tcataagatc  1500
catgtgtatg aaaagcacgc taattggact ttaactccat tgaagtccct cgactttgac  1560
acccttgtgg ataacatctc tgtggatcct gtgacagggg acctctgggt gggatgccat  1620
cccaacggaa tgcgaatctt ctactatgac ccaaagaatc ctcccggctc agaggtgctt  1680
cgaatccagg acattttatc cgaagagccc aaagtgacag tggtttatgc agaaaatggc  1740
actgtgttac agggcagcac ggtggccgct gtgtacaaag ggaaactgct gattggcaca  1800
gtgtttcaca aagctcttta ctgtgagctg                                   1830

SEQ ID NO: 144         moltype = AA  length = 610
FEATURE                Location/Qualifiers
REGION                 1..610
                       note = hVK3LP-[SCChinge-P238S-P331S Fc]-NGS-[G3C9 PON1]
source                 1..610
                       mol_type = protein
                       organism = synthetic construct
SEQUENCE: 144
METPAQLLFL LLLWLPDTTG EPKSSDKTHT CPPCPAPELL GGSSVFLFPP KPKDTLMISR  60
TPEVTCVVVD VSHEDPEVKF NWYVDGVEVH NAKTKPREEQ YNSTYRVVSV LTVLHQDWLN  120
GKEYKCKVSN KALPASIEKT ISKAKGQPRE PQVYTLPPSR DELTKNQVSL TCLVKGFYPS  180
```

```
DIAVEWESNG QPENNYKTTP PVLDSDGSFF LYSKLTVDKS RWQQGNVFSC SVMHEALHNH  240
YTQKSLSLSP GKVDGASSPV NVSSPSVQDI LFDGQKSSFQ TRFNVHREVT PVELPNCNLV  300
KGVDNGSEDL EILPNGLAFI SSGLKYPGIM SFDPDKSGKI LLMDLNEEDP VVLELGITGN  360
TLDISSFNPH GISTFTDEDN TVYLLVVNHP DSSSTVEVFK FQEEEKSLLH LKTIRHKLLP  420
SVNDIVAVGP EHFYATNDHY FADPYLKSWE MHLGLAWSFV TYYSPNDVRV VAEGFDFANG  480
INISPDGKYV YIAELLAHKI HVYEKHANWT LTPLKSLDFD TLVDNISVDP VTGDLWVGCH  540
PNGMRIFYYD PKNPPGSEVL RIQDILSEEP KVTVVYAENG TVLQGSTVAA VYKGKLLIGT  600
VFHKALYCEL                                                         610

SEQ ID NO: 145         moltype = DNA  length = 1830
FEATURE                Location/Qualifiers
misc_feature           1..1830
                       note = hVK3LP-[SCChinge-P238S-P331S Fc]-NGS-[M-IIG1 PON1]
                        DNA
source                 1..1830
                       mol_type = other DNA
                       organism = synthetic construct
SEQUENCE: 145
atggaaaccc cagcgcagct tctcttcctc ctgctactct ggctcccaga taccaccggt  60
gagcccaaat cttctgacaa aactcacaca tgtccaccgt gcccagcacc tgaactcctg  120
ggaggatcgt cagtcttcct cttcccccca aaacccaagg acaccctcat gatctcccgg  180
acccctgagg tcacatgcgt ggtggtggac gtgagccacg aagaccctga ggtcaagttc  240
aactggtacg tggacggcgt ggaggtgcat aatgccaaga caaagccgcg ggaggagcag  300
tacaacagca cgtaccgtgt ggtcagcgtc ctcaccgtcc tgcaccagga ctggctgaat  360
ggcaaggagt acaagtgcaa ggtctccaac aaagccctcc cagcctccat cgagaaaacc  420
atctccaaag ccaaagggca gccccgagaa ccacaggtgt acaccctgcc cccatcccgg  480
gatgagctga ccaagaacca ggtcagcctg acctgcctgg tcaaaggctt ctatcccagc  540
gacatcgccg tggagtggga gagcaatggg cagccggaga acaactacaa gaccacgcct  600
cccgtgctgg actccgacgg ctccttcttc ctctacagca agctcaccgt ggacaagagc  660
aggtggcagc aggggaacgt cttctcatgc tccgtgatgc atgaggctct gcacaaccac  720
tacacgcaga agagcctctc tctctctccg ggtaaagtcg acggagctag cagccccgtg  780
aacgtgagca gccccagcgt gcaggatatc ctcttcgatg gacagaagtc ttctttccaa  840
acacgattta atgttcaccg tgaagtaact ccagtggaac ttcctaactg taatttagtt  900
aaagggggttg acaatggttc tgaagacatt gaaatactgc ccaatggact ggctttcatc  960
agctccggag ttaagtatcc tggaataatg agctttgacc ctgataagtc tggaaagata  1020
cttctaatgg acctgaatga ggaagaccca gtagtgttgg aactgggcat tactggaaat  1080
acattggata tatcttcatt taaccctgct gggattagca cattcacaga tgaagataac  1140
actgtgtacc tactggtggt aaaccgacca gactcctcgt ccaccgtgga ggtgtttaaa  1200
tttcaagaag aagaaaaatc acttttgcat ctgaaaacca tcagacacaa gcttctgcct  1260
agtgtgaatg acattgtcgc tgtgggacct gaacactttt atgccacaaa tgatcactat  1320
tttgctgacc cttacttaaa atcctgggaa atgcatttgg gattagcgtg gtcatttgtt  1380
acttattata gtcccaatga tgttcgagta gtggcagaag gatttgatat ggctaacgga  1440
atcaacatct caccagacgg caagtatgtc tatatagctg agttgctggc tcataagatc  1500
catgtgtatg aaaagcacgc taattggact ttaactccat tgaagtccct cgactttgac  1560
acccttgtgg ataacatctc tgtggatcct gtgacagggg acctctgggt gggatgccat  1620
cccaacggaa tgcgattatt ctactatgac ccaaagaatc ctcccggctc agaggtgctt  1680
cgaatccagg acattttatc cgaagagccc aaagtgacag tggtttatgc agaaaatggc  1740
actgtgttac agggcagcag tgtggccgct gtgtacaaag ggaaactgct gattggcaca  1800
gtgtttcaca aagctcttta ctgtgagctg                                   1830

SEQ ID NO: 146         moltype = AA  length = 610
FEATURE                Location/Qualifiers
REGION                 1..610
                       note = hVK3LP-[SCChinge-P238S-P331S Fc]-NGS-[M-IIG1 PON1]
source                 1..610
                       mol_type = protein
                       organism = synthetic construct
SEQUENCE: 146
METPAQLLFL LLLWLPDTTG EPKSSDKTHT CPPCPAPELL GGSSVFLFPP KPKDTLMISR  60
TPEVTCVVVD VSHEDPEVKF NWYVDGVEVH NAKTKPREEQ YNSTYRVVSV LTVLHQDWLN  120
GKEYKCKVSN KALPASIEKT ISKAKGQPRE PQVYTLPPSR DELTKNQVSL TCLVKGFYPS  180
DIAVEWESNG QPENNYKTTP PVLDSDGSFF LYSKLTVDKS RWQQGNVFSC SVMHEALHNH  240
YTQKSLSLSP GKVDGASSPV NVSSPSVQDI LFDGQKSSFQ TRFNVHREVT PVELPNCNLV  300
KGVDNGSEDI EILPNGLAFI SSGVKYPGIM SFDPDKSGKI LLMDLNEEDP VVLELGITGN  360
TLDISSFNPA GISTFTDEDN TVYLLVVNRP DSSSTVEVFK FQEEEKSLLH LKTIRHKLLP  420
SVNDIVAVGP EHFYATNDHY FADPYLKSWE MHLGLAWSFV TYYSPNDVRV VAEGFDMANG  480
INISPDGKYV YIAELLAHKI HVYEKHANWT LTPLKSLDFD TLVDNISVDP VTGDLWVGCH  540
PNGMRLFYYD PKNPPGSEVL RIQDILSEEP KVTVVYAENG TVLQGSSVAA VYKGKLLIGT  600
VFHKALYCEL                                                         610

SEQ ID NO: 147         moltype = DNA  length = 2721
FEATURE                Location/Qualifiers
misc_feature           1..2721
                       note = hVK3LP-[hDNase1
                        N74K-G105R-A114F]-(g4s)6-[SSShinge-P238S-P331S
                        Fc]-NGS-[PON1 Q192K] DNA
source                 1..2721
                       mol_type = other DNA
                       organism = synthetic construct
```

-continued

SEQUENCE: 147
atggaaaccc cagcgcagct tctcttcctc ctgctactct ggctcccaga taccaccggt 60
ctgaagatcg cagccttcaa catccagaca tttggggaga ccaagatgtc caatgccacc 120
ctcgtcagct acattgtgca gatcctgagc cgctatgaca tcgccctggt ccaggaggtc 180
agagacagcc acctgactgc cgtggggaag ctgctggaca acctcaatca ggatgcacca 240
gacacctatc actacgtggt cagtgagcca ctgggacgga agagctataa ggagcgctac 300
ctgttcgtgt acaggcctga ccaggtgtct gcggtggaca gctactacta cgatgatggc 360
tgcgagccct gcaggaacga caccttcaac cgagagccat tcattgtcag gttcttctcc 420
cggttcacag aggtcaggga gtttgccatt gttcccctgc atgcggcccc gggggacgca 480
gtagccgaga tcgacgctct ctatgacgtc tacctggatg tccaagagaa atggggcttg 540
gaggacgtca tgttgatggg cgacttcaat gcgggctgca gctatgtgag accctcccag 600
tggtcatcca tccgcctgtg gacaagcccc accttccagt ggctgatccc cgacagcgct 660
gacaccacag ctacacccac gcactgtgcc tatgacagga tcgtggttgc agggatgctg 720
ctccgaggcg ccgttgttcc cgactcggct cttcccttta acttccaggc tgcctatggc 780
ctgagtgacc aactggccca agccatcagt gaccactatc cagtggaggt gatgctgaaa 840
gatctctccg gaggaggtgg ctcaggtggt ggaggatctg gaggaggtgg gagtggtgga 900
ggtggttctg gaggaggtgg tagtggaggt ggaggttcta ccggtctcga gcccaaatct 960
tctgacaaaa ctcacacatc tccaccgtcc ccagcacctg aactcctggg aggatcgtca 1020
gtcttcctct tccccccaaa acccaaggac accctcatga tctcccggac ccctgaggtc 1080
acatgcgtgg tggtggacgt gagccacgaa gaccctgagg tcaagttcaa ctggtacgtg 1140
gacggcgtgg aggtgcataa tgccaagaca aagccgcggg aggagcagta caacagcacg 1200
taccgtgtgg tcagcgtcct caccgtcctg caccaggact ggctgaatgg caaggagtac 1260
aagtgcaagg tctccaacaa agccctccca gcctccatcg agaaaaccat ctccaaagcc 1320
aaagggcagc cccgagaacc acaggtgtac accctgcccc catcccggga tgagctgacc 1380
aagaaccagg tcagcctgac ctgcctggtc aaaggcttct atcccagcga catcgccgtg 1440
gagtgggaga gcaatgggca gccggagaac aactacaaga ccacgcctcc cgtgctggac 1500
tccgacggct ccttcttcct ctacagcaag ctcaccgtgg acaagagcag gtggcagcag 1560
gggaacgtct tctcatgctc cgtgatgcat gaggctctgc acaaccacta cacgcagaag 1620
agcctctctc tctctccggg taaagtcgac ggagctagca gccccgtgaa cgtgagcagc 1680
cccagcgtgc aggatatcct cttcaggaac caccagtctt cttaccaaac acgacttaat 1740
gctctccgag aggtacaacc cgtagaactt cctaactgta atttagttaa aggaatcgaa 1800
actggctctg aagacttgga gatactgcct aatggactgg ctttcattag ctctggatta 1860
aagtatcctg gaataaagag cttcaacccc aacagtcctg gaaaaatact tctgatggac 1920
ctgaatgaag aagatccaac agtgttggaa ttggggatca ctggaagtaa atttgatgta 1980
tcttcattta accctcatgg gattagcaca ttcacagatg aagataatgc catgtacctc 2040
ctggtggtga accatccaga tgccaagtcc acagtggagt tgtttaaatt tcaagaagaa 2100
gaaaaatcgc ttttgcatct aaaaaccatc agacataaac ttctgcctaa tttgaatgat 2160
attgttgctg tgggacctga gcacttttat ggcacaaatg atcactattt tcttgacccc 2220
tacttaaaat cctgggagat gtatttgggt ttagcgtggt cgtatgttgt ctactatagt 2280
ccaagtgaag ttcgagtggt ggcagaagga tttgattttg ctaatggaat caacatttca 2340
cccgatggca agtatgtcta tatagctgag ttgctggctc ataagattca tgtgtatgaa 2400
aagcatgcta attggacttt aactccattg aagtcccttg actttaatac cctcgtggat 2460
aacatatctg tggatcctga gacaggagac ctttgggttg gatgccatcc caatggcatg 2520
aaaatcttct tctatgactc agagaatcct cctgcatcag aggtgcttcg aatccagaac 2580
attctaacag aagaacctaa agtgacacag gtttatgcag aaaatggcac agtgttgcaa 2640
ggcagtacag ttgcctctgt gtacaaaggg aaactgctga ttggcacagt gtttcacaaa 2700
gctctttact gtgagctcta a 2721

SEQ ID NO: 148 moltype = AA length = 906
FEATURE Location/Qualifiers
REGION 1..906
note = hVK3LP-[hDNase1 N74K-G105R-A114F]-(g4s)6-[SSShinge-P238S-P331S Fc]-NGS-[PON1 Q192K]
source 1..906
mol_type = protein
organism = synthetic construct
SEQUENCE: 148
METPAQLLFL LLLWLPDTTG LKIAAFNIQT FGETKMSNAT LVSYIVQILS RYDIALVQEV 60
RDSHLTAVGK LLDNLNQDAP DTYHYVVSEP LGRKSYKERY LFVYRPDQVS AVDSYYYDDG 120
CEPCRNDTFN REPFIVRFFS RFTEVREFAI VPLHAAPGDA VAEIDALYDV YLDVQEKWGL 180
EDVMLMGDFN AGCSYVRPSQ WSSIRLWTSP TFQWLIPDSA DTTATPTHCA YDRIVVAGML 240
LRGAVVPDSA LPFNFQAAYG LSDQLAQAIS DHYPVEVMLK DLSGGGGSGG GGSGGGGSGG 300
GGSGGGGSGG GGSTGLEPKS SDKTHTSPPS PAPELLGGSS VFLFPPKPKD TLMISRTPEV 360
TCVVVDVSHE DPEVKFNWYV DGVEVHNAKT KPREEQYNST YRVVSVLTVL HQDWLNGKEY 420
KCKVSNKALP ASIEKTISKA KGQPREPQVY TLPPSRDELT KNQVSLTCLV KGFYPSDIAV 480
EWESNGQPEN NYKTTPPVLD SDGSFFLYSK LTVDKSRWQQ GNVFSCSVMH EALHNHYTQK 540
SLSLSPGKVD GASSPVNVSS PSVQDILFRN HQSSYQTRLN ALREVQPVEL PNCNLVKGIE 600
TGSEDLEILP NGLAFISSGL KYPGIKSFNP NSPGKILLMD LNEEDPTVLE LGITGSKFDV 660
SSFNPHGIST FTDEDNAMYL LVVNHPDAKS TVELFKFQEE EKSLLHLKTI RHKLLPNLND 720
IVAVGPEHFY GTNDHYFLDP YLKSWEMYLG LAWSYVVYYS PSEVRVVAEG FDFANGINIS 780
PDGKYVYIAE LLAHKIHVYE KHANWTLTPL KSLDFNTLVD NISVDPETGD LWVGCHPNGM 840
KIFFYDSENP PASEVLRIQN ILTEEPKVTQ VYAENGTVLQ GSTVASVYKG KLLIGTVFHK 900
ALYCEL 906

SEQ ID NO: 149 moltype = AA length = 528
FEATURE Location/Qualifiers
REGION 1..528
note = [hDNase1 N74X-G105X-A114X]-[gs linker]-[SSShinge Fc]

```
VARIANT                 74
                        note = X is Lys, Arg, or His
VARIANT                 105
                        note = X is Lys, Arg, or His
VARIANT                 114
                        note = X is Phe, Glu, Met, Arg, or Tyr
VARIANT                 261..263
                        note = X is any naturally occurring non-cysteine amino acid
VARIANT                 264..283
                        note = X is Gly or Ser
VARIANT                 284..293
                        note = X is Gly or Ser or is absent
VARIANT                 294..296
                        note = X is any naturally occurring non-cysteine amino acid
VARIANT                 315..316
                        note = X is Leu or Ala
VARIANT                 319
                        note = X is Pro or Ser
VARIANT                 333
                        note = X is Met or Tyr
VARIANT                 335
                        note = X is Ser or Thr
VARIANT                 337
                        note = X is Thr or Glu
VARIANT                 346
                        note = X is Asp or Ala
VARIANT                 378
                        note = X is Asn, Ala, Gln, or Gly
VARIANT                 410
                        note = X is Pro, Ala, Gly, or Ser
VARIANT                 412
                        note = X is Pro, Ser, or Ala
VARIANT                 509
                        note = X is Met or Leu
VARIANT                 515
                        note = X is Asn or Ser
VARIANT                 528
                        note = X is Lys or is absent
source                  1..528
                        mol_type = protein
                        organism = synthetic construct
SEQUENCE: 149
LKIAAFNIQT FGETKMSNAT LVSYIVQILS RYDIALVQEV RDSHLTAVGK LLDNLNQDAP  60
DTYHYVVSEP LGRXSYKERY LFVYRPDQVS AVDSYYYDDG CEPCXNDTFN REPXIVRFFS  120
RFTEVREFAI VPLHAAPGDA VAEIDALYDV YLDVQEKWGL EDVMLMGDFN AGCSYVRPSQ  180
WSSIRLWTSP TFQWLIPDSA DTTATPTHCA YDRIVVAGML LRGAVVPDSA LPFNFQAAYG  240
LSDQLAQAIS DHYPVEVMLK XXXXXXXXXX XXXXXXXXXX XXXXXXXXXX XXXXXXEPKS  300
SDKTHTSPPS PAPEXXGGXS VFLFPPKPKD TLXIXRXPEV TCVVVXVSHE DPEVKFNWYV  360
DGVEVHNAKT KPREEQYXST YRVVSVLTVL HQDWLNGKEY KCKVSNKALX AXIEKTISKA  420
KGQPREPQVY TLPPSRDELT KNQVSLTCLV KGFYPSDIAV EWESNGQPEN NYKTTPPVLD  480
SDGSFFLYSK LTVDKSRWQQ GNVFSCSVXH EALHXHYTQK SLSLSPGX              528

SEQ ID NO: 150          moltype = AA  length = 528
FEATURE                 Location/Qualifiers
REGION                  1..528
                        note = [hDNase1 N74K-G105R-A114F]-[gs linker]-[SSShinge Fc]
VARIANT                 261..263
                        note = X is any naturally occurring non-cysteine amino acid
VARIANT                 264..283
                        note = X is Gly or Ser
VARIANT                 284..293
                        note = X is Gly or Ser or is absent
VARIANT                 294..296
                        note = X is any naturally occurring non-cysteine amino acid
VARIANT                 315..316
                        note = X is Leu or Ala
VARIANT                 319
                        note = X is Pro or Ser
VARIANT                 333
                        note = X is Met or Tyr
VARIANT                 335
                        note = X is Ser or Thr
VARIANT                 337
                        note = X is Thr or Glu
VARIANT                 346
                        note = X is Asp or Ala
VARIANT                 378
                        note = X is Asn, Ala, Gln, or Gly
VARIANT                 410
```

```
                        note = X is Pro, Ala, Gly, or Ser
VARIANT                 412
                        note = X is Pro, Ser, or Ala
VARIANT                 509
                        note = X is Met or Leu
VARIANT                 515
                        note = X is Asn or Ser
VARIANT                 528
                        note = X is Lys or is absent
source                  1..528
                        mol_type = protein
                        organism = synthetic construct
SEQUENCE: 150
LKIAAFNIQT FGETKMSNAT LVSYIVQILS RYDIALVQEV RDSHLTAVGK LLDNLNQDAP  60
DTYHYVVSEP LGRKSYKERY LFVYRPDQVS AVDSYYYDDG CEPCRNDTFN REPFIVRFFS  120
RFTEVREFAI VPLHAAPGDA VAEIDALYDV YLDVQEKWGL EDVMLMGDFN AGCSYVRPSQ  180
WSSIRLWTSP TFQWLIPDSA DTTATPTHCA YDRIVVAGML LRGAVVPDSA LPFNFQAAYG  240
LSDQLAQAIS DHYPVEVMLK XXXXXXXXXX XXXXXXXXXX XXXXXXXXXX XXXXXXEPKS  300
SDKTHTSPPS PAPEXXGGXS VFLFPPKPKD TLXIXRXPEV TCVVVXVSHE DPEVKFNWYV  360
DGVEVHNAKT KPREEQYXST YRVVSVLTVL HQDWLNGKEY KCKVSNKALX AXIEKTISKA  420
KGQPREPQVY TLPPSRDELT KNQVSLTCLV KGFYPSDIAV EWESNGQPEN NYKTTPPVLD  480
SDGSFFLYSK LTVDKSRWQQ GNVFSCSVXH EALHXHYTQK SLSLSPGX              528

SEQ ID NO: 151          moltype = DNA  length = 840
FEATURE                 Location/Qualifiers
misc_feature            1..840
                        note = hVK3LP-[hDNase1 N74K-G105R] DNA
source                  1..840
                        mol_type = other DNA
                        organism = synthetic construct
SEQUENCE: 151
atggaaaccc cagcgcagct tctcttcctc ctgctactct ggctcccaga taccaccggt  60
ctgaagatcg cagccttcaa catccagaca tttggggaga ccaagatgtc caatgccacc  120
ctcgtcagct acattgtgca gatcctgagc cgctatgaca tcgccctggt ccaggaggtc  180
agagacagcc acctgactgc cgtggggaag ctgctggaca acctcaatca ggatgcacca  240
gacacctatc actacgtggt cagtgagcca ctgggacgga agagctataa ggagcgctac  300
ctgttcgtgt acaggcctga ccaggtgtct gcggtggaca gctactacta cgatgatggc  360
tgcgagccct gcaggaacga caccttcaac cgagagccag ccattgtcag gttcttctcc  420
cggttcacag aggtcaggga gtttgccatt gttcccctgc atgcggcccc gggggacgca  480
gtagccgaga tcgacgctct ctatgacgtc tacctggatg tccaagagaa atggggcttg  540
gaggacgtca tgttgatggg cgacttcaat gcgggctgca gctatgtgag accctcccag  600
tggtcatcca tccgcctgtg gacaagcccc accttccagt ggctgatccc cgacagcgct  660
gacaccacag ctacacccac gcactgtgcc tatgacagga tcgtggttgc agggatgctg  720
ctccgaggcg ccgttgttcc cgactcggct cttcccttta acttccaggc tgcctatggc  780
ctgagtgacc aactggccca agccatcagt gaccactatc cagtggaggt gatgctgaaa  840

SEQ ID NO: 152          moltype = AA  length = 280
FEATURE                 Location/Qualifiers
REGION                  1..280
                        note = hVK3LP-[hDNase1 N74K-G105R]
source                  1..280
                        mol_type = protein
                        organism = synthetic construct
SEQUENCE: 152
METPAQLLFL LLLWLPDTTG LKIAAFNIQT FGETKMSNAT LVSYIVQILS RYDIALVQEV  60
RDSHLTAVGK LLDNLNQDAP DTYHYVVSEP LGRKSYKERY LFVYRPDQVS AVDSYYYDDG  120
CEPCRNDTFN REPAIVRFFS RFTEVREFAI VPLHAAPGDA VAEIDALYDV YLDVQEKWGL  180
EDVMLMGDFN AGCSYVRPSQ WSSIRLWTSP TFQWLIPDSA DTTATPTHCA YDRIVVAGML  240
LRGAVVPDSA LPFNFQAAYG LSDQLAQAIS DHYPVEVMLK                        280

SEQ ID NO: 153          moltype = AA  length = 528
FEATURE                 Location/Qualifiers
REGION                  1..528
                        note = [hDNase1 N74X-G105X]-[gs linker]-[SSShinge Fc]
VARIANT                 74
                        note = X is Lys, Arg, or His
VARIANT                 105
                        note = X is Lys, Arg, or His
VARIANT                 261..263
                        note = X is any naturally occurring non-cysteine amino acid
VARIANT                 264..283
                        note = X is Gly or Ser
VARIANT                 284..293
                        note = X is Gly or Ser or is absent
VARIANT                 294..296
                        note = X is any naturally occurring non-cysteine amino acid
VARIANT                 315..316
                        note = X is Leu or Ala
VARIANT                 319
```

```
                          note = X is Pro or Ser
VARIANT                   333
                          note = X is Met or Tyr
VARIANT                   335
                          note = X is Ser or Thr
VARIANT                   337
                          note = X is Thr or Glu
VARIANT                   346
                          note = X is Asp or Ala
VARIANT                   378
                          note = X is Asn, Ala, Gln, or Gly
VARIANT                   410
                          note = X is Pro, Ala, Gly, or Ser
VARIANT                   412
                          note = X is Pro, Ser, or Ala
VARIANT                   509
                          note = X is Met or Leu
VARIANT                   515
                          note = X is Asn or Ser
VARIANT                   528
                          note = X is Lys or is absent
source                    1..528
                          mol_type = protein
                          organism = synthetic construct
SEQUENCE: 153
LKIAAFNIQT FGETKMSNAT LVSYIVQILS RYDIALVQEV RDSHLTAVGK LLDNLNQDAP  60
DTYHYVVSEP LGRXSYKERY LFVYRPDQVS AVDSYYYDDG CEPCXNDTFN REPAIVRFFS  120
RFTEVREFAI VPLHAAPGDA VAEIDALYDV YLDVQEKWGL EDVMLMGDFN AGCSYVRPSQ  180
WSSIRLWTSP TFQWLIPDSA DTTATPTHCA YDRIVVAGML LRGAVVPDSA LPFNFQAAYG  240
LSDQLAQAIS DHYPVEVMLK XXXXXXXXXX XXXXXXXXXX XXXXXXXXXX XXXXXXEPKS  300
SDKTHTSPPS PAPEXXGGXS VFLFPPKPKD TLXIXRXPEV TCVVVXVSHE DPEVKFNWYV  360
DGVEVHNAKT KPREEQYXST YRVVSVLTVL HQDWLNGKEY KCKVSNKALX AXIEKTISKA  420
KGQPREPQVY TLPPSRDELT KNQVSLTCLV KGFYPSDIAV EWESNGQPEN NYKTTPPVLD  480
SDGSFFLYSK LTVDKSRWQQ GNVFSCSVXH EALHXHYTQK SLSLSPGX              528

SEQ ID NO: 154            moltype = AA  length = 528
FEATURE                   Location/Qualifiers
REGION                    1..528
                          note = [hDNase1 N74K-G105R]-[gs linker]-[SSShinge Fc]
VARIANT                   261..263
                          note = X is any naturally occurring non-cysteine amino acid
VARIANT                   264..283
                          note = X is Gly or Ser
VARIANT                   284..293
                          note = X is Gly or Ser or is absent
VARIANT                   294..296
                          note = X is any naturally occurring non-cysteine amino acid
VARIANT                   315..316
                          note = X is Leu or Ala
VARIANT                   319
                          note = X is Pro or Ser
VARIANT                   333
                          note = X is Met or Tyr
VARIANT                   335
                          note = X is Ser or Thr
VARIANT                   337
                          note = X is Thr or Glu
VARIANT                   346
                          note = X is Asp or Ala
VARIANT                   378
                          note = X is Asn, Ala, Gln, or Gly
VARIANT                   410
                          note = X is Pro, Ala, Gly, or Ser
VARIANT                   412
                          note = X is Pro, Ser, or Ala
VARIANT                   509
                          note = X is Met or Leu
VARIANT                   515
                          note = X is Asn or Ser
VARIANT                   528
                          note = X is Lys or is absent
source                    1..528
                          mol_type = protein
                          organism = synthetic construct
SEQUENCE: 154
LKIAAFNIQT FGETKMSNAT LVSYIVQILS RYDIALVQEV RDSHLTAVGK LLDNLNQDAP  60
DTYHYVVSEP LGRKSYKERY LFVYRPDQVS AVDSYYYDDG CEPCRNDTFN REPAIVRFFS  120
RFTEVREFAI VPLHAAPGDA VAEIDALYDV YLDVQEKWGL EDVMLMGDFN AGCSYVRPSQ  180
WSSIRLWTSP TFQWLIPDSA DTTATPTHCA YDRIVVAGML LRGAVVPDSA LPFNFQAAYG  240
```

```
LSDQLAQAIS DHYPVEVMLK XXXXXXXXXX XXXXXXXXXX XXXXXXXXXX XXXXXXEPKS  300
SDKTHTSPPS PAPEXXGGXS VFLFPPKPKD TLXIXRXPEV TCVVVXVSHE DPEVKFNWYV  360
DGVEVHNAKT KPREEQYXST YRVVSVLTVL HQDWLNGKEY KCKVSNKALX AXIEKTISKA  420
KGQPREPQVY TLPPSRDELT KNQVSLTCLV KGFYPSDIAV EWESNGQPEN NYKTTPPVLD  480
SDGSFFLYSK LTVDKSRWQQ GNVFSCSVXH EALHXHYTQK SLSLSPGX              528

SEQ ID NO: 155         moltype = AA  length = 538
FEATURE                Location/Qualifiers
REGION                 1..538
                       note = hVK3LP-[hDNase1
                        N96K-G127R]-(g4s)4-[SSShinge-P238S-P331S Fc]
source                 1..538
                       mol_type = protein
                       organism = synthetic construct
SEQUENCE: 155
METPAQLLFL LLLWLPDTTG LKIAAFNIQT FGETKMSNAT LVSYIVQILS RYDIALVQEV  60
RDSHLTAVGK LLDNLNQDAP DTYHYVVSEP LGRKSYKERY LFVYRPDQVS AVDSYYYDDG  120
CEPCRNDTFN REPAIVRFFS RFTEVREFAI VPLHAAPGDA VAEIDALYDV YLDVQEKWGL  180
EDVMLMGDFN AGCSYVRPSQ WSSIRLWTSP TFQWLIPDSA DTTATPTHCA YDRIVVAGML  240
LRGAVVPDSA LPFNFQAAYG LSDQLAQAIS DHYPVEVMLK DLSGGGGSGG GGSGGGGSGG  300
GGSTGLEPKS SDKTHTSPPS PAPELLGGSS VFLFPPKPKD TLMISRTPEV TCVVVDVSHE  360
DPEVKFNWYV DGVEVHNAKT KPREEQYNST YRVVSVLTVL HQDWLNGKEY KCKVSNKALP  420
ASIEKTISKA KGQPREPQVY TLPPSRDELT KNQVSLTCLV KGFYPSDIAV EWESNGQPEN  480
NYKTTPPVLD SDGSFFLYSK LTVDKSRWQQ GNVFSCSVMH EALHNHYTQK SLSLSPGK    538

SEQ ID NO: 156         moltype = AA  length = 548
FEATURE                Location/Qualifiers
REGION                 1..548
                       note = hVK3LP-[hDNase1
                        N96K-G127R]-(g4s)6-[SSShinge-P238S-P331S Fc]
source                 1..548
                       mol_type = protein
                       organism = synthetic construct
SEQUENCE: 156
METPAQLLFL LLLWLPDTTG LKIAAFNIQT FGETKMSNAT LVSYIVQILS RYDIALVQEV  60
RDSHLTAVGK LLDNLNQDAP DTYHYVVSEP LGRKSYKERY LFVYRPDQVS AVDSYYYDDG  120
CEPCRNDTFN REPAIVRFFS RFTEVREFAI VPLHAAPGDA VAEIDALYDV YLDVQEKWGL  180
EDVMLMGDFN AGCSYVRPSQ WSSIRLWTSP TFQWLIPDSA DTTATPTHCA YDRIVVAGML  240
LRGAVVPDSA LPFNFQAAYG LSDQLAQAIS DHYPVEVMLK DLSGGGGSGG GGSGGGGSGG  300
GGSGGGGSGG GGSTGLEPKS SDKTHTSPPS PAPELLGGSS VFLFPPKPKD TLMISRTPEV  360
TCVVVDVSHE DPEVKFNWYV DGVEVHNAKT KPREEQYNST YRVVSVLTVL HQDWLNGKEY  420
KCKVSNKALP ASIEKTISKA KGQPREPQVY TLPPSRDELT KNQVSLTCLV KGFYPSDIAV  480
EWESNGQPEN NYKTTPPVLD SDGSFFLYSK LTVDKSRWQQ GNVFSCSVMH EALHNHYTQK  540
SLSLSPGK                                                           548

SEQ ID NO: 157         moltype = DNA  length = 2713
FEATURE                Location/Qualifiers
misc_feature           1..2713
                       note = hVK3LP-[hDNase1
                        N74K-G105R]-(g4s)4-[SSShinge-P238S-P331S Fc]-NGS-[PON1
                        Q192K] DNA
source                 1..2713
                       mol_type = other DNA
                       organism = synthetic construct
SEQUENCE: 157
aagcttgccg ccatggaaac cccagcgcag cttctcttcc tcctgctact ctggctccca  60
gataccaccg gtctgaagat cgcagccttc aacatccaga catttgggga gaccaagatg  120
tccaatgcca ccctcgtcag ctacattgtg cagatcctga gccgctatga catcgccctg  180
gtccaggagg tcagagacag ccacctgact gccgtgggga agctgctgga caacctcaat  240
caggatgcac cagacaccta tcactacgtg gtcagtgagc cactgggacg gaagagctat  300
aaggagcgct acctgttcgt gtacaggcct gaccaggtgt ctgcggtgga cagctactac  360
tacgatgatg gctgcgagcc ctgcaggaac gacaccttca accgagagcc agccattgtc  420
aggttcttct cccggttcac agaggtcagg gagtttgcca ttgttcccct gcatgcggcc  480
ccgggggacg cagtagccga gatcgacgct ctctatgacg tctacctgga tgtccaagag  540
aaatggggct tggaggacgt catgttgatg ggcgacttca atgcgggctg cagctatgtg  600
agaccctccc agtggtcatc catccgcctg tggacaagcc ccaccttcca gtggctgatc  660
cccgacagcg ctgacaccac agctacaccc acgcactgtg cctatgacag gatcgtggtt  720
gcagggatgc tgctccgagg cgccgttgtt cccgactcgg ctcttccctt taacttccag  780
gctgcctatg gcctgagtga ccaactggcc caagccatca gtgaccacta tccagtggag  840
gtgatgctga aagatctctc cggaggaggt ggctcaggtg gtggaggatc tggaggaggt  900
gggagtggtg gaggtggttc taccggtctc gagcccaaat cttctgacaa aactcacaca  960
tctccaccgt ccccagcacc tgaactcctg ggaggatcgt cagtcttcct cttcccccca  1020
aaacccaagg acaccctcat gatctcccgg acccctgagg tcacatgcgt ggtggtggac  1080
gtgagccacg aagaccctga ggtcaagttc aactggtacg tggacggcgt ggaggtgcat  1140
aatgccaaga caaagccgcg ggaggagcag tacaacagca cgtaccgtgt ggtcagcgtc  1200
ctcaccgtcc tgcaccagga ctggctgaat ggcaaggagt acaagtgcaa ggtctccaac  1260
aaagccctcc cagcctccat cgagaaaacc atctccaaag ccaaagggca gccccgagaa  1320
ccacaggtgt acaccctgcc cccatcccgg gatgagctga ccaagaacca ggtcagcctg  1380
acctgcctgg tcaaaggctt ctatcccagc gacatcgccg tggagtggga gagcaatggg  1440
```

```
cagccggaga acaactacaa gaccacgcct cccgtgctgg actccgacgg ctccttcttc  1500
ctctacagca agctcaccgt ggacaagagc aggtggcagc aggggaacgt cttctcatgc  1560
tccgtgatgc atgaggctct gcacaaccac tacacgcaga agagcctctc tctctctccg  1620
ggtaaagtcg acggagctag cagccccgtg aacgtgagca gccccagcgt gcaggatatc  1680
ctcttcagga accaccagtc ttcttaccaa acacgactta atgctctccg agaggtacaa  1740
cccgtagaac ttcctaactg taatttagtt aaaggaatcg aaactggctc tgaagacttg  1800
gagatactgc ctaatggact ggctttcatt agctctggat taaagtatcc tggaataaag  1860
agcttcaacc ccaacagtcc tggaaaaata cttctgatgg acctgaatga agaagatcca  1920
acagtgttgg aattggggat cactggaagt aaatttgatg tatcttcatt taaccctcat  1980
gggattagca cattcacaga tgaagataat gccatgtacc tcctggtggt gaaccatcca  2040
gatgccaagt ccacagtgga gttgtttaaa tttcaagaag aagaaaaatc gcttttgcat  2100
ctaaaaacca tcagacataa acttctgcct aatttgaatg atattgttgc tgtgggacct  2160
gagcactttt atggcacaaa tgatcactat tttcttgacc cctacttaaa atcctgggag  2220
atgtatttgg gtttagcgtg gtcgtatgtt gtctactata gtccaagtga agttcgagtg  2280
gtggcagaag gatttgattt tgctaatgga atcaacattt cacccgatgg caagtatgtc  2340
tatatagctg agttgctggc tcataagatt catgtgtatg aaaagcatgc taattggact  2400
ttaactccat tgaagtccct tgactttaat accctcgtgg ataacatatc tgtggatcct  2460
gagacaggag acctttgggt tggatgccat cccaatggca tgaaaatctt cttctatgac  2520
tcagagaatc ctcctgcatc agaggtgctt cgaatccaga acattctaac agaagaacct  2580
aaagtgacac aggtttatgc agaaaatggc acagtgttgc aaggcagtac agttgcctct  2640
gtgtacaaag ggaaactgct gattggcaca gtgtttcaca aagctcttta ctgtgagctc  2700
taataatcta gaa                                                     2713

SEQ ID NO: 158          moltype = AA  length = 896
FEATURE                 Location/Qualifiers
REGION                  1..896
                        note = hVK3LP-[hDNase1
                         N74K-G105R]-(g4s)4-[SSShinge-P238S-P331S Fc]-NGS-[PON1
                         Q192K]
source                  1..896
                        mol_type = protein
                        organism = synthetic construct
SEQUENCE: 158
METPAQLLFL LLLWLPDTTG LKIAAFNIQT FGETKMSNAT LVSYIVQILS RYDIALVQEV  60
RDSHLTAVGK LLDNLNQDAP DTYHYVVSEP LGRKSYKERY LFVYRPDQVS AVDSYYYDDG  120
CEPCRNDTFN REPAIVRFFS RFTEVREFAI VPLHAAPGDA VAEIDALYDV YLDVQEKWGL  180
EDVMLMGDFN AGCSYVRPSQ WSSIRLWTSP TFQWLIPDSA DTTATPTHCA YDRIVVAGML  240
LRGAVVPDSA LPFNFQAAYG LSDQLAQAIS DHYPVEVMLK DLSGGGGSGG GGSGGGGSGG  300
GGSTGLEPKS SDKTHTSPPS PAPELLGGSS VFLFPPKPKD TLMISRTPEV TCVVVDVSHE  360
DPEVKFNWYV DGVEVHNAKT KPREEQYNST YRVVSVLTVL HQDWLNGKEY KCKVSNKALP  420
ASIEKTISKA KGQPREPQVY TLPPSRDELT KNQVSLTCLV KGFYPSDIAV EWESNGQPEN  480
NYKTTPPVLD SDGSFFLYSK LTVDKSRWQQ GNVFSCSVMH EALHNHYTQK SLSLSPGKVD  540
GASSPVNVSS PSVQDILFRN HQSSYQTRLN ALREVQPVEL PNCNLVKGIE TGSEDLEILP  600
NGLAFISSGL KYPGIKSFNP NSPGKILLMD LNEEDPTVLE LGITGSKFDV SSFNPHGIST  660
FTDEDNAMYL LVVNHPDAKS TVELFKFQEE EKSLLHLKTI RHKLLPNLND IVAVGPEHFY  720
GTNDHYFLDP YLKSWEMYLG LAWSYVVYYS PSEVRVVAEG FDFANGINIS PDGKYVYIAE  780
LLAHKIHVYE KHANWTLTPL KSLDFNTLVD NISVDPETGD LWVGCHPNGM KIFFYDSENP  840
PASEVLRIQN ILTEEPKVTQ VYAENGTVLQ GSTVASVYKG KLLIGTVFHK ALYCEL      896

SEQ ID NO: 159          moltype = DNA  length = 2743
FEATURE                 Location/Qualifiers
misc_feature            1..2743
                        note = hVK3LP-[hDNase1
                         N74K-G105R]-(g4s)6-[SSShinge-P238S-P331S Fc]-NGS-[PON1
                         Q192K] DNA
source                  1..2743
                        mol_type = other DNA
                        organism = synthetic construct
SEQUENCE: 159
aagcttgccg ccatggaaac cccagcgcag cttctcttcc tcctgctact ctggctccca  60
gataccaccg gtctgaagat cgcagccttc aacatccaga catttgggga gaccaagatg  120
tccaatgcca ccctcgtcag ctacattgtg cagatcctga gccgctatga catcgccctg  180
gtccaggagg tcagagacag ccacctgact gccgtgggga agctgctgga caacctcaat  240
caggatgcac cagacaccta tcactacgtg gtcagtgagc cactgggacg gaagagctat  300
aaggagcgct acctgttcgt gtacaggcct gaccaggtgt ctgcggtgga cagctactac  360
tacgatgatg gctgcgagcc ctgcaggaac gacaccttca accgagagcc agccattgtc  420
aggttcttct cccggttcac agaggtcagg gagtttgcca ttgttcccct gcatgcggcc  480
ccgggggacg cagtagccga gatcgacgct ctctatgacg tctacctgga tgtccaagag  540
aaatggggct tggaggacgt catgttgatg ggcgacttca atgcgggctg cagctatgtg  600
agaccctccc agtggtcatc catccgcctg tggacaagcc ccaccttcca gtggctgatc  660
cccgacagcg ctgacaccac agctacaccc acgcactgtg cctatgacag gatcgtggtt  720
gcagggatgc tgctccgagg cgccgttgtt cccgactcgg ctcttccctt taacttccag  780
gctgcctatg gcctgagtga ccaactggcc caagccatca gtgaccacta tccagtggag  840
gtgatgctga aagatctctc cggaggaggt ggctcaggtg gtggaggatc tggaggaggt  900
gggagtggtg gaggtggttc tggaggaggt ggtagtggag gtggaggttc taccggtctc  960
gagcccaaat cttctgacaa aactcacaca tctccaccgt ccccagcacc tgaactcctg  1020
ggaggatcgt cagtcttcct cttcccccca aaacccaagg acaccctcat gatctcccgg  1080
acccctgagg tcacatgcgt ggtggtggac gtgagccacg aagaccctga ggtcaagttc  1140
aactggtacg tggacggcgt ggaggtgcat aatgccaaga caaagccgcg ggaggagcag  1200
```

```
tacaacagca cgtaccgtgt ggtcagcgtc ctcaccgtcc tgcaccagga ctggctgaat  1260
ggcaaggagt acaagtgcaa ggtctccaac aaagccctcc cagcctccat cgagaaaacc  1320
atctccaaag ccaaagggca gccccgagaa ccacaggtgt acaccctgcc cccatcccgg  1380
gatgagctga ccaagaacca ggtcagcctg acctgcctgg tcaaaggctt ctatcccagc  1440
gacatcgccg tggagtggga gagcaatggg cagccggaga acaactacaa gaccacgcct  1500
cccgtgctgg actccgacgg ctccttcttc ctctacagca agctcaccgt ggacaagagc  1560
aggtggcagc aggggaacgt cttctcatgc tccgtgatgc atgaggctct gcacaaccac  1620
tacacgcaga agagcctctc tctctctccg ggtaaagtcg acggagctag cagccccgtg  1680
aacgtgagca gccccagcgt gcaggatatc ctcttcagga accaccagtc ttcttaccaa  1740
acacgactta atgctctccg agaggtacaa cccgtagaac ttcctaactg taatttagtt  1800
aaaggaatcg aaactggctc tgaagacttg gagatactgc ctaatggact ggctttcatt  1860
agctctggat taaagtatcc tggaataaag agcttcaacc ccaacagtcc tggaaaaata  1920
cttctgatgg acctgaatga agaagatcca acagtgttgg aattggggat cactggaagt  1980
aaatttgatg tatcttcatt taaccctcat gggattagca cattcacaga tgaagataat  2040
gccatgtacc tcctggtggt gaaccatcca gatgccaagt ccacagtgga gttgtttaaa  2100
tttcaagaag aagaaaaatc gcttttgcat ctaaaaacca tcagacataa acttctgcct  2160
aatttgaatg atattgttgc tgtgggacct gagcactttt atggcacaaa tgatcactat  2220
tttcttgacc cctacttaaa atcctgggag atgtatttgg gtttagcgtg gtcgtatgtt  2280
gtctactata gtccaagtga agttcgagtg gtggcagaag gatttgattt tgctaatgga  2340
atcaacattt cacccgatgg caagtatgtc tatatagctg agttgctggc tcataagatt  2400
catgtgtatg aaaagcatgc taattggact ttaactccat tgaagtccct tgactttaat  2460
accctcgtgg ataacatatc tgtggatcct gagacaggag acctttgggt tggatgccat  2520
cccaatggca tgaaaatctt cttctatgac tcagagaatc ctcctgcatc agaggtgctt  2580
cgaatccaga acattctaac agaagaacct aaagtgacac aggtttatgc agaaaatggc  2640
acagtgttgc aaggcagtac agttgcctct gtgtacaaag ggaaactgct gattggcaca  2700
gtgtttcaca aagctcttta ctgtgagctc taataatcta gaa                    2743

SEQ ID NO: 160          moltype = AA  length = 906
FEATURE                 Location/Qualifiers
REGION                  1..906
                        note = hVK3LP-[hDNase1
                         N74K-G105R]-(g4s)6-[SSShinge-P238S-P331S Fc]-NGS-[PON1
                         Q192K]
source                  1..906
                        mol_type = protein
                        organism = synthetic construct
SEQUENCE: 160
METPAQLLFL LLLWLPDTTG LKIAAFNIQT FGETKMSNAT LVSYIVQILS RYDIALVQEV  60
RDSHLTAVGK LLDNLNQDAP DTYHYVVSEP LGRKSYKERY LFVYRPDQVS AVDSYYYDDG  120
CEPCRNDTFN REPAIVRFFS RFTEVREFAI VPLHAAPGDA VAEIDALYDV YLDVQEKWGL  180
EDVMLMGDFN AGCSYVRPSQ WSSIRLWTSP TFQWLIPDSA DTTATPTHCA YDRIVVAGML  240
LRGAVVPDSA LPFNFQAAYG LSDQLAQAIS DHYPVEVMLK DLSGGGGSGG GGSGGGGSGG  300
GGSGGGGSGG GGSTGLEPKS SDKTHTSPPS PAPELLGGSS VFLFPPKPKD TLMISRTPEV  360
TCVVVDVSHE DPEVKFNWYV DGVEVHNAKT KPREEQYNST YRVVSVLTVL HQDWLNGKEY  420
KCKVSNKALP ASIEKTISKA KGQPREPQVY TLPPSRDELT KNQVSLTCLV KGFYPSDIAV  480
EWESNGQPEN NYKTTPPVLD SDGSFFLYSK LTVDKSRWQQ GNVFSCSVMH EALHNHYTQK  540
SLSLSPGKVD GASSPVNVSS PSVQDILFRN HQSSYQTRLN ALREVQPVEL PNCNLVKGIE  600
TGSEDLEILP NGLAFISSGL KYPGIKSFNP NSPGKILLMD LNEEDPTVLE LGITGSKFDV  660
SSFNPHGIST FTDEDNAMYL LVVNHPDAKS TVELFKFQEE EKSLLHLKTI RHKLLPNLND  720
IVAVGPEHFY GTNDHYFLDP YLKSWEMYLG LAWSYVVYYS PSEVRVVAEG FDFANGINIS  780
PDGKYVYIAE LLAHKIHVYE KHANWTLTPL KSLDFNTLVD NISVDPETGD LWVGCHPNGM  840
KIFFYDSENP PASEVLRIQN ILTEEPKVTQ VYAENGTVLQ GSTVASVYKG KLLIGTVFHK  900
ALYCEL                                                            906

SEQ ID NO: 161          moltype = DNA  length = 2721
FEATURE                 Location/Qualifiers
misc_feature            1..2721
                        note = hVK3LP-[hDNase1L3 R80A-R95A-N96A
                         NLS2delta]-(g4s)4-[SSShinge-P238S-P331S Fc]-NGS-[PON1
                         Q192K] DNA
source                  1..2721
                        mol_type = other DNA
                        organism = synthetic construct
SEQUENCE: 161
atggaaaccc cagcgcagct tctcttcctc ctgctactct ggctcccaga taccaccggt  60
atgaggatct gctccttcaa cgtcaggtcc tttggggaaa gcaagcagga agacaagaat  120
gccatggatg tcattgtgaa ggtcatcaaa cgctgtgaca tcatactcgt gatggaaatc  180
aaggacagca acaacaggat ctgccccata ctgatggaga agctgaacag aaattcagca  240
agaggcataa cgtacaacta tgtgattagc tctcggcttg gagcagctac atataaagaa  300
caatatgcct ttctctacaa ggaaaagctg gtgtctgtga agaggagtta tcactaccat  360
gactatcagg atggagacgc agatgtgttt tccagggagc cctttgtggt ctggttccaa  420
tctccccaca ctgctgtcaa agacttcgtg attatccccc tgcacaccac cccagagaca  480
tccgttaagg agatcgatga gttggttgag gtctacacgg acgtgaaaca ccgctggaag  540
gcggagaatt tcattttcat gggtgacttc aatgccggct gcagctacgt ccccaagaag  600
gcctggaaga acatccgctt gaggactgac cccaggtttg tttggctgat cggggaccaa  660
gaggacacca cggtgaagaa gagcaccaac tgtgcatatg acaggattgt gcttagagga  720
caagaaatcg tcagttctgt tgttcccaag tcaaacagtg tttttgactt ccagaaagct  780
tacaagctga ctgaagagga ggccctggat gtcagcgacc actttccagt tgaatttaaa  840
ctacagtctt caagggcctt caccaactca gatctctccg gaggaggtgg ctcaggtggt  900
```

```
ggaggatctg gaggaggtgg gagtggtgga ggtggttcta ccggtctcga gcccaaatct  960
tctgacaaaa ctcacacatc tccaccgtcc ccagcacctg aactcctggg aggatcgtca  1020
gtcttcctct tccccccaaa acccaaggac accctcatga tctcccggac ccctgaggtc  1080
acatgcgtgg tggtggacgt gagccacgaa gaccctgagg tcaagttcaa ctggtacgtg  1140
gacggcgtgg aggtgcataa tgccaagaca aagccgcggg aggagcagta caacagcacg  1200
taccgtgtgg tcagcgtcct caccgtcctg caccaggact ggctgaatgg caaggagtac  1260
aagtgcaagg tctccaacaa agccctccca gcctccatcg agaaaaccat ctccaaagcc  1320
aaagggcagc cccgagaacc acaggtgtac accctgcccc catcccggga tgagctgacc  1380
aagaaccagg tcagcctgac ctgcctggtc aaaggcttct atcccagcga catcgccgtg  1440
gagtgggaga gcaatgggca gccggagaac aactacaaga ccacgcctcc cgtgctggac  1500
tccgacggct ccttcttcct ctacagcaag ctcaccgtgg acaagagcag gtggcagcag  1560
gggaacgtct tctcatgctc cgtgatgcat gaggctctgc acaaccacta cacgcagaag  1620
agcctctctc tctctccggg taaagtcgac ggagctagca gccccgtgaa cgtgagcagc  1680
cccagcgtgc aggatatcct cttcaggaac caccagtctt cttaccaaac acgacttaat  1740
gctctccgag aggtacaacc cgtagaactt cctaactgta atttagttaa aggaatcgaa  1800
actggctctg aagacttgga gatactgcct aatggactgg ctttcattag ctctggatta  1860
aagtatcctg gaataaagag cttcaacccc aacagtcctg gaaaaatact tctgatggac  1920
ctgaatgaag aagatccaac agtgttggaa ttggggatca ctggaagtaa atttgatgta  1980
tcttcattta accctcatgg gattagcaca ttcacagatg aagataatgc catgtacctc  2040
ctggtggtga accatccaga tgccaagtcc acagtggagt tgtttaaatt tcaagaagaa  2100
gaaaaatcgc ttttgcatct aaaaaccatc agacataaac ttctgcctaa tttgaatgat  2160
attgttgctg tgggacctga gcacttttat ggcacaaatg atcactattt tcttgacccc  2220
tacttaaaat cctgggagat gtatttgggt ttagcgtggt cgtatgttgt ctactatagt  2280
ccaagtgaag ttcgagtggt ggcagaagga tttgattttg ctaatggaat caacatttca  2340
cccgatggca agtatgtcta tatagctgag ttgctggctc ataagattca tgtgtatgaa  2400
aagcatgcta attggacttt aactccattg aagtcccttg actttaatac cctcgtggat  2460
aacatatctg tggatcctga gacaggagac ctttgggttg gatgccatcc caatggcatg  2520
aaaatcttct tctatgactc agagaatcct cctgcatcag aggtgcttcg aatccagaac  2580
attctaacag aagaacctaa agtgacacag gtttatgcag aaaatggcac agtgttgcaa  2640
ggcagtacag ttgcctctgt gtacaaaggg aaactgctga ttggcacagt gtttcacaaa  2700
gctctttact gtgagctcta a                                           2721
```

```
SEQ ID NO: 162          moltype = AA  length = 906
FEATURE                 Location/Qualifiers
REGION                  1..906
                        note = hVK3LP-[hDNase1L3 R80A-R95A-N96A
                         NLS2delta]-(g4s)4-[SSShinge-P238S-P331S Fc]-NGS-[PON1
                         Q192K]
source                  1..906
                        mol_type = protein
                        organism = synthetic construct
SEQUENCE: 162
METPAQLLFL LLLWLPDTTG MRICSFNVRS FGESKQEDKN AMDVIVKVIK RCDIILVMEI  60
KDSNNRICPI LMEKLNRNSA RGITYNYVIS SRLGAATYKE QYAFLYKEKL VSVKRSYHYH  120
DYQDGDADVF SREPFVVWFQ SPHTAVKDFV IIPLHTTPET SVKEIDELVE VYTDVKHRWK  180
AENFIFMGDF NAGCSYVPKK AWKNIRLRTD PRFVWLIGDQ EDTTVKKSTN CAYDRIVLRG  240
QEIVSSVVPK SNSVFDFQKA YKLTEEEALD VSDHFPVEFK LQSSRAFTNS DLSGGGGSGG  300
GGSGGGGSGG GGSTGLEPKS SDKTHTSPPS PAPELLGGSS VFLFPPKPKD TLMISRTPEV  360
TCVVVDVSHE DPEVKFNWYV DGVEVHNAKT KPREEQYNST YRVVSVLTVL HQDWLNGKEY  420
KCKVSNKALP ASIEKTISKA KGQPREPQVY TLPPSRDELT KNQVSLTCLV KGFYPSDIAV  480
EWESNGQPEN NYKTTPPVLD SDGSFFLYSK LTVDKSRWQQ GNVFSCSVMH EALHNHYTQK  540
SLSLSPGKVD GASSPVNVSS PSVQDILFRN HQSSYQTRLN ALREVQPVEL PNCNLVKGIE  600
TGSEDLEILP NGLAFISSGL KYPGIKSFNP NSPGKILLMD LNEEDPTVLE LGITGSKFDV  660
SSFNPHGIST FTDEDNAMYL LVVNHPDAKS TVELFKFQEE EKSLLHLKTI RHKLLPNLND  720
IVAVGPEHFY GTNDHYFLDP YLKSWEMYLG LAWSYVVYYS PSEVRVVAEG FDFANGINIS  780
PDGKYVYIAE LLAHKIHVYE KHANWTLTPL KSLDFNTLVD NISVDPETGD LWVGCHPNGM  840
KIFFYDSENP PASEVLRIQN ILTEEPKVTQ VYAENGTVLQ GSTVASVYKG KLLIGTVFHK  900
ALYCEL                                                            906
```

```
SEQ ID NO: 163          moltype = DNA  length = 2721
FEATURE                 Location/Qualifiers
misc_feature            1..2721
                        note = hVK3LP-[hDNase1L3 R80S-R95S-N96S
                         NLS2delta]-(g4s)4-[SSShinge-P238S-P331S Fc]-NGS-[PON1
                         Q192K] DNA
source                  1..2721
                        mol_type = other DNA
                        organism = synthetic construct
SEQUENCE: 163
atggaaaccc cagcgcagct tctcttcctc ctgctactct ggctcccaga taccaccggt  60
atgaggatct gctccttcaa cgtcaggtcc tttggggaaa gcaagcagga agacaagaat  120
gccatggatg tcattgtgaa ggtcatcaaa cgctgtgaca tcatactcgt gatggaaatc  180
aaggacagca acaacaggat ctgccccata ctgatggaga agctgaacag aaattcatca  240
agaggcataa cgtacaacta tgtgattagc tctcggcttg gaagttctac atataaagaa  300
caatatgcct ttctctacaa ggaaaagctg gtgtctgtga agaggagtta tcactaccat  360
gactatcagg atggagacgc agatgtgttt tccagggagc cctttgtggt ctggttccaa  420
tctccccaca ctgctgtcaa agacttcgtg attatccccc tgcacaccac cccagagaca  480
tccgttaagg agatcgatga gttggttgag gtctacacgg acgtgaaaca ccgctggaag  540
gcggagaatt tcattttcat gggtgacttc aatgccggct gcagctacgt ccccaagaag  600
```

-continued

```
gcctggaaga acatccgctt gaggactgac cccaggtttg tttggctgat cggggaccaa  660
gaggacacca cggtgaagaa gagcaccaac tgtgcatatg acaggattgt gcttagagga  720
caagaaatcg tcagttctgt tgttcccaag tcaaacagtg tttttgactt ccagaaagct  780
tacaagctga ctgaagagga ggccctggat gtcagcgacc actttccagt tgaatttaaa  840
ctacagtctt caagggcctt caccaactca gatctctccg gaggaggtgg ctcaggtggt  900
ggaggatctg gaggaggtgg gagtggtgga ggtggttcta ccggtctcga gcccaaatct  960
tctgacaaaa ctcacacatc tccaccgtcc ccagcacctg aactcctggg aggatcgtca  1020
gtcttcctct tccccccaaa acccaaggac accctcatga tctcccggac ccctgaggtc  1080
acatgcgtgg tggtggacgt gagccacgaa gaccctgagg tcaagttcaa ctggtacgtg  1140
gacggcgtgg aggtgcataa tgccaagaca aagccgcggg aggagcagta caacagcacg  1200
taccgtgtgg tcagcgtcct caccgtcctg caccaggact ggctgaatgg caaggagtac  1260
aagtgcaagg tctccaacaa agccctccca gcctccatcg agaaaaccat ctccaaagcc  1320
aaagggcagc cccgagaacc acaggtgtac accctgcccc catcccggga tgagctgacc  1380
aagaaccagg tcagcctgac ctgcctggtc aaaggcttct atcccagcga catcgccgtg  1440
gagtgggaga gcaatgggca gccggagaac aactacaaga ccacgcctcc cgtgctggac  1500
tccgacggct ccttcttcct ctacagcaag ctcaccgtgg acaagagcag gtggcagcag  1560
gggaacgtct tctcatgctc cgtgatgcat gaggctctgc acaaccacta cacgcagaag  1620
agcctctctc tctctccggg taaagtcgac ggagctagca gccccgtgaa cgtgagcagc  1680
cccagcgtgc aggatatcct cttcaggaac caccagtctt cttaccaaac acgacttaat  1740
gctctccgag aggtacaacc cgtagaactt cctaactgta atttagttaa aggaatcgaa  1800
actggctctg aagacttgga gatactgcct aatggactgg ctttcattag ctctggatta  1860
aagtatcctg gaataaagag cttcaacccc aacagtcctg gaaaaatact tctgatggac  1920
ctgaatgaag aagatccaac agtgttggaa ttggggatca ctggaagtaa atttgatgta  1980
tcttcattta accctcatgg gattagcaca ttcacagatg aagataatgc catgtacctc  2040
ctggtggtga accatccaga tgccaagtcc acagtggagt tgtttaaatt tcaagaagaa  2100
gaaaaatcgc ttttgcatct aaaaaccatc agacataaac ttctgcctaa tttgaatgat  2160
attgttgctg tgggacctga gcacttttat ggcacaaatg atcactattt tcttgacccc  2220
tacttaaaat cctgggagat gtatttgggt ttagcgtggt cgtatgttgt ctactatagt  2280
ccaagtgaag ttcgagtggt ggcagaagga tttgattttg ctaatggaat caacatttca  2340
cccgatggca agtatgtcta tatagctgag ttgctggctc ataagattca tgtgtatgaa  2400
aagcatgcta attggacttt aactccattg aagtcccttg actttaatac cctcgtggat  2460
aacatatctg tggatcctga gacaggagac ctttgggttg gatgccatcc caatggcatg  2520
aaaatcttct tctatgactc agagaatcct cctgcatcag aggtgcttcg aatccagaac  2580
attctaacag aagaacctaa agtgacacag gtttatgcag aaaatggcac agtgttgcaa  2640
ggcagtacag ttgcctctgt gtacaaaggg aaactgctga ttggcacagt gtttcacaaa  2700
gctctttact gtgagctcta a                                             2721

SEQ ID NO: 164          moltype = AA  length = 906
FEATURE                 Location/Qualifiers
REGION                  1..906
                        note = hVK3LP-[hDNase1L3 R80S-R95S-N96S
                         NLS2delta]-(g4s)4-[SSShinge-P238S-P331S Fc]-NGS-[PON1
                         Q192K]
source                  1..906
                        mol_type = protein
                        organism = synthetic construct
SEQUENCE: 164
METPAQLLFL LLLWLPDTTG MRICSFNVRS FGESKQEDKN AMDVIVKVIK RCDIILVMEI  60
KDSNNRICPI LMEKLNRNSS RGITYNYVIS SRLGSSTYKE QYAFLYKEKL VSVKRSYHYH  120
DYQDGDADVF SREPFVVWFQ SPHTAVKDFV IIPLHTTPET SVKEIDELVE VYTDVKHRWK  180
AENFIFMGDF NAGCSYVPKK AWKNIRLRTD PRFVWLIGDQ EDTTVKKSTN CAYDRIVLRG  240
QEIVSSVVPK SNSVFDFQKA YKLTEEEALD VSDHFPVEFK LQSSRAFTNS DLSGGGGSGG  300
GGSGGGGSGG GGSTGLEPKS SDKTHTSPPS PAPELLGGSS VFLFPPKPKD TLMISRTPEV  360
TCVVVDVSHE DPEVKFNWYV DGVEVHNAKT KPREEQYNST YRVVSVLTVL HQDWLNGKEY  420
KCKVSNKALP ASIEKTISKA KGQPREPQVY TLPPSRDELT KNQVSLTCLV KGFYPSDIAV  480
EWESNGQPEN NYKTTPPVLD SDGSFFLYSK LTVDKSRWQQ GNVFSCSVMH EALHNHYTQK  540
SLSLSPGKVD GASSPVNVSS PSVQDILFRN HQSSYQTRLN ALREVQPVEL PNCNLVKGIE  600
TGSEDLEILP NGLAFISSGL KYPGIKSFNP NSPGKILLMD LNEEDPTVLE LGITGSKFDV  660
SSFNPHGIST FTDEDNAMYL LVVNHPDAKS TVELFKFQEE EKSLLHLKTI RHKLLPNLND  720
IVAVGPEHFY GTNDHYFLDP YLKSWEMYLG LAWSYVVYYS PSEVRVVAEG FDFANGINIS  780
PDGKYVYIAE LLAHKIHVYE KHANWTLTPL KSLDFNTLVD NISVDPETGD LWVGCHPNGM  840
KIFFYDSENP PASEVLRIQN ILTEEPKVTQ VYAENGTVLQ GSTVASVYKG KLLIGTVFHK  900
ALYCEL                                                              906
```

What is claimed is:

1. A fusion polypeptide comprising, from an amino terminal position to a carboxyl terminal position, T-L1-X-L2-P, wherein:

T is a biologically active RNase, wherein the RNase has at least 95% identity with the amino acid sequence shown in residues 29-156 of SEQ ID NO:22;

L1 is a first polypeptide linker, wherein L1 is optionally present;

X is an immunoglobulin heavy chain constant region, wherein the immunoglobulin heavy chain constant region is capable of forming dimers and specifically binding the neonatal Fc receptor (FcRn), wherein the immunoglobulin heavy chain constant region is a human immunoglobulin Fc region;

L2 is a second polypeptide linker comprising at least eight amino acid residues; and P is a biologically active paraoxonase, wherein the paraoxonase has at least 95% identity with the amino acid sequence shown in residues 16-355 or 26-355 of SEQ ID NO:6, and wherein the paraoxonase does not contain an amino terminal leader sequence corresponding to residues 1-15 of SEQ ID NO:6;

wherein the fusion polypeptide comprises an amino acid sequence having at least 95% identity with the amino acid sequence shown in residues 21-740 of SEQ ID NO:48.

2. The fusion polypeptide of claim 1, wherein the human Fc region is an Fc variant comprising one or more amino acid substitutions relative to the wild-type human sequence.

3. The fusion polypeptide of claim 2, wherein the Fc region is a human γ1 Fc region.

4. The fusion polypeptide of claim 2, wherein the Fc region is a human γ1 Fc variant in which Eu residue C220 is replaced by serine, Eu residue P238 is replaced by serine, and/or Eu residue P331 is replaced by serine.

5. The fusion polypeptide of claim 1, wherein the Fc region has the amino acid sequence shown in (i) residues 1-232 or 1-231 of SEQ ID NO:28, or (ii) residues 159-390 or 159-389 of SEQ ID NO:42.

6. The fusion polypeptide of claim 1, wherein the RNase has the amino acid sequence shown in residues 29-156 of SEQ ID NO:22.

7. The fusion polypeptide of claim 1, wherein the paraoxonase has the amino acid sequence shown in residues 16-355 of SEQ ID NO:6.

8. The fusion polypeptide of claim 1, wherein the fusion polypeptide comprises the amino acid sequence shown in residues 21-740 of SEQ ID NO:48.

9. A dimeric protein comprising a first fusion polypeptide and a second fusion polypeptide, wherein each of the first and second fusion polypeptides is a fusion polypeptide as defined in claim 1.

10. A polynucleotide encoding the fusion polypeptide of claim 1.

11. An expression cassette comprising a DNA segment encoding the fusion polypeptide of claim 1, wherein the DNA segment is operably linked to a promoter.

12. A vector comprising the expression cassette of claim 11.

13. A cultured cell into which has been introduced the expression cassette of claim 11, wherein the cell expresses the DNA segment.

14. A method of making a fusion polypeptide, the method comprising:

culturing a cell into which has been introduced the expression cassette of claim 11, wherein the cell expresses the DNA segment and the encoded fusion polypeptide is produced; and recovering the fusion polypeptide.

15. The method of claim 14, wherein the encoded fusion polypeptide is produced and recovered as a dimeric protein.

16. A composition comprising:

a dimeric protein of claim 9; and a pharmaceutically acceptable carrier.

* * * * *